(12) United States Patent
Germeroth et al.

(10) Patent No.: US 11,466,253 B2
(45) Date of Patent: Oct. 11, 2022

(54) METHODS FOR CULTURING CELLS AND KITS AND APPARATUS FOR SAME

(71) Applicant: Juno Therapeutics GmbH, Munich (DE)

(72) Inventors: Lothar Germeroth, Munich (DE); Christian Stemberger, Munich (DE); Patricia Gräf, Munich (DE); Keenan Bashour, Seattle, WA (US)

(73) Assignee: Juno Therapeutics GmbH, Munich (DE)

( * ) Notice: Subject to any disclaimer, the term of this patent is extended or adjusted under 35 U.S.C. 154(b) by 947 days.

(21) Appl. No.: 15/770,179

(22) PCT Filed: Oct. 20, 2016

(86) PCT No.: PCT/IB2016/001618
§ 371 (c)(1),
(2) Date: Apr. 20, 2018

(87) PCT Pub. No.: WO2017/068421
PCT Pub. Date: Apr. 27, 2017

(65) Prior Publication Data
US 2019/0136186 A1 May 9, 2019

Related U.S. Application Data

(60) Provisional application No. 62/245,261, filed on Oct. 22, 2015, provisional application No. 62/245,252, filed on Oct. 22, 2015.

(51) Int. Cl.
*C12N 5/0783* (2010.01)
*A61K 35/17* (2015.01)
*A61K 39/00* (2006.01)

(52) U.S. Cl.
CPC ........... *C12N 5/0636* (2013.01); *A61K 35/17* (2013.01); *A61K 2039/5158* (2013.01); *C12N 2501/51* (2013.01); *C12N 2501/515* (2013.01); *C12N 2501/998* (2013.01); *C12N 2533/20* (2013.01); *C12N 2533/50* (2013.01)

(58) Field of Classification Search
CPC ........... C12N 5/0636; C12N 2501/515; C12N 2533/50; C12N 2501/51; C12N 2501/998; A61K 35/17
See application file for complete search history.

(56) References Cited

U.S. PATENT DOCUMENTS

| | | |
|---|---|---|
| 4,235,871 A | 11/1980 | Papahadjopoulos et al. |
| 4,361,549 A | 11/1982 | Kung |
| 4,452,773 A | 6/1984 | Molday |
| 4,501,728 A | 2/1985 | Geho et al. |
| 4,690,915 A | 9/1987 | Rosenberg |
| 4,795,698 A | 1/1989 | Owen et al. |
| 4,837,028 A | 6/1989 | Allen |
| 4,851,341 A | 7/1989 | Hopp |
| 5,019,369 A | 5/1991 | Presant et al. |
| 5,087,616 A | 2/1992 | Myers et al. |
| 5,168,049 A | 12/1992 | Meade et al. |
| 5,200,084 A | 4/1993 | Liberti et al. |
| 5,219,740 A | 6/1993 | Miller et al. |
| 5,506,121 A | 4/1996 | Skerra |
| 5,853,721 A | 12/1998 | Gately et al. |
| 5,985,658 A | 11/1999 | Colinas |
| 6,013,480 A | 1/2000 | Grabstein et al. |
| 6,022,951 A | 2/2000 | Sano |
| 6,040,177 A | 3/2000 | Riddell et al. |
| 6,103,493 A | 8/2000 | Skerra et al. |

(Continued)

FOREIGN PATENT DOCUMENTS

| | | |
|---|---|---|
| CA | 2572334 | 1/2006 |
| CN | 1902491 A | 1/2007 |

(Continued)

OTHER PUBLICATIONS

Invitrogen. Healthy cells in = good data out. Cell isolation and Activation, p. 1-12 (Year: 2010).*
Turka et al. CD28 is an Inducible T Cell Surface Antigen That Transduces a Proliferative Signal in CD3+ Mature Thymocytes. Journal of Immunology. vol. 144. p. 1646-1653 (Year: 1990).*
Ahlers, J.D. et al. (Mar. 4, 2010). "Memories That Last Forever: Strategies for Optimizing Vaccine T-Cell Memory", *BLOOD* 115(9):1678-1689.
Alonso-Camino, V. et al. (May 2013, e-pub. May 21, 2013). "CARbodies: Human Antibodies Against Cell Surface Tumor Antigens Selected From Repertoires Displayed on T Cell Chimeric Antigen Receptors", 2(5):e93, 11 pages.
Ameres, S.et al. (2013). "Presentation of an Immunodominant Immediate-Early CD8+ T Cell Epitope Resists Human Cytomegalovirus Immunoevasion," *PLoS Pathog.* 9(5):e1003383, 15 pages.

(Continued)

*Primary Examiner* — Taeyoon Kim
(74) *Attorney, Agent, or Firm* — Morrison & Foerster LLP

(57) ABSTRACT

Provided herein are methods that relate, in some aspects, to the incubation or culturing, such as to induce stimulation of expansion (proliferation), activation, costimulation and/or survival, of a composition of cells, such as a population of lymphocytes. In some aspects, provided are methods and reagents for the stimulation, e.g., of expansion (proliferation), survival or persistence, activation, costimulation, or other effect, of cell populations that involve binding of agents to a molecule on the surface of the cells, thereby providing one or more signals to the cells. In some cases, the reagents are reagents containing a plurality of binding sites for agents, such as multimerization reagents, and thus the one or more agents are multimerized by reversibly binding to the reagent, e.g., thereby creating a stimulatory reagent (multimerized agent), having stimulatory agents multimerized thereon. In some aspects, the multimerized agent can provide for expansion or proliferation or other stimulation of a population of cells, and then such stimulatory agents can be removed by disruption of the reversible bond. Also provided are compositions, apparatus and methods of use thereof.

54 Claims, 48 Drawing Sheets
Specification includes a Sequence Listing.

(56) References Cited

U.S. PATENT DOCUMENTS

| | | |
|---|---|---|
| 6,153,441 A | 11/2000 | Appalbaum et al. |
| 6,156,493 A | 12/2000 | Stayton |
| 6,165,750 A | 12/2000 | Stayton |
| 6,184,358 B1 | 2/2001 | Loetscher et al. |
| 6,303,121 B1 | 10/2001 | Kwon |
| 6,352,694 B1 | 3/2002 | June |
| 6,368,813 B1 | 4/2002 | Reznuj et al. |
| 6,410,319 B1 | 6/2002 | Raubitschek et al. |
| 6,451,995 B1 | 9/2002 | Cheung et al. |
| 6,534,055 B1 | 3/2003 | June et al. |
| 6,569,997 B1 | 5/2003 | Kwon |
| 7,070,995 B2 | 7/2006 | Jensen |
| 7,265,209 B2 | 9/2007 | Jensen |
| 7,354,762 B2 | 4/2008 | Jensen |
| 7,446,191 B2 | 4/2008 | Jensen |
| 7,446,179 B2 | 11/2008 | Jensen et al. |
| 7,446,190 B2 | 11/2008 | Sadelain et al. |
| 7,482,000 B2 | 1/2009 | DeVaux |
| 7,494,656 B2 | 2/2009 | Bachmann |
| 7,547,438 B2 | 6/2009 | Thomas et al. |
| 7,553,932 B1 | 6/2009 | von Herrath et al. |
| 7,592,431 B2 | 9/2009 | Har-Noy |
| 7,662,381 B2 | 2/2010 | Cardarelli et al. |
| 7,704,708 B2 | 4/2010 | Wu et al. |
| 7,776,562 B2 | 8/2010 | Busch |
| 7,837,871 B2 | 11/2010 | Gjerde et al. |
| 7,935,339 B2 | 5/2011 | Martin-Villalba et al. |
| 7,981,632 B2 | 7/2011 | Schmidt |
| 8,071,374 B2 | 12/2011 | Har-Noy |
| 8,298,782 B2 | 10/2012 | Busch |
| 8,324,353 B2 | 12/2012 | Jensen |
| 8,339,645 B2 | 12/2012 | Nakawaki |
| 8,389,282 B2 | 3/2013 | Sadelain et al. |
| 8,398,282 B2 | 3/2013 | Kuhlman et al. |
| 8,449,874 B2 | 5/2013 | Bachmann |
| 8,460,668 B2 | 6/2013 | Cardarelli et al. |
| 8,479,118 B2 | 7/2013 | Lyndersay et al. |
| 8,481,029 B2 | 7/2013 | Glennie et al. |
| 8,735,330 B2 | 5/2014 | Geir |
| 8,735,540 B2 | 5/2014 | Schmidt |
| 9,023,604 B2 | 5/2015 | Schmidt et al. |
| 9,023,999 B2 | 5/2015 | Mori et al. |
| 9,102,737 B2 | 8/2015 | Chen et al. |
| 9,169,325 B2 | 10/2015 | Keler et al. |
| 9,309,320 B2 | 4/2016 | Martin-Villalba et al. |
| 10,228,312 B2 | 3/2019 | Stadler |
| 2001/0026932 A1 | 10/2001 | Thomas et al. |
| 2002/0131960 A1 | 9/2002 | Sadelain et al. |
| 2002/0142358 A1 | 10/2002 | Mikayama et al. |
| 2003/0108549 A1 | 6/2003 | Carter et al. |
| 2003/0170238 A1 | 9/2003 | Gruenberg et al. |
| 2003/0175850 A1 | 9/2003 | Ross et al. |
| 2004/0082012 A1 | 4/2004 | Busch et al. |
| 2004/0185048 A1 | 9/2004 | Strom et al. |
| 2006/0019319 A1 | 1/2006 | Billadeau et al. |
| 2006/0039902 A1 | 2/2006 | Young et al. |
| 2006/0106199 A1 | 5/2006 | Erdmann et al. |
| 2006/0159655 A1 | 7/2006 | Collins et al. |
| 2007/0077242 A1 | 4/2007 | Mikayama et al. |
| 2007/0241061 A1 | 10/2007 | Engstrom et al. |
| 2008/0131415 A1 | 6/2008 | Riddell |
| 2008/0255004 A1 | 10/2008 | Neurauter et al. |
| 2008/0279851 A1 | 11/2008 | Coyle et al. |
| 2010/0005098 A1 | 1/2010 | Millmore et al. |
| 2010/0068738 A1 | 3/2010 | Kawamura et al. |
| 2010/0196359 A1 | 8/2010 | Kato et al. |
| 2010/0267057 A1 | 10/2010 | Rakestraw et al. |
| 2011/0003380 A1 | 1/2011 | Miltenyi et al. |
| 2011/0053209 A1 | 3/2011 | Sheridan |
| 2012/0214187 A1 | 8/2012 | Lees et al. |
| 2012/0321665 A1 | 12/2012 | Bollyky et al. |
| 2013/0149337 A1 | 6/2013 | Cooper et al. |
| 2013/0254912 A1 | 9/2013 | Witte et al. |
| 2013/0287748 A1 | 10/2013 | Hjune et al. |
| 2014/0295458 A1 | 10/2014 | Schmidt |
| 2014/0314795 A1 | 10/2014 | Riddell |
| 2015/0024411 A1 | 1/2015 | Stadler |
| 2015/0307617 A1 | 10/2015 | Du et al. |
| 2016/0185870 A1 | 6/2016 | Van Eenennaam et al. |
| 2017/0037368 A1 | 2/2017 | Germeroth et al. |
| 2017/0037369 A1 | 2/2017 | Ramsborg et al. |
| 2017/0037370 A1 | 2/2017 | Kaiser et al. |
| 2017/0052176 A1 | 2/2017 | Carl et al. |
| 2019/0112576 A1 | 4/2019 | Germeroth et al. |
| 2021/0032297 A1 | 2/2021 | Schmidt et al. |
| 2021/0163893 A1 | 6/2021 | Westoby et al. |
| 2022/0002669 A1 | 1/2022 | Germeroth et al. |

FOREIGN PATENT DOCUMENTS

| | | |
|---|---|---|
| CN | 101 044 405 A | 9/2007 |
| CN | 101 226 118 A | 7/2008 |
| CN | 101 446 576 A | 6/2009 |
| CN | 101 535 466 A | 9/2009 |
| CN | 101622340 | 1/2010 |
| CN | 101 978 269 A | 2/2011 |
| DE | 19641876 | 4/1998 |
| EP | 452342 | 11/1994 |
| EP | 0638644 | 2/1995 |
| EP | 0700430 | 4/2005 |
| EP | 2425250 | 3/2012 |
| EP | 2487188 | 8/2012 |
| EP | 2537416 | 12/2012 |
| JP | 2006-516197 | 6/2006 |
| JP | 2006-524991 | 11/2006 |
| JP | 2009-531062 | 9/2009 |
| RU | 2249039 | 3/2005 |
| RU | 2469044 | 12/2012 |
| RU | 2515063 | 5/2014 |
| WO | WO-1986/002077 | 4/1986 |
| WO | WO-1992/008796 | 5/1992 |
| WO | WO-1994/028143 | 12/1994 |
| WO | WO-1996/023879 | 8/1996 |
| WO | WO-1996/024606 | 8/1996 |
| WO | WO-1998/040396 | 9/1998 |
| WO | WO-1999/061065 | 12/1999 |
| WO | WO-2000/14257 | 3/2000 |
| WO | WO-2001/004144 | 1/2001 |
| WO | WO-2001/056603 | 9/2001 |
| WO | WO-2001/083755 | 11/2001 |
| WO | WO-2002/054065 | 7/2002 |
| WO | WO-2002/077018 | 10/2002 |
| WO | WO-2003/024404 | 3/2003 |
| WO | WO-2003/029462 | 4/2003 |
| WO | WO-2003/090781 | 11/2003 |
| WO | WO-2004/104185 | 12/2004 |
| WO | WO-2005/047331 | 5/2005 |
| WO | WO-2005/050209 | 6/2005 |
| WO | WO-2006/044650 | 4/2006 |
| WO | WO-2006/054961 | 5/2006 |
| WO | WO-2006/058226 | 6/2006 |
| WO | WO-2007/001459 | 1/2007 |
| WO | WO-2007/112012 | 10/2007 |
| WO | WO-2008/011486 | 1/2008 |
| WO | WO-2008/051424 | 5/2008 |
| WO | WO-2008/054603 | 5/2008 |
| WO | WO 2008/100122 | 8/2008 |
| WO | WO-2008/140573 | 11/2008 |
| WO | WO-2009/072003 | 6/2009 |
| WO | WO-2009/097119 | 6/2009 |
| WO | WO-2009/092068 | 7/2009 |
| WO | WO 2009/095447 | 8/2009 |
| WO | WO-2009/145831 | 12/2009 |
| WO | WO-2010/033140 | 3/2010 |
| WO | WO-2010/080032 | 7/2010 |
| WO | WO-2010/120374 | 10/2010 |
| WO | WO-2011/107489 | 9/2011 |
| WO | WO-2012/017081 | 2/2012 |
| WO | WO-2012/058627 | 5/2012 |
| WO | WO-2012/087928 | 6/2012 |
| WO | WO-2012/129514 | 9/2012 |
| WO | WO-2013/011011 | 1/2013 |
| WO | WO-2013/038191 | 3/2013 |
| WO | WO-2013/071154 | 5/2013 |

(56) References Cited

FOREIGN PATENT DOCUMENTS

| WO | WO-2013/123061 | 8/2013 |
|---|---|---|
| WO | WO-2013/124474 | 8/2013 |
| WO | WO-2013/126726 | 8/2013 |
| WO | WO-2013/166321 | 11/2013 |
| WO | WO-2014/011489 | 1/2014 |
| WO | WO-2014/031687 | 2/2014 |
| WO | WO-2014/039044 | 3/2014 |
| WO | WO-2014/048920 | 4/2014 |
| WO | WO-2014/055668 | 4/2014 |
| WO | WO-2014/076277 | 5/2014 |
| WO | WO-2015/095895 | 7/2015 |
| WO | WO-2015/153513 | 10/2015 |
| WO | WO-2015/158868 | 10/2015 |
| WO | WO-2015/0162211 | 10/2015 |
| WO | WO-2015/164675 | 10/2015 |
| WO | WO-2015/189302 | 12/2015 |
| WO | WO-2015/197874 | 12/2015 |
| WO | WO-2016/059512 | 4/2016 |
| WO | WO-2016/166568 | 10/2016 |
| WO | WO-2017/068419 | 4/2017 |
| WO | WO-2017/068425 | 4/2017 |
| WO | WO-2017/096329 | 6/2017 |
| WO | WO-2018/134691 | 7/2018 |
| WO | WO-2018/197949 | 11/2018 |
| WO | WO-2020/033927 | 2/2020 |
| WO | WO-2020/089343 | 5/2020 |

OTHER PUBLICATIONS

Amstutz et al. (Aug. 2001). "In vitro Display Technologies: Novel Developments and Applications," *Curr Opin Biotechnol.* 12(4):400-5.

Arakawa et al. (Sep. 1996). "Cloning and sequencing of the VH and V kappa genes of an anti-CD3 monoclonal antibody, and construction of a mouse/human chimeric antibody," *J Biochem.* 120(3):657-662.

Argarana et al. (Feb. 25, 1986). "Molecular cloning and nucleotide sequence of the streptavidin gene," *Nucleic Acids Res.* 14(4):1871-1882.

Baccala et al., "Anti-IFN-α/β Receptor Antibody Treatment Ameliorates Disease in Lupus-Predisposed Mice," J Immunol (2012) 189(12):5976-5984.

Barret, D.M. et al. (2014, e-pub. Nov. 20, 2013). "Chimeric Antigen Receptor Therapy for Cancer," Annu Rev Med. (2014);65:333-347.

Bashour et al., "Functional Characterization of a T Cell Stimulation Reagent for the Production of Therapeutic Chimeric Antigen Receptor T Cells," Abstract of Poster, presented at American Society of Hematology Annual Meeting, Orlando, FL (Dec. 5, 2015) 1 page.

Bashour et al., "Functional Characterization of a T Cell Stimulation Reagent for the Production of Therapeutic Chimeric Antigen Receptor T Cells," Presentation of Poster, presented at American Society of Hematology Annual Meeting, Orlando, FL (Dec. 5, 2015).

Battaglia et al., "Interleukin-21 (IL-21) synergizes with IL-2 to enhance T-cell receptor-induced human T-cell proliferation and counteracts IL-2/transforming growth factor-β-induced regulatory T-cell development," Immunology. (2013) May;139(1):109-120.

Baum, C. et al. (Jun. 2006, e-pub. Apr. 24, 2006). "Retrovirus Vectors: Toward the Plentivirus?", Molecular Therapy 13(6)1050-1063.

Bazdar et al. "Interleukin-7 enhances proliferation responses to T-cell receptor stimulation in naïve CD4+ T cells from human immunodeficiency virus-infected persons," J Virol. (2007) Nov.; 81(22):12670-12674.

Bes, C. et al. (2003). "Mapping the Paratope of Anti-CD4 Recombinant Fab 13B8.2 by Combining Parallel Peptide Synthesis and Site-directed Mutagenesis", The Journal of Biological Chemistry 278(16):14266-14273.

Beste et al., "Small antibody-like proteins with prescribed ligand specificities derived from the lipocalin fold," Proc Natl Acad Sci U S A. Mar. 2, 1999;96(5):1898-1903.

Blair, P.J. et al. (Feb. 21, 2000). "Cd40 Ligand (Cd154) Triggers a Short-Term Cd4+ T Cell Activation Response That Results in Secretion of Immunomodulatory Cytokines and Apoptosis", J Exp Med. 191(4):651-660.

Boris-Lawrie, K.A. et al. (Feb. 1993). "Recent advances in retrovirus vector technology", *Curr Opin Genet Dev.* 3(1):102-109.

Brash, E.D. (May 1987). "Strontium Phosphate Transfection of Human Cells in Primary Culture: Stable Expression of the Simian Virus 40 Large-T-Antigen Gene in Primary Human Bronchial Epithelial Cells", *Mol. Cell. Biol.* 7(5):2031-2034.

Brentjens, R. et al. (Mar. 20, 2013). "CD19-targeted T cells rapidly induce molecular remissions in adults with chemotherapy-refractory acute lymphoblastic leukemia", Sci. Transl. Med. 5(177):177ra38, 19 pages.

Burns, J.C. et al. (Sep. 1993). "Vesicular stomatitis virus G glycoprotein pseudotyped retroviral vectors: concentration to very high titer and efficient gene transfer into mammalian and nonmammalian cells", Proc. Natl. Acad. Sci. U.S.A. 90(17):8033-8037.

Butler et al., "Ex Vivo Expansion of Human CD8+ T Cells Using Autologous CD4+ T Cell Help," PLoS ONE (2012) 7(1):e30229, 11 pages.

Carlens, S. (Oct. 2000). "Ex vivo T lymphocyte expansion for retroviral transduction: influence of serum-free media on variations in cell expansion rates and lymphocyte subset distribution", Exp Hematol 28(10):1137-1146.

Castro et al., "Anti-Interleukin 10 Receptor Monoclonal Antibody Is an Adjuvant for T Helper Cell Type 1 Responses to Soluble Antigen Only in the Presence of Lipopolysaccharide," J Exp Med (2000) 192(10):1529-1534.

Cavalieri, S. et al. (Jul. 15, 2003). "Human T lymphocytes transduced by lentiviral vectors in the absence of TCR activation maintain an intact immune competence", 102(2):497-505.

Cheadle et al., "Chimeric antigen receptors for T-cell based therapy," Methods Mol Biol. (2012) 907:645-66.

Chicaybam, L. et al. (Mar. 26, 2013). "An Efficient Low Cost Method for Gene Transfer to T Lymphocytes", Plos One 8(3):e60298, 11 pages.

Cho, S. H. et al. (Jun. 21, 2010). "Human mammalian cell sorting using a highly integrated microfabricated fluorescence-activated cell sorter (μFACS)", Lab. Chip. 10(12):1567-1573.

Chung et al., "Prevention of graft-versus-host disease by anti-IL-7Rα antibody," Blood (2007) 110:2803-2810.

Cieri, N. et al. (2015). "Generation of human memory stem T cells after haploidentical T-replete hematopoietic stem cell transplantation", Blood 125(8):2865-2874.

Cohen, C.J. (Nov. 1, 2005). "Recognition of Fresh Human Tumor by Human Peripheral Blood Lymphocytes Transduced with a Bicistronic Retroviral Vector Encoding a Murine Anti-p53 TCR", *J. Immunol.* 175(9):5799-5808.

Cooper, L.J.N. (Feb. 15, 2003). "T-cell clones can be rendered specific for CD19: toward the selective augmentation of the graft-versus-B-lineage leukemia effect", BLOOD 101(4):1637-1644.

Cornish et al., "Differential regulation of T-cell growth by IL-2 and IL-15," Blood. Jul. 15, 2006;108(2):600-608.

Davila, M. L. et al. (Apr. 9, 2013). "CD19 CAR-Targeted T Cells Induce Long-Term Remission and B Cell Aplasia in an Immunocompetent Mouse Model of B Cell Acute Lymphoblastic Leukemia", PLOS ONE 8(4):e61338, 14pgs.

Deng, Z.B. et al. (Jun. 2004). "An agonist human ICOS monoclonal antibody that induces T cell activation and inhibits proliferation of a myeloma cell line", Hybrid Hybridomics. 23(3):176-182.

Dienz et al., "The induction of antibody production by IL-6 is indirectly mediated by IL-21 produced by CD4+ T cells," J Exp Med. Jan. 16, 2009;206(1):69-78.

Facchetti et al., "Linker for Activation of T Cells (LAT), a Novel Immunohistochemical Marker for T Cells, NK Cells, Mast Cells, and Megakaryocytes Evaluation in Normal and Pathological Conditions," Am J Pathol (1999) 154(4):1037-1046.

Fairhead, M. et al. (Jan. 9, 2014). "Plug-and-Play Pairing via Defined Divalent Streptavidins", J Mol Biol. 426(1):199-214.

(56) References Cited

OTHER PUBLICATIONS

Fedorov, V.D. et al. (Dec. 11, 2013). "PD-1—and CTLA-4—Based Inhibitory Chimeric Antigen Receptors (iCARs) Divert Off-Target Immunotherapy Responses", Sci. Transl. Med. 5(215):215ra172, 25 pgs.
Flynn, K.J. et al. (2014, e-pub. Jul. 18, 2014). "Stem memory T cells (TSCM)—their role in cancer and HIV immunotherapies", Clinical & Translational Immunology 3(e20):1-7.
Frecha, C. et al. (Oct. 2010, e-pub. Aug. 24, 2010). "Advances in the Field of Lentivector-based Transduction of T and B Lymphocytes for Gene Therapy", Molecular Therapy 18(10):1748-1757.
Gattinoni, L. et al. (2012). "A human memory T-cell subset with stem cell-like properties", Nat Med 17(10):1290-1297.
Gattinoni, L. et al. (2012, e-pub. Sep. 21, 2012)."Paths to sternness: building the ultimate antitumour T cell", Nature Reviews Cancer 12(671):1-14.
Germeroth "IBA T-catch cell isolation in pipette tips" Apr. 23, 2014 Retrieved from the internet: URL:http://x.ymcdn.com/sites/www.celltherapysociety.org/resource/resmgr/2014_AnnualMtgPresentations/T2_L.Germeroth.pdf [Retrieved on Jan. 23, 2017].
Gill et al., "Biopharmaceutical drug discovery using novel protein scaffolds," Curr Opin Biotechnol. (2006) Dec.;17(6):653-658.
Godin, J. et al. (Oct. 2008). "Microfluidics and photonics for Bio-System-on-a-Chip: A review of advancements in technology towards a microfluidic flow cytometry chip", J Biophotonics. 1(5):355-376.
Guo et al., "Assessing agonistic potential of a candidate therapeutic anti-IL21R antibody," J Transl Med (2010) 8:50.
Hackett, P.B. et al. (Apr. 2010, e-pub. Jan. 26, 2010). "A Transposon and Transposase System for Human Application", Mol. Ther. 18(4):674-683.
He et al., "Agonist anti-human CD27 monoclonal antibody induces T cell activation and tumor immunity in human CD27-transgenic mice," J Immunol (2013) 191(8):4174-4183.
Hermans, I.F. et al. (2004). "The VITAL Assay: A Versatile Fluorometric Technique for Assessing CTL-and NKT-mediated Cytotoxicity Against Multiple Targets in Vitro and in Vivo", J. Immunological Methods 285(1):25-40.
Hodge et al., "IL-21 in the bone marrow microenvironment contributes to IgM secretion and proliferation of malignant cells in Waldenstrom macroglobulinemia," Blood (2012) 120:3774-3782.
Holliger, P. et al., "Diabodies": small bivalent and bispecific antibody fragments, Proc Natl Acad Sci U S A. Jul. 15, 1993;90(14):6444-6448.
Holt et al., Domain antibodies: proteins for therapy. Trends Biotechnol. Nov. 2003;21(11):484-490.
Hoshino et al., "Activation via the CD3 and CD16 pathway mediates interleukin-2-dependent autocrine proliferation of granular lymphocytes in patients with granular lymphocyte proliferative disorders," Blood. Dec. 15, 1991;78(12):3232-3240.
Howarth, M. et al. (Apr. 2006). "A monovalent streptavidin with a single femtomolar biotin binding site," Nat Methods 3(4):267-273.
Huang, X. et al. (2009). "DNA Transposons for Modification of Human Primary T Lymphocytes1," Methods in Mol Biol 506:115-126.
Hudecek et al., "Receptor affinity and extracellular domain modifications affect tumor recognition by ROR1-specific chimeric antigen receptor T cells," Clin Cancer Res. Jun. 15, 2013;19(12):3153-3164.
Hutten et al., New magnetic nanoparticles for biotechnology. J Biotechnol. Aug. 26, 2004;112(1-2):47-63.
Iliades et al., "Triabodies: single chain Fv fragments without a linker form trivalent trimers," FEBS Lett. Jun. 16, 1997;409(3):437-441.
Ill et al., "Design and construction of a hybrid immunoglobulin domain with properties of both heavy and light chain variable regions," Protein Eng. (1997) Aug.;10(8):949-957.
Itano et al., "IL-2 receptor γChain expression on CD34 positive hematopoietic progenitor cells from bone marrow and cord blood," Tohoku J. Exp. Med. (1996) 178:389-398.

Johnston, S.A. (1990). "Biolistic transformation: microbes to mice", Nature 346(6286):776-777.
Klebanoff, C.A. et al. (Nov. 2012). "Sorting through subsets: Which T cell populations mediate highly effective adoptive immunotherapy?", J Immunother 35(9):651-660.
Knabel et al., "Reversible MHC multimer staining for functional isolation of T-cell populations and effective adoptive transfer," Nat Med. Jun. 2002;8(6):631-637.
Kochenderfer, J. N. et al. (May 2013, e-pub. Apr. 2, 2013). "Treating B-cell cancerwith T cells expressing anti-CD19 chimeric antigen receptors", Nat Rev. Clin Oncol. 10(5):267-276.
Kondo et al., "Sharing of the interleukin-2 (IL-2) receptor gamma chain between receptors for IL-2 and IL-4," Science (1993) 262(5141):1874-1877.
Koste, L. et al. (May 2014, e-pub. Apr. 3, 2014). "T-cell receptor transfer into human T cells with ecotropic retroviral vectors", Gene Ther 21(5):533-538.
Kwon et al., "Quantitative evaluation of the relative cell permeability of peptoids and peptides," J Am Chem Soc. Feb. 14, 2007;129(6):1508-1509.
Lee et al., "Anti-IL-7 receptor-α reverses established type 1 diabetes in nonobese diabetic mice by modulating effector T-cell function," Proc Natl Acad Sci U.S.A (2012) 109(31):12674-12679.
Li, G. et al. (Jun. 27, 2013). "T-Bet and Eomes Regulate the Balance between the Effector/Central Memory T Cells versus Memory Stem Like T Cells", PLOS ONE 8(6):e67401, 1-10.
Li et al., "Comparison of anti-CD3 and anti-CD28-coated beads with soluble anti-CD3 for expanding human T cells: Differing impact on CD8 T cell phenotype and responsiveness to restimulation," J Transl Med. 2010; 8:104, 15 pages.
Li, Y. et al. (Mar. 2005, e-pub Feb. 20, 2005). "Directed evolution of human T-cell receptors with picomolar affinities by phage display", Nat Biotechnol. 23(3):349-354.
Lim et al. "Engineered Streptavidin Monomer and Dimer with Improved Stability and Function," Biochemistry (2010), 50:8682-91.
Lowman, "Bacteriophage display and discovery of peptide leads for drug development," Annu Rev Biophys Biomol Struct. (1997);26:401-424.
Lupton, S. D. et al. (Jun. 1991). "Dominant Positive and Negative Selection Using a Hygromycin Phosphotransferase-Thymidine Kinase Fusion Gene", Mol. and Cell Biol. 11(6):3374-3378.
Manuri, P.V.R. et al. (Apr. 2010). "piggyBac Transposon= Transposase System to Generate CD19-Specific T Cells for the Treatment of B-Lineage Malignancies", Human Gene Therapy 21:427-437.
Martin et al., "The affinity-selection of a minibody polypeptide inhibitor of human interleukin-6," EMBO J. Nov. 15, 1994;13(22):5303-5309.
Massoud et al., "Common γ-chain blocking peptide reduces in vitro immune activation markers in HTLV-1-associated myelopathy/tropical spastic paraparesis," PNAS (2015) 112(35):11030-11035.
Matsubara et al., "Transcription activator-like effector nuclease-mediated transduction of exogenous gene into IL2RG locus," Sci Rep (2014) 4:5043.
Melero et al., "Agonist antibodies to TNFR molecules that costimulate T and NK cells," Clin Cancer Res (2013) 19(5):1044-1053.
Miller, A.D. (Spring 1990). "Retrovirus Packaging Cells", Hum Gene Ther. 1(1):5-14.
Mittler, R.S. et al. (2004). "Anti-CD137 antibodies in the treatment of autoimmune disease and cancer", Immunol. Res. 29(1-3):197-208.
Morizono et al., "A versatile targeting system with lentiviral vectors bearing the biotin-adaptor peptide," J Gene Med. Aug. 2009;11(8):655-63.
Mosavi et al., "The ankyrin repeat as molecular architecture for protein recognition," Protein Sci. (2004) Jun.;13(6):1435-1448.
Moseley et al., "Interleukin-17 family and IL-17 receptors," Cytokine Growth Factor Rev (2003) 14(2):155-174.
Mullen, C. A. et al. (Jan. 1992). "Transfer of the bacterial gene for cytosine deaminase to mammalian cells confers lethal sensitivity to 5-fluorocytosine: A negative selection system", Proc. Natl. Acad. Sci. USA 89:33-37.

(56) References Cited

OTHER PUBLICATIONS

Noguchi et al., "Preparation and properties of the immunoconjugate composed of anti-human colon cancer monoclonal antibody and mitomycin C-dextran conjugate," Bioconjug Chem. (1992) Mar.-Apr.;3(2):132-7.
Papa et al., "Anti-IL-17 receptor antibody AMG 827 leads to rapid clinical response in subjects with moderate to severe psoriasis: results from a phase I, randomized, placebo-controlled trial," J Invest Dermatol (2012) 132(10):2466-2469.
Park, J-J. et al. (Feb. 2012, e-pub. Aug. 30, 2011). "Expression of anti-HVEM single-chain antibody on tumor cells induces tumor-specific immunity with long-term memory", Cancer Immunol Immunother 61(2):203-214.
Park, T. S. et al. (Nov. 2011). "Treating Cancer with Genetically Engineered T Cells", Trends Biotechnol. 29(11):550-557.
Parkhurst, M.R. et al. (Jan. 1, 2009). "Characterization of Genetically Modified T-Cell Receptors that Recognize the CEA:691-699 Peptide in the Context of HLA-A2.1 on Human Colorectal Cancer Cells", Clin. Cancer Res. 15(1):169-180.
Paulsen, M. et al. (Apr. 2011, e-pub. Nov. 5, 2010). "Modulation of CD4+ T-cell activation by CD95 co-stimulation", Cell Death Differ. 18(4):619-631.
Perez-Simon, "Anti-common γ-chain antibody: one for all in GVHD," Blood (2015) 125:424-426.
Riddell, S.R. et al. (Jun. 1992). "Phase I study of cellular adoptive immunotherapy using genetically modified CD8+ HIV-specific T cells for HIV seropositive patients undergoing allogeneic bone marrow transplant. The Fred Hutchinson Cancer Research Center and the University of Washington School of Medicine, Department of Medicine, Division of Oncology", 3(3):319-338.
Riddell et al., "Adoptive Therapy with Chimeric Antigen Receptor Modified T Cells of Defined Subset Composition," cancer J. (2014) 20(2): 141-144.
Rodi et al., "Phage-display technology—finding a needle in a vast molecular haystack," Curr Opin Biotechnol. (1999) Feb.;10(1):87-93.
Rong et al., "IL-17RD (Sef or IL-17RLM) interacts with IL-17 receptor and mediates IL-17 signaling," Cell Res (2009) 19(2):208-215.
Rosenberg, S.A. (Aug. 2011). "Cell transfer immunotherapy for metastatic solid cancer—what clinicians need to know", 8(10):577-585.
Sabatino et al., "Generation of clinical-grade CD19-specific CAR-modified CD8+ memory stem cells for the treatment of human B-cell malignancies," Blood. Jul. 28, 2016;128(4):519-28.
Sadelain, M. et al. (Apr. 2013, e-pub. Apr. 2, 2013). "The basic principles of chimeric antigen receptor (CAR) design", Cancer Disc. 3(4):388-398.
Scarpa, M. et al. (Feb. 1991). "Characterization of recombinant helper retroviruses from Moloney-based vectors in ecotropic and amphotropic packaging cell lines", Virology 180(2):849-852.
Schmitt et al., "Adoptive transfer and selective reconstitution of streptamer-selected cytomegalovirus-specific CD8+ T cells leads to virus clearance in patients after allogeneic peripheral blood stem cell transplantation," Transfusion. (2011) Mar.;51(3):591-9.
Sharma, N. et al. (Feb. 2013, e-pub. Feb. 26, 2013). "Efficient Sleeping Beauty DNA Transposition From DNA Minicircles", Mol Ther Nucleic Acids. 2(2):e74, 10 pages.
Silverman et al., "Multivalent avimer proteins evolved by exon shuffling of a family of human receptor domains," Nat Biotechnol. (2005) Dec.;23(12):1556-61.
Skerra, "Engineered protein scaffolds for molecular recognition," J Mol Recognit. (2000) Jul.-Aug.;13(4):167-87.
Smith et al., "Ex vivo expansion of human T cells for adoptive immunotherapy using the novel Xeno-free CTS Immune Cell Serum Replacement," Clinical & Translational Immunology (2015) 4:e31.
Stemberger et al., Novel Serial Positive Enrichment Technology Enables Clinical Multiparameter Cell Sorting. PLoS One. 2012;7(4):e35798 (11 pp).
Stone et al., "The assembly of single domain antibodies into bispecific decavalent molecules," J Immunol Methods. Jan. 10, 2007;318(1-2):88-94.
Taraban et al. (Dec. 2002, e-pub. ). "Expression and costimulatory effects of the TNF receptor superfamily members CD134 (OX40) and CD137 (4-1BB), and their role in the generation of anti-tumor immune responses", Eur J Immunol. 32(12):3617-3627.
Terakura, S. et al. (Jan. 5, 2012, e-pub. Oct. 26, 2011). "Generation of CD19-chimeric antigen receptor modified CD8+ T cells derived from virus-specific central memory T cells", Blood 119(1):72-82.
Themeli, M. et al. (Oct. 2013, e-pub. Aug. 11, 2013). "Generation of tumor-targeted human T lymphocytes from induced pluripotent stem cells for cancer therapy", Nat Biotechnol. 31(10):928-933.
Toy et al., "Cutting edge: interleukin 17 signals through a heteromeric receptor complex," J Immunol (2006) 177(1):36-39.
Traunecker et al., "Bispecific single chain molecules (Janusins) target cytotoxic lymphocytes on HIV infected cells," EMBO J. (1991) Dec.;10(12):3655-9.
Traunecker et al., "Janusin: new molecular design for bispecific reagents," Int J Cancer Suppl. (1992);7:51-2.
Tumaini et al., "Simplified process for the production of anti-CD19-CAR-engineered T cells," Cytotherapy. Nov. 2013;15(11):1406-15.
Turtle, C.J. et al. (Oct. 2012, e-pub. Jul. 18, 2012). "Engineered T cells For Anti-Cancer Therapy", Curr. Opin. Immunol. 24(5):633-639.
Van Tendeloo, VFI. et al. (2000). "High-level transgene expression in primary human T Tymphocytes and adult bone marrow CD341 cells via electroporation-mediated gene delivery", Gene Therapy 7(16):1431-1437.
Vanhove et al., "Selective blockade of CD28 and not CTLA-4 with a single-chain Fv-alpha1-antitrypsin fusion antibody," Blood. Jul. 15, 2003;102(2):564-570.
Varela-Rohena, A. et al. (Dec. 2008). "Control of HIV-1 immune escape by CD8 T-cells expressing enhanced T-cell receptor", Nat. Med. 14(12):1390-1395.
Verhoeyen, E. et al. (2009). "Lentiviral vector gene transfer into human T cells", Methods Mol Biol. 506(1):97-114.
Vitale et al., "NK-active cytokines IL-2, IL-12, and IL-15 selectively modulate specific protein kinase C (PKC) isoforms in primary human NK cells," Anat Rec. Feb. 1, 2002;266(2):87-92.
Volk et al., "The therapeutic efficacy of an anti-IL-2 receptor monoclonal antibody correlates with an increase in serum soluble IL-2 receptor levels," Clin Exp Immunol (1989) 76(1):121-125.
Voss, S. et al. (1997). "Mutagenesis of a flexible loop in Streptavidin Leads to Higher Affinity for the Strep-tag II Peptide and Improved Performance in Recombinant Protein Purification", Protein Engineering 10(8):975-982.
Wadhwa et al., "Receptor Mediated Glycotargeting," J. Drug Targeting (1995) 3:111.
Wang et al., "Clinical manufacturing of CAR T cells: foundation of a promising therapy," Mol Ther Oncolytics (2016) 3(16015):1-7.
Wang et al., "Phenotypic and functional attributes of lentivirus-modified CD19-specific human CD8+ central memory T cells manufactured at clinical scale," J Immunother. (2012) 35(9):689-701.
Wigler, M. et al. (May 1977). "Transfer of Purified Herpes Virus Thymidine Kinase Gene to Cultured Mouse Cells", Cell 2(11):223-232.
Wilson et al., "The use of mRNA display to select high-affinity protein-binding peptides," Proc Natl Acad Sci U S A. Mar. 27, 2001;98(7):3750-5.
Wu, R. et al. (Mar. 2012). "Adoptive T-cell Therapy Using Autologous Tumor-infiltrating Lymphocytes for Metastatic Melanoma: Current Status and Future Outlook", Cancer J. 18(2):160-175.
Wu, S.C. et al. (Jun. 17, 2005). "Engineering soluble monomeric streptavidin with reversible biotin binding capability", *J. Biol. Chem.*280(24):23225-23231.
Zhang et al., "CD137 promotes proliferation and survival of human B cells," J Immunol. Jan. 15, 2010;184(2):787-95.
Zhang et al., "LAT: the ZAP-70 tyrosine kinase substrate that links T cell receptor to cellular activation," Cell (1998) 92(1):83-92.

(56) References Cited

OTHER PUBLICATIONS

Zhang, M. et al. (Aug. 7, 2015). "A novel approach to make homogeneous protease-stable monovalent streptavidin", Biochem Biophys Res Commun. 463(4):1059-1063.
U.S. Appl. No. 16/231,188, filed Dec. 21, 2018, by Stadler et al. (Copy not provided). (Copy not submitted herewith pursuant to the waiver of 37 C.F. R. § 1.98(a)(2)(iii) issued by the Office on Sep. 21, 2004).
U.S. Appl. No. 16/231,193, filed Dec. 21, 2018, by Stadler et al. (Copy not provided). (Copy not submitted herewith pursuant to the waiver of 37 C.F. R. § 1.98(a)(2)(iii) issued by the Office on Sep. 21, 2004).
U.S. Appl. No. 15/770,177, filed Oct. 20, 2016, by Bashour et al. (Copy not provided). (Copy not submitted herewith pursuant to the waiver of 37 C.F. R. § 1 98(a)(2)(iii) issued by the Office on Sep. 21, 2004).
Anonymous, "Cross-linking reagents introduction to cross-linking single-step vs. multi-step reactions," Published on Jan. 1, 2005. Retrieved from http://www.korambiotech.com/upload/bbs/2/Cross-LinkingTechHB.pdf. Retrieved on Nov. 30, 2018.
Anonymous, "SMCC and Sulfo-SMCC," Published Jan. 1, 2018. Retrieved on https://assets.thermofisher.com/TFS-Assets/LSG/manuals/MAN0011295_SMCC_SulfoSMCC_UG.pdf. Retrieved on Dec. 3, 2018.
Anonymous, "Traut's reagent," Published on Jan. 1, 2012. Retrieved from https://assets.thermofisher.com/TFS-Assets/LSG/manuals/MAN0011238_Trauts_Reag_UG.pdf. Retrieved on Dec. 3, 2018.
Barrett et al., "The length and mode of termination of individual muscle fibers in the human Sartorius and posterior femoral muscles," Cell Tissues Organs (1962) 48(3):242-257.
Carpenter, E. L. et al., "Activation of human B cells by the agonist CD40 antibody CP-870,893 and augmentation with simultaneous toll-like receptor 9 stimulation," J Transl Med. Nov. 11, 2009;7:93, 10 pages.
Casalegno-Garduño et al., Multimer technologies for detection and adoptive transfer of antigen-specific T cells. Cancer Immunol Immunother. Feb. 2010;59(2):195-202.
Casati et al., "Enrichment, stimulation, and viral transduction of naive and central memory CD8+ T cells under GMP conditions for translational research towards the development of adoptive cell therapy of cancer patients," MACS&more (2013) 15:20-24.
Dainiak et al., Methods in Cell Separations. Adv Biochem Eng Biotechnol. 2007;106:1-18.
Dubel et al., "Bifunctional and multimeric complexes of streptavidin fused to single chain antibodies (scFv)," J Immunol Methods (1995) 178(2):201-209.
Hudson et al., "Engineered Antibodies," Nature Medicine (2003) 9(1):129-133.
Juntilla et al., "Single-step Strep-tag purification for the isolation and identification of protein complexes from mammalian cells," Proteomics. (2005) Apr.;5(5):1199-1203.
Kumar et al., "Cell separation using cryogel-based affinity chromatography",Nature Protocols, Nature Publishing Group, GB, vol. 5, No. 11, Nov. 1, 2010, pp. 1737-1747.
Kumar et al., Affinity binding of cells to cryogel adsorbents with immobilized specific ligands: effect of ligand coupling and matrix architecture. J Mol Recognit. Jan.-Feb. 2005;18(1):84-93.
Larvor et al., Measurement of the dissociation rate constant of antigen/antibody complexes in solution by enzyme-linked immunosorbent assay. J Immunol Methods. Apr. 15, 1994;170(2):167-175.
Levin et al., "Optimizing the affinity and specificity of proteins with molecular display," Mol BioSyst (2006) 2:49-57.
Liu et al., "Characterization of TectoRNA Assembly with Cationic Conjugated Polymers," J Am Chem Soc (2004) 126(13):4076-4077.
Melero, I. et al. (Mar. 1, 2013). "Clinical development of immunostimulatory monoclonal antibodies and opportunities for combination", Clin. Cancer Res. 19(5):997-1008.
Miltenyi et al., High Gradient Magnetic Cell Separation With MACS. Cytometry. 1990;11(2):231-238.

Padmanabhan et al., Purification of Transiently Transfected Cells by Magnetic Affinity Cell Sorting. J Immunogenet. Apr. 1989;16(2):91-102.
Plieva et al., "Characterization of supermacroporous monolithic polyacrylamide based matrices designed for chromatography of bioparticles," Journal of Chromatography (2004) 807(1):129-137.
Qiagen: "Strep-tagged Protein Purification Handbook For expressing, purifying, and detecting proteins carrying a Strep-tag II or a 6xHis tag and a Strep-tag II Two-step protein purification system His.Strep pQE-TriSystem Vector Set pQE-TriSystem Strep Vector Strep-Tactin Superflow and Superflow Cartridge", Apr. 1, 2007 (Apr. 1, 2007).
Riley et al., "Modulation of TCR-Induced transcriptional profiles by ligation of CD28, ICOS, and CTLA-4 receptors" (2002) PNAS vol. 99, No. 18 pp. 11790-11795.
Schmidt and Skerra, The Strep-tag system for one-step purification and high-affinity detection or capturing of proteins. Nat Protoc. 2007;2(6):1528-1535.
Schroeder, Nach Zellen Angeln. Faszination Forschung Jun. 30, 2010:28-37 Retrieved from the Internet: URL:http://portal.mytum.de/pressestelle/faszination-forschung/2010nr6/index html [retrieved on Nov. 16, 2012]-p. 34-p. 37 (English translation only).
Skerra et al., "Applications of a peptide ligand for streptavidin: the Strep-tag," Biomolecular Engineer (1999) 16(1-4):79-86.
ThermoFisher Scientific, Avidin-Biotein Interaction, retrieved from https://www.thermofisher.com/us/en/home/life-science/protein-biology/protein-biology-learning-center/protein-biology-resource-library/pierce-protein-methods/avidin-biotin-interaction.html on Apr. 9, 2019, pp. 1-7.
Trickett et al., "T cell stimulation and expansion using anti-CD3/CD28 beads" J. Immunol Methods (2003) 275(102):251-255.
Wang et al., "Clinical manufacturing of CAR T cells: foundation of a promising therapy," Mol Ther Oncolytics (2016) 3:16015.
Wang et al., Database Biosis. Database accession No. PREV200900325303.Abstract Only Mar. 2009: 1 page.
Wang et al., Generation of leukaemia antigen-specific donor lymphocyte infusions powered by streptamer-based selection. Bone Marrow Transplantation Mar. 2009;43(Suppl1):S73.
Wang et al., Open-Tubular Capillary Cell Affinity Chromatography: Single and Tandem Blood Cell Separation. Anal Chem. Mar. 15, 2008;80(6):2118-2124.
Wang et al: "Streptamer-based selection of WT1-specific CD8+ T cells for specific donor lymphocyte infusions", Experimental Hematology, vol. 38, No. 11, Nov. 1, 2010 (Nov. 1, 2010), pp. 1066-1073.
Xu et al., Aptamer-Based Microfluidic Device for Enrichment, Sorting, and Detection of Multiple Cancer Cells. Anal Chem. Sep. 1, 2009;81(17):7436-7442.
Arndt et al., "Analysis of TCR activation kinetics in primary human T cells upon focal or soluble stimulation," J Immunol Methods. Jan. 31, 2013;387(1-2):276-83.
Berg et al., "Sustained TCRsignaling is required for mitogen-activated protein kinase activation anddegranulation by cytotoxic T lymphocytes." 1998. J. Immunol. 161(6), 2919-2924.
Berger et al., "Adoptive transfer of effector CD8 T cells derived from central memory cells establishes persistent T cell memory in primates." (2008) J Clin Invest 118(1): 294-305.
Birnbaum et al., "Molecular architecture of the αβ cell receptor-CD3 complex." Proc Natl Acad Sci U S A. Dec. 9, 2014;111(49):17576-81. doi: 10.1073/pnas.1420936111.
Boerman et al., "Pretargeted radioimmunotherapy of cancer: progress step by step." Journal of Nuclear Medicine, (2003) 44(3); 400-411.
Brosseron et al. "Isolating peripheral lymphocytes by density gradient centrifugation and magnetic cell sorting" Methods Mol Biol (2015) 1295:33-42.
Busch et al., "Differing roles of inflammation and antigen in T cell proliferation and memory generation." J Immunol. (2000) 164(8); 4063-4070.
Carpentier et al., 2009. "T-cell artificial focal triggering tools: linking surface interactions with cell response." PLoS One (2009) 4(3), e4784.

(56) References Cited

OTHER PUBLICATIONS

Chang et al., "Identification and selective expansion of functionally superior T cells expressing chimeric antigen receptors," J Transl Med (2015) 13(1):161.
Chen et al., "Biotin IgM Antibodies in Human Blood: A Previously Unknown Factor Eliciting False Results in Biotinylation-Based Immunoassays," Plos One (2012); 7(8) e42376, pp. 1-8.
Choudhuri et al., "Signaling microdomains in T cells." FEBS Lett. (2010) 584(24); 4823-4831.
Clement et al., "Analysis of the monocyte Fc receptors and antibody-mediated cellular interactions required for the induction of T cell proliferation by anti-T3 antibodies." J Immunol. (1985) 135(1): 165-71.
Daniels et al., "Thymic Selection Threshold Defined by Compartmentalization of Ras/MAPK Signalling," Nature. Dec. 7, 2006; 444(7120): 724-729.
Davis et al., "The kinetic-segregation model: TCR triggering and beyond." Nat. Immunol. 7, 803-809 (2006).
Garlie et al., "T cells coactivated with immobilized anti-CD3 and anti-CD28 as potential immunotherapy for cancer." J. Immunother. (1999) 22(4); 336-345.
Grutzkau et al. "Small but mighty: how the MACS-technology based on nanosized superparamagnetic particles has helped to analyze the immune system within the last 20 years." Cytometry A. (Jul. 2010) 77(7): 643-647.
Hobson et al., "In situ transfection of target cells on solid surfaces by immobilized viral vectors," BMC Biotechnol (2003) 3(4):1-10.
Huppa et al., "T-cell-antigen recognition and the immunological synapse," Nat. Rev. Immunol. (2003) 3(12); 973-983.
Kato et al., "Development of Rous sarcoma Virus-like Particles Displaying hVV49 scFv for specific targeted drug delievery to human colon carcinoma cells," Pharm Res (2015) 32:3699-3707.
Kim et al., "The ABCs of Artificial Antigen Presentation," Nat Biotechnol (2004) Apr.;22(4):403-10.
Kleymann et al. "Engineered Fv Fragments as a Tool for the One-Step Purification of Integral Multisubunit Membrane Protein Complexes." Nat Biotechnol (1995) 13: 155-160.
Kohanski, R.A., Lane, M.D. "Monovalent avidin affinity columns" Methods Enzymol. 1990;184:194-200.
Kong et al., "Isolation of breast cancer stem cell and screening of specific polypeptide bonding to it," Chinese Journal of Cancer Prevention and Control (2013) 20(24):1892-1895.
Kubben et al. "Identification of differential protein interactors of lamin A and progerin," Nucleus (2010) 1(6): 513-525.
Lenschow et al., "CD28/B7 system of T cell costimulation." Annu Rev Immunol. 1996;14:233-58.
Levine et al., 1997. "Effects of CD28 costimulation on long-term proliferation of CD4+ T cells in the absence of exogenous feeder cells." J. Immunol. (1997) 159(12), 5921-5930.
Li et al.. "T cell receptor signalling in the control of regulatory T cell differentiation and function." Nat Rev Immunol. (2016) 16(4): 220-233. doi: 10.1038/nri.2016.26.
Li, Y. et al., "Comparison of anti-CD3 and anti-CD28-coated Beads With Soluble anti-CD3 for Expanding Human T Cells: Differing Impact on CD8 T Cell Phenotype and Responsiveness to Restimulation," J Transl Med (2010) 8: 104.
Lu et al., "A rapid cell expansion process for production of engineered autologous CAR-T cell therapies," Human Gene Therapy Methods (2016) 27(6):209-218.
Mehlhop-Williams et al., "Memory CD8+ T cells exhibit increased antigen threshold requirements for recall proliferation." J Exp Med. (2014) 211(2): 345-56. doi: 10.1084/jem.20131271.
Meyer et al., "Biodegradable nanoellipsoidal artificial antigen presenting cells for antigen specific T-cell activation." Small. (2015) 11(13):1519-1525. doi: 10.1002/smll.201402369.
Mittal et al. "Biotin-4-fluorescein based fluorescence quenching assay for determination of biotin binding capacity of streptavidin conjugated quantum dots." Bioconjug Chem. (2011) 22(3):362-368.

Nauerth et al., "Flow cytometry-based TCR-ligand Koff-rate assay for fast avidity screening of even very small antigen-specific T cell populations ex vivo." Cytometry A. (2016) 89(9):816-825. doi: 10.1002/cyto.a.22933.
Neeson et al., "Ex Vivo Culture of Chimeric Antigen Receptor T Cells Generates Functional CD8+ T Cells With Effector and Central Memory-Like Phenotype," Gene Ther (2010) 17(9): 1105-16.
Okamoto et al., "A Promising Vector for TCR Gene Therapy: Differential Effect of siRNA, 2A Peptide, and Disulfide Bond on the Introduced TCR Expression," Mol Ther Nucleic Acids. (2012) 1(12): e63. 11 pages.
Pearce EL. "Metabolism in T cell activation and differentiation," Curr. Opin. Immunol. (2010) 22(3), 314-320.
Poltorak et al., "TCR activation kinetics and feedback regulation in primary human T cells." Cell Commun Signal. Jan. 14, 2013;11:4. doi: 10.1186/1478-811X-11-4.
Pozarowski et al., "Analysis of Cell Cycle by Flow Cytometry," Methods Mol Biol. (2004) 281: 301-311.
Rapoport et al., "Restoration of immunity in lymphopenic individuals with cancer by vaccination and adoptive T-cell transfer." Nat Med. (2005) 11(11):1230-1237.
Riddell et al., "The use of anti-CD3 and anti-CD28 monoclonal antibodies to clone and expand human antigen-specific T cells." J Immunol Methods. (1990) 128(2): 189-201.
Rossy et al., "How Does the Kinase Lck Phosphorylate the T Cell Receptor? Spatial Organization as a Regulatory Mechanism," Front Immunol. (2012) 3:167.
Rudd et al.,"CD28 and CTLA-4 coreceptor expression and signal transduction." Immunol Rev. (2009) 229(1); 12-26.
Rybak, J.N., et al. "Purification of biotinylated proteins on streptavidin resin: a protocol for quantitative elution," Proteomics. 2004 4(8): 2296-2299.
Sanchez-Paulete et al., "Deciphering CD137 (4-1BB) signaling in T-cell costimulation for translation into successful cancer immunotherapy." Eur. J. Immunol. (2016) 46(3); 513-522. doi:10.1002/eji.201445388.
Sano et al., "A streptavidin-protein a chimera that allows one-step production of a variety of specific antibody conjugates," Nature (1991) 9:1378-1381.
Sawai et al., "A novel method of cell-specific mRNA transfection," Molecular Genetics of Metabolim (1998) 64:44-51.
Schmidt et al., "Development of the Twin-Strep-tag and its application for purification of recombinant proteins from cell culture supernatants." Protein Expression and Purification (2013) 92(1); 54-61.
Schmidt et al., "Molecular Interaction Between the Strep-tag Affinity Peptide and its Cognate Target, Streptavidin." Mol. Biol. (1996) 255(5); 753-766.
Schmidt et al., "The random peptide library-assisted engineering of a C-terminal affinity peptide, useful for the detection and purification of a functional Ig Fv fragment." Protein Eng. (1993) 6(1); 109-122.
Schroeder, Nach Zellen Angeln. Faszination Forschung Jun. 30, 2010:28-37 Retrieved from the Internet: URL:http://portal.mytum.de/pressestelle/faszination-forschung/2010nr6/index html [retrieved on Nov. 16, 2012]-p. 34-p. 37 (English translation provided).
Tsiotis et al. "Isolation and structural characterization of trimeric cyanobacterial photosystem I complex with the help of recombinant antibody fragments." Eur J Biochem. (Aug. 1, 1995) 231(3): 823-30.
Turtle et al., "Genetically retargeting CD8+ lymphocyte subsets for cancer immunotherapy." Curr Opin Immunol. (2011) 23(2); 299-305.
Van Panhuys et al., "T-cell-receptor-dependent signal intensity dominantly controls CD4(+) T cell polarization In Vivo." Immunity. (2014) 41(1): 63-74. doi: 10.1016/j.immuni.2014.06.003.
Van Stipdonk et al., "Naïve CTLs require a single brief period of antigenic stimulation for clonal expansion and differentiation." Nat Immunol. (2001) 2(5): 423-429.
Valle et al., "Heterogeneous CD3 Expression Levels in Differing T Cell Subsets Correlate with the In Vivo Anti-CD3-Mediated T Cell Modulation." J Immunol. (2015) 5: 2117-2127.

(56) References Cited

OTHER PUBLICATIONS

Wang et al., "A transgene-encoded cell surface polypeptide for selection, in vivo tracking, and ablation of engineered cells." Blood. (2011) 118(5):1255-1263.
Wang et al., "Dynamics of proximal signaling events after TCR/CD8-mediated induction of proliferation or apoptosis in mature CD8+ T cells." J. Immunol. (2008) 180(10); 6703-6712.
Williams et al., "Affinity recovery of moloney murine leukaemia virus," J Chromatography B (2005) 820(1):111-119.
Xia et al., "Enrichment of haploid spermatids in mice by flow sorting," Natl Journal of Andrology (2014) 20(2):106-110.
Xu et al., "Closely Related T-memory Stem Cells Correlate With in Vivo Expansion of CAR.CD19-T Cells and Are Preserved by IL-7 and IL-15," Blood (2014) 123 (24): 3750-3759.
Xu et al., "Multiparameter Comparative Analysis Reveals Differential Impacts of Various Cytokines on CART Cell Phenotype and Function Ex Vivo and in Vivo," Oncotarget (2016) 7(50): 82354-82368.
Yang et al., "In vitro generated anti-tumor T lymphocytes exhibit distinct subsets mimicking in vivo antigen-experienced cells." Cancer Immunol Immunother (2011) 60(5): 739-749.
Yang et al., "Targeting lentiviral vectors to specific cell types in vivo," PNAS USA (2006) 103(31):11479-11484.
Yarilin, "Immunology principles," M. Medicine (1999) 184-195, 339-347 (English Translation included).
Zhou X et al., "Lentivirus-mediated gene transfer and expression in established human tumor antigen-specific cytotoxic T cells and primayr unstimulated T cels," Human Gene Therapy, vol. 14 No. 11, Jul. 20, 2003 pp. 1089-1105.
Zufferey et al. "Self-Inactivating Lentivirus Vector for Safe and Efficient In Vivo Gene Delivery," J. Virol (1998) 72(12):9873-9880.
Zufferey et al. "Woodchuck Hepatitis Virus Posttranscriptional Regulatory Element Enhances Expression of Transgenes Delivered by Retroviral Vectors" 1999. J. Virol. vol. 73, No. 4, pp. 2886-2892.
U.S. Appl. No. 17/289,690, filed Apr. 28, 2021, by Germeroth et al. (Copy not provided). (Copy not submitted herewith pursuant to the waiver of 37 C.F. R. § 1.98(a)(2)(iii) issued by the Office on Sep. 21, 2004).
Aksoy et al., "Human primary T cells: A practical guide," Published on Jun. 19, 2018. Retrieved on Jan. 7, 2020. Retrieved from https://peerj.com/preprints/26993/.
Anonymous, "Optimization of Human T Cell Expansion Protocol: Effects of Early Cell Dilution," Published Oct. 2018. Retrieved on Jan. 7, 2020. Retrieved on https://cdn.stemcell.com/media/files/techbulletin/TB27143-Optimization_of_Human_T_Cell_Expansion_Protocol.pdf?_ga=2.128430788.931468903.1578439383-852611746.1578439383.
Bambauer et al., "LDL-apheresis: technical and clinical aspects," The Scientific World Journal (2012).
Godawat et al., "Period counter-current chromatography—design and operational considerations for integrated and continuous purification of proteins," Biotechnology journal (2012) 7(12):1496-1508.
Korndorfer et al., "Improved affinity of engineered streptavidin for the Strep-tag 11 peptide is due to a fixed open conformation of the lid-like loop at the binding site," Protein Sci (2002) 11:883-893.
Lada et al., "Quantitation of Integrated HIV Provirus by Pulsed-Field Gel Electrophoresis and Droplet Digital PCR," J Clin Microbiol (2018) 56(12): e01158-18.
Matic et al., "Fine Tuning and Efficient T Cell Activation with Stimulatory aCD3 Nanoarrays," Nano Letters (2013) 13:5090-5097.
Vormittag et al., "A Guide to Manufacturing CAR T Cell Therapies," Curr Opin Biotechnol (2018) 53: 164-181.
Zhao et al., "Development of the First World Health Organization Lentiviral Vector Standard: Toward the Production Control and Standardization of Lentivirus-Based Gene Therapy Products," Hum Gene Ther Methods (2017) 28 (4): 205-214.
U.S. Appl. No. 17/578,425, filed Jan. 18, 2022, by Bashour et al. (Copy not provided). (Copy not submitted herewith pursuant to the waiver of 37 C.F. R. § 1.98(a)(2)(iii) issued by the Office on Sep. 21, 2004).
Tarantula, Explanatory Biotechnological Dictionary (English translation only) (2009).
Corada et al., "Monoclonal antibodies directed to different regions of vascular endothelial cadherin extracellular domain affect adhesion and clustering of the protein and modulate endothelial permeability," Blood. (2001) 97(6):1679-84.
Kumar et al., "Integrated bioprocess for the production and isolation of urokinase from animal cell culture using supermacroporous cryogel matrices," Biotechnology and Bioengineering (2006) 93(4):636-646.
PADLAN,"X-Ray Crystallography of Antibodies," Adv Prot Chem (1996) 49:57-133.
Poirier et al. "CD28-specific immunomodulating antibodies: what can be learned from experimental models?" American Journal of Transplantation. Jul. 2012;12(7):1682-90.
Purification Technical Handbook (2010 retrieved from https://at.vwr.com/assetsvc/asset/de AT/id/20551553/contents).
Qureshi et al., "Development and characterization of a series of soluble tetrameric and monomeric streptavidin muteins with differential biotin binding affinities," The Journal of Biological Chemistry (2001) 276(49):46422-46428.
Sun et al., "Plug-and-go" strategy to manipulate streptavidin valencies, Bioconjugate Chem (2014) 25:1375-1380.
Walter et al., "Cutting edge: Predetermined Avidity of Human CD8 T cells expanded on calibrated MHC/Anti-CD28-Coated Microspheres," J Immunol (2003) 171:4973-4978.
Woolridge et al. "Anti-CD8 antibodies can inhibit or enhance peptide-MHC class I (pMHCI) multimer binding: this is paralleled by their effects on CTL activation and occurs in the absence of an interaction between pMHCI and CD8 on the cell surface." The Journal of Immunology (2003)171.12: 6650-6660.

* cited by examiner

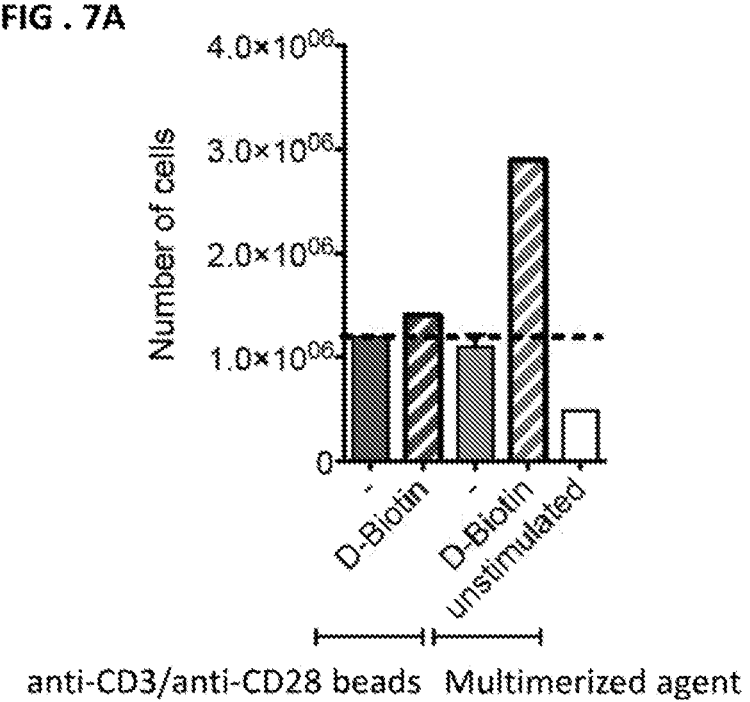

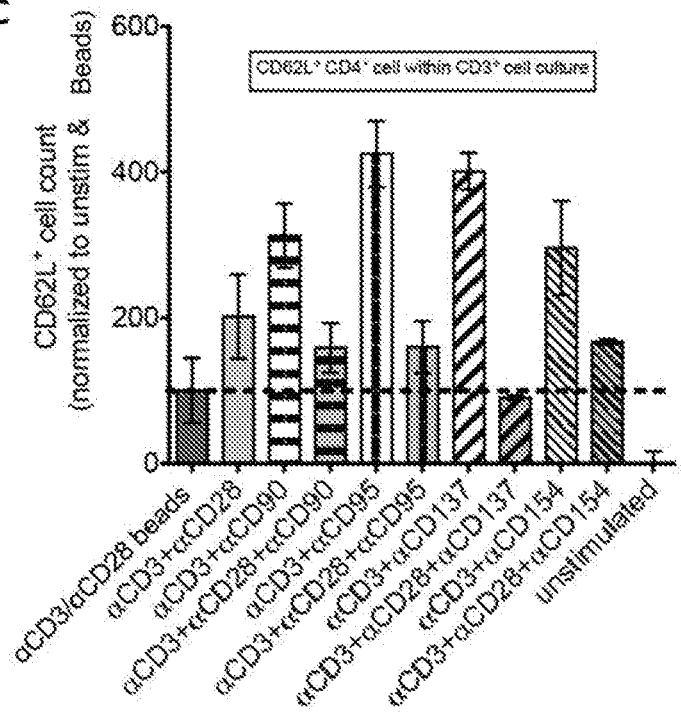
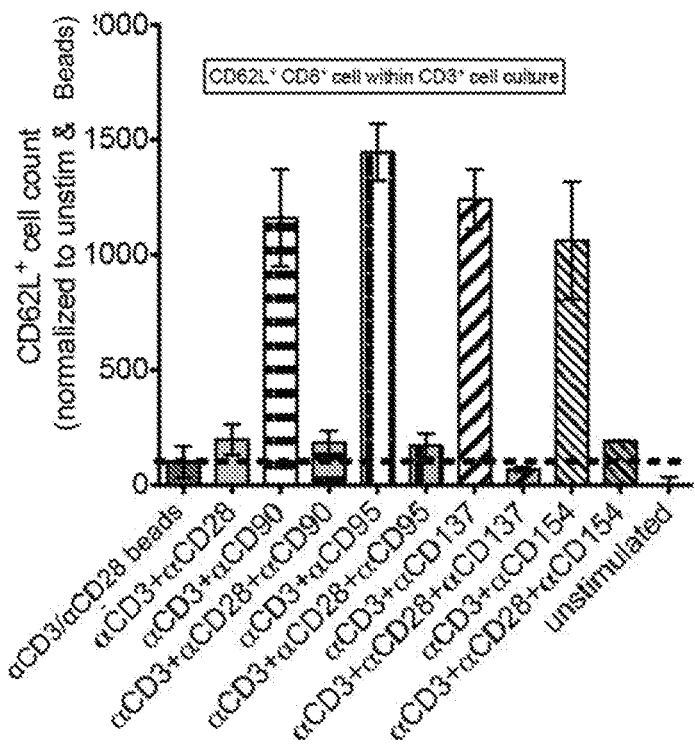

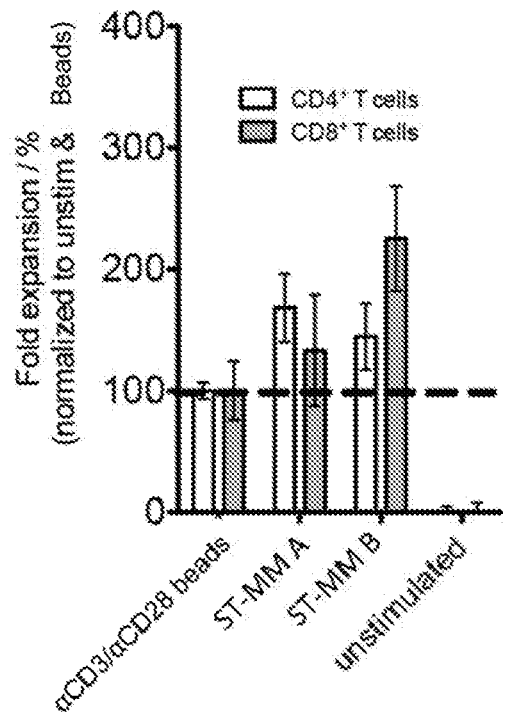
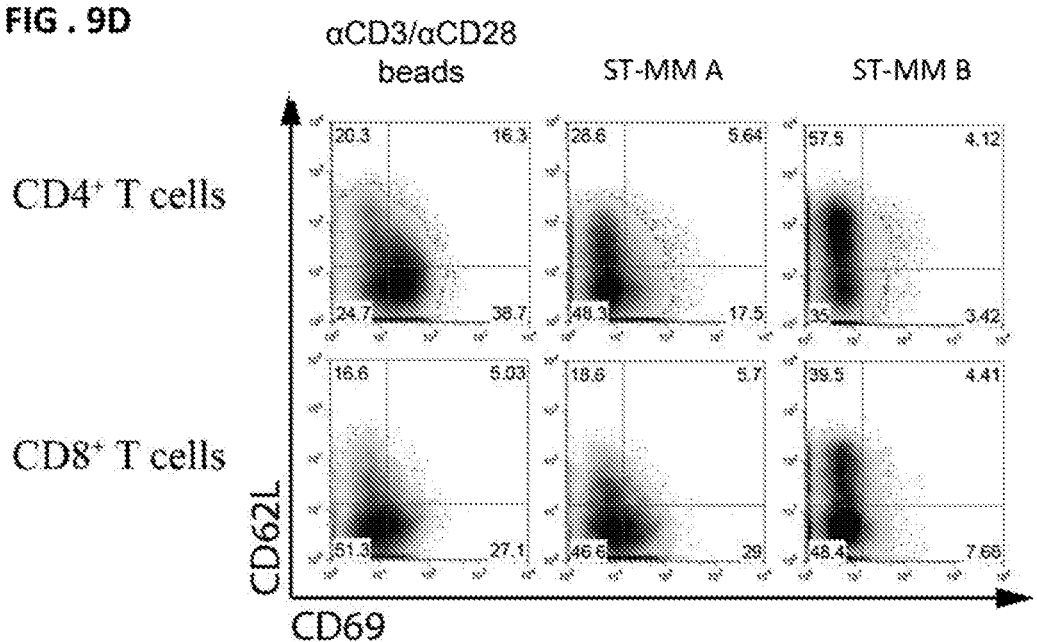

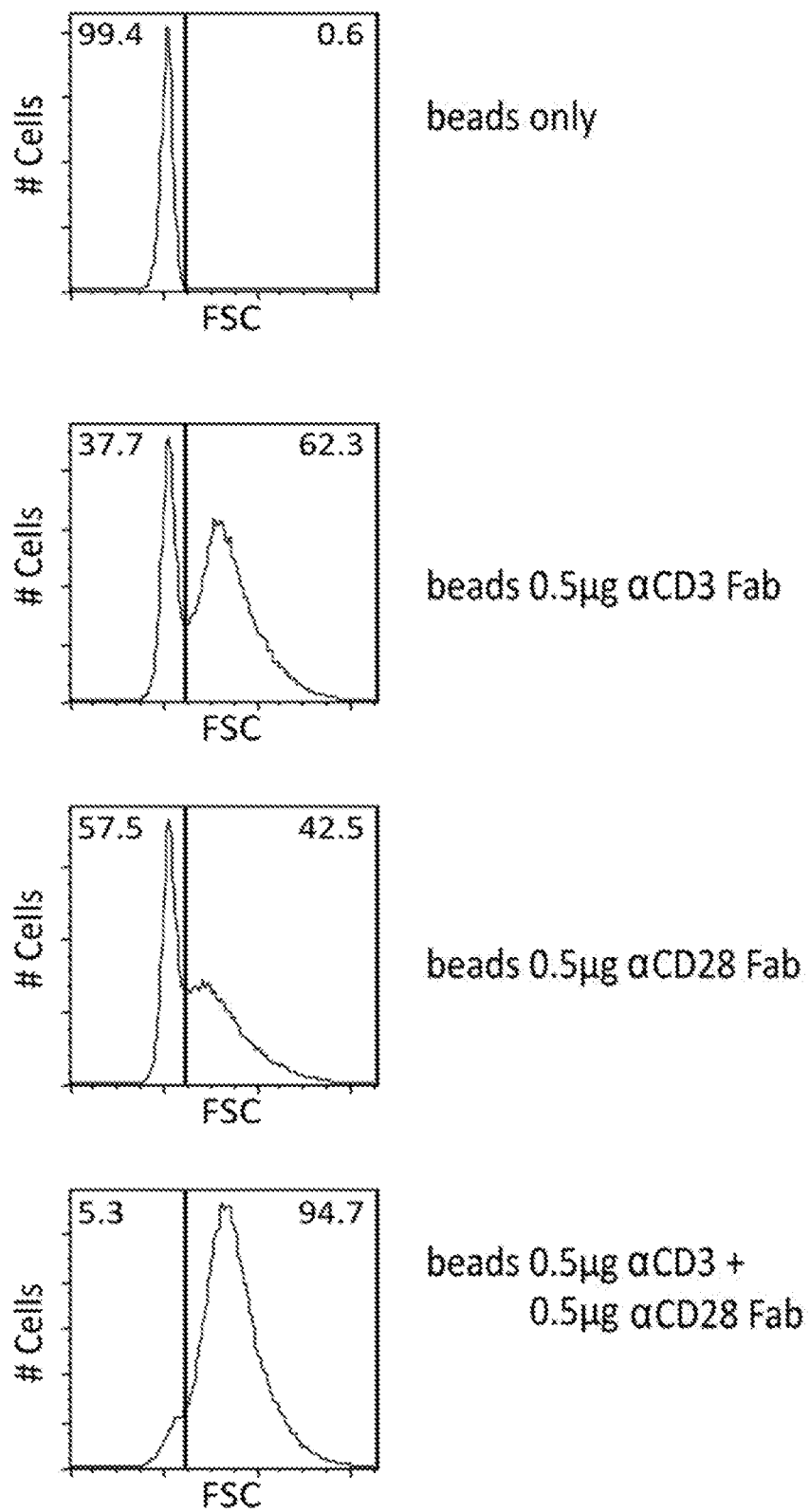

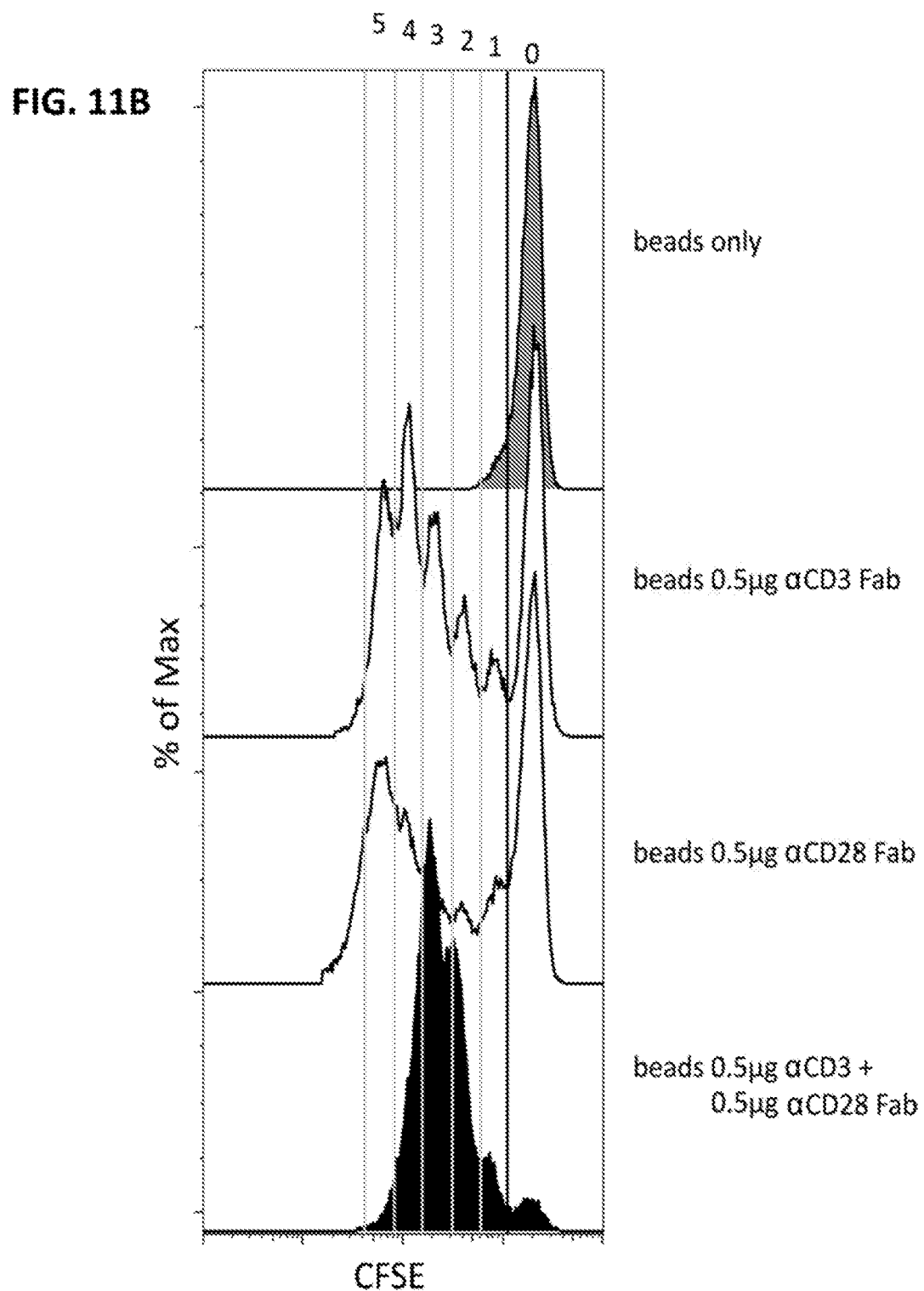

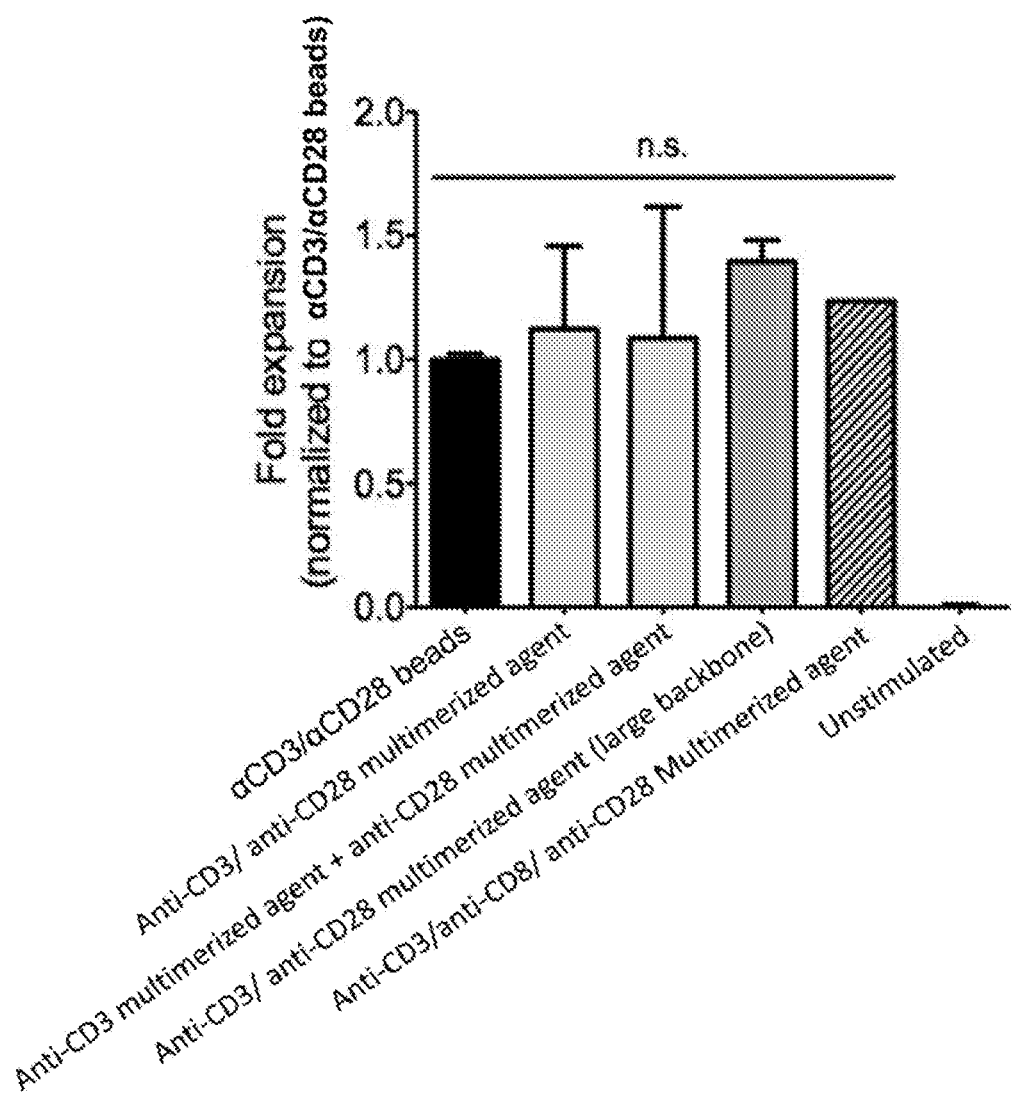

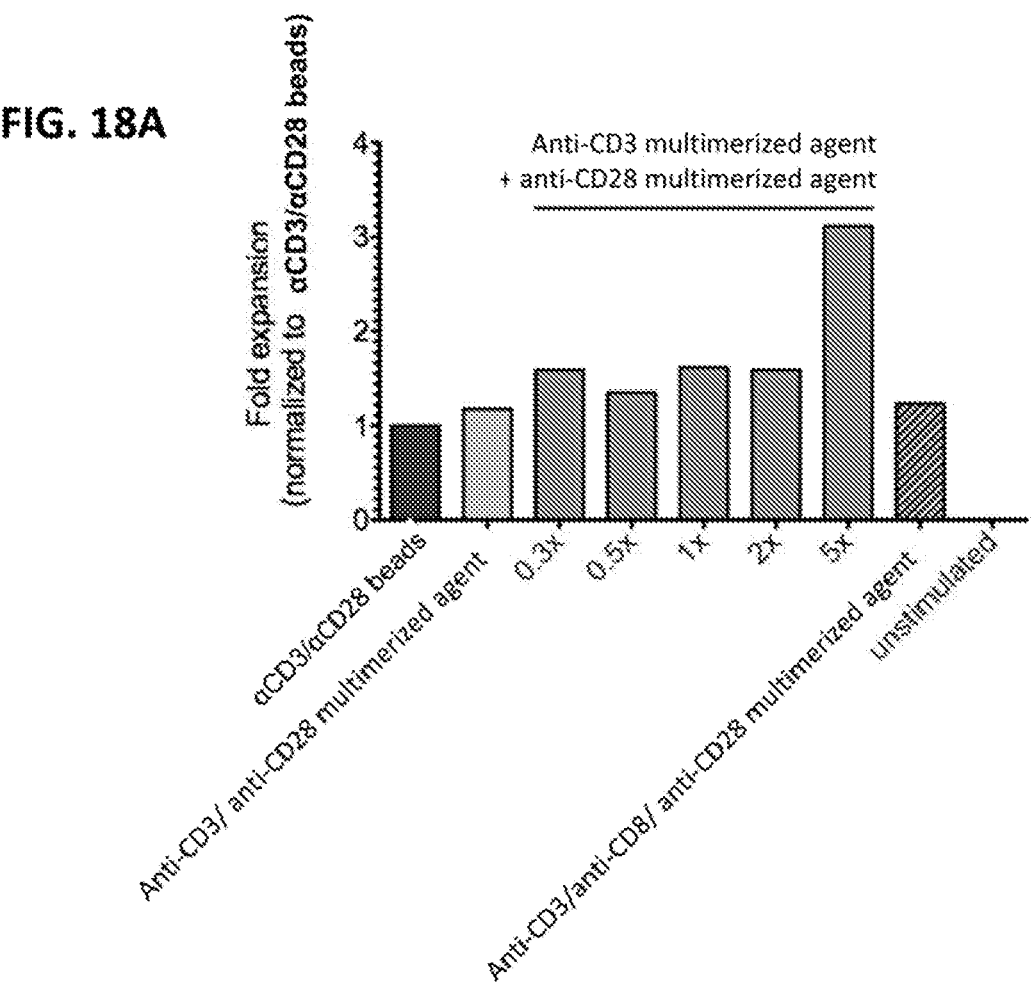

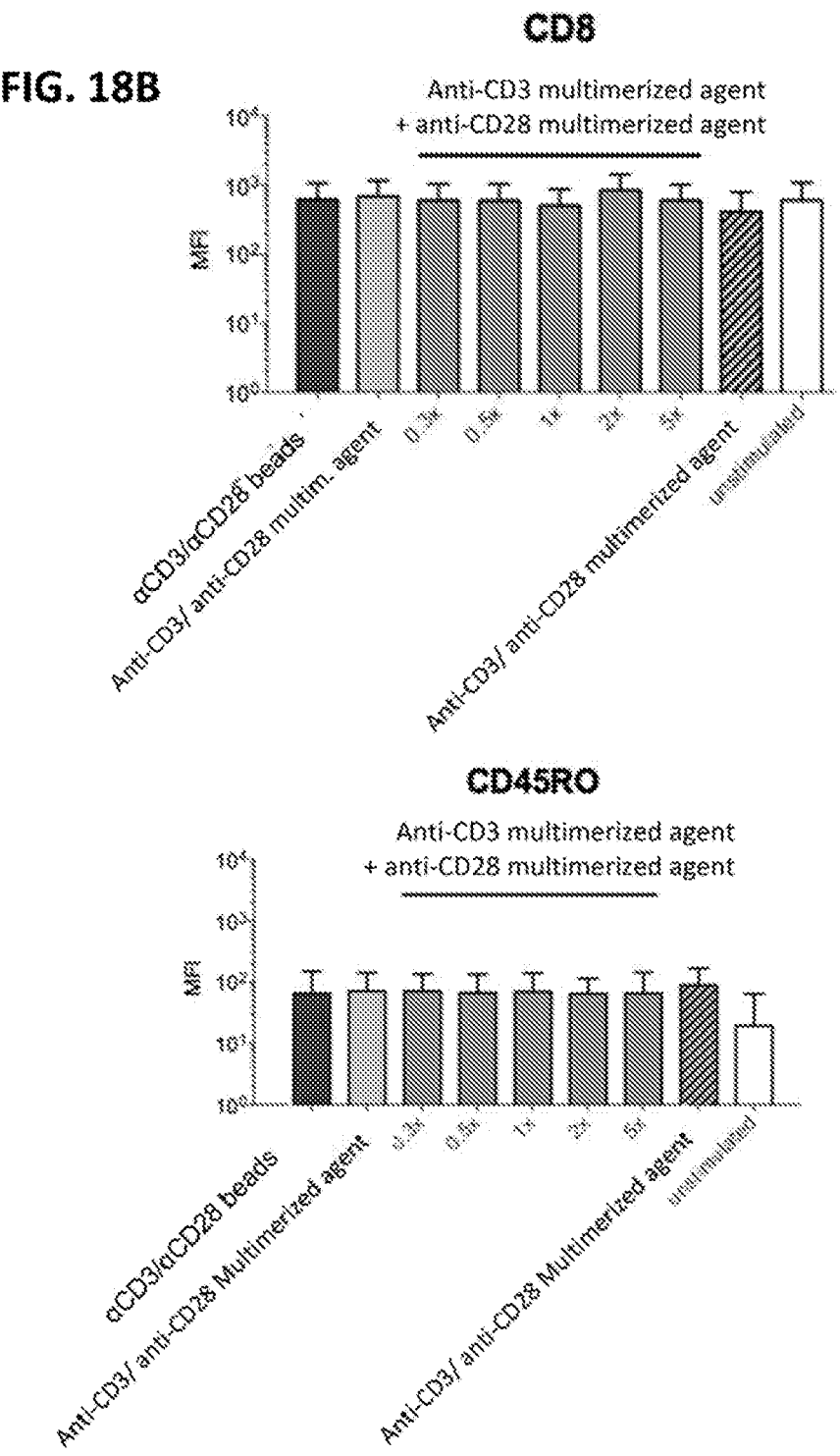

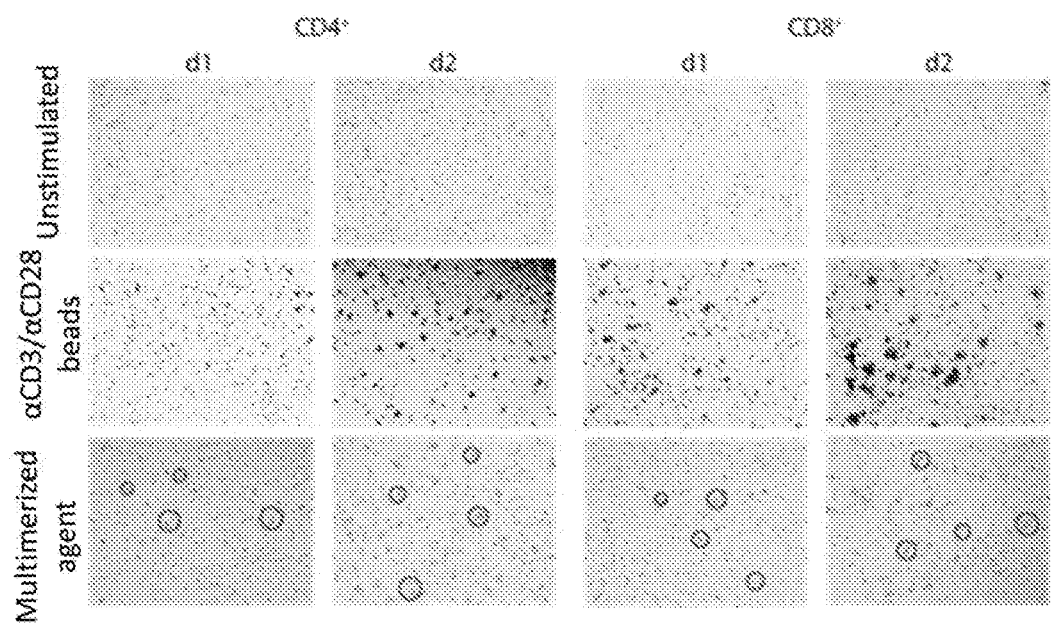

1: αCD3/αCD28 beads
2: αCD3/αCD28 multimerized agent + biotin d2
3: αCD3/αCD28 multimerized agent
4: unstimulated control

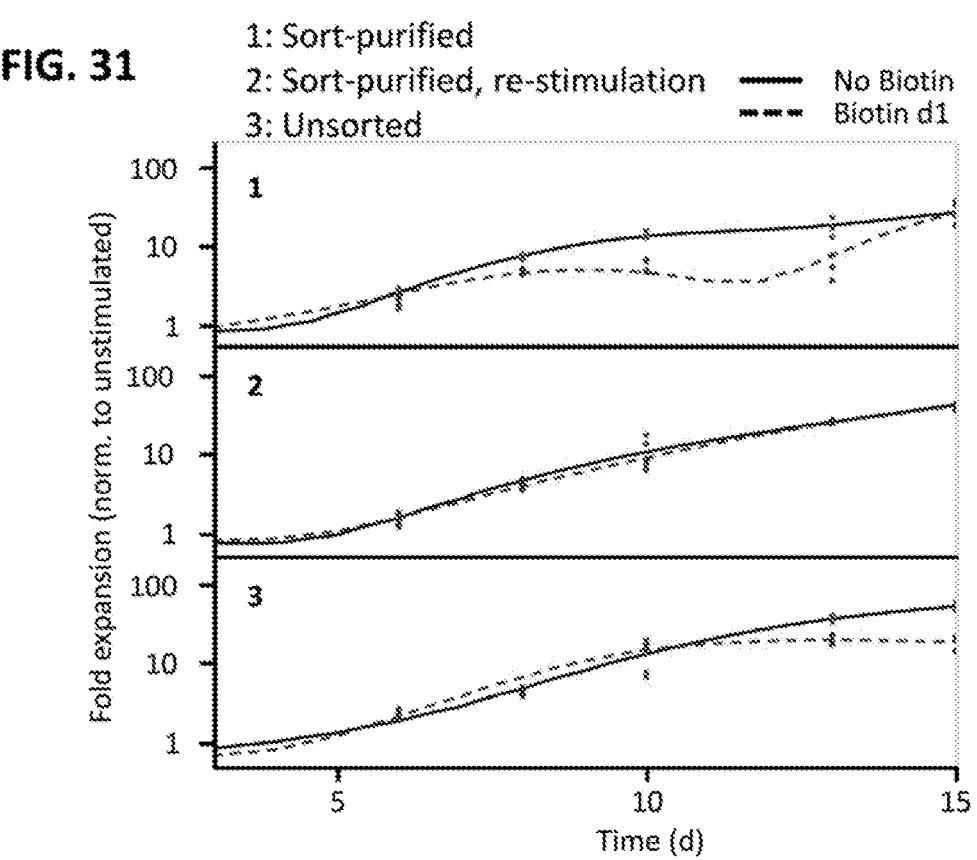

SEQUENCE LISTING

<160> NUMBER OF SEQ ID NOS: 81

<210> SEQ ID NO 1
<211> LENGTH: 159
<212> TYPE: PRT
<213> ORGANISM: Streptomyces avidinii
<220> FEATURE:
<223> OTHER INFORMATION: Streptavidin
<300> PUBLICATION INFORMATION:
<308> DATABASE ACCESSION NUMBER: UniProt No. P22629
<309> DATABASE ENTRY DATE: 1991-08-01

<400> SEQUENCE: 1

Asp Pro Ser Lys Asp Ser Lys Ala Gln Val Ser Ala Ala Glu Ala Gly
1               5                   10                  15

Ile Thr Gly Thr Trp Tyr Asn Gln Leu Gly Ser Thr Phe Ile Val Thr
            20                  25                  30

Ala Gly Ala Asp Gly Ala Leu Thr Gly Thr Tyr Glu Ser Ala Val Gly
        35                  40                  45

Asn Ala Glu Ser Arg Tyr Val Leu Thr Gly Arg Tyr Asp Ser Ala Pro
    50                  55                  60

Ala Thr Asp Gly Ser Gly Thr Ala Leu Gly Trp Thr Val Ala Trp Lys
65                  70                  75                  80

Asn Asn Tyr Arg Asn Ala His Ser Ala Thr Thr Trp Ser Gly Gln Tyr
                85                  90                  95

```
Val Gly Gly Ala Glu Ala Arg Ile Asn Thr Gln Trp Leu Leu Thr Ser
            100                 105                 110

Gly Thr Thr Glu Ala Asn Ala Trp Lys Ser Thr Leu Val Gly His Asp
        115                 120                 125

Thr Phe Thr Lys Val Lys Pro Ser Ala Ala Ser Ile Asp Ala Ala Lys
    130                 135                 140

Lys Ala Gly Val Asn Asn Gly Asn Pro Leu Asp Ala Val Gln Gln
145                 150                 155

<210> SEQ ID NO 2
<211> LENGTH: 126
<212> TYPE: PRT
<213> ORGANISM: Streptomyces avidinii
<220> FEATURE:
<223> OTHER INFORMATION: Minimal streptavidin

<400> SEQUENCE: 2

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Glu Ser
            20                  25                  30

Ala Val Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Ala Asn Ala Trp Lys Ser Thr Leu Val
            100                 105                 110

Gly His Asp Thr Phe Thr Lys Val Lys Pro Ser Ala Ala Ser
        115                 120                 125

<210> SEQ ID NO 3
<211> LENGTH: 159
<212> TYPE: PRT
<213> ORGANISM: Streptomyces avidinii
<220> FEATURE:
<223> OTHER INFORMATION: Mutein Streptavidin Val44-Thr45-Ala46-Arg47

<400> SEQUENCE: 3

Asp Pro Ser Lys Asp Ser Lys Ala Gln Val Ser Ala Ala Glu Ala Gly
1               5                   10                  15

Ile Thr Gly Thr Trp Tyr Asn Gln Leu Gly Ser Thr Phe Ile Val Thr
            20                  25                  30

Ala Gly Ala Asp Gly Ala Leu Thr Gly Thr Tyr Val Thr Ala Arg Gly
        35                  40                  45

Asn Ala Glu Ser Arg Tyr Val Leu Thr Gly Arg Tyr Asp Ser Ala Pro
    50                  55                  60

Ala Thr Asp Gly Ser Gly Thr Ala Leu Gly Trp Thr Val Ala Trp Lys
65                  70                  75                  80

Asn Asn Tyr Arg Asn Ala His Ser Ala Thr Thr Trp Ser Gly Gln Tyr
                85                  90                  95

Val Gly Gly Ala Glu Ala Arg Ile Asn Thr Gln Trp Leu Leu Thr Ser
            100                 105                 110

Gly Thr Thr Glu Ala Asn Ala Trp Lys Ser Thr Leu Val Gly His Asp
```

```
                115             120             125
Thr Phe Thr Lys Val Lys Pro Ser Ala Ala Ser Ile Asp Ala Ala Lys
        130             135             140

Lys Ala Gly Val Asn Asn Gly Asn Pro Leu Asp Ala Val Gln Gln
145             150             155

<210> SEQ ID NO 4
<211> LENGTH: 126
<212> TYPE: PRT
<213> ORGANISM: Streptomyces avidinii
<220> FEATURE:
<223> OTHER INFORMATION: Mutein Streptavidin Val44-Thr45-Ala46-Arg47

<400> SEQUENCE: 4

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
            20                  25                  30

Ala Arg Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Ala Asn Ala Trp Lys Ser Thr Leu Val
            100                 105                 110

Gly His Asp Thr Phe Thr Lys Val Lys Pro Ser Ala Ala Ser
        115                 120                 125

<210> SEQ ID NO 5
<211> LENGTH: 159
<212> TYPE: PRT
<213> ORGANISM: Streptomyces avidinii
<220> FEATURE:
<223> OTHER INFORMATION: Mutein Streptavidin Ile44-Gly45-Ala-46-Arg47

<400> SEQUENCE: 5

Asp Pro Ser Lys Asp Ser Lys Ala Gln Val Ser Ala Ala Glu Ala Gly
1               5                   10                  15

Ile Thr Gly Thr Trp Tyr Asn Gln Leu Gly Ser Thr Phe Ile Val Thr
            20                  25                  30

Ala Gly Ala Asp Gly Ala Leu Thr Gly Thr Tyr Ile Gly Ala Arg Gly
        35                  40                  45

Asn Ala Glu Ser Arg Tyr Val Leu Thr Gly Arg Tyr Asp Ser Ala Pro
    50                  55                  60

Ala Thr Asp Gly Ser Gly Thr Ala Leu Gly Trp Thr Val Ala Trp Lys
65                  70                  75                  80

Asn Asn Tyr Arg Asn Ala His Ser Ala Thr Thr Trp Ser Gly Gln Tyr
                85                  90                  95

Val Gly Gly Ala Glu Ala Arg Ile Asn Thr Gln Trp Leu Leu Thr Ser
            100                 105                 110

Gly Thr Thr Glu Ala Asn Ala Trp Lys Ser Thr Leu Val Gly His Asp
        115                 120                 125

Thr Phe Thr Lys Val Lys Pro Ser Ala Ala Ser Ile Asp Ala Ala Lys
    130                 135                 140
```

```
Lys Ala Gly Val Asn Gly Asn Pro Leu Asp Ala Val Gln Gln
145                 150                 155

<210> SEQ ID NO 6
<211> LENGTH: 126
<212> TYPE: PRT
<213> ORGANISM: Streptomyces avidinii
<220> FEATURE:
<223> OTHER INFORMATION: Mutein Streptavidin Ile44-Gly45-Ala-46-Arg47

<400> SEQUENCE: 6

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Ile Gly
            20                  25                  30

Ala Arg Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Ala Asn Ala Trp Lys Ser Thr Leu Val
            100                 105                 110

Gly His Asp Thr Phe Thr Lys Val Lys Pro Ser Ala Ala Ser
        115                 120                 125

<210> SEQ ID NO 7
<211> LENGTH: 8
<212> TYPE: PRT
<213> ORGANISM: Artificial Sequence
<220> FEATURE:
<223> OTHER INFORMATION: Streptavidin binding peptide, Strep-tag

<400> SEQUENCE: 7

Trp Arg His Pro Gln Phe Gly Gly
1               5

<210> SEQ ID NO 8
<211> LENGTH: 8
<212> TYPE: PRT
<213> ORGANISM: Artificial Sequence
<220> FEATURE:
<223> OTHER INFORMATION: Strep-tag II

<400> SEQUENCE: 8

Trp Ser His Pro Gln Phe Glu Lys
1               5

<210> SEQ ID NO 9
<211> LENGTH: 3
<212> TYPE: PRT
<213> ORGANISM: Artificial Sequence
<220> FEATURE:
<223> OTHER INFORMATION: Streptavidin Binding peptide
<220> FEATURE:
<221> NAME/KEY: VARIANT
<222> LOCATION: (3)...(3)
<223> OTHER INFORMATION: Xaa is Gln, Asp, or Met

<400> SEQUENCE: 9

His Pro Xaa
1
```

```
<210> SEQ ID NO 10
<211> LENGTH: 4
<212> TYPE: PRT
<213> ORGANISM: Artificial Sequence
<220> FEATURE:
<223> OTHER INFORMATION: Streptavidin Binding peptide

<400> SEQUENCE: 10

His Pro Gln Phe
1

<210> SEQ ID NO 11
<211> LENGTH: 8
<212> TYPE: PRT
<213> ORGANISM: Artificial Sequence
<220> FEATURE:
<223> OTHER INFORMATION: Streptavidin Binding peptide
<220> FEATURE:
<221> NAME/KEY: VARIANT
<222> LOCATION: (1)...(1)
<223> OTHER INFORMATION: Xaa is Trp, Lys or Arg
<220> FEATURE:
<221> NAME/KEY: VARIANT
<222> LOCATION: (2)...(2)
<223> OTHER INFORMATION: Xaa is any amino acid
<220> FEATURE:
<221> NAME/KEY: VARIANT
<222> LOCATION: (7)...(7)
<223> OTHER INFORMATION: Xaa is Gly or Glu
<220> FEATURE:
<221> NAME/KEY: VARIANT
<222> LOCATION: (8)...(8)
<223> OTHER INFORMATION: Xaa is Gly, Lys or Arg

<400> SEQUENCE: 11

Xaa Xaa His Pro Gln Phe Xaa Xaa
1               5

<210> SEQ ID NO 12
<211> LENGTH: 8
<212> TYPE: PRT
<213> ORGANISM: Artificial Sequence
<220> FEATURE:
<223> OTHER INFORMATION: Streptavidin Binding peptide
<220> FEATURE:
<221> NAME/KEY: VARIANT
<222> LOCATION: (2)...(2)
<223> OTHER INFORMATION: Xaa is any amino acid
<220> FEATURE:
<221> NAME/KEY: VARIANT
<222> LOCATION: (7)...(7)
<223> OTHER INFORMATION: Xaa is Gly or Glu
<220> FEATURE:
<221> NAME/KEY: VARIANT
<222> LOCATION: (8)...(8)
<223> OTHER INFORMATION: Xaa is Gly, Lys or Arg

<400> SEQUENCE: 12

Trp Xaa His Pro Gln Phe Xaa Xaa
1               5

<210> SEQ ID NO 13
<211> LENGTH: 28
<212> TYPE: PRT
<213> ORGANISM: Artificial Sequence
<220> FEATURE:
<223> OTHER INFORMATION: Sequential modules of streptavidin-binding
      peptide
<220> FEATURE:
<221> NAME/KEY: VARIANT
<222> LOCATION: (9)...(9)
```

```
<223> OTHER INFORMATION: Xaa is any amino acid
<220> FEATURE:
<221> NAME/KEY: VARIANT
<222> LOCATION: (10)...(10)
<223> OTHER INFORMATION: Xaa is any amino acid
<220> FEATURE:
<221> NAME/KEY: VARIANT
<222> LOCATION: (11)...(11)
<223> OTHER INFORMATION: Xaa is any amino acid
<220> FEATURE:
<221> NAME/KEY: VARIANT
<222> LOCATION: (12)...(12)
<223> OTHER INFORMATION: Xaa is any amino acid
<220> FEATURE:
<221> NAME/KEY: VARIANT
<222> LOCATION: (13)...(13)
<223> OTHER INFORMATION: Xaa is any amino acid
<220> FEATURE:
<221> NAME/KEY: VARIANT
<222> LOCATION: (14)...(14)
<223> OTHER INFORMATION: Xaa is any amino acid
<220> FEATURE:
<221> NAME/KEY: VARIANT
<222> LOCATION: (15)...(15)
<223> OTHER INFORMATION: Xaa is any amino acid
<220> FEATURE:
<221> NAME/KEY: VARIANT
<222> LOCATION: (16)...(16)
<223> OTHER INFORMATION: Xaa is any amino acid
<220> FEATURE:
<221> NAME/KEY: VARIANT
<222> LOCATION: (17)...(17)
<223> OTHER INFORMATION: Xaa is any amino acid or null
<220> FEATURE:
<221> NAME/KEY: VARIANT
<222> LOCATION: (18)...(18)
<223> OTHER INFORMATION: If Xaa at position 17 is any amino acid, then
      Xaa at position 18 is any amino acid. If Xaa at
      position 17 is null, then Xaa at position 18 is
      null.
<220> FEATURE:
<221> NAME/KEY: VARIANT
<222> LOCATION: (19)...(19)
<223> OTHER INFORMATION: If Xaa at position 17 is any amino acid, then
      Xaa at position 19 is any amino acid. If Xaa at
      position 17 is null, then Xaa at position 19 is
      null.
<220> FEATURE:
<221> NAME/KEY: VARIANT
<222> LOCATION: (20)...(20)
<223> OTHER INFORMATION: If Xaa at position 17 is any amino acid, then
      Xaa at position 20 is any amino acid. If Xaa at
      position 17 is null, then Xaa at position 20 is
      null.

<400> SEQUENCE: 13

Trp Ser His Pro Gln Phe Glu Lys Xaa Xaa Xaa Xaa Xaa Xaa Xaa Xaa
1               5                   10                  15

Xaa Xaa Xaa Xaa Trp Ser His Pro Gln Phe Glu Lys
            20                  25

<210> SEQ ID NO 14
<211> LENGTH: 28
<212> TYPE: PRT
<213> ORGANISM: Artificial Sequence
<220> FEATURE:
<223> OTHER INFORMATION: Sequential modules of streptavidin-binding
      peptide
<220> FEATURE:
<221> NAME/KEY: VARIANT
<222> LOCATION: (17)...(17)
<223> OTHER INFORMATION: Xaa is Gly or null
<220> FEATURE:
<221> NAME/KEY: VARIANT
<222> LOCATION: (18)...(18)
<223> OTHER INFORMATION: If Xaa at position 17 is Gly, then Xaa at
```

-continued

```
      position 18 is Gly. If Xaa at position 17 is null, then Xaa
      at position 18 is null
<220> FEATURE:
<221> NAME/KEY: VARIANT
<222> LOCATION: (19)...(19)
<223> OTHER INFORMATION: If Xaa at position 17 is Gly, then Xaa at
      position 19 is Gly. If Xaa at position 17 is null, then Xaa
      at position 19 is null
<220> FEATURE:
<221> NAME/KEY: VARIANT
<222> LOCATION: (20)...(20)
<223> OTHER INFORMATION: If Xaa at position 17 is Gly, then Xaa at
      position 20 is Ser. If Xaa at position 17 is null, then Xaa
      at position 20 is null

<400> SEQUENCE: 14

Trp Ser His Pro Gln Phe Glu Lys Gly Gly Gly Ser Gly Gly Gly Ser
1               5                   10                  15

Xaa Xaa Xaa Xaa Trp Ser His Pro Gln Phe Glu Lys
            20                  25

<210> SEQ ID NO 15
<211> LENGTH: 30
<212> TYPE: PRT
<213> ORGANISM: Artificial Sequence
<220> FEATURE:
<223> OTHER INFORMATION: Twin-Strep-tag

<400> SEQUENCE: 15

Ser Ala Trp Ser His Pro Gln Phe Glu Lys Gly Gly Gly Ser Gly Gly
1               5                   10                  15

Gly Ser Gly Gly Gly Ser Trp Ser His Pro Gln Phe Glu Lys
            20                  25                  30

<210> SEQ ID NO 16
<211> LENGTH: 30
<212> TYPE: PRT
<213> ORGANISM: Artificial Sequence
<220> FEATURE:
<223> OTHER INFORMATION: Twin-Strep-tag

<400> SEQUENCE: 16

Ser Ala Trp Ser His Pro Gln Phe Glu Lys Gly Gly Gly Ser Gly Gly
1               5                   10                  15

Gly Ser Gly Gly Ser Ala Trp Ser His Pro Gln Phe Glu Lys
            20                  25                  30

<210> SEQ ID NO 17
<211> LENGTH: 28
<212> TYPE: PRT
<213> ORGANISM: Artificial Sequence
<220> FEATURE:
<223> OTHER INFORMATION: Twin-Strep-tag

<400> SEQUENCE: 17

Trp Ser His Pro Gln Phe Glu Lys Gly Gly Gly Ser Gly Gly Gly Ser
1               5                   10                  15

Gly Gly Gly Ser Trp Ser His Pro Gln Phe Glu Lys
            20                  25

<210> SEQ ID NO 18
<211> LENGTH: 24
<212> TYPE: PRT
<213> ORGANISM: Artificial Sequence
<220> FEATURE:
<223> OTHER INFORMATION: Twin-Strep-tag
```

-continued

```
<400> SEQUENCE: 18

Trp Ser His Pro Gln Phe Glu Lys Gly Gly Gly Ser Gly Gly Gly Ser
1               5                   10                  15

Trp Ser His Pro Gln Phe Glu Lys
            20

<210> SEQ ID NO 19
<211> LENGTH: 28
<212> TYPE: PRT
<213> ORGANISM: Artificial Sequence
<220> FEATURE:
<223> OTHER INFORMATION: Twin-Strep-tag

<400> SEQUENCE: 19

Trp Ser His Pro Gln Phe Glu Lys Gly Gly Gly Ser Gly Gly Gly Ser
1               5                   10                  15

Gly Gly Ser Ala Trp Ser His Pro Gln Phe Glu Lys
            20                  25

<210> SEQ ID NO 20
<211> LENGTH: 9
<212> TYPE: PRT
<213> ORGANISM: Artificial Sequence
<220> FEATURE:
<223> OTHER INFORMATION: HA-tag

<400> SEQUENCE: 20

Tyr Pro Tyr Asp Val Pro Asp Tyr Ala
1               5

<210> SEQ ID NO 21
<211> LENGTH: 11
<212> TYPE: PRT
<213> ORGANISM: Artificial Sequence
<220> FEATURE:
<223> OTHER INFORMATION: VSV-G-tag

<400> SEQUENCE: 21

Tyr Thr Asp Ile Glu Met Asn Arg Leu Gly Lys
1               5                   10

<210> SEQ ID NO 22
<211> LENGTH: 11
<212> TYPE: PRT
<213> ORGANISM: Artificial Sequence
<220> FEATURE:
<223> OTHER INFORMATION: HSV-tag

<400> SEQUENCE: 22

Gln Pro Glu Leu Ala Pro Glu Asp Pro Glu Asp
1               5                   10

<210> SEQ ID NO 23
<211> LENGTH: 10
<212> TYPE: PRT
<213> ORGANISM: Artificial Sequence
<220> FEATURE:
<223> OTHER INFORMATION: T7 epitope

<400> SEQUENCE: 23

Ala Ser Met Thr Gly Gly Gln Gln Met Gly
1               5                   10

<210> SEQ ID NO 24
<211> LENGTH: 11
```

```
<212> TYPE: PRT
<213> ORGANISM: Artificial Sequence
<220> FEATURE:
<223> OTHER INFORMATION: HSV epitope

<400> SEQUENCE: 24

Gln Pro Glu Leu Ala Pro Glu Asp Pro Glu Asp
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Myc epitope

<400> SEQUENCE: 25

Glu Gln Lys Leu Ile Ser Glu Glu Asp Leu
1               5                   10

<210> SEQ ID NO 26
<211> LENGTH: 14
<212> TYPE: PRT
<213> ORGANISM: Artificial Sequence
<220> FEATURE:
<223> OTHER INFORMATION: V5-tag

<400> SEQUENCE: 26

Gly Lys Pro Ile Pro Asn Pro Leu Leu Gly Leu Asp Ser Thr
1               5                   10

<210> SEQ ID NO 27
<211> LENGTH: 126
<212> TYPE: PRT
<213> ORGANISM: Streptomyces avidinii
<220> FEATURE:
<223> OTHER INFORMATION: Mutein Streptavidin Val44-Thr45-Ala46-Arg47 and
      Glu117, Gly120, Try121 (mutein m1-9)

<400> SEQUENCE: 27

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
                20                  25                  30

Ala Arg Gly Asn Ala Glu Ser Arg Tyr Val Leu Thr Gly Arg Tyr Asp
            35                  40                  45

Ser Ala Pro Ala Thr Asp Gly Ser Gly Thr Ala Leu Gly Trp Thr Val
        50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Glu Asn Ala Gly Tyr Ser Thr Leu Val
                100                 105                 110

Gly His Asp Thr Phe Thr Lys Val Lys Pro Ser Ala Ala Ser
            115                 120                 125

<210> SEQ ID NO 28
<211> LENGTH: 139
<212> TYPE: PRT
<213> ORGANISM: Streptomyces avidinii
<220> FEATURE:
<223> OTHER INFORMATION: Mutein Streptavidin Val44-Thr45-Ala46-Arg47 and
      Glu117, Gly120, Try121 (mutein m1-9)
```

<400> SEQUENCE: 28

```
Asp Pro Ser Lys Asp Ser Lys Ala Gln Val Ser Ala Ala Glu Ala Gly
1               5                   10                  15

Ile Thr Gly Thr Trp Tyr Asn Gln Leu Gly Ser Thr Phe Ile Val Thr
                20                  25                  30

Ala Gly Ala Asp Gly Ala Leu Thr Gly Thr Tyr Val Thr Ala Arg Gly
            35                  40                  45

Asn Ala Glu Ser Arg Tyr Val Leu Thr Gly Arg Tyr Asp Ser Ala Pro
    50                  55                  60

Ala Thr Asp Gly Ser Gly Thr Ala Leu Gly Trp Thr Val Ala Trp Lys
65                  70                  75                  80

Asn Asn Tyr Arg Asn Ala His Ser Ala Thr Thr Trp Ser Gly Gln Tyr
                85                  90                  95

Val Gly Gly Ala Glu Ala Arg Ile Asn Thr Gln Trp Leu Leu Thr Ser
            100                 105                 110

Gly Thr Thr Glu Glu Asn Ala Gly Tyr Ser Thr Leu Val Gly His Asp
            115                 120                 125

Thr Phe Thr Lys Val Lys Pro Ser Ala Ala Ser
            130                 135
```

<210> SEQ ID NO 29
<211> LENGTH: 253
<212> TYPE: PRT
<213> ORGANISM: Artificial Sequence
<220> FEATURE:
<223> OTHER INFORMATION: Variable Heavy chain of Fab fragment m13B8.2

<400> SEQUENCE: 29

```
Ala Met Gln Val Gln Leu Lys Gln Ser Gly Pro Gly Leu Val Gln Pro
1               5                   10                  15

Ser Gln Ser Leu Ser Ile Thr Cys Thr Val Ser Gly Phe Ser Leu Thr
                20                  25                  30

Thr Phe Gly Val His Trp Val Arg Gln Ser Pro Gly Lys Gly Leu Glu
            35                  40                  45

Trp Leu Gly Val Ile Trp Ala Ser Gly Ile Thr Asp Tyr Asn Val Pro
    50                  55                  60

Phe Met Ser Arg Leu Ser Ile Thr Lys Asp Asn Ser Lys Ser Gln Val
65                  70                  75                  80

Phe Phe Lys Leu Asn Ser Leu Gln Pro Asp Asp Thr Ala Ile Tyr Tyr
                85                  90                  95

Cys Ala Lys Asn Asp Pro Gly Thr Gly Phe Ala Tyr Trp Gly Gln Gly
            100                 105                 110

Thr Leu Val Thr Val Ser Ala Gly Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205
```

```
Ser Asn Thr Lys Val Asp Lys Lys Val Glu Pro Lys Ser Cys Gly Ser
    210                 215                 220

Ala Trp Ser His Pro Gln Phe Glu Lys Gly Gly Gly Gly Gly
225                 230                 235                 240

Ser Gly Gly Ser Ala Trp Ser His Pro Gln Phe Glu Lys
                245                 250

<210> SEQ ID NO 30
<211> LENGTH: 218
<212> TYPE: PRT
<213> ORGANISM: Artificial Sequence
<220> FEATURE:
<223> OTHER INFORMATION: Variable Light chain of Fab Fragment m13B8.2

<400> SEQUENCE: 30

Ala Met Asp Ile Gln Met Thr Gln Ser Pro Ala Ser Leu Ser Ala Ser
1               5                   10                  15

Val Gly Glu Thr Val Thr Phe Thr Cys Arg Ala Ser Glu Met Ile Tyr
            20                  25                  30

Ser Tyr Leu Ala Trp Tyr Gln Gln Lys Gln Gly Lys Ser Pro Gln Leu
        35                  40                  45

Leu Val His Asp Ala Lys Thr Leu Ala Glu Gly Val Pro Ser Arg Phe
    50                  55                  60

Ser Gly Gly Ser Gly Thr Gln Phe Ser Leu Lys Ile Asn Thr Leu
65                  70                  75                  80

Gln Pro Glu Asp Phe Gly Thr Tyr Tyr Cys Gln Ala His Tyr Gly Asn
                85                  90                  95

Pro Pro Thr Phe Gly Gly Gly Thr Lys Leu Glu Ile Lys Arg Gly Ile
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys Gly Ser
    210                 215

<210> SEQ ID NO 31
<211> LENGTH: 119
<212> TYPE: PRT
<213> ORGANISM: Artificial Sequence
<220> FEATURE:
<223> OTHER INFORMATION: Variable Heavy chain of anti-CD3 antibody OKT3

<400> SEQUENCE: 31

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45
```

Gly Tyr Ile Asn Pro Ser Arg Gly Tyr Thr Asn Tyr Asn Gln Lys Phe
        50                  55                  60

Lys Asp Lys Ala Thr Leu Thr Thr Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115

<210> SEQ ID NO 32
<211> LENGTH: 106
<212> TYPE: PRT
<213> ORGANISM: Artificial Sequence
<220> FEATURE:
<223> OTHER INFORMATION: Variable Light chain of anti-CD3 antibody OKT3

<400> SEQUENCE: 32

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
                20                  25                  30

Asn Trp Tyr Gln Gln Lys Ser Gly Thr Ser Pro Lys Arg Trp Ile Tyr
            35                  40                  45

Asp Thr Ser Lys Leu Ala Ser Gly Val Pro Ala His Phe Arg Gly Ser
        50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Asn Pro Phe Thr
                85                  90                  95

Phe Gly Ser Gly Thr Lys Leu Glu Ile Asn
            100                 105

<210> SEQ ID NO 33
<211> LENGTH: 116
<212> TYPE: PRT
<213> ORGANISM: Artificial Sequence
<220> FEATURE:
<223> OTHER INFORMATION: Variable Heavy chain of anti-CD28 antibody
      CD28.3

<400> SEQUENCE: 33

Leu Gln Gln Ser Gly Ala Glu Leu Val Lys Pro Gly Ala Ser Val Arg
1               5                   10                  15

Leu Ser Cys Lys Ala Ser Gly Tyr Thr Phe Thr Glu Tyr Ile Ile His
                20                  25                  30

Trp Ile Lys Leu Arg Ser Gly Gln Gly Leu Glu Trp Ile Gly Trp Phe
            35                  40                  45

Tyr Pro Gly Ser Asn Asp Ile Gln Tyr Asn Ala Lys Phe Lys Gly Lys
        50                  55                  60

Ala Thr Leu Thr Ala Asp Lys Ser Ser Ser Thr Val Tyr Met Glu Leu
65                  70                  75                  80

Thr Gly Leu Thr Ser Glu Asp Ser Ala Val Tyr Phe Cys Ala Arg Arg
                85                  90                  95

Asp Asp Phe Ser Gly Tyr Asp Ala Leu Pro Tyr Trp Gly Gln Gly Thr
            100                 105                 110

```
Met Val Thr Val
        115

<210> SEQ ID NO 34
<211> LENGTH: 108
<212> TYPE: PRT
<213> ORGANISM: Artificial Sequence
<220> FEATURE:
<223> OTHER INFORMATION: Variable Light chain of anti-CD28 antibody
      CD28.3

<400> SEQUENCE: 34

Asp Ile Gln Met Thr Gln Ser Pro Ala Ser Leu Ser Val Ser Val Gly
1               5                   10                  15

Glu Thr Val Thr Ile Thr Cys Arg Thr Asn Glu Asn Ile Tyr Ser Asn
            20                  25                  30

Leu Ala Trp Tyr Gln Gln Lys Gln Gly Lys Ser Pro Gln Leu Leu Ile
        35                  40                  45

Tyr Ala Ala Thr His Leu Val Glu Gly Val Pro Ser Arg Phe Ser Gly
50                  55                  60

Ser Gly Ser Gly Thr Gln Tyr Ser Leu Lys Ile Thr Ser Leu Gln Ser
65                  70                  75                  80

Glu Asp Phe Gly Asn Tyr Tyr Cys Gln His Phe Trp Gly Thr Pro Cys
                85                  90                  95

Thr Phe Gly Gly Gly Thr Lys Leu Glu Ile Lys Arg
            100                 105

<210> SEQ ID NO 35
<211> LENGTH: 11
<212> TYPE: PRT
<213> ORGANISM: Artificial Sequence
<220> FEATURE:
<223> OTHER INFORMATION: MAT tag

<400> SEQUENCE: 35

His Asn His Arg His Lys His Gly Gly Gly Cys
1               5                   10

<210> SEQ ID NO 36
<211> LENGTH: 118
<212> TYPE: PRT
<213> ORGANISM: Artificial Sequence
<220> FEATURE:
<223> OTHER INFORMATION: anti-CD16 antibody 3G8 VH

<400> SEQUENCE: 36

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Arg Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Asp Lys Arg Tyr Asn Pro Ala
50                  55                  60

Leu Lys Ser Arg Leu Thr Ile Ser Lys Asp Thr Ser Ser Asn Gln Val
65                  70                  75                  80

Phe Leu Lys Ile Ala Ser Val Asp Thr Ala Asp Thr Ala Thr Tyr Tyr
                85                  90                  95

Cys Ala Gln Ile Asn Pro Ala Trp Phe Ala Tyr Trp Gly Gln Gly Thr
            100                 105                 110
```

```
Leu Val Thr Val Ser Ser
        115

<210> SEQ ID NO 37
<211> LENGTH: 111
<212> TYPE: PRT
<213> ORGANISM: Artificial Sequence
<220> FEATURE:
<223> OTHER INFORMATION: anti-CD16 antibody 3G8 VL

<400> SEQUENCE: 37

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Phe Asp
            20                  25                  30

Gly Asp Ser Phe Met Asn Trp Tyr Gln Gln Lys Pro Gly Gln Pro Pro
        35                  40                  45

Lys Leu Leu Ile Tyr Thr Thr Ser Asn Leu Glu Ser Gly Ile Pro Ala
    50                  55                  60

Arg Phe Ser Ala Ser Gly Ser Gly Thr Asp Phe Thr Leu Asn Ile His
65                  70                  75                  80

Pro Val Glu Glu Glu Asp Thr Ala Thr Tyr Tyr Cys Gln Gln Ser Asn
                85                  90                  95

Glu Asp Pro Tyr Thr Phe Gly Gly Gly Thr Lys Leu Glu Ile Lys
            100                 105                 110

<210> SEQ ID NO 38
<211> LENGTH: 9
<212> TYPE: PRT
<213> ORGANISM: Artificial Sequence
<220> FEATURE:
<223> OTHER INFORMATION: antigen-specific peptide

<400> SEQUENCE: 38

Cys Arg Val Leu Cys Cys Tyr Val Leu
1               5

<210> SEQ ID NO 39
<211> LENGTH: 9
<212> TYPE: PRT
<213> ORGANISM: Artificial Sequence
<220> FEATURE:
<223> OTHER INFORMATION: pp65 epitope of CMV (amino acids 341-350)

<400> SEQUENCE: 39

Gln Tyr Asp Pro Val Ala Ala Leu Phe
1               5

<210> SEQ ID NO 40
<211> LENGTH: 10
<212> TYPE: PRT
<213> ORGANISM: Artificial Sequence
<220> FEATURE:
<223> OTHER INFORMATION: pp65 epitope of CMV (amino acids 265-274)

<400> SEQUENCE: 40

Arg Pro His Glu Arg Asn Gly Phe Thr Val
1               5                   10

<210> SEQ ID NO 41
<211> LENGTH: 11
<212> TYPE: PRT
<213> ORGANISM: Artificial Sequence
<220> FEATURE:
```

<223> OTHER INFORMATION: hexon 5 epitope of adenovirus (amino acids
      114-124)

<400> SEQUENCE: 41

Cys Pro Tyr Ser Gly Thr Ala Tyr Asn Ser Leu
1               5                   10

<210> SEQ ID NO 42
<211> LENGTH: 314
<212> TYPE: PRT
<213> ORGANISM: Artificial Sequence
<220> FEATURE:
<223> OTHER INFORMATION: HLA-A*2402

<400> SEQUENCE: 42

Met Gly Ser His Ser Met Arg Tyr Phe Ser Thr Ser Val Ser Arg Pro
1               5                   10                  15

Gly Arg Gly Glu Pro Arg Phe Ile Ala Val Gly Tyr Val Asp Asp Thr
            20                  25                  30

Gln Phe Val Arg Phe Asp Ser Asp Ala Ala Ser Gln Arg Met Glu Pro
        35                  40                  45

Arg Ala Pro Trp Ile Glu Gln Glu Gly Pro Glu Tyr Trp Asp Glu Glu
    50                  55                  60

Thr Gly Lys Val Lys Ala His Ser Gln Thr Asp Arg Glu Asn Leu Arg
65                  70                  75                  80

Ile Ala Leu Arg Tyr Tyr Asn Gln Ser Glu Ala Gly Ser His Thr Leu
                85                  90                  95

Gln Met Met Phe Gly Cys Asp Val Gly Ser Asp Gly Arg Phe Leu Arg
            100                 105                 110

Gly Tyr His Gln Tyr Ala Tyr Asp Gly Lys Asp Tyr Ile Ala Leu Lys
        115                 120                 125

Glu Asp Leu Arg Ser Trp Thr Ala Ala Asp Met Ala Ala Gln Ile Thr
    130                 135                 140

Lys Arg Lys Trp Glu Ala Ala His Val Ala Glu Gln Gln Arg Ala Tyr
145                 150                 155                 160

Leu Glu Gly Thr Cys Val Asp Gly Leu Arg Arg Tyr Leu Glu Asn Gly
                165                 170                 175

Lys Glu Thr Leu Gln Arg Thr Asp Pro Pro Lys Thr His Met Thr His
            180                 185                 190

His Pro Ile Ser Asp His Glu Ala Thr Leu Arg Cys Trp Ala Leu Gly
        195                 200                 205

Phe Tyr Pro Ala Glu Ile Thr Leu Thr Trp Gln Arg Asp Gly Glu Asp
    210                 215                 220

Gln Thr Gln Asp Thr Glu Leu Val Glu Thr Arg Pro Ala Gly Asp Gly
225                 230                 235                 240

Thr Phe Gln Lys Trp Ala Ala Val Val Pro Ser Gly Glu Glu Gln
                245                 250                 255

Arg Tyr Thr Cys His Val Gln His Glu Gly Leu Pro Lys Pro Leu Thr
            260                 265                 270

Leu Arg Trp Glu Pro Pro Ser Gly Ser Ser Ala Trp Ser His Pro
        275                 280                 285

Gln Phe Glu Lys Gly Gly Gly Ser Gly Gly Gly Ser
    290                 295                 300

Ser Ala Trp Ser His Pro Gln Phe Glu Lys
305                 310

```
<210> SEQ ID NO 43
<211> LENGTH: 314
<212> TYPE: PRT
<213> ORGANISM: Artificial Sequence
<220> FEATURE:
<223> OTHER INFORMATION: HLA-B*0702

<400> SEQUENCE: 43

Met Gly Ser His Ser Met Arg Tyr Phe Tyr Thr Ser Val Ser Arg Pro
1               5                   10                  15

Gly Arg Gly Glu Pro Arg Phe Ile Ser Val Gly Tyr Val Asp Asp Thr
            20                  25                  30

Gln Phe Val Arg Phe Asp Ser Asp Ala Ala Ser Pro Arg Glu Glu Pro
        35                  40                  45

Arg Ala Pro Trp Ile Glu Gln Glu Gly Pro Glu Tyr Trp Asp Arg Asn
    50                  55                  60

Thr Gln Ile Tyr Lys Ala Gln Ala Gln Thr Asp Arg Glu Ser Leu Arg
65                  70                  75                  80

Asn Leu Arg Gly Tyr Tyr Asn Gln Ser Glu Ala Gly Ser His Thr Leu
                85                  90                  95

Gln Ser Met Tyr Gly Cys Asp Val Gly Pro Asp Gly Arg Leu Leu Arg
            100                 105                 110

Gly His Asp Gln Tyr Ala Tyr Asp Gly Lys Asp Tyr Ile Ala Leu Asn
        115                 120                 125

Glu Asp Leu Arg Ser Trp Thr Ala Ala Asp Thr Ala Ala Gln Ile Thr
    130                 135                 140

Gln Arg Lys Trp Glu Ala Ala Arg Glu Ala Glu Gln Arg Arg Ala Tyr
145                 150                 155                 160

Leu Glu Gly Glu Cys Val Glu Trp Leu Arg Arg Tyr Leu Glu Asn Gly
                165                 170                 175

Lys Asp Lys Leu Glu Arg Ala Asp Pro Pro Lys Thr His Val Thr His
            180                 185                 190

His Pro Ile Ser Asp His Glu Ala Thr Leu Arg Cys Trp Ala Leu Gly
        195                 200                 205

Phe Tyr Pro Ala Glu Ile Thr Leu Thr Trp Gln Arg Asp Gly Glu Asp
    210                 215                 220

Gln Thr Gln Asp Thr Glu Leu Val Glu Thr Arg Pro Ala Gly Asp Arg
225                 230                 235                 240

Thr Phe Gln Lys Trp Ala Ala Val Val Val Pro Ser Gly Glu Glu Gln
                245                 250                 255

Arg Tyr Thr Cys His Val Gln His Glu Gly Leu Pro Lys Pro Leu Thr
            260                 265                 270

Leu Arg Trp Glu Pro Pro Pro Ser Gly Ser Ser Ala Trp Ser His Pro
        275                 280                 285

Gln Phe Glu Lys Gly Gly Gly Ser Gly Gly Gly Ser Gly Gly Gly Ser
    290                 295                 300

Ser Ala Trp Ser His Pro Gln Phe Glu Lys
305                 310

<210> SEQ ID NO 44
<211> LENGTH: 321
<212> TYPE: PRT
<213> ORGANISM: Artificial Sequence
<220> FEATURE:
<223> OTHER INFORMATION: HLA-C*0702

<400> SEQUENCE: 44
```

Met Ala Leu Thr Glu Thr Trp Ala Cys Ser His Ser Met Arg Tyr Phe
1               5                   10                  15

Asp Thr Ala Val Ser Arg Pro Gly Arg Gly Glu Pro Arg Phe Ile Ser
            20                  25                  30

Val Gly Tyr Val Asp Asp Thr Gln Phe Val Arg Phe Asp Ser Asp Ala
            35                  40                  45

Ala Ser Pro Arg Gly Glu Pro Arg Ala Pro Trp Val Glu Gln Glu Gly
50                  55                  60

Pro Glu Tyr Trp Asp Arg Glu Thr Gln Lys Tyr Lys Arg Gln Ala Gln
65                  70                  75                  80

Ala Asp Arg Val Ser Leu Arg Asn Leu Arg Gly Tyr Tyr Asn Gln Ser
                85                  90                  95

Glu Asp Gly Ser His Thr Leu Gln Arg Met Ser Gly Cys Asp Leu Gly
            100                 105                 110

Pro Asp Gly Arg Leu Leu Arg Gly Tyr Asp Gln Ser Ala Tyr Asp Gly
            115                 120                 125

Lys Asp Tyr Ile Ala Leu Asn Glu Asp Leu Arg Ser Trp Thr Ala Ala
130                 135                 140

Asp Thr Ala Ala Gln Ile Thr Gln Arg Lys Leu Glu Ala Ala Arg Ala
145                 150                 155                 160

Ala Glu Gln Leu Arg Ala Tyr Leu Glu Gly Thr Cys Val Glu Trp Leu
                165                 170                 175

Arg Arg Tyr Leu Glu Asn Gly Lys Glu Thr Leu Gln Arg Ala Glu Pro
            180                 185                 190

Pro Lys Thr His Val Thr His His Pro Leu Ser Asp His Glu Ala Thr
            195                 200                 205

Leu Arg Cys Trp Ala Leu Gly Phe Tyr Pro Ala Glu Ile Thr Leu Thr
210                 215                 220

Trp Gln Arg Asp Gly Glu Asp Gln Thr Gln Asp Thr Glu Leu Val Glu
225                 230                 235                 240

Thr Arg Pro Ala Gly Asp Gly Thr Phe Gln Lys Trp Ala Ala Val Val
                245                 250                 255

Val Pro Ser Gly Gln Glu Gln Arg Tyr Thr Cys His Met Gln His Glu
            260                 265                 270

Gly Leu Gln Glu Pro Leu Thr Leu Ser Trp Glu Pro Ser Ser Gln Pro
            275                 280                 285

Thr Ile Gly Ser Ala Trp Ser His Pro Gln Phe Glu Lys Gly Gly Gly
290                 295                 300

Ser Gly Gly Gly Ser Gly Gly Ser Ala Trp Ser His Pro Gln Phe Glu
305                 310                 315                 320

Lys

<210> SEQ ID NO 45
<211> LENGTH: 100
<212> TYPE: PRT
<213> ORGANISM: Artificial Sequence
<220> FEATURE:
<223> OTHER INFORMATION: B2 microglobulin

<400> SEQUENCE: 45

Met Ile Gln Arg Thr Pro Lys Ile Gln Val Tyr Ser Arg His Pro Ala
1               5                   10                  15

Glu Asn Gly Lys Ser Asn Phe Leu Asn Cys Tyr Val Ser Gly Phe His
            20                  25                  30

Pro Ser Asp Ile Glu Val Asp Leu Leu Lys Asn Gly Glu Arg Ile Glu

```
            35                  40                  45
Lys Val Glu His Ser Asp Leu Ser Phe Ser Lys Asp Trp Ser Phe Tyr
 50                  55                  60

Leu Leu Tyr Tyr Thr Glu Phe Thr Pro Thr Glu Lys Asp Glu Tyr Ala
 65                  70                  75                  80

Cys Arg Val Asn His Val Thr Leu Ser Gln Pro Lys Ile Val Lys Trp
                 85                  90                  95

Asp Arg Asp Met
            100

<210> SEQ ID NO 46
<211> LENGTH: 10
<212> TYPE: PRT
<213> ORGANISM: Artificial Sequence
<220> FEATURE:
<223> OTHER INFORMATION: 10 amino acid tag from the collagen-binding
      domain of von Willebrand factor

<400> SEQUENCE: 46

Trp Arg Glu Pro Gly Arg Met Glu Leu Asn
 1               5                  10

<210> SEQ ID NO 47
<211> LENGTH: 283
<212> TYPE: PRT
<213> ORGANISM: Artificial Sequence
<220> FEATURE:
<223> OTHER INFORMATION: human CD19 extracellular domain with His-Tag

<400> SEQUENCE: 47

Pro Glu Glu Pro Leu Val Val Lys Val Glu Glu Gly Asp Asn Ala Val
 1               5                  10                  15

Leu Gln Cys Leu Lys Gly Thr Ser Asp Gly Pro Thr Gln Gln Leu Thr
                 20                  25                  30

Trp Ser Arg Glu Ser Pro Leu Lys Pro Phe Leu Lys Leu Ser Leu Gly
             35                  40                  45

Leu Pro Gly Leu Gly Ile His Met Arg Pro Leu Ala Ile Trp Leu Phe
 50                  55                  60

Ile Phe Asn Val Ser Gln Gln Met Gly Gly Phe Tyr Leu Cys Gln Pro
 65                  70                  75                  80

Gly Pro Pro Ser Glu Lys Ala Trp Gln Pro Gly Trp Thr Val Asn Val
                 85                  90                  95

Glu Gly Ser Gly Glu Leu Phe Arg Trp Asn Val Ser Asp Leu Gly Gly
            100                 105                 110

Leu Gly Cys Gly Leu Lys Asn Arg Ser Ser Glu Gly Pro Ser Ser Pro
        115                 120                 125

Ser Gly Lys Leu Met Ser Pro Lys Leu Tyr Val Trp Ala Lys Asp Arg
    130                 135                 140

Pro Glu Ile Trp Glu Gly Glu Pro Pro Cys Leu Pro Pro Arg Asp Ser
145                 150                 155                 160

Leu Asn Gln Ser Leu Ser Gln Asp Leu Thr Met Ala Pro Gly Ser Thr
                165                 170                 175

Leu Trp Leu Ser Cys Gly Val Pro Pro Asp Ser Val Ser Arg Gly Pro
            180                 185                 190

Leu Ser Trp Thr His Val His Pro Lys Gly Pro Lys Ser Leu Leu Ser
        195                 200                 205

Leu Glu Leu Lys Asp Asp Arg Pro Ala Arg Asp Met Trp Val Met Glu
    210                 215                 220
```

```
Thr Gly Leu Leu Leu Pro Arg Ala Thr Ala Gln Asp Ala Gly Lys Tyr
225                 230                 235                 240

Tyr Cys His Arg Gly Asn Leu Thr Met Ser Phe His Leu Glu Ile Thr
                245                 250                 255

Ala Arg Pro Val Leu Trp His Trp Leu Leu Arg Thr Gly Gly Trp Lys
            260                 265                 270

Ala His His His His His His His His
        275                 280
```

<210> SEQ ID NO 48
<211> LENGTH: 118
<212> TYPE: PRT
<213> ORGANISM: Artificial Sequence
<220> FEATURE:
<223> OTHER INFORMATION: anti-CD16 antibody 3G8 VH

<400> SEQUENCE: 48

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Arg Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Lys Arg Tyr Asn Pro Ala
    50                  55                  60

Leu Lys Ser Arg Leu Thr Ile Ser Lys Asp Thr Ser Asn Gln Val
65                  70                  75                  80

Phe Leu Lys Ile Ala Ser Val Asp Thr Ala Asp Thr Ala Thr Tyr Tyr
                85                  90                  95

Cys Ala Gln Ile Asn Pro Ala Trp Phe Ala Tyr Trp Gly Gln Gly Thr
            100                 105                 110

Leu Val Thr Val Ser Ser
        115
```

<210> SEQ ID NO 49
<211> LENGTH: 111
<212> TYPE: PRT
<213> ORGANISM: Artificial Sequence
<220> FEATURE:
<223> OTHER INFORMATION: anti-CD16 antibody 3G8 VL

<400> SEQUENCE: 49

```
Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Phe Asp
            20                  25                  30

Gly Asp Ser Phe Met Asn Trp Tyr Gln Gln Lys Pro Gly Gln Pro Pro
        35                  40                  45

Lys Leu Leu Ile Tyr Thr Thr Ser Asn Leu Glu Ser Gly Ile Pro Ala
    50                  55                  60

Arg Phe Ser Ala Ser Gly Ser Gly Thr Asp Phe Thr Leu Asn Ile His
65                  70                  75                  80

Pro Val Glu Glu Glu Asp Thr Ala Thr Tyr Tyr Cys Gln Gln Ser Asn
                85                  90                  95

Glu Asp Pro Tyr Thr Phe Gly Gly Gly Thr Lys Leu Glu Ile Lys
            100                 105                 110
```

```
<210> SEQ ID NO 50
<211> LENGTH: 133
<212> TYPE: PRT
<213> ORGANISM: Homo sapiens
<220> FEATURE:
<223> OTHER INFORMATION: IL-2

<400> SEQUENCE: 50

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 51
<211> LENGTH: 152
<212> TYPE: PRT
<213> ORGANISM: Homo sapiens
<220> FEATURE:
<223> OTHER INFORMATION: IL-7

<400> SEQUENCE: 51

Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
            20                  25                  30

Asn Cys Leu Asn Asn Glu Phe Asn Phe Phe Lys Arg His Ile Cys Asp
        35                  40                  45

Ala Asn Lys Glu Gly Met Phe Leu Phe Arg Ala Ala Arg Lys Leu Arg
    50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Val
                85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
        115                 120                 125

Cys Phe Leu Lys Arg Leu Leu Gln Glu Ile Lys Thr Cys Trp Asn Lys
    130                 135                 140

Ile Leu Met Gly Thr Lys Glu His
145                 150

<210> SEQ ID NO 52
<211> LENGTH: 133
```

```
<212> TYPE: PRT
<213> ORGANISM: Homo sapiens
<220> FEATURE:
<223> OTHER INFORMATION: IL-21

<400> SEQUENCE: 52

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser
    130

<210> SEQ ID NO 53
<211> LENGTH: 159
<212> TYPE: PRT
<213> ORGANISM: Homo sapiens
<220> FEATURE:
<223> OTHER INFORMATION: IL-1alpha

<400> SEQUENCE: 53

Ser Ala Pro Phe Ser Phe Leu Ser Asn Val Lys Tyr Asn Phe Met Arg
1               5                   10                  15

Ile Ile Lys Tyr Glu Phe Ile Leu Asn Asp Ala Leu Asn Gln Ser Ile
            20                  25                  30

Ile Arg Ala Asn Asp Gln Tyr Leu Thr Ala Ala Ala Leu His Asn Leu
        35                  40                  45

Asp Glu Ala Val Lys Phe Asp Met Gly Ala Tyr Lys Ser Ser Lys Asp
    50                  55                  60

Asp Ala Lys Ile Thr Val Ile Leu Arg Ile Ser Lys Thr Gln Leu Tyr
65                  70                  75                  80

Val Thr Ala Gln Asp Glu Asp Gln Pro Val Leu Leu Lys Glu Met Pro
                85                  90                  95

Glu Ile Pro Lys Thr Ile Thr Gly Ser Glu Thr Asn Leu Leu Phe Phe
            100                 105                 110

Trp Glu Thr His Gly Thr Lys Asn Tyr Phe Thr Ser Val Ala His Pro
        115                 120                 125

Asn Leu Phe Ile Ala Thr Lys Gln Asp Tyr Trp Val Cys Leu Ala Gly
    130                 135                 140

Gly Pro Pro Ser Ile Thr Asp Phe Gln Ile Leu Glu Asn Gln Ala
145                 150                 155

<210> SEQ ID NO 54
<211> LENGTH: 153
<212> TYPE: PRT
<213> ORGANISM: Homo sapiens
```

```
<220> FEATURE:
<223> OTHER INFORMATION: IL-1beta

<400> SEQUENCE: 54

Ala Pro Val Arg Ser Leu Asn Cys Thr Leu Arg Asp Ser Gln Gln Lys
1               5                   10                  15

Ser Leu Val Met Ser Gly Pro Tyr Glu Leu Lys Ala Leu His Leu Gln
            20                  25                  30

Gly Gln Asp Met Glu Gln Gln Val Val Phe Ser Met Ser Phe Val Gln
        35                  40                  45

Gly Glu Glu Ser Asn Asp Lys Ile Pro Val Ala Leu Gly Leu Lys Glu
    50                  55                  60

Lys Asn Leu Tyr Leu Ser Cys Val Leu Lys Asp Asp Lys Pro Thr Leu
65                  70                  75                  80

Gln Leu Glu Ser Val Asp Pro Lys Asn Tyr Pro Lys Lys Lys Met Glu
                85                  90                  95

Lys Arg Phe Val Phe Asn Lys Ile Glu Ile Asn Asn Lys Leu Glu Phe
            100                 105                 110

Glu Ser Ala Gln Phe Pro Asn Trp Tyr Ile Ser Thr Ser Gln Ala Glu
        115                 120                 125

Asn Met Pro Val Phe Leu Gly Gly Thr Lys Gly Gly Gln Asp Ile Thr
    130                 135                 140

Asp Phe Thr Met Gln Phe Val Ser Ser
145                 150

<210> SEQ ID NO 55
<211> LENGTH: 133
<212> TYPE: PRT
<213> ORGANISM: Homo sapiens
<220> FEATURE:
<223> OTHER INFORMATION: IL-15

<400> SEQUENCE: 55

Gly Ile His Val Phe Ile Leu Gly Cys Phe Ser Ala Gly Leu Pro Lys
1               5                   10                  15

Thr Glu Ala Asn Trp Val Asn Val Ile Ser Asp Leu Lys Lys Ile Glu
            20                  25                  30

Asp Leu Ile Gln Ser Met His Ile Asp Ala Thr Leu Tyr Thr Glu Ser
        35                  40                  45

Asp Val His Pro Ser Cys Lys Val Thr Ala Met Lys Cys Phe Leu Leu
    50                  55                  60

Glu Leu Gln Val Ile Ser Leu Glu Ser Gly Asp Ala Ser Ile His Asp
65                  70                  75                  80

Thr Val Glu Asn Leu Ile Ile Leu Ala Asn Asn Ser Leu Ser Ser Asn
                85                  90                  95

Gly Asn Val Thr Glu Ser Gly Cys Lys Glu Cys Glu Glu Leu Glu Glu
            100                 105                 110

Lys Asn Ile Lys Glu Phe Leu Gln Ser Phe Val His Ile Val Gln Met
        115                 120                 125

Phe Ile Asn Thr Ser
    130

<210> SEQ ID NO 56
<211> LENGTH: 138
<212> TYPE: PRT
<213> ORGANISM: Homo sapiens
<220> FEATURE:
<223> OTHER INFORMATION: Interferon (IFN)-gamma
```

<400> SEQUENCE: 56

Gln Asp Pro Tyr Val Lys Glu Ala Glu Asn Leu Lys Lys Tyr Phe Asn
1               5                   10                  15

Ala Gly His Ser Asp Val Ala Asp Asn Gly Thr Leu Phe Leu Gly Ile
            20                  25                  30

Leu Lys Asn Trp Lys Glu Glu Ser Asp Arg Lys Ile Met Gln Ser Gln
        35                  40                  45

Ile Val Ser Phe Tyr Phe Lys Leu Phe Lys Asn Phe Lys Asp Asp Gln
    50                  55                  60

Ser Ile Gln Lys Ser Val Glu Thr Ile Lys Glu Asp Met Asn Val Lys
65                  70                  75                  80

Phe Phe Asn Ser Asn Lys Lys Arg Asp Asp Phe Glu Lys Leu Thr
                85                  90                  95

Asn Tyr Ser Val Thr Asp Leu Asn Val Gln Arg Lys Ala Ile His Glu
            100                 105                 110

Leu Ile Gln Val Met Ala Glu Leu Ser Pro Ala Ala Lys Thr Gly Lys
        115                 120                 125

Arg Lys Arg Ser Gln Met Leu Phe Arg Gly
    130                 135

<210> SEQ ID NO 57
<211> LENGTH: 233
<212> TYPE: PRT
<213> ORGANISM: Homo sapiens
<220> FEATURE:
<223> OTHER INFORMATION: tumor necrosis factor (TNF)-alpha

<400> SEQUENCE: 57

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
    50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230

<210> SEQ ID NO 58
<211> LENGTH: 129
<212> TYPE: PRT
<213> ORGANISM: Homo sapiens
<220> FEATURE:
<223> OTHER INFORMATION: IL-4

<400> SEQUENCE: 58

His Lys Cys Asp Ile Thr Leu Gln Glu Ile Ile Lys Thr Leu Asn Ser
1               5                   10                  15

Leu Thr Glu Gln Lys Thr Leu Cys Thr Glu Leu Thr Val Thr Asp Ile
            20                  25                  30

Phe Ala Ala Ser Lys Asn Thr Thr Glu Lys Glu Thr Phe Cys Arg Ala
        35                  40                  45

Ala Thr Val Leu Arg Gln Phe Tyr Ser His His Glu Lys Asp Thr Arg
    50                  55                  60

Cys Leu Gly Ala Thr Ala Gln Gln Phe His Arg His Lys Gln Leu Ile
65                  70                  75                  80

Arg Phe Leu Lys Arg Leu Asp Arg Asn Leu Trp Gly Leu Ala Gly Leu
                85                  90                  95

Asn Ser Cys Pro Val Lys Glu Ala Asn Gln Ser Thr Leu Glu Asn Phe
            100                 105                 110

Leu Glu Arg Leu Lys Thr Ile Met Arg Glu Lys Tyr Ser Lys Cys Ser
        115                 120                 125

Ser

<210> SEQ ID NO 59
<211> LENGTH: 160
<212> TYPE: PRT
<213> ORGANISM: Homo sapiens
<220> FEATURE:
<223> OTHER INFORMATION: IL-10

<400> SEQUENCE: 59

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

```
Ile Phe Ile Asn Tyr Ile Glu Ala Tyr Met Thr Met Lys Ile Arg Asn
145                 150                 155                 160

<210> SEQ ID NO 60
<211> LENGTH: 165
<212> TYPE: PRT
<213> ORGANISM: Homo sapiens
<220> FEATURE:
<223> OTHER INFORMATION: interferon (IFN)-alpha2

<400> SEQUENCE: 60

Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
                20                  25                  30

Arg His Asp Phe Gly Phe Pro Gln Glu Glu Phe Gly Asn Gln Phe Gln
            35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
    115                 120                 125

Tyr Leu Lys Glu Lys Lys Tyr Ser Pro Cys Ala Trp Glu Val Val Arg
130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 61
<211> LENGTH: 165
<212> TYPE: PRT
<213> ORGANISM: Homo sapiens
<220> FEATURE:
<223> OTHER INFORMATION: interferon (IFN)-beta1

<400> SEQUENCE: 61

Met Ser Tyr Asp Val Leu Arg Tyr Gln Gln Arg Ser Ser Asn Leu Ala
1               5                   10                  15

Cys Gln Lys Leu Leu Gly Gln Leu Pro Gly Thr Pro Gln Tyr Cys Leu
                20                  25                  30

Glu Asp Arg Met Asn Phe Glu Val Pro Glu Glu Ile Met Gln Pro Pro
            35                  40                  45

Gln Phe Gln Lys Glu Asp Ala Val Leu Ile Ile His Glu Met Leu Gln
    50                  55                  60

Gln Ile Phe Gly Ile Leu Arg Arg Asn Phe Ser Ser Thr Gly Trp Asn
65                  70                  75                  80

Glu Thr Val Ile Lys Thr Ile Leu Val Glu Leu Asp Gly Gln Met Asp
                85                  90                  95

Asp Leu Glu Thr Ile Leu Glu Glu Ile Met Glu Glu Glu Asn Phe Pro
            100                 105                 110

Arg Gly Asp Met Thr Ile Leu His Leu Lys Lys Tyr Tyr Leu Ser Ile
    115                 120                 125
```

```
Leu Gln Tyr Leu Lys Ser Lys Glu Tyr Arg Ser Cys Ala Trp Thr Val
            130                 135                 140

Val Gln Val Glu Ile Leu Arg Asn Phe Ser Phe Leu Asn Arg Leu Thr
145                 150                 155                 160

Asp Tyr Leu Arg Asn
                165

<210> SEQ ID NO 62
<211> LENGTH: 197
<212> TYPE: PRT
<213> ORGANISM: Homo sapiens
<220> FEATURE:
<223> OTHER INFORMATION: IL-12alpha

<400> SEQUENCE: 62

Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
            20                  25                  30

Ala Arg Gln Thr Leu Glu Phe Tyr Pro Cys Thr Ser Glu Glu Ile Asp
        35                  40                  45

His Glu Asp Ile Thr Lys Asp Lys Thr Ser Thr Val Glu Ala Cys Leu
    50                  55                  60

Pro Leu Glu Leu Thr Lys Asn Glu Ser Cys Leu Asn Ser Arg Glu Thr
65                  70                  75                  80

Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
        115                 120                 125

Arg Gln Ile Phe Leu Asp Gln Asn Met Leu Ala Val Ile Asp Glu Leu
    130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
            180                 185                 190

Tyr Leu Asn Ala Ser
        195

<210> SEQ ID NO 63
<211> LENGTH: 306
<212> TYPE: PRT
<213> ORGANISM: Homo sapiens
<220> FEATURE:
<223> OTHER INFORMATION: IL-12beta

<400> SEQUENCE: 63

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
```

```
            50                  55                  60
Gln Tyr Thr Cys His Lys Gly Gly Glu Val Leu Ser His Ser Leu Leu
 65                  70                  75                  80

Leu Leu His Lys Lys Glu Asp Gly Ile Trp Ser Thr Asp Ile Leu Lys
                 85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser
305

<210> SEQ ID NO 64
<211> LENGTH: 132
<212> TYPE: PRT
<213> ORGANISM: Homo sapiens
<220> FEATURE:
<223> OTHER INFORMATION: IL-17

<400> SEQUENCE: 64

Gly Ile Thr Ile Pro Arg Asn Pro Gly Cys Pro Asn Ser Glu Asp Lys
 1               5                  10                  15

Asn Phe Pro Arg Thr Val Met Val Asn Leu Asn Ile His Asn Arg Asn
                20                  25                  30

Thr Asn Thr Asn Pro Lys Arg Ser Ser Asp Tyr Tyr Asn Arg Ser Thr
            35                  40                  45

Ser Pro Trp Asn Leu His Arg Asn Glu Asp Pro Glu Arg Tyr Pro Ser
        50                  55                  60

Val Ile Trp Glu Ala Lys Cys Arg His Leu Gly Cys Ile Asn Ala Asp
 65                  70                  75                  80

Gly Asn Val Asp Tyr His Met Asn Ser Val Pro Ile Gln Gln Glu Ile
                85                  90                  95

Leu Val Leu Arg Arg Glu Pro Pro His Cys Pro Asn Ser Phe Arg Leu
```

```
                    100                 105                 110
Glu Lys Ile Leu Val Ser Val Gly Cys Thr Cys Val Thr Pro Ile Val
                115                 120                 125
His His Val Ala
        130

<210> SEQ ID NO 65
<211> LENGTH: 103
<212> TYPE: PRT
<213> ORGANISM: Homo sapiens
<220> FEATURE:
<223> OTHER INFORMATION: CXCL9

<400> SEQUENCE: 65

Thr Pro Val Val Arg Lys Gly Arg Cys Ser Cys Ile Ser Thr Asn Gln
1               5                   10                  15
Gly Thr Ile His Leu Gln Ser Leu Lys Asp Leu Lys Gln Phe Ala Pro
                20                  25                  30
Ser Pro Ser Cys Glu Lys Ile Glu Ile Ile Ala Thr Leu Lys Asn Gly
            35                  40                  45
Val Gln Thr Cys Leu Asn Pro Asp Ser Ala Asp Val Lys Glu Leu Ile
        50                  55                  60
Lys Lys Trp Glu Lys Gln Val Ser Gln Lys Lys Lys Gln Lys Asn Gly
65                  70                  75                  80
Lys Lys His Gln Lys Lys Val Leu Lys Val Arg Lys Ser Gln Arg
                85                  90                  95
Ser Arg Gln Lys Lys Thr Thr
            100

<210> SEQ ID NO 66
<211> LENGTH: 77
<212> TYPE: PRT
<213> ORGANISM: Homo sapiens
<220> FEATURE:
<223> OTHER INFORMATION: CXCL10

<400> SEQUENCE: 66

Val Pro Leu Ser Arg Thr Val Arg Cys Thr Cys Ile Ser Ile Ser Asn
1               5                   10                  15
Gln Pro Val Asn Pro Arg Ser Leu Glu Lys Leu Glu Ile Ile Pro Ala
                20                  25                  30
Ser Gln Phe Cys Pro Arg Val Glu Ile Ile Ala Thr Met Lys Lys Lys
            35                  40                  45
Gly Glu Lys Arg Cys Leu Asn Pro Glu Ser Lys Ala Ile Lys Asn Leu
        50                  55                  60
Leu Lys Ala Val Ser Lys Glu Arg Ser Lys Arg Ser Pro
65                  70                  75

<210> SEQ ID NO 67
<211> LENGTH: 77
<212> TYPE: PRT
<213> ORGANISM: Homo sapiens
<220> FEATURE:
<223> OTHER INFORMATION: CCL19

<400> SEQUENCE: 67

Gly Thr Asn Asp Ala Glu Asp Cys Cys Leu Ser Val Thr Gln Lys Pro
1               5                   10                  15
Ile Pro Gly Tyr Ile Val Arg Asn Phe His Tyr Leu Leu Ile Lys Asp
                20                  25                  30
```

-continued

Gly Cys Arg Val Pro Ala Val Val Phe Thr Thr Leu Arg Gly Arg Gln
            35                  40                  45

Leu Cys Ala Pro Pro Asp Gln Pro Trp Val Glu Arg Ile Ile Gln Arg
 50                  55                  60

Leu Gln Arg Thr Ser Ala Lys Met Lys Arg Arg Ser Ser
 65                  70                  75

<210> SEQ ID NO 68
<211> LENGTH: 111
<212> TYPE: PRT
<213> ORGANISM: Homo sapiens
<220> FEATURE:
<223> OTHER INFORMATION: CCL21

<400> SEQUENCE: 68

Ser Asp Gly Gly Ala Gln Asp Cys Cys Leu Lys Tyr Ser Gln Arg Lys
 1               5                   10                  15

Ile Pro Ala Lys Val Val Arg Ser Tyr Arg Lys Gln Glu Pro Ser Leu
            20                  25                  30

Gly Cys Ser Ile Pro Ala Ile Leu Phe Leu Pro Arg Lys Arg Ser Gln
            35                  40                  45

Ala Glu Leu Cys Ala Asp Pro Lys Glu Leu Trp Val Gln Gln Leu Met
 50                  55                  60

Gln His Leu Asp Lys Thr Pro Ser Pro Gln Lys Pro Ala Gln Gly Cys
 65                  70                  75                  80

Arg Lys Asp Arg Gly Ala Ser Lys Thr Gly Lys Lys Gly Lys Gly Ser
                85                  90                  95

Lys Gly Cys Lys Arg Thr Glu Arg Ser Gln Thr Pro Lys Gly Pro
            100                 105                 110

<210> SEQ ID NO 69
<211> LENGTH: 127
<212> TYPE: PRT
<213> ORGANISM: Homo sapiens
<220> FEATURE:
<223> OTHER INFORMATION: CCL25

<400> SEQUENCE: 69

Gln Gly Val Phe Glu Asp Cys Cys Leu Ala Tyr His Tyr Pro Ile Gly
 1               5                   10                  15

Trp Ala Val Leu Arg Arg Ala Trp Thr Tyr Arg Ile Gln Glu Val Ser
            20                  25                  30

Gly Ser Cys Asn Leu Pro Ala Ala Ile Phe Tyr Leu Pro Lys Arg His
            35                  40                  45

Arg Lys Val Cys Gly Asn Pro Lys Ser Arg Glu Val Gln Arg Ala Met
 50                  55                  60

Lys Leu Leu Asp Ala Arg Asn Lys Val Phe Ala Lys Leu His His Asn
 65                  70                  75                  80

Thr Gln Thr Phe Gln Ala Gly Pro His Ala Val Lys Lys Leu Ser Ser
                85                  90                  95

Gly Asn Ser Lys Leu Ser Ser Ser Lys Phe Ser Asn Pro Ile Ser Ser
            100                 105                 110

Ser Lys Arg Asn Val Ser Leu Leu Ile Ser Ala Asn Ser Gly Leu
            115                 120                 125

<210> SEQ ID NO 70
<211> LENGTH: 4
<212> TYPE: PRT

<213> ORGANISM: Homo sapiens
<220> FEATURE:
<223> OTHER INFORMATION: Linker peptide

<400> SEQUENCE: 70

Gly Gly Gly Ser
1

<210> SEQ ID NO 71
<211> LENGTH: 1145
<212> TYPE: PRT
<213> ORGANISM: Homo sapiens
<220> FEATURE:
<223> OTHER INFORMATION: LFA-1alpha

<400> SEQUENCE: 71

Tyr Asn Leu Asp Val Arg Gly Ala Arg Ser Phe Ser Pro Pro Arg Ala
1               5                  10                  15

Gly Arg His Phe Gly Tyr Arg Val Leu Gln Val Gly Asn Gly Val Ile
            20                  25                  30

Val Gly Ala Pro Gly Glu Gly Asn Ser Thr Gly Ser Leu Tyr Gln Cys
        35                  40                  45

Gln Ser Gly Thr Gly His Cys Leu Pro Val Thr Leu Arg Gly Ser Asn
    50                  55                  60

Tyr Thr Ser Lys Tyr Leu Gly Met Thr Leu Ala Thr Asp Pro Thr Asp
65                  70                  75                  80

Gly Ser Ile Leu Ala Cys Asp Pro Gly Leu Ser Arg Thr Cys Asp Gln
                85                  90                  95

Asn Thr Tyr Leu Ser Gly Leu Cys Tyr Leu Phe Arg Gln Asn Leu Gln
            100                 105                 110

Gly Pro Met Leu Gln Gly Arg Pro Gly Phe Gln Glu Cys Ile Lys Gly
        115                 120                 125

Asn Val Asp Leu Val Phe Leu Phe Asp Gly Ser Met Ser Leu Gln Pro
    130                 135                 140

Asp Glu Phe Gln Lys Ile Leu Asp Phe Met Lys Asp Val Met Lys Lys
145                 150                 155                 160

Leu Ser Asn Thr Ser Tyr Gln Phe Ala Ala Val Gln Phe Ser Thr Ser
                165                 170                 175

Tyr Lys Thr Glu Phe Asp Phe Ser Asp Tyr Val Lys Arg Lys Asp Pro
            180                 185                 190

Asp Ala Leu Leu Lys His Val Lys His Met Leu Leu Leu Thr Asn Thr
        195                 200                 205

Phe Gly Ala Ile Asn Tyr Val Ala Thr Glu Val Phe Arg Glu Glu Leu
    210                 215                 220

Gly Ala Arg Pro Asp Ala Thr Lys Val Leu Ile Ile Ile Thr Asp Gly
225                 230                 235                 240

Glu Ala Thr Asp Ser Gly Asn Ile Asp Ala Ala Lys Asp Ile Ile Arg
                245                 250                 255

Tyr Ile Ile Gly Ile Gly Lys His Phe Gln Thr Lys Glu Ser Gln Glu
            260                 265                 270

Thr Leu His Lys Phe Ala Ser Lys Pro Ala Ser Glu Phe Val Lys Ile
        275                 280                 285

Leu Asp Thr Phe Glu Lys Leu Lys Asp Leu Phe Thr Glu Leu Gln Lys
    290                 295                 300

Lys Ile Tyr Val Ile Glu Gly Thr Ser Lys Gln Asp Leu Thr Ser Phe
305                 310                 315                 320

```
Asn Met Glu Leu Ser Ser Ser Gly Ile Ser Ala Asp Leu Ser Arg Gly
                325                 330                 335

His Ala Val Val Gly Ala Val Gly Ala Lys Asp Trp Ala Gly Gly Phe
                340                 345                 350

Leu Asp Leu Lys Ala Asp Leu Gln Asp Asp Thr Phe Ile Gly Asn Glu
                355                 360                 365

Pro Leu Thr Pro Glu Val Arg Ala Gly Tyr Leu Gly Tyr Thr Val Thr
        370                 375                 380

Trp Leu Pro Ser Arg Gln Lys Thr Ser Leu Leu Ala Ser Gly Ala Pro
385                 390                 395                 400

Arg Tyr Gln His Met Gly Arg Val Leu Leu Phe Gln Glu Pro Gln Gly
                405                 410                 415

Gly Gly His Trp Ser Gln Val Gln Thr Ile His Gly Thr Gln Ile Gly
                420                 425                 430

Ser Tyr Phe Gly Gly Glu Leu Cys Gly Val Asp Val Asp Gln Asp Gly
            435                 440                 445

Glu Thr Glu Leu Leu Leu Ile Gly Ala Pro Leu Phe Tyr Gly Glu Gln
        450                 455                 460

Arg Gly Gly Arg Val Phe Ile Tyr Gln Arg Arg Gln Leu Gly Phe Glu
465                 470                 475                 480

Glu Val Ser Glu Leu Gln Gly Asp Pro Gly Tyr Pro Leu Gly Arg Phe
                485                 490                 495

Gly Glu Ala Ile Thr Ala Leu Thr Asp Ile Asn Gly Asp Gly Leu Val
                500                 505                 510

Asp Val Ala Val Gly Ala Pro Leu Glu Glu Gln Gly Ala Val Tyr Ile
                515                 520                 525

Phe Asn Gly Arg His Gly Gly Leu Ser Pro Gln Pro Ser Gln Arg Ile
        530                 535                 540

Glu Gly Thr Gln Val Leu Ser Gly Ile Gln Trp Phe Gly Arg Ser Ile
545                 550                 555                 560

His Gly Val Lys Asp Leu Glu Gly Asp Gly Leu Ala Asp Val Ala Val
                565                 570                 575

Gly Ala Glu Ser Gln Met Ile Val Leu Ser Ser Arg Pro Val Val Asp
                580                 585                 590

Met Val Thr Leu Met Ser Phe Ser Pro Ala Glu Ile Pro Val His Glu
                595                 600                 605

Val Glu Cys Ser Tyr Ser Thr Ser Asn Lys Met Lys Glu Gly Val Asn
                610                 615                 620

Ile Thr Ile Cys Phe Gln Ile Lys Ser Leu Ile Pro Gln Phe Gln Gly
625                 630                 635                 640

Arg Leu Val Ala Asn Leu Thr Tyr Thr Leu Gln Leu Asp Gly His Arg
                645                 650                 655

Thr Arg Arg Arg Gly Leu Phe Pro Gly Gly Arg His Glu Leu Arg Arg
                660                 665                 670

Asn Ile Ala Val Thr Thr Ser Met Ser Cys Thr Asp Phe Ser Phe His
                675                 680                 685

Phe Pro Val Cys Val Gln Asp Leu Ile Ser Pro Ile Asn Val Ser Leu
            690                 695                 700

Asn Phe Ser Leu Trp Glu Glu Gly Thr Pro Arg Asp Gln Arg Ala
705                 710                 715                 720

Gln Gly Lys Asp Ile Pro Pro Ile Leu Arg Pro Ser Leu His Ser Glu
                725                 730                 735

Thr Trp Glu Ile Pro Phe Glu Lys Asn Cys Gly Glu Asp Lys Lys Cys
```

```
                    740                 745                 750
Glu Ala Asn Leu Arg Val Ser Phe Ser Pro Ala Arg Ser Arg Ala Leu
            755                 760                 765
Arg Leu Thr Ala Phe Ala Ser Leu Ser Val Glu Leu Ser Leu Ser Asn
        770                 775                 780
Leu Glu Glu Asp Ala Tyr Trp Val Gln Leu Asp Leu His Phe Pro Pro
785                 790                 795                 800
Gly Leu Ser Phe Arg Lys Val Glu Met Leu Lys Pro His Ser Gln Ile
                805                 810                 815
Pro Val Ser Cys Glu Glu Leu Pro Glu Glu Ser Arg Leu Leu Ser Arg
            820                 825                 830
Ala Leu Ser Cys Asn Val Ser Ser Pro Ile Phe Lys Ala Gly His Ser
        835                 840                 845
Val Ala Leu Gln Met Met Phe Asn Thr Leu Val Asn Ser Ser Trp Gly
    850                 855                 860
Asp Ser Val Glu Leu His Ala Asn Val Thr Cys Asn Asn Glu Asp Ser
865                 870                 875                 880
Asp Leu Leu Glu Asp Asn Ser Ala Thr Thr Ile Ile Pro Ile Leu Tyr
                885                 890                 895
Pro Ile Asn Ile Leu Ile Gln Asp Gln Glu Asp Ser Thr Leu Tyr Val
            900                 905                 910
Ser Phe Thr Pro Lys Gly Pro Lys Ile His Gln Val Lys His Met Tyr
        915                 920                 925
Gln Val Arg Ile Gln Pro Ser Ile His Asp His Asn Ile Pro Thr Leu
    930                 935                 940
Glu Ala Val Val Gly Val Pro Gln Pro Pro Ser Glu Gly Pro Ile Thr
945                 950                 955                 960
His Gln Trp Ser Val Gln Met Glu Pro Pro Val Pro Cys His Tyr Glu
                965                 970                 975
Asp Leu Glu Arg Leu Pro Asp Ala Ala Glu Pro Cys Leu Pro Gly Ala
            980                 985                 990
Leu Phe Arg Cys Pro Val Val Phe Arg Gln Glu Ile Leu Val Gln Val
        995                 1000                1005
Ile Gly Thr Leu Glu Leu Val Gly Glu Ile Glu Ala Ser Ser Met Phe
    1010                1015                1020
Ser Leu Cys Ser Ser Leu Ser Ile Ser Phe Asn Ser Lys His Phe
1025                1030                1035                1040
His Leu Tyr Gly Ser Asn Ala Ser Leu Ala Gln Val Val Met Lys Val
                1045                1050                1055
Asp Val Val Tyr Glu Lys Gln Met Leu Tyr Leu Tyr Val Leu Ser Gly
            1060                1065                1070
Ile Gly Gly Leu Leu Leu Leu Leu Ile Phe Ile Val Leu Tyr Lys
        1075                1080                1085
Val Gly Phe Phe Lys Arg Asn Leu Lys Glu Lys Met Glu Ala Gly Arg
    1090                1095                1100
Gly Val Pro Asn Gly Ile Pro Ala Glu Asp Ser Glu Gln Leu Ala Ser
1105                1110                1115                1120
Gly Gln Glu Ala Gly Asp Pro Gly Cys Leu Lys Pro Leu His Glu Lys
                1125                1130                1135
Asp Ser Glu Ser Gly Gly Gly Lys Asp
            1140                1145

<210> SEQ ID NO 72
```

<211> LENGTH: 747
<212> TYPE: PRT
<213> ORGANISM: Homo sapiens
<220> FEATURE:
<223> OTHER INFORMATION: LFA-1beta

<400> SEQUENCE: 72

```
Gln Glu Cys Thr Lys Phe Lys Val Ser Ser Cys Arg Glu Cys Ile Glu
1               5                   10                  15

Ser Gly Pro Gly Cys Thr Trp Cys Gln Lys Leu Asn Phe Thr Gly Pro
            20                  25                  30

Gly Asp Pro Asp Ser Ile Arg Cys Asp Thr Arg Pro Gln Leu Leu Met
        35                  40                  45

Arg Gly Cys Ala Ala Asp Asp Ile Met Asp Pro Thr Ser Leu Ala Glu
    50                  55                  60

Thr Gln Glu Asp His Asn Gly Gly Gln Lys Gln Leu Ser Pro Gln Lys
65                  70                  75                  80

Val Thr Leu Tyr Leu Arg Pro Gly Gln Ala Ala Ala Phe Asn Val Thr
                85                  90                  95

Phe Arg Arg Ala Lys Gly Tyr Pro Ile Asp Leu Tyr Tyr Leu Met Asp
            100                 105                 110

Leu Ser Tyr Ser Met Leu Asp Asp Leu Arg Asn Val Lys Lys Leu Gly
        115                 120                 125

Gly Asp Leu Leu Arg Ala Leu Asn Glu Ile Thr Glu Ser Gly Arg Ile
    130                 135                 140

Gly Phe Gly Ser Phe Val Asp Lys Thr Val Leu Pro Phe Val Asn Thr
145                 150                 155                 160

His Pro Asp Lys Leu Arg Asn Pro Cys Pro Asn Lys Glu Lys Glu Cys
                165                 170                 175

Gln Pro Pro Phe Ala Phe Arg His Val Leu Lys Leu Thr Asn Asn Ser
            180                 185                 190

Asn Gln Phe Gln Thr Glu Val Gly Lys Gln Leu Ile Ser Gly Asn Leu
        195                 200                 205

Asp Ala Pro Glu Gly Gly Leu Asp Ala Met Met Gln Val Ala Ala Cys
    210                 215                 220

Pro Glu Glu Ile Gly Trp Arg Asn Val Thr Arg Leu Leu Val Phe Ala
225                 230                 235                 240

Thr Asp Asp Gly Phe His Phe Ala Gly Asp Gly Lys Leu Gly Ala Ile
                245                 250                 255

Leu Thr Pro Asn Asp Gly Arg Cys His Leu Glu Asp Asn Leu Tyr Lys
            260                 265                 270

Arg Ser Asn Glu Phe Asp Tyr Pro Ser Val Gly Gln Leu Ala His Lys
        275                 280                 285

Leu Ala Glu Asn Asn Ile Gln Pro Ile Phe Ala Val Thr Ser Arg Met
    290                 295                 300

Val Lys Thr Tyr Glu Lys Leu Thr Glu Ile Ile Pro Lys Ser Ala Val
305                 310                 315                 320

Gly Glu Leu Ser Glu Asp Ser Ser Asn Val Val Gln Leu Ile Lys Asn
                325                 330                 335

Ala Tyr Asn Lys Leu Ser Ser Arg Val Phe Leu Asp His Asn Ala Leu
            340                 345                 350

Pro Asp Thr Leu Lys Val Thr Tyr Asp Ser Phe Cys Ser Asn Gly Val
        355                 360                 365

Thr His Arg Asn Gln Pro Arg Gly Asp Cys Asp Gly Val Gln Ile Asn
    370                 375                 380
```

Val Pro Ile Thr Phe Gln Val Lys Val Thr Ala Thr Glu Cys Ile Gln
385                 390                 395                 400

Glu Gln Ser Phe Val Ile Arg Ala Leu Gly Phe Thr Asp Ile Val Thr
            405                 410                 415

Val Gln Val Leu Pro Gln Cys Glu Cys Arg Cys Arg Asp Gln Ser Arg
        420                 425                 430

Asp Arg Ser Leu Cys His Gly Lys Gly Phe Leu Glu Cys Gly Ile Cys
        435                 440                 445

Arg Cys Asp Thr Gly Tyr Ile Gly Lys Asn Cys Glu Cys Gln Thr Gln
        450                 455                 460

Gly Arg Ser Ser Gln Glu Leu Glu Gly Ser Cys Arg Lys Asp Asn Asn
465                 470                 475                 480

Ser Ile Ile Cys Ser Gly Leu Gly Asp Cys Val Cys Gly Gln Cys Leu
                485                 490                 495

Cys His Thr Ser Asp Val Pro Gly Lys Leu Ile Tyr Gly Gln Tyr Cys
                500                 505                 510

Glu Cys Asp Thr Ile Asn Cys Glu Arg Tyr Asn Gly Gln Val Cys Gly
            515                 520                 525

Gly Pro Gly Arg Gly Leu Cys Phe Cys Gly Lys Cys Arg Cys His Pro
        530                 535                 540

Gly Phe Glu Gly Ser Ala Cys Gln Cys Glu Arg Thr Thr Glu Gly Cys
545                 550                 555                 560

Leu Asn Pro Arg Arg Val Glu Cys Ser Gly Arg Gly Arg Cys Arg Cys
                565                 570                 575

Asn Val Cys Glu Cys His Ser Gly Tyr Gln Leu Pro Leu Cys Gln Glu
            580                 585                 590

Cys Pro Gly Cys Pro Ser Pro Cys Gly Lys Tyr Ile Ser Cys Ala Glu
        595                 600                 605

Cys Leu Lys Phe Glu Lys Gly Pro Phe Gly Lys Asn Cys Ser Ala Ala
        610                 615                 620

Cys Pro Gly Leu Gln Leu Ser Asn Asn Pro Val Lys Gly Arg Thr Cys
625                 630                 635                 640

Lys Glu Arg Asp Ser Glu Gly Cys Trp Val Ala Tyr Thr Leu Glu Gln
                645                 650                 655

Gln Asp Gly Met Asp Arg Tyr Leu Ile Tyr Val Asp Glu Ser Arg Glu
            660                 665                 670

Cys Val Ala Gly Pro Asn Ile Ala Ala Ile Val Gly Gly Thr Val Ala
        675                 680                 685

Gly Ile Val Leu Ile Gly Ile Leu Leu Leu Val Ile Trp Lys Ala Leu
        690                 695                 700

Ile His Leu Ser Asp Leu Arg Glu Tyr Arg Arg Phe Glu Lys Glu Lys
705                 710                 715                 720

Leu Lys Ser Gln Trp Asn Asn Asp Asn Pro Leu Phe Lys Ser Ala Thr
                725                 730                 735

Thr Thr Val Met Asn Pro Lys Phe Ala Glu Ser
                740                 745

<210> SEQ ID NO 73
<211> LENGTH: 344
<212> TYPE: PRT
<213> ORGANISM: Homo sapiens
<220> FEATURE:
<223> OTHER INFORMATION: L-selectin

<400> SEQUENCE: 73

```
Asp Phe Leu Ala His His Gly Thr Asp Cys Trp Thr Tyr His Tyr Ser
1               5                   10                  15

Glu Lys Pro Met Asn Trp Gln Arg Ala Arg Arg Phe Cys Arg Asp Asn
                20                  25                  30

Tyr Thr Asp Leu Val Ala Ile Gln Asn Lys Ala Glu Ile Glu Tyr Leu
            35                  40                  45

Glu Lys Thr Leu Pro Phe Ser Arg Ser Tyr Tyr Trp Ile Gly Ile Arg
50                  55                  60

Lys Ile Gly Gly Ile Trp Thr Trp Val Gly Thr Asn Lys Ser Leu Thr
65                  70                  75                  80

Glu Glu Ala Glu Asn Trp Gly Asp Gly Glu Pro Asn Asn Lys Lys Asn
                85                  90                  95

Lys Glu Asp Cys Val Glu Ile Tyr Ile Lys Arg Asn Lys Asp Ala Gly
            100                 105                 110

Lys Trp Asn Asp Asp Ala Cys His Lys Leu Lys Ala Ala Leu Cys Tyr
            115                 120                 125

Thr Ala Ser Cys Gln Pro Trp Ser Cys Ser Gly His Gly Glu Cys Val
130                 135                 140

Glu Ile Ile Asn Asn Tyr Thr Cys Asn Cys Asp Val Gly Tyr Tyr Gly
145                 150                 155                 160

Pro Gln Cys Gln Phe Val Ile Gln Cys Glu Pro Leu Glu Ala Pro Glu
                165                 170                 175

Leu Gly Thr Met Asp Cys Thr His Pro Leu Gly Asn Phe Ser Phe Ser
            180                 185                 190

Ser Gln Cys Ala Phe Ser Cys Ser Glu Gly Thr Asn Leu Thr Gly Ile
            195                 200                 205

Glu Glu Thr Thr Cys Gly Pro Phe Gly Asn Trp Ser Ser Pro Glu Pro
210                 215                 220

Thr Cys Gln Val Ile Gln Cys Glu Pro Leu Ser Ala Pro Asp Leu Gly
225                 230                 235                 240

Ile Met Asn Cys Ser His Pro Leu Ala Ser Phe Ser Phe Thr Ser Ala
                245                 250                 255

Cys Thr Phe Ile Cys Ser Glu Gly Thr Glu Leu Ile Gly Lys Lys Lys
            260                 265                 270

Thr Ile Cys Glu Ser Ser Gly Ile Trp Ser Asn Pro Ser Pro Ile Cys
            275                 280                 285

Gln Lys Leu Asp Lys Ser Phe Ser Met Ile Lys Glu Gly Asp Tyr Asn
290                 295                 300

Pro Leu Phe Ile Pro Val Ala Val Met Val Thr Ala Phe Ser Gly Leu
305                 310                 315                 320

Ala Phe Ile Ile Trp Leu Ala Arg Arg Leu Lys Lys Gly Lys Lys Ser
                325                 330                 335

Lys Arg Ser Met Asn Asp Pro Tyr
            340

<210> SEQ ID NO 74
<211> LENGTH: 715
<212> TYPE: PRT
<213> ORGANISM: Homo sapiens
<220> FEATURE:
<223> OTHER INFORMATION: VCAM-1

<400> SEQUENCE: 74

Phe Lys Ile Glu Thr Thr Pro Glu Ser Arg Tyr Leu Ala Gln Ile Gly
1               5                   10                  15
```

```
Asp Ser Val Ser Leu Thr Cys Ser Thr Thr Gly Cys Glu Ser Pro Phe
            20                  25                  30

Phe Ser Trp Arg Thr Gln Ile Asp Ser Pro Leu Asn Gly Lys Val Thr
        35                  40                  45

Asn Glu Gly Thr Thr Ser Thr Leu Thr Met Asn Pro Val Ser Phe Gly
 50                  55                  60

Asn Glu His Ser Tyr Leu Cys Thr Ala Thr Cys Glu Ser Arg Lys Leu
 65                  70                  75                  80

Glu Lys Gly Ile Gln Val Glu Ile Tyr Ser Phe Pro Lys Asp Pro Glu
                 85                  90                  95

Ile His Leu Ser Gly Pro Leu Glu Ala Gly Lys Pro Ile Thr Val Lys
            100                 105                 110

Cys Ser Val Ala Asp Val Tyr Pro Phe Asp Arg Leu Glu Ile Asp Leu
        115                 120                 125

Leu Lys Gly Asp His Leu Met Lys Ser Gln Glu Phe Leu Glu Asp Ala
130                 135                 140

Asp Arg Lys Ser Leu Glu Thr Lys Ser Leu Glu Val Thr Phe Thr Pro
145                 150                 155                 160

Val Ile Glu Asp Ile Gly Lys Val Leu Val Cys Arg Ala Lys Leu His
                165                 170                 175

Ile Asp Glu Met Asp Ser Val Pro Thr Val Arg Gln Ala Val Lys Glu
            180                 185                 190

Leu Gln Val Tyr Ile Ser Pro Lys Asn Thr Val Ile Ser Val Asn Pro
        195                 200                 205

Ser Thr Lys Leu Gln Glu Gly Gly Ser Val Thr Met Thr Cys Ser Ser
210                 215                 220

Glu Gly Leu Pro Ala Pro Glu Ile Phe Trp Ser Lys Lys Leu Asp Asn
225                 230                 235                 240

Gly Asn Leu Gln His Leu Ser Gly Asn Ala Thr Leu Thr Leu Ile Ala
                245                 250                 255

Met Arg Met Glu Asp Ser Gly Ile Tyr Val Cys Glu Gly Val Asn Leu
            260                 265                 270

Ile Gly Lys Asn Arg Lys Glu Val Glu Leu Ile Val Gln Glu Lys Pro
        275                 280                 285

Phe Thr Val Glu Ile Ser Pro Gly Pro Arg Ile Ala Ala Gln Ile Gly
290                 295                 300

Asp Ser Val Met Leu Thr Cys Ser Val Met Gly Cys Glu Ser Pro Ser
305                 310                 315                 320

Phe Ser Trp Arg Thr Gln Ile Asp Ser Pro Leu Ser Gly Lys Val Arg
                325                 330                 335

Ser Glu Gly Thr Asn Ser Thr Leu Thr Leu Ser Pro Val Ser Phe Glu
            340                 345                 350

Asn Glu His Ser Tyr Leu Cys Thr Val Thr Cys Gly His Lys Lys Leu
        355                 360                 365

Glu Lys Gly Ile Gln Val Glu Leu Tyr Ser Phe Pro Arg Asp Pro Glu
370                 375                 380

Ile Glu Met Ser Gly Gly Leu Val Asn Gly Ser Ser Val Thr Val Ser
385                 390                 395                 400

Cys Lys Val Pro Ser Val Tyr Pro Leu Asp Arg Leu Glu Ile Glu Leu
                405                 410                 415

Leu Lys Gly Glu Thr Ile Leu Glu Asn Ile Glu Phe Leu Glu Asp Thr
            420                 425                 430
```

```
Asp Met Lys Ser Leu Glu Asn Lys Ser Leu Glu Met Thr Phe Ile Pro
        435                 440                 445

Thr Ile Glu Asp Thr Gly Lys Ala Leu Val Cys Gln Ala Lys Leu His
        450                 455                 460

Ile Asp Asp Met Glu Phe Glu Pro Lys Gln Arg Gln Ser Thr Gln Thr
465                 470                 475                 480

Leu Tyr Val Asn Val Ala Pro Arg Asp Thr Thr Val Leu Val Ser Pro
                485                 490                 495

Ser Ser Ile Leu Glu Gly Ser Ser Val Asn Met Thr Cys Leu Ser
                500                 505                 510

Gln Gly Phe Pro Ala Pro Lys Ile Leu Trp Ser Arg Gln Leu Pro Asn
        515                 520                 525

Gly Glu Leu Gln Pro Leu Ser Glu Asn Ala Thr Leu Thr Leu Ile Ser
        530                 535                 540

Thr Lys Met Glu Asp Ser Gly Val Tyr Leu Cys Glu Gly Ile Asn Gln
545                 550                 555                 560

Ala Gly Arg Ser Arg Lys Glu Val Glu Leu Ile Ile Gln Val Thr Pro
                565                 570                 575

Lys Asp Ile Lys Leu Thr Ala Phe Pro Ser Glu Ser Val Lys Glu Gly
            580                 585                 590

Asp Thr Val Ile Ile Ser Cys Thr Cys Gly Asn Val Pro Glu Thr Trp
            595                 600                 605

Ile Ile Leu Lys Lys Lys Ala Glu Thr Gly Asp Thr Val Leu Lys Ser
            610                 615                 620

Ile Asp Gly Ala Tyr Thr Ile Arg Lys Ala Gln Leu Lys Asp Ala Gly
625                 630                 635                 640

Val Tyr Glu Cys Glu Ser Lys Asn Lys Val Gly Ser Gln Leu Arg Ser
                645                 650                 655

Leu Thr Leu Asp Val Gln Gly Arg Glu Asn Asn Lys Asp Tyr Phe Ser
            660                 665                 670

Pro Glu Leu Leu Val Leu Tyr Phe Ala Ser Ser Leu Ile Ile Pro Ala
            675                 680                 685

Ile Gly Met Ile Ile Tyr Phe Ala Arg Lys Ala Asn Met Lys Gly Ser
            690                 695                 700

Tyr Ser Leu Val Glu Ala Gln Lys Ser Lys Val
705                 710                 715

<210> SEQ ID NO 75
<211> LENGTH: 999
<212> TYPE: PRT
<213> ORGANISM: Homo sapiens
<220> FEATURE:
<223> OTHER INFORMATION: VLA-4

<400> SEQUENCE: 75

Tyr Asn Val Asp Thr Glu Ser Ala Leu Leu Tyr Gln Gly Pro His Asn
1               5                   10                  15

Thr Leu Phe Gly Tyr Ser Val Val Leu His Ser His Gly Ala Asn Arg
            20                  25                  30

Trp Leu Leu Val Gly Ala Pro Thr Ala Asn Trp Leu Ala Asn Ala Ser
        35                  40                  45

Val Ile Asn Pro Gly Ala Ile Tyr Arg Cys Arg Ile Gly Lys Asn Pro
    50                  55                  60

Gly Gln Thr Cys Glu Gln Leu Gln Leu Gly Ser Pro Asn Gly Glu Pro
65                  70                  75                  80
```

```
Cys Gly Lys Thr Cys Leu Glu Glu Arg Asp Asn Gln Trp Leu Gly Val
                 85                  90                  95

Thr Leu Ser Arg Gln Pro Gly Glu Asn Gly Ser Ile Val Thr Cys Gly
            100                 105                 110

His Arg Trp Lys Asn Ile Phe Tyr Ile Lys Asn Glu Asn Lys Leu Pro
        115                 120                 125

Thr Gly Gly Cys Tyr Gly Val Pro Pro Asp Leu Arg Thr Glu Leu Ser
    130                 135                 140

Lys Arg Ile Ala Pro Cys Tyr Gln Asp Tyr Val Lys Lys Phe Gly Glu
145                 150                 155                 160

Asn Phe Ala Ser Cys Gln Ala Gly Ile Ser Ser Phe Tyr Thr Lys Asp
                165                 170                 175

Leu Ile Val Met Gly Ala Pro Gly Ser Ser Tyr Trp Thr Gly Ser Leu
            180                 185                 190

Phe Val Tyr Asn Ile Thr Thr Asn Lys Tyr Lys Ala Phe Leu Asp Lys
        195                 200                 205

Gln Asn Gln Val Lys Phe Gly Ser Tyr Leu Gly Tyr Ser Val Gly Ala
    210                 215                 220

Gly His Phe Arg Ser Gln His Thr Thr Glu Val Val Gly Gly Ala Pro
225                 230                 235                 240

Gln His Glu Gln Ile Gly Lys Ala Tyr Ile Phe Ser Ile Asp Glu Lys
                245                 250                 255

Glu Leu Asn Ile Leu His Glu Met Lys Gly Lys Lys Leu Gly Ser Tyr
            260                 265                 270

Phe Gly Ala Ser Val Cys Ala Val Asp Leu Asn Ala Asp Gly Phe Ser
        275                 280                 285

Asp Leu Leu Val Gly Ala Pro Met Gln Ser Thr Ile Arg Glu Glu Gly
    290                 295                 300

Arg Val Phe Val Tyr Ile Asn Ser Gly Ser Gly Ala Val Met Asn Ala
305                 310                 315                 320

Met Glu Thr Asn Leu Val Gly Ser Asp Lys Tyr Ala Ala Arg Phe Gly
                325                 330                 335

Glu Ser Ile Val Asn Leu Gly Asp Ile Asp Asn Asp Gly Phe Glu Asp
            340                 345                 350

Val Ala Ile Gly Ala Pro Gln Glu Asp Asp Leu Gln Gly Ala Ile Tyr
        355                 360                 365

Ile Tyr Asn Gly Arg Ala Asp Gly Ile Ser Ser Thr Phe Ser Gln Arg
    370                 375                 380

Ile Glu Gly Leu Gln Ile Ser Lys Ser Leu Ser Met Phe Gly Gln Ser
385                 390                 395                 400

Ile Ser Gly Gln Ile Asp Ala Asp Asn Asn Gly Tyr Val Asp Val Ala
                405                 410                 415

Val Gly Ala Phe Arg Ser Asp Ser Ala Val Leu Leu Arg Thr Arg Pro
            420                 425                 430

Val Val Ile Val Asp Ala Ser Leu Ser His Pro Glu Ser Val Asn Arg
        435                 440                 445

Thr Lys Phe Asp Cys Val Glu Asn Gly Trp Pro Ser Val Cys Ile Asp
    450                 455                 460

Leu Thr Leu Cys Phe Ser Tyr Lys Gly Lys Glu Val Pro Gly Tyr Ile
465                 470                 475                 480

Val Leu Phe Tyr Asn Met Ser Leu Asp Val Asn Arg Lys Ala Glu Ser
                485                 490                 495

Pro Pro Arg Phe Tyr Phe Ser Ser Asn Gly Thr Ser Asp Val Ile Thr
```

```
              500                 505                 510
    Gly Ser Ile Gln Val Ser Ser Arg Glu Ala Asn Cys Arg Thr His Gln
                515                 520                 525
    Ala Phe Met Arg Lys Asp Val Arg Asp Ile Leu Thr Pro Ile Gln Ile
            530                 535                 540
    Glu Ala Ala Tyr His Leu Gly Pro His Val Ile Ser Lys Arg Ser Thr
    545                 550                 555                 560
    Glu Glu Phe Pro Pro Leu Gln Pro Ile Leu Gln Gln Lys Lys Glu Lys
                    565                 570                 575
    Asp Ile Met Lys Lys Thr Ile Asn Phe Ala Arg Phe Cys Ala His Glu
                580                 585                 590
    Asn Cys Ser Ala Asp Leu Gln Val Ser Ala Lys Ile Gly Phe Leu Lys
            595                 600                 605
    Pro His Glu Asn Lys Thr Tyr Leu Ala Val Gly Ser Met Lys Thr Leu
            610                 615                 620
    Met Leu Asn Val Ser Leu Phe Asn Ala Gly Asp Asp Ala Tyr Glu Thr
    625                 630                 635                 640
    Thr Leu His Val Lys Leu Pro Val Gly Leu Tyr Phe Ile Lys Ile Leu
                    645                 650                 655
    Glu Leu Glu Glu Lys Gln Ile Asn Cys Glu Val Thr Asp Asn Ser Gly
                    660                 665                 670
    Val Val Gln Leu Asp Cys Ser Ile Gly Tyr Ile Tyr Val Asp His Leu
                675                 680                 685
    Ser Arg Ile Asp Ile Ser Phe Leu Leu Asp Val Ser Ser Leu Ser Arg
            690                 695                 700
    Ala Glu Glu Asp Leu Ser Ile Thr Val His Ala Thr Cys Glu Asn Glu
    705                 710                 715                 720
    Glu Glu Met Asp Asn Leu Lys His Ser Arg Val Thr Val Ala Ile Pro
                    725                 730                 735
    Leu Lys Tyr Glu Val Lys Leu Thr Val His Gly Phe Val Asn Pro Thr
                    740                 745                 750
    Ser Phe Val Tyr Gly Ser Asn Asp Glu Asn Glu Pro Glu Thr Cys Met
                755                 760                 765
    Val Glu Lys Met Asn Leu Thr Phe His Val Ile Asn Thr Gly Asn Ser
            770                 775                 780
    Met Ala Pro Asn Val Ser Val Glu Ile Met Val Pro Asn Ser Phe Ser
    785                 790                 795                 800
    Pro Gln Thr Asp Lys Leu Phe Asn Ile Leu Asp Val Gln Thr Thr Thr
                    805                 810                 815
    Gly Glu Cys His Phe Glu Asn Tyr Gln Arg Val Cys Ala Leu Glu Gln
                820                 825                 830
    Gln Lys Ser Ala Met Gln Thr Leu Lys Gly Ile Val Arg Phe Leu Ser
                835                 840                 845
    Lys Thr Asp Lys Arg Leu Leu Tyr Cys Ile Lys Ala Asp Pro His Cys
            850                 855                 860
    Leu Asn Phe Leu Cys Asn Phe Gly Lys Met Glu Ser Gly Lys Glu Ala
    865                 870                 875                 880
    Ser Val His Ile Gln Leu Glu Gly Arg Pro Ser Ile Leu Glu Met Asp
                    885                 890                 895
    Glu Thr Ser Ala Leu Lys Phe Glu Ile Arg Ala Thr Gly Phe Pro Glu
                    900                 905                 910
    Pro Asn Pro Arg Val Ile Glu Leu Asn Lys Asp Glu Asn Val Ala His
                915                 920                 925
```

```
Val Leu Leu Glu Gly Leu His His Gln Arg Pro Lys Arg Tyr Phe Thr
    930                 935                 940

Ile Val Ile Ile Ser Ser Leu Leu Leu Gly Leu Ile Val Leu Leu
945                 950                 955                 960

Leu Ile Ser Tyr Val Met Trp Lys Ala Gly Phe Phe Lys Arg Gln Tyr
                965                 970                 975

Lys Ser Ile Leu Gln Glu Glu Asn Arg Arg Asp Ser Trp Ser Tyr Ile
            980                 985                 990

Asn Ser Lys Ser Asn Asp Asp
            995

<210> SEQ ID NO 76
<211> LENGTH: 1065
<212> TYPE: PRT
<213> ORGANISM: Homo sapiens
<220> FEATURE:
<223> OTHER INFORMATION: LFA-1alpha Extracellular domain (ECD)

<400> SEQUENCE: 76

Tyr Asn Leu Asp Val Arg Gly Ala Arg Ser Phe Ser Pro Pro Arg Ala
1               5                   10                  15

Gly Arg His Phe Gly Tyr Arg Val Leu Gln Val Gly Asn Gly Val Ile
                20                  25                  30

Val Gly Ala Pro Gly Glu Gly Asn Ser Thr Gly Ser Leu Tyr Gln Cys
            35                  40                  45

Gln Ser Gly Thr Gly His Cys Leu Pro Val Thr Leu Arg Gly Ser Asn
        50                  55                  60

Tyr Thr Ser Lys Tyr Leu Gly Met Thr Leu Ala Thr Asp Pro Thr Asp
65                  70                  75                  80

Gly Ser Ile Leu Ala Cys Asp Pro Gly Leu Ser Arg Thr Cys Asp Gln
                85                  90                  95

Asn Thr Tyr Leu Ser Gly Leu Cys Tyr Leu Phe Arg Gln Asn Leu Gln
                100                 105                 110

Gly Pro Met Leu Gln Gly Arg Pro Gly Phe Gln Glu Cys Ile Lys Gly
            115                 120                 125

Asn Val Asp Leu Val Phe Leu Phe Asp Gly Ser Met Ser Leu Gln Pro
        130                 135                 140

Asp Glu Phe Gln Lys Ile Leu Asp Phe Met Lys Asp Val Met Lys Lys
145                 150                 155                 160

Leu Ser Asn Thr Ser Tyr Gln Phe Ala Ala Val Gln Phe Ser Thr Ser
                165                 170                 175

Tyr Lys Thr Glu Phe Asp Phe Ser Asp Tyr Val Lys Arg Lys Asp Pro
                180                 185                 190

Asp Ala Leu Leu Lys His Val Lys His Met Leu Leu Leu Thr Asn Thr
            195                 200                 205

Phe Gly Ala Ile Asn Tyr Val Ala Thr Glu Val Phe Arg Glu Glu Leu
        210                 215                 220

Gly Ala Arg Pro Asp Ala Thr Lys Val Leu Ile Ile Ile Thr Asp Gly
225                 230                 235                 240

Glu Ala Thr Asp Ser Gly Asn Ile Asp Ala Ala Lys Asp Ile Ile Arg
                245                 250                 255

Tyr Ile Ile Gly Ile Gly Lys His Phe Gln Thr Lys Glu Ser Gln Glu
                260                 265                 270

Thr Leu His Lys Phe Ala Ser Lys Pro Ala Ser Glu Phe Val Lys Ile
            275                 280                 285
```

```
Leu Asp Thr Phe Glu Lys Leu Lys Asp Leu Phe Thr Glu Leu Gln Lys
            290                 295                 300

Lys Ile Tyr Val Ile Glu Gly Thr Ser Lys Gln Asp Leu Thr Ser Phe
305                 310                 315                 320

Asn Met Glu Leu Ser Ser Gly Ile Ser Ala Asp Leu Ser Arg Gly
                325                 330                 335

His Ala Val Val Gly Ala Val Gly Ala Lys Asp Trp Ala Gly Gly Phe
            340                 345                 350

Leu Asp Leu Lys Ala Asp Leu Gln Asp Asp Thr Phe Ile Gly Asn Glu
                355                 360                 365

Pro Leu Thr Pro Glu Val Arg Ala Gly Tyr Leu Gly Tyr Thr Val Thr
            370                 375                 380

Trp Leu Pro Ser Arg Gln Lys Thr Ser Leu Leu Ala Ser Gly Ala Pro
385                 390                 395                 400

Arg Tyr Gln His Met Gly Arg Val Leu Leu Phe Gln Glu Pro Gln Gly
                405                 410                 415

Gly Gly His Trp Ser Gln Val Gln Thr Ile His Gly Thr Gln Ile Gly
                420                 425                 430

Ser Tyr Phe Gly Gly Glu Leu Cys Gly Val Asp Val Asp Gln Asp Gly
            435                 440                 445

Glu Thr Glu Leu Leu Leu Ile Gly Ala Pro Leu Phe Tyr Gly Glu Gln
            450                 455                 460

Arg Gly Gly Arg Val Phe Ile Tyr Gln Arg Arg Gln Leu Gly Phe Glu
465                 470                 475                 480

Glu Val Ser Glu Leu Gln Gly Asp Pro Gly Tyr Pro Leu Gly Arg Phe
                485                 490                 495

Gly Glu Ala Ile Thr Ala Leu Thr Asp Ile Asn Gly Asp Gly Leu Val
                500                 505                 510

Asp Val Ala Val Gly Ala Pro Leu Glu Glu Gln Gly Ala Val Tyr Ile
            515                 520                 525

Phe Asn Gly Arg His Gly Gly Leu Ser Pro Gln Pro Ser Gln Arg Ile
            530                 535                 540

Glu Gly Thr Gln Val Leu Ser Gly Ile Gln Trp Phe Gly Arg Ser Ile
545                 550                 555                 560

His Gly Val Lys Asp Leu Glu Gly Asp Gly Leu Ala Asp Val Ala Val
                565                 570                 575

Gly Ala Glu Ser Gln Met Ile Val Leu Ser Ser Arg Pro Val Val Asp
                580                 585                 590

Met Val Thr Leu Met Ser Phe Ser Pro Ala Glu Ile Pro Val His Glu
            595                 600                 605

Val Glu Cys Ser Tyr Ser Thr Ser Asn Lys Met Lys Glu Gly Val Asn
            610                 615                 620

Ile Thr Ile Cys Phe Gln Ile Lys Ser Leu Ile Pro Gln Phe Gln Gly
625                 630                 635                 640

Arg Leu Val Ala Asn Leu Thr Tyr Thr Leu Gln Leu Asp Gly His Arg
                645                 650                 655

Thr Arg Arg Arg Gly Leu Phe Pro Gly Gly Arg His Glu Leu Arg Arg
                660                 665                 670

Asn Ile Ala Val Thr Thr Ser Met Ser Cys Thr Asp Phe Ser Phe His
            675                 680                 685

Phe Pro Val Cys Val Gln Asp Leu Ile Ser Pro Ile Asn Val Ser Leu
            690                 695                 700
```

```
Asn Phe Ser Leu Trp Glu Glu Gly Thr Pro Arg Asp Gln Arg Ala
705                 710                 715                 720

Gln Gly Lys Asp Ile Pro Pro Ile Leu Arg Pro Ser Leu His Ser Glu
            725                 730                 735

Thr Trp Glu Ile Pro Phe Glu Lys Asn Cys Gly Glu Asp Lys Lys Cys
            740                 745                 750

Glu Ala Asn Leu Arg Val Ser Phe Ser Pro Ala Arg Ser Arg Ala Leu
            755                 760                 765

Arg Leu Thr Ala Phe Ala Ser Leu Ser Val Glu Leu Ser Leu Ser Asn
            770                 775                 780

Leu Glu Glu Asp Ala Tyr Trp Val Gln Leu Asp Leu His Phe Pro Pro
785                 790                 795                 800

Gly Leu Ser Phe Arg Lys Val Glu Met Leu Lys Pro His Ser Gln Ile
            805                 810                 815

Pro Val Ser Cys Glu Glu Leu Pro Glu Glu Ser Arg Leu Leu Ser Arg
            820                 825                 830

Ala Leu Ser Cys Asn Val Ser Ser Pro Ile Phe Lys Ala Gly His Ser
            835                 840                 845

Val Ala Leu Gln Met Met Phe Asn Thr Leu Val Asn Ser Ser Trp Gly
850                 855                 860

Asp Ser Val Glu Leu His Ala Asn Val Thr Cys Asn Asn Glu Asp Ser
865                 870                 875                 880

Asp Leu Leu Glu Asp Asn Ser Ala Thr Thr Ile Ile Pro Ile Leu Tyr
            885                 890                 895

Pro Ile Asn Ile Leu Ile Gln Asp Gln Glu Asp Ser Thr Leu Tyr Val
            900                 905                 910

Ser Phe Thr Pro Lys Gly Pro Lys Ile His Gln Val Lys His Met Tyr
            915                 920                 925

Gln Val Arg Ile Gln Pro Ser Ile His Asp His Asn Ile Pro Thr Leu
            930                 935                 940

Glu Ala Val Val Gly Val Pro Gln Pro Ser Glu Gly Pro Ile Thr
945                 950                 955                 960

His Gln Trp Ser Val Gln Met Glu Pro Val Pro Cys His Tyr Glu
            965                 970                 975

Asp Leu Glu Arg Leu Pro Asp Ala Ala Glu Pro Cys Leu Pro Gly Ala
            980                 985                 990

Leu Phe Arg Cys Pro Val Val Phe Arg Gln Glu Ile Leu Val Gln Val
            995                 1000                1005

Ile Gly Thr Leu Glu Leu Val Gly Glu Ile Glu Ala Ser Ser Met Phe
    1010                1015                1020

Ser Leu Cys Ser Ser Leu Ser Ile Ser Phe Asn Ser Ser Lys His Phe
1025                1030                1035                1040

His Leu Tyr Gly Ser Asn Ala Ser Leu Ala Gln Val Val Met Lys Val
            1045                1050                1055

Asp Val Val Tyr Glu Lys Gln Met Leu
            1060                1065

<210> SEQ ID NO 77
<211> LENGTH: 678
<212> TYPE: PRT
<213> ORGANISM: Homo sapiens
<220> FEATURE:
<223> OTHER INFORMATION: LFA-1beta Extracellular Domain (ECD)

<400> SEQUENCE: 77
```

```
Gln Glu Cys Thr Lys Phe Lys Val Ser Ser Cys Arg Glu Cys Ile Glu
1               5                   10                  15

Ser Gly Pro Gly Cys Thr Trp Cys Gln Lys Leu Asn Phe Thr Gly Pro
            20                  25                  30

Gly Asp Pro Asp Ser Ile Arg Cys Asp Thr Arg Pro Gln Leu Leu Met
        35                  40                  45

Arg Gly Cys Ala Ala Asp Asp Ile Met Asp Pro Thr Ser Leu Ala Glu
    50                  55                  60

Thr Gln Glu Asp His Asn Gly Gly Gln Lys Gln Leu Ser Pro Gln Lys
65                  70                  75                  80

Val Thr Leu Tyr Leu Arg Pro Gly Gln Ala Ala Phe Asn Val Thr
                85                  90                  95

Phe Arg Arg Ala Lys Gly Tyr Pro Ile Asp Leu Tyr Tyr Leu Met Asp
            100                 105                 110

Leu Ser Tyr Ser Met Leu Asp Asp Leu Arg Asn Val Lys Lys Leu Gly
        115                 120                 125

Gly Asp Leu Leu Arg Ala Leu Asn Glu Ile Thr Glu Ser Gly Arg Ile
    130                 135                 140

Gly Phe Gly Ser Phe Val Asp Lys Thr Val Leu Pro Phe Val Asn Thr
145                 150                 155                 160

His Pro Asp Lys Leu Arg Asn Pro Cys Pro Asn Lys Glu Lys Glu Cys
            165                 170                 175

Gln Pro Pro Phe Ala Phe Arg His Val Leu Lys Leu Thr Asn Asn Ser
        180                 185                 190

Asn Gln Phe Gln Thr Glu Val Gly Lys Gln Leu Ile Ser Gly Asn Leu
    195                 200                 205

Asp Ala Pro Glu Gly Gly Leu Asp Ala Met Met Gln Val Ala Ala Cys
    210                 215                 220

Pro Glu Glu Ile Gly Trp Arg Asn Val Thr Arg Leu Leu Val Phe Ala
225                 230                 235                 240

Thr Asp Asp Gly Phe His Phe Ala Gly Asp Gly Lys Leu Gly Ala Ile
            245                 250                 255

Leu Thr Pro Asn Asp Gly Arg Cys His Leu Glu Asp Asn Leu Tyr Lys
        260                 265                 270

Arg Ser Asn Glu Phe Asp Tyr Pro Ser Val Gly Gln Leu Ala His Lys
    275                 280                 285

Leu Ala Glu Asn Asn Ile Gln Pro Ile Phe Ala Val Thr Ser Arg Met
    290                 295                 300

Val Lys Thr Tyr Glu Lys Leu Thr Glu Ile Ile Pro Lys Ser Ala Val
305                 310                 315                 320

Gly Glu Leu Ser Glu Asp Ser Ser Asn Val Val Gln Leu Ile Lys Asn
            325                 330                 335

Ala Tyr Asn Lys Leu Ser Ser Arg Val Phe Leu Asp His Asn Ala Leu
        340                 345                 350

Pro Asp Thr Leu Lys Val Thr Tyr Asp Ser Phe Cys Ser Asn Gly Val
    355                 360                 365

Thr His Arg Asn Gln Pro Arg Gly Asp Cys Asp Gly Val Gln Ile Asn
    370                 375                 380

Val Pro Ile Thr Phe Gln Val Lys Val Thr Ala Thr Glu Cys Ile Gln
385                 390                 395                 400

Glu Gln Ser Phe Val Ile Arg Ala Leu Gly Phe Thr Asp Ile Val Thr
            405                 410                 415

Val Gln Val Leu Pro Gln Cys Glu Cys Arg Cys Arg Asp Gln Ser Arg
```

```
                420             425             430
Asp Arg Ser Leu Cys His Gly Lys Gly Phe Leu Glu Cys Gly Ile Cys
            435                 440             445

Arg Cys Asp Thr Gly Tyr Ile Gly Lys Asn Cys Glu Cys Gln Thr Gln
        450                 455             460

Gly Arg Ser Ser Gln Glu Leu Glu Gly Ser Cys Arg Lys Asp Asn Asn
465                 470                 475                 480

Ser Ile Ile Cys Ser Gly Leu Gly Asp Cys Val Cys Gly Gln Cys Leu
                485                 490                 495

Cys His Thr Ser Asp Val Pro Gly Lys Leu Ile Tyr Gly Gln Tyr Cys
            500                 505             510

Glu Cys Asp Thr Ile Asn Cys Glu Arg Tyr Asn Gly Gln Val Cys Gly
        515                 520             525

Gly Pro Gly Arg Gly Leu Cys Phe Cys Gly Lys Cys Arg Cys His Pro
530                 535             540

Gly Phe Glu Gly Ser Ala Cys Gln Cys Glu Arg Thr Thr Glu Gly Cys
545                 550             555                 560

Leu Asn Pro Arg Arg Val Glu Cys Ser Gly Arg Gly Arg Cys Arg Cys
            565                 570                 575

Asn Val Cys Glu Cys His Ser Gly Tyr Gln Leu Pro Leu Cys Gln Glu
            580                 585             590

Cys Pro Gly Cys Pro Ser Pro Cys Gly Lys Tyr Ile Ser Cys Ala Glu
            595                 600             605

Cys Leu Lys Phe Glu Lys Gly Pro Phe Gly Lys Asn Cys Ser Ala Ala
        610             615             620

Cys Pro Gly Leu Gln Leu Ser Asn Asn Pro Val Lys Gly Arg Thr Cys
625             630             635                 640

Lys Glu Arg Asp Ser Glu Gly Cys Trp Val Ala Tyr Thr Leu Glu Gln
            645             650             655

Gln Asp Gly Met Asp Arg Tyr Leu Ile Tyr Val Asp Glu Ser Arg Glu
            660             665             670

Cys Val Ala Gly Pro Asn
            675

<210> SEQ ID NO 78
<211> LENGTH: 294
<212> TYPE: PRT
<213> ORGANISM: Homo sapiens
<220> FEATURE:
<223> OTHER INFORMATION: L-selectin Extracellular Domain (ECD)

<400> SEQUENCE: 78

Trp Thr Tyr His Tyr Ser Glu Lys Pro Met Asn Trp Gln Arg Ala Arg
1               5                   10                  15

Arg Phe Cys Arg Asp Asn Tyr Thr Asp Leu Val Ala Ile Gln Asn Lys
            20                  25                  30

Ala Glu Ile Glu Tyr Leu Glu Lys Thr Leu Pro Phe Ser Arg Ser Tyr
        35                  40                  45

Tyr Trp Ile Gly Ile Arg Lys Ile Gly Gly Ile Trp Thr Trp Val Gly
    50                  55                  60

Thr Asn Lys Ser Leu Thr Glu Glu Ala Glu Asn Trp Gly Asp Gly Glu
65                  70                  75                  80

Pro Asn Asn Lys Lys Asn Lys Glu Asp Cys Val Glu Ile Tyr Ile Lys
            85                  90                  95

Arg Asn Lys Asp Ala Gly Lys Trp Asn Asp Asp Ala Cys His Lys Leu
```

```
                100             105             110
Lys Ala Ala Leu Cys Tyr Thr Ala Ser Cys Gln Pro Trp Ser Cys Ser
            115                 120             125
Gly His Gly Glu Cys Val Glu Ile Ile Asn Asn Tyr Thr Cys Asn Cys
        130                 135             140
Asp Val Gly Tyr Tyr Gly Pro Gln Cys Gln Phe Val Ile Gln Cys Glu
145                 150                 155                 160
Pro Leu Glu Ala Pro Glu Leu Gly Thr Met Asp Cys Thr His Pro Leu
                165                 170                 175
Gly Asn Phe Ser Phe Ser Ser Gln Cys Ala Phe Ser Cys Ser Glu Gly
            180                 185                 190
Thr Asn Leu Thr Gly Ile Glu Glu Thr Thr Cys Gly Pro Phe Gly Asn
        195                 200                 205
Trp Ser Ser Pro Glu Pro Thr Cys Gln Val Ile Gln Cys Glu Pro Leu
    210                 215                 220
Ser Ala Pro Asp Leu Gly Ile Met Asn Cys Ser His Pro Leu Ala Ser
225                 230                 235                 240
Phe Ser Phe Thr Ser Ala Cys Thr Phe Ile Cys Ser Glu Gly Thr Glu
                245                 250                 255
Leu Ile Gly Lys Lys Thr Ile Cys Glu Ser Ser Gly Ile Trp Ser
            260                 265                 270
Asn Pro Ser Pro Ile Cys Gln Lys Leu Asp Lys Ser Phe Ser Met Ile
        275                 280                 285
Lys Glu Gly Asp Tyr Asn
    290

<210> SEQ ID NO 79
<211> LENGTH: 674
<212> TYPE: PRT
<213> ORGANISM: Homo sapiens
<220> FEATURE:
<223> OTHER INFORMATION: VCAM-1 Extracellular Domain (ECD)

<400> SEQUENCE: 79

Phe Lys Ile Glu Thr Thr Pro Glu Ser Arg Tyr Leu Ala Gln Ile Gly
1               5                   10                  15
Asp Ser Val Ser Leu Thr Cys Ser Thr Thr Gly Cys Glu Ser Pro Phe
            20                  25                  30
Phe Ser Trp Arg Thr Gln Ile Asp Ser Pro Leu Asn Gly Lys Val Thr
        35                  40                  45
Asn Glu Gly Thr Thr Ser Thr Leu Thr Met Asn Pro Val Ser Phe Gly
    50                  55                  60
Asn Glu His Ser Tyr Leu Cys Thr Ala Thr Cys Glu Ser Arg Lys Leu
65                  70                  75                  80
Glu Lys Gly Ile Gln Val Glu Ile Tyr Ser Phe Pro Lys Asp Pro Glu
                85                  90                  95
Ile His Leu Ser Gly Pro Leu Glu Ala Gly Lys Pro Ile Thr Val Lys
            100                 105                 110
Cys Ser Val Ala Asp Val Tyr Pro Phe Asp Arg Leu Glu Ile Asp Leu
        115                 120                 125
Leu Lys Gly Asp His Leu Met Lys Ser Gln Glu Phe Leu Glu Asp Ala
    130                 135                 140
Asp Arg Lys Ser Leu Glu Thr Lys Ser Leu Glu Val Thr Phe Thr Pro
145                 150                 155                 160
Val Ile Glu Asp Ile Gly Lys Val Leu Val Cys Arg Ala Lys Leu His
```

```
                165                 170                 175
Ile Asp Glu Met Asp Ser Val Pro Thr Val Arg Gln Ala Val Lys Glu
                180                 185                 190
Leu Gln Val Tyr Ile Ser Pro Lys Asn Thr Val Ile Ser Val Asn Pro
                195                 200                 205
Ser Thr Lys Leu Gln Glu Gly Gly Ser Val Thr Met Thr Cys Ser Ser
210                 215                 220
Glu Gly Leu Pro Ala Pro Glu Ile Phe Trp Ser Lys Lys Leu Asp Asn
225                 230                 235                 240
Gly Asn Leu Gln His Leu Ser Gly Asn Ala Thr Leu Thr Leu Ile Ala
                245                 250                 255
Met Arg Met Glu Asp Ser Gly Ile Tyr Val Cys Glu Gly Val Asn Leu
                260                 265                 270
Ile Gly Lys Asn Arg Lys Glu Val Glu Leu Ile Val Gln Glu Lys Pro
                275                 280                 285
Phe Thr Val Glu Ile Ser Pro Gly Pro Arg Ile Ala Ala Gln Ile Gly
                290                 295                 300
Asp Ser Val Met Leu Thr Cys Ser Val Met Gly Cys Glu Ser Pro Ser
305                 310                 315                 320
Phe Ser Trp Arg Thr Gln Ile Asp Ser Pro Leu Ser Gly Lys Val Arg
                325                 330                 335
Ser Glu Gly Thr Asn Ser Thr Leu Thr Leu Ser Pro Val Ser Phe Glu
                340                 345                 350
Asn Glu His Ser Tyr Leu Cys Thr Val Thr Cys Gly His Lys Lys Leu
                355                 360                 365
Glu Lys Gly Ile Gln Val Glu Leu Tyr Ser Phe Pro Arg Asp Pro Glu
                370                 375                 380
Ile Glu Met Ser Gly Gly Leu Val Asn Gly Ser Ser Val Thr Val Ser
385                 390                 395                 400
Cys Lys Val Pro Ser Val Tyr Pro Leu Asp Arg Leu Glu Ile Glu Leu
                405                 410                 415
Leu Lys Gly Glu Thr Ile Leu Glu Asn Ile Glu Phe Leu Glu Asp Thr
                420                 425                 430
Asp Met Lys Ser Leu Glu Asn Lys Ser Leu Glu Met Thr Phe Ile Pro
                435                 440                 445
Thr Ile Glu Asp Thr Gly Lys Ala Leu Val Cys Gln Ala Lys Leu His
                450                 455                 460
Ile Asp Asp Met Glu Phe Glu Pro Lys Gln Arg Gln Ser Thr Gln Thr
465                 470                 475                 480
Leu Tyr Val Asn Val Ala Pro Arg Asp Thr Thr Val Leu Val Ser Pro
                485                 490                 495
Ser Ser Ile Leu Glu Glu Gly Ser Ser Val Asn Met Thr Cys Leu Ser
                500                 505                 510
Gln Gly Phe Pro Ala Pro Lys Ile Leu Trp Ser Arg Gln Leu Pro Asn
                515                 520                 525
Gly Glu Leu Gln Pro Leu Ser Glu Asn Ala Thr Leu Thr Leu Ile Ser
                530                 535                 540
Thr Lys Met Glu Asp Ser Gly Val Tyr Leu Cys Glu Gly Ile Asn Gln
545                 550                 555                 560
Ala Gly Arg Ser Arg Lys Glu Val Glu Leu Ile Ile Gln Val Thr Pro
                565                 570                 575
Lys Asp Ile Lys Leu Thr Ala Phe Pro Ser Glu Ser Val Lys Glu Gly
                580                 585                 590
```

```
Asp Thr Val Ile Ile Ser Cys Thr Cys Gly Asn Val Pro Glu Thr Trp
                595                 600                 605

Ile Ile Leu Lys Lys Lys Ala Glu Thr Gly Asp Thr Val Leu Lys Ser
            610                 615                 620

Ile Asp Gly Ala Tyr Thr Ile Arg Lys Ala Gln Leu Lys Asp Ala Gly
625                 630                 635                 640

Val Tyr Glu Cys Glu Ser Lys Asn Lys Val Gly Ser Gln Leu Arg Ser
                645                 650                 655

Leu Thr Leu Asp Val Gln Gly Arg Glu Asn Asn Lys Asp Tyr Phe Ser
                660                 665                 670

Pro Glu

<210> SEQ ID NO 80
<211> LENGTH: 943
<212> TYPE: PRT
<213> ORGANISM: Homo sapiens
<220> FEATURE:
<223> OTHER INFORMATION: VLA-4 Extracellular Domain (ECD)

<400> SEQUENCE: 80

Asn Val Asp Thr Glu Ser Ala Leu Leu Tyr Gln Gly Pro His Asn Thr
1               5                   10                  15

Leu Phe Gly Tyr Ser Val Val Leu His Ser His Gly Ala Asn Arg Trp
            20                  25                  30

Leu Leu Val Gly Ala Pro Thr Ala Asn Trp Leu Ala Asn Ala Ser Val
        35                  40                  45

Ile Asn Pro Gly Ala Ile Tyr Arg Cys Arg Ile Gly Lys Asn Pro Gly
    50                  55                  60

Gln Thr Cys Glu Gln Leu Gln Leu Gly Ser Pro Asn Gly Glu Pro Cys
65                  70                  75                  80

Gly Lys Thr Cys Leu Glu Glu Arg Asp Asn Gln Trp Leu Gly Val Thr
                85                  90                  95

Leu Ser Arg Gln Pro Gly Glu Asn Gly Ser Ile Val Thr Cys Gly His
            100                 105                 110

Arg Trp Lys Asn Ile Phe Tyr Ile Lys Asn Glu Asn Lys Leu Pro Thr
        115                 120                 125

Gly Gly Cys Tyr Gly Val Pro Pro Asp Leu Arg Thr Glu Leu Ser Lys
    130                 135                 140

Arg Ile Ala Pro Cys Tyr Gln Asp Tyr Val Lys Lys Phe Gly Glu Asn
145                 150                 155                 160

Phe Ala Ser Cys Gln Ala Gly Ile Ser Ser Phe Tyr Thr Lys Asp Leu
                165                 170                 175

Ile Val Met Gly Ala Pro Gly Ser Ser Tyr Trp Thr Gly Ser Leu Phe
            180                 185                 190

Val Tyr Asn Ile Thr Thr Asn Lys Tyr Lys Ala Phe Leu Asp Lys Gln
        195                 200                 205

Asn Gln Val Lys Phe Gly Ser Tyr Leu Gly Tyr Ser Val Gly Ala Gly
    210                 215                 220

His Phe Arg Ser Gln His Thr Thr Glu Val Val Gly Gly Ala Pro Gln
225                 230                 235                 240

His Glu Gln Ile Gly Lys Ala Tyr Ile Phe Ser Ile Asp Glu Lys Glu
                245                 250                 255

Leu Asn Ile Leu His Glu Met Lys Gly Lys Lys Leu Gly Ser Tyr Phe
            260                 265                 270
```

```
Gly Ala Ser Val Cys Ala Val Asp Leu Asn Ala Asp Gly Phe Ser Asp
            275                 280                 285

Leu Leu Val Gly Ala Pro Met Gln Ser Thr Ile Arg Glu Glu Gly Arg
290                 295                 300

Val Phe Val Tyr Ile Asn Ser Gly Ser Gly Ala Val Met Asn Ala Met
305                 310                 315                 320

Glu Thr Asn Leu Val Gly Ser Asp Lys Tyr Ala Ala Arg Phe Gly Glu
                325                 330                 335

Ser Ile Val Asn Leu Gly Asp Ile Asp Asn Asp Gly Phe Glu Asp Val
            340                 345                 350

Ala Ile Gly Ala Pro Gln Glu Asp Asp Leu Gln Gly Ala Ile Tyr Ile
            355                 360                 365

Tyr Asn Gly Arg Ala Asp Gly Ile Ser Ser Thr Phe Ser Gln Arg Ile
370                 375                 380

Glu Gly Leu Gln Ile Ser Lys Ser Leu Ser Met Phe Gly Gln Ser Ile
385                 390                 395                 400

Ser Gly Gln Ile Asp Ala Asp Asn Asn Gly Tyr Val Asp Val Ala Val
                405                 410                 415

Gly Ala Phe Arg Ser Asp Ser Ala Val Leu Leu Arg Thr Arg Pro Val
                420                 425                 430

Val Ile Val Asp Ala Ser Leu Ser His Pro Glu Ser Val Asn Arg Thr
            435                 440                 445

Lys Phe Asp Cys Val Glu Asn Gly Trp Pro Ser Val Cys Ile Asp Leu
            450                 455                 460

Thr Leu Cys Phe Ser Tyr Lys Gly Lys Glu Val Pro Gly Tyr Ile Val
465                 470                 475                 480

Leu Phe Tyr Asn Met Ser Leu Asp Val Asn Arg Lys Ala Glu Ser Pro
                485                 490                 495

Pro Arg Phe Tyr Phe Ser Ser Asn Gly Thr Ser Asp Val Ile Thr Gly
                500                 505                 510

Ser Ile Gln Val Ser Ser Arg Glu Ala Asn Cys Arg Thr His Gln Ala
            515                 520                 525

Phe Met Arg Lys Asp Val Arg Asp Ile Leu Thr Pro Ile Gln Ile Glu
530                 535                 540

Ala Ala Tyr His Leu Gly Pro His Val Ile Ser Lys Arg Ser Thr Glu
545                 550                 555                 560

Glu Phe Pro Pro Leu Gln Pro Ile Leu Gln Gln Lys Lys Glu Lys Asp
                565                 570                 575

Ile Met Lys Lys Thr Ile Asn Phe Ala Arg Phe Cys Ala His Glu Asn
                580                 585                 590

Cys Ser Ala Asp Leu Gln Val Ser Ala Lys Ile Gly Phe Leu Lys Pro
            595                 600                 605

His Glu Asn Lys Thr Tyr Leu Ala Val Gly Ser Met Lys Thr Leu Met
            610                 615                 620

Leu Asn Val Ser Leu Phe Asn Ala Gly Asp Asp Ala Tyr Glu Thr Thr
625                 630                 635                 640

Leu His Val Lys Leu Pro Val Gly Leu Tyr Phe Ile Lys Ile Leu Glu
                645                 650                 655

Leu Glu Glu Lys Gln Ile Asn Cys Glu Val Thr Asp Asn Ser Gly Val
                660                 665                 670

Val Gln Leu Asp Cys Ser Ile Gly Tyr Ile Tyr Val Asp His Leu Ser
            675                 680                 685

Arg Ile Asp Ile Ser Phe Leu Leu Asp Val Ser Ser Leu Ser Arg Ala
```

-continued

```
            690                 695                 700

Glu Glu Asp Leu Ser Ile Thr Val His Ala Thr Cys Glu Asn Glu Glu
705                 710                 715                 720

Glu Met Asp Asn Leu Lys His Ser Arg Val Thr Val Ala Ile Pro Leu
                725                 730                 735

Lys Tyr Glu Val Lys Leu Thr Val His Gly Phe Val Asn Pro Thr Ser
                740                 745                 750

Phe Val Tyr Gly Ser Asn Asp Glu Asn Glu Pro Glu Thr Cys Met Val
                755                 760                 765

Glu Lys Met Asn Leu Thr Phe His Val Ile Asn Thr Gly Asn Ser Met
770                 775                 780

Ala Pro Asn Val Ser Val Glu Ile Met Val Pro Asn Ser Phe Ser Pro
785                 790                 795                 800

Gln Thr Asp Lys Leu Phe Asn Ile Leu Asp Val Gln Thr Thr Thr Gly
                805                 810                 815

Glu Cys His Phe Glu Asn Tyr Gln Arg Val Cys Ala Leu Glu Gln Gln
                820                 825                 830

Lys Ser Ala Met Gln Thr Leu Lys Gly Ile Val Arg Phe Leu Ser Lys
                835                 840                 845

Thr Asp Lys Arg Leu Leu Tyr Cys Ile Lys Ala Asp Pro His Cys Leu
850                 855                 860

Asn Phe Leu Cys Asn Phe Gly Lys Met Glu Ser Gly Lys Glu Ala Ser
865                 870                 875                 880

Val His Ile Gln Leu Glu Gly Arg Pro Ser Ile Leu Glu Met Asp Glu
                885                 890                 895

Thr Ser Ala Leu Lys Phe Glu Ile Arg Ala Thr Gly Phe Pro Glu Pro
                900                 905                 910

Asn Pro Arg Val Ile Glu Leu Asn Lys Asp Glu Asn Val Ala His Val
                915                 920                 925

Leu Leu Glu Gly Leu His His Gln Arg Pro Lys Arg Tyr Phe Thr
930                 935                 940

<210> SEQ ID NO 81
<211> LENGTH: 126
<212> TYPE: PRT
<213> ORGANISM: Homo sapiens
<220> FEATURE:
<223> OTHER INFORMATION: IL-9

<400> SEQUENCE: 81

Gln Gly Cys Pro Thr Leu Ala Gly Ile Leu Asp Ile Asn Phe Leu Ile
1                 5                   10                  15

Asn Lys Met Gln Glu Asp Pro Ala Ser Lys Cys His Cys Ser Ala Asn
                20                  25                  30

Val Thr Ser Cys Leu Cys Leu Gly Ile Pro Ser Asp Asn Cys Thr Arg
                35                  40                  45

Pro Cys Phe Ser Glu Arg Leu Ser Gln Met Thr Asn Thr Thr Met Gln
                50                  55                  60

Thr Arg Tyr Pro Leu Ile Phe Ser Arg Val Lys Lys Ser Val Glu Val
65                  70                  75                  80

Leu Lys Asn Asn Lys Cys Pro Tyr Phe Ser Cys Glu Gln Pro Cys Asn
                85                  90                  95
```

```
Gln Thr Thr Ala Gly Asn Ala Leu Thr Phe Leu Lys Ser Leu Leu Glu
            100                 105                 110

Ile Phe Gln Lys Glu Lys Met Arg Gly Met Arg Gly Lys Ile
            115                 120                 125
```

METHODS FOR CULTURING CELLS AND KITS AND APPARATUS FOR SAME

CROSS-REFERENCE TO RELATED APPLICATIONS

This application is a U.S. National Stage of International Application No. PCT/IB2016/001618 filed Oct. 20, 2016, which claims priority from U.S. provisional application No. 62/245,252 filed Oct. 22, 2015, entitled "Methods for Culturing Cells and Kits and Apparatus for Same," and U.S. provisional application No. 62/245,261 filed Oct. 22, 2015, entitled "Methods for Culturing Cells and Kits and Apparatus for Same," the contents of each of which is incorporated by reference in its entirety.

INCORPORATION BY REFERENCE OF SEQUENCE LISTING

The present application is being filed with a Sequence Listing in electronic format. The Sequence Listing is provided as a file entitled 735042003600SeqList.txt, created Jan. 10, 2019, which is 134,782 bytes in size. The information in electronic format of the Sequence Listing is incorporated by reference in its entirety.

FIELD

The present disclosure relates in some aspects to the incubation or culturing, such as to induce stimulation of expansion (proliferation), activation, costimulation and/or survival, of a composition of cells such as a population of lymphocytes. In some aspects, the disclosure provides methods and reagents for the stimulation, e.g., of expansion (proliferation), survival or persistence, activation, costimulation, or other effect, of cell populations that involve binding of agents to a molecule on the surface of the cells, thereby providing one or more signals to the cells. In some cases, the reagents are reagents containing a plurality of binding sites for agents, such as multimerization reagents, and thus the one or more agents are multimerized by reversibly binding to the reagent, e.g., thereby creating a stimulatory reagent (multimerized agent), having stimulatory agents multimerized thereon. In some aspects, the multimerized agent can provide for expansion or proliferation or other stimulation of a population of cells, and then such stimulatory agents can be removed by disruption of the reversible bond. Also provided are compositions, apparatus and methods of use thereof.

BACKGROUND

Various strategies are available for stimulating T cell populations in vitro, including for expanding antigen-specific T cells in vitro for use in adoptive cellular immunotherapy or cancer therapy in which infusions of such T cells have been shown to have anti-tumor reactivity in a tumor-bearing host or for use to treat viral infections. Improved strategies are needed for expanding cell populations in vitro, including for research, diagnostic and therapeutic purposes. Provided are reagents, methods, articles of manufacture and kits that meet such needs.

SUMMARY

Provided herein are methods for incubating cells and compositions thereof, such as for culturing such cells, using reversible reagents for inducing or modulating a signal in a target cell. In some embodiments, the cells are T cells.

In some aspects the method involves incubating a composition containing T cells in the presence of an agent, such as a receptor-binding agent, e.g., a stimulatory agent. The receptor-binding agent (e.g., stimulatory agent) may be reversibly bound to a reagent containing a plurality of binding sites capable of reversibly binding to the receptor-binding agent. In some aspects, the receptor-binding agent is capable of specifically binding to a molecule on the surface of the cells, e.g., T cells, such as in a manner that induces or modulates a signal in the cells, e.g., the T cells in the composition. In some embodiments, the methods involve features, such as particular steps, selection of particular agents and/or selection of particular reagents, which allow the control or adjustment of the type or strength or duration of the signal received or modulated via the reagent, and/or of properties of the output composition or cell population(s) ultimately generated by the methods. In some embodiments, such features are possible due to advantageous properties of the agents and reagents, such as the reversibility of binding of the individual components of the agents or reagents, and thus, the reversibility of the binding of the multimerized agents and the cells. Such properties of the reagents can be exploited to achieve control in a number of ways. For example, in some embodiments, the methods, via reversibility of binding, include exerting temporal control of the signal, controlling the duration of the period in which the cells are in contact with the multimerized agents, and/or the duration of the signaling induced thereby.

In some embodiments, the methods involve control, e.g., precise control, of the length of the time period under which such agents are bound to cells. For example, this may be done by actively reversing such binding at a particular timepoint, and in some cases while still maintaining the cells for an additional time period other culture conditions, such as incubation at a physiological temperature and/or with various nutrients. Thus, as opposed to other methods which simply involve the termination of all or substantially all signals received by the cells, the provided methods in some aspects allow the specific termination or disruption of signals delivered by particular reagents.

Likewise, in some embodiments, the reversibility allows the reagents to be modular in nature, permitting the substitution of one or more components thereof without engineering or new reagents, e.g., by simply reversing binding and combining with additional agents or reagents, under conditions where reversible binding is induced. For example, by being able to reversibly bind various stimulatory agents to the same multimerization reagent, either at the same time or at different times, the user of the provided methods and compositions may adjust the nature of the particular signal being delivered, e.g., by substituting one or more stimulatory agent for another one or more stimulatory agent, such as to induce a stronger or weaker or qualitatively different signal, depending on the desired outcome.

In some embodiments, temporal control and modularity are used in combination, e.g., by incubating cells in the presence of one agent for a certain period of time, inducing reversal of binding by disruption, followed by incubation in the presence of other or more different agents or reagents. For example, in one embodiment, T cells are initially stimulated with a reagent to deliver a particular strength or quality of signal, and after a certain period of time, such signal is disrupted and a qualitatively or quantitatively different (e.g., stronger or weaker or activating different signaling pathways or known to be important for different differentiation pathways) signal is substituted. In some embodiments, such control provides advantages, for example, allowing the user to maximize desired outcomes (e.g., expansion or persistence) while avoiding undesirable outcomes such as exhaustion or anergy.

In some embodiments, temporal control is achieved by disrupting the reversible binding of the reagents or agents, such as by the addition of a substance. For example, in some embodiments, within a period of time, e.g., within 5 days after initiation of the incubation, and/or within a certain percentage of the total length of the incubation, such as within $1/5$, $1/4$, $1/3$, or $1/2$ of the time, the reversible binding between the receptor-binding agent and the reagent is disrupted. Thus, in some cases the method results in the generation of cultured T cells.

In some embodiments, the incubation is performed under conditions in which the receptor-binding agent specifically binds to the molecule, thereby inducing or modulating the signal in one or more T cells in the composition.

In some embodiments, the disruption of the binding between the receptor-binding agent and the reagent is effected more than 30 minutes after the initiation of the incubation. For example, in some aspects, the disruption of the binding between the receptor-binding agent and the reagent is effected between 1 hour and 4 days after initiation of the incubation, between 6 hours and 3 days after initiation of the incubation, between 12 hours and 2 days after initiation of the incubation, or between 1 day and 3 days after initiation of the incubation. In some cases, the disruption of the binding between the receptor-binding agent and the reagent is effected between about 1 hour and about 4 days after initiation of the incubation, between about 6 hours and about 3 days after initiation of the incubation, between about 12 hours and about 2 days after initiation of the incubation, or between about 1 day and about 3 days after initiation of the incubation. In some aspects, the disruption is effected greater than or equal to about 1 hour after initiation of said incubation and within 1 day, 2 days, 3 days or 4 days after initiation of the incubation. In some embodiments, binding of the receptor-binding agent is capable of initiating or does initiates a TCR/CD3 complex-associated signal in the T cells. In some aspects, the receptor-binding agent specifically binds to a member of a TCR/CD3 complex. In some instances, the receptor-binding agent specifically binds to CD3.

In some embodiments, the molecule (the molecule on the surface of the T cells) is a component of the TCR/CD3 complex or is CD3. In some aspects, the molecule is a first molecule and the receptor-binding agent is further capable of specifically binding to a second molecule on the surface of one or more of the T cells. In some cases the second molecule is capable of inducing or enhancing, dampening, or modifying a signal delivered through the first molecule in the T cells.

In some aspects, the receptor-binding agent includes a binding partner C1. In some aspects, the plurality of binding sites contained by the reagent includes two or more binding sites, Z1. In some instances, the two or binding sites Z1 each are capable of binding to the binding partner C1 to form the reversible bond between the receptor-binding agent and the reagent. In some embodiments, the disruption of the binding between the receptor-binding agent and the reagent includes introducing to the cells a composition containing a substance capable of reversing the bond between the receptor-binding agent and the reagent.

In some embodiments, the receptor-binding agent is a first receptor-binding agent and the incubation is further carried out in the presence of a second receptor-binding agent, which is capable of specifically binding to a second molecule on the surface of one or more of the T cells. In some embodiments, the binding of the second receptor-binding agent to the second molecule or does enhance, dampen, or modify a signal delivered through the first molecule in the T cells.

In some embodiments, the reagent contains a plurality of binding sites capable of reversibly binding to the second receptor-binding agent. In some such cases, the second receptor-binding agent is reversibly bound to the reagent. In some aspects, the plurality of binding sites capable of reversibly binding to the first receptor-binding agent and the plurality of binding sites capable of reversibly binding to the second receptor-binding agent can be the same or can be different.

In some aspects, the second receptor-binding agent includes a binding partner C1 or C2, which is capable of reversibly binding to the two or more binding sites Z1. In some such instances, the first and second receptor-binding agents are reversibly bound to the reagent via the two or more binding sites Z1. In some cases, the second receptor-binding agent contains a binding partner C2 and the reagent further contains a plurality of binding sites Z2. The plurality of binding sites Z2 may be capable of binding to the binding partner C2 to form the reversible bond between the second receptor-binding agent and the reagent. In some aspects, C2 and C1 are the same or substantially the same, or contain the same or substantially the same moiety. In some instances, Z1 and Z2 are the same or substantially the same or contain the same or substantially the same moiety.

In some cases, the reagent is a first reagent and the incubation is carried out in the presence of at least a second reagent which is reversibly bound to the second receptor-binding agent. In some embodiments, the incubation is performed under conditions in which the second receptor-binding agent specifically binds to the second molecule. In some such aspects, the bind of the second receptor-binding agent to the second molecule induces or modulates a signal, e.g., that enhances, dampens, or modifies a signal delivered through the first molecule in the T cells.

In some embodiments, said disruption includes introducing to the cells a composition that contains a substance capable of reversing the bond between the first receptor-binding agent and the reagent and/or the second receptor-binding agent and the reagent. In some embodiments, said disruption terminates or lessens the signal induced or modulated by the first receptor-binding agent and terminates or lessens the signal induced or modulated by the second receptor-binding agent.

Provided herein in some embodiments is a method for culturing T cells that includes incubating a composition containing T cells in the presence of a first receptor-binding agent that is capable of specifically binding to a first molecule expressed on the surface of the T cells. In some aspects, the binding of the first receptor-binding agent to the first molecule induces or modulates a TCR/CD3 complex-associated signal in the T cell. In some such embodiments, the composition further is incubated in the presence of a second receptor-binding agent that is reversibly bound to a reagent containing a plurality of binding sites capable of reversibly binding to the second receptor-binding agent. In some aspects, the second receptor-binding agent is capable of specifically binding to a second molecule on the surface of the T cells. In some cases, the binding of the second receptor-binding agent to the second molecule induces or modulates a second signal in the T cell, such as to enhance, dampen or modify a signal delivered through the first molecule. In some aspects, within 5 days after initiation of the incubation, the reversible binding between the second receptor-binding agent and the reagent is disrupted, thereby generating cultured T cells.

In some embodiments, the second signal enhances, dampens or modifies a signal delivered through the first molecule in the T cells.

In some embodiments of any of the methods provided herein, the incubation is performed under conditions in which the first receptor-binding agent specifically binds to the first molecule and/or the second receptor-binding agent specifically binds to the second molecule, thereby inducing or modulating one or more signals in the T cells. In some embodiments, said disruption is carried out greater than 30 minutes after initiation of said incubation. In some embodiments, said disruption is carried out between 1 hour and 4 days after initiation of said incubation, between 6 hours and 3 days after initiation of said incubation, between 12 hours and 2 days after initiation of said incubation or between 1 day and 3 days after initiation of said incubation; or said disruption is carried out between about 1 hour and about 4 days after initiation of said incubation, between about 6 hours and about 3 days after initiation of said incubation, between about 12 hours and about 2 days after initiation of said incubation or between about 1 day and about 3 days after initiation of said incubation; or said disruption is carried out greater than or equal to about 1 hour after initiation of said incubation and within 1 day, 2 days, 3 days or 4 days after initiation of said incubation.

In some embodiments, the second receptor-binding agent includes a binding partner C1. In some such embodiments, the plurality of binding sites contained by the reagent includes two or more binding sites, Z1, which each are capable of binding to the binding partner C1 to form the reversible bond between the second receptor-binding agent and the reagent.

In some embodiments of any of the methods provided herein, the second signal is a signal other than a TCR/CD3 complex-associated signal; the second signal is capable of enhancing or potentiating a TCR/CD3 complex-associated signal; or the second molecule is a costimulatory molecule, accessory molecule, cytokine receptor, chemokine receptor, immune checkpoint molecule or is a member of the TNF family or the TNF receptor family. In some embodiments, the second molecule is selected from among CD28, CD90 (Thy-1), CD95 (Apo-/Fas), CD137 (4-1BB), CD154 (CD40L), ICOS, LAT, CD27, OX40 and HVEM. In some embodiments, the second molecule is CD28.

In some embodiments, the second molecule is or includes an adhesion molecule or is a factor that induces cytokine production, chemokine production and/or expression of an adhesion molecule.

In some embodiments, the second receptor-binding agent specifically binds to a cytokine receptor selected from among IL-2R, IL-1R, IL-15R, IFN-gammaR, TNF-alphaR, IL-4R, IL-10R, Type I IFNR, IL-12R, IL-15R, IL-17R, TNFR1 and TNFR2. In some embodiments, the second receptor-binding agent is a ligand that specifically binds to a cytokine receptor selected from among IL-2R, IL-1R, IL-15R, IFN-gammaR, TNF-alphaR, IL-4R, IL-10R, Type I IFNR, IL-12R, IL-15R, IL-17R, TNFR1 and TNFR2; and/or the second receptor-binding agent is a ligand selected from among IL-2, IL-1, IL-15, IFN-gamma, TNF-alpha, IL-4, IL-10, IL-12, IL-15, IL-17 and TNF, or is a biologically active fragment thereof. In some embodiments, the second receptor-binding agent specifically binds to a cytokine receptor selected from among IL-12R, IFN-gammaR, IL-4R and IL-17R; or the second receptor-binding agent is a ligand selected from among IL-2, IL-4, IL-7, IL-10, IL-15 and IL-17 or is a biologically active fragment thereof.

In some embodiments, the second receptor-binding agent specifically binds to a cytokine receptor selected from among IL-7R, IL-21R and CD132 (IL receptor common gamma chain). In some embodiments, the second receptor-binding agent is a ligand that specifically binds to a cytokine receptor selected from among IL-7R, IL-21R and CD132 (IL receptor common gamma chain); and/or the second receptor-binding agent is a ligand selected from among IL-7, IL-21, IL-2, IL-4, IL-9 and IL-15, or is a biologically active fragment thereof. In some embodiments, the second receptor-binding agent specifically binds to a cytokine receptor selected from among IL-7R, IL-21R and CD132 (IL receptor common gamma chain); or the second receptor-binding agent is a ligand selected from among IL-7, IL-21, IL-2, IL-4, IL-9 and IL-15, or is a biologically active fragment thereof.

In some embodiments, the second receptor-binding agent specifically binds to a chemokine receptor selected from among CCR1, CCR2, CCR3, CCR4, CCR5, CCR7, CCR9, CXCR1, CXCR3 and CXCR4. In some embodiments, the second receptor-binding agent is a ligand that specifically binds to a cytokine receptor selected from among CCR1, CCR2, CCR3, CCR4, CCR5, CCR7, CCR9, CXCR1, CXCR3 and CXCR4; or the second receptor-binding agent is a ligand selected from among CXCL9, CXCL10, CCL19, CCL21 and CCL25 or is a biologically active fragment thereof. In some embodiments, the second receptor-binding agent specifically binds to a chemokine receptor selected from among CXCR3, CCR7, CXCR1 and CXCR4; or the second receptor-binding agent is a ligand selected from among CXCL9, CXCL10, CCL19, CCL21 and CCL25 or is a biologically active fragment thereof.

In some embodiments, the adhesion molecule is selected from among CD44, CD31, CD18/CD11a (LFA-1), CD29, CD54 (ICAM-1), CD62L (L-selectin), and CD29/CD49d (VLA-4), CD106 (VCAM-1) or is a biologically active fragment thereof. In some embodiments, the adhesion molecule is selected from among LFA-1, L-selectin, VCAM-1 and VLA-4 or is a biologically active fragment thereof.

In some embodiments, the factor is a nuclear factor. In some embodiments, the factor is a retinoic acid receptor-related orphan receptor gamma (RORgamma) or RORalpha.

In some embodiments, said disruption includes introducing to the cells a composition that contains a substance capable of reversing the bond between the second receptor-binding agent and the reagent. In some embodiments, said disruption terminates or lessens the signal induced or modulated by the second receptor-binding agent. For example, in some embodiments, the second molecule is CD28 and the disruption terminates or lessens the CD28 costimulatory signal in the T cells.

In some embodiments, the incubation is further carried out in the presence of a third receptor-binding agent, which is capable of specifically binding to a third molecule on the surface of one or more of the T cells.

In some embodiments of any of the methods provided herein, the first receptor-binding agent specifically binds to a first molecule expressed on the surface of the T cells in a manner that induces or modulates a TCR/CD3 complex-associated signal in the T cell; the second receptor-binding agent specifically binds to the second molecule, thereby inducing or modulating a second signal in the T cells; and the third receptor-binding agent specifically binds to a third molecule on the surface of the T cells that induces or modulates a further signal in the cell.

In some embodiments, the first molecule is CD3.

In some embodiments, the second signal enhances, dampens or modifies a signal delivered through the first molecule. In some embodiments, the second molecule is a costimulatory molecule, accessory molecule, cytokine receptor, chemokine receptor, immune checkpoint molecule or is a member of the TNF family or the TNF receptor family. In some embodiments, the second molecule is selected from among CD28, CD90 (Thy-1), CD95 (Apo-/Fas), CD137 (4-1BB), CD154 (CD40L), ICOS, LAT, CD27, OX40 and HVEM. In some embodiments, the second molecule is CD28.

In some embodiments, the third molecule is a cytokine receptor, a chemokine receptor, or is or includes an adhesion molecule or is a factor that induces cytokine production, chemokine production and/or expression of an adhesion molecule. In some embodiments, the third receptor-binding agent specifically binds to a cytokine receptor selected from among IL-2R, IL-1R, IL-15R, IFN-gammaR, TNF-alphaR, IL-4R, IL-10R, Type I IFNR, IL-12R, IL-15R, IL-17R, TNFR1 and TNFR2. In some embodiments, the third receptor-binding agent is a ligand that specifically binds to a cytokine receptor selected from among IL-2R, IL-1R, IL-15R, IFN-gammaR, TNF-alphaR, IL-4R, IL-10R, Type I IFNR, IL-12R, IL-15R, IL-17R, TNFR1 and TNFR2; and/or the third receptor-binding agent is a ligand selected from among IL-2, IL-1, IL-15, IFN-gamma, TNF-alpha, IL-4, IL-10, IL-12, IL-15, IL-17 and TNF, or is a biologically active fragment thereof.

In some embodiments, the third receptor-binding agent specifically binds to a cytokine receptor selected from among IL-12R, IFN-gammaR, IL-4R and IL-17R; or the third receptor-binding agent is a ligand selected from among IL-2, IL-4, IL-7, IL-10, IL-15 and IL-17 or is a biologically active fragment thereof. In some embodiments, the third receptor-binding agent specifically binds to a cytokine receptor selected from among IL-7R, IL-21R and CD132 (IL receptor common gamma chain). In some embodiments, the third receptor-binding agent is a ligand that specifically binds to a cytokine receptor selected from among IL-7R, IL-21R and CD132 (IL receptor common gamma chain); and/or the third receptor-binding agent is a ligand selected from among IL-7, IL-21, IL-2, IL-4, IL-9 and IL-15, or is a biologically active fragment thereof. In some embodiments, the third receptor-binding agent specifically binds to a cytokine receptor selected from among IL-7R, IL-21R and CD132 (IL receptor common gamma chain); or the third receptor-binding agent is a ligand selected from among IL-7, IL-21, IL-2, IL-4, IL-9 and IL-15, or is a biologically active fragment thereof.

In some embodiments, the third receptor-binding agent specifically binds to a chemokine receptor selected from among CCR1, CCR2, CCR3, CCR4, CCR5, CCR7, CCR9, CXCR1, CXCR3 and CXCR4. In some embodiments: the third receptor-binding agent is a ligand that specifically binds to a cytokine receptor selected from among CCR1, CCR2, CCR3, CCR4, CCR5, CCR7, CCR9, CXCR1, CXCR3 and CXCR4; or the third receptor-binding agent is a ligand selected from among CXCL9, CXCL10, CCL19, CCL21 and CCL25 or is a biologically active fragment thereof. In some embodiments, the third receptor-binding agent specifically binds to a chemokine receptor selected from among CXCR3, CCR7, CXCR1 and CXCR4; or the third receptor-binding agent is a ligand selected from among CXCL9, CXCL10, CCL19, CCL21 and CCL25 or is a biologically active fragment thereof.

In some embodiments, the adhesion molecule is selected from among CD44, CD31, CD18/CD11a (LFA-1), CD29, CD54 (ICAM-1), CD62L (L-selectin), and CD29/CD49d (VLA-4), CD106 (VCAM-1) or is a biologically active fragment thereof. In some embodiments, the adhesion molecule is selected from among LFA-1, L-selectin, VCAM-1 and VLA-4 or is a biologically active fragment thereof.

In some embodiments, the factor is a nuclear factor. In some embodiments, the factor is a retinoic acid receptor-related orphan receptor gamma (RORgamma) or RORalpha.

In some embodiments, the third receptor-binding agent is reversibly bound to the first reagent or the second reagent; or the incubation is carried out in the presence of a further reagent that is reversibly bound to the third receptor-binding agent.

In some embodiments of any of the methods provided herein, the method also includes, after said disruption, further incubating the composition that contains the T cells. In some embodiments, the incubation and further incubation are carried out in the same vessel; and/or the further incubation is carried out in the presence of the substance; and/or the method does not comprise removing the substance, receptor-binding agent, second receptor-binding agent and/or reagent from the cell composition prior to the further incubation.

In some embodiments, the incubation and/or further incubation is carried out at or about 37° C.±2° C.; and/or the incubation and/or further incubation is carried out in the presence of a further agent that is capable of delivering a signal to T cells. In some embodiments, the further agent is capable of enhancing or inducing proliferation of T cells, CD4+ T cells and/or CD8+ T cells. In some embodiments, the further agent is a cytokine selected from among IL-2, IL-15 and IL-7. In some embodiments, the further incubation is carried out for a time that is no more than 14 days, no more than 12 days, no more than 10 days, no more than 8 days or no more than 6 days.

Provided herein are methods for culturing T cells that include: incubating a composition that contains T cells in the presence of a receptor-binding agent that specifically binds to a CD28 molecule on the surface of T cells under conditions to effect signaling through CD28 in the cells; and within 5 days after initiation of said incubation, eliminating or reducing the binding of the receptor-binding agent and the CD28 molecule, whereby the CD28 signaling is terminated or lessened in the cells, thereby generating cultured T cells. In some embodiments, the elimination or reduction is carried out within 4 days, within 3 days, within 2 days or within 1 day after initiation of the incubation.

In some instances, the elimination or reduction is effected within 4 days, within 3 days, within 2 days or within 1 day after initiation of the incubation. In some cases, the eliminating or reducing includes washing the cells, whereby any receptor-binding agent that is not specifically bound to CD28 is removed or reduced from the composition. In some aspects, the eliminating includes reversing the binding interaction between the receptor-binding agent and the CD28 molecule, further including washing the cells to remove or reduce the receptor-binding agent from the composition.

In some aspects, during at least a portion of the incubation and/or subsequent to the incubation, T cells in the composition are incubated in the presence of an agent that specifically binds a molecule of the TCR/CD3 complex, whereby a TCR/CD3 complex-associated signal is induced or modulated in the cells.

Provided herein in some aspects is a method for culturing T cells including incubating a composition containing T cells in the presence of a receptor-binding agent. In some embodiments, the receptor-binding agent is reversibly bound to a reagent containing a plurality of binding sites capable of reversibly binding to the receptor-binding agent. In some cases, the receptor-binding agent is capable of specifically binding to a molecule on the surface of the target cells other than CD28, CD3 or CD40 in a manner that induces or modulates a signal in the target cells and/or alters a function of the target cells, thereby generating cultured target cells. In some embodiments, the molecule is not CD137 and/or the receptor-binding agent does not specifically bind to CD137.

In some aspects, the incubation is performed under conditions in which the receptor-binding agent specifically binds to the molecule, thereby inducing or modulating the signal in the T cells. In some embodiments, the signal is not a TCR/CD3 complex-associated signal.

In some embodiments, the signal is not a TCR/CD3 complex-associated signal.

In some embodiments, the receptor-binding agent includes a binding partner C1. In some such embodiments, the plurality of binding sites of the reagent includes two or more binding sites, Z1, which each are capable of binding to the binding partner C1 to form the reversible bond between the receptor-binding agent and the reagent.

In some embodiments, the molecule is selected from among CD90 (Thy-1), CD95 (Apo-/Fas), CD137 (4-1BB), CD154 (CD40L), ICOS, LAT, CD27, OX40 and HVEM; and/or the receptor-binding agent specifically binds to CD90 (Thy-1), CD95 (Apo-/Fas), CD137 (4-1BB), CD154 (CD40L), ICOS, LAT, CD27, OX40 or HVEM.

In some embodiments, the receptor-binding agent is a second receptor-binding agent and the molecule is a second molecule, and the incubation is further carried out in the presence of a first receptor-binding agent, which is capable of specifically binding to a first molecule on the surface of one or more of the T cells, which first molecule is optionally capable of inducing or modulating a first signal in one or more T cells in the composition. In some embodiments, the first receptor-binding agent is reversibly bound to the reagent, said reagent that includes a plurality of binding sites for the first receptor-binding agent and the second receptor-binding agent; or the first receptor-binding agent is reversibly bound to a second reagent that includes a plurality of binding sites capable of reversibly binding to the first receptor-binding agent.

In some embodiments, the first receptor-binding agent is capable of initiating a TCR/CD3 complex-associated signal in the T cells. In some aspects, the first receptor-binding agent specifically binds to a member of a TCR/CD3 complex. In some cases, the first receptor-binding agent specifically binds to CD3.

In some embodiments, the specific binding of the second receptor-binding agent to the second molecule is capable of enhancing, dampening or modifying a signal delivered through the first molecule. In some cases, the specific binding of the second receptor-binding agent to the second molecule is capable of enhancing or potentiating a TCR/CD3 complex-associated signal.

Provided herein in some embodiments is a method for culturing T cells, which method includes incubating a composition containing T cells in the presence of a first receptor-binding agent which is reversibly bound to a reagent containing a plurality of binding sites capable of reversibly binding to the first receptor-binding agent. In some cases, first receptor-binding agent is capable of specifically binding to a first molecule on the surface of the T cells, such as to induce or modulate a TCR/CD3 complex-associated signal in T cells in the composition. In some embodiments, the method includes incubating the composition containing the T cells in the presence of a second receptor-binding agent which may be reversibly bound to the reagent further containing a plurality of binding sites for the second receptor-binding agent or to a second reagent containing a plurality of binding sites capable of reversibly binding to the second receptor-binding agent. In some aspects, the second receptor-binding agent is capable of specifically binding to a second molecule on the surface of T cells such as to induce or modulate a second signal in T cells in the composition. In some aspects, the second molecule is other than CD28. In some embodiments, the incubation is performed under conditions in which the signal and/or second signal are induced or modulated in T cells in the composition, thereby generating cultured T cells.

In some embodiments, the first receptor-binding agent specifically binds to a member of a TCR/CD3 complex and/or the first receptor-binding agent specifically binds to CD3.

In some instances, the specific binding of the second receptor-binding agent to the second molecule is capable of inducing or modulating a signal other than a TCR/CD3 complex-associated signal. In some aspects, the specific binding of the second receptor-binding agent to the second molecule is capable of enhancing, dampening or modifying a signal delivered through the first molecule. In some embodiments, the specific binding of the second receptor-binding agent to the second molecule is capable of enhancing or potentiating a TCR/CD3 complex-associated signal.

In some embodiments, the molecule, which can be the second molecule, is CD90 (Thy-1), CD95 (Apo-/Fas), CD137, (4-1BB), CD154 (CD40L), ICOS, LAT, CD27, OX40 or HVEM. In some aspects, the receptor-binding agent, which can be the second receptor-binding agent, specifically binds to CD90 (Thy-1), CD95 (Apo-/Fas), CD137 (4-1BB), CD154 (CD40L), ICOS, LAT, CD27, OX40 or HVEM. In some embodiments, the molecule, which can be a second molecule, is not CD137 and/or the receptor-binding agent, which can be the second receptor-binding agent, does not specifically bind to CD137.

In some aspects, the first receptor-binding agent and the second receptor-binding agent reversibly bind to the reagent. In some embodiments, the first receptor-binding agent and second receptor-binding agent each individually include a binding partner C1, and the plurality of binding sites includes two or more binding site, Z1, which each are capable of binding to the binding partner C1 to form the reversible bond between the first and second receptor-binding agent and the reagent. In other embodiments, the first receptor-binding agent includes a binding partner C1, the second receptor-binding agent includes a binding partner C2, and the plurality of binding sites includes two or more binding sites, Z1, which each are capable of binding to the binding partner C1 and the binding partner C2 to form the reversible bond between the first and second receptor-binding agent and the reagent. In still further embodiments, the first receptor-binding agent includes a binding partner C1, the second receptor binding agent includes a binding partner C2, and the plurality of binding sites includes two or more binding site, Z1, which each are capable of binding to the binding partner C1 to form the reversible bond between the first receptor-binding agent and the reagent and two or more binding site, Z2, which each are capable of binding to the binding partner C2 to form the reversible bond between the second receptor-binding agent and the reagent.

In some embodiments, the receptor-binding agent specifically binds to a cytokine receptor selected from among IL-2R, IL-1R, IL-15R, IFN-gammaR, TNF-alphaR, IL-4R, IL-10R, Type I IFNR, IL-12R, IL-15R, IL-17R, TNFR1 and TNFR2. In some embodiments, the receptor-binding agent is a ligand that specifically binds to a cytokine receptor selected from among IL-2R, IL-1R, IL-15R, IFN-gammaR, TNF-alphaR, IL-4R, IL-10R, Type I IFNR, IL-12R, IL-15R, IL-17R, TNFR1 and TNFR2; and/or the receptor-binding agent is a ligand selected from among IL-2, IL-1, IL-15, IFN-gamma, TNF-alpha, IL-4, IL-10, IL-12, IL-15, IL-17 and TNF, or is a biologically active fragment thereof. In some embodiments, the receptor-binding agent specifically binds to a cytokine receptor selected from among IL-12R, IFN-gammaR, IL-4R and IL-17R; or the receptor-binding agent is a ligand selected from among IL-2, IL-4, IL-7, IL-10, IL-15 and IL-17 or is a biologically active fragment thereof.

In some embodiments, the receptor-binding agent specifically binds to a cytokine receptor selected from among IL-7R, IL-21R and CD132 (IL receptor common gamma chain). In some embodiments, the receptor-binding agent is a ligand that specifically binds to a cytokine receptor selected from among IL-7R, IL-21R and CD132 (IL receptor common gamma chain); and/or the receptor-binding agent is a ligand selected from among IL-7, IL-21, IL-2, IL-4, IL-9 and IL-15, or is a biologically active fragment thereof. In some embodiments, the receptor-binding agent specifically binds to a cytokine receptor selected from among IL-7R, IL-21R and CD132 (IL receptor common gamma chain); or the receptor-binding agent is a ligand selected from among IL-7, IL-21, IL-2, IL-4, IL-9 and IL-15, or is a biologically active fragment thereof.

In some embodiments, the receptor-binding agent specifically binds to a chemokine receptor selected from among CCR1, CCR2, CCR3, CCR4, CCR5, CCR7, CCR9, CXCR1, CXCR3 and CXCR4. In some embodiments, the receptor-binding agent is a ligand that specifically binds to a cytokine receptor selected from among CCR1, CCR2, CCR3, CCR4, CCR5, CCR7, CCR9, CXCR1, CXCR3 and CXCR4; or the receptor-binding agent is a ligand selected from among CXCL9, CXCL10, CCL19, CCL21 and CCL25 or is a biologically active fragment thereof. In some embodiments, the receptor-binding agent specifically binds to a chemokine receptor selected from among CXCR3, CCR7, CXCR1 and CXCR4; or the receptor-binding agent is a ligand selected from among CXCL9, CXCL10, CCL19, CCL21 and CCL25 or is a biologically active fragment thereof.

In some embodiments, the adhesion molecule is selected from among CD44, CD31, CD18/CD11a (LFA-1), CD29, CD54 (ICAM-1), CD62L (L-selectin), and CD29/CD49d (VLA-4), CD106 (VCAM-1) or is a biologically active fragment thereof. In some embodiments, the adhesion molecule is selected from among LFA-1, L-selectin, VCAM-1 and VLA-4 or is a biologically active fragment thereof.

In some embodiments, the factor is a nuclear factor. In some embodiments, the factor is a retinoic acid receptor-related orphan receptor gamma (RORgamma) or RORalpha.

In some embodiments of any of the methods provided herein, the incubation is performed under conditions in which the receptor-binding agent specifically binds to the molecule, thereby inducing or modulating the signal in the target cells and/or altering a function in the target cells. In some embodiments, the receptor-binding agent includes a binding partner C1, and the plurality of binding sites includes two or more binding site, Z1, which each are capable of binding to the binding partner C1 to form the reversible bond between the receptor-binding agent and the reagent. In some embodiments, the receptor-binding agent is an additional receptor-binding agent and the molecule is an additional molecule, and the incubation is further carried out in the presence of a first receptor-binding agent, which is capable of specifically binding to a first molecule on the surface of one or more of the T cells, which first molecule is optionally capable of inducing or modulating a first signal in one or more T cells in the composition.

In some embodiments, the first receptor-binding agent is reversibly bound to the reagent, said reagent that includes a plurality of binding sites for the first receptor-binding agent and the additional receptor-binding agent; or the first receptor-binding agent is reversibly bound to a second reagent that includes a plurality of binding sites capable of reversibly binding to the first receptor-binding agent. In some embodiments, the first receptor-binding agent is capable of initiating a TCR/CD3 complex-associated signal in the T cells; and/or the first receptor-binding agent specifically binds to a member of a TCR/CD3 complex; and/or the first receptor-binding agent specifically binds to CD3.

In some embodiments, the first receptor-binding agent includes a binding partner C2, and the plurality of binding sites includes two or more binding site, Z2, which each are capable of binding to the binding partner C2 to form the reversible bond between the first receptor-binding agent and the reagent.

In some embodiments, the incubation is further carried out in the presence of a second receptor-binding agent, which is capable of specifically binding to a second molecule on the surface of one or more of the T cells, which second molecule is optionally capable of inducing or modulating a signal in target cells in the composition to enhance, dampen or modify a signal delivered through the first molecule.

In some embodiments, the second signal is a signal other than a TCR/CD3 complex-associated signal; the second signal is capable of enhancing or potentiating a TCR/CD3 complex-associated signal; or the second molecule is a costimulatory molecule, accessory molecule, cytokine receptor, chemokine receptor, immune checkpoint molecule or is a member of the TNF family or the TNF receptor family. In some embodiments, the second molecule is selected from among CD90 (Thy-1), CD95 (Apo-/Fas), CD137 (4-1BB), CD154 (CD40L), ICOS, LAT, CD27, OX40 and HVEM; and/or the second receptor-binding agent specifically binds to CD90 (Thy-1), CD95 (Apo-/Fas), CD137 (4-1BB), CD154 (CD40L), ICOS, LAT, CD27, OX40 or HVEM. In some embodiments, the second molecule is selected from among CD28 and CD137. In some embodiments, the second molecule is CD28.

Provided herein are methods for culturing target cells, which method includes incubating a composition containing target cells in the presence of a receptor-binding agent. The receptor-binding agent may be reversibly bound to a reagent that is a streptavidin analog or mutein containing a plurality of binding sites capable of reversibly binding to the receptor-binding agent. In some cases, the receptor-binding agent is capable of specifically binding to a molecule on the surface of the target cells, such as to induce or modulate a signal in target cells in the composition. In some aspects, the mutein streptavidin includes a net negative charge or exhibits an isoelectric point less than the streptavidin mutein comprising the sequence set forth in SEQ ID NO:4 or 6, thereby generating cultured target cells.

Provided herein in some aspects is a method for culturing target cells, the method including incubating a composition containing target cells in the presence of a receptor-binding agent that is reversibly bound to a reagent that is a streptavidin analog or mutein containing a plurality of binding sites capable of reversibly binding to the receptor-binding agent. In some embodiments, the receptor-binding agent is capable of specifically binding to a molecule on the surface of the target cells in a manner that induces or modulates a signal in target cells in the composition. In some cases, the streptavidin analog or mutein exhibits a higher affinity for a streptavidin-binding peptide containing the sequence of amino acids Trp-Ser-His-Pro-Gln-Phe-Glu-Lys (SEQ ID NO: 8) than a streptavidin or mutein containing the sequence of amino acids set forth in any of SEQ ID NOS: 1-6, thereby generating cultured target cells.

In some embodiments, the incubation is performed under conditions in which the receptor-binding agent specifically binds to the molecule, thereby inducing or modulating the signal in one or more target cells in the composition.

In some instances, the plurality of binding sites of the reagent includes two or more binding sites, Z1. In some cases, the receptor-binding agent includes a binding partner C1, which is capable of reversibly binding to the binding site Z1, wherein the reversible binding between C1 and Z1 effects the reversible binding between the receptor-binding agent and the reagent. In some embodiments, the streptavidin analog or mutein includes a plurality of binding sites Z1, and a plurality of receptor-binding agents are reversibly bound to the reagent.

In some embodiments, the target cells comprise immune cells. For example, in some embodiments, the target cells comprise blood cells; the target cells comprise leukocytes; the target cells comprise lymphocytes; the target cells comprise B cells; the target cells comprise a B cell population; the target cells comprise T cells; the target cells comprise a T cell population; and/or the target cells comprise natural killer (NK) cells. In some embodiments, the target cells comprise antigen-specific T cells or a population thereof, a T helper cell or population thereof, a cytotoxic T cell or population thereof, a memory T cell or population thereof, a regulatory T cell or population thereof, an NK cell or population thereof, antigen-specific B cells or a population thereof, a memory B cell or population thereof, or a regulatory B cell or population thereof. In some embodiments, the target cells are T cells.

In some embodiments, the molecule is present on the surface of T cells, and the receptor-binding agent is capable of inducing or modulating a signal in T cells in the composition. In some aspects, the receptor-binding agent is capable of initiating a TCR/CD3 complex-associated signal in the T cells and/or the receptor-binding agent specifically binds to a member of a TCR/CD3 complex. In some cases, the receptor-binding agent, specifically binds to CD3. In some instances, the molecule is a first molecule and the receptor-binding agent is capable of specifically binding to the first molecule and, in some cases, a second molecule on the surface of one or more of the target cells. In some embodiments, binding to the second molecule is capable of enhancing, dampening, or modifying a signal delivered through the first molecule.

In some embodiments, the molecule is a first molecule and the receptor-binding agent is capable of specifically binding to the first molecule and a second molecule on the surface of one or more of the target cells, which binding to the second molecule induces or modulates a signal in the target cells. In some embodiments, binding to the second molecule is optionally capable of enhancing, dampening, or modifying a signal delivered through the first molecule.

, the receptor-binding agent is a first receptor-binding agent and the incubation is further carried out in the presence of a second receptor-binding agent. The second receptor-binding agent may be capable of specifically binding to a second molecule on the surface of one or more of the target cells. In some cases, binding of the second receptor-binding agent to the second molecule is capable of inducing or modulating a signal to enhance, dampen, or modify a signal delivered through the first molecule.

In some embodiments, the incubation is performed under conditions in which the second receptor-binding agent specifically binds to the second molecule, thereby inducing or modulating a signal in target cells in the composition to enhance, dampen or modify a signal delivered through the first molecule. In some embodiments, the streptavidin mutein or analog includes a plurality of binding sites capable of reversibly binding to the second receptor-binding agent, whereby the second receptor-binding agent is reversibly bound to the streptavidin mutein or analog.

In some embodiments, the second receptor-binding agent includes a binding partner C1 or C2, which is capable of reversibly binding to the two or more binding sites Z2 present in the streptavidin analog or mutein.

In some cases, the additional molecule is CD28, CD90 (Thy-1), CD95 (Apo-/Fas), CD137 (4-1BB), CD154 (CD40L), ICOS, LAT, CD27, OX40 or HVEM. In some embodiments, the second receptor-binding agent specifically binds to CD28, CD90 (Thy-1), CD95 (Apo-/Fas), CD137 (4-1BB), CD154 (CD40L), ICOS, LAT, CD27, OX40 or HVEM. In some aspects, the additional molecule is CD40 and CD137. In some instances, the second receptor-binding agent specifically binds to CD40 or CD137.

In some embodiments, the second molecule is or includes an adhesion molecule or is a factor that induces cytokine production, chemokine production and/or expression of an adhesion molecule.

In some embodiments, the second receptor-binding agent specifically binds to a cytokine receptor selected from among IL-2R, IL-1R, IL-15R, IFN-gammaR, TNF-alphaR, IL-4R, IL-10R, Type I IFNR, IL-12R, IL-15R, IL-17R, TNFR1 and TNFR2. In some embodiments, the second receptor-binding agent is a ligand that specifically binds to a cytokine receptor selected from among IL-2R, IL-1R, IL-15R, IFN-gammaR, TNF-alphaR, IL-4R, IL-10R, Type I IFNR, IL-12R, IL-15R, IL-17R, TNFR1 and TNFR2; and/or the second receptor-binding agent is a ligand selected from among IL-2, IL-1, IL-15, IFN-gamma, TNF-alpha, IL-4, IL-10, IL-12, IL-15, IL-17 and TNF, or is a biologically active fragment thereof. In some embodiments, the second receptor-binding agent specifically binds to a cytokine receptor selected from among IL-12R, IFN-gammaR, IL-4R and IL-17R; or the second receptor-binding agent is a ligand selected from among IL-2, IL-4, IL-7, IL-10, IL-15 and IL-17 or is a biologically active fragment thereof.

In some embodiments, the second receptor-binding agent specifically binds to a cytokine receptor selected from among IL-7R, IL-21R and CD132 (IL receptor common gamma chain). In some embodiments, the second receptor-binding agent is a ligand that specifically binds to a cytokine receptor selected from among IL-7R, IL-21R and CD132 (IL receptor common gamma chain); and/or the second receptor-binding agent is a ligand selected from among IL-7, IL-21, IL-2, IL-4, IL-9 and IL-15, or is a biologically active fragment thereof. In some embodiments, the second receptor-binding agent specifically binds to a cytokine receptor selected from among IL-7R, IL-21R and CD132 (IL receptor common gamma chain); or the second receptor-binding agent is a ligand selected from among IL-7, IL-21, IL-2, IL-4, IL-9 and IL-15, or is a biologically active fragment thereof.

In some embodiments, the second receptor-binding agent specifically binds to a chemokine receptor selected from among CCR1, CCR2, CCR3, CCR4, CCR5, CCR7, CCR9, CXCR1, CXCR3 and CXCR4. In some embodiments, the second receptor-binding agent is a ligand that specifically binds to a cytokine receptor selected from among CCR1, CCR2, CCR3, CCR4, CCR5, CCR7, CCR9, CXCR1, CXCR3 and CXCR4; or the second receptor-binding agent is a ligand selected from among CXCL9, CXCL10, CCL19, CCL21 and CCL25 or is a biologically active fragment thereof. In some embodiments, the second receptor-binding agent specifically binds to a chemokine receptor selected from among CXCR3, CCR7, CXCR1 and CXCR4; or the second receptor-binding agent is a ligand selected from among CXCL9, CXCL10, CCL19, CCL21 and CCL25 or is a biologically active fragment thereof.

In some embodiments, the adhesion molecule is selected from among CD44, CD31, CD18/CD11a (LFA-1), CD29, CD54 (ICAM-1), CD62L (L-selectin), and CD29/CD49d (VLA-4), CD106 (VCAM-1) or is a biologically active fragment thereof. In some embodiments, the adhesion molecule is selected from among LFA-1, L-selectin, VCAM-1 and VLA-4 or is a biologically active fragment thereof.

In some embodiments, the factor is a nuclear factor. In some embodiments, the factor is a retinoic acid receptor-related orphan receptor gamma (RORgamma) or RORalpha.

, the second receptor-binding agent includes a plurality of different receptor-binding agents, each of which is capable of individually binding to the same or different second molecule on the surface of T cells in the composition to collectively induce or modulate one or more signals in the cells.

In some embodiments, the method further includes disrupting the reversible binding between the first and/or second receptor-binding agent and the reagent. In some aspects, the disruption is effected within 14 days after initiation of the incubation, within 12 days after initiation of the incubation, within 10 days after initiation of the incubation within 8 days after initiation of the incubation or within 6 days after initiation of the incubation.

In some embodiments, at least a portion of the incubation is carried out in the presence of a further agent that is capable of delivering a signal to T cells. In some cases, the further agent is capable of enhancing or inducing proliferation of T cells, CD4+ T cells and/or CD8+ T cells. In some embodiments, the further agent is a cytokine such as IL-2, IL-15 or IL-7. In some instances, the further agent does not specifically bind to CD28 and/or induce CD28 signaling.

In some embodiments, the T cells or target cells are primary cells from a subject. In some cases, the T cells or target cells are directly isolated from a subject. In some embodiments, the T cells are unfractionated T cells, are enriched or isolated CD3+ T cells, are enriched or isolated CD4+ T cells, or are enriched or isolated CD8+ T cells. In some embodiments, prior to the incubating the T cells are not enriched for CD62L+ cells and/or are not enriched for naïve T cells. In some cases, the T cells or target cells are human cells.

In some aspects, the reagent has a size that is less than 20 nm, less than 10 nm, less than 5 nm or less than 1 nm. In some instances, the reagent has a density of less than 1.2 g/cm3 or less than 1.0 g/cm3.

In some embodiments, the reagent is not, and is not bound to or associated with, a solid support, stationary phase, a bead, a microparticle, a magnetic particle, and/or a matrix during said incubation; and/or the reagent is flexible, does not contain a metal or magnetic core, is comprised entirely or primarily of organic multimer, is not spherical, is not substantially spherical or uniform in shape and/or is not rigid.

In some embodiments, the reagent is not bound to a support or a solid support during said incubation. In some embodiments, the reagent is bound to a support during at least a portion of the incubation, whereby a plurality of the T cells or target cells are reversibly immobilized on the support during at least a portion of the incubation. In some embodiments, the support is or includes a stationary phase; and/or the support is or includes a solid support.

In some embodiments, the receptor-binding agent, which can be the first receptor-binding agent, contains only one binding site, such as B2. In some aspects, the receptor-binding agent, which can be the first receptor-binding agent, specifically binds to the molecule in a monovalent manner. In some embodiments, the second receptor-binding agent contains only one binding site, such as B4. In some cases, the second receptor-binding agent specifically binds to the molecule in a monovalent manner. In some embodiments, the binding site, such as B2 or B4, contains an antibody combining site.

In some aspects, the receptor-binding agent, which can be a first receptor-binding agent, and/or the second receptor-binding agent each individually is an antibody fragment, a monovalent antibody fragment, a proteinaceous binding molecule with antibody-like binding properties, a molecule containing Ig domains, a cytokine, a chemokine, an aptamer, or MHC molecule or binding fragments thereof. In some such aspects, the receptor-binding agent, which can be the first receptor-binding agent, and/or the second receptor-binding agent include an antibody fragment, a Fab fragment, a divalent antibody fragment such as a F(ab')$_2$-fragment or a divalent single-chain Fv (scFv) fragment. In some cases, the receptor-binding agent, which can be the first receptor-binding agent, and/or the second receptor-binding agent is a monovalent antibody fragment such as a Fab fragment, an Fv fragment or an scFv fragment. In some instances, the receptor-binding agent, which can be the first receptor-binding agent, and/or the second receptor-binding agent is a proteinaceous binding molecule with antibody-like binding properties, such as an aptamer, mutein based on a polypeptide of the lipocalin family, glubody, protein based on the ankyrin scaffold, protein based on the crystalline scaffold, adnectin or an avimer.

In some embodiments, the receptor-binding agent, which can be the first receptor-binding agent, includes an agent that specifically binds to CD3. The agent that specifically binds CD3 can be an anti-CD3-antibody, a divalent antibody fragment of an anti-CD3 antibody, a monovalent antibody fragment of an anti-CD3-antibody, or a proteinaceous CD3 binding molecule with antibody-like binding properties. In some embodiments, the second receptor-binding agent includes an agent that specifically binds to CD28, CD90, CD95, CD137, CD154, ICOS, LAT, CD27, OX40 and/or HVEM. The agent that specifically binds to CD28, CD90, CD95, CD137, CD154, ICOS, LAT, CD27, OX40 and/or HVEM can be an anti-CD28-antibody, a divalent antibody fragment of an anti-CD28 antibody, an antibody fragment of an anti-CD28-antibody, a proteinaceous CD28 binding molecule with antibody-like binding properties, an anti-CD90-antibody, a divalent antibody fragment of an anti-CD90 antibody, an antibody fragment of an anti-CD90-antibody, a proteinaceous CD90 binding molecule with antibody-like binding properties, an anti-CD95-antibody, a divalent antibody fragment of an anti-CD95 antibody, an antibody fragment of an anti-CD95-antibody, a proteinaceous CD95 binding molecule with antibody-like binding properties, an anti-CD154-antibody, a divalent antibody fragment of an anti-CD154 antibody, a monovalent antibody fragment of an anti-CD154-antibody, a proteinaceous CD154 binding molecule with antibody-like binding properties, an anti-CD137-antibody, a divalent antibody fragment of an anti-CD137 antibody, a monovalent antibody fragment of an anti-CD137-antibody, a proteinaceous CD137 binding molecule with antibody-like binding properties, an anti-ICOS-antibody, a divalent antibody fragment of an anti-ICOS antibody, an antibody fragment of an anti-ICOS-antibody, a proteinaceous ICOS binding molecule with antibody-like binding properties, an anti-LAT-antibody, a divalent antibody fragment of an anti-LAT antibody, an antibody fragment of an anti-LAT-antibody, a proteinaceous LAT binding molecule with antibody-like binding properties, an anti-CD27-antibody, a divalent antibody fragment of an anti-CD27 antibody, an antibody fragment of an anti-CD27-antibody, a proteinaceous CD27 binding molecule with antibody-like binding properties, an anti-OX40-antibody, a divalent antibody fragment of an anti-OX40 antibody, an antibody fragment of an anti-OX40-antibody, a proteinaceous OX40 binding molecule with antibody-like binding properties, an anti-HVEM-antibody, a divalent antibody fragment of an anti-HVEM antibody, an antibody fragment of an anti-HVEM-antibody, a proteinaceous HVEM binding molecule with antibody-like binding properties, 4-1BB ligand, or any mixture thereof.

In some embodiments of any of the methods provided herein, the receptor-binding agent comprise an antibody fragment; the receptor-binding agent comprise a Fab fragment; the receptor-binding agent is a divalent antibody fragment selected from among a F(ab')$_2$-fragment and a divalent single-chain Fv (scFv) fragment; the receptor-binding agent is a monovalent antibody fragment selected from among a Fab fragment, an Fv fragment and an scFv fragment; and/or the receptor-binding agent is a proteinaceous binding molecule with antibody-like binding properties selected from among aptamers, muteins based on a polypeptide of the lipocalin family, glubodies, proteins based on the ankyrin scaffold, proteins based on the crystalline scaffold, adnectins and avimers.

In some embodiments of any of the methods provided herein, the reagent is or contains streptavidin, avidin, an analog or mutein of streptavidin that reversibly binds biotin, a biotin analog or a biologically active fragment thereof; an analog or mutein of avidin or streptavidin that reversibly binds a streptavidin-binding peptide; a reagent that includes at least two chelating groups K, wherein the at least two chelating groups are capable of binding to a transition metal ion; an agent capable of binding to an oligohistidine affinity tag; an agent capable of binding to a glutathione-S-transferase; calmodulin or an analog thereof; an agent capable of binding to calmodulin binding peptide (CBP); an agent capable of binding to a FLAG-peptide; an agent capable of binding to an HA-tag; an agent capable of binding to maltose binding protein (MBP); an agent capable of binding to an HSV epitope; an agent capable of binding to a myc epitope; or an agent capable of binding to a biotinylated carrier protein.

In some embodiments, the reagent is or contains a streptavidin analog or mutein or an avidin analog or mutein that reversibly binds to biotin or a biologically active fragment; a streptavidin analog or mutein or an avidin analog or mutein that reversibly binds to a biotin analog or a biologically active fragment; and/or a streptavidin analog or mutein or an avidin analog or mutein that reversibly binds to a streptavidin-binding peptide.

In some embodiments, the reagent is an oligomer or polymer of streptavidin, avidin, an analog or mutein of streptavidin that reversibly binds biotin or a biologically active fragment; a streptavidin or avidin analog or mutein that reversibly binds a streptavidin-binding peptide; a reagent that includes at least two chelating groups K, wherein the at least two chelating groups are capable of binding to a transition metal ion; an agent capable of binding to an oligohistidine affinity tag; an agent capable of binding to a glutathione-S-transferase; calmodulin or an analog thereof; an agent capable of binding to calmodulin binding peptide (CBP); an agent capable of binding to a FLAG-peptide; an agent capable of binding to an HA-tag; an agent capable of binding to maltose binding protein (MBP); an agent capable of binding to an HSV epitope; an agent capable of binding to a myc epitope; or an agent capable of binding to a biotinylated carrier protein. In some embodiments, the reagent includes an oligomer or polymer of streptavidin, avidin, a streptavidin analog or mutein or and an avidin analog or mutein. In some aspects, individual molecules of the oligomer or polymer are crosslinked by a polysaccharide or a bifunctional linker.

In some embodiments, the plurality of binding sites Z include at least 2, 4, 8, 12, 16, 20, 24, 28, 32, 36, 40, 44, 48, 52, 56, 60, 64, 72 or more binding sites.

In some aspects, the streptavidin-binding peptide is Trp-Ser-His-Pro-Gln-Phe-Glu-Lys (SEQ ID NO: 8), Trp-Ser-His-Pro-Gln-Phe-Glu-Lys-(GlyGlyGlySer)3-Trp-Ser-His-Pro-Gln-Phe-Glu-Lys ((SEQ ID NO: 17), Trp-Ser-His-Pro-Gln-Phe-Glu-Lys-(GlyGlyGlySer)2-Trp-Ser-His-Pro-Gln-Phe-Glu-Lys (SEQ ID NO: 18) or Trp-Ser-His-Pro-Gln-Phe-Glu-Lys-(GlyGlyGlySer)2Gly-Gly-Ser-Ala-Trp-Ser-His-Pro-Gln-Phe-Glu-Lys (SEQ ID NO: 19).

In some embodiments, the reagent includes a streptavidin analog or mutein containing the amino acid sequence Val44-Thr45-Ala46-Arg47 or Ile44-Gly45-Ala46-Arg47 at sequence positions corresponding to positions 44 to 47 with reference to positions in streptavidin in the sequence of amino acids set forth in SEQ ID NO: 1. In some embodiments, the streptavidin analog or mutein includes the amino acid sequence Val44-Thr45-Ala46-Arg47 at sequence positions corresponding to positions 44 to 47 with reference to positions in streptavidin in the sequence of amino acids set forth in SEQ ID NO:1.

In some embodiments, the streptavidin analog or mutein includes the sequence of amino acids set forth in any of SEQ ID NOS: 3-6. In some aspects, the streptavidin analog or mutein includes a sequence of amino acids that exhibits at least 85%, 86%, 87%, 88%, 89%, 89%, 90%, 91%, 92%, 93%, 94%, 95%, 96%, 97%, 98%, 99% or more sequence identity to any of SEQ ID NOS:3-6 and contains the amino acid sequence corresponding to Val44-Thr45-Ala46-Arg47 or Ile44-Gly45-Ala46-Arg47. In some embodiments, the streptavidin analog or mutein reversibly binds to biotin or a biologically active form thereof, a biotin analog or mutein or a biologically active fragment thereof or a streptavidin-binding peptide. In some embodiments, the streptavidin analog or mutein binds a functional fragment of any of the above sequences that reversibly binds to biotin or a biologically active form thereof, a biotin analog or mutein or a biologically active fragment thereof or a streptavidin-binding peptide.

In some embodiments, the streptavidin analog or mutein further contains an amino acid replacement or replacements at a position corresponding to 117, 120 and/or 121 with reference to positions in streptavidin in the sequence of amino acids set forth in SEQ ID NO: 1. In some embodiments, the amino acid replacement or replacements are selected from among Glu117, Asp117, Arg117, Ser120, Ala120, Gly120, Trp121, Tyr121 or Phe121. In some embodiments, the amino acid replacement or replacements are Glu117, Gly120 or Tyr121.

In some embodiments, the streptavidin analog or mutein contains the sequence of amino acids set forth in SEQ ID NO: 27 or 28. In some aspects, the streptavidin analog or mutein contains a sequence of amino acids that exhibits at least 85%, 86%, 87%, 88%, 89%, 89%, 90%, 91%, 92%, 93%, 94%, 95%, 96%, 97%, 98%, 99% or more sequence identity to SEQ ID NOS:28 and contains the amino acid sequence corresponding to Val44, Thr45, Ala46, Arg47, Glu117, Gly120 and Tyr121. In some embodiments, the streptavidin analog or mutein reversibly binds to biotin or a biologically active fragment, a biotin analog or mutein or a biologically active fragment thereof or a streptavidin-binding peptide. In some embodiments, the streptavidin analog or mutein reversibly binds a functional fragment any of the above sequences that reversibly binds to biotin or a biologically active fragment, a biotin analog or mutein or a biologically active fragment thereof or a streptavidin-binding peptide.

In some embodiments, the binding partner C1 and/or the binding partner C2, independently, includes a streptavidin-binding peptide such as Trp-Ser-His-Pro-Gln-Phe-Glu-Lys (SEQ ID NO: 8), Trp-Ser-His-Pro-Gln-Phe-Glu-Lys-(GlyGlyGlySer)3-Trp-Ser-His-Pro-Gln-Phe-Glu-Lys ((SEQ ID NO: 17), Trp-Ser-His-Pro-Gln-Phe-Glu-Lys-(GlyGlyGlySer)2-Trp-Ser-His-Pro-Gln-Phe-Glu-Lys (SEQ ID NO: 18) or Trp-Ser-His-Pro-Gln-Phe-Glu-Lys-(GlyGlyGlySer)2Gly-Gly-Ser-Ala-Trp-Ser-His-Pro-Gln-Phe-Glu-Lys (SEQ ID NO: 19);

In some embodiments, the disruption includes introducing to the cells a composition containing a substance capable of reversing the bond between the receptor-binding agent, which can be the first receptor-binding agent, and/or the second-receptor-binding agent and the reagent. In some embodiments, the substance is a free binding partner and/or is a competition agent. In some embodiments, the substance in the composition is not detrimental to the T cells or to the target cells. In some aspects, the addition of the substance does not reduce the percentage of surviving T cells or target cells to less than 90%, 80%, 70%, 60%, or 50%, as compared to incubation of the T cells or target cells, respectively, under comparable or the same conditions, without the substance. In some embodiments, the disruption terminates or lessens the signal induced or modulated by one or both of the receptor-binding agent or second receptor-binding agent in the T cells or the target cells.

In some embodiments, the reagent is or contains a streptavidin, avidin, a streptavidin analog or mutein or and an avidin analog or mutein or biologically active fragments thereof. In some embodiments, the substance contains a streptavidin-binding peptide, biotin or a biologically active fragment, optionally a D-biotin, or a biotin analog or biologically active fragment.

In some embodiments, the substance is a streptavidin-binding peptide such as Trp-Ser-His-Pro-Gln-Phe-Glu-Lys (SEQ ID NO: 8), Trp-Ser-His-Pro-Gln-Phe-Glu-Lys-(GlyGlyGlySer)3-Trp-Ser-His-Pro-Gln-Phe-Glu-Lys ((SEQ ID NO: 17), Trp-Ser-His-Pro-Gln-Phe-Glu-Lys-(GlyGlyGlySer)2-Trp-Ser-His-Pro-Gln-Phe-Glu-Lys (SEQ ID NO: 18) or Trp-Ser-His-Pro-Gln-Phe-Glu-Lys-(GlyGlyGlySer)2Gly-Gly-Ser-Ala-Trp-Ser-His-Pro-Gln-Phe-Glu-Lys (SEQ ID NO: 19). In some embodiments, the substance is C1 or an analog thereof or is C2 or an analog thereof.

In some embodiments, the dissociation constant ($K_D$) for the reversible binding between the binding site Z1 and the binding partner C1 and/or for the reversible binding between the binding site Z2 and the binding partner C2 is in the range of 10-2 M to 10-13 M.

In some embodiments, prior to the incubation, cells are contacted with a selection agent that specifically binds to a marker contained by T cells or target cells of the composition, thereby generating or obtaining the composition containing the T cells or target cells. In some embodiments, at least a portion of the incubation is carried out in the presence of a selection agent that specifically binds to a marker comprised by T cells or target cells of the composition, and the cultured T cells are enriched for T cells or target cells containing the marker.

In some embodiments, the selection agent is reversibly bound to the reagent, and the reagent further contains a plurality of binding sites capable of specifically binding the selection agent. In some aspects, the selection agent is reversibly bound to a second reagent containing a plurality of binding sites capable of specifically binding to the selection agent.

In some embodiments, the induction or modulation of the signal effects an increase in expansion (proliferation) and/or activation of the cultured T cells compared to incubation of T cells in the absence of the induction or modulation of the signal. In some embodiments, the increase is at least 2-fold, 3-fold, 4-fold, 5-fold, 6-fold, 7-fold, 8-fold, 9-fold, 10-fold or greater. In some embodiments, the induction or modulation of the additional or second signal increases expansion (proliferation) and/or activation of the T cells compared to incubation of T cells in the absence of the induction or modulation of the additional or second signal. In some embodiments, the increase is at least 2-fold, 3-fold, 4-fold, 5-fold, 6-fold, 7-fold, 8-fold, 9-fold, 10-fold or greater.

In some embodiments, the method increases expansion and/or proliferation of T cells in the composition, alters the metabolic profile of T cells in the composition, alters the subset of CD8+ T cells in the composition; and/or increases the percentage of long-lived memory T cells in the composition, each compared to the T cells in the composition prior to the incubation, subsequent to the incubation but in the absence of the disruption or subsequent to the incubation but in the presence of an agent that specifically binds CD28 and/or induces or modulates CD28 signaling.

In some embodiments, the methods result in cultured T cells in which the number or percentage of CD3+ T cells, CD4+ T cells or CD8+ cells is increased at least 2-fold, 3-fold, 4-fold, 5-fold, 6-fold, 7-fold, 8-fold, 9-fold or 10-fold compared to the number or percentage of CD3+ T cells, CD4+ T cells or CD8+ T cells, respectively, in the composition prior to the incubation, subsequent to the incubation but in the absence of the disruption, or subsequent to an analogous incubation but performed in the presence of an agent that specifically binds CD28 and/or induces or modulates CD28 signaling. In some embodiments, the methods result in cultured T cells in which the ratio of CD8+ T cells or the relative or normalized ratio of CD8+ T cells in the composition is increased at least 2-fold, 3-fold, 4-fold, 5-fold, 6-fold, 7-fold, 8-fold, 9-fold or 10-fold compared to the ratio or the relative or normalized ratio of CD8+ T cells in the composition prior to the incubation, subsequent to the incubation but in the absence of the disruption, or subsequent to an analogous incubation but in the presence of an agent that specifically binds CD28 and/or induces or modulates CD28 signaling. In some embodiments, the methods result in cultured T cells in which the number or percentage of CD62L+, optionally long-lived memory T cells or memory stem cells ($T_{SCM}$), in the composition is increased at least 2-fold, 3-fold, 4-fold, 5-fold, 6-fold, 7-fold, 8-fold, 9-fold or 10-fold compared to the number or percentage of the corresponding population of cells, either CD62L+, long-lived memory T cells or $T_{SCM}$, in the composition prior to the incubation, subsequent to the incubation but in the absence of the disruption, or subsequent to an analogous incubation but in the presence of an agent that specifically binds CD28 and/or induces or modulates CD28 signaling.

In some embodiments, the cultured T cells contain greater than 35%, 40%, 45%, 50%, 60%, 70%, 80% or 90% of a T cell subset containing a phenotype that is surface positive for CD62L (CD62L+) as a percentage of the total T cells in the composition or the total cells in the composition.

In some embodiments, the T cell subset further includes a phenotype including CD127+; and/or any one or more of CD45RA+, CD45RO−, CCR7+ and CD27+ and any one or more of t-bet$^{low}$, IL-7Ra+, CD95+, IL-2Rβ+, CXCR3+ and LFA-1+.

In some embodiments, the T cell subset includes a low level of TCR rearrangement excisions circles (TREC); and/or expresses a proliferation marker, which can be Ki-67; and/or exhibits the capacity to proliferate in the presence of a stimulatory agent; and/or exhibits the capacity to produce a cytokine such as IFN-gamma, TNF or IL-2 in the presence of a stimulatory agent.

In some embodiments, the stimulatory agent is an antigen, a homeostatic cytokine, such as IL-15 and/or IL-17, or is an agent that is capable of initiating a TCR/CD3 complex-associated signal in the T cells.

In some embodiments, the T cell subset is or contains long-lived memory T cells. In some embodiments, the T cell subset is or includes T memory stem cells ($T_{SCM}$).

In some embodiments, the method further includes introducing a recombinant nucleic acid molecule into T cells or target cells of the population. In some such aspects, the nucleic acid molecule may encode a recombinant protein, whereby cells express the recombinant protein. In some embodiments, the recombinant receptor is a chimeric antigen receptor or transgenic T cell receptor (TCR). In some aspects, the method is performed in vitro or ex vivo.

In some embodiments, the method further includes administering the cultured cells to a subject having a disease or condition.

Provided herein in some aspects is a composition containing a plurality of cultured T cells or target cells produced by the methods provided herein, and optionally a pharmaceutically acceptable excipient.

In some embodiments, after addition of the substance, the cells have not been incubated in vitro or ex vivo at a temperature greater than 30° C. for more than 24 hours, more than 48 hours, more than 72 hours or more than 96 hours.

Also provided herein are articles of manufacture that include: a) a reagent that includes a plurality of binding sites capable of binding to a receptor-binding agent; and b) the receptor-binding agent which i) is reversibly bound to the reagent and ii) is capable of specifically binding to a molecule on the surface of T cells in a manner that induces or modulates a signal in T cells. In some embodiments the molecule is not CD28, CD3, or CD40.

In some embodiments, binding the molecule induces or modulates a signal in a T cell other than a TCR/CD3 complex-associated signal; and/or binding the molecule enhances or potentiates a TCR/CD3 complex-associated signal. In some embodiments, the molecule is selected from among CD90 (Thy-1), CD95 (Apo-/Fas), CD137 (4-1BB), CD154 (CD40L), ICOS, LAT, CD27, OX40 and HVEM. In some embodiments, the molecule is not CD137.

In some embodiments, the receptor-binding agent specifically binds to a cytokine receptor, specifically binds to a chemokine receptor, is or includes an adhesion molecule or is a factor that induces cytokine production, chemokine production and/or expression of an adhesion molecule.

In some embodiments, the receptor-binding agent specifically binds to a cytokine receptor selected from among IL-2R, IL-1R, IL-15R, IFN-gammaR, TNF-alphaR, IL-4R, IL-10R, Type I IFNR, IL-12R, IL-15R, IL-17R, TNFR1 and TNFR2. In some embodiments, the receptor-binding agent is a ligand that specifically binds to a cytokine receptor selected from among IL-2R, IL-1R, IL-15R, IFN-gammaR, TNF-alphaR, IL-4R, IL-10R, Type I IFNR, IL-12R, IL-15R, IL-17R, TNFR1 and TNFR2; and/or the receptor-binding agent is a ligand selected from among IL-2, IL-1, IL-15, IFN-gamma, TNF-alpha, IL-4, IL-10, IL-12, IL-15, IL-17 and TNF, or is a biologically active fragment thereof. In some embodiments, the receptor-binding agent specifically binds to a cytokine selected from among IL-12R, IFN-gammaR, IL-4R and IL-17R; or the receptor-binding agent is a ligand selected from among IL-2, IL-4, IL-7, IL-10, IL-15 and IL-17 or is a biologically active fragment thereof.

In some embodiments, the second receptor-binding agent specifically binds to a cytokine receptor selected from among IL-7R, IL-21R and CD132 (IL receptor common gamma chain). In some embodiments, the second receptor-binding agent is a ligand that specifically binds to a cytokine receptor selected from among IL-7R, IL-21R and CD132 (IL receptor common gamma chain); and/or the second receptor-binding agent is a ligand selected from among IL-7, IL-21, IL-2, IL-4, IL-9 and IL-15, or is a biologically active fragment thereof. In some embodiments, the second receptor-binding agent specifically binds to a cytokine receptor selected from among IL-7R, IL-21R and CD132 (IL receptor common gamma chain); or the second receptor-binding agent is a ligand selected from among IL-7, IL-21, IL-2, IL-4, IL-9 and IL-15, or is a biologically active fragment thereof.

In some embodiments, the receptor-binding agent specifically binds to a chemokine receptor selected from among CCR1, CCR2, CCR3, CCR4, CCR5, CCR7, CCR9, CXCR1, CXCR3 and CXCR4. In some embodiments, the receptor-binding agent is a ligand that specifically binds to a cytokine receptor selected from among CCR1, CCR2, CCR3, CCR4, CCR5, CCR7, CCR9, CXCR1, CXCR3 and CXCR4; or the receptor-binding agent is a ligand selected from among CXCL9, CXCL10, CCL19, CCL21 and CCL25 or is a biologically active fragment thereof. In some embodiments, the receptor-binding agent specifically binds to a cytokine selected from among CXCR3, CCR7, CXCR1 and CXCR4; or the receptor-binding agent is a ligand selected from among CXCL9, CXCL10, CCL19, CCL21 and CCL25 or is a biologically active fragment thereof.

In some embodiments, the adhesion molecule is selected from among CD44, CD31, CD18/CD11a (LFA-1), CD29, CD54 (ICAM-1), CD62L (L-selectin), and CD29/CD49d (VLA-4), CD106 (VCAM-1) or is a biologically active fragment thereof. In some embodiments, the adhesion molecule is selected from among LFA-1, L-selectin, VCAM-1 and VLA-4 or is a biologically active fragment thereof.

In some embodiments, the factor is a nuclear factor. In some embodiments, the factor is a retinoic acid receptor-related orphan receptor gamma (RORgamma) or RORalpha.

Provided herein are methods for culturing target cells that include incubating a composition that contains target cells in the presence of one or more receptor-binding agent, wherein the receptor-binding agent reversibly bound to a reagent that is a streptavidin analog or mutein containing a plurality of binding sites capable of binding to an agent. In some aspects, the streptavidin analog or mutein includes a net negative charge or exhibits an isoelectric point less than the streptavidin mutein comprising the sequence of amino acids set forth in SEQ ID NO:4 or 6 and/or exhibits a higher affinity for a streptavidin-binding peptide containing the sequence of amino acids Trp-Ser-His-Pro-Gln-Phe-Glu-Lys (SEQ ID NO: 8) than a streptavidin or mutein containing the sequence of amino acids set forth in any of SEQ ID NOS: 1-6. In some embodiments, the agent is reversibly bound to the reagent and is capable of specifically binding to a molecule on the surface of a cell.

In some embodiments, the receptor-binding agent includes a binding partner C1. In some aspects, the plurality of binding sites includes two or more binding sites, Z1, which each are capable of binding to the binding partner C1 to form the reversible bond between the receptor-binding agent or agent and the reagent.

In some embodiments, the agent is a selection agent or a receptor-binding agent.

In some embodiments, the agent is a receptor-binding agent that specifically binds to a molecule that is or includes a member of a TCR/CD3 complex, CD3, a costimulatory molecule, accessory molecule, cytokine receptor, chemokine receptor, immune checkpoint molecule or is a member of the TNF family or the TNF receptor family or is or includes an adhesion molecule or is a factor that induces cytokine production, chemokine production and/or expression of an adhesion molecule.

In some embodiments, the receptor-binding agent is a second receptor-binding agent and the molecule is a second molecule, and the reagent further includes: c) a plurality of binding sites capable of reversibly binding to a first receptor-binding agent and d) the first receptor-binding agent which i) is reversibly bound to the reagent and ii) is capable of specifically binding to a first molecule on the surface of a T cell.

In some embodiments, the agent or the first receptor-binding agent specifically binds to a member of a TCR/CD3 complex and/or the first receptor-binding agent specifically binds to CD3.

In some embodiments, the first receptor-binding agent and second receptor-binding agent each individually contains a binding partner C1, and the plurality of binding sites includes two or more binding site, Z1, which each are capable of binding to the binding partner C1 to form the reversible bond between the first and second receptor-binding agent and the reagent. In some aspects, the first receptor-binding agent contains a binding partner C1, the second receptor-binding agent contains a binding partner C2, and the plurality of binding sites include two or more binding sites, Z1, which each are capable of binding to the binding partner C1 and the binding partner C2 to form the reversible bond between the first and second receptor-binding agent and the reagent. In some embodiments, the first receptor-binding agent contains a binding partner C1, the second receptor binding agent contains a binding partner C2, and the plurality of binding sites includes two or more binding sites, Z1, which each are capable of binding to the binding partner C1 to form the reversible bond between the first receptor-binding agent and the reagent and two or more binding sites, Z2, which each are capable of binding to the binding partner C2 to form the reversible bond between the second receptor-binding agent and the reagent.

In some embodiments, the reagent has a size that is less than 20 nm, less than 10 nm, less than 5 nm or less than 1 nm. In some embodiments, the reagent has a density of less than 1.2 g/cm3 or less than 1.0 g/cm3. In some embodiments, the reagent is not bound to a support or solid support. In some instances, the reagent is bound or immobilized to a support. In some cases, the support is a solid support or a stationary phase. In some aspects, the support includes a bead, a particle, a nanoparticle or a microsphere.

In some embodiments, the agent individually is selected from among an antibody fragment, a monovalent antibody fragment, a proteinaceous binding molecule with antibody-like binding properties, a molecule containing Ig domains, and binding fragments thereof.

In some embodiments, the agent, the receptor-binding agent, which can be the second receptor-binding agent, and/or the first receptor-binding agent contains an antibody fragment. In some aspects, the agent, the receptor-binding agent, which can be the second receptor-binding agent, and/or the first receptor-binding agent contains a Fab fragment. In some cases, the agent, the receptor-binding agent, which can be the second receptor-binding agent, and/or the first receptor-binding agent is a divalent antibody fragment such as a F(ab')$_2$-fragment or a divalent single-chain Fv (scFv) fragment. In some embodiments, the agent, the receptor-binding agent, which can be the second receptor-binding agent, and/or the first receptor-binding agent is a monovalent antibody fragment selected from among a Fab fragment, an Fv fragment and an scFv fragment.

In some embodiments, the agent or first receptor-binding agent includes an agent that specifically binds to CD3. In some embodiments, the agent that specifically binds CD3 is an anti-CD3-antibody, a divalent antibody fragment of an anti-CD3 antibody, a monovalent antibody fragment of an anti-CD3-antibody, or a proteinaceous CD3 binding molecule with antibody-like binding properties. In some embodiments, the agent or receptor-binding agent, which can be the second receptor-binding agent, includes an agent that specifically binds to CD90, CD95, CD137, CD154, ICOS, LAT, CD27, OX40 and HVEM, such as an anti-CD90-antibody, a divalent antibody fragment of an anti-CD90 antibody, an antibody fragment of an anti-CD90-antibody, a proteinaceous CD90 binding molecule with antibody-like binding properties, an anti-CD95-antibody, a divalent antibody fragment of an anti-CD95 antibody, an antibody fragment of an anti-CD95-antibody, a proteinaceous CD95 binding molecule with antibody-like binding properties, an anti-CD154-antibody, a divalent antibody fragment of an anti-CD154 antibody, a monovalent antibody fragment of an anti-CD154-antibody, a proteinaceous CD154 binding molecule with antibody-like binding properties, an anti-CD137-antibody, a divalent antibody fragment of an anti-CD137 antibody, a monovalent antibody fragment of an anti-CD137-antibody, a proteinaceous CD137 binding molecule with antibody-like binding properties, an anti-ICOS-antibody, a divalent antibody fragment of an anti-ICOS antibody, a monovalent antibody fragment of an anti-ICOS-antibody, a proteinaceous ICOS binding molecule with antibody-like binding properties, an anti-LAT-antibody, a divalent antibody fragment of an anti-LAT antibody, a monovalent antibody fragment of an anti-LAT-antibody, a proteinaceous LAT binding molecule with antibody-like binding properties, an anti-CD27-antibody, a divalent antibody fragment of an anti-CD27 antibody, a monovalent antibody fragment of an anti-CD27-antibody, a proteinaceous CD27 binding molecule with antibody-like binding properties, an anti-OX40-antibody, a divalent antibody fragment of an anti-OX40 antibody, a monovalent antibody fragment of an anti-OX40-antibody, a proteinaceous OX40 binding molecule with antibody-like binding properties, an anti-HVEM-antibody, a divalent antibody fragment of an anti-HVEM antibody, a monovalent antibody fragment of an anti-HVEM-antibody, a proteinaceous HVEM binding molecule with antibody-like binding properties, or any mixture thereof.

In some embodiments, the reagent is or contains streptavidin, avidin, a streptavidin analog or mutein or and an avidin analog or mutein. In some embodiments, the reagent includes an oligomer or polymer of streptavidin, avidin, a streptavidin analog or mutein or and an avidin analog or mutein.

Provided herein in some aspects is a kit, including the reagent disclosed herein and optionally instructions for use. In some embodiments, the kit contains a substance capable of reversing the bond between the receptor-binding agent and the reagent. In some embodiments, the kit contains a reagent containing a plurality of binding sites capable of reversibly binding to a receptor-binding agent. In some aspects, the receptor-binding agent is reversibly bound to the reagent and is capable of specifically binding to a molecule expressed on the surface of target cells. In some instances, binding to the molecule induces or modulates a signal in the target cells. In some cases the kit contains a substance capable of reversing the bond between the receptor-binding agent and the reagent.

In some embodiments, the target cells are T cells. In some embodiments, the reagent is or includes streptavidin, avidin, a streptavidin analog or mutein or and an avidin analog or mutein. In some embodiments, the reagent includes an oligomer or polymer of streptavidin, avidin, a streptavidin analog or mutein or and an avidin analog or mutein.

In some embodiments, the substance includes a streptavidin-binding peptide, biotin or a biologically active fragment, optionally a D-biotin, or a biotin analog or biologically active fragment.

In some embodiments, the reagent has a size that is less than 20 nm, less than 10 nm, less than 5 nm or less than 1 nm. In some embodiments, the reagent has a density of less than 1.2 g/cm3 or less than 1.0 g/cm3. In some embodiments, the reagent is not bound to a support or solid support.

Provided herein in some aspects is a composition including a plurality of T cells genetically engineered to express a recombinant receptor that specifically binds to a target antigen. In some cases, greater than 35%, 40%, 50%, 60%, 70%, 80% or 90% of the cells include a T cell subset containing a surface phenotype that is CD3+, CD4+ or CD8+ and CD62L+ and one or more of CD127+, CD45RA+, CD45RO−, CCR7+ and CD27+ and one or more of t-bet$^{low}$, IL-7Ra+, CD95+, IL-2Rβ+, CXCR3+ and LFA-1+ as a percentage of the total T cells in the composition or the total cells in the composition. In some embodiments, prior to or during the genetic engineering, the plurality of T cells containing the T cell subset were not incubated in the presence of a GSK-P inhibitor; were not incubated in the presence of a recombinant homeostatic cytokine, optionally IL-7 or IL-15; or were not enriched for CD62L+ cells. In some embodiments, the composition does not contain a GSK-P inhibitor or a recombinant homeostatic cytokine, optionally IL-7 or IL-15.

In some embodiments, the T cell subset includes at least $5 \times 10^6$, at least $1 \times 10^6$ or at least $2 \times 10^6$ cells.

Provided herein in some embodiments is a composition including a plurality of T cells genetically engineered to express a recombinant receptor that specifically binds to a target antigen. In some aspects, the genetically engineered T cells are derived from transducing a population of T cells containing a T cell subset containing a surface phenotype that is CD3+, CD4+ or CD8+ and CD62L+ and one or more of CD127+, CD45RA+, CD45RO−, CCR7+ and CD27+ and one or more of t-bet$^{low}$, IL-7Ra+, CD95+, IL-2Rβ+, CXCR3+ and LFA-1+. In some embodiments, the T cell subset is present at a greater percentage of the total T cells in the population or a greater number of total T cells in the population compared to a population containing primary T cells that were isolated or enriched from a human subject based on surface expression of one or markers containing the phenotype. In some embodiments, the T cell subset is present at a greater percentage of the total T cells in the population or a greater number of total T cells in the population compared to a population of T cells that were incubated in the presence of a GSK-P inhibitor. In some embodiments, the T cell subset is present at a greater percentage of the total T cells in the population or a greater number of total T cells in the population compared to a population of T cells that were incubated in the presence of a recombinant homeostatic cytokine, optionally IL-7 or IL-15. In some embodiments, the T cell subset is present at a greater percentage of the total T cells in the population or a greater number of total T cells in the population compared to a population of T cells that were stimulated by anti-CD3 and anti-CD8, but in which the stimulation or activation was for greater than 1 day, 2 days, 3 days, 4 days or 5 days and/or the stimulation was not disrupted in the presence of biotin or a biotin analog.

In some embodiments, the T cell subset is present in the population at or about greater than 35%, 40%, 50%, 60%, 70%, 80% or 90% as a percentage of the total T cells in the population. In some embodiments, the T cell subset includes at least $5 \times 10^6$ cells, $1 \times 10^6$ cells, $2 \times 10^6$ cells or more.

In some embodiments, the composition is a pharmaceutical composition.

Provided herein in some aspects is a method of treatment including administering to a subject having a disease or condition a composition, e.g., pharmaceutical composition, as described herein.

In some embodiments, the cells include a recombinant receptor, such as a chimeric antigen receptor (CAR) or TCR. In some aspects, the recombinant receptor, such as CAR or transgenic TCR specifically binds to an antigen associated with the disease or condition.

In some embodiments, the disease or condition is a cancer, and autoimmune disease or disorder, or an infectious disease.

BRIEF DESCRIPTION OF THE DRAWINGS

FIG. 1(A-E) provides schematic representations of exemplary embodiments.

FIG. 5(A-C) shows the temporal effect of adding D-Biotin on T cell expansion following stimulation of T cells with an anti-CD3/anti-CD28 Fabs that were reversibly bound to an oligomeric mutein streptavidin reagent.

FIG. 6(A-F) shows features resulting from short-term activation of CD3+ T cells with anti-CD3/anti-CD28 Fabs that were reversibly bound to an oligomeric mutein streptavidin reagent in which D-Biotin was added one day after initiation of stimulation.

FIG. 7(A-C) shows features resulting from short-term activation of CD8+ T cells with anti-CD3/anti-CD28 Fabs that were reversibly bound to an oligomeric mutein streptavidin reagent in which D-Biotin was added one day after initiation of stimulation using the experimental conditions and timeline set forth in FIG. 6A. FIG. 7A shows the CD8+ cell count (degree of expansion) in cultures at day 7 under the indicated conditions. The dashed horizontal line indicates the number of cells expanded in the anti-CD3/anti-CD28 beads positive control without D-Biotin addition.

FIG. 8(A-F) shows features resulting from stimulation of CD3+ T cells with an oligomeric mutein streptavidin reagent reversibly bound by anti-CD3 Fab and various co-stimulatory molecules. FIGS. 8C and 8D show normalized number of either CD62L+/CD4+(FIG. 8C) or CD62L+/CD8+(FIG. 8D) cells within the CD3+ cell cultures at day 6 for the indicated conditions. The resulting numbers of CD62L+/CD4+ or CD62L+/CD8+ cells expanded in the positive control (anti-CD3/anti-CD28 beads) were set to 100% as indicated by the horizontal lines.

FIG. 9(A-D) shows features resulting from stimulation of CD3+ T cells with either an oligomeric mutein streptavidin (Strep-Tactin®; ST-MM A) reagent or an oligomeric mutein streptavidin (Strep-Tactin® XT; ST-MM B) reagent, each reversibly bound by anti-CD3 and anti-CD28. FIG. 9C shows the number of CD4+ or CD8+ cells normalized to the numbers of CD4+ or CD8+ cells in the unstimulated control. The horizontal line represents the numbers of CD4+ or CD8+ cells expanded in the positive anti-CD3/anti-CD28 beads control. FIG. 9D shows flow cytometric analysis of CD62L and CD69 surface expression in cultures at day 5 for the indicated conditions.

10A shows the cell count (degree of expansion) in cultures at day 6 under the indicated conditions. The dashed horizontal line indicates the number of cells expanded in the positive control (anti-CD3/anti-CD28 beads).

FIG. 11(A-C) shows the results of an experiment in which CD3+ T responder cells were proliferated after being stimulated in vitro with αCD3 Fab and αCD28 Fab fragments that were reversibly immobilized on beads coated with the streptavidin mutein Strep-Tactin®. FIG. 11A is a histogram showing size-distribution (forward scatter) of stimulated cells, FIG. 11B depicts histograms representing the degree of proliferation according to the number of cells per cell division that are indicated on top of FIG. 11B (0 represents undivided cells; 5 represents cells that have gone through at least 5 divisions)

FIG. 12(A-E) shows the results of an experiment in which CD3+ T responder cells were proliferated after being stimulated in vitro with reversible αCD3/αCD28 Fab fragments that were reversibly immobilized on soluble oligomeric streptavidin mutein acting a soluble reagent. For the experiments the results of which are shown in FIG. 12, 300,000 CD3+ responder T cells (Tresp) were labeled with 2 uM Carboxyfluorescein succinimidyl ester (CFSE) and stimulated with varying amounts of a preparation of soluble oligomeric streptavidin mutein on which a combination of αCD3 Fab fragment and αCD28 Fab both carrying a Strep-tag as streptavidin binding peptide at the heavy chain were immobilized. ("1×" corresponds to 3 µg oligomeric streptavidin mutein functionalized with 0.5 µg αCD3Fab and 0.5 µg αCD28 Fab; numbers indicate fold amount of "1×"). Tresp cells either left unstimulated or were stimulated with blank oligomeric streptavidin muteins (no Fab) served as negative control. Tresp cells were seeded in duplicates in 48-well plates along with 300,000 CD3 negative autologous feeder cells (irradiated with 30Gy) in 1 ml cell culture medium supplemented with 20 U/ml interleukin 2 (IL-2). Cells were incubated at 37° C. without media exchange and proliferation was analyzed according to CFSE dilution after 5 days by FACS analysis (FIG. 12B). FIG. 12A shows size distribution of cells after 5 days in culture. Histograms show live CD3+ cells, while

FIG. 17(A-B) shows the yield and phenotype of expansion of purified CD8+ T responder cells stimulated in vitro with αCD3/αCD28 Fab fragments that were reversibly immobilized on two kinds of soluble oligomeric streptavidin muteins acting a soluble reagent. The first kind of oligomeric streptavidin mutein was the fraction of the oligomeric streptavidin mutein (obtained in Example 3 (conventional backbone), the second kind of this oligomeric streptavidin mutein used as soluble reagent was the soluble oligomer described above and referred herein as "large" backbone. In these experiments, the fraction of the oligomeric conventional streptavidin mutein (n≥3) was also used as a reagent that were either functionalized with single Fab fragments (third bar in FIG. 17A and FIG. 17B) or with a combination of αCD3 Fab and αCD28 Fab-fragments. Furthermore to the combined stimulation with αCD3/αCD28 Fab fragments, also an additional αCD8 Fab fragment (commercially available from IBA GmbH, Göttingen, Germany) was immobilized in order to test whether it is possible to preferentially stimulate a specific T cell subpopulation. FIG. 17A shows a graph of bars that represent the degree of proliferation according to the number of cells harvested at day 6 compared to the negative controls (unstimulated purified CD8+ T responder cells) and normalized to the positive control (purified CD8+ T responder stimulated with commercially available anti-CD3/anti-CD28 beads (beads on which αCD3 and αCD28 monoclonal antibodies are irreversible immobilized).

FIG. 18(A-B) shows the yield and phenotype for the expansion of purified CD8+ T responder cells stimulated in vitro with αCD3/αCD28 Fab fragments that were reversibly immobilized on soluble oligomeric streptavidin mutein acting as a soluble reagent that were either functionalized with single Fab fragments or with a combination of Fab-fragments (as already described above). In these experiments, the CD8+ T responder cells were stimulated with the soluble reagent (the soluble oligomeric streptavidin mutein (1 mg/ml) of Example 3) which was functionalized with varying amounts of αCD3 Fab and αCD28 Fab fragments, optionally together with the αCD8 Fab fragment described above. The term "1×" corresponds to 1.5 µg oligomeric streptavidin mutein functionalized with 0.5 µg αCD3 Fab fragment alone and 1.5 µg oligomeric streptavidin mutein functionalized with 0.5 µg αCD28 Fab alone), or 30 of a preparation of oligomeric streptavidin mutein loaded with 0.5 µg αCD3 Fab fragment and 0.5 µg αCD28 Fab, or 4.5 µl of a preparation of oligomeric streptavidin mutein loaded with 0.5 µg strep-tagged αCD3 Fab, 0.5 µg strep-tagged αCD8 Fab and 0.5 µg strep-tagged αCD28 Fab. Accordingly, the term "2×" corresponds to 3.0 µg oligomeric streptavidin mutein functionalized with 1 µg αCD3 Fab fragment alone and 3.0 µg oligomeric streptavidin mutein functionalized with 1 µg αCD28 Fab alone, meaning that twice the amount of immobilized αCD3 Fab fragment was used. Untreated Tresp cells served as negative control and purified CD8+ T responder stimulated with commercially available anti-CD3/anti-CD28 beads (beads on which αCD3 and αCD28 monoclonal antibodies are irreversible immobilized) as positive control. FIG. 18A shows a graph in which the bars represent the degree of proliferation according to the number of cells harvested at day 5 compared to the negative controls and normalized to the positive control. FIG. 18B shows FACS analysis of CD8 and CD45RO surface expression after cell culture.

FIG. 19(A-B) shows the expansion of purified CD3+ T responder cells stimulated in vitro with αCD3/αCD28 Fab fragments that were reversibly immobilized on the soluble oligomeric streptavidin mutein of Example 3 that served as a soluble reagent. In one experiment, in addition to αCD3/αCD28 Fab fragments, also an αCD8 Fab fragment commercially available from IBA GmbH, Göttingen, Germany (catalogue number 6-8000-203) was immobilized on the soluble oligomer of the streptavidin mutein in order to test whether it is possible to preferentially stimulate in vitro the CD8+ T cell subpopulation within the bulk CD3+ culture with a reagent having reversibly immobilized thereon also an αCD8 Fab fragment. In more detail, 500,000 purified CD3+ responder T cells (Tresp) were stimulated with 30 of a preparation of oligomeric streptavidin mutein (1 mg/ml) loaded with a combination of 0.5 µg of the αCD3 Fab and 0.5 µg of the αCD28 Fab. As an alternative approach, 4.5 µl of the oligomeric streptavidin mutein were loaded with 0.5 µg αCD3 Fab, 0.5 µg αCD8 Fab and 0.5 µg αCD28 Fab described above. Unstimulated Tresp cells served as negative control and Tresp stimulated with anti-CD3/anti-CD28 beads (beads on which αCD3 and αCD28 monoclonal antibodies are irreversible immobilized) served as positive control.

FIG. 23(A-B) shows early cluster formation of T cells after activation of purified CD4+ and CD8+ T responder cells stimulated in vitro with αCD3/αCD28 Fab fragments that were reversibly immobilized on the soluble oligomeric streptavidin mutein (n>3) described in Example 3. FIG. 23A depicts the results for CD4+ T cells and FIG. 23B depicts the results for the CD8+ T cells. Data for the Tresp stimulated with the soluble multimerization reagent (the oligomeric streptavidin mutein), the Tresp stimulated with the commercially available anti-CD3/anti-CD28 beads (positive control) and the unstimulated T cells (negative control) are shown.

FIG. 24 (A-F) shows the kinetics of selective antigen-specific (Ag-specific) expansion out of a bulk population of purified CD3+CD62L+CD45RA-$T_{CM}$ responder cells that were stimulated in vitro with both a peptide:MHC molecule complex (that acts as first agent that provides a primary activation signal to the cells) and αCD28 Fab fragment (that acts as second agent that binds the accessory molecule on the surface of the cells) and unstimulated T cells (negative control) are shown. Both, the complex of antigen-specific peptide with the MHC molecule and the αCD28 Fab fragment were reversibly immobilized on the same soluble oligomeric streptavidin mutein (with n≥3) described in Example 3. The peptide used for the antigen-specific expansion in FIG. 24A was the peptide CRVLCCYVL (SEQ ID NO: 38), amino acids 309-317 of the immediate-early 1 protein restricted by the HLA-C702 MHC molecule (described in Ameres et al., PLOS Pathogens, May 2013, vol. 9, issue 5, e1003383) representing an HLA-C7/IE-1 epitope that is specific for cytomegalovirus (CMV). The MHC I molecule that presents the peptide carries at its C-terminus of the heavy chain the streptavidin binding peptide (SAWSHPQFEK(GGGS)$_2$GGSAWSHPQFEK (SEQ ID NO: 16), that is commercially available as "Twin-Strep-Tag®" from IBA GmbH, Göttingen, Germany).

FIG. 31 shows the expansion capacity of CD3+ T cells that were stimulated with the multimerized agent reversibly bound with αCD3/αCD28 Fabs and further cultured (1) after sorting for dividing cells and not further stimulated (sort-purified), (2) after sorting for dividing cells and re-stimulated with the multimerized agent (sort-purified, re-stimulation) or (3) without sorting or further re-stimulation (unsorted). D-Biotin was added at day 1 after further culture for all conditions (dashed line).

DETAILED DESCRIPTION

Figure 1A:
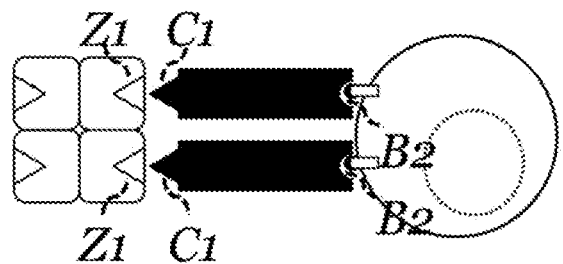
FIG. 1A shows a schematic representation of a reagent (or representative portion thereof) with a plurality of binding sites for reversible binding to agents. In this case, the reagent is shown as capable of reversibly binding to two agents, each of which is capable of specifically binding to a molecule on a cell. The reagent has a plurality of binding sites, including a plurality of the binding site, Z1, each capable of reversibly binding to the agents. The first and second agents, which, in some cases, can be the same, in the schematic representation shown each contain at least one binding partner C1. Binding partner C1 reversibly binds to binding site Z1. The first and second agents each also contain a binding site, B2, which can specifically bind to a molecule on the surface of a cell, which, in some cases, can be on the same cell. Here, the first and second agents are shown specifically binding to molecules on the same cell.
Figure 1B:
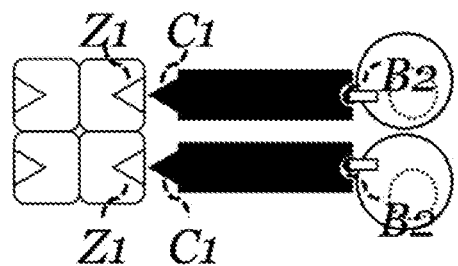
FIG. 1B shows a schematic representation of a reagent with a plurality of binding sites, capable of reversibly binding to a first and second agent, which agents are each capable of specifically binding to a molecule on a first and second cell, respectively. The reagent has a plurality of binding sites Z1, each capable of reversibly binding to an agent. The first and second agents, which, in some cases, can be the same, each contain a binding partner C1, which reversibly binds to binding site Z1. The first and second agents each contain a binding site B2, which can specifically bind to a molecule on the surface of a cell, which, in some cases, can be on the same cell or a different cell. Here, the first agent is bound to a molecule on the surface of a first cell and the second agent is bound to a molecule on the surface of a second cell.
Figure 1C:
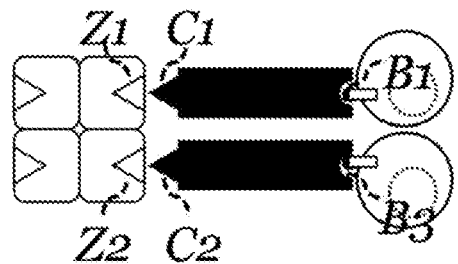
FIG. 1C shows a reagent capable of reversibly binding to a first and second agents, which agents are each capable of specifically binding to a molecule on a first and second cell, respectively. The reagent has a plurality of binding sites Z1 and Z2, which can be the same or different, each capable of reversibly binding to one or both of the agents. The first agent contains a binding partner C1, which reversibly binds to Z1; the second agent contains a binding partner C2, which can reversibly bind to Z2. In some cases, C1 and C2 are different. In some cases, C1 and C2 are the same or substantially the same. The first agent contains a binding site B1, which can specifically bind to a molecule on the surface of a cell and the second agent contains at least one binding site B3, which can specifically bind to a molecule on the surface of a cell. Binding sites B1 and B3 in some cases bind to two different cell surface molecules, or different epitopes on a single molecule, or the same or different molecules on the surface of different cells. Here, the first agent is shown as being bound, via B1, to a molecule on the surface of a first cell, and the second agent is bound, via B3, to a molecule on the surface of a second cell.
Figure 1D:
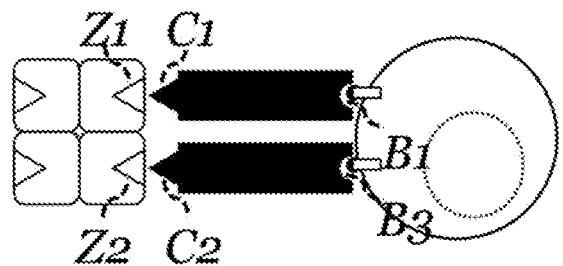
FIG. 1D shows a reagent capable of reversibly binding to a first and second agent, such as selection agents, which are each capable of specifically binding to a molecule on a cell. The reagent has a plurality of binding sites, including Z1 and Z2, which can be the same or different, each capable of reversibly binding to an agent. The first agent contains a binding partner C1 that can specifically bind to binding site Z1 and the second agent contains at least one binding partner C2 that can specifically bind to binding site Z2. In some cases, C1 and C2 are different. In some cases, C1 and C2 are the same or substantially the same. The first agent contains a binding site B1, which can specifically bind to a molecule on the surface of a cell and the second agent contains a binding site B3, which can specifically bind to a molecule on the surface of a cell. In some embodiments, the first agent and second agent can be a selection agent. Binding sites Bland B3 can bind the same or different molecules (e.g. receptor) on the surface of a cell, the same or different epitopes on a molecule, or the same or different molecules on the surface of different cells. Here, the first agent is bound to a first molecule on the surface of a cell and the second agent is bound to a second molecule on the surface of the same cell.
Figure 1E:
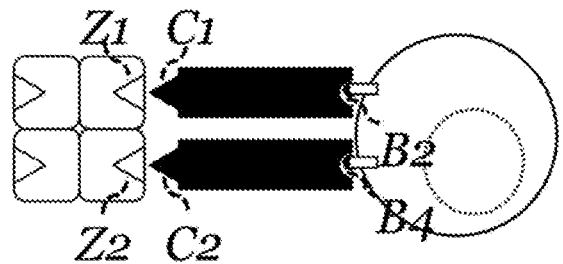
FIG. 1E shows a reagent reversibly bound to a first and second agent, which agents are each capable of specifically binding to a molecule on a cell. The reagent has a plurality of binding sites, including Z1 and Z2, which can be the same or different, each capable of reversibly binding to an agent. The first agent contains a binding partner C1 that can reversibly bind to Z1 of the reagent and the second agent contains a binding partner C2 that can reversibly bind to Z2. In some cases, C1 and C2 are different. In some cases, C1 and C2 are the same or substantially the same. The first agent contains at least one binding site B2, which can specifically bind to a molecule on the surface of a cell and the second agent contains at least one binding site B4, which can specifically bind to a molecule on the surface of a cell. In some embodiments, the first agent and second agent can be stimulatory agents. Binding sites B2 and B4 can bind the same or different molecules on the surface of a cell, the same or different epitopes on a molecule, or the same or different molecules on the surface of different cells. Here, the first agent is bound to a first molecule on the surface of a cell and the second agent is bound to a second molecule on the surface of the same cell.
Figure 2A:
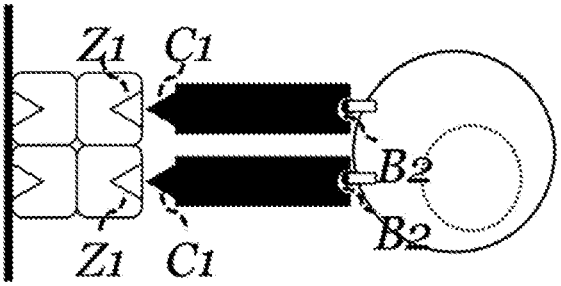
FIG. 2(A-E), which includes FIGS. 2A-2E, provide schematic representations of exemplary embodiments as shown in FIGS. 1A-1E, respectively, except that the depicted reagents are shown as being immobilized on a support, such as a stationary phase.
Figure 2B:
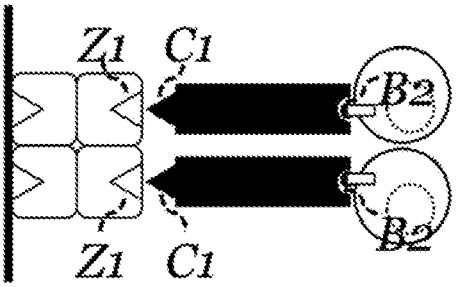
Figure 2C:
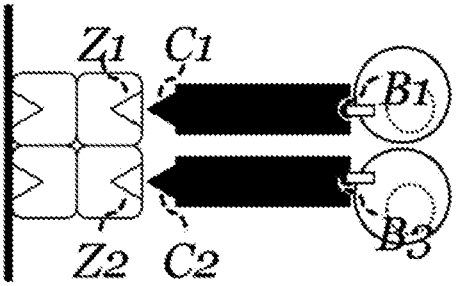
Figure 2D:
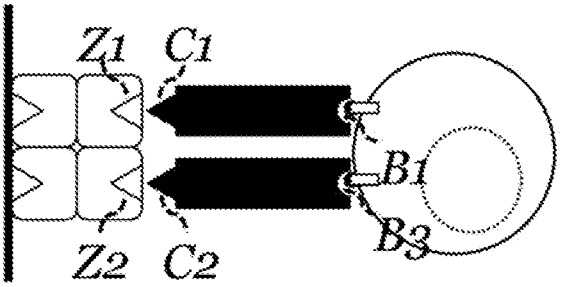
Figure 2E:
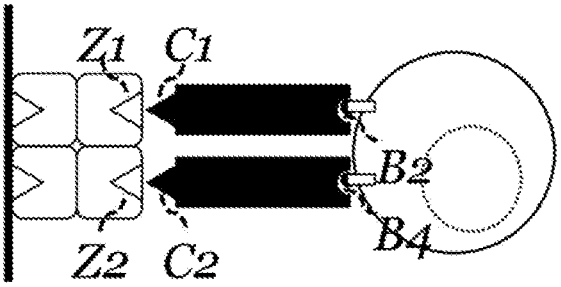

Provided herein is a method for stimulating, e.g., expanding, inducing survival or persistence of, differentiation of, a composition of target cells, such as T cells. In some embodiments, the methods relates to reversible reagent systems capable of binding to molecules on the surface of a target cells, such as a receptor binding molecule, thereby providing a signal to the cells, which, in some cases, can be a primary activation signal. In some embodiments, the methods employ reagents, which can be multimerization reagent having bound thereon one or more agents, e.g. a first agent, second agent, etc. that provides a signal to the cells, such as a primary activation signal and/or an accessory or costimulatory signal. In some embodiments, the primary activation signal may as such be sufficient to activate the cells to expand/proliferate. This first agent can either be bound reversibly or also irreversibly to the multimerization reagent. The multimerization reagent may have bound thereto also a second agent that stimulates an accessory molecule on the surface of the cells. The second agent, when binding to the accessory molecule on the surface on the surface of the cells, may thereby stimulate the activated cells to expand. Also this second agent can either be bound reversibly or also irreversibly to the multimerization reagent. In some aspects, one or more additional agents also can be employed to modulate or induce additional signals in cells. In some embodiments, the provided methods involve temporally controlling stimulation of cells by time-controlled disruption of the reversible reagent or reagents.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference. For example, the contents of International PCT Application No. PCT/EP2015/058339 is incorporated by reference in its entirety.

The section headings used herein are for organizational purposes only and are not to be construed as limiting the subject matter described.

I. Overview of Methods and Systems for Modulating or Stimulating Cells Using Reversible Reagents In some embodiments, the methods involve incubating, such as contacting, a plurality of cells comprising target cells, with one or more multimerization reagent having reversibly bound thereto an agent. In some embodiments, the multimerization reagent may either be immobilized on a solid support or soluble, whereby during at least a portion of the incubation of cells the cells are contacted with the multimerization reagent. In one aspect, the method disclosed herein is a serial expansion of a population of cells in which a complete population of lymphocytes is stimulated/expanded, the reagents necessary for the expansion are then removed by chromatography on a suitable stationary phase. In some embodiments, the expanded/stimulated cells, which are the cultured cells, are optionally transfected with e.g. a T cell receptor or a chimeric antigen receptor (CAR) and, in some aspects, can be subjected to a second stimulation expansion with a different stimulatory molecule that binds to the introduced T cell receptor or the chimeric antigen receptor.

Methods of expanding T cell populations in vitro in the absence of exogenous growth factors or low amounts of exogenous growth factors are known in the art (see e.g. U.S. Pat. No. 6,352,694 B1 and European Patent EP 0 700 430 B1). In general, such methods employ a solid phase surfaces of greater than 1 µM to which various binding agents (e.g. anti-CD3 antibody and/or anti-CD28 antibody) are immobilized. For example, anti-CD3/anti-CD28 beads anti-CD3/anti-CD28 beads (Invitrogen) are commercially available reagents for T cell expansion, which are uniform, 4.5 µm superparamagnetic, sterile, non-pyrogenic polystyrene beads coated with a mixture of affinity purified monoclonal antibodies against the CD3 and CD28 cell surface molecules on human T cells. However, in some cases, such magnetic beads are, for example, difficult to integrate into a method to expand cells under conditions required for clinical trials or therapeutic purposes since it has to be made sure that these magnetic beads are completely removed before administering the expanded T cells to a patient.

In some embodiments, the methods provided herein address these concerns. In some aspects, the provided reagents are reversible, such that the stimulating agents can be removed from the cell composition. Also, in some aspects, the reagent, e.g. multimerization reagent, to which the stimulating agents are bound is not immobilized on a support, such as not immobilized on a solid support or surface. Thus, in some aspects, the reagent, e.g. multimerization reagent, is flexible and not rigid. In some embodiments, the reagent can adapt or conform to the cell surface. In some embodiments, it is possible to immobilize the reagent on a support, such as a solid support, including a stationary phase. In some embodiments, such methods can be used in concert with selection methods using similar selection agents in which one or more target cells can be selected and, simultaneously or sequentially, exposed to the stimulatory agents. Hence, in some aspects, the stimulation of particular cells or subsets of cells can be biased by selection and isolation in together with stimulation.

Figure 3:
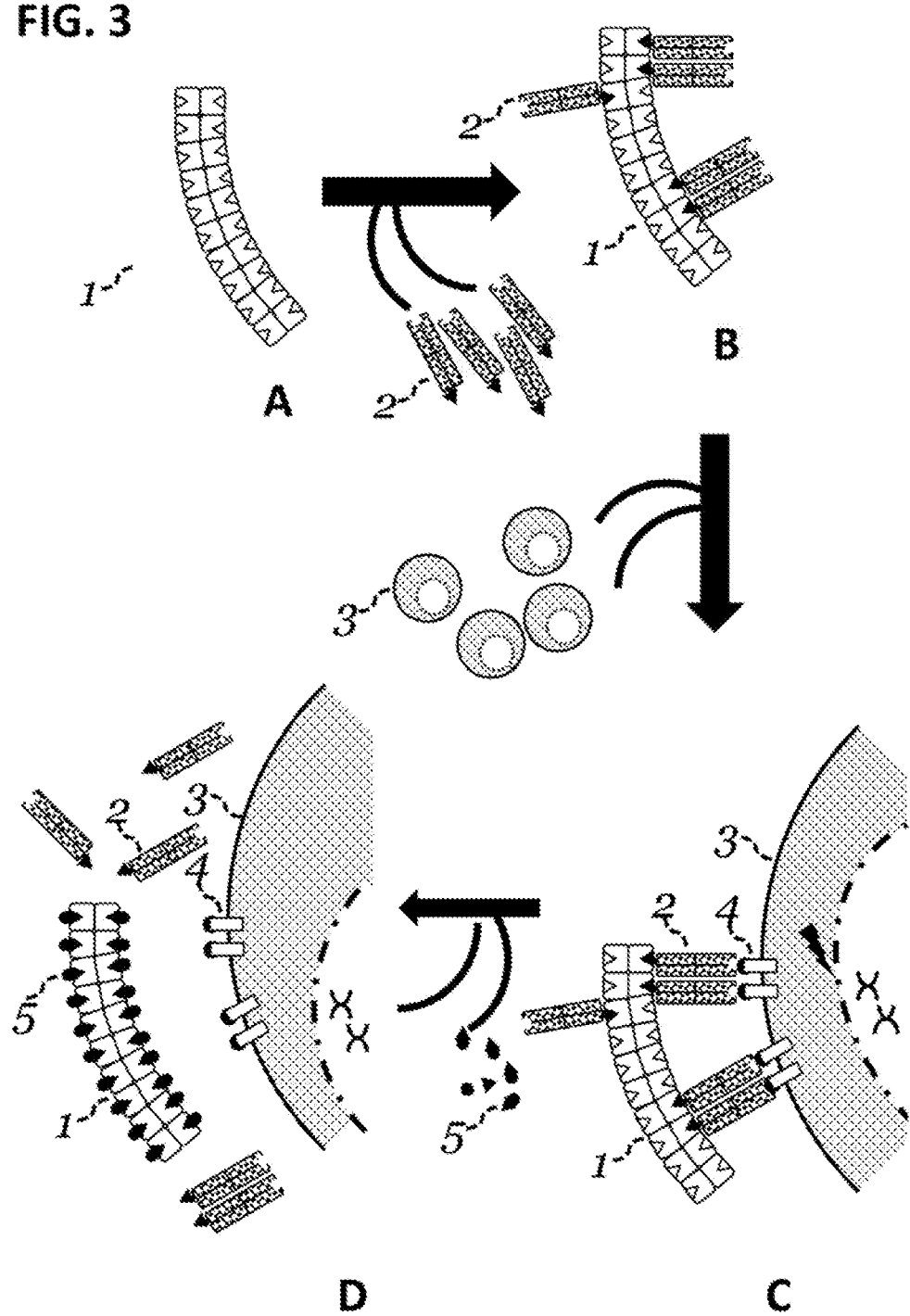
FIG. 3 provides a schematic representation of exemplary embodiments in which oligomeric reagents are used to multimerize stimulatory agents and the resulting complexes incubated with cells to deliver signals to the cells, followed by reversal of the binding. Panel A shows an oligomeric reagent 1, which is shown as not bound to any support and as being flexible. Stimulatory agents 2, which are shown here as Fab fragments and are capable of specifically binding to a molecule on the surface of a cell, are combined with the reagent. The agents comprise a binding partner (e.g. binding partner C) that is capable of reversibly binding to a binding site (e.g. binding site Z) on the reagent, multimerizing the agents. Panel B depicts the binding partner reversibly binding to a binding site on the reagent. Cells 3 are added to the system. Panel C depicts the multimerized agents (Fab fragments) specifically binding to the molecules 4 on the surface of a cell 3. In Panel C, the depicted agents are stimulatory receptor-binding agents, (e.g. a first receptor-binding agent and/or a second receptor-binding agent), which can induce or modulate a signal in a cell upon binding of the agent, to the molecule on the cell. As shown in Panel D, a substance 5, such as a competitive reagent (e.g. biotin), is added to the composition, which can be a substance that exhibits a higher binding affinity for the binding site on the reagent than for the binding partner on the agent, thereby disrupting the reversible binding between the reagent 1 and the agent 2. In some cases, the agent, e.g., Fab fragment also can dissociate from its interaction with the molecule 4 on the cell 3. In some cases, this can disrupt, lessen and/or terminate the signaling in the cell.
Figure 4:
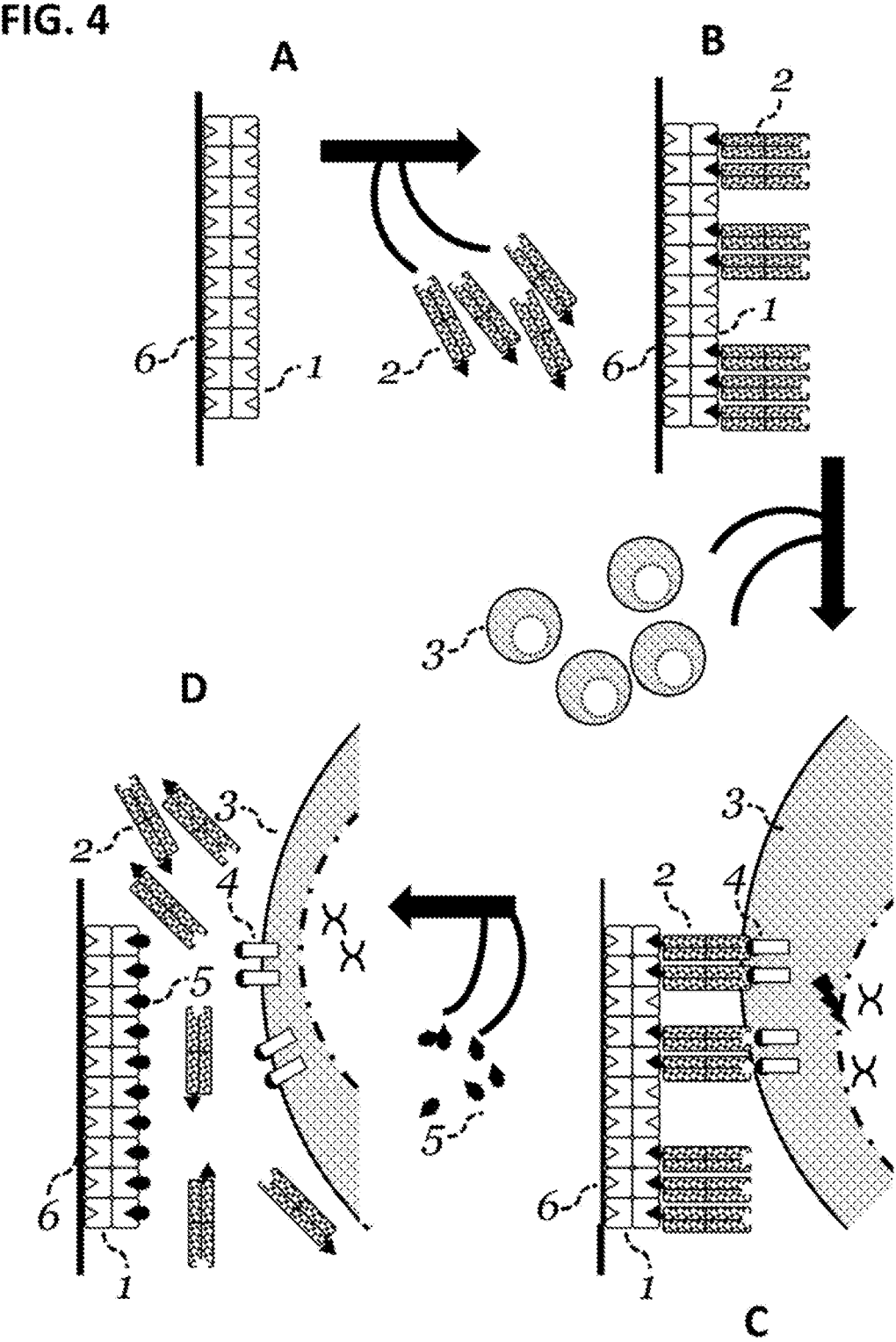
FIG. 4 provides a schematic representation of exemplary embodiments of a reversible system attached to a support, such as a solid support or a surface, including a stationary phase. Panel A shows a support 6 containing the reagent 1. Agents 2, such as Fab fragments, that are capable of specifically binding to a molecule on the surface of a cell are added to the system. The agents 2, such as Fab fragments, comprise a binding partner (e.g. binding partner C) that is capable of reversibly binding to a binding site (e.g. binding site Z) on the reagent. Panel B depicts the binding partner reversibly binding to a binding site on the reagent. Cells 3 are added to the system. Panel C depicts the agents 2, e.g. Fab fragments, binding to the molecules 4 on the surface of a cell 3. In some embodiments, the scFvs comprise a receptor-binding agent or a selection agent. In some embodiments, the agents, e.g. Fab fragments, can be a receptor-binding agent or a selection agent. Panel C depicts an exemplary receptor-binding agent or agents (e.g. a first receptor-binding agent and/or a second receptor-binding agent), which can induce or modulate a signal in a cell upon binding of the agent, e.g. Fab fragment, to the molecule on the cell. A substance 5, such as a competitive reagent (e.g. biotin), is added, which can be a substance that exhibits a higher binding affinity for the binding site on the reagent than for the binding partner on the agent, e.g. Fab fragment, thereby disrupting binding between the reagent and the agent. Panel D depicts disruption of the binding between the agent 2, e.g. Fab fragment, and the reagent, thereby resulting in dissociation of the reagent from the agent, and thereby the cell. In some cases, the agent, e.g. Fab fragment, also can dissociate from its interaction with the molecule 4 on the cell 3. In some cases, this can disrupt, lessen and/or terminate the signaling in the cell.

In some embodiments, the provided methods involve incubating or culturing, e.g. contacting, a composition of cells with a reagent, e.g. multimerization reagent to which is bound one or more receptor-binding agents (e.g. stimulatory agents) (see e.g. FIGS. 3 and 4). In some embodiments, after contacting the cell composition with the multimerization reagent and usually incubating the cell population with the multimerization reagent, the population of cells forms complexes/is bound to the multimerization agent via the first agent. The other cell populations contained in the initial sample that lack the specific cell surface molecule do not bind to the multimerization reagent. In this respect, it is noted that the cell population usually has multiple copies of the cell surface molecule on its surface and binding of these multiple copies is typically needed for stimulation or activation.

Thus, the multimerization agent provide typically more than one binding site, e.g. Z1, in which, in some cases, a plurality of agents can be reversibly bound to present the first agent, second agent and/or other agents in a sufficient density to the population of cells. In this respect, it is noted that a multimerization agent can as such have multiple binding sites, e.g., Z1, for example, a streptavidin mutein (being a homo-tetramer) in its native state has four such binding sites, e.g. Z1, and can further be oligomerized. In some cases, a reagent may have only one binding site, e.g. Z1, for the reversible binding of a binding partner, e.g. C1. Such an example is multimeric calmodulin. Calmodulin as such has only one binding site for calmodulin binding peptides. However, calmodulin can be biotinylated and then reacted with streptavidin-oligomers (see also below), thereby providing a multimerization reagent in which multiple calmodulin molecules are presented in high density on a "scaffold", thereby providing multimeric calmodulin.

In some embodiments, after incubation or other suitable time at which stimulation is desired to be disrupted, the binding between the binding partner C, e.g. C1 of a reversibly bound agent and the binding site Z, e.g. Z1, of the multimerization reagent is disrupted by disrupting the respective reversible bond. In some cases, the disruption may be achieved by adding a competitor to the incubation/reaction mixture containing the population of cells being bound to the multimerization reagent. For competitive disruption (which can be understood as being a competitive elution) of the reversible bond between the binding partner C, e.g. C1, of a reversibly bound agent and the binding site Z, e.g. Z1 of the multimerization reagent, the incubation mixture/population of cells can be contacted with a free first binding partner C, e.g. C1, or an analog of said first binding partner C that is capable of disrupting the bond between the first binding partner and the binding site Z, e.g. Z1. In the example of the binding partner C, e.g. C1, being a streptavidin binding peptide that binds to biotin binding site of streptavidin, the first free partner may be the corresponding free streptavidin binding peptide or an analogue that binds competitively. Such an analogue can, for example, be biotin or a biotin derivate such as desthiobiotin.

In some embodiments, the addition of the free partner or the analog thereof results in displacement of the binding partner C, e.g. C1, from the multimerization reagent and thus, since the binding partner is comprised in the reversibly bound agent, displacement of such agent from the multimerization reagent is achieved. This displacement of the agent in turn results in a dissociation of the first agent from the cell surface molecule, in particular if the binding affinity of the bond between the first agent and the cell surface receptor has a dissociation constant ($K_D$) in the range of $10^{-2}$ M to $10^{-13}$ M and is thus also reversible. Due to this dissociation, in some aspects, the stimulation of the cell population is also terminated.

In some embodiments, the binding affinity of antibody molecules towards their antigen, including for example, a cell surface receptor molecule is usually in the affinity range of a $K_D$ of about $10^{-7}$ M to about $10^{-13}$ M. Thus, conventional monoclonal antibodies can be used as an agent (first or second, receptor-binding, e.g. stimulatory agent, or selection agent). In some embodiments, in order to avoid any unwanted avidity effects that lead to a stronger binding, monoclonal antibodies can also be used in form of their monovalent antibody fragments such as Fab-fragments or single chain Fv fragments.

The provided method has the advantage that the time period of the stimulation or expansion of the cell population can be exactly controlled and thus also the functional status of the cell population can be closely controlled. As described herein, short-term activation of cells, such as T cells, by addition of a substance, such as a competitive agent (e.g. biotin or an analog) within 5 days after stimulation results in proliferation and stimulation of cells, but alters one or more characteristics or features of the cells, such as CD4 or CD8 T cell percentage, CD8/CD4 ratio, phenotypic markers and/or differentiation state. For example, results described herein show that that the ability to temporally control the signal using embodiments of the provided reagents can result in an increase in a less-differentiated, long-lived population T cells such as long-lived memory T cells. In some cases, temporal control of the signal, e.g., by disruption of multimerized agent binding using a competition substance, can be used to tailor or adjust the relative expansion and/or persistence of particular subpopulations compared to others (e.g., CD4+ vs CD8+).

In some embodiments, due to the dissociation of the reversibly bound agent or agents from the cell surface molecule, the provided method has the added advantage that the stimulated cell population is free of stimulating agents at the end of the stimulation period. Also, in some embodiments, all other reagents used in the method, namely the agents (e.g. first or second, receptor-binding agents, e.g. stimulatory agents, or selection agents) as well as the competition reagent of the binding partner C, e.g. C1, or the analog thereof can be easily removed from the stimulated cell population via a "removal cartridge" (see e.g. described in International Patent App. Pub. No. WO 2013/124474). In some cases, for example in which the multimerization reagent is immobilized on a solid support, such as a bioreactor surface or a magnetic bead, it is being held back. Thus, the use of a removal cartridge for removal of the free agent and the competition reagent, can include loading the elution sample (e.g. sample obtained after disruption of the reversible binding) onto a second chromatography column.

In some embodiments, this chromatography column has a suitable stationary phase that is both an affinity chromatography matrix and, at the same time, can act as gel permeation matrix. In some aspects, this affinity chromatography matrix has an affinity reagent immobilized thereon. In some embodiments, the affinity reagent may, for instance, be streptavidin, a streptavidin mutein, avidin, an avidin mutein or a mixture thereof. In some embodiments the agent (e.g. first or second, receptor-binding agents, e.g. stimulatory agents, or selection agents), the competition reagent of the binding partner C, C1, bind to the affinity reagent, thereby being immobilized on the chromatography matrix. As a result the elution sample containing the isolated and expanded cell population is being depleted of the agent (e.g. first or second, receptor-binding agents, e.g. stimulatory agents, or selection agents) and the competition reagent. In some embodiments, the cultured composition is free of any reactants, which in some aspects is an advantageous for use in connection with diagnostic applications (for example, further FACS™ sorting) or for any cell based therapeutic application.

In some embodiments, the ability to remove the reagent and other components from the composition has the further advantage of being able to avoid any solid support such as magnetic beads. In some embodiments, this means there is no risk or minimal risk of contamination of the activated T cells by such magnetic beads. In some embodiments, this also means that a process that is compliant with GMP standards can be more easily established compared to other methods, such as the use of Dynabeads in which additional measures have to be taken to ensure that the final expanded T cell population is free of magnetic beads. Furthermore, in some embodiments, the use of a soluble multimerization agent makes it much easier to remove the same from the activated cell population (T cells, B cells or also natural killer cells) since the cells can be simple sedimented by centrifugation and the supernatant, including the soluble multimerization agent can be discarded. Alternatively, the soluble multimerization agent can be removed from the expanded cell population in a gel permeations matrix of the removal cartridge, such as described above (e.g. International Patent App. Pub. No. WO 2013/124474). In some embodiments, since no solid phase (e.g. magnetic beads) are present, the present invention also provides for an automated closed system for expansion of the cells that can be integrated into known cell expansion systems such as the Xuri Cell Expansion System W25 and WAVE Bioreactor 2/10 System, available from GE Healthcare (Little Chalfont, Buckinghamshire, United Kingdom) or the Quantum® Cell Expansion System, available from TerumoBCT Inc. (Lakewood, Colo., USA).

In some aspects, the methods provided herein can include a population of cells that carry at least two specific cell surface molecules. In some embodiments, a first cell surface molecule is involved in a primary activation signal to the cell population, while the second cell surface molecule is an accessory molecule on the cell surface that is involved in providing a stimulus to the cells. In some embodiments, the cell population is contacted with a multimerization reagent in which is reversibly bound a first agent that provides a primary activation signal to the cells and a second agent that induces or modulates an additional signal, such as stimulates an accessory molecule on the surface of the cells. The population of cells may, for example, be a T cell population in which the cell surface molecule is a TCR/CD3 complex and the cell surface molecule is the accessory molecule CD28. Further, as described herein, targeting other accessory molecules also is contemplated, such as one or more of CD90 (Thy-1), CD95 (Apo-/Fas), CD137 (4-1BB), CD154 (CD40L), ICOS, LAT, CD27, OX40 and HVEM. In some aspects, stimulation through such other accessory molecules can result in an increase in a less-differentiated, and, in some cases, a long-lived population T cells such as long-lived memory T cells as compared to conventional stimulation through CD28. In some embodiments, binding of both the TCR/CD3 complex as the primary activation signal and binding of the accessory molecule (e.g. CD28 or other accessory molecule) can be necessary for expansion/proliferation of T cells.

In some embodiments as described, the population of cells may alternatively or additionally be stimulated in the presence of a multimerization reagent that is reversibly bound to an agent that targets or binds a molecule on the surface of the cell to provide an additional signal that modulates survival, proliferation and/or one or more other properties of the cells. Such targeted molecules include, but are not limited to, cytokine receptors, chemokine receptors or adhesion molecules. In some aspects, stimulation through such additional molecules can result in one or other improved features of the stimulated or cultured cells, including, for example, increased persistence, survival and/or less exhausted phenotype or activity.

In some embodiments, the methods provided herein also can be further combined to include at least one selection agent reversibly bound to the same reagent, e.g. same multimerization reagent, as the receptor-binding agent, e.g. either or both of the first or second and/or additional receptor-binding agent (e.g. stimulatory agent). In some cases, it is possible to enhance or increase one or more features resulting from the incubation or culture, such as stimulation of expansion (proliferation), activation, costimulation, and/or survival, in a subset of T cells which can be reversibly selected in the presence of the at least one or more selection agent in an incubation or culture that occurs also in the presence of the one or more stimulatory agents. For example, as shown in examples herein, the degree of expansion in a composition of T cells was selectively increased in CD8+ cells when such cells were incubated with a multimerized agent to which was reversibly bound an anti-CD8 antibody in addition to the anti-CD3 antibody and anti-CD28 antibody stimulatory agents. In some embodiments, one or more features resulting from the incubation or culture, such as stimulation of expansion (proliferation), activation, costimulation, and/or survival, can be increased at least 1.5-fold, at least 2.0-fold, at least 3.0-fold, at least 4.0-fold, at least 5.0-fold, at least 6.0-fold, at least 7.0-fold, at least 8.0-fold, at least 9.0-fold, at least 10.0-fold or more in a subset of T cell in the cultured composition that are positive for a selection marker when incubated in the presence of the one or more stimulatory agents and the selection agent that specifically binds to the selection marker compared to the incubation only in the presence of the one of more stimulatory agents but not the selection agent. This biasing or selectivity of cell, such as T cell, features permits one to control the end points features of specific subsets or populations of T cells. In some embodiments, the selection marker can be any selection marker as described herein. In some embodiments, the selection marker is selected from among CD25, CD28, CD62L, CCR7, CD27, CD127, CD3, CD4, CD8, CD45RA, and/or CD45RO.

In some embodiments, the multimerization reagent comprises at least one binding site Z, e.g. Z1, for the reversible binding of the agent, e.g. first agent, and the agent, e.g. first agent, also comprises at least one binding partner C, e.g. C1, wherein the binding partner C, e.g. C1, is able of reversibly binding to the binding site Z, e.g. Z1, of the multimerization reagent. Thus, the agent, e.g. first agent, when contacted or incubated with the multimerization agent, can be reversibly bound to the multimerization reagent via the reversible bond formed between the binding partner C, e.g. C1, and the binding site Z, e.g. Z1. In addition, one or more further agents, e.g. the second agent, can comprises a binding partner C, e.g. C2, wherein the binding partner C2 is able of being reversibly bound to a binding site Z, e.g. Z2, respectively, of the multimerization reagent. In some embodiments, the one or more additional agents, e.g. second agent, when it is contacted or incubated with the multimerization agent, is reversibly bound to the multimerization reagent via the reversible bond formed between the binding partner C, e.g. C1 and the binding site Z, e.g. Z2. In some cases, C1 and C2 can be the same or substantially the same and/or comprise the same or substantially the same moiety. In some cases, Z1 and Z2 can be the same or substantially the same and/or comprise the same or substantially the same moiety.

In some embodiments, using as binding partners C1 and C2, moieties that bind to the same binding site of the multimerization agent has the advantage that the same competition reagent (of the first binding partner C1 and also of the second binding partner C2) or analog thereof can be used to disrupt, and in some cases terminate, the expansion of the population of target cells (e.g. T cells) and to release this population of target cells (e.g. T cells) from the multimerization agent.

In some cases for producing the binding agents (e.g. e.g. first, second and/or additional, receptor-binding agents, e.g. stimulatory agents, or selection agents) to comprise a binding partner C, the binding partner C, e.g. C1 or C2, can be provided by the respective expression vector used for the recombinant production of the agent (e.g. antibody fragment) so that the binding partner C, e.g. C1 or C2, is part of a fusion peptide with the agent at either the N-terminus or C-terminus. In some embodiments, in the context of an agent that is an antibody or antigen-binding fragment, the binding partner C, e.g. C1 or C2, can be present at the C-terminus of either the light or the heavy chain. Also this methodology of cloning a recombinant protein, such as the variable domains of an antibody molecule, and recombinantly producing a respective protein, e.g. antibody fragment, is well known to the person skilled in the art, see for example, Skerra, A. (1994). In some embodiments, an antibody molecule can be generated of artificial binding molecules with antibody like properties against a given target, such as CD3 or CD28 or other accessory or stimulatory agent molecules as described, such as by well-known evolutive methods such as phage display (reviewed, e.g., in Kay, B. K. et al. (1996) *Phage Display of Peptides and Proteins—A Laboratory Manual*, 1$^{st}$ Ed., Academic Press, New York N.Y.; Lowman, H. B. (1997) *Annu. Rev. Biophys. Biomol. Struct.* 26, 401-424, or Rodi, D. J., and Makowski, L. (1999) *Curr. Opin. Biotechnol.* 10, 87-93), ribosome display (reviewed in Amstutz, P. et al. (2001) *Curr. Opin. Biotechnol.* 12, 400-405) or mRNA display as reported in Wilson, D. S. et al. (2001) *Proc. Natl. Acad. Sci. USA* 98, 3750-3755.

II. Reversible Reagent Systems and Related Uses

In some embodiments, the methods employ reversible systems in which at least one agent (e.g., a receptor-binding agent or selection agent) capable of binding to a molecule on the surface of a cell (cell surface molecule), is reversibly associated with a reagent. In some cases, the reagent contains a plurality of binding sites capable of reversibly binding to the agent (e.g., receptor-binding agent or selection agent). In some cases, the reagent is a multimerization reagent. In some embodiments, the at least one agent (e.g., receptor-binding agent or selection agent) contains at least one binding site B that can specifically bind an epitope or region of the molecule and also contains a binding partner C that specifically binds to at least one binding site Z of the reagent. In some cases, the binding interaction between the binding partner C and the at least one binding site Z is a non-covalent interaction. In some embodiments, the binding interaction, such as non-covalent interaction, between the binding partner C and the at least one binding site Z is reversible.

In some embodiments, the reversible association can be mediated in the presence of a substance, such as a competition reagent (also called an eluent reagent), that is or contains a binding site that also is able to bind to the at least one binding site Z. Generally, the substance (e.g. competition reagent) can act as a competitor due to a higher binding affinity for the binding site Z present in the reagent and/or due to being present at higher concentrations than the binding partner C, thereby detaching and/or dissociating the binding partner C from the reagent. In some embodiments, the affinity of the substance (e.g. competition reagent) for the at least one binding site Z is greater than the affinity of the binding partner C of the agent (e.g., receptor-binding agent or selection agent) for the at least one binding site Z. Thus, in some cases, the bond between the binding site Z of the reagent and the binding partner C of the agent (e.g., receptor-binding agent or selection agent) can be disrupted by addition of the substance (e.g. competition reagent), thereby rendering the association of the agent (e.g., receptor-binding agent or selection agent) and reagent reversible.

Reagents that can be used in such reversible systems are described and known in the art, see e.g., U.S. Pat. Nos. 5,168,049; 5,506,121; 6,103,493; 7,776,562; 7,981,632; 8,298,782; 8,735,540; 9,023,604; and International published PCT Appl. Nos. WO2013/124474 and WO2014/076277. Non-limiting examples of reagents and binding partners capable of forming a reversible interaction, as well as substances (e.g. competition reagents) capable of reversing such binding, are described below.

A. Reagent

In some embodiments, the reagent contains one or a plurality of binding sites Z that are capable of reversibly binding to a binding partners C comprised by the agent (e.g., receptor-binding agent or selection agent). In some embodiments, the reagent contains a plurality of binding sites Z, which each are able to specifically bind to the binding partner C that is included in the agent (e.g., receptor-binding agent or selection agent), such that the reagent is capable of reversibly binding to a plurality of agents (e.g., receptor-binding agent or selection agent), e.g., is a multimerization reagent. In some embodiments, the reagent is an oligomer or polymer of individual molecules (e.g. monomers) or complexes that make up an individual molecule (e.g. tetramer), each containing at least one binding site Z. In some embodiments, the reagent contains at least two binding sites Z, at least three binding sites Z, at least four binding sites Z, such as at least 5, 6, 7, 8, 9, 10, 11, 12, 13, 14, 15, 16, 17, 18, 19, 20, 24, 28, 32, 36, 40, 44, 48, 52, 56, 60, 64, 68, 72 or more binding sites Z. The binding sites can all be the same or the plurality of binding sites can contain one or more different binding sites (e.g., Z1, Z2, Z3, etc.).

In some embodiments, two or more agents (e.g., receptor-binding agents or selection agents) associate with, such as are reversibly bound to, the reagent, such as via the one or plurality of binding sites Z present on the reagent. In some cases, this results in the agents (e.g., receptor-binding agents or selection agents) being closely arranged to each other such that an avidity effect can take place if a target cell having (at least two copies of) a cell surface molecule is brought into contact with the agent (e.g., receptor-binding agent or selection agent) that has one or more binding sites B able to bind the particular molecule.

In some embodiments, two or more different agents (e.g., receptor-binding agents or selection agents) that are the same, i.e. containing the same binding site B, can be reversibly bound to the reagent. In some embodiments, it is possible to use at least two different (kinds of) agents (e.g., receptor-binding agents or selection agents), and in some cases, three or four different (kinds of) agents, e.g. two or more different receptor-binding agents and/or selection agent. For example, in some embodiments, the reagent can be reversibly bound to a first agent (e.g., receptor-binding agent or selection agent) containing a binding site B1, B2, B3 or B4, etc. and a second agent (e.g., receptor-binding agent or selection agent) containing another binding site, e.g. another of a binding site B1, B2, B3 or B4. In some cases, the binding site of the first agent and the second agent can be the same. For example, in some aspects, each of the at least two agents (e.g. receptor-binding agent or selection agent) can bind to the same molecule. In some cases, the binding site of the first agent and the second agent can be different. In some aspects, each of the at least two agents (e.g. receptor-binding agent or selection agent) can bind to a different molecule, such as a first molecule, second molecule and so on. In some cases, the different molecules, such as cell surface molecules, can be present on the same target cell. In other cases, the different molecules, such as cell surface molecules, can be present on different target cells that are present in the same population of cells. In some case, a third, fourth and so on agent (e.g., receptor-binding agent or selection agent) can be associated with the same reagent, each containing a further different binding site.

In some embodiments, the two or more different agents (e.g., receptor-binding agents or selection agents) contain the same binding partner C. In some embodiments, the two or more different agents (e.g., receptor-binding agents or selection agents) contain different binding partners. In some aspects, a first agent (e.g., receptor-binding agent or selection agent) can have a binding partner C1 that can specifically bind to a binding site Z1 present on the reagent and a second agent (e.g., receptor-binding agents or selection agent) can have a binding partner C2 that can specifically bind to the binding site Z1 or to a binding site Z2 present on the reagent. Thus, in some instances, the plurality of binding sites Z comprised by the reagent includes binding sites Z1 and Z2, which are capable of reversibly binding to binding partners C1 and C2, respectively, comprised by the agent (e.g., receptor-binding agent or selection agent). In some embodiments, C1 and C2 are the same, and/or Z1 and Z2 are the same. In other aspects, one or more of the plurality of binding sites Z can be different. In other instances, one or more of the plurality of binding partners C may be different. It is within a level of a skilled artisan to choose any combination of different binding partners C that are compatible with a reagent containing the binding sites Z, as long as each of the binding partners C are able to interact, such as specifically bind, with one of the binding sites Z.

In some embodiments, the reagent is a streptavidin, a streptavidin mutein or analog, avidin, an avidin mutein or analog (such as neutravidin) or a mixture thereof, in which such reagent contains one or more binding sites Z for reversible association with a binding partner C. In some embodiments, the binding partner C can be a biotin, a biotin derivative or analog, or a streptavidin-binding peptide or other molecule that is able to specifically bind to streptavidin, a streptavidin mutein or analog, avidin or an avidin mutein or analog. In some embodiments, the reagent is or contains streptavidin, avidin, an analog or mutein of streptavidin, or an analog or mutein or avidin that reversibly binds biotin, a biotin analog or a biologically active fragment thereof. In some embodiments, the reagent is or contains an analog or mutein of streptavidin or an analog or mutein of avidin that reversibly binds a streptavidin-binding peptide. In some embodiments, the substance (e.g. competitive reagent) can be a biotin, a biotin derivative or analog or a streptavidin-binding peptide capable of competing for binding with the binding partner C for the one or more binding sites Z. In some embodiments, the binding partner C and the substance (e.g. competitive reagent) are different, and the substance (e.g. competitive reagent) exhibits a higher binding affinity for the one or more binding sites Z compared to the affinity of the binding partner.

In some embodiments, the streptavidin can be wild-type streptavidin, streptavidin muteins or analogs, such as streptavidin-like polypeptides. Likewise, avidin, in some aspects, includes wild-type avidin or muteins or analogs of avidin such as neutravidin, a deglycosylated avidin with modified arginines that typically exhibits a more neutral pi and is available as an alternative to native avidin. Generally, deglycosylated, neutral forms of avidin include those commercially available forms such as "Extravidin", available through Sigma Aldrich, or "NeutrAvidin" available from Thermo Scientific or Invitrogen, for example.

In some embodiments, the reagent is a streptavidin or a streptavidin mutein or analog. In some embodiments, wild-type streptavidin (wt-streptavidin) has the amino acid sequence disclosed by Argarana et al., Nucleic Acids Res. 14 (1986) 1871-1882 (SEQ ID NO: 1). In general, streptavidin naturally occurs as a tetramer of four identical subunits, i.e. it is a homo-tetramer, where each subunit contains a single binding site for biotin, a biotin derivative or analog or a biotin mimic. An exemplary sequence of a streptavidin subunit is the sequence of amino acids set forth in SEQ ID NO: 1, but such a sequence also can include a sequence present in homologs thereof from other *Streptomyces* species. In particular, each subunit of streptavidin may exhibit a strong binding affinity for biotin with an equilibrium dissociation constant ($K_D$) on the order of about $10^{-14}$ M. In some cases, streptavidin can exist as a monovalent tetramer in which only one of the four binding sites is functional (Howarth et al. (2006) *Nat. Methods*, 3:267-73; Zhang et al. (2015) *Biochem. Biophys. Res. Commun.*, 463:1059-63)), a divalent tetramer in which two of the four binding sites are functional (Fairhead et al. (2013) *J. Mol. Biol.*, 426:199-214), or can be present in monomeric or dimeric form (Wu et al. (2005) *J. Biol. Chem.*, 280:23225-31; Lim et al. (2010) *Biochemistry*, 50:8682-91).

In some embodiments, streptavidin may be in any form, such as wild-type or unmodified streptavidin, such as a streptavidin from a *Streptomyces* species or a functionally active fragment thereof that includes at least one functional subunit containing a binding site for biotin, a biotin derivative or analog or a biotin mimic, such as generally contains at least one functional subunit of a wild-type streptavidin from *Streptomyces avidinii* set forth in SEQ ID NO: 1 or a functionally active fragment thereof. For example, in some embodiments, streptavidin can include a fragment of wild-type streptavidin, which is shortened at the N- and/or C-terminus. Such minimal streptavidins include any that begin N-terminally in the region of amino acid positions 10 to 16 of SEQ ID NO: 1 and terminate C-terminally in the region of amino acid positions 133 to 142 of SEQ ID NO: 1. In some embodiments, a functionally active fragment of streptavidin contains the sequence of amino acids set forth in SEQ ID NO: 2. In some embodiments, streptavidin, such as set forth in SEQ ID NO: 2, can further contain an N-terminal methionine at a position corresponding to Ala13 with numbering set forth in SEQ ID NO: 1. Reference to the position of residues in streptavidin or streptavidin muteins is with reference to numbering of residues in SEQ ID NO: 1.

In some aspects, streptavidin muteins include polypeptides that are distinguished from the sequence of an unmodified or wild-type streptavidin by one or more amino acid substitutions, deletions, or additions, but that include at least one functional subunit containing a binding site for biotin, a biotin derivative or analog or a streptavidin-binding peptide. In some aspects, streptavidin-like polypeptides and streptavidin muteins can be polypeptides which essentially are immunologically equivalent to wild-type streptavidin and are in particular capable of binding biotin, biotin derivatives or biotin analogues with the same or different affinity as wt-streptavidin. In some cases, streptavidin-like polypeptides or streptavidin muteins may contain amino acids which are not part of wild-type streptavidin or they may include only a part of wild-type streptavidin. In some embodiments, streptavidin-like polypeptides are polypeptides which are not identical to wild-type streptavidin, since the host does not have the enzymes which are required in order to transform the host-produced polypeptide into the structure of wild-type streptavidin. In some embodiments, streptavidin also may be present as streptavidin tetramers and streptavidin dimers, in particular streptavidin homotetramers, streptavidin homodimers, streptavidin heterotetramers and streptavidin heterodimers. Generally, each subunit normally has a binding site for biotin or biotin analogues or for streptavidin-binding peptides. Examples of streptavidins or streptavidin muteins are mentioned, for example, in WO 86/02077, DE 19641876 A1, U.S. Pat. No. 6,022,951, WO 98/40396 or WO 96/24606.

In some embodiments, a streptavidin mutein can contain amino acids that are not part of an unmodified or wild-type streptavidin or can include only a part of a wild-type or unmodified streptavidin. In some embodiments, a streptavidin mutein contains at least one subunit that can have one more amino acid substitutions (replacements) compared to a subunit of an unmodified or wild-type streptavidin, such as compared to the wild-type streptavidin subunit set forth in SEQ ID NO: 1 or a functionally active fragment thereof, e.g. set forth in SEQ ID NO: 2. In some embodiments, at least one subunit of a streptavidin mutein can have at least 1, 2, 3, 4, 5, 6, 7, 8, 9, 10, 11, 12, 13, 14, 15, 16, 17, 18, 19 or 20 amino acid differences compared to a wild-type or unmodified streptavidin and/or contains at least one subunit that comprising an amino acid sequence that exhibits at least 85%, 86%, 87%, 88%, 89%, 90%, 91%, 92%, 93%, 94%, 95%, 96%, 97%, 98%, 99% or more sequence identity to the sequence of amino acids set forth in SEQ ID NO: 1 or 2, where such streptavidin mutein exhibits functional activity to bind biotin, a biotin derivative or analog or biotin mimic. In some embodiments, the amino acid replacements (substitutions) are conservative or non-conservative mutations. Examples of streptavidin muteins are known in the art, see e.g., U.S. Pat. Nos. 5,168,049; 5,506,121; 6,022,951; 6,156,493; 6,165,750; 6,103,493; or 6,368,813; or International published PCT App. No. WO2014/076277.

In some embodiments, streptavidin or a streptavidin mutein includes proteins containing one or more than one functional subunit containing one or more binding sites Z for biotin, a biotin derivative or analog or a streptavidin-binding peptide, such as two or more, three or more, four or more, and, in some cases, 5, 6, 7, 8, 9, 10, 11, 12 or more functional subunits. In some embodiments, streptavidin or streptavidin mutein can include a monomer; a dimer, including a heterodimer or a homodimer; a tetramer, including a homotetramer, a heterotetramer, a monovalent tetramer or a divalent tetramer; or can include higher ordered multimers or oligomers thereof.

In some embodiments, the binding affinity of streptavidin or a streptavidin mutein for a peptide ligand binding partner is less than $1 \times 10^{-4}$ M, $5 \times 10^{-4}$ M, $1 \times 10^{-5}$ M, $5 \times 10^{-5}$ M, $1 \times 10^{-6}$ M, $5 \times 10^{-6}$ M or $1 \times 10^{-7}$ M, but generally greater than $1\times10^{-13}$ M, $1\times10^{-12}$ M or $1\times10^{-11}$ M. For example, peptide sequences (Strep-tags), such as those disclosed in U.S. Pat. No. 5,506,121, can act as biotin mimics and demonstrate a binding affinity for streptavidin, e.g., with a $K_D$ of approximately between $10^{-4}$ M and $10^{-5}$M. In some cases, the binding affinity can be further improved by making a mutation within the streptavidin molecule, see e.g. U.S. Pat. No. 6,103,493 or International published PCT App. No. WO2014/076277. In some embodiments, binding affinity can be determined by methods known in the art, such as any described below.

In some embodiments, the reagent, such as a streptavidin or streptavidin mutein, exhibits binding affinity for a peptide ligand binding partner, which peptide ligand binding partner can be the binding partner C present in the agent (e.g., receptor-binding agent or selection agent). In some embodiments, the peptide sequence contains a sequence with the general formula set forth in SEQ ID NO: 9, such as contains the sequence set forth in SEQ ID NO: 10. In some embodiments, the peptide sequence has the general formula set forth in SEQ ID NO: 11, such as set forth in SEQ ID NO: 12. In one example, the peptide sequence is Trp-Arg-His-Pro-Gln-Phe-Gly-Gly (also called Strep-Tag®, set forth in SEQ ID NO: 7). In one example, the peptide sequence is Trp-Ser-His-Pro-Gln-Phe-Glu-Lys (also called Strep-Tag® II, set forth in SEQ ID NO: 8). In some embodiments, the peptide ligand contains a sequential arrangement of at least two streptavidin-binding modules, wherein the distance between the two modules is at least 0 and not greater than 50 amino acids, wherein one binding module has 3 to 8 amino acids and contains at least the sequence His-Pro-Xaa (SEQ ID NO: 9), where Xaa is glutamine, asparagine, or methionine, and wherein the other binding module has the same or different streptavidin peptide ligand, such as set forth in SEQ ID NO: 11 (see e.g. International Published PCT Appl. No. WO02/077018; U.S. Pat. No. 7,981,632). In some embodiments, the peptide ligand contains a sequence having the formula set forth in any of SEQ ID NO: 13 or 14. In some embodiments, the peptide ligand has the sequence of amino acids set forth in any of SEQ ID NOS: 15-19.

In some embodiments, the reagent is or contains a streptavidin mutein. In some embodiments, the streptavidin muteins contain one or more mutations (e.g. amino acid replacements) compared to wild-type streptavidin set forth in SEQ ID NO: 1 or a biologically active portion thereof. For example, biologically active portions of streptavidin can include streptavidin variants that are shortened at the N- and/or the C-terminus, which in some cases is called a minimal streptavidin. In some embodiments, an N-terminally shortened minimal streptavidin, to which any of the mutations can be made, begins N-terminally in the region of the amino acid positions 10 to 16 and terminates C-terminally in the region of the amino acid positions 133 to 142 compared to the sequence set forth in SEQ ID NO: 1. In some embodiments, an N-terminally shortened streptavidin, to which any of the mutations can be made, contains the amino acid sequence set forth in SEQ ID NO: 2. In some embodiments, the minimal streptavidin contains an amino acid sequence from position Ala13 to Ser139 and optionally has an N-terminal methionine residue instead of Ala13. For purposes herein, the numbering of amino acid positions refers throughout to the numbering of wt-streptavidin set forth in SEQ ID NO: 1 (e.g. Argarana et al., Nucleic Acids Res. 14 (1986), 1871-1882, cf. also FIG. 3).

In some embodiments, the streptavidin mutein is a mutant as described in U.S. Pat. No. 6,103,493. In some embodiments, the streptavidin mutein contains at least one mutation within the region of amino acid positions 44 to 53, based on the amino acid sequence of wild-type streptavidin, such as set forth in SEQ ID NO: 1. In some embodiments, the streptavidin mutein contains a mutation at one or more residues 44, 45, 46, and/or 47. In some embodiments, the streptavidin mutein contains a replacement of Glu at position 44 of wild-type streptavidin with a hydrophobic aliphatic amino acid, e.g. Val, Ala, Ile or Leu, any amino acid at position 45, an aliphatic amino acid, such as a hydrophobic aliphatic amino acid at position 46 and/or a replacement of Val at position 47 with a basic amino acid, e.g. Arg or Lys, such as generally Arg. In some embodiments, Ala is at position 46 and/or Arg is at position 47 and/or Val or Ile is at position 44. In some embodiments, the streptavidin mutant contains residues $Val^{44}$-$Thr^{45}$-$Ala^{46}$-$Arg^{47}$, such as set forth in exemplary streptavidin muteins containing the sequence of amino acids set forth in SEQ ID NO: 3 or SEQ ID NO: 4 (also known as streptavidin mutant 1, SAM1). In some embodiments, the streptavidin mutein contains residues $Ile^{44}$-$Gly^{45}$-$Ala^{46}$-$Arg^{47}$, such as set forth in exemplary streptavidin muteins containing the sequence of amino acids set forth in SEQ ID NO: 5 or 6 (also known as SAM2). In some cases, such streptavidin mutein are described, for example, in U.S. Pat. No. 6,103,493, and are commercially available under the trademark Strep-Tactin®.

In some embodiment, the streptavidin mutein is a mutant as described in International Published PCT Appl. Nos. WO 2014/076277. In some embodiments, the streptavidin mutein contains at least two cysteine residues in the region of amino acid positions 44 to 53 with reference to amino acid positions set forth in SEQ ID NO: 1. In some embodiments, the cysteine residues are present at positions 45 and 52 to create a disulfide bridge connecting these amino acids. In such an embodiment, amino acid 44 is typically glycine or alanine and amino acid 46 is typically alanine or glycine and amino acid 47 is typically arginine. In some embodiments, the streptavidin mutein contains at least one mutation or amino acid difference in the region of amino acids residues 115 to 121 with reference to amino acid positions set forth in SEQ ID NO: 1. In some embodiments, the streptavidin mutein contains at least one mutation at amino acid position 117, 120 and 121 and/or a deletion of amino acids 118 and 119 and substitution of at least amino acid position 121.

In some embodiments, the streptavidin mutein contains a mutation at a position corresponding to position 117, which mutation can be to a large hydrophobic residue like Trp, Tyr or Phe or a charged residue like Glu, Asp or Arg or a hydrophilic residue like Asn or Gln, or, in some cases, the hydrophobic residues Leu, Met or Ala, or the polar residues Thr, Ser or His. In some embodiments, the mutation at position 117 is combined with a mutation at a position corresponding to position 120, which mutation can be to a small residue like Ser or Ala or Gly, and a mutation at a position corresponding to position 121, which mutation can be to a hydrophobic residue, such as a bulky hydrophobic residue like Trp, Tyr or Phe. In some embodiments, the mutation at position 117 is combined with a mutation at a position corresponding to position 120 of wildtype streptavidin set forth in SEQ ID NO:1 or a biologically active fragment thereof, which mutation can be a hydrophobic residue such as Leu, Be, Met, or Val or, generally, Tyr or Phe, and a mutation at a position corresponding to position 121 compared to positions of wildtype streptavidin set forth in SEQ ID NO:1 or a biologically active fragment thereof, which mutation can be to a small residue like Gly, Ala, or Ser, or with Gln, or with a hydrophobic residue like Leu, Val, Ile, Trp, Tyr, Phe, or Met. In some embodiments, such muteins also can contain residues Val44-Thr45-Ala46-Arg47 or residues Ile44-Gly45-Ala46-Arg47. In some embodiments, the streptavidin mutein contains the residues Val44, Thr45, Ala46, Arg47, Glu117, Gly120 and Tyr121. In some embodiments, the mutein streptavidin contains the sequence of amino acids set forth in SEQ ID NO:27 or SEQ ID NO:28, or a sequence of amino acids that exhibits at least 85%, 86%, 87%, 88%, 89%, 90%, 91%, 92%, 93%, 94%, 95%, 96%, 97%, 98%, 99% or more sequence identity to the sequence of amino acids set forth in SEQ ID NO: 27 or SEQ ID NO: 28, contains the residues Val44, Thr45, Ala46, Arg47, Glu117, Gly120 and Tyr121 and exhibits functional activity to bind to biotin, a biotin analog or a streptavidin-binding peptide.

In some embodiments, a streptavidin mutein can contain any of the above mutations in any combination, and the resulting streptavidin mutein may exhibit a binding affinity that is less than $2.7 \times 10^{-4}$ M for the peptide ligand (Trp-Arg-His-Pro-Gln-Phe-Gly-Gly; also called Strep-Tag®, set forth in SEQ ID NO: 7) and/or less than $1.4 \times 10^{-4}$ M for the peptide ligand (Trp-Ser-His-Pro-Gln-Phe-Glu-Lys; also called Strep-Tag® II, set forth in SEQ ID NO: 8) and/or is less than $1 \times 10^{-4}$ M, $5 \times 10^{-4}$ M, $1 \times 10^{-5}$ M, $5 \times 10^{-5}$ M, $1 \times 10^{-6}$ M, $5 \times 10^{-6}$ M or $1 \times 10^{-7}$ M, but generally greater than $1 \times 10^{-13}$ M, $1 \times 10^{-12}$ M or $1 \times 10^{-11}$ M for any of the peptide ligands set forth in any of SEQ ID NOS:7-19.

In some embodiments, the streptavidin mutein exhibits the sequence of amino acids set forth in any of SEQ ID NOs: 3-6 27 or 28, or a sequence of amino acids that exhibits at least 90%, 91%, 92%, 93%, 94%, 95%, 96%, 97%, 98%, 99% or more sequence identity to the sequence of amino acids set forth in any of SEQ ID NO: 3-6, 27 or 28, and exhibits a binding affinity that is less than $2.7 \times 10^{-4}$ M for the peptide ligand (Trp-Arg-His-Pro-Gln-Phe-Gly-Gly; also called Strep-Tag®, set forth in SEQ ID NO: 7) and/or less than $1.4 \times 10^{-4}$ M for the peptide ligand (Trp-Ser-His-Pro-Gln-Phe-Glu-Lys; also called Strep-Tag® II, set forth in SEQ ID NO: 8) and/or is less than $1 \times 10^{-4}$ M, $5 \times 10^{-4}$ M, $1 \times 10^{-5}$ M, $5 \times 10^{-5}$ M, $1 \times 10^{-6}$ M, $5 \times 10^{-6}$ M or $1 \times 10^{-7}$ M, but generally greater than $1 \times 10^{-13}$ M, $1 \times 10^{-12}$ M or $1 \times 10^{-11}$ M for any of the peptide ligands set forth in any of SEQ ID NOS:7-19.

In some embodiments, the streptavidin mutein also exhibits binding to other streptavidin ligands, such as but not limited to, biotin, iminobiotin, lipoic acid, desthiobiotin, diaminobiotin, HABA (hydroxyazobenzene-benzoic acid) and/or dimethyl-HABA. In some embodiments, the streptavidin mutein exhibits a binding affinity for another streptavidin ligand, such as biotin or desthiobiotin, that is greater than the binding affinity of the streptavidin mutein for a biotin mimic peptide ligand, such as set forth in any of SEQ ID NOS: 7-19. Thus, in some embodiments, biotin or a biotin analog or derivative (e.g. desthiobiotin) can be employed as a competition reagent in the provided methods. For example, as an example, the interaction of a mutein streptavidin designated Strep-Tactin® (e.g. containing the sequence set forth in SEQ ID NO: 4) with the peptide ligand designated Strep-Tag® II (e.g. set forth in SEQ ID NO: 8) is characterized by a binding affinity with a $K_D$ of approximately $10^{-6}$ M compared to approximately $10^{-13}$ M for the bitoin-streptavidin interaction. In some cases, biotin, which can bind with high affinity to the Strep-Tactin® with a $K_D$ of between or between about $10^{-10}$ and $10^{-13}$ M, can compete with Strep-Tag® II for the binding site.

In some cases, the reagent contains at least two chelating groups K that may be capable of binding to a transition metal ion. In some embodiments, the reagent may be capable of binding to an oligohistidine affinity tag, a glutathione-S-transferase, calmodulin or an analog thereof, calmodulin binding peptide (CBP), a FLAG-peptide, an HA-tag, maltose binding protein (MBP), an HSV epitope, a myc epitope, and/or a biotinylated carrier protein.

In some embodiments, the reagent is an oligomer or polymer. In some embodiments, the oligomer or polymer can be generated by linking directly or indirectly individual molecules of the protein as it exists naturally, either by linking directly or indirectly individual molecules of a monomer or a complex of subunits that make up an individual molecule (e.g. linking directly or indirectly dimers, trimers, tetramers, etc. of a protein as it exists naturally). For example, a tetrameric homodimer or heterodimer of streptavidin or avidin may be referred to as an individual molecule or smallest building block of a respective oligomer or polymer. In some embodiments, the oligomer or polymer can contain linkage of at least 2 individual molecules of the protein (e.g. is a 2-mer), or can be at least a 3-mer, 4-mer, 5-mer, 6-mer, 7-mer, 8-mer, 9-mer, 10-mer, 11-mer, 12-mer, 13-mer, 14-mer, 15-mer, 16-mer, 17-mer, 18-mer, 19-mer, 20-mer, 25-mer, 30-mer, 35-mer, 40-mer, 45-mer or 50-mer of individual molecules of the protein (e.g., monomers, tetramers).

Oligomers can be generated using any methods known in the art, such as any described in published U.S. Patent Application No. US2004/0082012. In some embodiments, the oligomer or polymer contains two or more individual molecules that may be crosslinked, such as by a polysaccharide or a bifunctional linker.

In some embodiments, the oligomer or polymer is obtained by crosslinking individual molecules or a complex of subunits that make up an individual molecule in the presence of a polysaccharide. In some embodiments, oligomers or polymers can be prepared by the introduction of carboxyl residues into a polysaccharide, e.g. dextran. In some aspects, individual molecules of the reagent (e.g., monomers, tetramers) can be coupled via primary amino groups of internal lysine residues and/or the free N-terminus to the carboxyl groups in the dextran backbone using conventional carbodiimide chemistry. In some embodiments, the coupling reaction is performed at a molar ratio of about 60 moles of individual molecules of the reagent (e.g., monomers, tetramers) per mole of dextran.

In some embodiments the reagent is an oligomer or a polymer of one or more streptavidin or avidin or of any analog or mutein of streptavidin or an analog or mutein of avidin (e.g. neutravidin). In some embodiments, the binding site Z is a natural biotin binding site of avidin or streptavidin for which there can be up to four binding sites in an individual molecule (e.g. a tetramer contains four binding sites Z), whereby a homo-tetramer can contain up to 4 binding sites that are the same, i.e. Z1, whereas a hetero-tetramer can contain up to 4 binding sites that may be different, e.g. containing Z1 and Z2. In some embodiments, the oligomer is generated or produced from a plurality of individual molecules (e.g. a plurality of homo-tetramers) of the same streptavidin, streptavidin mutein, avidin or avidin mutein, in which case each binding site Z, e.g. Z1, of the oligomer is the same. For example, in some cases, an oligomer can contain a plurality of binding sites Z1, such as at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 40, 45, 50 or more binding sites Z1. In some embodiments, the oligomer is generated or produced from a plurality of individual molecules that can be hetero-tetramers of a streptavidin, streptavidin mutein, avidin or avidin mutein and/or from a plurality of two or more different individual molecules (e.g. different homo-tetramers) of streptavidin, streptavidin mutein, avidin or avidin mutein that differ in their binding sites Z, e.g. Z1 and Z2, in which case a plurality of different binding sites Z, e.g. Z1 and Z2, may be present in the oligomer. For example, in some cases, an oligomer can contain a plurality of binding sites Z1 and a plurality of binding sites Z, which, in combination, can include at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 40, 45, 50 or more combined binding sites Z1 and Z2.

In some cases, the respective oligomer or polymer may be crosslinked by a polysaccharide. In one embodiment, oligomers or polymers of streptavidin or of avidin or of analogs of streptavidin or of avidin (e.g., neutravidin) can be prepared by the introduction of carboxyl residues into a polysaccharide, e. g. dextran, essentially as described in Noguchi, A, et al., Bioconjugate Chemistry (1992) 3, 132-137 in a first step. In some such aspects, streptavidin or avidin or analogs thereof then may be linked via primary amino groups of internal lysine residue and/or the free N-terminus to the carboxyl groups in the dextran backbone using conventional carbodiimide chemistry in a second step. In some cases, cross-linked oligomers or polymers of streptavidin or avidin or of any analog of streptavidin or avidin may also be obtained by crosslinking via bifunctional molecules, serving as a linker, such as glutardialdehyde or by other methods described in the art.

In some embodiments, the oligomer or polymer is obtained by crosslinking individual molecules or a complex of subunits that make up an individual molecule using a bifunctional linker or other chemical linker, such as glutardialdehyde or by other methods known in the art. In some aspects, cross-linked oligomers or polymers of streptavidin or avidin or of any mutein or analog of streptavidin or avidin may be obtained by crosslinking individual streptavidin or avidin molecules via bifunctional molecules, serving as a linker, such as glutardialdehyde or by other methods described in the art. It is, for example, possible to generate oligomers of streptavidin muteins by introducing thiol groups into the streptavidin mutein (this can, for example, be done by reacting the streptavidin mutein with 2-iminothiolan (Trauts reagent) and by activating, for example in a separate reaction, amino groups available in the streptavidin mutein. In some embodiments, this activation of amino groups can be achieved by reaction of the streptavidin mutein with a commercially available heterobifunctional crosslinker such as sulfosuccinimidyl 4-(N-maleimidomethyl)cyclohexane-1-carboxylate (sulfo SMCC) or Succinimidyl-6-[(β-maleimidopropionamido)hexanoate (SMPH). In some such embodiments, the two reaction products so obtained are mixed together, typically leading to the reaction of the thiol groups contained in the one batch of modified streptavidin mutein with the activated (such as by maleimide functions) amino acids of the other batch of modified streptavidin mutein. In some cases, by this reaction, multimers/oligomers of the streptavidin mutein are formed. These oligomers can have any suitable number of individual molecules, such as at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 40, 45, 50 or more, and the oligomerization degree can be varied according to the reaction condition.

In some embodiments, the oligomeric or polymeric reagent can be isolated via size exclusion chromatography and any desired fraction can be used as the reagent. For example, in some embodiments, after reacting the modified streptavidin mutein, in the presence of 2-iminothiolan and a heterobifunctional crosslinker such as sulfo SMCC, the oligomeric or polymeric reagent can be isolated via size exclusion chromatography and any desired fraction can be used as the reagent. In some embodiments, the oligomers do not have (and do not need to have) a single molecular weight but they may observe a statistical weight distribution such as Gaussian distribution. In some cases, any oligomer with more than three streptavidin or mutein tetramers, e.g., homotetramers or heterotetramers, can be used as a soluble reagent, such as generally 3 to 50 tetramers, e.g., homotetramers or heterotetramers, 10 to 40 tetramers, e.g., homotetramers or heterotetramers, or 25 to 35 tetramers, e.g., homotetramers or heterotetramers. The oligomers might have, for example, from 3 to 25 streptavidin mutein tetramers, e.g., homotetramers or heterotetramers. In some aspects, with a molecular weight of about 50 kDa for streptavidin muteins, the soluble oligomers can have a molecular weight from about 150 kDa to about 2000 kDa, about 150 kDa to about 1500 kDa, about 150 kDa to about 1250 kDa, about 150 kDa to 1000 kDa, about 150 kDa to about 500 kDa or about 150 kDa to about 300 kDa, about 300 kDa to about 2000 kDa, about 300 kDa to about 1500 kDa, about 300 kDa to about 1250 kDa, about 300 kDa to 1000 kDa, about 300 kDa to about 500 kDa, about 500 kDa to about 2000 kDa, about 500 kDa to about 1500 kDa, about 500 kDa to about 1250 kDa, about 500 kDa to 1000 kDa, about 1000 kDa to about 2000 kDa, about 1000 kDa to about 1500 kDa, about 1000 kDa to about 1250 kDa, about 1250 kDa to about 2000 kDa or about 1500 kDa to about 2000 kDa. Generally, because each streptavidin molecule/mutein has four biotin binding sites, such a reagent can provide 12 to 160 binding sites Z, such as 12 to 100 binding sites Z.

B. Format of Reagent

1. Support

In some embodiments, the reagent is comprised on a support, such as a solid support or surface, e.g., bead, or a stationary phase (chromatography matrix). In some such embodiments, the reagent is reversibly immobilized on the support. In some cases, the reagent is immobilized to the support via covalent bonds. In some aspects, the reagent is reversibly immobilized to the support non-covalently.

In some embodiments, the support is a solid support. Any solid support (surface) can be used for the reversible immobilization of the reagent. Illustrative examples of solid supports on which the reagent can be immobilized include a magnetic bead, a polymeric bead, a cell culture plate, a microtiter plate, a membrane, or a hollow fiber. In some aspects, hollow fibers can be used as a bioreactor in the Quantum® Cell Expansion System, available from TerumoBCT Inc. (Lakewood, Colo., USA). In some embodiments, the reagent is covalently attached to the solid support. In other embodiments, non-covalent interactions can also be used for immobilization, for example on plastic substrates. In some embodiments, the reagent can, for example, be a streptavidin or avidin mutein that reversibly binds a streptavidin binding peptide. Such streptavidin muteins can be covalently attached to any surface, for example, resin (beads) used for chromatography purification and are commercially available in such form from IBA GmbH, Göttingen, for example, as Strep-Tactin® Sepharose, Strep-Tactin® Superflow®, Strep-Tactin® Superflow® high capacity or Strep-Tactin® MacroPrep®. Other illustrative examples that are readily commercially available are immobilized metal affinity chromatography (IMAC) resins such as the TALON® resins (Westburg, Leusden, The Netherlands) that can be used for the reversible immobilization of oligohistidine tagged (his-tagged) proteins, such as for the reversible binding of an agent (e.g., receptor-binding agent or selection agent) that contains as a binding partner C an oligohistidine tag such as a penta- or hexa-histidine tag. Other examples include calmodulin sepharose available from GE Life Sciences which can be used together with an agent (e.g., receptor-binding agent or selection agent) that contains a calmodulin binding peptide as a binding partner C or sepharose, to which glutathion is coupled. In some such cases, the binding partner C is glutathion-S-transferase.

In some embodiments, the support contains a stationary phase. Thus, in some embodiments, the reagent is comprised on a stationary phase (also called chromatography matrix). In some such embodiments, the reagent is reversibly immobilized on the stationary phase. In some cases, the reagent is reversibly immobilized to the stationary phase via covalent bonds. In some aspects, the reagent is reversibly immobilized to the stationary phase non-covalently.

Any material may be employed as a chromatography matrix. In general, a suitable chromatography material is essentially innocuous, i.e. not detrimental to cell viability, such as when used in a packed chromatography column under desired conditions. In some embodiments, the stationary phase remains in a predefined location, such as a predefined position, whereas the location of the sample is being altered. Thus, in some embodiments the stationary phase is the part of a chromatographic system through which the mobile phase flows (either by flow through or in a batch mode) and where distribution of the components contained in the liquid phase (either dissolved or dispersed) between the phases occurs.

In some embodiments, the chromatography matrix has the form of a solid or semisolid phase, whereas the sample that contains the target cell to be isolated/separated is a fluid phase. The chromatography matrix can be a particulate material (of any suitable size and shape) or a monolithic chromatography material, including a paper substrate or membrane. Thus, in some aspects, the chromatography can be both column chromatography as well as planar chromatography. In some embodiments, in addition to standard chromatography columns, columns allowing a bidirectional flow such as PhyTip® columns available from PhyNexus, Inc. San Jose, Calif., U.S.A. or pipette tips can be used for column based/flow through mode based methods. Thus, in some cases, pipette tips or columns allowing a bidirectional flow are also comprised by chromatography columns useful in the present methods. In some cases, such as where a particulate matrix material is used, the particulate matrix material may, for example, have a mean particle size of about 5 µm to about 200 µm, or from about 5 µm to about 400 µm, or from about 5 µm to about 600 µm. In some aspects, the chromatography matrix may, for example, be or include a polymeric resin or a metal oxide or a metalloid oxide. In some aspects, such as where planar chromatography is used, the matrix material may be any material suitable for planar chromatography, such as conventional cellulose-based or organic polymer based membranes (for example, a paper membrane, a nitrocellulose membrane or a polyvinylidene difluoride (PVDF) membrane) or silica coated glass plates. In one embodiment, the chromatography matrix/stationary phase is a non-magnetic material or non-magnetizable material.

In some embodiments, non-magnetic or non-magnetizable chromatography stationary phases that are suitable in the present methods include derivatized silica or a crosslinked gel. In some aspects, a crosslinked gel may be based on a natural polymer, such as on a polymer class that occurs in nature. For example, a natural polymer on which a chromatography stationary phase may be based is a polysaccharide. In some cases, a respective polysaccharide is generally crosslinked. An example of a polysaccharide matrix includes, but is not limited to, an agarose gel (for example, Superflow™ agarose or a Sepharose® material such as Superflow™ Sepharose® that are commercially available in different bead and pore sizes) or a gel of crosslinked dextran(s). A further illustrative example is a particulate cross-linked agarose matrix, to which dextran is covalently bonded, that is commercially available (in various bead sizes and with various pore sizes) as Sephadex® or Superdex®, both available from GE Healthcare. Another illustrative example of such a chromatography material is Sephacryl® which is also available in different bead and pore sizes from GE Healthcare.

In some embodiments, a crosslinked gel may also be based on a synthetic polymer, such as on a polymer class that does not occur in nature. In some aspects, such a synthetic polymer on which a chromatography stationary phase is based is a polymer that has polar monomer units, and which is therefore in itself polar. Thus, in some cases, such a polar polymer is hydrophilic. Hydrophilic molecules, also termed lipophobic, in some aspects contain moieties that can form dipole-dipole interactions with water molecules. In general, hydrophobic molecules, also termed lipophilic, have a tendency to separate from water.

Illustrative examples of suitable synthetic polymers are polyacrylamide(s), a styrene-divinylbenzene gel and a copolymer of an acrylate and a diol or of an acrylamide and a diol. An illustrative example is a polymethacrylate gel, commercially available as a Fractogel®. A further example is a copolymer of ethylene glycol and methacrylate, commercially available as a Toyopearl®. In some embodiments, a chromatography stationary phase may also include natural and synthetic polymer components, such as a composite matrix or a composite or a co-polymer of a polysaccharide and agarose, e.g. a polyacrylamide/agarose composite, or of a polysaccharide and N,N'-methylenebisacrylamide. An illustrative example of a copolymer of a dextran and N,N'-methylenebisacrylamide is the above-mentioned Sephacryl® series of material. In some embodiments, a derivatized silica may include silica particles that are coupled to a synthetic or to a natural polymer. Examples of such embodiments include, but are not limited to, polysaccharide grafted silica, polyvinylpyrrolidone grafted silica, polyethylene oxide grafted silica, poly(2-hydroxyethylaspartamide) silica and poly(N-isopropylacrylamide) grafted silica.

In some embodiments, the chromatography matrix is a gel filtration matrix, for example, when used in a removal cartridge as described herein. Generally, a gel filtration can be characterized by the property that it is designed to undergo. Hence, a gel filtration matrix in some aspects allows the separation of cells or other biological entities largely on the basis of their size. In some such aspects, the respective chromatography matrix is typically a particulate porous material as mentioned above. The chromatography matrix may have a certain exclusion limit, which is typically defined in terms of a molecular weight above which molecules are entirely excluded from entering the pores. In some embodiments, the respective molecular weight defining the size exclusion limit may be selected to be below the weight corresponding to the weight of a target cell. In such an embodiment, the target cell is prevented from entering the pores of the size exclusion chromatography matrix. Likewise, a stationary phase may have pores that are of a size that is smaller than the size of a chosen target cell. In illustrative embodiments chromatography matrix has a mean pore size of 0 to about 500 nm.

In some embodiments, components present in a sample such as agents (e.g., receptor-binding agents or selection agents) or a competition reagent may have a size that is below the exclusion limit of the pores and thus can enter the pores of the chromatography matrix. In some aspects, of such components that are able to partially or fully enter the pore volume, larger molecules, with less access to the pore volume can elute first, whereas the smallest molecules typically elute last. In some embodiments, the exclusion limit of the chromatography matrix is selected to be below the maximal width of the target cell. Hence, in some aspects, components that have access to the pore volume can remain longer in/on the chromatography matrix than target cell. Thus, in some cases, target cells can be collected in the eluate of a chromatography column separately from other matter/components of a sample. Therefore, in some aspects, components such as an agent (e.g., receptor-binding agent or selection agent), or where applicable a competition reagent, may elute at a later point of time from a gel filtration matrix than the target cell. In some embodiments, this effect can be further increased, such as if the gel permeation matrix contains a reagent (such as covalently bound thereon) that contains binding sites Z that are able to bind agents (e.g., receptor-binding agents or selection agents) and/or a competition reagent present in a sample. In some cases, the agent (e.g., receptor-binding agent or selection agent) and/or the competition reagent can be bound by the binding sites Z of the reagent and thereby immobilized on the matrix. In some aspects, this method is carried out in a removal cartridge.

In some embodiments, a chromatography matrix employed in the present methods may also include magnetically attractable matter such as one or more magnetically attractable particles or a ferrofluid. A respective magnetically attractable particle may comprise a reagent with a binding site that is capable of binding a target cell. In some cases, magnetically attractable particles may contain diamagnetic, ferromagnetic, paramagnetic or superparamagnetic material. In general, superparamagnetic material responds to a magnetic field with an induced magnetic field without a resulting permanent magnetization. Magnetic particles based on iron oxide are for example commercially available as Dynabeads from Dynal Biotech, as magnetic MicroBeads from Miltenyi Biotec, as magnetic porous glass beads from CPG Inc., as well as from various other sources, such as Roche Applied Science, BIOCLON, BioSource International Inc., micromod, AMBION, Merck, Bangs Laboratories, Polysciences, or Novagen Inc., to name only a few. Magnetic nanoparticles based on superparamagnetic Co and FeCo, as well as ferromagnetic Co nanocrystals have been described, for example by Hutten, A. et al. (J. Biotech. (2004), 112, 47-63). In other embodiments, a chromatography matrix employed in the present methods is void of any magnetically attractable matter.

In some embodiments, provided is an apparatus that contains at least one arrangement of a first and a second stationary phase, such as chromatography column for selection of cells (a selection cartridge) and a second chromatography column (a removal cartridge) for removal of reagents. The apparatus may comprise a plurality of arrangements of first and second stationary phases (chromatography columns) being fluidly connected in series. The apparatus may comprise a sample inlet being fluidly connected to the first stationary phase of the first arrangement of the first and second stationary phases. In some embodiments, the apparatus may also comprise a sample outlet for cells, the sample outlet being fluidly connected to the second stationary phase of the last of the at least one arrangement of a first and second stationary phases for chromatography. In some aspects, the apparatus may also comprise a competition reagent container that is fluidly connected to at least one of the first stationary phases of the arrangements of the first and second stationary phases.

2. Soluble

In some embodiments, the reagent is not bound to a solid support, i.e. it is present in soluble form or is soluble. In principle, the same reagent can be used as in the case of a reagent that is immobilized on a support, such as a solid support or stationary phase. For example, any of the exemplary of reagents described above can be used without immobilizing or attaching such reagent to a support, e.g. not attaching solid support or stationary phase. In some embodiments, the reagent contains a plurality of binding sites, Z, for reversibly binding to a binding agent via interaction with a binding partner, C. In some cases, the reagent is an oligomer or polymer of individual molecules or an oligomer or polymer of a complex of subunits that make up the individual molecule (e.g. oligomers or polymers of a dimeric, trimeric or tetrameric protein). In some embodiments, the reagent can, for example, be a streptavidin mutein oligomer, a calmodulin oligomer, a compound (oligomer) that provides least two chelating groups K, wherein the at least two chelating groups are capable of binding to a transition metal ion, thereby rendering the reagent capable of binding to an oligohistidine affinity tag, multimeric glutathione-S-transferase, or a biotinylated carrier protein.

In some embodiments, the reagent is characterized by the absence of a solid support (surface) attached to the reagent. For example, in some embodiments, the reagent does not comprise or is not attached (directly or indirectly) to a particle, bead, nanoparticle, microsphere or other solid support. In some embodiments, the reagent is not rigid, inflexible or stiff or does not comprise or is not attached to a rigid, inflexible, or stiff surface. In some embodiments, the reagent is flexible or substantially flexible. In some cases, the reagent is able to adjust or adapt to the form of the surface of the cells. In some embodiments, the reagent does not or does not comprise a shape that is spherical or substantially spherical.

In some embodiments, substantially all, i.e. more than 80%, 85%, 90%, 91%, 92%, 93%, 94%, 95%, 96%, 97%, 98%, 99% or more of the reagent is, is composed of or contains organic material. For example, in some embodiments, more than 80%, 85%, 90%, 91%, 92%, 93%, 94%, 95%, 96%, 97%, 98%, 99% or more of the reagent is, is composed of or contains lipids, carbohydrates, proteins, peptides or mixtures thereof. In some embodiments, the reagent is, is composed of or contains an essential absence of inorganic material, an inorganic core, e.g. metal, e.g. iron, synthetic or inorganic polymers, such as styrene polymers, e.g. polystyrene, latex, silica or magnetic cores. For example, in some embodiments, the relative percentage of inorganic material of the reagent or that is comprised as part of the reagent is less than 20%, 15%, 10%, 5% or less.

In some embodiments, the majority (i.e. more than 50%), such as more than 60%, 70%, 80%, 90%, 95%, 99% or more of the total volume of the reagent in aqueous solution consists of the individual protein molecules that comprise the reagent, such as oligomers or polymers of individual molecules or a complex of subunits that make up an individual molecule (e.g. tetrameric molecule). In some embodiments, the total density of the soluble reagent is less than 1.2 g/cm$^3$, 1.1 g/cm$^3$, 1.0 g/cm$^3$ or less.

In some embodiments, the soluble reagent, e.g. not being attached to a support or solid support (e.g. is not attached to a bead), has a relatively small size, such as generally less than or about less than 20 nM in size, such as less than or about less than 15 nM, less than or about less than 10 nM, less than or about less than 5 nM or smaller.

In some embodiments, the soluble reagent, e.g. not being attached to a support or solid support (e.g. is not attached to a bead), is biologically inert, i.e. it is non-toxic to living cells. In some embodiments, the reagent may be biodegradable, for example, it can be degraded by enzymatic activity or cleared by phagocytic cells.

In some embodiments, it is possible to react the reagent (e.g. a streptavidin or mutein, such as tetrameric streptavidin muteins) to a carrier, such as an organic carrier. In some aspects, in addition to a reaction with a polysaccharide, it is also possible to use physiologically or pharmaceutically acceptable proteins such as serum albumin (for example human serum albumin (HSA) or bovine serum albumin (BSA)) as carrier protein. In such a case, the reagent, such as streptavidin or a streptavidin mutein (either as individual tetramer or also in the form of oligomers), can be coupled to the carrier protein via non-covalent interaction. In some such embodiments, biotinylated BSA (which is commercially available from various suppliers such as ThermoFisher Scientific, Sigma Aldrich or Vectorlabs, to name only a few) can be reacted with the reagent (e.g. streptavidin mutein). In some aspects, some of the reagent oligomers (e.g. streptavidin oligomers) can non-covalently bind via one or more binding sites Z to the biotinylated carrier protein, leaving the majority of the binding sites Z of the oligomer available for binding the agent (e.g., receptor-binding agent or selection agent) and any further agent as described herein. Thus, by such an approach a soluble reagent with a multitude of binding sites Z can be prepared.

In other embodiments, a reagent, such as a streptavidin mutein (either as an individual tetramer or also in the form of an oligomer), can be covalently coupled to a synthetic carrier such as a polyethylene glycol (PEG) molecule. Any suitable PEG molecule can be used for this purpose, for example, and the PEG molecule and the respective reagent can be soluble. Typically, PEG molecules up to a molecular weight of 1000 Da are soluble in water or culture media that may be used in the present methods. In some cases, such PEG based reagent can be prepared using commercially available activated PEG molecules (for example, PEG-NHS derivatives available from NOF North America Corporation, Irvine, Calif., USA, or activated PEG derivatives available from Creative PEGWorks, Chapel Hills, N.C., USA) with amino groups of the streptavidin mutein.

C. Agents

In some embodiments the agent (e.g., receptor-binding agent or selection agent) has one or binding sites, B, for binding to the molecule on the surface of the cell, e.g. cell surface molecule. Thus, in some instances, the agent (e.g., receptor-binding agent or selection agent) contains a binding site B or a plurality of binding sites B, wherein the specific binding between the agent (receptor-binding agent or selection agent) and the molecule on the surface of the target cells contains interaction between B and the molecule. In some embodiments, the agent contains only a single binding site, i.e. is monovalent. In some embodiments the agent (e.g., receptor-binding agent or selection agent) has at least two, such as a plurality of binding sites B including three, four or five binding sites B capable of binding to the cell surface molecule. In some such aspects, the at least two or plurality of binding sites B may be identical. In some embodiments, one or more of the at least two or plurality of binding sites B may be different (e.g. B1 and B2).

In some embodiments, one or more different agents (e.g. one or more different receptor-binding agent, selection agent or other agent that binds to a molecule on a cell) are reversibly bound to the reagent. In some embodiments, at least 2, 3, 4 or more different agents are reversibly bound to the same reagent. In some embodiments, at least two different agents are reversibly bound to the same reagent, whereby each reagent comprises a binding site B or a plurality of binding sites B for specific binding between the agent and the molecule. In some embodiments, the at least two or more agents contain the same binding site B, e.g. for the binding the same or substantially the same molecule. In some embodiments, the at least two or more agents contain different binding sites B, e.g. for the binding to different molecules. In some embodiments, a first agent (e.g. a first receptor-binding agent or a first selection agent) contains a binding site B1, B2, B3, B4, etc. and a second agent (e.g. a second receptor-binding agent or second selection agent) contains another of a binding site B1, B2, B3, B4, etc. In some embodiments, a first agent (e.g. a first selection agent) contains a binding site B1 and a second agent (e.g. second selection agent) contains a binding site B3. In some embodiments, a first agent (e.g. a first receptor-binding agent) contains a binding site B2 and a second agent (e.g. a second receptor-binding agent) contains a binding site B4. In any of such embodiments, the first agent and second agent can contain a binding partner, C1 or C2. In some embodiments, C1 and C2 can be the same. In some embodiments, C1 and C2 are different. In some embodiments, the first agent and second agent contain the same binding partner, C1.

In some cases, the dissociation constant ($K_D$) of the binding between the agent (e.g., via the binding site B) and the binding site Z of the reagent may have a value in the range from about $10^{-2}$ M to about $10^{-13}$ M or from about $10^{-3}$ M to about $10^{-12}$ M or from about $10^{-4}$ M to about $10^{-11}$M, or from about $10^{-5}$M to about $10^{-10}$M. In some embodiments, the dissociation constant ($K_D$) for the binding between the binding agent and the molecule is of low affinity, for example, in the range of a $K_D$ of about $10^{-3}$ to about $10^{-7}$ M. In some embodiments, the dissociation constant ($K_D$) for the binding between the binding agent and the molecule is of high affinity, for example, in the range of a $K_D$ of about $10^{-7}$ to about $1\times10^{-10}$ M.

In some embodiments, the dissociation of the binding of the agent via the binding site B and the molecule occurs sufficiently fast, for example, to allow the target cell to be only transiently stained or associated with the agent after disruption of the reversible bond between the reagent and the agent. In some cases, when expressed in terms of the $k_{off}$ rate (also called dissociation rate constant for the binding between the agent (via the binding site B) and the molecule, the $k_{off}$ rate is about $0.5\times10^{-4}$ sec$^{-1}$ or greater, about $1\times10^{-4}$ sec$^{-1}$ or greater, about $2\times10^{-4}$ sec$^{-1}$ or greater, about $3\times10^{-4}$ sec$^{-1}$ or greater, about $4\times10^{-4}$ sec$^{-1}$ of greater, about $5\times10^{-4}$ sec$^{-1}$ or greater, about $1\times10^{-3}$ sec$^{-1}$ or greater, about $1.5\times10^{-3}$ sec$^{-1}$ or greater, about $2\times10^{-3}$ sec$^{-1}$ or greater, about $3\times10^{-3}$ sec$^{-1}$ or greater, about $4\times10^{-3}$ sec$^{-1}$, about $5\times10^{-3}$ sec$^{-1}$ or greater, about $1\times10^{-2}$ sec or greater, or about $5\times10^{-1}$ sec$^{-1}$ or greater. It is within the level of a skilled artisan to empirically determine the $k_{off}$ rate range suitable for a particular agent and cell molecule interaction (see e.g. U.S. published application No. US2014/0295458). For example, an agent with a rather high $k_{off}$ rate of, for example, greater than $4.0\times10^{-4}$ sec$^{-1}$ may be used so that, after the disruption of the binding complexes, most of the agent can be removed or dissociated within one hour. In other cases, an agent with a lower $k_{off}$ rate of, for example, $1.0\times10^{-4}$ sec$^{-1}$, may be used, so that after the disruption of the binding complexes, most of the agent may be removed or dissociated from the cell within about 3 and a half hours.

In some embodiments, the $K_D$ of this bond as well as the $K_D$, $K_A$, $k_{off}$ and $k_{on}$ rate of the bond formed between the binding site B of the agent (e.g., receptor-binding agent or selection agent) and the cell surface molecule can be determined by any suitable means, for example, by fluorescence titration, equilibrium dialysis or surface plasmon resonance.

In some aspects, the cell surface molecule is a molecule against which an agent, such as a binding agent, (e.g., receptor-binding agent or selection agent) may be directed. In some embodiments, the cell surface molecule is a peptide or a protein, such as a receptor, e.g., a membrane receptor protein. In some embodiments, the receptor is a lipid, a polysaccharide or a nucleic acid. In some embodiments, a cell surface molecule that is a protein may be a peripheral membrane protein or an integral membrane protein. The cell surface molecule may in some embodiments have one or more domains that span the membrane. As a few illustrative examples, a membrane protein with a transmembrane domain may be a G-protein coupled receptor, such as an odorant receptors, a rhodopsin receptor, a rhodopsin pheromone receptor, a peptide hormone receptor, a taste receptor, a GABA receptor, an opiate receptor, a serotonin receptor, a Ca$^{2+}$ receptor, melanopsin, a neurotransmitter receptor, such as a ligand gated, a voltage gated or a mechanically gated receptor, including the acetylcholine, the nicotinic, the adrenergic, the norepinephrine, the catecholamines, the L-DOPA-, a dopamine and serotonin (biogenic amine, endorphin/enkephalin) neuropeptide receptor, a receptor kinase such as serine/threonine kinase, a tyrosine kinase, a porin/channel such as a chloride channel, a potassium channel, a sodium channel, an OMP protein, an ABC transporter (ATP-Binding Cassette-Transporter) such as amino acid transporter, the Na-glucose transporter, the Na/iodide transporter, an ion transporter such as Light Harvesting Complex, cytochrome c oxidase, ATPase Na/K, H/K, Ca, a cell adhesion receptor such as metalloprotease, an integrin or a cadherin.

In some embodiments, the cell surface molecule may be an antigen defining a desired cell population or subpopulation, for instance a population or subpopulation of blood cells, e.g., lymphocytes (e.g., T cells, T-helper cells, for example, CD4+ T-helper cells, B cells or natural killer cells), monocytes, or stem cells, e.g. CD34-positive peripheral stem cells or Nanog or Oct-4 expressing stem cells. Examples of T-cells include cells such as CMV-specific CD8+ T-lymphocytes, cytotoxic T-cells, memory T-cells and regulatory T-cells (Treg). An illustrative example of Treg is CD4 CD25 CD45RA Treg cells and an illustrative example of memory T-cells is CD62L CD8+ specific central memory T-cells. The cell surface molecule may also be a marker for a tumor cell.

As described above, in some embodiments, the agent, such as a binding agent, (e.g., receptor-binding agent or selection agent) has, in addition to the binding site B that is able to bind the cell surface molecule, a binding partner C. In some aspects, this binding partner C is able to bind to a binding site Z of the reagent wherein the reagent has one or more binding sites Z for the binding partner C. In some embodiments, the non-covalent bond that may be formed between the binding partner C that is included in the agent (e.g., receptor-binding agent or selection agent) and the binding site(s) Z of the reagent may be of any desired strength and affinity, and may be disruptable or reversible under conditions under which the method is performed. The agent (e.g., receptor-binding agent or selection agent) may include at least one, including two, three or more additional binding partners C and the reagent may include at least two, such as three, four, five, six, seven, eight or more binding sites Z for the binding partner C that is included in the agent (e.g., receptor-binding agent or selection agent). As described in U.S. Pat. Nos. 7,776,562, 8,298,782 or International Patent App. Pub. No. WO 2002/054065, any combination of a binding partner C and a reagent with one or more corresponding binding sites Z can be chosen, for example, such that the binding partner C and the binding site Z are able to reversibly bind in a complex, such as to cause an avidity effect.

The binding partner C included in the agent (e.g., receptor-binding agent or selection agent) may for instance be hydrocarbon-based (including polymeric) and include nitrogen-, phosphorus-, sulphur-, carben-, halogen- or pseudohalogen groups. In some aspects, it may be an alcohol, an organic acid, an inorganic acid, an amine, a phosphine, a thiol, a disulfide, an alkane, an amino acid, a peptide, an oligopeptide, a polypeptide, a protein, a nucleic acid, a lipid, a saccharide, an oligosaccharide, or a polysaccharide. As further examples, it may also be a cation, an anion, a polycation, a polyanion, a polycation, an electrolyte, a polyelectrolyte, a carbon nanotube or carbon nanofoam. Generally, such a binding partner C has a higher affinity to the binding site of the reagent than to other matter. Examples of a respective binding partner C include, but are not limited to, a crown ether, an immunoglobulin, a fragment thereof and a proteinaceous binding molecule with antibody-like functions.

In some embodiments, the binding partner C that is included in the agent (e.g., receptor-binding agent or selection agent) includes biotin and the reagent includes a streptavidin analog or an avidin analog that reversibly binds to biotin. In some embodiments the binding partner C that is included in the agent (e.g., receptor-binding agent or selection agent) includes a biotin analog that reversibly binds to streptavidin or avidin, and the reagent includes streptavidin, avidin, a streptavidin analog or an avidin analog that reversibly binds to the respective biotin analog. In some embodiments, the binding partner C that is included in the agent (e.g., receptor-binding agent or selection agent) includes a streptavidin or avidin binding peptide and the reagent includes streptavidin, avidin, a streptavidin analog or an avidin analog that reversibly binds to the respective streptavidin or avidin binding peptide.

In some embodiments, the reagent is a streptavidin, such as a streptavidin mutein including any described above (e.g. set forth in SEQ ID NOS: 3-6), and the binding partner C that is included in the agent (e.g. receptor-binding agent or selection agent) may include a streptavidin-binding peptide. In some embodiments, the streptavidin-binding peptide may include a sequence with the general formula set forth in SEQ ID NO: 9, such as contains the sequence set forth in SEQ ID NO: 10. In some embodiments, the peptide sequence has the general formula set forth in SEQ ID NO: 11, such as set forth in SEQ ID NO: 12. In one example, the peptide sequence is Trp-Arg-His-Pro-Gln-Phe-Gly-Gly (also called Strep-Tag®, set forth in SEQ ID NO: 7). In one example, the peptide sequence is Trp-Ser-His-Pro-Gln-Phe-Glu-Lys (also called Strep-Tag® II, set forth in SEQ ID NO: 8). In some embodiments, the peptide ligand contains a sequential arrangement of at least two streptavidin-binding modules, wherein the distance between the two modules is at least 0 and not greater than 50 amino acids, wherein one binding module has 3 to 8 amino acids and contains at least the sequence His-Pro-Xaa (SEQ ID NO: 9), where Xaa is glutamine, asparagine, or methionine, and wherein the other binding module has the same or different streptavidin peptide ligand, such as set forth in SEQ ID NO: 11 (see e.g. International Published PCT Appl. No. WO02/077018; U.S. Pat. No. 7,981,632). In some embodiments, the peptide ligand contains a sequence having the formula set forth in any of SEQ ID NO: 13 or 14. In some embodiments, the peptide ligand has the sequence of amino acids set forth in any of SEQ ID NOS: 15-19. In most cases, all these streptavidin binding peptides bind to the same binding site, namely the biotin binding site of streptavidin. If one or more of such streptavidin binding peptides is used as binding partners C, e.g. C1 and C2, the multimerization reagent is typically a streptavidin mutein.

In some embodiments, the streptavidin-binding peptide may be further modified. In some embodiments, the streptavidin-binding peptide may include the peptide sequence is Trp-Ser-His-Pro-Gln-Phe-Glu-Lys (also called Strep-Tag® II, set forth in SEQ ID NO: 8) conjugated with a nickel charged trisNTA (also called His-STREPPER or His/Strep-Tag® II Adapter).

In some embodiment the binding partner C of the agent (e.g., receptor-binding agent or selection agent) includes a moiety known to the skilled artisan as an affinity tag. In such an embodiment, the reagent may include a corresponding binding partner, for example, an antibody or an antibody fragment, known to bind to the affinity tag. As a few illustrative examples of known affinity tags, the binding partner C that is included in the agent (e.g., receptor-binding agent or selection agent) may include dinitrophenol or digoxigenin, oligohistidine, polyhistidine, an immunoglobulin domain, maltose-binding protein, glutathione-S-transferase (GST), chitin binding protein (CBP) or thioredoxin, calmodulin binding peptide (CBP), FLAG-peptide, the HA-tag (sequence: Tyr-Pro-Tyr-Asp-Val-Pro-Asp-Tyr-Ala) (SEQ ID NO: 20), the VSV-G-tag (sequence: Tyr-Thr-Asp-Ile-Glu-Met-Asn-Arg-Leu-Gly-Lys) (SEQ ID NO: 21), the HSV-tag (sequence: Gln-Pro-Glu-Leu-Ala-Pro-Glu-Asp-Pro-Glu-Asp) (SEQ ID NO: 22), the T7 epitope (Ala-Ser-Met-Thr-Gly-Gly-Gln-Gln-Met-Gly) (SEQ ID NO: 22), maltose binding protein (MBP), the HSV epitope of the sequence Gln-Pro-Glu-Leu-Ala-Pro-Glu-Asp-Pro-Glu-Asp (SEQ ID NO: 24) of herpes simplex virus glycoprotein D, the "myc" epitope of the transcription factor c-myc of the sequence Glu-Gln-Lys-Leu-Ile-Ser-Glu-Glu-Asp-Leu (SEQ ID NO: 25), the V5-tag (sequence: Gly-Lys-Pro-Ile-Pro-Asn-Pro-Leu-Leu-Gly-Leu-Asp-Ser-Thr) (SEQ ID NO: 26), or glutathione-S-transferase (GST). In such embodiments, the complex formed between the one or more binding sites Z of the reagent which may be an antibody or antibody fragment, and the antigen can be disrupted competitively by adding the free antigen, i.e. the free peptide (epitope tag) or the free protein (such as MBP or CBP). In some embodiments, the affinity tag might also be an oligonucleotide tag. In some cases, such an oligonucleotide tag may, for instance, be used to hybridize to an oligonucleotide with a complementary sequence, linked to or included in the reagent.

Further examples of a suitable binding partner C include, but are not limited to, a lectin, protein A, protein G, a metal, a metal ion, nitrilo triacetic acid derivatives (NT A), RGD-motifs, a dextrane, polyethyleneimine (PEI), a redox polymer, a glycoproteins, an aptamers, a dye, amylose, maltose, cellulose, chitin, glutathione, calmodulin, gelatine, polymyxin, heparin, NAD, NADP, lysine, arginine, benzamidine, poly U, or oligo-dT. Lectins such as Concavalin A are known to bind to polysaccharides and glycosylated proteins. An illustrative example of a dye is a triazine dye such as Cibacron blue F3G-A (CB) or Red HE-3B, which specifically bind NADH-dependent enzymes. Typically, Green A binds to Co A proteins, human serum albumin, and dehydrogenases. In some cases, the dyes 7-aminoactinomycin D and 4',6-diamidino-2-phenylindole bind to DNA. Generally, cations of metals such as Ni, Cd, Zn, Co, or Cu, are typically used to bind affinity tags such as an oligohistidine containing sequence, including the hexahistidine or the His-Asn-His-Arg-His-Lys-His-Gly-Gly-Gly-Cys tag (MAT tag) (SEQ ID NO: 35), and N-methacryloyl-(L)-cysteine methyl ester.

In some embodiments the binding between the binding partner C that is included in the agent (e.g., receptor-binding agent or selection agent) and the one or more binding sites Z of the reagent occurs in the presence of a divalent, a trivalent or a tetravalent cation. In this regard, in some embodiments the reagent includes a divalent, a trivalent or a tetravalent cation, typically held, e.g. complexed, by means of a suitable chelator. In some embodiments, the binding partner C that is included in the agent (e.g., receptor-binding agent or selection agent) may include a moiety that includes, e.g. complexes, a divalent, a trivalent or a tetravalent cation. Examples of a respective metal chelator, include, but are not limited to, ethylenediamine, ethylene-diaminetetraacetic acid (EDTA), ethylene glycol tetraacetic acid (EGTA), diethylenetri-aminepentaacetic acid (DTPA), N,N-bis(carboxymethyl)glycine (also called nitrilotriacetic acid, NTA), 1,2-bis(o-aminophenoxy)ethane-N,N,N',N'-tetraacetic acid (BAPTA), 2,3-dimer-capto-1-propanol (dimercaprol), porphine and heme. As an example, EDTA forms a complex with most monovalent, divalent, trivalent and tetravalent metal ions, such as e.g. silver ($Ag^+$), calcium ($Ca^{2+}$), manganese ($Mn^{2+}$), copper ($Cu^{2+}$), iron ($Fe^{2+}$), cobalt ($Co^+$) and zirconium ($Zr^{4+}$), while BAPTA is specific for $Ca^{2+}$. As an illustrative example, a standard method used in the art is the formation of a complex between an oligohistidine tag and copper ($Cu^{2+}$), nickel ($Ni^{2+}$), cobalt ($Co^{2+}$), or zinc ($Zn^{2+}$) ions, which are presented by means of the chelator nitrilotriacetic acid (NTA).

In some embodiments, the binding partner C that is included in the agent (e.g., receptor-binding agent or selection agent) includes a calmodulin binding peptide and the reagent includes multimeric calmodulin as described in U.S. Pat. No. 5,985,658, for example. In some embodiments, the binding partner C that is included in the agent (e.g., receptor-binding agent or selection agent) includes a FLAG peptide and the reagent includes an antibody that binds to the FLAG peptide, e.g. the FLAG peptide, which binds to the monoclonal antibody 4E11 as described in U.S. Pat. No. 4,851,341. In one embodiment, the binding partner C that is included in the agent (e.g., receptor-binding agent or selection agent) includes an oligohistidine tag and the reagent includes an antibody or a transition metal ion binding the oligohistidine tag. In some cases, the disruption of all these binding complexes may be accomplished by metal ion chelation, e.g. calcium chelation, for instance by adding EDTA or EGTA. In some embodiments, calmodulin, antibodies such as 4E11 or chelated metal ions or free chelators may be multimerized by conventional methods, e.g. by biotinylation and complexation with streptavidin or avidin or oligomers thereof or by the introduction of carboxyl residues into a polysaccharide, e.g. dextran, essentially as described in Noguchi, A, et al. Bioconjugate Chemistry (1992) 3, 132-137 in a first step and linking calmodulin or antibodies or chelated metal ions or free chelators via primary amino groups to the carboxyl groups in the polysaccharide, e.g. dextran, backbone using conventional carbodiimide chemistry in a second step. In some such embodiments, the binding between the binding partner C that is included in the agent (e.g., receptor-binding agent or selection agent) and the one or more binding sites Z of the reagent can be disrupted by metal ion chelation. The metal chelation may, for example, be accomplished by addition of EGTA or EDTA.

In some embodiments, the agent (e.g., receptor-binding agent or selection agent), which specifically bind to the cell surface molecule, may for instance be comprised by an antibody, a fragment thereof, or a proteinaceous binding molecule with antibody-like functions. In some embodiments, the binding site B of the agent is an antibody combining site, such as is or contains one or more complementarity determining regions (CDRs) of an antibody. Examples of (recombinant) antibody fragments include, but are not limited to, Fab fragments, Fv fragments, single-chain Fv fragments (scFv), a divalent antibody fragment such as an $F(ab')_2F(ab')_2$-fragment, diabodies, triabodies (Iliades, P., et al., FEB S Lett (1997) 409, 437-441), decabodies (Stone, E., et al., Journal of Immunological Methods (2007) 318, 88-94) and other domain antibodies (Holt, L. J., et al., Trends Biotechnol. (2003), 21, 11, 484-490). In some embodiments, the agent (e.g., receptor-binding agent or selection agent) may comprise a bivalent proteinaceous artificial binding molecule such as a dimeric lipocalin mutein that is also known as "duocalin".

In some embodiments, the agent (e.g., receptor-binding agent or selection agent) may have a single binding site B, i.e., it may be monovalent. Examples of monovalent agents (e.g., receptor-binding agents or selection agents) include, but are not limited to, a monovalent antibody fragment, a proteinaceous binding molecule with antibody-like binding properties or an MHC molecule. Examples of monovalent antibody fragments include, but are not limited to a Fab fragment, an Fv fragment, and a single-chain Fv fragment (scFv), including a divalent single-chain Fv fragment.

In some embodiments, the agent is an antibody or an antigen-binding fragment thereof, such as a Fab fragments, Fv fragments, single-chain Fv fragments (scFv), a divalent antibody fragment such as an $F(ab')_2$-fragment. In some embodiments, the agent is or is derived from a parental antibody that is known to bind to a cell molecule of interest. Various antibody molecules or fragments thereof against cell surface molecules are well known in the art and any of a variety of such can be used as agents in the methods herein. In some embodiments, the agent is an antibody or fragment thereof that contains one or more amino acid replacements in the variable heavy chain of a parental or reference antibody, for example, to generate an antibody with an altered affinity or that exhibits a sufficiently fast off-rate as described above. For example, exemplary of such mutations are known the context of mutants of the anti-CD4 antibody 13B8.2 (see e.g., U.S. Pat. No. 7,482,000, U.S. Patent Appl. Pub. No. US2014/0295458 or International Patent App. Pub. No. WO2013/124474), and any of such mutations can be generated in another parental or reference antibody.

In some aspects, the agent (e.g., receptor-binding agent or selection agent) that can be monovalent, for example comprise a monovalent antibody fragment or a monovalent artificial binding molecule (proteinaceous or other) such as a mutein based on a polypeptide of the lipocalin family (also known as "Anticalin®"), or a bivalent molecule such as an antibody or a fragment in which both binding sites are retained such as an $F(ab')_2$ fragment.

An example of a proteinaceous binding molecule with antibody-like functions includes a mutein based on a polypeptide of the lipocalin family (see for example, WO 03/029462, Beste et al., Proc. Natl. Acad. Sci. U.S.A. (1999) 96, 1898-1903). Generally, lipocalins, such as the bilin binding protein, the human neutrophil gelatinase-associated lipocalin, human Apo lipoprotein D or human tear lipocalin possess natural ligand-binding sites that can be modified so that they bind a given target. Further examples of a proteinaceous binding molecule with antibody-like binding properties that can be used as agent (e.g., receptor-binding agent or selection agent) that specifically binds to the cell surface molecule include, but are not limited to, the so-called glubodies (see e.g. International Patent App. Pub. No. WO 96/23879), proteins based on the ankyrin scaffold (Mosavi, L. K., et al., Protein Science (2004) 13, 6, 1435-1448) or crystalline scaffold (e.g. International Patent App. Pub. No. WO 01/04144) the proteins described in Skerra, J. Mol. Recognit. (2000) 13, 167-187, AdNectins, tetranectins and avimers. Generally, avimers, including multivalent avimer proteins evolved by exon shuffling of a family of human receptor domains, contain so called A-domains that occur as strings of multiple domains in several cell surface receptors (Silverman, J., et al., Nature Biotechnology (2005) 23, 1556-1561). Adnectins, generally derived from a domain of human fibronectin, typically contain three loops that can be engineered for immunoglobulin-like binding to targets (Gill, D. S. & Damle, N. K., Current Opinion in Biotechnology (2006) 17, 653-658). Tetranectins, generally derived from the respective human homotrimeric protein, likewise typically contain loop regions in a C-type lectin domain that can be engineered for desired binding. Peptoids, which can, in some cases, act as protein ligands, typically are oligo(N-alkyl) glycines that differ from peptides in that the side chain is connected to the amide nitrogen rather than the carbon atom. Peptoids are typically resistant to proteases and other modifying enzymes and can have a much higher cell permeability than peptides (see e.g. Kwon, Y.-U., and Kodadek, T., J. Am. Chem. Soc. (2007) 129, 1508-1509).

Further examples of suitable proteinaceous binding molecules include, but are not limited to, an EGF-like domain, a Kringle-domain, a fibronectin type I domain, a fibronectin type II domain, a fibronectin type III domain, a PAN domain, a Gla domain, a SRCR domain, a Kunitz/Bovine pancreatic trypsin Inhibitor domain, tendamistat, a Kazal-type serine protease inhibitor domain, a Trefoil (P-type) domain, a von Willebrand factor type C domain, an Anaphylatoxin-like domain, a CUB domain, a thyroglobulin type I repeat, LDL-receptor class A domain, a Sushi domain, a Link domain, a Thrombospondin type I domain, an immunoglobulin domain or a an immunoglobulin-like domain (for example, domain antibodies or camel heavy chain antibodies), a C-type lectin domain, a MAM domain, a von Willebrand factor type A domain, a Somatomedin B domain, a WAP-type four disulfide core domain, a F5/8 type C domain, a Hemopexin domain, an SH2 domain, an SH3 domain, a Laminin-type EGF-like domain, a C2 domain, "Kappabodies" (Ill et al. Protein Eng (1997) 10, 949-57, a so called "minibody" (Martin et al., EMBO J (1994) 13, 5303-5309), a diabody (Holliger et al., PNAS USA (1993) 90, 6444-6448), a so called "Janusis" (Traunecker et al., EMBO J (1991) 10, 3655-3659, or Traunecker et al., Int J Cancer (1992) Suppl 7, 51-52), a nanobody, a microbody, an affilin, an affibody, a knottin, ubiquitin, a zinc-finger protein, an autofluorescent protein or a leucine-rich repeat protein. In some embodiments, a nucleic acid molecule with antibody-like functions can be an aptamer. Generally, an aptamer folds into a defined three-dimensional motif and shows high affinity for a given target structure.

1. Receptor-Binding Agents

In some embodiments, the agent is a receptor-binding agent. In some embodiments, the receptor-binding agent binds to a molecule (e.g. receptor) on the surface of a cell, which binding between the agent and the molecule is capable of inducing or modulating a signal in the cells. In some instances, the cell surface molecule (e.g. receptor) is a signaling molecule. In some such cases, the receptor-binding agent is capable of specifically binding to a signaling molecule expressed by one or more of the cells. In some instances, the receptor-binding agent is a stimulatory agent, which can be any agent that is capable of inducing a signal in a cell (e.g. a T cell) upon binding to a cell surface molecule, such as a receptor.

In some embodiments, the signal can be immunostimulatory, in which case the receptor-binding agent or stimulatory agent is capable of inducing or modulating a signal that is involved in or that does stimulate an immune response by the cell (e.g. T cell), e.g. increase immune cell proliferation or expansion, immune cell activation, immune cell differentiation, cytokine secretion, cytotoxic activity or one or more other functional activities of an immune cell. In some embodiment, the signal can be inhibitory, in which case the receptor-binding agent or stimulatory agent is capable of inducing or modulating a signal in the cell (e.g. T cell) that is involved in or that does inhibit an immune response, e.g. inhibits or decreases immune cell proliferation or expansion, immune cell activation, immune cell differentiation, cytokine secretion, cytotoxic activity or one or more other functional activities of an immune cell. In some embodiments, the receptor-binding agent, e.g., stimulatory agent, is an agonist of the receptor, an antagonist of the receptor or a mixed agonist/antagonist of the receptor.

In some embodiments, the receptor-binding agent, e.g., stimulatory agent is a first receptor-binding agent, e.g., first stimulatory agent. In some aspects, the first receptor-binding agent, e.g., first stimulatory agent, binds to a first molecule, such as a receptor molecule, on the surface of the cells. Thus, in some cases, the first receptor-binding agent, e.g., first stimulatory agent, induces or modulates a signal. In some aspects, the inducing or modulating of a signal by the first receptor-binding agent, e.g., first stimulatory agent, effects the activation, stimulation, and/or expansion (proliferation) of the cells. Thus, in some cases, the first receptor-binding agent, e.g., first stimulatory agent, provides a primary activation signal to the cells, thereby activating the cells. In some embodiments, the first receptor-binding agent, e.g., first stimulatory agent, provides T cell activation signal 1 (e.g., signal via T cell receptor (TCR) engagement).

In some embodiments, incubating or culturing cells in accord with the provided methods is performed or carried out in the presence of one or more agents. In some embodiments, incubating or culturing cells is in the presence of the first receptor-binding agent, e.g. as described above, and one or more second receptor-binding agent, e.g., second stimulatory agent.

In some aspects, the receptor-binding agent, e.g., stimulatory agent, is a second receptor-binding agent, e.g., second stimulatory agent. In some cases, the second receptor-binding agent, e.g., second stimulatory agent, binds to a molecule on the surface of the cells, such as a cell surface molecule, e.g., receptor molecule. In some embodiments, the second receptor-binding agent, e.g., second stimulatory agent, induces or modulates a signal, e.g., a second or an additional signal. In some embodiments, the second receptor-binding agent, e.g., second stimulatory agent, is capable of enhancing, dampening, or modifying a signal delivered through the first molecule.

In some aspects, the second receptor-binding agent, e.g., second stimulatory agent, may enhance or potentiate a signal induced by the first receptor-binding agent, e.g., first stimulatory agent. In some embodiments, the second receptor-binding agent, e.g., second stimulatory agent, binds to an accessory molecule and/or can stimulate or induce an accessory or secondary and/or additional signal in the cell. In some aspects, the second receptor-binding agent, e.g., second stimulatory agent, binds to a co-stimulatory molecule and/or provides a costimulatory signal. In some embodiments, the second receptor-binding agent, e.g., second stimulatory agent, provides T cell activation signal 2 (e.g., co-stimulatory signal). In some embodiments, the second receptor-binding agent, e.g., second stimulatory agent, provides T cell activation signal 3 (e.g., cytokine signals, accessory signals, survival signals and/or environmental signals).

In some embodiments, the receptor-binding agent, e.g., stimulatory agent, which can be the second receptor-binding agent, e.g., second stimulatory agent, binds, e.g. specifically binds, to a molecule, e.g., a second molecule, that can be a costimulatory molecule, an accessory molecule, a cytokine receptor, a chemokine receptor, an immune checkpoint molecule, an adhesion molecule, a member of the TNF family or the TNF receptor family and/or a Wnt receptor or co-receptor, e.g., the Frizzled (Fz) family of receptors.

In some embodiments, incubating or culturing cells in accord with the provided methods is performed or carried out in the presence of three or more agents, such as three or more binding agents. In some embodiments, incubating or culturing cells is in the presence of one or more additional receptor-binding agents, e.g., third receptor-binning agent, that modulate one or more additional signal. For example, in some embodiments, the incubating or culturing the cells in accord with the provided methods is performed or carried out in the presence of at least three different receptor-binding agent, e.g., a first receptor-binding agent, e.g., first stimulatory agent, providing a primary T cell activation signal, e.g., signal 1 (e.g., signal via T cell receptor (TCR) engagement); a second receptor-binding agent, e.g., second stimulatory agent, providing signal 2 (e.g., co-stimulatory signal or accessory signal), and an additional (e.g. third) receptor-binding agent, e.g., an additional stimulatory agent, providing signal 3 (e.g., cytokine signals, survival signals and/or environmental signals). Any number of the receptor-binding agents, e.g., stimulatory agents, can be selected in any combination for any of the methods described herein.

In some embodiments, the receptor-binding agent, e.g., the first, second and/or additional (e.g. third) receptor-binding agent, e.g., stimulatory agent, may be a binding agent that specifically binds a receptor, e.g., a receptor expressed on the surface of the cell. In some cases, the receptor-binding agent, e.g., stimulatory agent, is an antibody or an antigen-binding fragment thereof. In some cases, the receptor-binding agent, e.g., the first, second and/or additional receptor-binding agent, e.g., stimulatory agent, that specifically binds receptor may be selected from the group consisting of an anti-receptor antibody, a divalent antibody fragment of an anti-receptor antibody, a monovalent antibody fragment of an anti-receptor antibody, and a proteinaceous receptor binding molecule with antibody-like binding properties. The divalent antibody fragment may be a F(ab')₂-fragment, or a divalent single-chain Fv fragment while the monovalent antibody fragment may be selected from the group consisting of an Fab fragment, an Fv fragment, and a single-chain Fv fragment (scFv). In some cases, a proteinaceous receptor binding molecule with antibody-like binding properties may be an aptamer, a mutein based on a polypeptide of the lipocalin family, a glubody, a protein based on the ankyrin scaffold, a protein based on the crystalline scaffold, an adnectin, or an avimer. In some cases, the receptor-binding agent, e.g., the first, second and/or additional receptor-binding agent, e.g., stimulatory agent, that specifically binds receptor is an antibody or an antigen-binding fragment thereof, e.g., an Fab fragment.

In some embodiments, the receptor-binding agent, e.g., the first, second and/or additional (e.g. third) receptor-binding agent, e.g., stimulatory agent, may be a ligand that binds, e.g., specifically binds, to the receptor. In some embodiments, the receptor-binding agent, e.g., the first, second and/or additional receptor-binding agent, is an endogenous ligand, a cognate ligand, a synthetic ligand and/or a portion, a variant or modified forms thereof. For example, in some embodiments, the receptor-binding agent is a cytokine that binds to a cytokine receptor. In some embodiments, the receptor-binding agent is a chemokine that binds to a chemokine receptor. In some embodiments, the receptor-binding agent is an extracellular domain or a portion of a cytokine or chemokine or of an adhesion molecule that binds to a cell surface adhesion molecule. In some embodiments, the receptor-binding agent, e.g. stimulatory agent, can be an extracellular domain or a portion thereof, of an endogenous ligand and/or a cognate ligand that is itself a cell-surface or transmembrane protein.

In some embodiments, the receptor-binding agent, e.g., the first, second and/or additional (e.g. third) receptor-binding agent, e.g., stimulatory agent, binds to a molecule on the surface of a cell that may be a lymphocyte including, but not limited a B cell, a T cell or a natural killer cell. Illustrative examples of cells are B cells carrying CD40 or CD137 (both cell population can be proliferated upon binding of only a first agent that provides an activation signal, for example 4-1BB ligand; or an αCD40 antibody molecule or an αCD137 antibody molecule (see for example Zhang et al., 2010, J Immunol, 184:787-795)). Other illustrative examples for agents (either first or second) that may be used for the expansion of B cells are agents that bind to IgG, CD19, CD28 or CD14, for example αCD19, αIgG, αCD28, or αCD14 antibody molecules or antigen binding portions thereof. It is also envisioned that first or second agents for the expansion of B cell may comprise ligands for toll like receptors or interleukins, such as IL-21 (see for example Dienz O, et al. 2009. J. Exp. Med. 206:69). It is noted that lipopolysaccharide dependent activation of B cells is also encompassed in the present invention, as a lipopolysaccharide can also be used as first agent and can be equipped with a binding partner C1 as used herein.

Other illustrative examples of suitable cell populations include T cell population that expand after being activated by binding of a first agent to TCR/CD3 and binding of a second agent to an accessory molecule on the T cell such as CD28. In this case, the first agent stimulates a TCR/CD3 complex-associated signal in the T cells and the second agent provides a secondary stimulus by binding CD28 as accessory molecule. Agents that can be used for the expansion of T cells may also include interleukins, such as IL-2, IL-7, IL-15, or IL-21 (see for example Cornish et al. 2006, Blood. 108(2):600-8, Bazdar and Sieg, 2007, Journal of Virology, 2007, 81(22):12670-12674, Battalia et al., 2013, Immunology, 139(1):109-120). Other illustrative examples for agents that may be used for the expansion of T cells are agents that bind to CD8, CD45 or CD90, such as αCD8, αCD45 or αCD90 antibodies. Illustrative examples of T cell population including antigen-specific T cells, T helper cells, cytotoxic T cells, memory T cell (an illustrative example of memory T-cells are CD62L⁺CD8⁺ specific central memory T cells) or regulatory T cells (an illustrative example of Treg are CD4⁺CD25⁺CD45RA⁺ Treg cells).

Another illustrative example of a suitable cell population includes natural killer cells (NK cells), which may for example be expanded with agents that bind to CD16 or CD56, such as for example αCD16 or αCD56 antibodies. In illustrative example for such an αCD16 antibody is the antibody 3G8 with a VH sequence set forth in SEQ ID NO: 48 and a VL sequence set forth in SEQ ID NO: 49 (see for example Hoshino et al., Blood. 1991 Dec. 15; 78(12):3232-40.). Another agent that may be used for expansion of NK cells may be IL-15 (see for example Vitale et al. 2002. The Anatomical Record. 266:87-92). Yet another illustrative example of a suitable cell population includes monocytes, which may for instance be expanded using an agent that binds to CD14, such as an αCD14 antibody molecule.

In some aspects, the receptor-binding agent, e.g., stimulatory agent, specifically targets a molecule expressed on the surface of the target cells in which the molecule is a TCR or a chimeric antigen receptor. For example, the molecule expressed on the surface of the target cell is selected from a T cell or B cell antigen receptor complex, a CD3 chain, a CD3 zeta, an antigen-binding portion of a T cell receptor or a B cell receptor, or a chimeric antigen receptor. In some cases, the receptor binding agent targets peptide:MHC class I complexes.

In some embodiments, the stimulatory agent binds to a His-tagged extracellular domain of a molecule expressed on the surface of the target cells. In some cases, the stimulator agent contains the peptide sequence Trp-Ser-His-Pro-Gln-Phe-Glu-Lys (also called Strep-Tag® II, set forth in SEQ ID NO: 8) conjugated with a nickel charged trisNTA (also called His-STREPPER or His/Strep-Tag® II Adapter). In some embodiments, the molecule expressed on the surface of the target cells that is His-tagged is CD19.

In some aspects, the receptor-binding agent, e.g., stimulatory agent, specifically binds to the antibody portion of the recombinant receptor, e.g., CAR. In some cases, the antibody portion of the recombinant receptor includes at least a portion of an immunoglobulin constant region, such as a hinge region, e.g., an IgG4 hinge region, and/or a CH1/CL and/or Fc region. In some embodiments, the constant region or portion is of a human IgG, such as IgG4 or IgG1. In some cases, the reagent is loaded with αIgG that recognizes the IgG4 spacer.

In some embodiments, two or more receptor-binding agents are reversibly bound to the same reagent (e.g. multimerization reagent), such as to the same oligomeric streptavidin mutein reagent. In some embodiments, two or more receptor-binding agents, e.g. a first receptor-binding agent, second receptor-binding agent and/or one or more additional (e.g. third) receptor-binding agent, are reversibly bound to the same reagent (e.g. multimerization reagent) via the plurality of binding sites capable of reversibly binding to the two or more receptor-binding agents.

In some embodiments, two or more receptor-binding agents are reversibly bound to two or more different reagents (e.g. multimerization reagent), such as two or more different oligomeric streptavidin mutein reagent. In some such embodiments, at least one receptor-binding agent, e.g. a first receptor-binding agent) is reversibly bound to a first reagent (e.g. a first multimerization reagent) via the plurality of binding sites capable of reversibly binding to the receptor-binding agent and at least one or more additional receptor-binding agent (e.g. a second receptor-binding agent or third receptor-binding agent) is reversibly bound to a second reagent (e.g. a second multimerization reagent) via the plurality of binding sites capable of reversibly binding to the receptor-binding agent.

a. Receptor-Binding Agents Stimulating T Cell Activation

In some embodiments, the first receptor-binding agent, e.g., first stimulatory agent, may stimulate a TCR/CD3 complex-associated signal (e.g., signal 1 via engagement of the TCR) in the cells, e.g., T cells. In some aspects, the first receptor-binding agent, e.g., first stimulatory agent, may be a binding agent that specifically binds CD3. In some cases, a first receptor-binding agent, e.g., first stimulatory agent, that specifically binds CD3 may be selected from the group consisting of an anti-CD3 antibody, a divalent antibody fragment of an anti-CD3 antibody, a monovalent antibody fragment of an anti-CD3 antibody, and a proteinaceous CD3 binding molecule with antibody-like binding properties. The divalent antibody fragment may be a F(ab')$_2$-fragment, or a divalent single-chain Fv fragment while the monovalent antibody fragment may be selected from the group consisting of a Fab fragment, an Fv fragment, and a single-chain Fv fragment (scFv). In some cases, a proteinaceous CD3 binding molecule with antibody-like binding properties may be an aptamer, a mutein based on a polypeptide of the lipocalin family, a glubody, a protein based on the ankyrin scaffold, a protein based on the crystalline scaffold, an adnectin, or an avimer.

In some embodiments, an anti-CD3 Fab fragment can be derived from the CD3 binding monoclonal antibody produced by the hybridoma cell line OKT3 (ATCC® CRL-8001™; see also U.S. Pat. No. 4,361,549). The variable domain of the heavy chain and the variable domain of the light chain of the anti-CD3 antibody OKT3 are described in Arakawa et al., J. Biochem. 120, 657-662 (1996) and comprise the amino acid sequences set forth in SEQ ID NOS:31 and 32, respectively.

b. Receptor-Binding Agent Stimulating Co-Stimulatory and/or Accessory Signal

In some embodiments, the receptor-binding agent, e.g., the second receptor-binding agent, e.g. stimulatory agent, binds to a molecule that provides a co-stimulatory or accessory signal, to the cell expressing the molecule, e.g., a T cell or a B cell. In some embodiments, the receptor-binding agent, e.g., stimulatory agent, binds to a molecule that stimulates or activates a T cell activation signal 2, e.g., co-stimulatory signal, to the cell expressing the molecule, e.g., a T cell. In some embodiments, the receptor-binding agent provides an accessory signal to the cell expressing the molecule, e.g., a T cell.

In any of the embodiments provided herein, the receptor-binding agent, e.g., the second receptor-binding agent, e.g. stimulatory agent, may be a binding agent that specifically binds a receptor, e.g., a receptor expressed on the surface of the cell.

In some embodiments, the receptor-binding agent, e.g., stimulatory agent, is an antibody or an antigen-binding fragment thereof, e.g., an antibody or antigen binding fragment thereof that binds to a cell surface molecule that stimulates or activates a T cell activation signal 2, e.g., co-stimulatory signal, upon binding of the agent. In some cases, the receptor-binding agent, e.g., the first, second and/or additional receptor-binding agent, e.g., stimulatory agent, that specifically binds receptor may be selected from the group consisting of an anti-receptor antibody, a divalent antibody fragment of an anti-receptor antibody, a monovalent antibody fragment of an anti-receptor antibody, and a proteinaceous receptor binding molecule with antibody-like binding properties. The divalent antibody fragment may be a F(ab')$_2$-fragment, or a divalent single-chain Fv fragment while the monovalent antibody fragment may be selected from the group consisting of an Fab fragment, an Fv fragment, and a single-chain Fv fragment (scFv). In some cases, a proteinaceous receptor binding molecule with antibody-like binding properties may be an aptamer, a mutein based on a polypeptide of the lipocalin family, a glubody, a protein based on the ankyrin scaffold, a protein based on the crystalline scaffold, an adnectin, or an avimer. In some cases, the receptor-binding agent, e.g., the first, second and/or additional receptor-binding agent, e.g., stimulatory agent, that specifically binds receptor is an antibody or an antigen-binding fragment thereof, e.g., an Fab fragment.

In some embodiments, the receptor-binding agent, e.g., stimulatory agent, may be a ligand that binds, e.g., specifically binds, to the receptor, e.g., a cell surface molecule that stimulates or activates a T cell activation signal 2, e.g., co-stimulatory signal, upon binding of the agent. In some embodiments, the receptor-binding agent, e.g., the first, second and/or additional receptor-binding agent, is an endogenous ligand, a cognate ligand, a synthetic ligand and/or a portion, a variant or modified forms thereof. In some embodiments, the receptor-binding agent, e.g. stimulatory agent, can be an extracellular domain or a portion thereof, of an endogenous ligand and/or a cognate ligand.

In some embodiments, the receptor-binding agent, e.g., stimulatory agent is capable of binding to any one or more of CD28, CD5, CD4, CD8, MHCI, MHCII, CTLA-4, ICOS, PD-1, OX40, CD27L (CD70), 4-1BBL, CD30L and LIGHT. In some embodiments, the receptor-binding agent, e.g. stimulatory agent, can be an antibody, divalent antibody (e.g. a F(ab')$_2$-fragment or a divalent single-chain Fv fragment), monovalent antibody (e.g. a Fab fragment, an Fv fragment, or a single-chain Fv fragment (scFv)) or ligand to any one or more of CD28, CD5, CD4, CD8, MHCI, MHCII, CTLA-4, ICOS, PD-1, OX40, CD27L (CD70), 4-1BBL, CD30L and LIGHT, in which such agent is capable of inducing or modeling a signal in the cells upon binding of the receptor-binding agent, e.g., stimulatory agent to the molecule.

In some embodiments, the receptor-binding agent, e.g. stimulatory agent, can be a ligand to any one or more of CD28, CD5, CD4, CD8, MHCI, MHCII, CTLA-4, ICOS, PD-1, OX40, CD27L (CD70), 4-1BBL, CD30L and LIGHT, in which such agent is capable of inducing or modeling a signal in the cells upon binding of the receptor-binding agent, e.g., stimulatory agent to the molecule. In some embodiments, the receptor-binding agent, e.g. stimulatory agent, can be an extracellular domain or a portion thereof, of an endogenous ligand and/or a cognate ligand. For example, in some embodiments, the receptor-binding agent is or contains the extracellular domain or a portion thereof, of B7-1 (CD80), B7-2 (CD86), ICOS-L, PD-L1, OX40L, CD27, 4-1BB (CD137) and/or CD30.

In some embodiments, the receptor-binding agent, e.g., stimulatory agent, is capable of specifically binding to a molecule on the surface of the target cells other than CD28, CD3, CD137 or CD40. In some cases, the binding of the receptor-binding agent, e.g., stimulatory agent, to the molecule on the surface of the target cells other than CD28, CD3, CD137 or CD40 induces or modulates a signal in the target cells and/or alters a function of the target cells, thereby generating cultured target cells.

In some embodiments, the receptor-binding agent, e.g., stimulatory agent is capable of binding to any one or more of a member of the TNF family or the TNF receptor family, e.g., a member of the TNF receptor superfamily, and/or a Wnt receptor or co-receptor, e.g., the Frizzled (Fz) family of receptors.

In some embodiments, the molecule on the cell is a member of the TNF receptor superfamily, such as Tumor necrosis factor receptor 1 (CD120a), Tumor necrosis factor receptor 2 (CD120b), Lymphotoxin beta receptor (CD18), OX40 (CD134), CD40 (Bp50), Fas receptor (Apo-1, CD95), Decoy receptor 3 (TR6, M68), CD27 (S152, Tp55), CD30 (Ki-1), 4-1BB (CD137), Death receptor 4 (TRAILR1, Apo-2, CD261), Death receptor 5 (TRAILR2, CD262), Decoy receptor 1 (TRAILR3, LIT, TRID, CD263), Decoy receptor 2 (TRAILR4, TRUNDD, CD264), RANK (CD265), Osteoprotegerin (OCIF, TR1), TWEAK receptor (Fn14, CD266), TACI (IGAD2, CD267), BAFF receptor (CD268), Herpesvirus entry mediator (ATAR, TR2, CD270), Nerve growth factor receptor (p75NTR, CD271), B-cell maturation antigen (TNFRSF13A, CD269), Glucocorticoid-induced TNFR-related (AITR, CD357), TROY (TAJ, TRADE), Death receptor 6 (CD358), Death receptor 3 (Apo-3, TRAMP, LARD, WS-1) or Ectodysplasin A2 receptor (XEDAR).

In some cases, the receptor-binding agent that specifically binds the TNF receptor superfamily protein is an antibody or an antigen-binding fragment thereof, e.g., an Fab fragment. In some embodiments, the receptor-binding agent that specifically binds the TNF receptor superfamily protein may be a ligand that binds, e.g., specifically binds, to the receptor, and/or an extracellular domain or a portion thereof. In some embodiments, the ligand is or includes TNFα, Lymphotoxin beta (TNF-C), OX40L, CD154, FasL, FasL, LIGHT, TL1A, CD70, Siva, CD153, 4-1BB ligand, TRAIL, RANKL, TWEAK, APRIL, BAFF, CAMLG, BAFF, LIGHT, NGF, BDNF, NT-3, NT-4, BAFF, GITR ligand, TL1A or EDA-A2, or an extracellular domain or a portion thereof of any of the transmembrane proteins.

In some embodiments, the molecule on the cell is a Wnt receptor or co-receptor, receptors, such a Frizzled (Fz) family receptor, a lipoprotein receptor-related protein (LRP)-5/6, receptor tyrosine kinase (RTK), and receptor-related orphan receptor 2 (ROR2). In some embodiments, the molecule on the cell is, e.g., Frizzled-1 (FZD1), Frizzled-2 (FZD2), Frizzled-3 (FZD3), Frizzled-4 (FZD4), Frizzled-5 (FZD5), Frizzled-6 (FZD6), Frizzled-7 (FZD7), Frizzled-8 (FZD8), Frizzled-9 (FZD9) or Frizzled-10 (FZD10).

In some cases, the receptor-binding agent that specifically binds the Wnt receptor or co-receptor is an antibody or an antigen-binding fragment thereof, e.g., an Fab fragment. In some embodiments, the receptor-binding agent that specifically binds Wnt receptor or co-receptor may be a ligand that binds, e.g., specifically binds, to the receptor. In some embodiments, the ligand is or includes, e.g., WNT1, WNT2, WNT2B, WNT3, WNT3A, WNT4, WNT5A, WNT5B, WNT6, WNT7A, WNT7B, WNT8A, WNT8B, WNT9A, WNT9B, WNT10A, WNT10B, WNT11 or WNT16.

In some embodiments, the receptor-binding agent, e.g., stimulatory agent is capable of binding to any one or more of CD28, CD90 (Thy-1), CD95 (Apo-/Fas), CD137 (4-1BB), CD154 (CD40L), ICOS, LAT, CD27, OX40 and HVEM. In some embodiments, the receptor-binding agent, e.g. stimulatory agent, can be an antibody, divalent antibody (e.g. a F(ab')$_2$-fragment or a divalent single-chain Fv fragment), monovalent antibody (e.g. a Fab fragment, an Fv fragment, or a single-chain Fv fragment (scFv)) or ligand to any one or more of CD28, CD90 (Thy-1), CD95 (Apo-/Fas), CD137 (4-1BB), CD154 (CD40L), ICOS, LAT, CD27, OX40 and HVEM, in which such agent is capable of inducing or modeling a signal in the cells upon binding of the receptor-binding agent, e.g., stimulatory agent to the molecule.

In some embodiments, the receptor-binding agent, e.g. stimulatory agent, can be a ligand to any one or more of CD28, 4-1BB (CD137), CD40, CD40L, Linker for Activation of T cells (LAT), CD27, OX40 (CD134) and herpesvirus entry mediator (HVEM), in which such agent is capable of inducing or modeling a signal in the cells upon binding of the receptor-binding agent, e.g., stimulatory agent to the molecule. In some embodiments, the receptor-binding agent, e.g. stimulatory agent, can be an extracellular domain or a portion thereof, of an endogenous ligand and/or a cognate ligand. For example, in some embodiments, the receptor-binding agent is or contains the extracellular domain or a portion thereof, of B7-1 (CD80), B7-2 (CD86), 4-1BBL, CD40, CD40L, CD27L (CD70) and/or OX40L.

In some embodiments, the molecule on the cell, e.g., T cell, may be CD28 and the receptor-binding agent, e.g., stimulatory agent (e.g. which can be the second receptor-binding agent, e.g., second stimulatory agent) specifically binds CD28.

In some embodiments, the molecule on the cell, e.g., T cell, may be CD28 and the receptor-binding agent, e.g., stimulatory agent (e.g. which can be the second receptor-binding agent, e.g., second stimulatory agent) specifically binds CD28. In some aspects, the receptor-binding agent, e.g., stimulatory agent (e.g. which can be the second receptor-binding agent, e.g., second stimulatory agent) that specifically binds CD28 may be selected from the group consisting of an anti-CD28 antibody, a divalent antibody fragment of an anti-CD28 antibody, a monovalent antibody fragment of an anti-CD28 antibody, and a proteinaceous CD28 binding molecule with antibody-like binding properties. The divalent antibody fragment may be an F(ab')$_2$-fragment, or a divalent single-chain Fv fragment while the monovalent antibody fragment may be selected from the group consisting of a Fab fragment, an Fv fragment, and a single-chain Fv fragment (scFv). A proteinaceous CD28 binding molecule with antibody-like binding properties may be an aptamer, a mutein based on a polypeptide of the lipocalin family, a glubody, a protein based on the ankyrin scaffold, a protein based on the crystalline scaffold, an adnectin, and an avimer.

In some embodiments, an anti-CD28 Fab fragment can be derived from antibody CD28.3 (deposited as a synthetic single chain Fv construct under GenBank Accession No. AF451974.1; see also Vanhove et al., BLOOD, 15 Jul. 2003, Vol. 102, No. 2, pages 564-570) the heavy and light chain of which comprise SEQ ID NO: 33 and 34, respectively.

In some embodiments, the molecule on the cell, e.g., T cell or B cell, may be CD137 and the receptor-binding agent, e.g., stimulatory agent (e.g. which can be the second receptor-binding agent, e.g., second stimulatory agent) specifically binds CD137. In some aspects, the receptor-binding agent, e.g., stimulatory agent (e.g. which can be the second receptor-binding agent, e.g., second stimulatory agent) that specifically binds CD137 may be selected from the group consisting of an anti-CD137 antibody, a divalent antibody fragment of an anti-CD137 antibody, a monovalent antibody fragment of an anti-CD137 antibody, and a proteinaceous CD137 binding molecule with antibody-like binding properties. The antibody or antigen-binding fragment can be derived from any known in the art. For example, the anti-CD137 antibody can be LOB12, IgG2a or LOB12.3, IgG1 as described in Taraban et al. Eur J Immunol. 2002 December; 32(12):3617-27. See also e.g. U.S. Pat. Nos. 6,569,997, 6,303,121, Mittler et al. Immunol Res. 2004; 29(1-3):197-208.

In some embodiments, the molecule on the cell, e.g. B cell, may be CD40 and the receptor-binding agent, e.g., stimulatory agent, (e.g. which can be the second receptor-binding agent, e.g., second stimulatory agent) specifically binds CD40. In some aspects, the receptor-binding agent (which can be the second receptor-binding agent, e.g., second stimulatory agent) that specifically binds CD40 may be selected from the group consisting of an anti-CD40 antibody, a divalent antibody fragment of an anti-CD40 antibody, a monovalent antibody fragment of an anti-CD40 antibody, and a proteinaceous CD40 binding molecule with antibody-like binding properties. The antibody or antigen-binding fragment can be derived from any known in the art. For example, the anti-CD40 antibody can be chimeric monoclonal anti-human CD40 antibody Teneliximab and anti-human CD40 (Affymetrix cat. no. 14-0409-80), or any described in e.g., US 2002/0142358, US 2007/0077242, WO 2001/083755, Zhang et al., 2010, J Immunol, 184:787-795.

In some embodiments, the molecule on the cell, e.g., T cell, may be CD40L (CD154) and the receptor-binding agent, e.g., stimulatory agent, (e.g. which can be the second receptor-binding agent, e.g., second stimulatory agent) specifically binds CD40L. In some aspects, the receptor-binding agent, e.g., stimulatory agent, (e.g. which can be the second receptor-binding agent, e.g., second stimulatory agent) that specifically binds CD40L may be selected from the group consisting of an anti-CD40L antibody, a divalent antibody fragment of an anti-CD40L antibody, a monovalent antibody fragment of an anti-CD40L antibody, and a proteinaceous CD40L binding molecule with antibody-like binding properties. The antibody or antigen-binding fragment can be derived from any known in the art. For example, the anti-CD40L antibody can in some aspects be Hu5C8, as described in Blair et al. JEM vol. 191 no. 4 651-660. See also e.g. WO1999061065, US20010026932, U.S. Pat. No. 7,547,438, WO2001056603.

In some embodiments, the molecule on the cell, e.g., T cell, may be inducible T cell Costimulator (ICOS) and the receptor-binding agent, e.g., stimulatory agent, (e.g. which can be the second receptor-binding agent, e.g., second stimulatory agent) specifically binds ICOS. In some aspects, the receptor-binding agent, e.g., stimulatory agent, (e.g. which can be the second receptor-binding agent, e.g., second stimulatory agent) that specifically binds ICOS may be selected from the group consisting of an anti-ICOS antibody, a divalent antibody fragment of an anti-ICOS antibody, a monovalent antibody fragment of an anti-ICOS antibody, and a proteinaceous ICOS binding molecule with antibody-like binding properties. The antibody or antigen-binding fragment can be derived from any known in the art. See, e.g., US20080279851 and Deng et al. Hybrid Hybridomics. 2004 June; 23(3):176-82.

In some embodiments, the molecule on the cell, e.g., T cell, may be Linker for Activation of T cells (LAT) and the receptor-binding agent, e.g., stimulatory agent, (e.g. which can be the second receptor-binding agent, e.g., second stimulatory agent) specifically binds LAT. In some aspects, the receptor-binding agent, e.g., stimulatory agent, (e.g. which can be the second receptor-binding agent, e.g., second stimulatory agent) that specifically binds LAT may be selected from the group consisting of an anti-LAT antibody, a divalent antibody fragment of an anti-LAT antibody, a monovalent antibody fragment of an anti-LAT antibody, and a proteinaceous LAT binding molecule with antibody-like binding properties. The antibody or antigen-binding fragment can be derived from any known in the art. See, e.g., Zhang et al., Cell. 1998 Jan. 9; 92(1):83-92 and Facchetti et al., Am J Pathol. 1999 April; 154(4): 1037-1046.

In some embodiments, the molecule on the cell, e.g., T cell, may be CD27 and the receptor-binding agent, e.g., stimulatory agent, (e.g. which can be the second receptor-binding agent, e.g., second stimulatory agent) specifically binds CD27. In some aspects, the receptor-binding agent, e.g., stimulatory agent, (e.g. which can be the second receptor-binding agent, e.g., second stimulatory agent) that specifically binds CD27 may be selected from the group consisting of an anti-CD27 antibody, a divalent antibody fragment of an anti-CD27 antibody, a monovalent antibody fragment of an anti-CD27 antibody, and a proteinaceous CD27 binding molecule with antibody-like binding properties. The antibody or antigen-binding fragment can be derived from any known in the art. See, e.g. WO2008051424, U.S. Pat. Nos. 9,023,999, 8,481,029, 9,169,325, 9,102,737, US 2016/0185870, and He et al., J Immunol. 2013 Oct. 15; 191(8):4174-83.

In some embodiments, the molecule on the cell, e.g., T cell, may be OX40 (CD134) and the receptor-binding agent, e.g., stimulatory agent, (e.g. which can be the second receptor-binding agent, e.g., second stimulatory agent) specifically binds OX40. In some aspects, the receptor-binding agent, e.g., stimulatory agent, (e.g. which can be the second receptor-binding agent, e.g., second stimulatory agent) that specifically binds OX40 may be selected from the group consisting of an anti-OX40 antibody, a divalent antibody fragment of an anti-OX40 antibody, a monovalent antibody fragment of an anti-OX40 antibody, and a proteinaceous OX40 binding molecule with antibody-like binding properties. The antibody or antigen-binding fragment can be derived from any known in the art. See, e.g., US 2010/0196359, US 2015/0307617, WO 2015/153513, WO203038191 and Melero et al. Clin Cancer Res. 2013 Mar. 1; 19(5):1044-53.

In some embodiments, the molecule on the cell, e.g., T cell, may be herpesvirus entry mediator (HVEM) and the receptor-binding agent, e.g., stimulatory agent, (e.g. which can be the second receptor-binding agent, e.g., second stimulatory agent) specifically binds HVEM. In some aspects, the receptor-binding agent, e.g., stimulatory agent, (e.g. which can be the second receptor-binding agent, e.g., second stimulatory agent) that specifically binds HVEM may be selected from the group consisting of an anti-HVEM antibody, a divalent antibody fragment of an anti-HVEM antibody, a monovalent antibody fragment of an anti-HVEM antibody, and a proteinaceous HVEM binding molecule with antibody-like binding properties. The antibody or antigen-binding fragment can be derived from any known in the art. See, e.g. WO2006054961, WO2007001459, Park et al. Cancer Immunol Immunother. 2012 February; 61(2):203-14.

In some embodiments, the molecule on the cell, e.g., T cell, may be CD90 and the receptor-binding agent, e.g., stimulatory agent (e.g. which can be the second receptor-binding agent, e.g., second stimulatory agent) specifically binds CD90. In some aspects, the receptor-binding agent, e.g., stimulatory agent (e.g. which can be the second receptor-binding agent, e.g., second stimulatory agent) that specifically binds CD90 may be selected from the group consisting of an anti-CD90 antibody, a divalent antibody fragment of an anti-CD90 antibody, a monovalent antibody fragment of an anti-CD90 antibody, and a proteinaceous CD90 binding molecule with antibody-like binding properties. The antibody or antigen-binding fragment can be derived from any known in the art. See, e.g., anti-human CD90 antibody clone 5E10 (Stemcell Technologies, Cat. no. 60045 or BD Biosciences cat. no. 550402) and anti-CD90 antibody G7 (Biolegend, cat. no. 105201).

In some embodiments, the molecule on the cell, e.g., T cell, may be CD95 and the receptor-binding agent, e.g., stimulatory agent (e.g. which can be the second receptor-binding agent, e.g., second stimulatory agent) specifically binds CD95. In some aspects, the receptor-binding agent, e.g., stimulatory agent (e.g. which can be the second receptor-binding agent, e.g., second stimulatory agent) that specifically binds CD95 may be selected from the group consisting of an anti-CD95 antibody, a divalent antibody fragment of an anti-CD95 antibody, a monovalent antibody fragment of an anti-CD95 antibody, and a proteinaceous CD95 binding molecule with antibody-like binding properties. The antibody or antigen-binding fragment can be derived from any known in the art. For example, in some aspects, the anti-CD95 antibody can be monoclonal mouse anti-human CD95 CH11 (Upstate Biotechnology, Lake Placid, N.Y.) or can be anti-CD95 mAb 7C11 or anti-APO-1, such as any described in e.g., WO 2015/197874, U.S. Pat. Nos. 9,309,320, 7,935,339 and Paulsen et al. *Cell Death & Differentiation* 18.4 (2011): 619-631.

c. Receptor-Binding Agent Providing Additional Signal

In some embodiments, the molecule on the cell, e.g., T cell, to which the receptor-binding agent, which may be a second or an additional receptor-binding agent, binds to a cell surface molecule that stimulates or activates a cytokine signal, chemokine signal, cell adhesion signal, T cell activation signal 3 or additional signals, e.g., environmental signals, upon binding of the agent. In some embodiments, the molecule on the cell, e.g., T cell, to which the receptor-binding agent, which may be a second or an additional receptor-binding agent, specifically binds, is a cytokine receptor or a chemokine receptor. In some cases, the receptor-binding agent, e.g., additional receptor-binding agent, is or contains an adhesion molecule, is a factor that induces cytokine production, chemokine production, expression of an adhesion molecule, and/or is involved in stimulating and/or modulating an accessory signal and/or an additional signal, e.g., an environmental signal.

In any of the embodiments provided herein, the receptor-binding agent, e.g., the first, second and/or additional receptor-binding agent, e.g., stimulatory agent, may be a binding agent that specifically binds a receptor, e.g., a receptor expressed on the surface of the cell.

In some embodiments, the receptor-binding agent, e.g., stimulatory agent, is an antibody or an antigen-binding fragment thereof, e.g., an antibody or antigen binding fragment thereof that binds to a cell surface molecule that stimulates or activates a cytokine signal, chemokine signal, cell adhesion signal, T cell activation signal 3 or additional signals, e.g., environmental signals, upon binding of the agent. In some cases, the receptor-binding agent, e.g., the first, second and/or additional receptor-binding agent, e.g., stimulatory agent, that specifically binds receptor may be selected from the group consisting of an anti-receptor antibody, a divalent antibody fragment of an anti-receptor antibody, a monovalent antibody fragment of an anti-receptor antibody, and a proteinaceous receptor binding molecule with antibody-like binding properties. The divalent antibody fragment may be a F(ab')$_2$-fragment, or a divalent single-chain Fv fragment while the monovalent antibody fragment may be selected from the group consisting of an Fab fragment, an Fv fragment, and a single-chain Fv fragment (scFv). In some cases, a proteinaceous receptor binding molecule with antibody-like binding properties may be an aptamer, a mutein based on a polypeptide of the lipocalin family, a glubody, a protein based on the ankyrin scaffold, a protein based on the crystalline scaffold, an adnectin, or an avimer. In some cases, the receptor-binding agent, e.g., the first, second and/or additional receptor-binding agent, e.g., stimulatory agent, that specifically binds receptor is an antibody or an antigen-binding fragment thereof, e.g., an Fab fragment.

In some embodiments, the receptor-binding agent, e.g., stimulatory agent, may be a ligand that binds, e.g., specifically binds, to the receptor, e.g., a cell surface molecule that stimulates or activates a cytokine signal, chemokine signal, cell adhesion signal, T cell activation signal 3 or additional signals, e.g., environmental signals, upon binding of the agent. In some embodiments, the receptor-binding agent, e.g., the first, second and/or additional receptor-binding agent, is an endogenous ligand, a cognate ligand, a synthetic ligand and/or a portion, a variant or modified forms thereof. In some embodiments, the receptor-binding agent, e.g. stimulatory agent, can be an extracellular domain or a portion thereof, of an endogenous ligand and/or a cognate ligand.

In some embodiments, the receptor-binding agent, e.g., a second or an additional receptor-binding agent, is or contains a ligand that specifically binds to a cytokine receptor. In some embodiments, the receptor-binding agent, e.g., a second or an additional receptor-binding agent, is or comprises a ligand of the cytokine receptor, e.g., a cytokine or a portion thereof.

Exemplary cytokine receptors include, but are not limited to, IL-2R, IL-7R, IL-21R, CD132 (IL receptor common gamma chain), IL-1R, IL-15R, IFN-gammaR, TNF-alphaR, IL-4R, IL-10R, Type I IFNR, IL-12R, IL-17R, TNFR1 and TNFR2. Exemplary ligands, e.g., cytokines, include, but are not limited to, IL-2, IL-7, IL-21, IL-1, IL-15, IFN-gamma, TNF-alpha, IL-4, IL-10, Type I interferons (e.g., IFNα and/or IFNβ), IL-12, IL-17, IL-9 and TNF, and biologically active fragments thereof.

In some embodiments, the receptor-binding agent, e.g., a second or an additional receptor-binding agent, is an antibody or antigen-binding fragment thereof, that specifically binds to a cytokine receptor. In some cases, the receptor-binding agent, e.g., a second or an additional receptor-binding agent, that specifically binds cytokine receptor may be selected from the group consisting of an anti-(cytokine receptor) antibody, a divalent antibody fragment of an anti-(cytokine receptor) antibody, a monovalent antibody fragment of an anti-(cytokine receptor) antibody, and a proteinaceous cytokine receptor binding molecule with antibody-like binding properties. The divalent antibody fragment may be a F(ab')$_2$-fragment, or a divalent single-chain Fv fragment while the monovalent antibody fragment may be selected from the group consisting of a Fab fragment, an Fv fragment, and a single-chain Fv fragment (scFv).

In some embodiments, the receptor-binding agent, e.g., additional receptor-binding agent, is or contains a ligand that specifically binds to a chemokine receptor. In some embodiments, the receptor-binding agent, e.g., a second or an additional receptor-binding agent, is or comprises a ligand of the chemokine receptor, e.g., a chemokine or a portion thereof.

Exemplary chemokine receptors include, but are not limited to, CCR1, CCR2, CCR3, CCR4, CCR5, CCR7, CCR9, CXCR1, CXCR3 and CXCR4. Exemplary ligands, e.g., chemokines, include but are not limited to, CXCL9, CXCL10, CCL19, CCL21 and CCL25 or biologically active fragments thereof.

In some embodiments, the receptor-binding agent, e.g., a second or an additional receptor-binding agent, is an antibody or antigen-binding fragment thereof, that specifically binds to a chemokine receptor. In some cases, the receptor-binding agent, e.g., a second or an additional receptor-binding agent, that specifically binds chemokine receptor may be selected from the group consisting of an anti-(chemokine receptor) antibody, a divalent antibody fragment of an anti-(chemokine receptor) antibody, a monovalent antibody fragment of an anti-(chemokine receptor) antibody, and a proteinaceous chemokine receptor binding molecule with antibody-like binding properties. The divalent antibody fragment may be a F(ab')$_2$-fragment, or a divalent single-chain Fv fragment while the monovalent antibody fragment may be selected from the group consisting of a Fab fragment, an Fv fragment, and a single-chain Fv fragment (scFv).

In some cases, the receptor-binding agent that specifically binds the adhesion molecule or factors that induce cytokine is an antibody or an antigen-binding fragment thereof, e.g., an Fab fragment. In some embodiments, the receptor-binding agent that specifically binds the adhesion molecule or factors that induce cytokine may be a ligand that binds, e.g., specifically binds, to the receptor. In some embodiments, the receptor-binding agent is an endogenous ligand, a cognate ligand, a synthetic ligand and/or a portion, a variant or modified forms thereof, of the adhesion molecule and/or the receptor. In some embodiments, the receptor-binding agent, e.g. stimulatory agent, can be an extracellular domain or a portion thereof, of an endogenous ligand and/or a cognate ligand that is itself a cell-surface or transmembrane protein.

In some instances, the molecule on the cell, e.g., adhesion molecule, is CD44, CD31, CD18/CD11a (LFA-1; full length alpha and beta chain sequence set forth in SEQ ID NOS: 71 and 72 respectively), CD29, CD54 (ICAM-1), CD62L (L-selectin; full length sequence set forth in SEQ ID NO:73), CD29/CD49d (VLA-4; full length sequence set forth in SEQ ID NO:75), CD106 (VCAM-1; full length sequence set forth in SEQ ID NO:74) or is a biologically active fragment thereof. In some embodiments, the receptor-binding agent is an antibody or an antigen-binding fragment thereof that binds, e.g., specifically binds to an adhesion molecule, e.g., CD44, CD31, CD18/CD11a (LFA-1), CD29, CD54 (ICAM-1), CD62L (L-selectin), CD29/CD49d (VLA-4), CD106 (VCAM-1) or is a biologically active fragment thereof. In some embodiments, the receptor-binding agent is a ligand or a portion thereof, that binds, e.g., specifically binds to an adhesion molecule, e.g., CD44, CD31, CD18/CD11a (LFA-1), CD29, CD54 (ICAM-1), CD62L (L-selectin), CD29/CD49d (VLA-4), CD106 (VCAM-1). Such receptor-binding agents include an agent that is or comprises an extracellular domain (ECD) or a portion thereof, of an endogenous ligand and/or a cognate ligand of an adhesion molecule. In some embodiments, the receptor-binding agent is an extracellular domain or a portion thereof, of an adhesion molecule, and can bind one or more adhesion molecules on the surface of a cell. Exemplary of such receptor-binding agents include the extracellular domain of LFA-1α (ECD set forth in SEQ ID NO:77); LFA-1β (ECD set forth in SEQ ID NO:78); L-selectin (ECD set forth in SEQ ID NO:79); VCAM-1 (ECD set forth in SEQ ID NO:80); and VLA-4 (ECD set forth in SEQ ID NO:81), or any portion thereof.

In some embodiments, the factor that induces cytokine production, chemokine production and/or expression of an adhesion molecule is or contains a nuclear factor, such as a retinoic acid receptor-related orphan receptor gamma (RORgamma) or RORalpha.

In some embodiments, the receptor-binding agent, e.g., a second or an additional receptor-binding agent, is or contains a ligand that specifically binds to a cytokine receptor.

In some embodiments, the molecule on the cell, e.g., T cell, may be IL-2R and the receptor-binding agent, e.g., stimulatory agent, (e.g. which can be an additional receptor-binding agent, e.g., additional stimulatory agent) specifically binds IL-2R. In some aspects, the receptor-binding agent, e.g., stimulatory agent, (e.g. which can be an additional receptor-binding agent, e.g., additional stimulatory agent) that specifically binds IL-2R may be selected from the group consisting of an anti-IL-2R antibody, a divalent antibody fragment of an anti-IL-2R antibody, a monovalent antibody fragment of an anti-IL-2R antibody, and a proteinaceous IL-2R binding molecule with antibody-like binding properties. The antibody or antigen-binding fragment can be derived from any known in the art. For example, in some cases, the antibody or antigen-binding fragment may be any as described in, e.g., EP 2425250, US 2011/0053209, WO 2009/145831, US 2010/0055098, and Volk et al., Clin Exp Immunol. 1989 April; 76(1): 121-125.

In some embodiments, the molecule on the cell, e.g., T cell, may be IL-7R (CD127) and the receptor-binding agent, e.g., stimulatory agent, (e.g. which can be the second receptor-binding agent, e.g., second stimulatory agent) specifically binds IL-7R. In some aspects, the receptor-binding agent, e.g., stimulatory agent, (e.g. which can be the second receptor-binding agent, e.g., second stimulatory agent) that specifically binds IL-7R may be selected from the group consisting of an anti-IL-7R antibody, a divalent antibody fragment of an anti-IL-7R antibody, a monovalent antibody fragment of an anti-IL-7R antibody, and a proteinaceous IL-7R binding molecule with antibody-like binding properties. The antibody or antigen-binding fragment can be derived from any known in the art. For example, in some cases, the antibody or antigen-binding fragment may be any as described in, e.g., WO 2016/059512, WO 2015/189302, Lee et al., Proc Natl Acad Sci USA. 2012 Jul. 31; 109(31): 12674-9, and Chung et al., Blood (2007) 110(8):2803-2810.

In some embodiments, the molecule on the cell, e.g., T cell, may be IL-21R (CD360) and the receptor-binding agent, e.g., stimulatory agent, (e.g. which can be the second receptor-binding agent, e.g., second stimulatory agent) specifically binds IL-21R. In some aspects, the receptor-binding agent, e.g., stimulatory agent, (e.g. which can be the second receptor-binding agent, e.g., second stimulatory agent) that specifically binds IL-21R may be selected from the group consisting of an anti-IL-21R antibody, a divalent antibody fragment of an anti-IL-21R antibody, a monovalent antibody fragment of an anti-IL-21R antibody, and a proteinaceous IL-21R binding molecule with antibody-like binding properties. The antibody or antigen-binding fragment can be derived from any known in the art. For example, in some cases, the antibody or antigen-binding fragment may be any as described in, e.g., US 2006/0159655, US 2006/0039902, US 2003/0108549, and Guo et al., J Transl Med. 2010; 8: 50.

In some embodiments, the molecule on the cell, e.g., T cell, may be the IL receptor common gamma chain (γc; or CD132) and the receptor-binding agent, e.g., stimulatory agent, (e.g. which can be the second receptor-binding agent, e.g., second stimulatory agent) specifically binds the common gamma chain. The common gamma chain (γc; or CD132), also known as interleukin-2 receptor subunit gamma or IL-2RG, is a cytokine receptor subunit that is common to the receptor complexes for interleukin receptors: IL-2R, IL-4R, IL-7R, IL-9R, IL-15R and IL-21R. In some aspects, the receptor-binding agent, e.g., stimulatory agent, (e.g. which can be the second receptor-binding agent, e.g., second stimulatory agent) that specifically binds the common gamma chain may be selected from the group consisting of an anti-γc or anti-CD132 antibody, a divalent antibody fragment of an anti-γc or anti-CD132 antibody, a monovalent antibody fragment of an anti-γc or anti-CD132 antibody, and a proteinaceous common gamma chain binding molecule with antibody-like binding properties. The antibody or antigen-binding fragment can be derived from any known in the art. For example, in some cases, the antibody or antigen-binding fragment may be any as described in, e.g., anti-γc or anti-CD132 antibody TUGh4 (AB_2123585 (BioLegend Cat. No. 338607) or AB_2123584 (BioLegend Cat. No. 338608)), Itano et al. 1996. J. Exp. Med. 178:389, Kondo et al. 1993. Science 262:1874, Hodge et al. 2012. Blood. 120:3774, Matsubara et al. 2014. Sci Rep. 4:5043 and Massoud et al. 2015. PNAS. 112: 11030-11035, Pérez-Simón, Blood 2015 125:424-426.

In some embodiments, the molecule on the cell, e.g., T cell, may be IL-1R (CD121), such as IL-1R1 or IL-1R2, and the receptor-binding agent, e.g., stimulatory agent, (e.g. which can be the second receptor-binding agent, e.g., second stimulatory agent) specifically binds IL-1R. In some aspects, the receptor-binding agent, e.g., stimulatory agent, (e.g. which can be the second receptor-binding agent, e.g., second stimulatory agent) that specifically binds IL-1R may be selected from the group consisting of an anti-IL-1R antibody, a divalent antibody fragment of an anti-IL-1R antibody, a monovalent antibody fragment of an anti-IL-1R antibody, and a proteinaceous IL-1R binding molecule with antibody-like binding properties. The antibody or antigen-binding fragment can be derived from any known in the art. For example, in some cases, the antibody or antigen-binding fragment may be, e.g., human IL-1R1 antibody (R&D Systems cat. no. AF269).

In some embodiments, the molecule on the cell, e.g., T cell, may be IL-15R (CD215), and the receptor-binding agent, e.g., stimulatory agent, (e.g. which can be the second receptor-binding agent, e.g., second stimulatory agent) specifically binds IL-15R. In some aspects, the receptor-binding agent, e.g., stimulatory agent, (e.g. which can be the second receptor-binding agent, e.g., second stimulatory agent) that specifically binds IL-15R may be selected from the group consisting of an anti-IL-15R antibody, a divalent antibody fragment of an anti-IL-15R antibody, a monovalent antibody fragment of an anti-IL-15R antibody, and a proteinaceous IL-15R binding molecule with antibody-like binding properties. The antibody or antigen-binding fragment can be derived from any known in the art. For example, in some cases, the antibody or antigen-binding fragment may be any as described in, e.g., US 2004/0185048, U.S. Pat. No. 6,013,480 or may be anti-human IL-15R antibody eBioJM7A4 (Affymetrix cat. no. 12-7159-41).

In some embodiments, the molecule on the cell, e.g., T cell, may be interferon gamma receptor (IFNγR; CD119) and the receptor-binding agent, e.g., stimulatory agent, (e.g. which can be an additional receptor-binding agent, e.g., additional stimulatory agent) specifically binds IFNγR. In some aspects, the receptor-binding agent, e.g., stimulatory agent, (e.g. which can be an additional receptor-binding agent, e.g., additional stimulatory agent) that specifically binds IFNγR may be selected from the group consisting of an anti-IFNγR antibody, a divalent antibody fragment of an anti-IFNγR antibody, a monovalent antibody fragment of an anti-IFNγR antibody, and a proteinaceous IFNγR binding molecule with antibody-like binding properties. The antibody or antigen-binding fragment can be derived from any known in the art. For example, in some cases, the antibody or antigen-binding fragment may be, e.g., anti-human CD119 (IFN gamma Receptor 1) antibody GIR 208 (eBioscience cat. no. 13-1199-80) and anti-human IFN gamma receptor antibody ab25448 (Abcam cat. no. ab25448).

In some embodiments, the molecule on the cell, e.g., T cell, may be tumor necrosis factor alpha receptor (TNFαR), e.g., including TNFR1 (CD120a) and TNFR2 (CD120b), and the receptor-binding agent, e.g., stimulatory agent, (e.g. which can be an additional receptor-binding agent, e.g., additional stimulatory agent) specifically binds TNFαR. In some aspects, the receptor-binding agent, e.g., stimulatory agent, (e.g. which can be an additional receptor-binding agent, e.g., additional stimulatory agent) that specifically binds TNFαR may be selected from the group consisting of an anti-TNFαR antibody, a divalent antibody fragment of an anti-TNFαR antibody, a monovalent antibody fragment of an anti-TNFαR antibody, and a proteinaceous TNFαR binding molecule with antibody-like binding properties. The antibody or antigen-binding fragment can be derived from any known in the art. For example, in some cases, the antibody or antigen-binding fragment may be any as described in, WO 2012/087928, WO 2010/120374 and anti-human IFN gamma receptor antibody ab19139 (Abcam cat. no. ab19139) and ab74315 (Abcam cat. no. ab74315).

In some embodiments, the molecule on the cell, e.g., T cell, may be IL-4R and the receptor-binding agent, e.g., stimulatory agent, (e.g. which can be an additional receptor-binding agent, e.g., additional stimulatory agent) specifically binds IL-4R. In some aspects, the receptor-binding agent, e.g., stimulatory agent, (e.g. which can be an additional receptor-binding agent, e.g., additional stimulatory agent) that specifically binds IL-4R may be selected from the group consisting of an anti-IL-4R antibody, a divalent antibody fragment of an anti-IL-4R antibody, a monovalent antibody fragment of an anti-IL-4R antibody, and a proteinaceous IL-4R binding molecule with antibody-like binding properties. The antibody or antigen-binding fragment can be derived from any known in the art. For example, in some aspects, the antibody or antigen binding fragment may be any as described in WO2005047331.

In some embodiments, the molecule on the cell, e.g., T cell, may be IL-10R and the receptor-binding agent, e.g., stimulatory agent, (e.g. which can be an additional receptor-binding agent, e.g., additional stimulatory agent) specifically binds IL-10R. In some aspects, the receptor-binding agent, e.g., stimulatory agent, (e.g. which can be an additional receptor-binding agent, e.g., additional stimulatory agent) that specifically binds IL-10R may be selected from the group consisting of an anti-IL-10R antibody, a divalent antibody fragment of an anti-IL-10R antibody, a monovalent antibody fragment of an anti-IL-10R antibody, and a proteinaceous IL-10R binding molecule with antibody-like binding properties. The antibody or antigen-binding fragment can be derived from any known in the art. For example, in some aspects, the antibody or antigen binding fragment may be any as described in U.S. Pat. Nos. 7,553,932, 8,071,374, Castro et al., J Exp Med. 2000 Nov. 20; 192(10): 1529-34 or anti-IL-10R antibody 9D7 (ThermoFisher cat. no. 06-1067).

In some embodiments, the molecule on the cell, e.g., T cell, may be Interferon type I receptor, e.g., IFNα receptor (IFNAR), including IFNAR1 and IFNAR2, and the receptor-binding agent, e.g., stimulatory agent, (e.g. which can be an additional receptor-binding agent, e.g., additional stimulatory agent) specifically binds IFNAR. In some aspects, the receptor-binding agent, e.g., stimulatory agent, (e.g. which can be an additional receptor-binding agent, e.g., additional stimulatory agent) that specifically binds IFNAR may be selected from the group consisting of an anti-IFNAR antibody, a divalent antibody fragment of an anti-IFNAR antibody, a monovalent antibody fragment of an anti-IFNAR antibody, and a proteinaceous IFNAR binding molecule with antibody-like binding properties. The antibody or antigen-binding fragment can be derived from any known in the art. For example, in some cases, the antibody or antigen-binding fragment may be any as described in, e.g., US 2013/0254912, U.S. Pat. Nos. 7,662,381, 8,460,668, Baccala et al., J. Immunol. 2012, 189(12):5976-5984 and anti-IFNAR2 antibody clone MMHAR-2 (PBL Sciences cat. no. 21385-1).

In some embodiments, the molecule on the cell, e.g., T cell, may be IL-12R and the receptor-binding agent, e.g., stimulatory agent, (e.g. which can be an additional receptor-binding agent, e.g., additional stimulatory agent) specifically binds IL-12R. In some aspects, the receptor-binding agent, e.g., stimulatory agent, (e.g. which can be an additional receptor-binding agent, e.g., additional stimulatory agent) that specifically binds IL-12R may be selected from the group consisting of an anti-IL-12R antibody, a divalent antibody fragment of an anti-IL-12R antibody, a monovalent antibody fragment of an anti-IL-12R antibody, and a proteinaceous IL-12R binding molecule with antibody-like binding properties. The antibody or antigen-binding fragment can be derived from any known in the art. For example, in some cases, the antibody or antigen-binding fragment may be any as described in EP0638644 or U.S. Pat. No. 5,853,721.

In some embodiments, the molecule on the cell, e.g., T cell, may be IL-17R (CD217) and the receptor-binding agent, e.g., stimulatory agent, (e.g. which can be an additional receptor-binding agent, e.g., additional stimulatory agent) specifically binds IL-17R. In some aspects, the receptor-binding agent, e.g., stimulatory agent, (e.g. which can be an additional receptor-binding agent, e.g., additional stimulatory agent) that specifically binds IL-17R may be selected from the group consisting of an anti-IL-17R antibody, a divalent antibody fragment of an anti-IL-17R antibody, a monovalent antibody fragment of an anti-IL-17R antibody, and a proteinaceous IL-17R binding molecule with antibody-like binding properties. The antibody or antigen-binding fragment can be derived from any known in the art. For example, in some cases, the antibody or antigen-binding fragment may be any as described in WO2008054603, EP2487188, Papp et al., J Invest Dermatol. 2012 October; 132(10):2466-9, Moseley et al., 2003. Cytokine Growth Factor Rev. 14:155, Rong et al., 2009. Cell. Res. 19:208, Toy et al., 2006. J. Immunol. 177:36, or anti-human CD217 antibody clone W15177A (Biolegend).

In some embodiments, the receptor-binding agent, e.g., stimulatory agent, (e.g. which can be an additional receptor-binding agent, e.g., additional stimulatory agent) can include a ligand of a stimulatory receptor or other receptor capable of inducing a signal in the cell, such as an IL-2 ligand or a biologically active portion thereof. In some aspects, the IL-2 ligand has the amino acid sequence set forth in SEQ ID NO: 50 or is a variant thereof that exhibits at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity with the sequence set forth in SEQ ID NO: 50, or is a biologically active portion thereof, wherein the variant or biologically active portion thereof retains activity to bind to the receptor and/or a functional activity to modulate one or more signals to the receptor.

In some embodiments, the receptor-binding agent, e.g., stimulatory agent, (e.g. which can be an additional receptor-binding agent, e.g., additional stimulatory agent) can include a ligand of a stimulatory receptor or other receptor capable of inducing a signal in the cell, such as an IL-7 ligand or a biologically active portion thereof. In some aspects, the IL-7 ligand has the amino acid sequence set forth in SEQ ID NO: 51 or is a variant thereof that exhibits at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity with the sequence set forth in SEQ ID NO: 51, or is a biologically active portion thereof, wherein the variant or biologically active portion thereof retains activity to bind to the receptor and/or a functional activity to modulate one or more signals to the receptor.

In some embodiments, the receptor-binding agent, e.g., stimulatory agent, (e.g. which can be an additional receptor-binding agent, e.g., additional stimulatory agent) can include a ligand of a stimulatory receptor or other receptor capable of inducing a signal in the cell, such as an IL-21 ligand or a biologically active portion thereof. In some aspects, the IL-21 ligand has the amino acid sequence set forth in SEQ ID NO: 52 or is a variant thereof that exhibits at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity with the sequence set forth in SEQ ID NO: 52, or is a biologically active portion thereof, wherein the variant or biologically active portion thereof retains activity to bind to the receptor and/or a functional activity to modulate one or more signals to the receptor.

In some embodiments, the receptor-binding agent, e.g., stimulatory agent, (e.g. which can be an additional receptor-binding agent, e.g., additional stimulatory agent) can include a ligand of a stimulatory receptor or other receptor capable of inducing a signal in the cell, such as an IL-1 ligand or a biologically active portion thereof. In some aspects, the IL-1 ligand has the amino acid sequence set forth in SEQ ID NO: 53 and/or 54 (IL-1α or IL-1β, respectively) or is a variant thereof that exhibits at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity with the sequence set forth in SEQ ID NO: 53 and/or 54 (IL-1α or IL-1β, respectively), or is a biologically active portion thereof, wherein the variant or biologically active portion thereof retains activity to bind to the receptor and/or a functional activity to modulate one or more signals to the receptor.

In some embodiments, the receptor-binding agent, e.g., stimulatory agent, (e.g. which can be an additional receptor-binding agent, e.g., additional stimulatory agent) can include a ligand of a stimulatory receptor or other receptor capable of inducing a signal in the cell, such as an IL-15 ligand or a biologically active portion thereof. In some aspects, the IL-15 ligand has the amino acid sequence set forth in SEQ ID NO: 55 or is a variant thereof that exhibits at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity with the sequence set forth in SEQ ID NO: 55, or is a biologically active portion thereof, wherein the variant or biologically active portion thereof retains activity to bind to the receptor and/or a functional activity to modulate one or more signals to the receptor.

In some embodiments, the receptor-binding agent, e.g., stimulatory agent, (e.g. which can be an additional receptor-binding agent, e.g., additional stimulatory agent) can include a ligand of a stimulatory receptor or other receptor capable of inducing a signal in the cell, such as an IL-9 ligand or a biologically active portion thereof. In some aspects, the IL-9 ligand has the amino acid sequence set forth in SEQ ID NO: 81 or is a variant thereof that exhibits at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity with the sequence set forth in SEQ ID NO: 81, or is a biologically active portion thereof, wherein the variant or biologically active portion thereof retains activity to bind to the receptor and/or a functional activity to modulate one or more signals to the receptor.

In some embodiments, the receptor-binding agent, e.g., stimulatory agent, (e.g. which can be an additional receptor-binding agent, e.g., additional stimulatory agent) can include a ligand of a stimulatory receptor or other receptor capable of inducing a signal in the cell, such as an IFNγ ligand or a biologically active portion thereof. In some aspects, the IFNγ ligand has the amino acid sequence set forth in SEQ ID NO: 56 or is a variant thereof that exhibits at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity with the sequence set forth in SEQ ID NO: 56, or is a biologically active portion thereof, wherein the variant or biologically active portion thereof retains activity to bind to the receptor and/or a functional activity to modulate one or more signals to the receptor.

In some embodiments, the receptor-binding agent, e.g., stimulatory agent, (e.g. which can be an additional receptor-binding agent, e.g., additional stimulatory agent) can include a ligand of a stimulatory receptor or other receptor capable of inducing a signal in the cell, such as a TNFα ligand or a biologically active portion thereof. In some aspects, the TNFα ligand has the amino acid sequence set forth in SEQ ID NO: 57 or is a variant thereof that exhibits at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity with the sequence set forth in SEQ ID NO: 57, or is a biologically active portion thereof, wherein the variant or biologically active portion thereof retains activity to bind to the receptor and/or a functional activity to modulate one or more signals to the receptor.

In some embodiments, the receptor-binding agent, e.g., stimulatory agent, (e.g. which can be an additional receptor-binding agent, e.g., additional stimulatory agent) can include a ligand of a stimulatory receptor or other receptor capable of inducing a signal in the cell, such as an IL-4 ligand or a biologically active portion thereof. In some aspects, the IL-4 ligand has the amino acid sequence set forth in SEQ ID NO: 58 or is a variant thereof that exhibits at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity with the sequence set forth in SEQ ID NO: 58, or is a biologically active portion thereof, wherein the variant or biologically active portion thereof retains activity to bind to the receptor and/or a functional activity to modulate one or more signals to the receptor.

In some embodiments, the receptor-binding agent, e.g., stimulatory agent, (e.g. which can be an additional receptor-binding agent, e.g., additional stimulatory agent) can include a ligand of a stimulatory receptor or other receptor capable of inducing a signal in the cell, such as an IL-10 ligand or a biologically active portion thereof. In some aspects, the IL-10 ligand has the amino acid sequence set forth in SEQ ID NO: 59 or is a variant thereof that exhibits at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity with the sequence set forth in SEQ ID NO: 59, or is a biologically active portion thereof, wherein the variant or biologically active portion thereof retains activity to bind to the receptor and/or a functional activity to modulate one or more signals to the receptor.

In some embodiments, the receptor-binding agent, e.g., stimulatory agent, (e.g. which can be an additional receptor-binding agent, e.g., additional stimulatory agent) can include a ligand of a stimulatory receptor or other receptor capable of inducing a signal in the cell, such as a Type I interferon, e.g., IFNα, IFNβ, IFNκ, IFNδ, IFNε, IFNτ, IFNω, and IFNζ (also known as limitin) or a biologically active portion thereof. In some aspects, the Type I interferon is IFN-α or IFN-β which has the amino acid sequence set forth in SEQ ID NO: 60 or 61 (IFN-α2 or IFN-β1, respectively) or is a variant thereof that exhibits at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity with the sequence set forth in SEQ ID NO: 60 or 61, or is a biologically active portion thereof, wherein the variant or biologically active portion thereof retains activity to bind to the receptor and/or a functional activity to modulate one or more signals to the receptor.

In some embodiments, the receptor-binding agent, e.g., stimulatory agent, (e.g. which can be an additional receptor-binding agent, e.g., additional stimulatory agent) can include a ligand of a stimulatory receptor or other receptor capable of inducing a signal in the cell, such as an IL-12 ligand or a biologically active portion thereof. In some aspects, the IL-12 ligand has the amino acid sequence set forth in SEQ ID NO: 62 and/or 63 (IL-12a or IL-12β, respectively) or is a variant thereof that exhibits at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity with the sequence set forth in SEQ ID NO: 62 and/or 63 (IL-12a or IL-12β, respectively), or is a biologically active portion thereof, wherein the variant or biologically active portion thereof retains activity to bind to the receptor and/or a functional activity to modulate one or more signals to the receptor.

In some embodiments, the receptor-binding agent, e.g., stimulatory agent, (e.g. which can be an additional receptor-binding agent, e.g., additional stimulatory agent) can include a ligand of a stimulatory receptor or other receptor capable of inducing a signal in the cell, such as an IL-17 ligand or a biologically active portion thereof. In some aspects, the IL-17 ligand has the amino acid sequence set forth in SEQ ID NO: 64 or is a variant thereof that exhibits at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity with the sequence set forth in SEQ ID NO: 64, or is a biologically active portion thereof, wherein the variant or biologically active portion thereof retains activity to bind to the receptor and/or a functional activity to modulate one or more signals to the receptor.

In some embodiments, the receptor-binding agent, e.g., a second or an additional receptor-binding agent, is or contains a ligand that specifically binds to a chemokine receptor.

In some embodiments, the molecule on the cell, e.g., T cell, may be CXCR3 and the receptor-binding agent, e.g., stimulatory agent, (e.g. which can be an additional receptor-binding agent, e.g., additional stimulatory agent) specifically binds CXCR3. In some aspects, the receptor-binding agent, e.g., stimulatory agent, (e.g. which can be an additional receptor-binding agent, e.g., additional stimulatory agent) that specifically binds CXCR3 may be selected from the group consisting of an anti-CXCR3 antibody, a divalent antibody fragment of an anti-CXCR3 antibody, a monovalent antibody fragment of an anti-CXCR3 antibody, and a proteinaceous CXCR3 binding molecule with antibody-like binding properties. The antibody or antigen-binding fragment can be derived from any known in the art. For example, in some aspects, the antibody or antigen-binding fragment can be any as described in WO2003024404.

In some embodiments, the molecule on the cell, e.g., T cell, may be CCR7 and the receptor-binding agent, e.g., stimulatory agent, (e.g. which can be an additional receptor-binding agent, e.g., additional stimulatory agent) specifically binds CCR7. In some aspects, the receptor-binding agent, e.g., stimulatory agent, (e.g. which can be an additional receptor-binding agent, e.g., additional stimulatory agent) that specifically binds CCR7 may be selected from the group consisting of an anti-CCR7 antibody, a divalent antibody fragment of an anti-CCR7 antibody, a monovalent antibody fragment of an anti-CCR7 antibody, and a proteinaceous CCR7 binding molecule with antibody-like binding properties. The antibody or antigen-binding fragment can be derived from any known in the art. For example, in some aspects, the antibody or antigen-binding fragment can be any as described in U.S. Pat. No. 6,153,441.

In some embodiments, the molecule on the cell, e.g., T cell, may be CXCR1 and the receptor-binding agent, e.g., stimulatory agent, (e.g. which can be an additional receptor-binding agent, e.g., additional stimulatory agent) specifically binds CXCR1. In some aspects, the receptor-binding agent, e.g., stimulatory agent, (e.g. which can be an additional receptor-binding agent, e.g., additional stimulatory agent) that specifically binds CXCR1 may be selected from the group consisting of an anti-CXCR1 antibody, a divalent antibody fragment of an anti-CXCR1 antibody, a monovalent antibody fragment of an anti-CXCR1 antibody, and a proteinaceous CXCR1 binding molecule with antibody-like binding properties. The antibody or antigen-binding fragment can be derived from any known in the art. For example, in some aspects, the antibody or antigen-binding fragment can be anti-CXCR1 antibody [42705.111] (Abcam; ab10400).

In some embodiments, the molecule on the cell, e.g., T cell, may be CXCR4 and the receptor-binding agent, e.g., stimulatory agent, (e.g. which can be an additional receptor-binding agent, e.g., additional stimulatory agent) specifically binds CXCR4. In some aspects, the receptor-binding agent, e.g., stimulatory agent, (e.g. which can be an additional receptor-binding agent, e.g., additional stimulatory agent) that specifically binds CXCR4 may be selected from the group consisting of an anti-CXCR4 antibody, a divalent antibody fragment of an anti-CXCR4 antibody, a monovalent antibody fragment of an anti-CXCR4 antibody, and a proteinaceous CXCR4 binding molecule with antibody-like binding properties. The antibody or antigen-binding fragment can be derived from any known in the art. For example, in some aspects, the antibody or antigen-binding fragment can be any as described in WO2003024404.

In some embodiments, the receptor-binding agent, e.g., stimulatory agent, (e.g. which can be an additional receptor-binding agent, e.g., additional stimulatory agent) can include a ligand of a stimulatory receptor or other receptor capable of inducing a signal in the cell, such as a CXCL9 ligand or a biologically active portion thereof. In some aspects, the CXCL9 ligand has the amino acid sequence set forth in SEQ ID NO: 65 or is a variant thereof that exhibits at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity with the sequence set forth in SEQ ID NO: 65, or is a biologically active portion thereof, wherein the variant or biologically active portion thereof retains activity to bind to the receptor and/or a functional activity to modulate one or more signals to the receptor.

In some embodiments, the receptor-binding agent, e.g., stimulatory agent, (e.g. which can be an additional receptor-binding agent, e.g., additional stimulatory agent) can include a ligand of a stimulatory receptor or other receptor capable of inducing a signal in the cell, such as a CXCL10 ligand or a biologically active portion thereof. In some aspects, the CXCL10 ligand has the amino acid sequence set forth in SEQ ID NO: 66 or is a variant thereof that exhibits at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity with the sequence set forth in SEQ ID NO: 66, or is a biologically active portion thereof, wherein the variant or biologically active portion thereof retains activity to bind to the receptor and/or a functional activity to modulate one or more signals to the receptor.

In some embodiments, the receptor-binding agent, e.g., stimulatory agent, (e.g. which can be an additional receptor-binding agent, e.g., additional stimulatory agent) can include a ligand of a stimulatory receptor or other receptor capable of inducing a signal in the cell, such as a CCL19 ligand or a biologically active portion thereof. In some aspects, the CCL19 ligand has the amino acid sequence set forth in SEQ ID NO: 67 or is a variant thereof that exhibits at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity with the sequence set forth in SEQ ID NO: 67, or is a biologically active portion thereof, wherein the variant or biologically active portion thereof retains activity to bind to the receptor and/or a functional activity to modulate one or more signals to the receptor.

In some embodiments, the receptor-binding agent, e.g., stimulatory agent, (e.g. which can be an additional receptor-binding agent, e.g., additional stimulatory agent) can include a ligand of a stimulatory receptor or other receptor capable of inducing a signal in the cell, such as a CCL21 ligand or a biologically active portion thereof. In some aspects, the CCL21 ligand has the amino acid sequence set forth in SEQ ID NO: 68 or is a variant thereof that exhibits at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity with the sequence set forth in SEQ ID NO: 68, or is a biologically active portion thereof, wherein the variant or biologically active portion thereof retains activity to bind to the receptor and/or a functional activity to modulate one or more signals to the receptor.

In some embodiments, the receptor-binding agent, e.g., stimulatory agent, (e.g. which can be an additional receptor-binding agent, e.g., additional stimulatory agent) can include a ligand of a stimulatory receptor or other receptor capable of inducing a signal in the cell, such as a CCL25 ligand or a biologically active portion thereof. In some aspects, the CCL25 ligand has the amino acid sequence set forth in SEQ ID NO: 69 or is a variant thereof that exhibits at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity with the sequence set forth in SEQ ID NO: 69, or is a biologically active portion thereof, wherein the variant or biologically active portion thereof retains activity to bind to the receptor and/or a functional activity to modulate one or more signals to the receptor.

In some cases, the receptor-binding agent, e.g., additional receptor-binding agent, is or contains an adhesion molecule or is a factor that induces cytokine production, chemokine production, expression of an adhesion molecule, and/or is involved in stimulating and/or modulating an accessory signal and/or an additional signal.

In some embodiments, the molecule on the cell, e.g., T cell, may be CD62L and the receptor-binding agent, e.g., stimulatory agent, (e.g. which can be an additional receptor-binding agent, e.g., additional stimulatory agent) specifically binds CD62L. In some aspects, the receptor-binding agent, e.g., stimulatory agent, (e.g. which can be an additional receptor-binding agent, e.g., additional stimulatory agent) that specifically binds CD62L may be selected from the group consisting of an anti-CD62L antibody, a divalent antibody fragment of an anti-CD62L antibody, a monovalent antibody fragment of an anti-CD62L antibody, and a proteinaceous CD62L binding molecule with antibody-like binding properties. The antibody or antigen-binding fragment can be derived from any known in the art, e.g., antibody DREG56 (e.g. ATCC HB300); See, e.g., Stemberger et al. 2012 PLoS One. 2012; 7(4):e35798.

In some embodiments, the molecule on the cell, e.g., T cell, may be RORγt and the receptor-binding agent, e.g., stimulatory agent, (e.g. which can be an additional receptor-binding agent, e.g., additional stimulatory agent) specifically binds RORγt. In some aspects, the receptor-binding agent, e.g., stimulatory agent, (e.g. which can be an additional receptor-binding agent, e.g., additional stimulatory agent) that specifically binds RORγt may be selected from the group consisting of an anti-RORγt antibody, a divalent antibody fragment of an anti-RORγt antibody, a monovalent antibody fragment of an anti-RORγt antibody, and a proteinaceous RORγt binding molecule with antibody-like binding properties. The antibody or antigen-binding fragment can be derived from any known in the art. For example, in some aspects, the antibody or antigen-binding fragment can be any as described in CA2572334.

In some embodiments, the molecule on the cell, e.g., T cell, may be RORα and the receptor-binding agent, e.g., stimulatory agent, (e.g. which can be an additional receptor-binding agent, e.g., additional stimulatory agent) specifically binds RORα. In some aspects, the receptor-binding agent, e.g., stimulatory agent, (e.g. which can be an additional receptor-binding agent, e.g., additional stimulatory agent) that specifically binds RORα may be selected from the group consisting of an anti-RORα antibody, a divalent antibody fragment of an anti-RORα antibody, a monovalent antibody fragment of an anti-RORα antibody, and a proteinaceous RORα binding molecule with antibody-like binding properties. The antibody or antigen-binding fragment can be derived from any known in the art. For example, the anti-RORα antibody is RORα Antibody H-65 (Santa Cruz Biotechnology cat. no. sc-28612).

2. Selection Agents

In some embodiments, the agent is a selection agent. In some embodiments, the selection agent binds to a molecule on the surface of a cell, such as a cell surface molecule. In some instances, the cell surface molecule is a selection marker. In some such cases, the selection agent is capable of specifically binding to a selection marker expressed by one or more of the cells. In some embodiments, a selection agent or agents that are reversibly bound to a reagent can be used to facilitate selection or isolation of cells.

In any of the embodiments provided herein, the receptor-binding agent, e.g., the first, second and/or additional receptor-binding agent, e.g., stimulatory agent, may be a binding agent that specifically binds a receptor, e.g., a receptor expressed on the surface of the cell. In some cases, the receptor-binding agent, e.g., the first, second and/or additional receptor-binding agent, e.g., stimulatory agent, that specifically binds receptor may be selected from the group consisting of an anti-receptor antibody, a divalent antibody fragment of an anti-receptor antibody, a monovalent antibody fragment of an anti-receptor antibody, and a proteinaceous receptor binding molecule with antibody-like binding properties. The divalent antibody fragment may be a F(ab')$_2$-fragment, or a divalent single-chain Fv fragment while the monovalent antibody fragment may be selected from the group consisting of an Fab fragment, an Fv fragment, and a single-chain Fv fragment (scFv). In some cases, a proteinaceous receptor binding molecule with antibody-like binding properties may be an aptamer, a mutein based on a polypeptide of the lipocalin family, a glubody, a protein based on the ankyrin scaffold, a protein based on the crystalline scaffold, an adnectin, or an avimer. In some cases, the receptor-binding agent, e.g., the first, second and/or additional receptor-binding agent, e.g., stimulatory agent, that specifically binds receptor is an antibody or an antigen-binding fragment thereof, e.g., an Fab fragment.

In some aspects, the cell surface molecule, e.g., selection marker, may be an antigen defining a desired cell population or subpopulation, for instance a population or subpopulation of blood cells, e. g. lymphocytes (e.g. T cells, T-helper cells, for example, CD4+ T-helper cells, B cells or natural killer cells), monocytes, or stem cells, e.g. CD34-positive peripheral stem cells or Nanog or Oct-4 expressing stem cells. In some embodiments, the selection marker can be a marker expressed on the surface of T cells or a subset of T cells, such as CD25, CD28, CD62L, CCR7, CD27, CD127, CD3, CD4, CD8, CD45RA, and/or CD45RO. Examples of T-cells include cells such as CMV-specific CD8+ T-lymphocytes, cytotoxic T-cells, memory T-cells and regulatory T-cells (Treg). An illustrative example of Treg includes CD4 CD25 CD45RA Treg cells and an illustrative example of memory T-cells includes CD62L CD8+ specific central memory T-cells. The cell surface molecule, e.g., selection marker, may also be a marker for a tumor cell.

In some embodiments, the selection marker may be CD4 and the selection agent specifically binds CD4. In some aspects, the selection agent that specifically binds CD4 may be selected from the group consisting of an anti-CD4 antibody, a divalent antibody fragment of an anti-CD4 antibody, a monovalent antibody fragment of an anti-CD4 antibody, and a proteinaceous CD4 binding molecule with antibody-like binding properties. In some embodiments, an anti-CD4 antibody, such as a divalent antibody fragment or a monovalent antibody fragment (e.g. CD4 Fab fragment) can be derived from antibody 13B8.2 or a functionally active mutant of 13B8.2 that retains specific binding for CD4. For example, exemplary mutants of antibody 13B8.2 or m13B8.2 are described in U.S. Pat. No. 7,482,000, U.S. Patent Appl. No. US2014/0295458 or International Patent Application Pub. No. WO2013/124474; and Bes, C, et al. J Biol Chem 278, 14265-14273 (2003). The mutant Fab fragment termed "m13B8.2" carries the variable domain of the CD4 binding murine antibody 13B8.2 and a constant domain containing constant human CH1 domain of type gamma for the heavy chain and the constant human light chain domain of type kappa, as described in U.S. Pat. No. 7,482,000. In some embodiments, the anti-CD4 antibody, e.g. a mutant of antibody 13B8.2, contains the amino acid replacement H91A in the variable light chain, the amino acid replacement Y92A in the variable light chain, the amino acid replacement H35A in the variable heavy chain and/or the amino acid replacement R53A in the variable heavy chain, each by Kabat numbering. In some aspects, compared to variable domains of the 13B8.2 Fab fragment in m13B8.2 the His residue at position 91 of the light chain (position 93 in SEQ ID NO: 30) is mutated to Ala and the Arg residue at position 53 of the heavy chain (position 55 in SEQ ID NO: 29) is mutated to Ala. In some embodiments, the reagent that is reversibly bound to anti-CD4 or a fragment thereof is commercially available or derived from a reagent that is commercially available (e.g. catalog No. 6-8000-206 or 6-8000-205 or 6-8002-100; IBA GmbH, Gottingen, Germany).

In some embodiments, the selection marker may be CD8 and the selection agent specifically binds CD8. In some aspects, the selection agent that specifically binds CD8 may be selected from the group consisting of an anti-CD8 antibody, a divalent antibody fragment of an anti-CD8 antibody, a monovalent antibody fragment of an anti-CD8 antibody, and a proteinaceous CD8 binding molecule with antibody-like binding properties. In some embodiments, an anti-CD8 antibody, such as a divalent antibody fragment or a monovalent antibody fragment (e.g. CD8 Fab fragment) can be derived from antibody OKT8 (e.g. ATCC CRL-8014) or a functionally active mutant thereof that retains specific binding for CD8. In some embodiments, the reagent that is reversibly bound to anti-CD8 or a fragment thereof is commercially available or derived from a reagent that is commercially available (e.g. catalog No. 6-8003 or 6-8000-201; IBA GmbH, Gottingen, Germany).

In some embodiments, the selection marker may be CD3 and the selection agent specifically binds CD3. In some aspects, the selection agent that specifically binds CD3 may be selected from the group consisting of an anti-CD3 antibody, a divalent antibody fragment of an anti-CD3 antibody, a monovalent antibody fragment of an anti-CD3 antibody, and a proteinaceous CD3 binding molecule with antibody-like binding properties. In some embodiments, an anti-CD3 antibody, such as a divalent antibody fragment or a monovalent antibody fragment (e.g. CD3 Fab fragment) can be derived from antibody OKT3 (e.g. ATCC CRL-8001; See, e.g., Stemberger et al. PLoS One. 2012; 7(4): e35798) or a functionally active mutant thereof that retains specific binding for CD3. In some embodiments, the reagent that is reversibly bound to anti-CD3 or a fragment thereof is commercially available or derived from a reagent that is commercially available (e.g. catalog No. 6-8000-201, 6-8001-100; IBA GmbH, Gottingen, Germany).

In some embodiments, the selection marker may be CD25 and the selection agent specifically binds CD25. In some aspects, the selection agent that specifically binds CD25 may be selected from the group consisting of an anti-CD25 antibody, a divalent antibody fragment of an anti-CD25 antibody, a monovalent antibody fragment of an anti-CD25 antibody, and a proteinaceous CD25 binding molecule with antibody-like binding properties. In some embodiments, an anti-CD25 antibody, such as a divalent antibody fragment or a monovalent antibody fragment (e.g. CD25 Fab fragment) can be derived from antibody FRT5 (See, e.g., Stemberger et al. 2012. PLoS One. 2012; 7(4):e35798) or a functionally active mutant thereof that retains specific binding for CD25. In some embodiments, the reagent that is reversibly bound to anti-CD4 or a fragment thereof is commercially available or derived from a reagent that is commercially available (e.g. catalog No. 6-8000-205 or 6-8000-207 or 6-8004-050; IBA GmbH, Gottingen, Germany).

In some embodiments, the selection marker may be CD62L and the selection agent specifically binds CD62L. In some aspects, the selection agent that specifically binds CD62L may be selected from the group consisting of an anti-CD62L antibody, a divalent antibody fragment of an anti-CD62L antibody, a monovalent antibody fragment of an anti-CD62L antibody, and a proteinaceous CD62L binding molecule with antibody-like binding properties. In some embodiments, an anti-CD62L antibody, such as a divalent antibody fragment or a monovalent antibody fragment (e.g. CD62L Fab fragment) can be derived from antibody DREG56 (e.g. ATCC HB300; See, e.g., Stemberger et al. 2012, PLoS One. 2012; 7(4):e35798) or a functionally active mutant thereof that retains specific binding for CD62L. In some embodiments, the reagent that is reversibly bound to anti-CD62L or a fragment thereof is commercially available or derived from a reagent that is commercially available (e.g. catalog No. 6-8000-204 or 6-8005-050; IBA GmbH, Gottingen, Germany).

In some embodiments, the selection marker may be CD45RA and the selection agent specifically binds CD45RA. In some aspects, the selection agent that specifically binds CD45RA may be selected from the group consisting of an anti-CD45RA antibody, a divalent antibody fragment of an anti-CD45RA antibody, a monovalent antibody fragment of an anti-CD45RA antibody, and a proteinaceous CD45RA binding molecule with antibody-like binding properties. In some embodiments, an anti-CD45RA antibody, such as a divalent antibody fragment or a monovalent antibody fragment (e.g. CD45RA Fab fragment) can be derived from antibody MEM56 (e.g. Millipore 05-1413;

See, e.g., Stemberger et al. 2012, PLoS One. 2012; 7(4): e35798) or a functionally active mutant thereof that retains specific binding for CD45RA. In some embodiments, the reagent that is reversibly bound to anti-CD45RA or a fragment thereof is commercially available or derived from a reagent that is commercially available (e.g. catalog No. 6-8000-208 or 6-8007-050; IBA GmbH, Gottingen, Germany).

In some embodiments, the selection marker may be CD45RO and the selection agent specifically binds CD45RO. In some aspects, the selection agent that specifically binds CD45RO may be selected from the group consisting of an anti-CD45RO antibody, a divalent antibody fragment of an anti-CD45RO antibody, a monovalent antibody fragment of an anti-CD45RO antibody, and a proteinaceous CD45RO binding molecule with antibody-like binding properties. In some embodiments, the reagent that is reversibly bound to anti-CD45RO or a fragment thereof is commercially available or derived from a reagent that is commercially available (e.g. catalog No. 6-8000-209 or 6-8012-020; IBA GmbH, Gottingen, Germany).

In some embodiments, the selection marker may be CD154 and the selection agent specifically binds CD154. In some aspects, the selection agent that specifically binds CD154 may be selected from the group consisting of an anti-CD154 antibody, a divalent antibody fragment of an anti-CD154 antibody, a monovalent antibody fragment of an anti-CD154 antibody, and a proteinaceous CD154 binding molecule with antibody-like binding properties. In some embodiments, the reagent that is reversibly bound to anti-CD154 or a fragment thereof is commercially available or derived from a reagent that is commercially available (e.g. catalog No. 6-8000-202 or 6-5510-050; IBA GmbH, Gottingen, Germany).

In some embodiments, the selection marker may be CD16 and the selection agent specifically binds CD16. In some aspects, the selection agent that specifically binds CD16 may be selected from the group consisting of an anti-CD16 antibody, a divalent antibody fragment of an anti-CD16 antibody, a monovalent antibody fragment of an anti-CD16 antibody, and a proteinaceous CD16 binding molecule with antibody-like binding properties. In some embodiments, the reagent that is reversibly bound to anti-CD16 or a fragment thereof is commercially available or derived from a reagent that is commercially available. In some aspects, the CD16 binding molecule comprises the heavy chain and/or light chain sequences set forth in SEQ ID NO: 36 and/or 37, respectively.

III. Methods of Culturing Cells

Provided herein are methods of culturing cells which include incubating a composition containing target cells (e.g. T cells) in the presence of an agent (e.g. first, second and/or additional), receptor-binding agents, e.g. stimulatory agents, or selection agents) that is capable of binding to a molecule on the surface of targets cells (e.g. T cells) in the composition and that is reversibly bound to a reagent containing a plurality of binding sites capable of reversibly binding to the agent. In some embodiments, the incubation is performed under conditions in which the agent binds, such as specifically binds, to the molecule on the cell. In some cases, for certain receptor-binding agents (e.g. stimulatory agents), such binding can induce or modulate a signal in target cells (e.g. T cells) in the compositions, such as a primary signal or accessory signal as described. In some embodiments, binding of the agent to the molecule results in one or more of the stimulation, activation, expansion (proliferation) and/or differentiation of target cells in the composition.

In some embodiments, the provided method can be used for selectively inducing ex vivo expansion of a population of cells such as B cells, T cells or natural killer cells. In some cases, the stimulation can be in the absence of exogenous growth factors, such as lymphokines, and accessory cells. In some embodiments, the proliferation of these cells such as B cells or T cells can be induced without the need for antigen, thus providing an expanded cell population such as a T cell population which is polyclonal with respect to antigen reactivity. The methods disclosed herein may provide for sustained proliferation of a selected population of T cells such as CD4+ or CD8+ T cells over an extended period of time to yield a multi-fold increase in the number of these cells relative to the original T cell population. In general, in case of a (clonal) expansion of a lymphocyte population as described herein, all progeny may share the same antigen specificity as the cell population that was selected for expansion.

In some embodiments, the methods relate to expanding a population of antigen specific T cells. In some embodiments, to produce a population of antigen specific T cells, T cells are contacted with an antigen in a form suitable to trigger a primary activation signal in the T cell, i.e., the antigen is presented to the T cell such that a signal is triggered in the T cell through the TCR/CD3 complex. For example, the antigen can be presented to the T cell by an antigen presenting cell in conjunction with an MHC molecule. An antigen presenting cell, such as a B cell, macrophage, monocyte, dendritic cell, Langerhans cell, or other cell which can present antigen to a T cell, can be incubated with the T cell in the presence of the antigen (e.g., a soluble antigen) such that the antigen presenting cell presents the antigen to the T cell. Alternatively, a cell expressing an antigen of interest can be incubated with the T cell. For example, a tumor cell expressing tumor-associated antigens can be incubated with a T cell together to induce a tumor-specific response. Similarly, a cell infected with a pathogen, e.g., a virus, which presents antigens of the pathogen can be incubated with a T cell. Following antigen specific activation of a population of T cells, the cells can be expanded in accordance with the provided methods. For example, after antigen specificity has been established, T cells can be expanded by culture with an anti-CD3 antibody (used as first agent) and an anti-CD28 antibody (used as second agent) according to the methods described herein. In another embodiment, the first agent can be an MHC I: peptide complex, which binds to an antigen specific T cell population. In such an embodiment, any antigen specific peptide that is known and that can be complexed with the respective MHC I molecule can be used. Alternatively, it is also possible to use as first agent the natural ligand of a receptor that triggers of cell expansion. For example, the extracellular domain of CD19 can be used to cause the activation of intracellular signaling cascades of cells transduced to express chimeric CD19 binding antigen receptor (CAR). Exemplary aspects of the above are shown in Examples.

In some embodiments, provided is an in vitro-method of culturing a population of cells, comprising contacting a sample comprising a composition comprising a plurality of cells with a multimerization reagent. The multimerization reagent has reversibly immobilized thereon (bound thereto) an agent (first, second and/or additional, receptor-binding, e.g. stimulatory agent, or selection agent), which can be used for the selection, stimulation, expansion and/or differentiation of cells. In some embodiments, an agent, e.g. first agent, that provides a primary activation signal to the cells, wherein the multimerization reagent comprising at least one binding site Z1 for the reversible binding of the first agent. The first agent comprises at least one binding partner C1, wherein the binding partner C1 is able of reversibly binding to the binding site Z1 of the multimerization reagent, wherein the first agent is bound to the multimerization reagent via the reversible bond formed between the binding partner C1 and the binding site Z1. The first agent binds to a receptor molecule on the surface of the cells, thereby providing a primary activation signal to the cells and thereby activating the cells.

In some embodiments, the multimerization reagent is immobilized on a support, such as a solid surface. In some embodiments, the multimerization reagent is not bound to a support, such as not bound to a solid surface or stationary phase.

For example, in some embodiments, provided is an in vitro-method of expanding a population of cells, comprising contacting a sample comprising a population of cells with a multimerization reagent, wherein the multimerization reagent is not immobilized on a solid support, i.e. is in a soluble form, and has bound thereto an agent (first or second, receptor-binding, e.g. stimulatory agent, or selection agent), which can be used for the selection, stimulation, expansion and/or differentiation of cells. In some embodiments, an agent, e.g. first agent, that provides a primary activation signal to the cells is reversibly bound to the multimerization reagent. The multimerization reagent comprises at least one binding site, e.g. Z1 for the binding of the first agent, wherein the first agent comprises at least one binding partner, e.g. C1, wherein the binding partner C1 is able of binding to the binding site Z1 of the multimerization reagent. In some embodiments, the first agent is bound to the multimerization reagent via the bond formed between the binding partner C1 and the binding site Z1, and the first agent binds to a receptor molecule on the surface of the cells, thereby providing a primary activation signal to the cells and thereby activating the cells. In some embodiments, when a soluble multimerization agent is used, the bond between the binding part C, e.g. C1 and the binding site Z, e.g. Z1 does not need to be reversible.

In some embodiments, the provided methods also include the use of a multimerization reagent having bound thereto one or more additional agents, e.g. a second agent or a third agent, such as targeting an accessory or co-stimulatory molecules or other signaling molecule on the cell, that stimulates one or more additional signal, e.g. costimulatory or accessory signal. In some cases, the multimerization agent is immobilized on a support, e.g. a solid support or stationary phase. In some embodiments, the multimerization agent is not immobilized on a support, i.e. is in soluble form.

In some embodiments, the one or more additional agent, e.g. second agent, comprises a binding partner C (e.g. C1, C2, C3, etc.) that is able of being reversibly bound to a binding site Z (e.g. Z1, Z2, Z3, etc.). In some embodiment, the one or more additional agent, e.g. second agent, comprises a binding partner, e.g. C2, wherein the binding partner, e.g. C2 is able of being reversibly bound to a binding site, e.g. Z2 of the multimerization reagent, wherein the second agent is bound to the multimerization reagent via the reversible bond formed between the binding partner C2 and the binding site Z2. In some embodiments, the bond formed between the binding partner C1 and the binding site Z1 may be reversible and the bond formed between the binding partner C2 and the binding site Z2 may be revers-ible. In this case, the dissociation constant ($K_D$) for the reversible binding between said binding site Z1 and said binding partner C1 and/or for the reversible binding between said binding site Z2 and said binding partner C2 may be in the range of $10^{-2}$ M to $10^{-13}$ M. In some aspects, such as when the multimerization reagent is not bound to a support (e.g. not bound to a solid support or stationary phase), the bond formed between the binding partner C1 and the binding site Z1 may be irreversible and/or also the bond formed between the binding partner C2 and the binding site Z2 may be irreversible In some cases, the one or more additional agent, e.g. second agent, binds to the accessory molecule on the surface on the surface of the cells, thereby stimulating the activated cells. In this embodiment, the first agent may stimulate a TCR/CD3 complex-associated signal in the T cells and may be a binding agent that specifically binds CD3. In this embodiment the accessory molecule on the T cell may be CD28 and the second agent that binds the accessory molecule is a binding reagent that specifically binds CD28. Alternatively, in some embodiments, it is found that targeting other accessory molecules also can be employed, which can, in some cases, alter, such as improve, one or more features, properties or characteristics of the cultured cells. In some embodiments, the accessory molecule can be one or more of CD90, CD95, CD137, CD154, ICOS, LAT, CD27, OX40 or HVEM (e.g. an anti-CD90 antibody, an anti-CD95 antibody, an anti-CD137 antibody, and an anti-CD154 antibody, anti-ICOS antibody, anti-LAT antibody, anti-CD27 antibody, anti-OX40 antibody or anti-HVEM antibody, respectively. Exemplary agents, such as receptor-binding agents (e.g. stimulatory agents), are described below.

In some embodiments, the one or more additional agent, e.g. third agent, binds to an additional molecule that modulates survival, proliferation and/or one or more other properties of the cells. Such targeted molecules include, but are not limited to, cytokine receptors, chemokine receptors or adhesion molecules. In some aspects, stimulation through such additional molecules can result in one or other improved features of the stimulated or cultured cells, including, for example, increased persistence, survival and/or less exhausted phenotype or activity. Exemplary agents, such as receptor-binding agents (e.g. stimulatory agents), are described below.

In some embodiments, the provided method may be carried out at any temperature at which the viability of the cell population is at least essentially uncompromised. In some embodiments, the condition at which incubation or culture is carried out include any conditions that are at least essentially not harmful, not detrimental or at least essentially not compromising viability, for example, under which the percentage of the population of cells that are to be expanded with full viability, is at least 70%, including at least 75%, at least 80%, at least 85%, at least 90%, at least 92%, at least 95%, at least 97%, at least 98%, at least 99% or at least 99.5%. In some embodiments, the provided method is carried out at a temperature of about 20° C. or higher. Depending on the cell population to be expanded a suitable temperature range may for instance be from about 20° C. to about 45° C., including from about 25° C. to about 40° C., or from about 32° C. to 37° C. In some embodiments a method according to the invention is carried out at a constant temperature value, or at a selected temperature value±about 5° C., ±about 4° C., ±about 3° C., ±about 2° C., ±about 1° C. or ±about 0.5° C. The person skilled in the art is able to empirically determine a suitable temperature, taking into account the nature of the cells and the expansion conditions. Typically human cells are expanded at a temperature such as 37° C.

In accordance with the disclosure herein, also provided are multimerized agents, or composition comprising multimerization reagents reversibly bound to one or more receptor-binding agents, that care capable of stimulating, e.g. expanding or modulating a signal, in a population of cells. Such a multimerized agent that is capable of stimulating, e.g. expanding or modulating a signal, in a population of cells is a multimerization reagent that is not bound to a support (e.g. in soluble form) and comprises at least one binding site Z, e.g. Z1, for the reversible binding of a first agent that provides a primary activation signal to the cells, wherein the multimerization reagent has reversibly bound thereto said first agent that provides a primary activation signal to the cells; wherein the first agent comprises at least one binding partner C, e.g. C1, wherein the binding partner C1 is able of reversibly binding to the at least one binding site Z1 of the multimerization reagent, wherein the first agent is bound to the multimerization reagent via the reversible bond formed between the binding partner C1 and the binding site Z1. It should be noted here that such a multimerization agent can have immobilized thereon any of the first agent that are described herein.

In some embodiments, a multimerized agent provided herein may further comprise at least one binding site, e.g. Z2 for the reversible binding of a second agent that stimulates an accessory molecule on the surface of the cells, wherein the multimerization reagent has reversibly bound thereto the second agent that stimulates an accessory molecule on the surface of the cells, wherein the second agent comprises a binding partner, e.g. C2, wherein the binding partner C2 is able of binding to the at least one binding site Z2 of the multimerization reagent. In this embodiment the second agent is bound to the multimerization reagent via the bond formed between the binding partner C2 and the binding site Z2. In some embodiments, the second agent is any that can bind to CD90, CD95, CD137, CD154, ICOS, LAT, CD27, OX40 or HVEM (e.g. an anti-CD90 antibody, an anti-CD95 antibody, an anti-CD137 antibody, and an anti-CD154 antibody, anti-ICOS antibody, anti-LAT antibody, anti-CD27 antibody, anti-OX40 antibody or anti-HVEM antibody, respectively).

In some embodiments, a multimerized agent provided herein may further comprise at least one binding site, e.g. Z that is the same or different from Z1 or Z2, for the reversible binding of an additional agent that binds to an additional molecule that modulates survival, proliferation and/or one or more other properties of the cells, wherein the multimerization reagent has reversibly bound thereto the additional agent that stimulates an accessory molecule on the surface of the cells, wherein the additional agent comprises a binding partner, e.g. C that is the same or different from C1 or C2, wherein the binding partner C is able of binding to the at least one binding site Z of the multimerization reagent.

In some embodiments, the culturing of the composition containing target cells (e.g. T cells) with the multimerized agent (e.g. anti-CD3/anti-CD28 mutein streptavidin or oligomer thereof) can be carried out in a bioreactor such as a hollow-fiber bioreactor (e.g. hollow fiber bioreactor of the Quantum® cell expansion system) or a plastic bag bioreactor (e.g. Cellbag® used in Xuri Cell Expansion System W25 from GE Healthcare).

In some embodiments, the method further includes contacting the cultured target cells (e.g. T cells) in the reaction mixture (e.g. containing the target cells, e.g. T cells, bound to the multimerization reagent via, for example, the first agent and the second agent) with (i) a competition reagent (e.g. free first binding partner C, e.g. C1) or an analog thereof capable of disrupting the bond between the first binding partner, e.g. C1 and the binding site, e.g. Z1 and/or (such as if necessary) (ii) a second competition reagent, e.g. free second binding partner, e.g. C2, or an analog thereof, capable of disrupting the bond between the second binding partner C2 and the binding site Z2. By so doing the reversible bond between said binding partner C1 of the first agent and said binding sites Z1 as well as the reversible bond between said binding partner C2 of the second agent and said binding site Z2 of said multimerization reagent is disrupted, thereby releasing in an eluate the T cells bound to the multimerization reagent via the first agent and the second agent and disrupting the stimulation and/or expansion of the T cells.

In some embodiments, the competition reagent (e.g. the first and/or second competition reagent) is added within 5 days after initiation of the incubation, such as within 4 days, 3 days, 2 days or 1 day after initiation of the incubation. Hence, by controlling the time at which the stimulation is disrupted, one or more particular features of the cultured T cells eluted from the multimerized agent can be altered as described herein.

In some embodiments, the method further includes separating or removing one or more of the components remaining after the reversible dissociation of components. In some embodiments, any unbound or residual biotin in the cultured target cells (e.g. T cells) can be separated or removed. In some embodiments, the multimerization reagent is removed or separated from the cells in the cultured target cell composition. For example, in some embodiments, the separation/removal might be carried out using a second stationary phase. For this purpose, a mixture comprising the target cells (e.g. T cells) and the soluble multimerization reagent are exposed, before or after being applied onto the first stationary phase described above, to chromatography on a suitable second stationary phase. This secondary stationary phase may be a gel filtration matrix and/or affinity chromatography matrix, wherein the gel filtration and/or affinity chromatography matrix comprises an affinity reagent. The affinity reagent comprised on the chromatography resin include a binding partner D that (specifically) binds to the binding site Z1 and/or binding site Z2, if present, of the multimerization reagent, thereby immobilizing the multimerization reagent on the stationary phase. If a streptavidin based multimerization reagent is used and both first and second agents have a streptavidin binding peptide as binding partner C1 or C2, the binding partner D that is comprised in the affinity reagent of this second stationary phase can be biotin. The soluble oligomer of streptavidin or of a streptavidin mutein that is used as multimerization reagent then binds to the biotin that is usually covalently coupled to a chromatography matrix such as biotin-Sepharose™ that is commercially available. In some such embodiments, the cultured cells (e.g. cultured T cells) can be recovered away from the multimerization reagent.

A. Cells

In some embodiments, the sample of the cell population can be from any suitable source, typically all sample of a body tissue or a body fluid such as blood. In the latter case, the sample might for example, be a population of peripheral blood mononucleated cells (PBMC) that can be obtained by standard isolation methods such a Ficoll gradient of blood cells. The cell population to be stimulated or expanded can however also be in purified form and might have been isolated using an reversible cell staining/isolation technology as described patent in U.S. Pat. Nos. 7,776,562, 8,298,782, International Patent App. Pub. No. WO02/054065 or International Patent App. Pub. No. WO2013/011011. Alternatively, the population of cells can also be obtained by cell sorting via negative magnetic immunoadherence as described in U.S. Pat. No. 6,352,694 B1 or European Patent EP 0 700 430 B1. If an isolation method described here is used in basic research, the sample might be cells of in vitro cell culture experiments. The sample will typically have been prepared in form of a fluid, such as a solution or dispersion.

Cells contained in the composition containing target cells generally are eukaryotic cells, such as mammalian cells, and typically are human cells. In some embodiments, the cells are derived from the blood, bone marrow, lymph, or lymphoid organs, or are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). The cells typically are primary cells, such as those isolated directly from a subject and/or isolated from a subject and frozen.

In some embodiments, the reversibly-bound agents, such as multimerized agents, provided herein are capable of expanding a lymphocyte population or a subpopulation contained in the lymphocyte population. The lymphocyte population to be expanded may any suitable population, for example, a B cell population, a T cell population, or a natural killer cell population. The T-cell population may be an antigen-specific T cell population, a T helper cell population, a cytotoxic T cell, a memory T cell, a regulatory T cell, or a natural killer T cell population. Accordingly, in such embodiments of the multimerized agent the first agent is able to stimulate a TCR/CD3 complex-associated signal in the T cells. The first agent present in the multimerized agent may thus be binding reagent that specifically binds CD3, while the second agent that binds the accessory molecule, such as may be a binding agent that specifically binds CD28, CD137 CD90, CD95, CD137, CD154, ICOS, LAT, CD27, OX40 or HVEM.

In some embodiments, the cells include one or more subsets of T cells or other cell types, such as whole T cell populations, CD3+, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. Among the methods include off-the-shelf methods. In some aspects, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, as described herein, and re-introducing them into the same patient, before or after cryopreservation.

In some embodiments, the T cells, such as CD3+, CD4+ or CD8+ cells, are not further enriched for another marker. In some embodiments, the T cells are not further enriched for CD62L+ cells.

Among the sub-types and subpopulations of T cells and/or of CD4+ and/or of CD8+ T cells are naïve T ($T_N$) cells, effector T cells ($T_{EFF}$), memory T cells and sub-types thereof, such as stem cell memory T ($T_{SCM}$), central memory T ($T_{CM}$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, the cells are natural killer (NK) cells. In some embodiments, the cells are monocytes or granulocytes, e.g., myeloid cells, macrophages, neutrophils, dendritic cells, mast cells, eosinophils, and/or basophils.

Preparation of Cells

In some embodiments, preparation of the cells includes one or more culture and/or preparation steps. The cells may be isolated from a sample, such as a biological sample, e.g., one obtained from or derived from a subject. In some embodiments, the subject from which the cells are isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered.

Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, or pig.

In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contain cells other than red blood cells and platelets.

In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished a semi-automated "flow-through" centrifuge (for example, the Cobe 2991 cell processor, Baxter) according to the manufacturer's instructions. In some aspects, a washing step is accomplished by tangential flow filtration (TFF) according to the manufacturer's instructions. In some embodiments, the cells are resuspended in a variety of biocompatible buffers after washing, such as, for example, $Ca^{++}/Mg^{++}$ free PBS. In certain embodiments, components of a blood cell sample are removed and the cells directly resuspended in culture media.

In some embodiments, the methods include density-based cell separation methods, such as the preparation of white blood cells from peripheral blood by lysing the red blood cells and centrifugation through a Percoll or Ficoll gradient.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. Separation methods may include any of those disclosed herein, including methods using reversible reagent systems, e.g., agents (such as receptor binding agents or selection agents) and reagents as described herein.

In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population.

The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

For example, in some aspects, specific subpopulations of T cells, such as cells positive or expressing high levels of one or more surface markers, e.g., $CD28^+$, $CD62L^+$, $CCR7^+$, $CD27^+$, $CD127^+$, $CD4^+$, $CD8^+$, $CD45RA^+$, and/or $CD45RO^+$ T cells, are isolated by positive or negative selection techniques.

For example, $CD3^+$, $CD28^+$ T cells can be positively selected using CD3/CD28 conjugated magnetic beads (e.g., DYNABEADS M-450 CD3/CD28 T Cell Expander).

In some embodiments, isolation is carried out by enrichment for a particular cell population by positive selection, or depletion of a particular cell population, by negative selection. In some embodiments, positive or negative selection is accomplished by incubating cells with one or more antibodies or other binding agent that specifically bind to one or more surface markers expressed or expressed ($marker^+$) at a relatively higher level ($marker^{high}$) on the positively or negatively selected cells, respectively.

In some embodiments, T cells are separated from a PBMC sample by negative selection of markers expressed on non-T cells, such as B cells, monocytes, or other white blood cells, such as CD14. In some aspects, a $CD4^+$ or $CD8^+$ selection step is used to separate $CD4^+$ helper and $CD8^+$ cytotoxic T cells. Such $CD4^+$ and $CD8^+$ populations can be further sorted into sub-populations by positive or negative selection for markers expressed or expressed to a relatively higher degree on one or more naive, memory, and/or effector T cell subpopulations.

In some embodiments, $CD8^+$ cells are further enriched for or depleted of naive, central memory, effector memory, and/or central memory stem cells, such as by positive or negative selection based on surface antigens associated with the respective subpopulation. In some embodiments, enrichment for central memory T ($T_{CM}$) cells is carried out to increase efficacy, such as to improve long-term survival, expansion, and/or engraftment following administration, which in some aspects is particularly robust in such subpopulations. See Terakura et al. (2012) Blood. 1:72-82; Wang et al. (2012) *J Immunother.* 35(9):689-701. In some embodiments, combining $T_{CM}$-enriched $CD8^+$ T cells and $CD4^+$ T cells further enhances efficacy.

In embodiments, memory T cells are present in both $CD62L^+$ and $CD62L^-$ subsets of $CD8^+$ peripheral blood lymphocytes. PBMC can be enriched for or depleted of $CD62L^-CD8^+$ and/or $CD62L^+CD8^+$ fractions, such as using anti-CD8 and anti-CD62L antibodies.

In some embodiments, the enrichment for central memory T ($T_{CM}$) cells is based on positive or high surface expression of CD45RO, CD62L, CCR7, CD28, CD3, and/or CD 127; in some aspects, it is based on negative selection for cells expressing or highly expressing CD45RA and/or granzyme B. In some aspects, isolation of a $CD8^+$ population enriched for $T_{CM}$ cells is carried out by depletion of cells expressing CD4, CD14, CD45RA, and positive selection or enrichment for cells expressing CD62L. In one aspect, enrichment for central memory T ($T_{CM}$) cells is carried out starting with a negative fraction of cells selected based on CD4 expression, which is subjected to a negative selection based on expression of CD14 and CD45RA, and a positive selection based on CD62L. Such selections in some aspects are carried out simultaneously and in other aspects are carried out sequentially, in either order. In some aspects, the same CD4 expression-based selection step used in preparing the CD8+ cell population or subpopulation, also is used to generate the CD4+ cell population or sub-population, such that both the positive and negative fractions from the CD4-based separation are retained and used in subsequent steps of the methods, optionally following one or more further positive or negative selection steps.

CD4+ T helper cells are sorted into naïve, central memory, and effector cells by identifying cell populations that have cell surface antigens. CD4+ lymphocytes can be obtained by standard methods. In some embodiments, naive CD4+ T lymphocytes are CD45RO−, CD45RA+, CD62L+, CD4+ T cells. In some embodiments, central memory CD4+ cells are CD62L+ and CD45RO+. In some embodiments, effector CD4+ cells are CD62L− and CD45RO−.

In one example, to enrich for CD4+ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection. For example, in some embodiments, the cells and cell populations are separated or isolated using immunomagnetic (or affinitymagnetic) separation techniques (reviewed in Methods in Molecular Medicine, vol. 58: Metastasis Research Protocols, Vol. 2: Cell Behavior In vitro and In vivo, p 17-25 Edited by: S. A. Brooks and U. Schumacher© Humana Press Inc., Totowa, N.J.).

In some aspects, the sample or composition of cells to be separated is incubated with small, magnetizable or magnetically responsive material, such as magnetically responsive particles or microparticles, such as paramagnetic beads (e.g., such as Dynalbeads or MACS beads). The magnetically responsive material, e.g., particle, generally is directly or indirectly attached to a binding partner, e.g., an antibody, that specifically binds to a molecule, e.g., surface marker, present on the cell, cells, or population of cells that it is desired to separate, e.g., that it is desired to negatively or positively select.

In some embodiments, the magnetic particle or bead contains a magnetically responsive material bound to a specific binding member, such as an antibody or other binding partner. There are many well-known magnetically responsive materials used in magnetic separation methods. Suitable magnetic particles include those described in Molday, U.S. Pat. No. 4,452,773, and in European Patent Specification EP 452342 B, which are hereby incorporated by reference. Colloidal sized particles, such as those described in Owen U.S. Pat. No. 4,795,698, and Liberti et al., U.S. Pat. No. 5,200,084 are other examples.

The incubation generally is carried out under conditions whereby the antibodies or binding partners, or molecules, such as secondary antibodies or other reagents, which specifically bind to such antibodies or binding partners, which are attached to the magnetic particle or bead, specifically bind to cell surface molecules if present on cells within the sample.

In some aspects, the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some aspects, a combination of positive and negative selection is performed during the same selection step, where the positive and negative fractions are retained and further processed or subject to further separation steps.

In certain embodiments, the magnetically responsive particles are coated in primary antibodies or other binding partners, secondary antibodies, lectins, enzymes, or streptavidin. In certain embodiments, the magnetic particles are attached to cells via a coating of primary antibodies specific for one or more markers. In certain embodiments, the cells, rather than the beads, are labeled with a primary antibody or binding partner, and then cell-type specific secondary antibody- or other binding partner (e.g., streptavidin)-coated magnetic particles, are added. In certain embodiments, streptavidin-coated magnetic particles are used in conjunction with biotinylated primary or secondary antibodies.

In some embodiments, the magnetically responsive particles are left attached to the cells that are to be subsequently incubated, cultured and/or engineered; in some aspects, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, magnetizable particles or antibodies conjugated to cleavable linkers, etc. In some embodiments, the magnetizable particles are biodegradable.

In some embodiments, the affinity-based selection is via magnetic-activated cell sorting (MACS) (Miltenyi Biotech, Auburn, Calif.). Magnetic Activated Cell Sorting (MACS) systems are capable of high-purity selection of cells having magnetized particles attached thereto. In certain embodiments, MACS operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain embodiments, the non-target cells are labelled and depleted from the heterogeneous population of cells.

In certain embodiments, the isolation or separation is carried out using a system, device, or apparatus that carries out one or more of the isolation, cell preparation, separation, processing, incubation, culture, and/or formulation steps of the methods. In some aspects, the system is used to carry out each of these steps in a closed or sterile environment, for example, to minimize error, user handling and/or contamination. In one example, the system is a system as described in International Patent App. Pub. No. WO2009/072003, or US 20110003380 A1.

In some embodiments, the system or apparatus carries out one or more, e.g., all, of the isolation, processing, engineering, and formulation steps in an integrated or self-contained system, and/or in an automated or programmable fashion. In some aspects, the system or apparatus includes a computer and/or computer program in communication with the system or apparatus, which allows a user to program, control, assess the outcome of, and/or adjust various aspects of the processing, isolation, engineering, and formulation steps.

In some aspects, the separation and/or other steps is carried out using CliniMACS system (Miltenyi Biotec), for example, for automated separation of cells on a clinical-scale level in a closed and sterile system. Components can include an integrated microcomputer, magnetic separation unit, peristaltic pump, and various pinch valves. The integrated computer in some aspects controls all components of the instrument and directs the system to perform repeated procedures in a standardized sequence. The magnetic separation unit in some aspects includes a movable permanent magnet and a holder for the selection column. The peristaltic pump controls the flow rate throughout the tubing set and, together with the pinch valves, ensures the controlled flow of buffer through the system and continual suspension of cells.

The CliniMACS system in some aspects uses antibody-coupled magnetizable particles that are supplied in a sterile, non-pyrogenic solution. In some embodiments, after labelling of cells with magnetic particles the cells are washed to remove excess particles. A cell preparation bag is then connected to the tubing set, which in turn is connected to a bag containing buffer and a cell collection bag. The tubing set consists of pre-assembled sterile tubing, including a pre-column and a separation column, and are for single use only. After initiation of the separation program, the system automatically applies the cell sample onto the separation column. Labelled cells are retained within the column, while unlabeled cells are removed by a series of washing steps. In some embodiments, the cell populations for use with the methods described herein are unlabeled and are not retained in the column. In some embodiments, the cell populations for use with the methods described herein are labeled and are retained in the column. In some embodiments, the cell populations for use with the methods described herein are eluted from the column after removal of the magnetic field, and are collected within the cell collection bag.

In certain embodiments, separation and/or other steps are carried out using the CliniMACS Prodigy system (Miltenyi Biotec). The CliniMACS Prodigy system in some aspects is equipped with a cell processing unity that permits automated washing and fractionation of cells by centrifugation. The CliniMACS Prodigy system can also include an onboard camera and image recognition software that determines the optimal cell fractionation endpoint by discerning the macroscopic layers of the source cell product. For example, peripheral blood may be automatically separated into erythrocytes, white blood cells and plasma layers. The CliniMACS Prodigy system can also include an integrated cell cultivation chamber which accomplishes cell culture protocols such as, e.g., cell differentiation and expansion, antigen loading, and long-term cell culture. Input ports can allow for the sterile removal and replenishment of media and cells can be monitored using an integrated microscope. See, e.g., Klebanoff et al. (2012) *J Immunother.* 35(9): 651-660, Terakura et al. (2012) Blood. 1:72-82, and Wang et al. (2012) *J Immunother.* 35(9):689-701.

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system (see, e.g., WO 2010/033140, Cho et al. (2010) *Lab Chip* 10, 1567-1573; and Godin et al. (2008) J Biophoton. 1(5):355-376. In both cases, cells can be labeled with multiple markers, allowing for the isolation of well-defined T cell subsets at high purity.

In some embodiments, the antibodies or binding partners are labeled with one or more detectable marker, to facilitate separation for positive and/or negative selection. For example, separation may be based on binding to fluorescently labeled antibodies. In some examples, separation of cells based on binding of antibodies or other binding partners specific for one or more cell surface markers are carried in a fluidic stream, such as by fluorescence-activated cell sorting (FACS), including preparative scale (FACS) and/or microelectromechanical systems (MEMS) chips, e.g., in combination with a flow-cytometric detection system. Such methods allow for positive and negative selection based on multiple markers simultaneously.

In some embodiments, the preparation methods include steps for freezing, e.g., cryopreserving, the cells, either before or after isolation, incubation, and/or engineering. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some aspects may be used. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are then frozen to −80° C. at a rate of 1° per minute and stored in the vapor phase of a liquid nitrogen storage tank.

In some embodiments, the cells are incubated and/or cultured prior to or in connection with genetic engineering. The incubation steps can include culture, cultivation, stimulation, activation, and/or propagation. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR component and/or costimulatory receptor, e.g., anti-CD3, anti-CD28, for example, bound to solid support such as a bead, and/or one or more cytokines. Optionally, the expansion method may further comprise the step of adding anti-CD3 and/or anti-CD28 antibody to the culture medium (e.g., at a concentration of at least about 0.5 ng/ml). In some embodiments, the stimulating agents include IL-2 and/or IL-15, for example, an IL-2 concentration of at least about 10 units/mL.

In some aspects, incubation is carried out in accordance with techniques such as those described in U.S. Pat. No.

6,040,177 to Riddell et al., Klebanoff et al. (2012) J Immunother. 35(9): 651-660, Terakura et al. (2012) Blood. 1:72-82, and/or Wang et al. (2012) J Immunother. 35(9):689-701.

In some embodiments, the T cells are expanded by adding to the composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division. In some aspects, the feeder cells are added to culture medium prior to the addition of the populations of T cells.

In some embodiments, the stimulating conditions include temperature suitable for the growth of human T lymphocytes, for example, at least about 25 degrees Celsius, generally at least about 30 degrees, and generally at or about 37 degrees Celsius. Optionally, the incubation may further comprise adding non-dividing EBV-transformed lymphoblastoid cells (LCL) as feeder cells. LCL can be irradiated with gamma rays in the range of about 6000 to 10,000 rads. The LCL feeder cells in some aspects is provided in any suitable amount, such as a ratio of LCL feeder cells to initial T lymphocytes of at least about 10:1.

In embodiments, antigen-specific T cells, such as antigen-specific CD4+ and/or CD8+ T cells, are obtained by stimulating naive or antigen specific T lymphocytes with antigen. For example, antigen-specific T cell lines or clones can be generated to cytomegalovirus antigens by isolating T cells from infected subjects and stimulating the cells in vitro with the same antigen.

B. Apparatus and Articles of Manufactures

In some embodiments, also provided is an apparatus or article of manufacture. In some embodiments, provided is an arrangement of a bioreactor and a first stationary phase for chromatography. The bioreactor is suitable for the expansion of cells, and the stationary phase is suitable for cell separation and removal of reagents. The first stationary phase is a gel filtration matrix and/or affinity chromatography matrix, wherein the gel filtration and/or affinity chromatography matrix comprises an affinity reagent, such as a multimerization reagent as described, wherein the reagent comprises a binding site Z (e.g. Z1) specifically binding to a binding partner C (e.g. C1) comprised in a first agent and/or the affinity reagent, such as a multimerization reagent as described, comprises a binding site Z (e.g. Z2) specifically binding to a binding partner C (e.g. C2) comprised in a second agent. In some embodiments, the gel filtratin and/or affinity chromatography matrix comprises an affinity reagent, such as a multimerization reagent as described, comprises the reagent comprises a binding site Z (e.g. the same or different from the first or second agent) specifically binding to a binding partner C comprised in the additional agent (e.g. the same or different from that comprised in the first or second agent). The first stationary phase is thereby being suitable of immobilizing thereon the first agent, the second agent and/or the additional agent, the binding partner C, such as the first binding partner C1 and/or the free second binding partner C2. In addition the bioreactor and the stationary phase are fluidly connected. This arrangement can be used in the serial expansion as explained above and can be integrated into known cell expansion systems such as the Quantum® cell expansion system) or the Xuri Cell Expansion System W25.

In this arrangement the first stationary phase is either comprised in a chromatography column or is a planar stationary phase. The arrangement may further comprise a second stationary phase which is fluidly connected to the first stationary phase. The secondary stationary phase may be a gel filtration matrix and/or affinity chromatography matrix, wherein the gel filtration and/or affinity chromatography matrix comprises an affinity reagent. This affinity reagent may comprise a binding partner D that (specifically) binds to the binding site Z1 of the multimerization reagent, thereby being suitable of immobilizing the multimerization reagent on the stationary phase.

Also provided is an apparatus for purification (e.g. selection) and culture, such as stimulation or expansion, of a composition of cells, the apparatus comprising at least one arrangement of a bioreactor and a first stationary phase or a second stationary phase for chromatography as defined above.

The apparatus may further comprise a plurality of arrangements of a bioreactor and a stationary phase being fluidly connected in series.

The apparatus may comprise a sample inlet being fluidly connected to the bioreactor of the arrangement of a bioreactor and the stationary phase for chromatography. The apparatus may also comprise a sample outlet for purified and expanded target cells, the sample outlet being fluidly connected to the stationary phase of the last of the at least one arrangement of a bioreactor and the stationary phase for chromatography.

In some embodiments, the apparatus may be designed as a functionally closed system.

C. Exemplary Features of Cultured Cells

In some embodiments, the cultured target cells, (e.g. cultured T cells), which can include cultured cells generated or produced in accord with the methods provided herein, exhibit one or more specified phenotypic and/or functional features, based on or related to their proliferation capacity, surface marker expression, differentiation state, activation state and/or metabolic profile. In some embodiments, the culturing of the target cells (e.g. culturing of T cells) in accord with any of the provided methods results in a change in a parameter associated with the function (e.g. increase or decrease of a functional activity) or phenotype (e.g. higher or lower expression of a marker or markers) of cells compared to the corresponding or respective function or phenotype of cells in the composition prior to incubation in accord with methods provided herein. In some embodiments, the cultured T cells exhibit the change with respect to a parameter from among expansion and/or proliferation capacity, CD4+/CD8+ T cell distribution or ratio, surface marker expression, functional activity, or metabolic profile.

In some embodiments, the change in the parameter as measured in the cultured T cells is compared or with reference to the same or similar parameter as measured in a reference T cell composition or preparation. Typically, T cells in the reference T cell composition or preparation include or are derived from the same or substantially the same composition of T cells prior to incubation with the reversibly-bound agent (e.g. multimerized agent, such as incubation with a stimulatory agent reversibly bound to an oligomeric mutein streptavidin), except such cells were not subject to the incubation or were subject to a different incubation. In some embodiments, the reference T cell preparation is subject to the incubation using substantially the same protocol or conditions (e.g. type of stimulatory agents or agent, format of stimulatory agent or agents, substantially the same starting cell numbers, washes, presence or absence of additional reagents, timing of incubation, temperature of incubation), except at least one aspect, and in some cases only one aspect, of such incubation in a reference T cell preparation is different than in the incubation producing the cultured T cells. In some embodiments, the reference T cell preparation is one in which incubation is not performed using a multimerization reagent, but instead in which the receptor-binding agents, e.g. stimulatory agents, are presented on an alternative formation, such as directly and/or non-reversbily bound or conjugated to a support (e.g. solid support), e.g. a bead, particle, magnetic particle or bead, nanoparticle or microsphere.

In some embodiments, the reference T cell composition or preparation is the composition containing T cells prior to incubation with a reversibly-bound agent (e.g. multimerized agent, such as incubation with a stimulatory agent reversibly bound to an oligomeric mutein streptavidin).

In some embodiments, the cultured T cells are generated by incubation with a reversibly-bound agent (e.g. multimerized agent, such as incubation with a stimulatory agent reversibly bound to an oligomeric mutein streptavidin) for less than 5 days and/or where the association of such agent with one or more molecules on the cell is disrupted (e.g. in the presence of a competition reagent, e.g. biotin or a biotin analog), such as disrupted within 5 days of initiation of incubation with such agent. For example, in some aspects, cultured T cells are generated or produced following incubation with a reversibly-bound agent (e.g. multimerized agent, such as incubation with a stimulatory agent reversibly bound to an oligomeric mutein streptavidin) as described herein, wherein the incubation is terminated and/or disrupted within 5 days after initiation of such incubation (such as within or about 4, 3, 2, or 1 day, or less), and/or where a competing agent (e.g. biotin) that dissociates the reversibly-bound agent from the cells is added to the incubated cells within 5 days after initiation of such incubation (such as within or about 4, 3, 2, or 1 day, or less). In some embodiments, the reference T cell preparation is generated or produced following incubation with the same or substantially the same reversibly-bound agent (e.g. multimerized agent, such as incubation with a stimulatory agent reversibly bound to an oligomeric mutein streptavidin), but where the incubation is performed for greater than 5 days, is not terminated and/or disrupted to lessen or terminate the signal induced or modulated in the cell, and/or where the T cell preparation is produced without the addition of a competing agent (e.g. biotin or biotin analog) that dissociates the reagent from the cells.

In some embodiments, the cultured T cells are generated by incubation with a reversibly-bound agent (e.g. multimerized agent, such as incubation with a stimulatory agent reversibly bound to an oligomeric mutein streptavidin) in which the receptor-binding agent (e.g. stimulatory agent) is one that does not bind to CD28 and/or induce signaling, i.e. is not an anti-CD28 antibody or fragment thereof. For example, in some embodiments, the cultured T cells are produced or generated following incubation with a reversibly-bound reagent in which one or more stimulatory agents are reversibly bound to a mutein streptavidin in which at least one stimulatory agent is specific for CD3 (e.g. anti-CD3 antibody or fragment thereof) and a second stimulatory agent can be specific for one or more of CD90, CD95, CD137, CD154, ICOS, LAT, CD27, OX40 or HVEM (e.g. an anti-CD90 antibody, an anti-CD95 antibody, an anti-CD137 antibody, and an anti-CD154 antibody, anti-ICOS antibody, anti-LAT antibody, anti-CD27 antibody, anti-OX40 antibody or anti-HVEM antibody, respectively, or antigen-binding fragments thereof). In some embodiments, the reference T cell preparation is a T cell culture generated or produced following incubation with a reversibly-bound agent (e.g. multimerized agent, such as incubation with a stimulatory agent reversibly bound to an oligomeric mutein streptavidin), but where the reagent comprises an agent that specifically binds CD28 and/or induces or modulates CD28 signaling. For example, in some embodiments, the reference T cell preparation is generated or produced following incubation of a T cell composition with anti-CD3/anti-CD28 Dynabeads®, anti-CD3/anti-CD28 ExPact® beads or other anti-CD3/anti-CD28 stimulatory agent. In some embodiments, such other anti-CD3/anti-CD28 stimulatory agent is one in which the antibody reagents are bound to a support (e.g. solid support), e.g. a bead, particle, magnetic particle or bead, nanoparticle or microsphere. In some embodiments, the cultured T cells are prepared by incubation with a reversibly-bound agent (e.g. multimerized agent, such as incubation with a stimulatory agent reversibly bound to an oligomeric mutein streptavidin) that is soluble, i.e. not bound to a support (e.g. solid support).

For example, in some embodiments, there are provided cultured T cells, such as prepared according to any of the methods provided herein, wherein the cultured T cells are generated or produced following incubation with a reversibly-bound agent as described herein (e.g. multimerized agent, such as incubation with a stimulatory agent reversibly bound to an oligomeric mutein streptavidin), in which the cultured T cells are characterized by an enhanced expansion and/or proliferation capacity compared to a reference T cell composition or preparation. In some embodiments, the enhanced expansion and/or proliferation capacity comprises an increase in the number or percentage of CD3+ T cells, CD4+ T cells, and/or CD8+ T cells in the cultured T cells by at least about 2-fold (such as by at least about any of 3-fold, 4-fold, 5-fold, 6-fold, 7-fold, 8-fold, 9-fold, 10-fold, or more) compared to the number or percentage of CD3+ T cells, CD4+ T cells, and/or CD8+ T cells, respectively, in the reference T cell composition or preparation.

In some embodiments, there are provided cultured T cells, such as prepared according to any of the methods provided herein, wherein the cultured T cells are generated or produced following incubation with a reversibly-bound agent as described herein (e.g. multimerized agent, such as incubation with a stimulatory agent reversibly bound to an oligomeric mutein streptavidin), in which the cultured T cells are characterized by an enhanced expansion and/or proliferation capacity of CD3+ T cells compared to a reference T cell culture. In some embodiments, the enhanced expansion and/or proliferation capacity comprises an increase in the number or percentage of CD3+ T cells in the cultured T cells by at least about 2-fold (such as by at least about any of 3-fold, 4-fold, 5-fold, 6-fold, 7-fold, 8-fold, 9-fold, 10-fold, or more) compared to the number or percentage of CD3+ T cells in the reference T cell composition or preparation.

In some embodiments, there are provided cultured T cells, such as prepared according to any of the methods provided herein, wherein the cultured T cells are generated or produced following incubation with a reversibly-bound agent as described herein (e.g. multimerized agent, such as incubation with a stimulatory agent reversibly bound to an oligomeric mutein streptavidin), in which the cultured T cells are characterized by an enhanced expansion and/or proliferation capacity of CD4+ T cells compared to a reference T cell composition or preparation. In some embodiments, the enhanced expansion and/or proliferation capacity comprises an increase in the number or percentage of CD4+ T cells in the cultured T cells by at least about 2-fold (such as by at least about any of 3-fold, 4-fold, 5-fold, 6-fold, 7-fold, 8-fold, 9-fold, 10-fold, or more) compared to the number or percentage of CD4+ T cells in the reference T cell composition or preparation.

In some embodiments, there are provided cultured T cells, such as prepared according to any of the methods provided herein, wherein the cultured T cells are generated or produced following incubation with a reversibly-bound agent as described herein (e.g. multimerized agent, such as incubation with a stimulatory agent reversibly bound to an oligomeric mutein streptavidin), in which the cultured T cells are characterized by an enhanced expansion and/or proliferation capacity of CD8+ T cells compared to a reference T cell composition or preparation. In some embodiments, the enhanced expansion and/or proliferation capacity comprises an increase in the number or percentage of CD8+ T cells in the cultured T cells by at least about 2-fold (such as by at least about any of 3-fold, 4-fold, 5-fold, 6-fold, 7-fold, 8-fold, 9-fold, 10-fold, or more) compared to the number or percentage of CD8+ T cells in the reference T cell composition or preparation.

In some embodiments, there are provided cultured T cells, such as prepared according to any of the methods provided herein, wherein the cultured T cells are generated or produced following incubation with a reversibly-bound agent as described herein (e.g. multimerized agent, such as incubation with a stimulatory agent reversibly bound to an oligomeric mutein streptavidin), in which the cultured T cells are characterized by an altered CD8+/CD4+ T cell distribution or normalized T cell distribution, such as an altered CD8+/CD4+ ratio or normalized CD8+/CD4+ T cell ratio, compared to a reference T cell composition or preparation. The CD8+/CD4+ ratio or normalized ratio can be increased or decreased. In some embodiments, the altered CD8+/CD4+ T cell ratio results from an increase in the number or percentage or normalized number or percentage of CD8+ T cells in the cultured T cells relative or compared to the number or percentage or normalized number or percentage in a reference composition or preparation. In some embodiments, number of CD8+ T cells in the cultured T cells is increased by at least about 2-fold (such as by at least about any of 3-fold, 4-fold, 5-fold, 6-fold, 7-fold, 8-fold, 9-fold, 10-fold, or more) compared to the number or percentage of CD8+ T cells or the normalized number or percentage of CD8+ T cells in the reference T cell composition or preparation. In some embodiments, the ratio of CD8+/CD4+ T cells or the normalized ratio of CD8+/CD4+ is increased by at least about 2-fold (such as by at least about any of 3-fold, 4-fold, 5-fold, 6-fold, 7-fold, 8-fold, 9-fold, 10-fold, or more) compared to the ratio of CD8+/CD4+ T cells or the normalized ratio of CD8+/CD4+ in the reference T cell composition or preparation. In some embodiments, the number, percentage or ratio in the cultured T cells or in a composition or preparation is normalized to the number, percentage or ratio in the starting composition containing the T cells prior to the incubation.

In some embodiments, there are provided cultured T cells prepared according to any of the methods provided herein, wherein the cultured T cells are generated or produced following incubation with a reversibly-bound agent as described herein (e.g. multimerized agent, such as incubation with a stimulatory agent reversibly bound to an oligomeric mutein streptavidin), and wherein the cultured T cells are characterized by an altered surface marker expression profile compared to a reference T cell composition or preparation. In some embodiments, the altered surface marker expression profile is due to a change in the number or percentage of one or more subsets of T cells that are positive, negative, high or low for one or more surface markers selected from CD45RA, CD45RO, CD62L, CD69, CCR7, CD27, CD28, CD122, T-bet, IL-7Rα, CD95, IL-2Rβ, CXCR3, LFA-1, KLRG1. In some embodiments, the number or percentage of the T cell subset in the cultured T cells is increased at least about 2-fold (such as by at least about any of 3-fold, 4-fold, 5-fold, 6-fold, 7-fold, 8-fold, 9-fold, 10-fold, or more) compared to the number or percentage of the subset of T cells in the reference composition or preparation.

In some embodiments, the T cell subset in the cultured T cells (e.g. a T cell subset that is increased in the cultured T cells compared to the reference composition or preparation) exhibits a decreased or reduced differentiation or activation state compared to the reference T cell composition or preparation. In some embodiments, the T cell subset is not or does not include an effector T cell ($T_E$) or effector memory T cell ($T_{EM}$) phenotype. In some embodiments, the subset of T cells contains a surface phenotype that is one or more of CD62L+, CCR7$^+$, CD27$^+$, CD28$^+$, or KLRG1$^{low/-}$. In some embodiments, such a subset of T cells in the cultured T cells is increased by at least about 2-fold (such as by at least about any of 3-fold, 4-fold, 5-fold, 6-fold, 7-fold, 8-fold, 9-fold, 10-fold, or more) compared to the number or percentage of the subset of T cells in the reference T cell composition or culture.

In some embodiments, the T cell subset in the cultured T cells (e.g. a T cell subset that is increased in the cultured T cells compared to the reference composition or preparation) is positive for CD62L and/or IL-7Rα (CD127) and/or negative or low for t-bet. In some embodiments, the subset of T cells is positive for CD45RA and/or negative or low for CD45RO. In some embodiments, the subset of T cells is positive for one or more of CCR7, CD45RA, CD62L, CD27, CD28, IL-7Rα (CD127), CD95, IL-2Rβ, CXCR3, and LFA-1, and/or negative for CD45RO. In some embodiments, such a subset of T cells in the cultured T cells is increased by at least about 2-fold (such as by at least about any of 3-fold, 4-fold, 5-fold, 6-fold, 7-fold, 8-fold, 9-fold, 10-fold, or more) compared to the number or percentage of the subset of T cells in the reference T cell composition or culture.

In some embodiments, the T cell subset in the cultured T cells (e.g. a T cell subset that is increased in the cultured T cells compared to the reference composition or preparation) is or includes cells that are positive for CD62L (CD62L+). In some embodiments, such a subset of T cells in the cultured T cells is increased by at least about 2-fold (such as by at least about any of 3-fold, 4-fold, 5-fold, 6-fold, 7-fold, 8-fold, 9-fold, 10-fold, or more) compared to the number or percentage of the subset of T cells in the reference T cell composition or culture.

In some embodiments, the T cell subset in the cultured T cells (e.g. a T cell subset that is increased in the cultured T cells compared to the reference composition or preparation) is or includes cells that are CD62L+ and a) any one or more of CD45RA$^{low/+}$, CD45RO$^{low/+}$, CCR7+ and CD27+ and b) any one or more of t-bet$^{low}$, IL-7Ra+(CD127+), CD95+, IL-2Rβ+, CXCR3+ and LFA-1+. In some embodiments, the T cell subset also can be CD3+, CD4+, or CD8+. In some embodiments, such a subset of T cells in the cultured T cells is increased by at least about 2-fold (such as by at least about any of 3-fold, 4-fold, 5-fold, 6-fold, 7-fold, 8-fold, 9-fold, 10-fold, or more) compared to the number or percentage of the subset of T cells in the reference T cell composition or culture.

In some embodiments, the T cell subset, such as a CD62L+ T cell subset, in the cultured T cells are or include or share phenotypic characteristics with memory T cells or particular subsets thereof, such as long-lived memory T cells. In some embodiments, such memory T cells are central memory T cells ($T_{CM}$) or T memory stem cells ($T_{SCM}$) cells. In some embodiments, the memory T cells are $T_{SCM}$ cells. $T_{SCM}$ cells may be described as having one or more phenotypic differences or functional features compared to other memory T cell subsets or compared to naïve T cells, such as being less differentiated or more naïve (see e.g., Ahlers and Belyakov (2010) Blood, 115:1678); Cieri et al. (2015) Blood, 125:2865; Flynn et al. (2014) Clinical & Translational Immunology, 3, e20; Gattinoni et al. (2012) Nat. Med., 17:1290-1297; Gattinoni et al. (2012) Nat. Reviews, 12:671; Li et al. (2013) PLOS ONE, 8:e67401; and published PCT Appl. No. WO2014/039044). In some cases, $T_{SCM}$ cells are thought to be the only memory T cells able to generate effector T cells and all three subsets of memory T cells ($T_{SCM}$, $T_{CM}$, and $T_{EM}$). In some aspects, $T_{SCM}$ cells have the highest survival and proliferation response to antigenic or homeostatic stimuli of all the memory T cell subsets, and the least attrition absent cognate antigen. In some embodiments, the less-differentiated $T_{SCM}$ cells may exhibit greater expansion, long-term viability, and target cell destruction following adoptive transfer than other memory T cells, and thus may be able to mediate more effective treatment with fewer transferred cells than would be possible for either $T_{CM}$ or $T_{EM}$ cells.

In some aspects, examples of phenotypic or functional features that have been reported or are known for $T_{SCM}$ cells include, for example, that such cells a) are CD45RO$^-$, CCR7$^+$, CD45RA$^+$, CD62L$^+$, CD27$^+$, CD28$^+$, IL-7Rα$^+$, CD95$^+$, IL-2Rβ$^+$, CXCR3$^+$, and LFA-1$^+$; b) are CD45RA$^+$, CCR7$^+$, CD62L$^+$, and CD95$^+$; c) are CD45RA$^+$, CD45RO$^+$, CCR7$^+$, CD62L$^+$, CD27$^+$, CD28$^+$, CD95$^+$, and IL-2Rβ$^+$; d) are CD45RO$^-$, CD45RA$^+$, CCR7$^+$, CD62L$^+$, CD27$^+$, CD28$^+$, CD127$^+$, and CD95$^+$; e) are CD45RA$^+$, CD44$^{+/-}$, CD62L$^+$, CD127$^+$, IL-2Rβ$^+$, CD28$^+$, CD43$^-$, KLRG1$^-$, Peforin$^-$, and GranzymeB$^-$; f) express high levels of CCR7, CD62L, CD27, and CD28, intermediate levels of CD95 and IL-2Rβ, low levels of CD45RA, and do not express CD45RO or KLRG-1; or g) express high levels of CD62L, low levels of CD44 and t-bet, and are Sca-1$^+$; and/or have intermediate IL-2-producing capacity, low IFNγ-producing capacity, low cytotoxicity, and high self-renewal capacity.

In some embodiments, the T cell subset in the cultured T cells (e.g. a T cell subset that is increased in the cultured T cells compared to the reference composition or preparation) is or includes memory T cells, such as long-lived memory T cells. In some embodiments, the memory T cells are central memory ($T_{CM}$) T cells. In some embodiments, the T cell subset has a phenotypic characteristic CD45RA-, CD45RO$^{low/+}$, CCR7+, CD62L+, CD27+, CD28+, CD95+ CD122+ and/or KLGR1$^{low}$. In some embodiments, such a subset of T cells in the cultured T cells is increased by at least about 2-fold (such as by at least about any of 3-fold, 4-fold, 5-fold, 6-fold, 7-fold, 8-fold, 9-fold, 10-fold, or more) compared to the number or percentage of the subset of T cells in the reference T cell composition or culture.

In some embodiments, the memory T cells are stem central memory ($T_{SCM}$) T cells. In some embodiments, the T cell subset has a phenotypic characteristic CD45RA$^{low/+}$, CD45RO$^{low/+}$, CCR7+, CD62L+, CD27+, CD28+, CD95+, CD122+ and/or KLGR1-. In some embodiments, the T cell subset has a phenotypic characteristic CD45RA$^{low/+}$, CD45RO$^-$, CCR7+, CD62L+, CD27+, CD28+, CD95+, CD122+ and/or KLGR1-. In some embodiments, the T cell subset has a phenotypic characteristic CD45RO$^-$, CCR7$^+$, CD45RA$^+$, CD62L$^+$, CD27$^+$, CD28$^+$, IL-7Rα$^+$, CD95$^+$, IL-2Rβ$^+$, CXCR3$^+$, and/or LFA-1$^+$. In some embodiments, the T cell subset has a phenotypic characteristic CD45RA$^+$, CCR7$^+$, CD62L$^+$, and/or CD95$^+$. In some embodiments, the T cell subset has a phenotypic characteristic CD45RA$^+$, CD45RO$^+$, CCR7$^+$, CD62L$^+$, CD27$^+$, CD28$^+$, CD95$^+$, and/or IL-2Rβ$^+$. In some embodiments, the T cell subset has a phenotypic characteristic CD45RO$^-$, CD45RA$^+$, CCR7$^+$, CD62L$^+$, CD27$^+$, CD28$^+$, CD127$^+$, and/or CD95$^+$. In some embodiments, the T cell subset has a phenotypic characteristic CD45RA$^+$, CD44$^{+/-}$, CD62L$^+$, CD127$^+$, IL-2Rβ$^+$, CD28$^+$, CD43$^-$, KLRG1$^-$, Peforin$^-$, and/or GranzymeB$^-$. In some embodiments, the T cell subset expresses high levels of CCR7, CD62L, CD27, and/or CD28, intermediate levels of CD95 and/or IL-2R13, low levels of CD45RA, and/or does not express CD45RO and/or KLRG-1. In some embodiments, the T cell subset expresses high levels of CD62L, low levels of CD44 and t-bet, and/or is Sca-1$^+$. In some embodiments, the T cell subset has a phenotypic characteristic intermediate IL-2-producing capacity, low IFNγ-producing capacity, low cytotoxicity, and/or high self-renewal capacity. In some embodiments, such a subset of T cells in the cultured T cells is increased by at least about 2-fold (such as by at least about any of 3-fold, 4-fold, 5-fold, 6-fold, 7-fold, 8-fold, 9-fold, 10-fold, or more) compared to the number or percentage of the subset of T cells in the reference T cell composition or culture.

In some embodiments, the subset of T cells, such as any subset of T cells described above, is present at a greater percentage of the total T cells in the cultured T cells or a greater number of total T cells in the cultured T cells compared to a reference T cell composition or preparation. In some embodiments, the percentage of the T cell subset in the cultured T cells as a percentage of the total T cells or total cells in the culture is at least 35%, 40%, 45%, 50%, 55%, 60%, 65%, 70%, 75%, 80%, 85%, 90%, 95% or more. In some embodiments, the percentage of the T cell subset in the cultured cells, such as any T cell subset described above, is greater, e.g. at least 1.5-fold greater, at least 2-fold, at least 3-fold, at least 4-fold, at least 5-fold or more greater, than the corresponding percentage of the subset of cells in a T cell in a T cell composition isolated or enriched directly from a human subject based on surface expression of one or markers comprising the phenotype, but without the incubation or culture. In some embodiments, the total number, relative number or normalized number of the T cells subset in the cultured cells, such as any T cell subset described above, is greater, e.g. at least 1.5-fold greater, at least 2-fold, at least 3-fold, at least 4-fold, at least 5-fold or more greater, than the number, relative number or normalized number of the T cell subset in a reference T cell composition or preparation, such as any reference T cell composition or preparation described above, e.g. the T cell composition prior to the incubation with the reversibly-bound agent (e.g. multimerized agent, such as incubation with a stimulatory agent reversibly bound to an oligomeric mutein streptavidin) in accord with any of the methods provided herein. In some embodiments, the number of T cells corresponding to the T cell subset present in the T cell culture is at least or at least about 1×10$^6$ cells, 2×10$^6$ cells, 3×10$^6$ cells, 4×10$^6$ cells, 5×10$^6$ cells or more.

In some embodiments, the T cell subset is CD62L+ and/or IL-7Rα+ (CD127+) and the percentage of the CD62L+ and/or IL-7Rα+ (CD127+) subset in the cultured T cells as a percentage of the total T cells or total cells in the culture is at least 35%, 40%, 45%, 50%, 55%, 60%, 65%, 70%, 75%, 80%, 85%, 90%, 95% or more. In some embodiments, the T cell subset is CD45RA-, CD45RO$^{low/+}$, and/or KLRG1$^{low}$ and the percentage of the CD45RA-, CD45RO$^{low/+}$, and/or KLRG1$^{low}$ subset in the cultured T cells as a percentage of the total T cells or total cells in the culture is at least 35%, 40%, 45%, 50%, 55%, 60%, 65%, 70%, 75%, 80%, 85%, 90%, 95% or more. In some embodiments, the T cell subset is CD45RA$^{low/+}$, CD45RO$^{low/+}$, and/or KLRG1$^-$ and the percentage of the CD45RA$^{low/+}$, CD45RO$^{low}$, and/or KLRG1$^-$ subset in the cultured T cells as a percentage of the total T cells or total cells in the culture is at least 35%, 40%, 45%, 50%, 55%, 60%, 65%, 70%, 75%, 80%, 85%, 90%, 95% or more.

In some embodiments, the T cell subset is or includes T$_{CM}$ cells. In some embodiments, the percentage of the T$_{CM}$ subset in the cultured T cells as a percentage of the total T cells or total cells in the culture is at least 35%, 40%, 45%, 50%, 55%, 60%, 65%, 70%, 75%, 80%, 85%, 90%, 95% or more.

In some embodiments, the T cell subset is or includes T$_{SCM}$ cells. In some embodiments, the percentage of the T$_{SCM}$ subset in the cultured T cells as a percentage of the total T cells or total cells in the culture is at least 35%, 40%, 45%, 50%, 55%, 60%, 65%, 70%, 75%, 80%, 85%, 90%, 95% or more.

In some embodiments, the subset of T cells, such as CD62L+ T cells, have or exhibit a) a low level of TCR rearrangement excisions circles (TREC); and/or b) express a proliferation marker (e.g., Ki-67); and/or c) exhibit the capacity to proliferate in the presence of a stimulatory agent; and/or d) exhibit a capacity to produce a cytokine selected from among IFN-gamma, TNF and IL-2 in the presence of a stimulatory agent; and/or e) are refractory to attrition in the absence of a stimulatory agent; and/or f) are able to generate T$_{SCM}$, T$_{CM}$, T$_{EM}$, and T$_{EFF}$ cells; and/or g) have low cytotoxicity; and/or h) can produce the same or greater response following adoptive transfer of fewer cells than with T$_{CM}$ or T$_{EM}$ cells. In some embodiments, the stimulatory agent is an antigen, a homeostatic cytokine (e.g., IL-15 or IL-17), or is an agent that is capable of initiating a TCR/CD3 complex-associated signal in the T cells. In some embodiments, the capacity to produce a cytokine comprises a low capacity to produce IFNγ and/or an intermediate capacity to produce IL-2.

In some embodiments, there are provided cultured T cells, such as prepared according to any of the methods provided herein, wherein the cultured T cells are generated or produced following incubation as described herein, and wherein the cultured T cells are characterized by a modified functional activity profile compared to a reference T cell composition or preparation. In some embodiments, the cultured T cells or a specific subset of T cells present in the culture exhibits an altered functional activity profile compared to a reference composition or preparation or compared to the subset of T cells in the reference composition or preparation, such as a functional activity that is altered (e.g. increased or decreased) at least 1.5-fold, 2-fold, 3-fold, 4-fold, 5-fold, 6-fold, 7-fold, 8-fold, 9-fold, 10-fold. In some embodiments, the functional activity is selected from one or more of a) a low level of TCR rearrangement excisions circles (TREC); and/or b) expression of a proliferation marker (e.g., Ki-67); and/or c) the capacity to proliferate in the presence of a stimulatory agent; and/or d) the capacity to produce a cytokine selected from among IFN-gamma, TNF and IL-2 in the presence of a stimulatory agent; and/or e) are refractory to attrition in the absence of a stimulatory agent; and/or f) are able to generate T$_{SCM}$, T$_{CM}$, T$_{EM}$, and T$_{EFF}$ cells; and/or g) have low cytotoxicity. In some embodiments, the stimulatory agent is an antigen, a homeostatic cytokine (e.g., IL-15 or IL-17), or is an agent that is capable of initiating a TCR/CD3 complex-associated signal in the T cells. In some embodiments, the capacity to produce a cytokine comprises a low capacity to produce IFNγ and/or an intermediate capacity to produce IL-2. In some embodiments, the subset of T cells comprises memory T cells, such as long-lived memory T cells, in the cultured T cells. In some embodiments, the memory T cells are T$_{SCM}$ cells In some embodiments, the cultured T cells or a specific subset of T cells present in the culture can produce the same or greater response following adoptive transfer of fewer cells than can be achieved by a reference composition or preparation or by the subset of T cells in the reference composition or preparation. In some embodiments, such response is achieved with at least about 2-fold (such as by at least about any of 3-fold, 4-fold, 5-fold, 6-fold, 7-fold, 8-fold, 9-fold, 10-fold, or more) fewer cells. In some embodiments, the response is increased or is greater by at least about 2-fold (such as by at least about any of 3-fold, 4-fold, 5-fold, 6-fold, 7-fold, 8-fold, 9-fold, 10-fold, or more).

In some embodiments, the percentage of the T cell subset in the cultured cells, such as any T cell subset described above, is greater, e.g. at least 1.5-fold greater, at least 2-fold, at least 3-fold, at least 4-fold, at least 5-fold or more greater, than the corresponding subset of cells in a preparation of T cells that were incubated in the presence of a GSK-P inhibitor. In some embodiments, the composition of cultured T cells does not contain a GSK-P inhibitor.

In some embodiments, the percentage of the T cell subset in the cultured cells, such as any T cell subset described above, is greater, e.g. at least 1.5-fold greater, at least 2-fold, at least 3-fold, at least 4-fold, at least 5-fold or more greater, than the corresponding subset of cells that were incubated in the presence of a recombinant homeostatic cytokine, optionally IL-7 or IL-15. In some embodiments, the composition of cultured T cells does not contain a recombinant (e.g. exogenous) IL-7 cytokine or a recombinant (e.g. exogenous) IL-15 cytokine.

In some embodiments, the composition of cultured T cells was produced or generated in accord with any of the methods provided herein in which a substance, such as a competition agent, was added to T cells to disrupt, such as to lessen and/or terminate, the signaling of the stimulatory agent or agents. In some embodiments, the composition of cultured T cells contains the presence of a substance, such as a competition agent, e.g. biotin or a biotin analog, e.g. D-Biotin. In some embodiments, the substance, such as a competition agent, e.g. biotin or a biotin analog, e.g. D-Biotin, is present in an amount that is at least 1.5-fold greater, at least 2-fold, at least 3-fold, at least 4-fold, at least 5-fold, at least 10-fold, at least 100-fold, at least 1000-fold or more greater than the amount of the substance in a reference composition or preparation of cultured T cells in which the substance was not added exogenously during the incubation. In some embodiments, the amount of the substance, such as a competition agent, e.g. biotin or a biotin analog, e.g. D-Biotin, in the composition of cultured T cells is from or from about 10 μM to 100 μM, 100 μM to 1 mM, 100 μM to 500 μM or 10 μM to 100 μM.

IV. Methods of Genetically Engineering Cultured Cells, Antigen Receptors and Genetically Engineered Cells In some embodiments, the cultured cells contain or are engineered to contain an engineered receptor, e.g., an engineered antigen receptor, such as a chimeric antigen receptor (CAR), or a T cell receptor (TCR). Also provided are populations of such cells, compositions containing such cells and/or enriched for such cells, such as in which cells of a certain type such as T cells or CD8+ or CD4+ cells are enriched or selected. Among the compositions are pharmaceutical compositions and formulations for administration, such as for adoptive cell therapy. Also provided are therapeutic methods for administering the cells and compositions to subjects, e.g., patients.

Thus, in some embodiments, the cultured cells include one or more nucleic acids introduced via genetic engineering, and thereby express recombinant or genetically engineered products of such nucleic acids. In some embodiments, gene transfer is accomplished by first stimulating the cultured cells, such as by combining it with a stimulus that induces a response such as proliferation, survival, and/or activation, e.g., as measured by expression of a cytokine or activation marker, followed by transduction of the activated cells, and expansion in culture to numbers sufficient for clinical applications.

In some contexts, overexpression of a stimulatory factor (for example, a lymphokine or a cytokine) may be toxic to a subject. Thus, in some contexts, the engineered cells include gene segments that cause the cells to be susceptible to negative selection in vivo, such as upon administration in adoptive immunotherapy. For example, in some aspects, the cultured cells are engineered so that they can be eliminated as a result of a change in the in vivo condition of the patient to which they are administered. The negative selectable phenotype may result from the insertion of a gene that confers sensitivity to an administered agent, for example, a compound. Negative selectable genes include the Herpes simplex virus type I thymidine kinase (HSV-I TK) gene (Wigler et al., Cell 2: 223, 1977) which confers ganciclovir sensitivity; the cellular hypoxanthine phosphribosyltransferase (HPRT) gene, the cellular adenine phosphoribosyltransferase (APRT) gene, bacterial cytosine deaminase, (Mullen et al., Proc. Natl. Acad. Sci. USA. 89:33 (1992)). In some aspects, the cultured cells further are engineered to promote expression of cytokines or other factors.

A. Nucleic Acids Encoding Antigen Receptors, e.g. Chimeric Antigen Receptors

Provided are methods, nucleic acids, compositions, and kits for producing the genetically engineered cells. The genetic engineering generally involves introduction of a nucleic acid encoding the recombinant or engineered component into a composition containing the cultured cells, such as by retroviral transduction, transfection, or transformation.

In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

1. Chimeric Antigen Receptors (CARs)

The cells generally express recombinant receptors, such as antigen receptors including functional non-TCR antigen receptors, e.g., chimeric antigen receptors (CARs), and other antigen-binding receptors such as transgenic T cell receptors (TCRs). Also among the receptors are other chimeric receptors.

Exemplary antigen receptors, including CARs, and methods for engineering and introducing such receptors into cells, include those described, for example, in International Patent App. Pub. Nos. WO200014257, WO2013126726, WO2012/129514, WO2014031687, WO2013/166321, WO2013/071154, WO2013/123061 U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416,and/or those described by Sadelain et al., Cancer Discov. 2013 April; 3(4): 388-398; Davila et al. (2013) PLoS ONE 8(4): e61338; Turtle et al., Curr. Opin. Immunol., 2012 October; 24(5): 633-39; Wu et al., Cancer, 2012 Mar. 18(2): 160-75. In some aspects, the antigen receptors include a CAR as described in U.S. Pat. No. 7,446,190, and those described in International Patent App. Pub. No. WO/2014055668 A1. Examples of the CARs include CARs as disclosed in any of the aforementioned publications, such as WO2014031687, U.S. Pat. Nos. 8,339,645, 7,446,179, US 2013/0149337, U.S. Pat. Nos. 7,446,190, 8,389,282, Kochenderfer et al., 2013, Nature Reviews Clinical Oncology, 10, 267-276 (2013); Wang et al. (2012) J. Immunother. 35(9): 689-701; and Brentjens et al., Sci Transl Med. 2013 5(177). See also WO2014031687, U.S. Pat. Nos. 8,339,645, 7,446,179, US 2013/0149337, U.S. Pat. Nos. 7,446,190, and 8,389,282. The chimeric receptors, such as CARs, generally include an extracellular antigen binding domain, such as a portion of an antibody molecule, generally a variable heavy ($V_H$) chain region and/or variable light ($V_L$) chain region of the antibody, e.g., an scFv antibody fragment.

In some embodiments, the antigen targeted by the receptor is a polypeptide. In some embodiments, it is a carbohydrate or other molecule. In some embodiments, the antigen is selectively expressed or overexpressed on cells of the disease or condition, e.g., the tumor or pathogenic cells, as compared to normal or non-targeted cells or tissues. In other embodiments, the antigen is expressed on normal cells and/or is expressed on the engineered cells.

Antigens targeted by the receptors in some embodiments include orphan tyrosine kinase receptor ROR1, tEGFR, Her2, L1-CAM, CD19, CD20, CD22, mesothelin, CEA, and hepatitis B surface antigen, anti-folate receptor, CD23, CD24, CD30, CD33, CD38, CD44, EGFR, EGP-2, EGP-4, EPHa2, ErbB2, 3, or 4, FBP, fetal acethycholine e receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, PSCA, NKG2D Ligands, NY-ESO-1, MART-1, gp100, oncofetal antigen, ROR1, TAG72, VEGF-R2, carcinoembryonic antigen (CEA), prostate specific antigen, PSMA, Her2/neu, estrogen receptor, progesterone receptor, ephrinB2, CD123, c-Met, GD-2, and MAGE A3, CE7, Wilms Tumor 1 (WT-1), a cyclin, such as cyclin A1 (CCNA1), and/or biotinylated molecules, and/or molecules expressed by HIV, HCV, HBV or other pathogens.

In some embodiments, the CAR binds a pathogen-specific antigen. In some embodiments, the CAR is specific for viral antigens (such as HIV, HCV, HBV, etc.), bacterial antigens, and/or parasitic antigens.

In some embodiments, the antibody portion of the recombinant receptor, e.g., CAR, further includes at least a portion of an immunoglobulin constant region, such as a hinge region, e.g., an IgG4 hinge region, and/or a CH1/CL and/or Fc region. In some embodiments, the constant region or portion is of a human IgG, such as IgG4 or IgG1. In some aspects, the portion of the constant region serves as a spacer region between the antigen-recognition component, e.g., scFv, and transmembrane domain. The spacer can be of a length that provides for increased responsiveness of the cell following antigen binding, as compared to in the absence of the spacer. Exemplary spacers, e.g., hinge regions, include those described in International Patent App. Pub. No. WO2014031687. In some examples, the spacer is or is about 12 amino acids in length or is no more than 12 amino acids in length. Exemplary spacers include those having at least about 10 to 229 amino acids, about 10 to 200 amino acids, about 10 to 175 amino acids, about 10 to 150 amino acids, about 10 to 125 amino acids, about 10 to 100 amino acids, about 10 to 75 amino acids, about 10 to 50 amino acids, about 10 to 40 amino acids, about 10 to 30 amino acids, about 10 to 20 amino acids, or about 10 to 15 amino acids, and including any integer between the endpoints of any of the listed ranges. In some embodiments, a spacer region has about 12 amino acids or less, about 119 amino acids or less, or about 229 amino acids or less. Exemplary spacers include IgG4 hinge alone, IgG4 hinge linked to CH2 and CH3 domains, or IgG4 hinge linked to the CH3 domain.

This antigen recognition domain generally is linked to one or more intracellular signaling components, such as signaling components that mimic activation through an antigen receptor complex, such as a TCR complex, in the case of a CAR, and/or signal via another cell surface receptor. Thus, in some embodiments, the antigen-binding component (e.g., antibody) is linked to one or more transmembrane and intracellular signaling domains. In some embodiments, the transmembrane domain is fused to the extracellular domain. In one embodiment, a transmembrane domain that naturally is associated with one of the domains in the receptor, e.g., CAR, is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 epsilon, CD45, CD4, CD5, CDS, CD9, CD16, CD22, CD33, CD37, CD64, CD80, CD86, CD134, CD137, and/or CD154. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain. In some embodiments, the linkage is by linkers, spacers, and/or transmembrane domain(s).

Among the intracellular signaling domains are those that mimic or approximate a signal through a natural antigen receptor, a signal through such a receptor in combination with a costimulatory receptor, and/or a signal through a costimulatory receptor alone. In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the cytoplasmic signaling domain of the CAR.

The receptor, e.g., the CAR, generally includes at least one intracellular signaling component or components. In some embodiments, the receptor includes an intracellular component of a TCR complex, such as a TCR CD3 chain that mediates T-cell activation and cytotoxicity, e.g., CD3 zeta chain. Thus, in some aspects, the antigen-binding portion is linked to one or more cell signaling modules. In some embodiments, cell signaling modules include CD3 transmembrane domain, CD3 intracellular signaling domains, and/or other CD transmembrane domains. In some embodiments, the receptor, e.g., CAR, further includes a portion of one or more additional molecules such as Fc receptor γ, CD8, CD4, CD25, or CD16. For example, in some aspects, the CAR or other chimeric receptor includes a chimeric molecule between CD3-zeta (CD3-ζ) or Fc receptor γ and CD8, CD4, CD25 or CD16.

In some embodiments, upon ligation of the CAR or other chimeric receptor, the cytoplasmic domain or intracellular signaling domain of the receptor activates at least one of the normal effector functions or responses of the immune cell, e.g., T cell engineered to express the CAR. For example, in some contexts, the CAR induces a function of a T cell such as cytolytic activity or T-helper activity, such as secretion of cytokines or other factors. In some embodiments, a truncated portion of an intracellular signaling domain of an antigen receptor component or costimulatory molecule is used in place of an intact immunostimulatory chain, for example, if it transduces the effector function signal. In some embodiments, the intracellular signaling domain or domains include the cytoplasmic sequences of the T cell receptor (TCR), and in some aspects also those of co-receptors that in the natural context act in concert with such receptors to initiate signal transduction following antigen receptor engagement.

In the context of a natural TCR, full activation generally requires not only signaling through the TCR, but also a costimulatory signal. Thus, in some embodiments, to promote full activation, a component for generating secondary or co-stimulatory signal is also included in the CAR. In other embodiments, the CAR does not include a component for generating a costimulatory signal. In some aspects, an additional CAR is expressed in the same cell and provides the component for generating the secondary or costimulatory signal.

T cell activation is in some aspects described as being mediated by two classes of cytoplasmic signaling sequences: those that initiate antigen-dependent primary activation through the TCR (primary cytoplasmic signaling sequences), and those that act in an antigen-independent manner to provide a secondary or co-stimulatory signal (secondary cytoplasmic signaling sequences). In some aspects, the CAR includes one or both of such signaling components.

In some aspects, the CAR includes a primary cytoplasmic signaling sequence that regulates primary activation of the TCR complex. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences include those derived from TCR zeta, FcR gamma, FcR beta, CD3 gamma, CD3 delta, CD3 epsilon, CDS, CD22, CD79a, CD79b, and CD66d. In some embodiments, cytoplasmic signaling molecule(s) in the CAR contain(s) a cytoplasmic signaling domain, portion thereof, or sequence derived from CD3 zeta.

In some embodiments, the CAR includes a signaling domain and/or transmembrane portion of a costimulatory receptor, such as CD28, 4-1BB, OX40, DAP10, and ICOS.

In some aspects, the same CAR includes both the activating and costimulatory components.

In some embodiments, the activating domain is included within one CAR, whereas the costimulatory component is provided by another CAR recognizing another antigen. In some embodiments, the CARs include activating or stimulatory CARs, costimulatory CARs, both expressed on the same cell (see WO2014/055668). In some aspects, the cells include one or more stimulatory or activating CAR and/or a costimulatory CAR. In some embodiments, the cells further include inhibitory CARs (iCARs, see Fedorov et al., Sci. Transl. Medicine, 5(215) (December, 2013), such as a CAR recognizing an antigen other than the one associated with and/or specific for the disease or condition whereby an activating signal delivered through the disease-targeting CAR is diminished or inhibited by binding of the inhibitory CAR to its ligand, e.g., to reduce off-target effects.

In certain embodiments, the intracellular signaling domain comprises a CD28 transmembrane and signaling domain linked to a CD3 (e.g., CD3-zeta) intracellular domain. In some embodiments, the intracellular signaling domain comprises a chimeric CD28 and CD137 (4-1BB, TNFRSF9) co-stimulatory domains, linked to a CD3 zeta intracellular domain.

In some embodiments, the CAR encompasses one or more, e.g., two or more, costimulatory domains and an activation domain, e.g., primary activation domain, in the cytoplasmic portion. Exemplary CARs include intracellular components of CD3-zeta, CD28, and 4-1BB.

In some embodiments, the CAR or other antigen receptor further includes a marker, such as a cell surface marker, which may be used to confirm transduction or engineering of the cell to express the receptor, such as a truncated version of a cell surface receptor, such as truncated EGFR (tEGFR). In some aspects, the marker includes all or part (e.g., truncated form) of CD34, a NGFR, or epidermal growth factor receptor (e.g., tEGFR). In some embodiments, the nucleic acid encoding the marker is operably linked to a polynucleotide encoding for a linker sequence, such as a cleavable linker sequence, e.g., T2A. See WO2014031687.

In some embodiments, the marker is a molecule, e.g., cell surface protein, not naturally found on T cells or not naturally found on the surface of T cells, or a portion thereof.

In some embodiments, the molecule is a non-self molecule, e.g., non-self protein, i.e., one that is not recognized as "self" by the immune system of the host into which the cells will be adoptively transferred.

In some embodiments, the marker serves no therapeutic function and/or produces no effect other than to be used as a marker for genetic engineering, e.g., for selecting cells successfully engineered. In other embodiments, the marker may be a therapeutic molecule or molecule otherwise exerting some desired effect, such as a ligand for a cell to be encountered in vivo, such as a costimulatory or immune checkpoint molecule to enhance and/or dampen responses of the cells upon adoptive transfer and encounter with ligand.

In some cases, CARs are referred to as first, second, and/or third generation CARs. In some aspects, a first generation CAR is one that solely provides a CD3-chain induced signal upon antigen binding; in some aspects, a second-generation CARs is one that provides such a signal and costimulatory signal, such as one including an intracellular signaling domain from a costimulatory receptor such as CD28 or CD137; in some aspects, a third generation CAR is one that includes multiple costimulatory domains of different costimulatory receptors.

In some embodiments, the chimeric antigen receptor includes an extracellular portion containing an antibody or antibody fragment. In some aspects, the chimeric antigen receptor includes an extracellular portion containing the antibody or fragment and an intracellular signaling domain. In some embodiments, the antibody or fragment includes an scFv and the intracellular domain contains an ITAM. In some aspects, the intracellular signaling domain includes a signaling domain of a zeta chain of a CD3-zeta (CD3) chain. In some embodiments, the chimeric antigen receptor includes a transmembrane domain linking the extracellular domain and the intracellular signaling domain. In some aspects, the transmembrane domain contains a transmembrane portion of CD28. In some embodiments, the chimeric antigen receptor contains an intracellular domain of a T cell costimulatory molecule. In some aspects, the T cell costimulatory molecule is CD28 or 41BB.

The terms "polypeptide" and "protein" are used interchangeably to refer to a polymer of amino acid residues, and are not limited to a minimum length. Polypeptides, including the provided receptors and other polypeptides, e.g., linkers or peptides, may include amino acid residues including natural and/or non-natural amino acid residues. The terms also include post-expression modifications of the polypeptide, for example, glycosylation, sialylation, acetylation, and phosphorylation. In some aspects, the polypeptides may contain modifications with respect to a native or natural sequence, as long as the protein maintains the desired activity. These modifications may be deliberate, as through site-directed mutagenesis, or may be accidental, such as through mutations of hosts which produce the proteins or errors due to PCR amplification.

In some embodiments, the receptor, e.g., the CAR, expressed by the cells in the consecutive dose contains at least one immunoreactive epitope as the receptor, e.g., the CAR, expressed by the cells of the first dose. In some aspects, the receptor, e.g., the CAR, expressed by the cells administered in the consecutive dose is identical to the receptor, e.g., the CAR, expressed by the first dose or is substantially identical to the receptor, e.g., the CAR, expressed by the cells of administered in the first dose.

The recombinant receptors, such as CARs, expressed by the cells administered to the subject in the various doses generally recognize or specifically bind to a molecule that is expressed in, associated with, and/or specific for the disease or condition or cells thereof being treated. Upon specific binding to the molecule, e.g., antigen, the receptor generally delivers an immunostimulatory signal, such as an ITAM-transduced signal, into the cell, thereby promoting an immune response targeted to the disease or condition. For example, in some embodiments, the cells in the first dose express a CAR that specifically binds to an antigen expressed by a cell or tissue of the disease or condition or associated with the disease or condition.

2. TCRs

In some embodiments, the genetically engineered antigen receptors include recombinant T cell receptors (TCRs) and/or TCRs cloned from naturally occurring T cells. In some embodiments, a high-affinity T cell clone for a target antigen (e.g., a cancer antigen) is identified, isolated from a patient, and introduced into the cells. In some embodiments, the TCR clone for a target antigen has been generated in transgenic mice engineered with human immune system genes (e.g., the human leukocyte antigen system, or HLA). See, e.g., tumor antigens (see, e.g., Parkhurst et al. (2009) Clin Cancer Res. 15:169-180 and Cohen et al. (2005) J Immunol. 175:5799-5808. In some embodiments, phage display is used to isolate TCRs against a target antigen (see, e.g., Varela-Rohena et al. (2008) *Nat Med.* 14:1390-1395 and Li (2005) *Nat Biotechnol.* 23:349-354.

In some embodiments, after the T-cell clone is obtained, the TCR alpha and beta chains are isolated and cloned into a gene expression vector. In some embodiments, the TCR alpha and beta genes are linked via a picornavirus 2A ribosomal skip peptide so that both chains are coexpression. In some embodiments, genetic transfer of the TCR is accomplished via retroviral or lentiviral vectors, or via transposons (see, e.g., Baum et al. (2006) Molecular Therapy: The Journal of the American Society of Gene Therapy. 13:1050-1063; Frecha et al. (2010) Molecular Therapy: The Journal of the American Society of Gene Therapy. 18:1748-1757; an Hackett et al. (2010) Molecular Therapy: The Journal of the American Society of Gene Therapy. 18:674-683.

3. Multi-Targeting

In some embodiments, the cells and methods include multi-targeting strategies, such as expression of two or more genetically engineered receptors on the cell, each recognizing the same of a different antigen and typically each including a different intracellular signaling component. Such multi-targeting strategies are described, for example, in International Patent App. Pub. No. WO 2014055668 A1 (describing combinations of activating and costimulatory CARs, e.g., targeting two different antigens present individually on off-target, e.g., normal cells, but present together only on cells of the disease or condition to be treated) and Fedorov et al., Sci. Transl. Medicine, 5(215) (December, 2013) (describing cells expressing an activating and an inhibitory CAR, such as those in which the activating CAR binds to one antigen expressed on both normal or non-diseased cells and cells of the disease or condition to be treated, and the inhibitory CAR binds to another antigen expressed only on the normal cells or cells which it is not desired to treat).

For example, in some embodiments, the cells include a receptor expressing a first genetically engineered antigen receptor (e.g., CAR or TCR) which is capable of inducing an activating signal to the cell, generally upon specific binding to the antigen recognized by the first receptor, e.g., the first antigen. In some embodiments, the cell further includes a second genetically engineered antigen receptor (e.g., CAR or TCR), e.g., a chimeric costimulatory receptor, which is capable of inducing a costimulatory signal to the immune cell, generally upon specific binding to a second antigen recognized by the second receptor. In some embodiments, the first antigen and second antigen are the same. In some embodiments, the first antigen and second antigen are different.

In some embodiments, the first and/or second genetically engineered antigen receptor (e.g. CAR or TCR) is capable of inducing an activating signal to the cell. In some embodiments, the receptor includes an intracellular signaling component containing ITAM or ITAM-like motifs. In some embodiments, the activation induced by the first receptor involves a signal transduction or change in protein expression in the cell resulting in initiation of an immune response, such as ITAM phosphorylation and/or initiation of ITAM-mediated signal transduction cascade, formation of an immunological synapse and/or clustering of molecules near the bound receptor (e.g. CD4 or CD8, etc.), activation of one or more transcription factors, such as NF-κB and/or AP-1, and/or induction of gene expression of factors such as cytokines, proliferation, and/or survival.

In some embodiments, the first and/or second receptor includes intracellular signaling domains of costimulatory receptors such as CD28, CD137 (4-1 BB), OX40, and/or ICOS. In some embodiments, the first and second receptor include an intracellular signaling domain of a costimulatory receptor that are different. In one embodiment, the first receptor contains a CD28 costimulatory signaling region and the second receptor contain a 4-1BB co-stimulatory signaling region or vice versa.

In some embodiments, the first and/or second receptor includes both an intracellular signaling domain containing ITAM or ITAM-like motifs and an intracellular signaling domain of a costimulatory receptor.

In some embodiments, the first receptor contains an intracellular signaling domain containing ITAM or ITAM-like motifs and the second receptor contains an intracellular signaling domain of a costimulatory receptor. The costimulatory signal in combination with the activating signal induced in the same cell is one that results in an immune response, such as a robust and sustained immune response, such as increased gene expression, secretion of cytokines and other factors, and T cell mediated effector functions such as cell killing.

In some embodiments, neither ligation of the first receptor alone nor ligation of the second receptor alone induces a robust immune response. In some aspects, if only one receptor is ligated, the cell becomes tolerized or unresponsive to antigen, or inhibited, and/or is not induced to proliferate or secrete factors or carry out effector functions. In some such embodiments, however, when the plurality of receptors are ligated, such as upon encounter of a cell expressing the first and second antigens, a desired response is achieved, such as full immune activation or stimulation, e.g., as indicated by secretion of one or more cytokine, proliferation, persistence, and/or carrying out an immune effector function such as cytotoxic killing of a target cell.

In some embodiments, the two receptors induce, respectively, an activating and an inhibitory signal to the cell, such that binding by one of the receptor to its antigen activates the cell or induces a response, but binding by the second inhibitory receptor to its antigen induces a signal that suppresses or dampens that response. Examples are combinations of activating CARs and inhibitory CARs or iCARs. Such a strategy may be used, for example, in which the activating CAR binds an antigen expressed in a disease or condition but which is also expressed on normal cells, and the inhibitory receptor binds to a separate antigen which is expressed on the normal cells but not cells of the disease or condition.

In some embodiments, the multi-targeting strategy is employed in a case where an antigen associated with a particular disease or condition is expressed on a non-diseased cell and/or is expressed on the engineered cell itself, either transiently (e.g., upon stimulation in association with genetic engineering) or permanently. In such cases, by requiring ligation of two separate and individually specific antigen receptors, specificity, selectivity, and/or efficacy may be improved.

In some embodiments, the plurality of antigens, e.g., the first and second antigens, are expressed on the cell, tissue, or disease or condition being targeted, such as on the cancer cell. In some aspects, the cell, tissue, disease or condition is multiple myeloma or a multiple myeloma cell. In some embodiments, one or more of the plurality of antigens generally also is expressed on a cell which it is not desired to target with the cell therapy, such as a normal or non-diseased cell or tissue, and/or the engineered cells themselves. In such embodiments, by requiring ligation of multiple receptors to achieve a response of the cell, specificity and/or efficacy is achieved.

B. Vectors and Methods for Genetic Engineering

Various methods for the introduction of genetically engineered components, e.g., antigen receptors, e.g., CARs or TCRs, are well known and may be used with the provided methods and compositions. Exemplary methods include those for transfer of nucleic acids encoding the receptors, including via viral, e.g., retroviral or lentiviral, transduction, transposons, and electroporation.

In some embodiments, recombinant nucleic acids are transferred into cultured cells using recombinant infectious virus particles, such as, e.g., vectors derived from simian virus 40 (SV40), adenoviruses, adeno-associated virus (AAV). In some embodiments, recombinant nucleic acids are transferred into T cells using recombinant lentiviral vectors or retroviral vectors, such as gamma-retroviral vectors (see, e.g., Koste et al. (2014) Gene Therapy 2014 Apr. 3. doi: 10.1038/gt.2014.25; Carlens et al. (2000) Exp Hematol 28(10): 1137-46; Alonso-Camino et al. (2013) Mol Ther Nucl Acids 2, e93; Park et al., Trends Biotechnol. 2011 Nov. 29(11): 550-557.

In some embodiments, the retroviral vector has a long terminal repeat sequence (LTR), e.g., a retroviral vector derived from the Moloney murine leukemia virus (MoMLV), myeloproliferative sarcoma virus (MPSV), murine embryonic stem cell virus (MESV), murine stem cell virus (MSCV), spleen focus forming virus (SFFV), or adeno-associated virus (AAV). Most retroviral vectors are derived from murine retroviruses. In some embodiments, the retroviruses include those derived from any avian or mammalian cell source. The retroviruses typically are amphotropic, meaning that they are capable of infecting host cells of several species, including humans. In one embodiment, the gene to be expressed replaces the retroviral gag, pol and/or env sequences. A number of illustrative retroviral systems have been described (e.g., U.S. Pat. Nos. 5,219,740; 6,207,453; 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109.

Methods of lentiviral transduction are known. Exemplary methods are described in, e.g., Wang et al. (2012) *J. Immunother.* 35(9): 689-701; Cooper et al. (2003) *Blood.* 101: 1637-1644; Verhoeyen et al. (2009) *Methods Mol Biol.* 506: 97-114; and Cavalieri et al. (2003) Blood. 102(2): 497-505.

In some embodiments, recombinant nucleic acids are transferred into T cells via electroporation (see, e.g., Chicaybam et al., (2013) *PLoS ONE* 8(3): e60298 and Van Tedeloo et al. (2000) *Gene Therapy* 7(16): 1431-1437). In some embodiments, recombinant nucleic acids are transferred into T cells via transposition (see, e.g., Manuri et al. (2010) Hum Gene Ther 21(4): 427-437; Sharma et al. (2013) *Molec Ther Nucl Acids* 2, e74; and Huang et al. (2009) *Methods Mol Biol* 506: 115-126). Other methods of introducing and expressing genetic material in immune cells include calcium phosphate transfection (e.g., as described in Current Protocols in Molecular Biology, John Wiley & Sons, New York. N.Y.), protoplast fusion, cationic liposome-mediated transfection; tungsten particle-facilitated microparticle bombardment (Johnston, Nature, 346: 776-777 (1990)); and strontium phosphate DNA co-precipitation (Brash et al., Mol. Cell Biol., 7: 2031-2034 (1987)).

Other approaches and vectors for transfer of the nucleic acids encoding the recombinant products are those described, e.g., in International Patent App. Pub. No. WO2014055668, and U.S. Pat. No. 7,446,190.

In some embodiments, the cells, e.g., T cells, may be transfected either during or after expansion e.g. with a T cell receptor (TCR) or a chimeric antigen receptor (CAR). This transfection for the introduction of the gene of the desired receptor can be carried out with any suitable retroviral vector, for example. The genetically modified cell population can then be liberated from the initial stimulus (the CD3/CD28 stimulus, for example) and subsequently be stimulated with a second type of stimulus e.g. via a de novo introduced receptor). This second type of stimulus may include an antigenic stimulus in form of a peptide/MHC molecule, the cognate (cross-linking) ligand of the genetically introduced receptor (e.g. natural ligand of a CAR) or any ligand (such as an antibody) that directly binds within the framework of the new receptor (e.g. by recognizing constant regions within the receptor). See, for example, Cheadle et al., "Chimeric antigen receptors for T-cell based therapy" Methods Mol Biol. 2012; 907:645-66 or Barrett et al., Chimeric Antigen Receptor Therapy for Cancer Annual Review of Medicine Vol. 65: 333-347 (2014).

Among additional nucleic acids, e.g., genes for introduction are those to improve the efficacy of therapy, such as by promoting viability and/or function of transferred cells; genes to provide a genetic marker for selection and/or evaluation of the cells, such as to assess in vivo survival or localization; genes to improve safety, for example, by making the cell susceptible to negative selection in vivo as described by Lupton S. D. et al., *Mol. and Cell Biol.,* 11:6 (1991); and Riddell et al., *Human Gene Therapy* 3:319-338 (1992); see also the publications of PCT/US91/08442 and PCT/US94/05601 by Lupton et al. describing the use of bifunctional selectable fusion genes derived from fusing a dominant positive selectable marker with a negative selectable marker. See, e.g., Riddell et al., U.S. Pat. No. 6,040,177, at columns 14-17.

In some cases, a vector may be used that does not require that the cells, e.g., T cells, are activated. In some such instances, the cells may be selected and/or transduced prior to activation. Thus, the cells may be engineered prior to, or subsequent to the culturing of the cells as described herein, and in some cases at the same time as or during at least a portion of the culturing. In some embodiments, the cells that to be engineered are the cultured cells, or in some cases, cells may be transduced prior to performing the culturing as described herein.

V. Compositions, Formulations and Methods of Administration

Also provided are compositions containing the engineered receptor (e.g., engineered antigen receptor), such as CAR or TCR, and compositions containing the engineered cells, including pharmaceutical compositions and formulations. Also provided are compositions containing a plurality of cultured T cells or target cells produced by any of the methods provided herein, and optionally a pharmaceutically acceptable excipient. Also provided are methods of using and uses of the compositions, such as in the treatment of diseases, conditions, and disorders in which the antigen is expressed, or in detection, diagnostic, and prognostic methods.

A. Compositions/Formulations

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

In some aspects, the choice of carrier is determined in part by the particular cell and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulation or composition may also contain more than one active ingredients useful for the particular indication, disease, or condition being treated with the cells, preferably those with activities complementary to the cell, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. In some embodiments, the cells or antibodies are administered in the form of a salt, e.g., a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

Active ingredients may be entrapped in microcapsules, in colloidal drug delivery systems (for example, liposomes, albumin microspheres, microemulsions, nano-particles and nanocapsules) or in macroemulsions. In certain embodiments, the pharmaceutical composition is formulated as an inclusion complex, such as cyclodextrin inclusion complex, or as a liposome. Liposomes can serve to target the host cells (e.g., T-cells or NK cells) to a particular tissue. Many methods are available for preparing liposomes, such as those described in, for example, Szoka et al., Ann. Rev. Biophys. Bioeng., 9: 467 (1980), and U.S. Pat. Nos. 4,235,871, 4,501,728, 4,837,028, and 5,019,369.

The pharmaceutical composition in some aspects can employ time-released, delayed release, and sustained release delivery systems such that the delivery of the composition occurs prior to, and with sufficient time to cause, sensitization of the site to be treated. Many types of release delivery systems are available and known. Such systems can avoid repeated administrations of the composition, thereby increasing convenience to the subject and the physician.

The pharmaceutical composition in some embodiments contains cells in amounts effective to treat or prevent the disease or condition, such as a therapeutically effective or prophylactically effective amount. Therapeutic or prophylactic efficacy in some embodiments is monitored by periodic assessment of treated subjects. For repeated administrations over several days or longer, depending on the condition, the treatment is repeated until a desired suppression of disease symptoms occurs. However, other dosage regimens may be useful and can be determined. The desired dosage can be delivered by a single bolus administration of the composition, by multiple bolus administrations of the composition, or by continuous infusion administration of the composition.

The cells may be administered using standard administration techniques, formulations, and/or devices. Provided are formulations and devices, such as syringes and vials, for storage and administration of the compositions. Administration of the cells can be autologous or heterologous. For example, immunoresponsive cells or progenitors can be obtained from one subject, and administered to the same subject or a different, compatible subject. Peripheral blood derived immunoresponsive cells or their progeny (e.g., in vivo, ex vivo or in vitro derived) can be administered via localized injection, including catheter administration, systemic injection, localized injection, intravenous injection, or parenteral administration. When administering a therapeutic composition (e.g., a pharmaceutical composition containing a genetically modified immunoresponsive cell), it will generally be formulated in a unit dosage injectable form (solution, suspension, emulsion).

Formulations include those for oral, intravenous, intraperitoneal, subcutaneous, pulmonary, transdermal, intramuscular, intranasal, buccal, sublingual, or suppository administration. In some embodiments, the cell populations are administered parenterally. The term "parenteral," as used herein, includes intravenous, intramuscular, subcutaneous, rectal, vaginal, and intraperitoneal administration. In some embodiments, the cell populations are administered to a subject using peripheral systemic delivery by intravenous, intraperitoneal, or subcutaneous injection.

Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyoi (for example, glycerol, propylene glycol, liquid polyethylene glycol) and suitable mixtures thereof.

Sterile injectable solutions can be prepared by incorporating the cells in a solvent, such as in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin.

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

B. Methods of Administration

Provided are methods of administering the cells, populations, and compositions, and uses of such cells, populations, and compositions to treat or prevent diseases, conditions, and disorders, including cancers. In some embodiments, the cells, populations, and compositions are administered to a subject or patient having the particular disease or condition to be treated, e.g., via adoptive cell therapy, such as adoptive T cell therapy. In some embodiments, cells and compositions prepared by the provided methods, such as engineered compositions and end-of-production compositions following incubation and/or other processing steps, are administered to a subject, such as a subject having or at risk for the disease or condition. In some aspects, the methods thereby treat, e.g., ameliorate one or more symptom of, the disease or condition, such as by lessening tumor burden in a cancer expressing an antigen recognized by an engineered T cell.

Methods for administration of cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8(10):577-85). See, e.g., Themeli et al. (2013) *Nat Biotechnol.* 31(10): 928-933; Tsukahara et al. (2013) *Biochem Biophys Res Commun* 438(1): 84-9; Davila et al. (2013) *PLoS ONE* 8(4): e61338.

As used herein, a "subject" is a mammal, such as a human or other animal, and typically is human. In some embodiments, the subject, e.g., patient, to whom the cells, cell populations, or compositions are administered is a mammal, typically a primate, such as a human. In some embodiments, the primate is a monkey or an ape. The subject can be male or female and can be any suitable age, including infant, juvenile, adolescent, adult, and geriatric subjects. In some embodiments, the subject is a non-primate mammal, such as a rodent.

As used herein, "treatment" (and grammatical variations thereof such as "treat" or "treating") refers to complete or partial amelioration or reduction of a disease or condition or disorder, or a symptom, adverse effect or outcome, or phenotype associated therewith. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. The terms do not imply complete curing of a disease or complete elimination of any symptom or effect(s) on all symptoms or outcomes.

As used herein, "delaying development of a disease" means to defer, hinder, slow, retard, stabilize, suppress and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

"Preventing," as used herein, includes providing prophylaxis with respect to the occurrence or recurrence of a disease in a subject that may be predisposed to the disease but has not yet been diagnosed with the disease. In some embodiments, the provided cells and compositions are used to delay development of a disease or to slow the progression of a disease.

As used herein, to "suppress" a function or activity is to reduce the function or activity when compared to otherwise same conditions except for a condition or parameter of interest, or alternatively, as compared to another condition. For example, cells that suppress tumor growth reduce the rate of growth of the tumor compared to the rate of growth of the tumor in the absence of the cells.

An "effective amount" of an agent, e.g., a pharmaceutical formulation, cells, or composition, in the context of administration, refers to an amount effective, at dosages/amounts and for periods of time necessary, to achieve a desired result, such as a therapeutic or prophylactic result.

A "therapeutically effective amount" of an agent, e.g., a pharmaceutical formulation or cells, refers to an amount effective, at dosages and for periods of time necessary, to achieve a desired therapeutic result, such as for treatment of a disease, condition, or disorder, and/or pharmacokinetic or pharmacodynamic effect of the treatment. The therapeutically effective amount may vary according to factors such as the disease state, age, sex, and weight of the subject, and the populations of cells administered. In some embodiments, the provided methods involve administering the cells and/or compositions at effective amounts, e.g., therapeutically effective amounts.

A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The disease or condition that is treated can be any in which expression of an antigen is associated with and/or involved in the etiology of a disease condition or disorder, e.g. causes, exacerbates or otherwise is involved in such disease, condition, or disorder. Exemplary diseases and conditions can include diseases or conditions associated with malignancy or transformation of cells (e.g. cancer), autoimmune or inflammatory disease, or an infectious disease, e.g. caused by a bacterial, viral or other pathogen. Exemplary antigens, which include antigens associated with various diseases and conditions that can be treated, are described above. In particular embodiments, the chimeric antigen receptor or transgenic TCR specifically binds to an antigen associated with the disease or condition.

Thus, the provided methods and uses include methods and uses for adoptive cell therapy. In some embodiments, the methods include administration of the cells or a composition containing the cells to a subject, tissue, or cell, such as one having, at risk for, or suspected of having the disease, condition or disorder. In some embodiments, the cells, populations, and compositions are administered to a subject having the particular disease or condition to be treated, e.g., via adoptive cell therapy, such as adoptive T cell therapy. In some embodiments, the cells or compositions are administered to the subject, such as a subject having or at risk for the disease or condition, ameliorate one or more symptom of the disease or condition.

In some embodiments, the cell therapy, e.g., adoptive T cell therapy, is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject. The cells can be administered by any suitable means. Dosing and administration may depend in part on whether the administration is brief or chronic. Various dosing schedules include but are not limited to single or multiple administrations over various timepoints, bolus administration, and pulse infusion.

In certain embodiments, the cells, or individual populations of sub-types of cells, are administered to the subject at a range of about one million to about 100 billion cells and/or that amount of cells per kilogram of body weight, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges and/or per kilogram of body weight. Again, dosages may vary depending on attributes particular to the disease or disorder and/or patient and/or other treatments. In some embodiments, the cells are administered as part of a combination treatment, such as simultaneously with or sequentially with, in any order, another therapeutic intervention, such as an antibody or engineered cell or receptor or agent, such as a cytotoxic or therapeutic agent. The cells in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells are administered prior to the one or more additional therapeutic agents. In some embodiments, the cells are administered after the one or more additional therapeutic agents. In some embodiments, the one or more additional agents includes a cytokine, such as IL-2, for example, to enhance persistence. In some embodiments, the methods comprise administration of a chemotherapeutic agent.

Following administration of the cells, the biological activity of the engineered cell populations in some embodiments is measured, e.g., by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable method known in the art, such as cytotoxicity assays described in, for example, Kochenderfer et al., J. Immunotherapy, 32(7): 689-702 (2009), and Herman et al. J. Immunological Methods, 285(1): 25-40 (2004). In certain embodiments, the biological activity of the cells is measured by assaying expression and/or secretion of one or more cytokines, such as CD107a, IFNγ, IL-2, and TNF. In some aspects the biological activity is measured by assessing clinical outcome, such as reduction in tumor burden or load.

In certain embodiments, the engineered cells are further modified in any number of ways, such that their therapeutic or prophylactic efficacy is increased. For example, the engineered CAR or TCR expressed by the population can be conjugated either directly or indirectly through a linker to a targeting moiety. The practice of conjugating compounds, e.g., the CAR or TCR, to targeting moieties is known in the art. See, for instance, Wadwa et al., J. Drug Targeting 3: 111 (1995), and U.S. Pat. No. 5,087,616.

VI. Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

As used herein, the singular forms "a," "an," and "the" include plural referents unless the context clearly dictates otherwise. For example, "a" or "an" means "at least one" or "one or more." It is understood that aspects and variations described herein include "consisting" and/or "consisting essentially of" aspects and variations.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X".

As used herein, a composition refers to any mixture of two or more products, substances, or compounds, including cells. It may be a solution, a suspension, liquid, powder, a paste, aqueous, non-aqueous or any combination thereof.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors." Among the vectors are viral vectors, such as retroviral, e.g., gammaretroviral and lentiviral vectors.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

As used herein, "enriching" when referring to one or more particular cell type or cell population, refers to increasing the number or percentage of the cell type or population, e.g., compared to the total number of cells in or volume of the composition, or relative to other cell types, such as by positive selection based on markers expressed by the population or cell, or by negative selection based on a marker not present on the cell population or cell to be depleted. The term does not require complete removal of other cells, cell type, or populations from the composition and does not require that the cells so enriched be present at or even near 100% in the enriched composition.

As used herein, a statement that a cell or population of cells is "positive" for a particular marker refers to the detectable presence on or in the cell of a particular marker, typically a surface marker. When referring to a surface marker, the term refers to the presence of surface expression as detected by flow cytometry, for example, by staining with an antibody that specifically binds to the marker and detecting said antibody, wherein the staining is detectable by flow cytometry at a level substantially above the staining detected carrying out the same procedure with an isotype-matched control under otherwise identical conditions and/or at a level substantially similar to that for cell known to be positive for the marker, and/or at a level substantially higher than that for a cell known to be negative for the marker.

As used herein, a statement that a cell or population of cells is "negative" for a particular marker refers to the absence of substantial detectable presence on or in the cell of a particular marker, typically a surface marker. When referring to a surface marker, the term refers to the absence of surface expression as detected by flow cytometry, for example, by staining with an antibody that specifically binds to the marker and detecting said antibody, wherein the staining is not detected by flow cytometry at a level substantially above the staining detected carrying out the same procedure with an isotype-matched control under otherwise identical conditions, and/or at a level substantially lower than that for cell known to be positive for the marker, and/or at a level substantially similar as compared to that for a cell known to be negative for the marker.

The term "expression", as used herein, refers to the process by which a polypeptide is produced based on the encoding sequence of a nucleic acid molecule, such as a gene. The process may include transcription, post-transcriptional control, post-transcriptional modification, translation, post-translational control, post-translational modification, or any combination thereof.

As used herein, a control refers to a sample that is substantially identical to the test sample, except that it is not treated with a test parameter, or, if it is a plasma sample, it can be from a normal volunteer not affected with the condition of interest. A control also can be an internal control.

VII. Exemplary Embodiments

Among the provided embodiments are:

1. A method for culturing T cells, the method comprising:

(a) incubating a composition comprising T cells in the presence of a receptor-binding agent which i) is reversibly bound to a reagent comprising a plurality of binding sites capable of reversibly binding to the receptor-binding agent and ii) is capable of specifically binding to a molecule on the surface of the T cells in a manner that induces or modulates a signal in T cells in the composition; and (b) within 5 days after initiation of said incubation, disrupting the reversible binding between the receptor-binding agent and the reagent, thereby generating cultured T cells.

2. The method of embodiment 1, wherein the incubation is performed under conditions in which the receptor-binding agent specifically binds to the molecule, thereby inducing or modulating the signal in one or more T cells in the composition.

3. The method of embodiment 1 or embodiment 2, wherein said disruption is effected greater than 30 minutes after initiation of said incubation.

4. The method of any of embodiments 1-3, wherein:

said disruption is effected between 1 hour and 4 days after initiation of said incubation, between 6 hours and 3 days after initiation of said incubation, between 12 hours and 2 days after initiation of said incubation or between 1 day and 3 days after initiation of said incubation; or said disruption is effected between about 1 hour and about 4 days after initiation of said incubation, between about 6 hours and about 3 days after initiation of said incubation, between about 12 hours and about 2 days after initiation of said incubation or between about 1 day and about 3 days after initiation of said incubation; or said disruption is effected greater than or equal to about 1 hour after initiation of said incubation and within 1 day, 2 days, 3 days or 4 days after initiation of said incubation.

5. The method of any of embodiments 1-4, wherein:

the receptor-binding agent is capable of initiating a TCR/CD3 complex-associated signal in the T cells; and/or the receptor-binding agent specifically binds to a member of a TCR/CD3 complex; and/or the receptor-binding agent specifically binds to CD3.

6. The method of any of embodiments 1-5, wherein the molecule is a component of the TCR/CD3 complex or is CD3.

7. The method of any of embodiments 1-6, wherein the molecule is a first molecule and the receptor-binding agent is further capable of specifically binding to a second molecule on the surface of one or more of the T cells, which second molecule is optionally capable of inducing or enhancing, dampening, or modifying a signal delivered through the first molecule in the T cells.

8. The method of any of embodiments 1-7, wherein:

the receptor-binding agent comprises a binding partner C1; and the plurality of binding sites comprises two or more binding sites, Z1, which each are capable of binding to the binding partner C1 to form the reversible bond between the receptor-binding agent and the reagent.

9. The method of any of embodiments 1-8, wherein said disruption comprises introducing to the cells a composition comprising a substance capable of reversing the bond between the receptor-binding agent and the reagent.

10. The method of any of embodiments 1-9, wherein the receptor-binding agent is a first receptor-binding agent and the incubation is further carried out in the presence of a second receptor-binding agent, which is capable of specifically binding to a second molecule on the surface of one or more of the T cells, which second molecule is optionally capable of enhancing, dampening, or modifying a signal delivered through the first molecule in the T cells.

11. The method of embodiment 10, wherein the reagent comprises a plurality of binding sites capable of reversibly binding to the second receptor-binding agent, whereby the second receptor-binding agent is reversibly bound to the reagent.

12. The method of embodiment 11, wherein the plurality of binding sites capable of reversibly binding to the first receptor-binding agent and the plurality of binding sites capable of reversibly binding to the second receptor-binding agent can be the same or different.

13. The method of embodiment 11 or embodiment 12, wherein:

the second receptor-binding agent comprises a binding partner C1 or C2, which is capable of reversibly binding to the two or more binding sites Z1, whereby the first and second receptor-binding agents are reversibly bound to the reagent via the two or more binding sites Z1; and/or the second receptor-binding agent comprises a binding partner C2 and the reagent further comprises a plurality of binding sites Z2, which is capable of binding to the binding partner C2 to form the reversible bond between the second receptor-binding agent and the reagent.

14. The method of embodiment 13, wherein:

C2 and C1 are the same or substantially the same, or contain the same or substantially the same moiety; and/or Z1 and Z2 are the same or substantially the same or contain the same or substantially the same moiety.

15. The method of any of embodiments 1-14, wherein the reagent is a first reagent and the incubation is carried out in the presence of at least a second reagent which is reversibly bound to the second receptor-binding agent.

16. The method of any of embodiments 10-15, wherein the incubation is performed under conditions in which the second receptor-binding agent specifically binds to the second molecule, thereby inducing or modulating a signal that enhances, dampens, or modifies a signal delivered through the first molecule in the T cells.

17. The method of any of embodiments 7-16, wherein said disruption comprises introducing to the cells a composition comprising a substance capable of reversing the bond between the first receptor-binding agent and the reagent and/or the second receptor-binding agent and the reagent.

18. The method of any of embodiments 7-17, wherein said disruption terminates or lessens the signal induced or modulated by the first receptor-binding agent and terminates or lessens the signal induced or modulated by the second receptor-binding agent.

19. A method for culturing T cells, the method comprising:

(a) incubating a composition comprising T cells in the presence of:

i) a first receptor-binding agent that is capable of specifically binding to a first molecule expressed on the surface of the T cells in a manner that induces or modulates a TCR/CD3 complex-associated signal in the T cell; and ii) a second receptor-binding agent which i) is reversibly bound to a reagent comprising a plurality of binding sites capable of reversibly binding to the second receptor-binding agent and ii) is capable of specifically binding to a second molecule on the surface of the T cells in a manner to induce or modulate a second signal in the T cells to enhance, dampen or modify a signal delivered through the first molecule; and (b) within 5 days after initiation of said incubation, disrupting the reversible binding between the second receptor-binding agent and the reagent, thereby generating cultured T cells.

20. The method of embodiment 19, wherein the incubation is performed under conditions in which the first receptor-binding agent specifically binds to the first molecule and/or the second receptor-binding agent specifically binds to the second molecule, thereby inducing or modulating one or more signals in the T cells.

21. The method of embodiment 19 or embodiment 20, wherein:

the second receptor-binding agent comprises a binding partner C1; and the plurality of binding sites comprises two or more binding sites, Z1, which each are capable of binding to the binding partner C1 to form the reversible bond between the second receptor-binding agent and the reagent.

22. The method of any of embodiments 7-21, wherein:

the second signal is a signal other than a TCR/CD3 complex-associated signal;

the second signal is capable of enhancing or potentiating a TCR/CD3 complex-associated signal; or the second molecule is a costimulatory molecule, accessory molecule, cytokine receptor, chemokine receptor, immune checkpoint molecule or is a member of the TNF family or the TNF receptor family.

23. The method of any of embodiments 7-22, wherein the second molecule is selected from among CD28, CD90 (Thy-1), CD95 (Apo-/Fas), CD137 (4-1BB), CD154 (CD40L), ICOS, LAT, CD27, OX40 and HVEM.

24. The method of any of embodiments 7-23, wherein the second molecule is CD28.

25. The method of any of embodiments 7-24, wherein said disruption comprises introducing to the cells a composition comprising a substance capable of reversing the bond between the second receptor-binding agent and the reagent, which can be the second reagent.

26. The method of any of embodiments 7-25, wherein:

said disruption terminates or lessens the signal induced or modulated by the second receptor-binding agent; or the additional molecule is CD28 and the disruption terminates or lessens the CD28 costimulatory signal in the T cells.

27. The method of any of embodiments 1-26, comprising, after said disruption, further incubating the composition comprising the T cells.

28. The method of embodiment 27, wherein:

the incubation and further incubation are carried out in the same vessel; and/or the further incubation is carried out in the presence of the substance; and/or the method does not comprise removing the substance, receptor-binding agent, second receptor-binding agent and/or reagent from the cell composition prior to the further incubation.

29. The method of any of embodiments 1-28, wherein:

the incubation and/or further incubation is carried out at or about 37° C.±2° C.; and/or the incubation and/or further incubation is carried out in the presence of a further agent that is capable of delivering a signal to T cells.

30. The method embodiment 29, wherein the further agent is capable of enhancing or inducing proliferation of T cells, CD4+ T cells and/or CD8+ T cells.

31. The method of embodiment 30, wherein the further agent is a cytokine selected from among IL-2, IL-15 and IL-7.

32. The method of any of embodiments 27-32, wherein the further incubation is carried out for a time that is no more than 14 days, no more than 12 days, no more than 10 days, no more than 8 days or no more than 6 days.

33. A method for culturing T cells, comprising:

incubating a composition comprising T cells in the presence of a receptor-binding agent that specifically binds to a CD28 molecule on the surface of T cells under conditions to effect signaling through CD28 in the cells; and within 5 days after initiation of said incubation, eliminating or reducing the binding of the receptor-binding agent and the CD28 molecule, whereby the CD28 signaling is terminated or lessened in the cells, thereby generating cultured T cells.

34. The method of embodiment 33, wherein the elimination or reduction is effected within 4 days, within 3 days, within 2 days or within 1 day after initiation of the incubation.

35. The method of embodiment 33 or embodiment 34, wherein the eliminating or reducing comprises:

washing the cells, whereby any receptor-binding agent that is not specifically bound to CD28 is removed or reduced from the composition; or reversing the binding interaction between the receptor-binding agent and the CD28 molecule, optionally further comprising washing the cells to remove or reduce the receptor-binding agent from the composition.

36. The method of any of embodiments 33-35, wherein during at least a portion of the incubation and/or subsequent to the incubation, incubating T cells in the composition in the presence of an agent that specifically binds a molecule of the TCR/CD3 complex, whereby a TCR/CD3 complex-associated signal is induced or modulated in the cells.

37. A method for culturing T cells, comprising incubating a composition comprising T cells in the presence of a receptor-binding agent which is i) reversibly bound to a reagent comprising a plurality of binding sites capable of reversibly binding to the receptor-binding agent; and ii) is capable of specifically binding to a molecule on the surface of the T cells other than CD28 or CD3 in a manner that induces or modulates a signal in T cells, thereby generating cultured T cells.

38. The method of embodiment 37, wherein the incubation is performed under conditions in which the receptor-binding agent specifically binds to the molecule, thereby inducing or modulating the signal in the T cells.

39. The method of embodiment 37 or embodiment 38, wherein the signal is not a TCR/CD3 complex-associated signal.

40. The method of any of embodiments 37-39, wherein the receptor-binding agent comprises a binding partner C1, and the plurality of binding sites comprises two or more binding site, Z1, which each are capable of binding to the binding partner C1 to form the reversible bond between the receptor-binding agent and the reagent.

41. The method of any of embodiments 37-40, wherein the receptor-binding agent is a second receptor-binding agent and the molecule is a second molecule, and the incubation is further carried out in the presence of a first receptor-binding agent, which is capable of specifically binding to a first molecule on the surface of one or more of the T cells, which first molecule is optionally capable of inducing or modulating a first signal in one or more T cells in the composition.

42. The method of embodiment 41, wherein:
the first receptor-binding agent is reversibly bound to the reagent, said reagent comprising a plurality of binding sites for the first receptor-binding agent and the second receptor-binding agent; or
the first receptor-binding agent is reversibly bound to a second reagent comprising a plurality of binding sites capable of reversibly binding to the first receptor-binding agent.

43. The method of embodiment 41 or embodiment 42, wherein:
the first receptor-binding agent is capable of initiating a TCR/CD3 complex-associated signal in the T cells; and/or
the first receptor-binding agent specifically binds to a member of a TCR/CD3 complex; and/or
the first receptor-binding agent specifically binds to CD3.

44. The method of any of embodiments 41-43, wherein:
the specific binding of the second receptor-binding agent to the second molecule is capable of enhancing, dampening or modifying a signal delivered through the first molecule; or
the specific binding of the second receptor-binding agent to the second molecule is capable of enhancing or potentiating a TCR/CD3 complex-associated signal.

45. A method for culturing T cells, comprising incubating a composition comprising T cells in the presence of:
i) a first receptor-binding agent which i) is reversibly bound to a reagent comprising a plurality of binding sites capable of reversibly binding to the first receptor-binding agent and ii) is capable of specifically binding to a first molecule on the surface of the T cells in a manner to induce or modulate a TCR/CD3 complex-associated signal in T cells in the composition; and
ii) a second receptor-binding agent which i) is reversibly bound to the reagent further comprising a plurality of binding sites for the second receptor-binding agent or to a second reagent comprising a plurality of binding sites capable of reversibly binding to the second receptor-binding agent and ii) is capable of specifically binding to a second molecule on the surface of T cells in a manner to induce or modulate a second signal in T cells in the composition, said second molecule being other than CD28, and
wherein the incubation is performed under conditions in which the signal and/or second signal are induced or modulated in T cells in the composition, thereby generating cultured T cells.

46. The method of embodiment 44, wherein the first receptor-binding agent specifically binds to a member of a TCR/CD3 complex and/or the first receptor-binding agent specifically binds to CD3.

47. The method of embodiment 45 or embodiment 46, wherein:
the specific binding of the second receptor-binding agent to the second molecule is capable of inducing or modulating a signal other than a TCR/CD3 complex-associated signal; and/or
the specific binding of the second receptor-binding agent to the second molecule is capable of enhancing, dampening or modifying a signal delivered through the first molecule; or
the specific binding of the second receptor-binding agent to the second molecule is capable of enhancing or potentiating a TCR/CD3 complex-associated signal.

48. The method of any of embodiments 37-47, wherein:
the molecule, which can be the second molecule, is selected from among CD90 (Thy-1), CD95 (Apo-/Fas), CD137, (4-1BB), CD154 (CD40L), ICOS, LAT, CD27, OX40 and HVEM; and/or
the receptor-binding agent, which can be the second receptor-binding agent, specifically binds to CD90 (Thy-1), CD95 (Apo-/Fas), CD137 (4-1BB), CD154 (CD40L), ICOS, LAT, CD27, OX40 or HVEM.

49. The method of any of embodiments 37-48, wherein the molecule, which can be a second molecule, is not CD137 and/or the receptor-binding agent, which can be the second receptor-binding agent, does not specifically bind to CD137.

50. The method of any of embodiments 42-49, wherein:
the first receptor-binding agent and the second receptor-binding agent reversibly bind to the reagent; and
either:
i) the first receptor-binding agent and second receptor-binding agent each individually comprise a binding partner C1, and the plurality of binding sites comprises two or more binding site, Z1, which each are capable of binding to the binding partner C1 to form the reversible bond between the first and second receptor-binding agent and the reagent; or
ii) the first receptor-binding agent comprises a binding partner C1, the second receptor-binding agent comprises a binding partner C2, and the plurality of binding sites comprises two or more binding sites, Z1, which each are capable of binding to the binding partner C1 and the binding partner C2 to form the reversible bond between the first and second receptor-binding agent and the reagent; or
iii) the first receptor-binding agent comprises a binding partner C1, the second receptor binding agent comprises a binding partner C2, and the plurality of binding sites comprises two or more binding site, Z1, which each are capable of binding to the binding partner C1 to form the reversible bond between the first receptor-binding agent and the reagent and two or more binding site, Z2, which each are capable of binding to the binding partner C2 to form the reversible bond between the second receptor-binding agent and the reagent.

51. A method for culturing target cells, comprising incubating a composition comprising target cells in the presence of a receptor-binding agent that is i) reversibly bound to a reagent that is a streptavidin analog or mutein comprising a plurality of binding sites capable of reversibly binding to the receptor-binding agent; and ii) is capable of specifically binding to a molecule on the surface of the target cells in a manner that induces or modulates a signal in target cells in the composition, wherein the mutein streptavidin comprises a net negative charge or exhibits an isoelectric point of less than the isoelectric point of the streptavidin mutein set forth in SEQ ID NO:4 or SEQ ID NO:6, thereby generating cultured target cells.

52. A method for culturing target cells, comprising incubating a composition comprising target cells in the presence of a receptor-binding agent that is i) reversibly bound to a reagent that is a streptavidin analog or mutein comprising a plurality of binding sites capable of reversibly binding to the receptor-binding agent; and ii) is capable of specifically binding to a molecule on the surface of the target cells in a manner that induces or modulates a signal in target cells in the composition, wherein the streptavidin analog or mutein exhibits a higher affinity for a streptavidin-binding peptide comprising the sequence of amino acids Trp-Ser-His-Pro-Gln-Phe-Glu-Lys (SEQ ID NO: 8) than a streptavidin or mutein comprising the sequence of amino acids set forth in any of SEQ ID NOS: 1-6, thereby generating cultured target cells.

53. The method of embodiment 51 or embodiment 52, wherein the incubation is performed under conditions in which the receptor-binding agent specifically binds to the molecule, thereby inducing or modulating the signal in one or more target cells in the composition.

54. The method of any of embodiments 51-53, wherein:
the plurality of binding sites comprise two or more binding sites, Z1; and
the receptor-binding agent comprises a binding partner C1, which is capable of reversibly binding to the binding site Z1, wherein the reversible binding between C1 and Z1 effects the reversible binding between the receptor-binding agent and the reagent.

55. The method of embodiment 54, wherein the streptavidin analog or mutein comprises a plurality of binding sites Z1, wherein a plurality of receptor-binding agents are reversibly bound to the reagent.

56. The method of any of embodiments 51-56, wherein:
the target cells comprise blood cells;
the target cells comprise leukocytes;
the target cells comprise lymphocytes;
the target cells comprise B cells;
the target cells comprise a B cell population;
the target cells comprise T cells;
the target cells comprise a T cell population; and/or
the target cells comprise natural killer (NK) cells.

57. The method of any of embodiments 51-56, wherein the target cells comprise antigen-specific T cells or a population thereof, a T helper cell or population thereof, a cytotoxic T cell or population thereof, a memory T cell or population thereof, a regulatory T cell or population thereof, an NK cell or population thereof, antigen-specific B cells or a population thereof, a memory B cell or population thereof, or a regulatory B cell or population thereof.

58. The method of any of embodiments 51-57, wherein the target cells are T cells.

59. The method of any of embodiments 51-58, wherein the molecule is present on the surface of T cells, wherein the receptor-binding agent is capable of inducing or modulating a signal in T cells in the composition.

60. The method of any of embodiments 51-59, wherein:
the receptor-binding agent is capable of initiating a TCR/CD3 complex-associated signal in the T cells; and/or
the receptor-binding agent specifically binds to a member of a TCR/CD3 complex; and/or
the receptor-binding agent, specifically binds to CD3.

61. The method of any of embodiments 51-60, wherein the molecule is a first molecule and the receptor-binding agent is capable of specifically binding to the first molecule and a second molecule on the surface of one or more of the target cells, which binding to the second molecule is optionally capable of enhancing, dampening, or modifying a signal delivered through the first molecule.

62. The method of any of embodiments 51-61, wherein the receptor-binding agent is a first receptor-binding agent and the incubation is further carried out in the presence of a second receptor-binding agent, which is capable of specifically binding to a second molecule on the surface of one or more of the target cells, which binding to the second molecule is optionally capable of inducing or modulating a signal to enhance, dampen, or modify a signal delivered through the first molecule.

63. The method of embodiment 62, wherein the incubation is performed under conditions in which the second receptor-binding agent specifically binds to the second molecule, thereby inducing or modulating a signal in target cells in the composition to enhance, dampen or modify a signal delivered through the first molecule.

64. The method of embodiment 62 or embodiment 63, wherein the streptavidin mutein or analog comprises a plurality of binding sites capable of reversibly binding to the second receptor-binding agent, whereby the second receptor-binding agent is reversibly bound to the streptavidin mutein or analog.

65. The method of embodiment 64, wherein the second receptor-binding agent comprises a binding partner C1 or C2, which is capable of reversibly binding to the two or more binding sites Z2 present in the streptavidin analog or mutein.

66. The method of any of embodiments 61-65, wherein:
the additional molecule is selected from among CD28, CD90 (Thy-1), CD95 (Apo-/Fas), CD137 (4-1BB), CD154 (CD40L), ICOS, LAT, CD27, OX40 and HVEM; and/or
the second receptor-binding agent specifically binds to CD28, CD90 (Thy-1), CD95 (Apo-/Fas), CD137 (4-1BB), CD154 (CD40L), ICOS, LAT, CD27, OX40 or HVEM.

67. The method of any of embodiments 61-66, wherein:
the additional molecule is selected from among CD40 and CD137; and/or
the second receptor-binding agent specifically binds to CD40 or CD137.

68. The method of any of embodiments 11-67, wherein the second receptor-binding agent comprises a plurality of different receptor-binding agents, each of which is capable of individually binding to the same or different second molecule on the surface of T cells in the composition to collectively induce or modulate one or more signals in the cells.

69. The method of any of embodiments 37-68, further comprising disrupting the reversible binding between the first and/or second receptor-binding agent and the reagent.

70. The method of embodiment 69, wherein the disruption is effected within 14 days after initiation of the incubation, within 12 days after initiation of the incubation, within 10 days after initiation of the incubation within 8 days after initiation of the incubation or within 6 days after initiation of the incubation.

71. The method of any of embodiments 37-70, wherein at least a portion of the incubation is carried out in the presence of a further agent that is capable of delivering a signal to T cells.

72. The method embodiment 71, wherein the further agent is capable of enhancing or inducing proliferation of T cells, CD4+ T cells and/or CD8+ T cells.

73. The method of embodiment 71 or embodiment 72, wherein the further agent is a cytokine selected from among IL-2, IL-15 and IL-7.

74. The method of any of embodiments 71-73, wherein the further agent does not specifically bind to CD28 and/or induce CD28 signaling.

75. The method of any of embodiments 1-74, wherein the T cells or target cells are primary cells from a subject 76. The method of any of embodiments 1-75, wherein the T cells or target cells are directly isolated from a subject.

77. The method of any of embodiments 1-50 and 57-76, wherein the T cells are unfractionated T cells, are enriched or isolated CD3+ T cells, are enriched or isolated CD4+ T cells or are enriched or isolated CD8+ T cells.

78. The method of any of embodiments 1-50 and 57-77, wherein prior to the incubating the T cells are not enriched for CD62L+ cells and/or are not enriched for naïve T cells.

79. The method of any of embodiments 1-78, wherein the T cells or target cells are human cells.

80. The method of any of embodiments 1-80, wherein:
the reagent has a size that is less than 20 nm, less than 10 nm, less than 5 nm or less than 1 nm; or
the reagent has a density of less than 1.2 g/cm$^3$ or less than 1.0 g/cm$^3$.

81. The method of any of embodiments 1-80, wherein the reagent is not bound to a support or a solid support during said incubation.

82. The method of any of embodiments 1-80, wherein the reagent is bound to a support during at least a portion of the incubation, whereby a plurality of the T cells or target cells are reversibly immobilized on the support during at least a portion of the incubation.

83. The method of embodiment 82, wherein the support is a solid support or a stationary phase.

84. The method of any of embodiments 1-83, wherein:
the receptor-binding agent, which can be the first receptor-binding agent, comprises only one of said binding sites, B2; and/or
the receptor-binding agent, which can be the first receptor-binding agent, specifically binds to the molecule in a monovalent manner.

85. The method of any of embodiments 1-84, wherein:
the second receptor-binding agent comprises only one of said binding sites, B4; and/or
the second receptor-binding agent specifically binds to the molecule in a monovalent manner.

86. The method of embodiment 84 or embodiment 85, wherein the binding site, B2 and/or B4, comprises an antibody combining site.

87. The method of any of embodiments 1-86, wherein the receptor-binding agent, which can be a first receptor-binding agent, and/or the second receptor-binding agent each individually are selected from among an antibody fragment, a monovalent antibody fragment, a proteinaceous binding molecule with antibody-like binding properties, a molecule containing Ig domains, a cytokine, a chemokine, an aptamer, and MHC molecule and binding fragments thereof.

88. The method of any of embodiments 1-87, wherein:
the receptor-binding agent, which can be the first receptor-binding agent, and/or the second receptor-binding agent comprise an antibody fragment;
the receptor-binding agent, which can be a first receptor-binding agent, and/or the second receptor-binding agent comprise a Fab fragment;
the receptor-binding agent, which can be the first receptor-binding agent, and/or the second receptor-binding agent are is a divalent antibody fragment selected from among a F(ab')$_2$-fragment and a divalent single-chain Fv (scFv) fragment;
the receptor-binding agent, which can be the first receptor-binding agent, and/or the second receptor-binding agent is a monovalent antibody fragment selected from among a Fab fragment, an Fv fragment and an scFv fragment; and/or
the receptor-binding agent, which can be the first receptor-binding agent, and/or the second receptor-binding agent is a proteinaceous binding molecule with antibody-like binding properties selected from among aptamers, muteins based on a polypeptide of the lipocalin family, glubodies, proteins based on the ankyrin scaffold, proteins based on the crystalline scaffold, adnectins and avimers.

89. The method of any of embodiments 1-88, wherein:
the receptor-binding agent, which can be the first receptor-binding agent, comprises an agent that specifically binds to CD3, which optionally is selected from the group consisting of an anti-CD3-antibody, a divalent antibody fragment of an anti-CD3 antibody, a monovalent antibody fragment of an anti-CD3-antibody, and a proteinaceous CD3 binding molecule with antibody-like binding properties, and/or
the second receptor-binding agent comprises an agent that specifically binds to CD28, CD90, CD95, CD137, CD154, ICOS, LAT, CD27, OX40 and/or HVEM, which optionally is selected from the group consisting of an anti-CD28-antibody, a divalent antibody fragment of an anti-CD28 antibody, an antibody fragment of an anti-CD28-antibody, a proteinaceous CD28 binding molecule with antibody-like binding properties, an anti-CD90-antibody, a divalent antibody fragment of an anti-CD90 antibody, an antibody fragment of an anti-CD90-antibody, a proteinaceous CD90 binding molecule with antibody-like binding properties, an anti-CD95-antibody, a divalent antibody fragment of an anti-CD95 antibody, an antibody fragment of an anti-CD95-antibody, a proteinaceous CD95 binding molecule with antibody-like binding properties, an anti-CD154-antibody, a divalent antibody fragment of an anti-CD154 antibody, a monovalent antibody fragment of an anti-CD154-antibody, a proteinaceous CD154 binding molecule with antibody-like binding properties, an anti-CD137-antibody, a divalent antibody fragment of an anti-CD137 antibody, a monovalent antibody fragment of an anti-CD137-antibody, a proteinaceous CD137 binding molecule with antibody-like binding properties, an anti-ICOS-antibody, a divalent antibody fragment of an anti-ICOS antibody, an antibody fragment of an anti-ICOS-antibody, a proteinaceous ICOS binding molecule with antibody-like binding properties, an anti-LAT-antibody, a divalent antibody fragment of an anti-LAT antibody, an antibody fragment of an anti-LAT-antibody, a proteinaceous LAT binding molecule with antibody-like binding properties, an anti-CD27-antibody, a divalent antibody fragment of an anti-CD27 antibody, an antibody fragment of an anti-CD27-antibody, a proteinaceous CD27 binding molecule with antibody-like binding properties, an anti-OX40-antibody, a divalent antibody fragment of an anti-OX40 antibody, an antibody fragment of an anti-OX40-antibody, a proteinaceous OX40 binding molecule with antibody-like binding properties, an anti-HVEM-antibody, a divalent antibody fragment of an anti-HVEM antibody, an antibody fragment of an anti-HVEM-antibody, a proteinaceous HVEM binding molecule with antibody-like binding properties, and 4-1BB ligand, and any mixture thereof.

90. The method of any of embodiments 1-50 and 68-89, wherein the reagent is or comprises streptavidin, avidin, an analog or mutein of streptavidin that reversibly binds biotin, a biotin analog or a biologically active fragment thereof; an analog or mutein of avidin or streptavidin that reversibly binds a streptavidin-binding peptide; a reagent that comprises at least two chelating groups K, wherein the at least two chelating groups are capable of binding to a transition metal ion; an agent capable of binding to an oligohistidine affinity tag; an agent capable of binding to a glutathione-S-transferase; calmodulin or an analog thereof; an agent capable of binding to calmodulin binding peptide (CBP); an agent capable of binding to a FLAG-peptide; an agent capable of binding to an HA-tag; an agent capable of binding to maltose binding protein (MBP); an agent capable of binding to an HSV epitope; an agent capable of binding to a myc epitope; or an agent capable of binding to a biotinylated carrier protein.

91. The method of any of embodiments 1-94, wherein:
the reagent is or comprises a streptavidin analog or mutein or an avidin analog or mutein that reversibly binds to biotin or a biologically active fragment;

the reagent is or comprises a streptavidin analog or mutein or an avidin analog or mutein that reversibly binds to a biotin analog or a biologically active fragment; and/or the reagent is or comprises a streptavidin analog or mutein or an avidin analog or mutein that reversibly binds to a streptavidin-binding peptide.

92. The method of any of embodiments 1-91, wherein the reagent is an oligomer or polymer of streptavidin, avidin, an analog or mutein of streptavidin that reversibly binds biotin or a biologically active fragment; a streptavidin or avidin analog or mutein that reversibly binds a streptavidin-binding peptide; a reagent that comprises at least two chelating groups K, wherein the at least two chelating groups are capable of binding to a transition metal ion; an agent capable of binding to an oligohistidine affinity tag; an agent capable of binding to a glutathione-S-transferase; calmodulin or an analog thereof; an agent capable of binding to calmodulin binding peptide (CBP); an agent capable of binding to a FLAG-peptide; an agent capable of binding to an HA-tag; an agent capable of binding to maltose binding protein (MBP); an agent capable of binding to an HSV epitope; an agent capable of binding to a myc epitope; or an agent capable of binding to a biotinylated carrier protein.

93. The method of any of embodiments 1-92, wherein the reagent comprises an oligomer or polymer of streptavidin, avidin, a streptavidin analog or mutein or and an avidin analog or mutein.

94. The method of embodiment 92 or embodiment 93, wherein individual molecules of the oligomer or polymer are crosslinked by a polysaccharide or a bifunctional linker.

95. The method of any of embodiments 1-94, wherein the plurality of binding sites comprises at least 2, 4, 8, 12, 16, 20, 24, 28, 32, 36, 40, 44, 48, 52, 56, 60, 64, 72 or more binding sites.

96. The method of any of embodiments 90-95, wherein the streptavidin-binding peptide is selected from the group consisting of Trp-Ser-His-Pro-Gln-Phe-Glu-Lys (SEQ ID NO: 8), Trp-Ser-His-Pro-Gln-Phe-Glu-Lys-(GlyGlyGlySer)$_3$-Trp-Ser-His-Pro-Gln-Phe-Glu-Lys (SEQ ID NO: 17), Trp-Ser-His-Pro-Gln-Phe-Glu-Lys-(GlyGlyGlySer)$_2$-Trp-Ser-His-Pro-Gln-Phe-Glu-Lys (SEQ ID NO: 18) and Trp-Ser-His-Pro-Gln-Phe-Glu-Lys-(GlyGlyGlySer)$_2$Gly-Gly-Ser-Ala-Trp-Ser-His-Pro-Gln-Phe-Glu-Lys (SEQ ID NO: 19).

97. The method of any of embodiments 1-96, wherein:
the reagent comprises a streptavidin analog or mutein comprising the amino acid sequence Val$^{44}$-Thr$^{45}$-Ala$^{46}$-Arg$^{47}$ or Ile$^{44}$-Gly$^{45}$-Ala$^{46}$-Arg$^{47}$ at sequence positions corresponding to positions 44 to 47 with reference to positions in streptavidin in the sequence of amino acids set forth in SEQ ID NO:1; or
the streptavidin analog or mutein comprises the amino acid sequence Val$^{44}$-Thr$^{45}$-Ala$^{46}$-Arg$^{47}$ at sequence positions corresponding to positions 44 to 47 with reference to positions in streptavidin in the sequence of amino acids set forth in SEQ ID NO:1.

98. The method of any of embodiments 1-51 and 68-97, wherein the streptavidin analog or mutein comprises:
a) the sequence of amino acids set forth in any of SEQ ID NOS: 3-6, 27 and 28;
b) a sequence of amino acids that exhibits at least 85%, 86%, 87%, 88%, 89%, 89%, 90%, 91%, 92%, 93%, 94%, 95%, 96%, 97%, 98%, 99% or more sequence identity to any of SEQ ID NOS:3-6, 27 and 28 and contains the amino acid sequence corresponding to Val$^{44}$-Thr45-Ala46-Arg$^{47}$ or Ile$^{44}$-Gly$^{45}$-Ala$^{46}$-Arg$^{47}$ and that reversibly binds to biotin or a biologically active form thereof, a biotin analog or mutein or a biologically active fragment thereof or a streptavidin-binding peptide; or
c) a functional fragment of a) or b) that reversibly binds to biotin or a biologically active form thereof, a biotin analog or mutein or a biologically active fragment thereof or a streptavidin-binding peptide.

99. The method of embodiment 97 or embodiment 98, wherein the streptavidin analog or mutein further comprises an amino acid replacement or replacements at a position corresponding to 117, 120 and/or 121 with reference to positions in streptavidin in the sequence of amino acids set forth in SEQ ID NO:1.

100. The method of embodiment 99, wherein:
the amino acid replacement or replacements are selected from among Glu117, Asp117, Arg117, Ser120, Ala120, Gly120, Trp121, Tyr121 or Phe121; or
the amino acid replacement or replacements are selected from one or more of Glu117, Gly120 or Tyr121; or
the amino acid replacements are selected from Glu117, Gly120 or Tyr121.

101. The method of any of embodiments 51-100, wherein the streptavidin analog or mutein comprises:
a) the sequence of amino acids set forth in SEQ ID NO: 27 or 28;
b) a sequence of amino acids that exhibits at least 85%, 86%, 87%, 88%, 89%, 89%, 90%, 91%, 92%, 93%, 94%, 95%, 96%, 97%, 98%, 99% or more sequence identity to SEQ ID NOS:28 and contains the amino acid sequence corresponding to Val$^{44}$, Thr$^{45}$, Ala$^{46}$, Arg$^{47}$, Glu$^{117}$, Gly$^{120}$ and Tyr$^{121}$ and reversibly binds to biotin or a biologically active fragment, a biotin analog or mutein or a biologically active fragment thereof or a streptavidin-binding peptide; or
c) a functional fragment of a) or b) that reversibly binds to biotin or a biologically active fragment, a biotin analog or mutein or a biologically active fragment thereof or a streptavidin-binding peptide.

102. The method of any of embodiments 1-101, wherein the binding partner C1 and/or the binding partner C2, independently, comprises a streptavidin-binding peptide selected from the group consisting of Trp-Ser-His-Pro-Gln-Phe-Glu-Lys (SEQ ID NO: 8), Trp-Ser-His-Pro-Gln-Phe-Glu-Lys-(GlyGlyGlySer)$_3$-Trp-Ser-His-Pro-Gln-Phe-Glu-Lys (SEQ ID NO: 17), Trp-Ser-His-Pro-Gln-Phe-Glu-Lys-(GlyGlyGlySer)$_2$-Trp-Ser-His-Pro-Gln-Phe-Glu-Lys (SEQ ID NO: 18) and Trp-Ser-His-Pro-Gln-Phe-Glu-Lys-(GlyGlyGlySer)$_2$Gly-Gly-Ser-Ala-Trp-Ser-His-Pro-Gln-Phe-Glu-Lys (SEQ ID NO: 19);

103. The method of any of embodiments 1-36 and 69-102, wherein said disruption comprises introducing to the cells a composition comprising a substance capable of reversing the bond between the receptor-binding agent, which can be the first receptor-binding agent, and/or the second-receptor-binding agent and the reagent.

104. The method of embodiment 103, wherein the substance is a free binding partner and/or is a competition agent.

105. The method of embodiment 103 or embodiment 104, wherein the substance in the composition is not detrimental to the T cells or to the target cells and/or wherein the addition of said substance does not reduce the percentage of surviving T cells or target cells to less than 90%, 80%, 70%, 60%, or 50%, as compared to incubation of the T cells or target cells, respectively, under comparable or the same conditions, without the substance.

106. The method of any of embodiments 1-36 and 69-105, wherein said disruption terminates or lessens the signal induced or modulated by one or both of the receptor-binding agent or second receptor-binding agent in the T cells or the target cells.

107. The method of any of embodiments 10-18, 22-32 and 69-107, wherein:

the reagent is or comprises a streptavidin, avidin, a streptavidin analog or mutein or and an avidin analog or mutein or biologically active fragments thereof; and the substance comprises a streptavidin-binding peptide, biotin or a biologically active fragment, optionally a D-biotin, or a biotin analog or biologically active fragment.

108. The method of embodiment 107, wherein:

the substance is a streptavidin-binding peptide is selected from the group consisting of Trp-Ser-His-Pro-Gln-Phe-Glu-Lys (SEQ ID NO: 8), Trp-Ser-His-Pro-Gln-Phe-Glu-Lys-(GlyGlyGlySer)$_3$-Trp-Ser-His-Pro-Gln-Phe-Glu-Lys (SEQ ID NO: 17), Trp-Ser-His-Pro-Gln-Phe-Glu-Lys-(GlyGlyGlySer)$_2$-Trp-Ser-His-Pro-Gln-Phe-Glu-Lys (SEQ ID NO: 18) and Trp-Ser-His-Pro-Gln-Phe-Glu-Lys-(GlyGlyGlySer)$_2$Gly-Gly-Ser-Ala-Trp-Ser-His-Pro-Gln-Phe-Glu-Lys (SEQ ID NO: 19); and/or the substance is C1 or an analog thereof or is C2 or an analog thereof.

109. The method of any of embodiments 1-108, wherein:

the dissociation constant ($K_D$) for the reversible binding between said binding site Z1 and said binding partner C1 and/or for the reversible binding between said binding site Z2 and said binding partner C2 is in the range of 10-2 M to 10-13 M.

110. The method of any of embodiments 1-109, wherein:

prior to the incubation, contacting cells with a selection agent that specifically binds to a marker comprised by T cells or target cells of the composition, thereby generating or obtaining the composition comprising the T cells or target cells; or at least a portion of the incubation is carried out further in the presence of a selection agent that specifically binds to a marker comprised by T cells or target cells of the composition, wherein the cultured T cells are enriched for T cells or target cells comprising the marker.

111. The method of embodiment 110, wherein:

the selection agent is reversibly bound to the reagent, said reagent further comprising a plurality of binding sites capable of specifically binding the selection agent; or the selection agent is reversibly bound to a second reagent comprising a plurality of binding sites capable of specifically binding to the selection agent.

112. The method of any of embodiments 1-110, wherein the induction or modulation of the signal effects an increase in expansion (proliferation) and/or activation of the cultured T cells compared to incubation of T cells in the absence of the induction or modulation of the signal.

113. The method of embodiment 112, wherein the increase is at least 2-fold, 3-fold, 4-fold, 5-fold, 6-fold, 7-fold, 8-fold, 9-fold, 10-fold or greater.

114. The method of any of embodiments 7-113, wherein the induction or modulation of the additional or second signal increases expansion (proliferation) and/or activation of the T cells compared to incubation of T cells in the absence of the induction or modulation of the additional or second signal.

115. The method of embodiment 114, wherein the increase is at least 2-fold, 3-fold, 4-fold, 5-fold, 6-fold, 7-fold, 8-fold, 9-fold, 10-fold or greater.

116. The method of any of embodiments 1-115, wherein the method increases expansion and/or proliferation of T cells in the composition, alters the metabolic profile of T cells in the composition, alters the subset of CD8+ T cells in the composition; and/or increases the percentage of long-lived memory T cells in the composition, each compared to the T cells in the composition prior to the incubation, subsequent to the incubation but in the absence of the disruption or subsequent to the incubation but in the presence of an agent that specifically binds CD28 and/or induces or modulates CD28 signaling.

117. The method of any of embodiments 1-116, wherein the methods result in cultured T cells in which:

the number or percentage of CD3+ T cells, CD4+ T cells or CD8+ cells is increased at least 2-fold, 3-fold, 4-fold, 5-fold, 6-fold, 7-fold, 8-fold, 9-fold or 10-fold compared to the number or percentage of CD3+ T cells, CD4+ T cells or CD8+ T cells, respectively, in the composition prior to the incubation, subsequent to the incubation but in the absence of the disruption, or subsequent to an analogous incubation but performed in the presence of an agent that specifically binds CD28 and/or induces or modulates CD28 signaling;

the ratio of CD8+ T cells or the relative or normalized ratio of CD8+ T cells in the composition is increased at least 2-fold, 3-fold, 4-fold, 5-fold, 6-fold, 7-fold, 8-fold, 9-fold or 10-fold compared to the ratio or the relative or normalized ratio of CD8+ T cells in the composition prior to the incubation, subsequent to the incubation but in the absence of the disruption, or subsequent to an analogous incubation but in the presence of an agent that specifically binds CD28 and/or induces or modulates CD28 signaling;

the number or percentage of CD62L+, optionally long-lived memory T cells or memory stem cells ($T_{SCM}$), in the composition is increased at least 2-fold, 3-fold, 4-fold, 5-fold, 6-fold, 7-fold, 8-fold, 9-fold or 10-fold compared to the number or percentage of the corresponding population of cells, either CD62L+, long-lived memory T cells or $T_{SCM}$, in the composition prior to the incubation, subsequent to the incubation but in the absence of the disruption, or subsequent to an analogous incubation but in the presence of an agent that specifically binds CD28 and/or induces or modulates CD28 signaling.

118. The method of any of embodiments 1-117, wherein the cultured T cells comprise greater than 35%, 40%, 45%, 50%, 60%, 70%, 80% or 90% of a T cell subset comprising a phenotype that is surface positive for CD62L (CD62L+) as a percentage of the total T cells in the composition or the total cells in the composition.

119. The method of embodiment 118, wherein the T cell subset further comprises a phenotype comprising:

a) CD127+; and/or b) any one or more of CD45RA+, CD45RO−, CCR7+ and CD27+ and any one or more of t-bet$^{low}$, IL-7Rα+, CD95+, IL-2Rβ+, CXCR3+ and LFA-1+.

120. The method of embodiment 118 or embodiment 119, wherein the T cell subset:

a) comprises a low level of TCR rearrangement excisions circles (TREC); and/or b) expresses a proliferation marker, which optionally is Ki-67; and/or c) exhibits the capacity to proliferate in the presence of a stimulatory agent; and/or d) exhibits the capacity to produce a cytokine selected from among IFN-gamma, TNF and IL-2 in the presence of a stimulatory agent.

121. The method of embodiment 120, wherein the stimulatory agent is an antigen, a homeostatic cytokine, optionally IL-15 and/or IL-17, or is an agent that is capable of initiating a TCR/CD3 complex-associated signal in the T cells.

122. The method of any of embodiments 118-121, wherein the T cell subset is or comprises long-lived memory T cells.

123. The method of any of embodiments 118-122, wherein the T cell subset is or comprises T memory stem cells ($T_{SCM}$).

124. The method of any of embodiments 1-123, further comprising introducing a recombinant nucleic acid molecule into T cells or target cells of the population, which nucleic acid molecule encodes a recombinant protein, whereby cells express the recombinant protein.

125. The method of embodiment 124, wherein the recombinant receptor is a chimeric antigen receptor or transgenic T cell receptor (TCR).

126. The method of any of embodiments 1-125, wherein the method is performed in vitro or ex vivo.

127. The method of any of embodiments 1-126, further comprising administering the cultured cells to a subject having a disease or condition.

128. A composition, comprising a plurality of cultured T cells or target cells produced by the method of any of embodiments 1-127, and optionally a pharmaceutically acceptable excipient.

129. The composition of embodiment 128, wherein after addition of the substance, the cells have not been incubated in vitro or ex vivo at a temperature greater than 30° C. for more than 24 hours, more than 48 hours, more than 72 hours or more than 96 hours.

130. An article of manufacture, comprising:
a) a reagent comprising a plurality of binding sites capable of binding to a receptor-binding agent; and
b) the receptor-binding agent which i) is reversibly bound to the reagent and ii) is capable of specifically binding to a molecule on the surface of T cells in a manner that induces or modulates a signal in T cells, wherein the molecule is not CD28 or CD3.

131. The article of manufacture of embodiment 130, wherein:
binding the molecule induces or modulates a signal in a T cell other than a TCR/CD3 complex-associated signal; and/or
binding the molecule enhances or potentiates a TCR/CD3 complex-associated signal.

132. The article of manufacture of embodiment 130 or embodiment 131, wherein the molecule is selected from among CD90 (Thy-1), CD95 (Apo-/Fas), CD137 (4-1BB), CD154 (CD40L), ICOS, LAT, CD27, OX40 and HVEM.

133. The article of manufacture of any of embodiments 130-132, wherein the molecule is not CD137.

134. An article of manufacture, comprising:
a) a reagent that is a streptavidin analog or mutein comprising a plurality of binding sites capable of binding to an agent, wherein the streptavidin analog or mutein comprises a net negative charge or exhibits an isoelectric point less than the streptavidin mutein comprising the sequence of amino acids set forth in SEQ ID NO:4 or 6 and/or exhibits a higher affinity for a streptavidin-binding peptide comprising the sequence of amino acids Trp-Ser-His-Pro-Gln-Phe-Glu-Lys (SEQ ID NO: 8) than a streptavidin or mutein comprising the sequence of amino acids set forth in SEQ ID NO: 4 or 6; and
b) the agent which i) is reversibly bound to the reagent and ii) is capable of specifically binding to a molecule on the surface of a cell.

135. The article of manufacture of any of embodiments 130-134, wherein:
the receptor-binding agent or agent comprises a binding partner C1; and
the plurality of binding sites comprises two or more binding site, Z1, which each are capable of binding to the binding partner C1 to form the reversible bond between the receptor-binding agent or agent and the reagent.

136. The article of manufacture of any of embodiments 130-133, wherein the receptor-binding agent is a second receptor-binding agent and the molecule is a second molecule, and the reagent further comprises: c) a plurality of binding sites capable of reversibly binding to a first receptor-binding agent and d) the first receptor-binding agent which i) is reversibly bound to the reagent and ii) is capable of specifically binding to a first molecule on the surface of a T cell.

137. The article of manufacture of embodiment 134 or embodiment 136, wherein the agent or the first receptor-binding agent specifically binds to a member of a TCR/CD3 complex and/or the first receptor-binding agent specifically binds to CD3.

138. The article of manufacture of embodiment 136 or embodiment 137, wherein:
i) the first receptor-binding agent and second receptor-binding agent each individually comprise a binding partner C1, and the plurality of binding sites comprises two or more binding site, Z1, which each are capable of binding to the binding partner C1 to form the reversible bond between the first and second receptor-binding agent and the reagent; or
ii) the first receptor-binding agent comprises a binding partner C1, the second receptor-binding agent comprises a binding partner C2, and the plurality of binding sites comprise two or more binding sites, Z1, which each are capable of binding to the binding partner C1 and the binding partner C2 to form the reversible bond between the first and second receptor-binding agent and the reagent; or
iii) the first receptor-binding agent comprises a binding partner C1, the second receptor binding agent comprises a binding partner C2, and the plurality of binding sites comprises two or more binding site, Z1, which each are capable of binding to the binding partner C1 to form the reversible bond between the first receptor-binding agent and the reagent and two or more binding site, Z2, which each are capable of binding to the binding partner C2 to form the reversible bond between the second receptor-binding agent and the reagent.

139. The article of manufacture of any of embodiments 130-139, wherein:
the reagent has a size that is less than 20 nm, less than 10 nm, less than 5 nm or less than 1 nm; or
the reagent has a density of less than 1.2 g/cm$^3$ or less than 1.0 g/cm$^3$.

140. The article of manufacture of any of embodiments 130-139, wherein the reagent is not bound to a support or solid support.

141. The article of manufacture of any of embodiments 130-140, wherein the reagent is bound or immobilized to a support.

142. The article of manufacture of embodiment 141, wherein the support is a solid support or a stationary phase.

143. The article of manufacture of embodiment 141 or embodiment 142, wherein the support comprises a bead, a particle, a nanoparticle or a microsphere.

144. The article of manufacture of any of embodiments 130-143, wherein the agent, the receptor-binding agent, which can be a first receptor-binding agent, and/or the second receptor-binding agent each individually are selected from among an antibody fragment, a monovalent antibody fragment, a proteinaceous binding molecule with antibody-like binding properties, a molecule containing Ig domains, and binding fragments thereof.

145. The article of manufacture of any of embodiments 130-144, wherein:
the agent, the receptor-binding agent, which can be the second receptor-binding agent, and/or the first receptor-binding agent comprise an antibody fragment;
the agent, the receptor-binding agent, which can be the second receptor-binding agent, and/or the first receptor-binding agent comprise a Fab fragment;
the agent, the receptor-binding agent, which can be the second receptor-binding agent, and/or the first receptor-binding agent are is a divalent antibody fragment selected from among a F(ab')$_2$-fragment and a divalent single-chain Fv (scFv) fragment; or
the agent, the receptor-binding agent, which can be the second receptor-binding agent, and/or the first receptor-binding agent is a monovalent antibody fragment selected from among a Fab fragment, an Fv fragment and an scFv fragment.

146. The article of manufacture of any of embodiments 130-145, wherein:
the agent or first receptor-binding agent comprises an agent that specifically binds to CD3, which optionally is selected from the group consisting of an anti-CD3-antibody, a divalent antibody fragment of an anti-CD3 antibody, a monovalent antibody fragment of an anti-CD3-antibody, and a proteinaceous CD3 binding molecule with antibody-like binding properties, and/or
the agent or receptor-binding agent, which can be the second receptor-binding agent, comprises an agent that specifically binds to CD90, CD95, CD137, CD154, ICOS, LAT, CD27, OX40 or HVEM, which optionally is selected from the group consisting of an anti-CD90-antibody, a divalent antibody fragment of an anti-CD90 antibody, an antibody fragment of an anti-CD90-antibody, a proteinaceous CD90 binding molecule with antibody-like binding properties, an anti-CD95-antibody, a divalent antibody fragment of an anti-CD95 antibody, an antibody fragment of an anti-CD95-antibody, a proteinaceous CD95 binding molecule with antibody-like binding properties, an anti-CD154-antibody, a divalent antibody fragment of an anti-CD154 antibody, a monovalent antibody fragment of an anti-CD154-antibody, a proteinaceous CD154 binding molecule with antibody-like binding properties, an anti-CD137-antibody, a divalent antibody fragment of an anti-CD137 antibody, a monovalent antibody fragment of an anti-CD137-antibody, a proteinaceous CD137 binding molecule with antibody-like binding properties, an anti-ICOS-antibody, a divalent antibody fragment of an anti-ICOS antibody, a monovalent antibody fragment of an anti-ICOS-antibody, a proteinaceous ICOS binding molecule with antibody-like binding properties, an anti-LAT-antibody, a divalent antibody fragment of an anti-LAT antibody, a monovalent antibody fragment of an anti-LAT-antibody, a proteinaceous LAT binding molecule with antibody-like binding properties, an anti-CD27-antibody, a divalent antibody fragment of an anti-CD27 antibody, a monovalent antibody fragment of an anti-CD27-antibody, a proteinaceous CD27 binding molecule with antibody-like binding properties, an anti-OX40-antibody, a divalent antibody fragment of an anti-OX40 antibody, a monovalent antibody fragment of an anti-OX40-antibody, a proteinaceous OX40 binding molecule with antibody-like binding properties, an anti-HVEM-antibody, a divalent antibody fragment of an anti-HVEM antibody, a monovalent antibody fragment of an anti-HVEM-antibody, a proteinaceous HVEM binding molecule with antibody-like binding properties, and any mixture thereof.

147. The article of manufacture of any of embodiments 130-147, wherein:
the reagent is or comprises streptavidin, avidin, a streptavidin analog or mutein or and an avidin analog or mutein; or
the reagent comprises an oligomer or polymer of streptavidin, avidin, a streptavidin analog or mutein or and an avidin analog or mutein.

148. A kit, comprising the article of manufacture of any of embodiments 130-147 and optionally instructions for use.

149. The kit of embodiment 148, further comprising a substance capable of reversing the bond between the receptor-binding agent and the reagent 150. A kit, comprising:
a) a reversible reagent comprising i) a reagent comprising a plurality of binding sites capable of reversibly binding to a receptor-binding agent; and ii) the receptor-binding agent that is reversibly bound to the reagent and is capable of specifically binding to a molecule expressed on the surface of target cells, and optionally wherein binding to the molecule induces or modulates a signal in the target cells; and
b) a substance capable of reversing the bond between the receptor-binding agent and the reagent.

151. The kit of embodiment 150, wherein the target cells are T cells.

151. The kit of embodiment 150 or embodiment 151, wherein:
the reagent is or comprises streptavidin, avidin, a streptavidin analog or mutein or and an avidin analog or mutein; or
the reagent comprises an oligomer or polymer of streptavidin, avidin, a streptavidin analog or mutein or and an avidin analog or mutein.

152. The kit of any of embodiments 149-151, wherein the substance comprises a streptavidin-binding peptide, biotin or a biologically active fragment, optionally a D-biotin, or a biotin analog or biologically active fragment.

153. The kit of any of embodiments 150-152, wherein:
the reagent has a size that is less than 20 nm, less than 10 nm, less than 5 nm or less than 1 nm; or
the reagent has a density of less than 1.2 g/cm$^3$ or less than 1.0 g/cm$^3$.

154. The kit of any of embodiments 150-153, wherein the reagent is not bound to a support or solid support.

155. A composition, comprising a plurality of T cells genetically engineered to express a recombinant receptor that specifically binds to a target antigen, wherein:
greater than 35%, 40%, 50%, 60%, 70%, 80% or 90% of the cells comprise a T cell subset comprising a surface phenotype that is CD3+, CD4+ or CD8+ and CD62L+ and one or more of CD127+, CD45RA+, CD45RO−, CCR7+ and CD27+ and one or more of t-bet$^{low}$, IL-7Ra+, CD95+, IL-2Rβ+, CXCR3+ and LFA-1+ as a percentage of the total T cells in the composition or the total cells in the composition; and either or both:
a) prior to or during the genetic engineering, the plurality of T cells comprising the T cell subset:
i) were not incubated in the presence of a GSK-P inhibitor;
ii) were not incubated in the presence of a recombinant homeostatic cytokine, optionally IL-7 or IL-15; or
iii) were not enriched for CD62L+ cells; or
b) the composition does not comprise a GSK-P inhibitor or a recombinant homeostatic cytokine, optionally IL-7 or IL-15.

156. The composition of embodiment 155, wherein the T cell subset comprises at least $5\times10^6$, at least $1\times10^6$ or at least $2\times10^6$ cells.

157. A composition, comprising a plurality of T cells genetically engineered to express a recombinant receptor that specifically binds to a target antigen, wherein:

the genetically engineered T cells are derived from transducing a population of T cells comprising a T cell subset comprising a surface phenotype that is CD3+, CD4+ or CD8+ and CD62L+ and one or more of CD127+, CD45RA+, CD45RO−, CCR7+ and CD27+ and one or more of t-bet$^{low}$, IL-7Rα+, CD95+, IL-2Rβ+, CXCR3+ and LFA-1+, wherein the T cell subset is present at a greater percentage of the total T cells in the population or a greater number of total T cells in the population compared to either:

a) a population comprising primary T cells that were isolated or enriched from a human subject based on surface expression of one or markers comprising the phenotype; or b) a population of T cells that were incubated in the presence of a GSK-P inhibitor;

c) a population of T cells that were incubated in the presence of a recombinant homeostatic cytokine, optionally IL-7 or IL-15; or d) a population of T cells that were stimulated by anti-CD3 and anti-CD8, but in which the stimulation or activation was for greater than 1 day, 2 days, 3 days, 4 days or 5 days and/or the stimulation was not disrupted in the presence of biotin or a biotin analog.

158. The composition of embodiment 156, wherein:

the T cell subset is present in the population at or about greater than 35%, 40%, 50%, 60%, 70%, 80% or 90% as a percentage of the total T cells in the population; or the T cell subset comprises at least 5×106 cells, 1×106 cells, 2×106 cells or more.

159. The composition of any of embodiments 155-158 that is a pharmaceutical composition.

160. A method of treatment, comprising administering to a subject having a disease or condition the composition of embodiment 128, embodiment 129 and any of embodiments 154-158.

161. The method of treatment of embodiment 160, wherein the cells comprise a recombinant receptor, chimeric antigen receptor or TCR and the recombinant receptor, chimeric antigen receptor or transgenic TCR specifically binds to an antigen associated with the disease or condition.

162. The method of treatment of embodiment 160 or embodiment 161, wherein the disease or condition is a cancer, and autoimmune disease or disorder, or an infectious disease.

163. A method for culturing target cells, comprising incubating a composition comprising target cells in the presence of a receptor-binding agent which is i) reversibly bound to a reagent comprising a plurality of binding sites capable of reversibly binding to the receptor-binding agent; and ii) is capable of specifically binding to a molecule on the surface of the target cells other than CD28, CD3, CD137 or CD40 in a manner that induces or modulates a signal in the target cells and/or alters a function of the target cells, thereby generating cultured target cells.

164. The method of embodiment 163, wherein the receptor-binding agent specifically binds to a cytokine receptor, specifically binds to a chemokine receptor, is or comprises an adhesion molecule or is a factor that induces cytokine production, chemokine production and/or expression of an adhesion molecule.

165. The method of embodiment 163 or embodiment 164, wherein the receptor-binding agent specifically binds to a cytokine receptor selected from among IL-2R, IL-1R, IL-15R, IFN-gammaR, TNF-alphaR, IL-4R, IL-10R, Type I IFNR, IL-12R, IL-15R, IL-17R, TNFR1, TNFR2, IL-7R, IL-21R and CD132 (IL receptor common gamma chain).

166. The method of any of embodiments 163-165, wherein:

the receptor-binding agent is a ligand that specifically binds to a cytokine receptor selected from among IL-2R, IL-1R, IL-15R, IFN-gammaR, TNF-alphaR, IL-4R, IL-10R, Type I IFNR, IL-12R, IL-15R, IL-17R, TNFR1, TNFR2, IL-7R, IL-21R and CD132 (IL receptor common gamma chain); and/or the receptor-binding agent is a ligand selected from among IL-2, IL-1, IL-15, IFN-gamma, TNF-alpha, IL-4, IL-10, IL-12, IL-15, IL-17, TNF, IL-7, IL-21 and IL-9, or is a biologically active fragment thereof.

167. The method of any of embodiments 163-165, wherein:

the receptor-binding agent specifically binds to a cytokine selected from among IL-12R, IFN-gammaR, IL-4R and IL-17R; or the receptor-binding agent is a ligand selected from among IL-2, IL-4, IL-7, IL-10, IL-15 and IL-17 or is a biologically active fragment thereof.

168. The method of embodiment 163 or embodiment 164, wherein the receptor-binding agent specifically binds to a chemokine receptor selected from among CCR1, CCR2, CCR3, CCR4, CCR5, CCR7, CCR9, CXCR1, CXCR3 and CXCR4.

169. The method of embodiment 163, embodiment 164 or embodiment 168, wherein:

the receptor-binding agent is a ligand that specifically binds to a cytokine receptor selected from among CCR1, CCR2, CCR3, CCR4, CCR5, CCR7, CCR9, CXCR1, CXCR3 and CXCR4; or the receptor-binding agent is a ligand selected from among CXCL9, CXCL10, CCL19, CCL21 and CCL25 or is a biologically active fragment thereof.

170. The method of any of embodiment 163, embodiment 164, embodiment 168 or embodiment 169, wherein:

the receptor-binding agent specifically binds to a cytokine selected from among CXCR3, CCR7, CXCR1 and CXCR4; or the receptor-binding agent is a ligand selected from among CXCL9, CXCL10, CCL19, CCL21 and CCL25 or is a biologically active fragment thereof.

171. The method of embodiment 163 or embodiment 164, wherein the adhesion molecule is selected from among CD44, CD31, CD18/CD11a (LFA-1), CD29, CD54 (ICAM-1), CD62L (L-selectin), and CD29/CD49d (VLA-4), CD106 (VCAM-1) or is a biologically active fragment thereof.

172. The method of embodiment 171, wherein the adhesion molecule is selected from among LFA-1, L-selectin, VCAM-1 and VLA-4 or is a biologically active fragment thereof.

173. The method of embodiment 163 or embodiment 164, wherein the factor is a nuclear factor.

174. The method of embodiment 163, embodiment 164 or embodiment 173, wherein the factor is a retinoic acid receptor-related orphan receptor gamma (RORgamma) or RORalpha.

175. The method of any of embodiments 163-174, wherein:

the target cells comprise blood cells;
the target cells comprise leukocytes;
the target cells comprise lymphocytes;
the target cells comprise B cells;

the target cells comprise a B cell population;
the target cells comprise T cells;
the target cells comprise a T cell population; and/or
the target cells comprise natural killer (NK) cells.

176. The method of any of embodiments 163-175, wherein the target cells comprise immune cells.

177. The method of any of embodiments 163-176, wherein the target cells comprise antigen-specific T cells or a population thereof, a T helper cell or population thereof, a cytotoxic T cell or population thereof, a memory T cell or population thereof, a regulatory T cell or population thereof, an NK cell or population thereof, antigen-specific B cells or a population thereof, a memory B cell or population thereof, or a regulatory B cell or population thereof.

178. The method of any of embodiments 163-177, wherein the target cells are T cells.

179. The method of any of embodiments 163-178, wherein the target cells are primary cells from a subject.

180. The method of any of embodiments 163-179, wherein the incubation is performed under conditions in which the receptor-binding agent specifically binds to the molecule, thereby inducing or modulating the signal in the target cells and/or altering a function in the target cells.

181. The method of any of embodiments 163-180, wherein the receptor-binding agent comprises a binding partner C1, and the plurality of binding sites comprises two or more binding site, Z1, which each are capable of binding to the binding partner C1 to form the reversible bond between the receptor-binding agent and the reagent.

182. The method of any of embodiments 163-181, wherein the receptor-binding agent is an additional receptor-binding agent and the molecule is an additional molecule, and the incubation is further carried out in the presence of a first receptor-binding agent, which is capable of specifically binding to a first molecule on the surface of one or more of the T cells, which first molecule is optionally capable of inducing or modulating a first signal in one or more T cells in the composition.

183. The method of embodiment 182, wherein:
the first receptor-binding agent is reversibly bound to the reagent, said reagent comprising a plurality of binding sites for the first receptor-binding agent and the additional receptor-binding agent; or
the first receptor-binding agent is reversibly bound to a second reagent comprising a plurality of binding sites capable of reversibly binding to the first receptor-binding agent.

184. The method of embodiment 182 or embodiment 183, wherein:
the first receptor-binding agent is capable of initiating a TCR/CD3 complex-associated signal in the T cells; and/or
the first receptor-binding agent specifically binds to a member of a TCR/CD3 complex; and/or
the first receptor-binding agent specifically binds to CD3.

185. The method of any of embodiments 182-184, wherein the first receptor-binding agent comprises a binding partner C2, and the plurality of binding sites comprises two or more binding site, Z2, which each are capable of binding to the binding partner C2 to form the reversible bond between the first receptor-binding agent and the reagent.

186. The method of any of embodiments 182-185, wherein the incubation is further carried out in the presence of a second receptor-binding agent, which is capable of specifically binding to a second molecule on the surface of one or more of the T cells, which second molecule is optionally capable of inducing or modulating a signal in target cells in the composition to enhance, dampen or modify a signal delivered through the first molecule.

187. The method of embodiment 186, wherein:
the second signal is a signal other than a TCR/CD3 complex-associated signal;
the second signal is capable of enhancing or potentiating a TCR/CD3 complex-associated signal; or
the second molecule is a costimulatory molecule, accessory molecule, cytokine receptor, chemokine receptor, immune checkpoint molecule or is a member of the TNF family or the TNF receptor family.

188. The method of any of embodiments 186 or embodiment 187, wherein the second molecule is selected from among CD28 and CD137.

189. The method of any of embodiments 186-188, wherein the second molecule is
CD28.

190. The method of any of embodiments 186-188, wherein the second receptor-binding agent comprises a binding partner C3, and the plurality of binding sites comprises two or more binding site, Z3, which each are capable of binding to the binding partner C3 to form the reversible bond between the first receptor-binding agent and the reagent.

191. The method of any of embodiments 163-190, wherein:
C1 and C2, C1 and C3, C2 and C3 or C1, C2 and C3 are the same or substantially the same, or contain the same or substantially the same moiety;
Z1 and Z2, Z1 and Z3, Z2 and Z3 or Z1, Z2 and Z3 are the same or substantially the same or contain the same or substantially the same moiety.

192. The method of any of embodiments 163-191, wherein the reagent is immobilized, or is capable of being immobilized, on a support for at least a portion of the incubation, whereby the receptor-binding agent (additional, first and/or second) is immobilized, or is capable of being immobilized on the support.

193. The method of embodiment 192, wherein:
the support is or comprises a stationary phase; and/or
the support is or comprises a solid support.

194. The method of any of embodiments 163-191, wherein:
the reagent is not, and is not bound to or associated with, a solid support, stationary phase, a bead, a microparticle, a magnetic particle, and/or a matrix during said incubation; and/or
the reagent is flexible, does not contain a metal or magnetic core, is comprised entirely or primarily of organic multimer, is not spherical, is not substantially spherical or uniform in shape and/or is not rigid;
the reagent has a size that is less than 20 nm, less than 10 nm, less than 5 nm or less than 1 nm; or
the reagent has a density of less than 1.2 g/cm$^3$ or less than 1.0 g/cm$^3$.

195. The method of any of embodiments 163-194, wherein:
the receptor-binding agent, which can be the additional receptor-binding agent, comprises a binding site, B1; and/or
the receptor-binding agent, which can be the additional receptor-binding agent, comprises only one of said binding sites, B1; and/or
the receptor-binding agent, which can be the additional receptor-binding agent, specifically binds to the molecule in a monovalent manner.

196. The method of any of embodiments 163-195, wherein:

the first receptor-binding agent comprises a binding site, B2; and/or the first receptor-binding agent comprises only one of said binding sites, B2; and/or the first receptor-binding agent specifically binds to the molecule in a monovalent manner.

197. The method of any of embodiments 163-196, wherein:

the second receptor-binding agent comprises a binding site, B4; and/or the second receptor-binding agent comprises only one of said binding sites, B4; and/or the second receptor-binding agent specifically binds to the molecule in a monovalent manner.

198. The method of any of embodiments 195-197, wherein the binding site, B2 and/or B4, comprises an antibody combining site.

199. The method of any of embodiments 163-198, wherein the receptor-binding agent, which can be an additional receptor-binding agent is selected from among a cytokine, a chemokine, or an adhesion molecule.

200. The method of any of embodiments 163-199, wherein the receptor-binding agent (additional, first and/or additional) each individually are selected from among an antibody fragment, a monovalent antibody fragment, a proteinaceous binding molecule with antibody-like binding properties, a molecule containing Ig domains, an aptamer, and MHC molecule and binding fragments thereof.

201. The method of any of embodiments 163-200, wherein:

the receptor-binding agent (additional, first and/or additional) comprise an antibody fragment;

the receptor-binding agent (additional, first and/or additional) comprise a Fab fragment;

the receptor-binding agent (additional, first and/or additional) are is a divalent antibody fragment selected from among a F(ab')$_2$-fragment and a divalent single-chain Fv (scFv) fragment;

the receptor-binding agent (additional, first and/or additional) is a monovalent antibody fragment selected from among a Fab fragment, an Fv fragment and an scFv fragment; and/or the receptor-binding agent (additional, first and/or additional) is a proteinaceous binding molecule with antibody-like binding properties selected from among aptamers, muteins based on a polypeptide of the lipocalin family, glubodies, proteins based on the ankyrin scaffold, proteins based on the crystalline scaffold, adnectins and avimers.

202. The method of any of embodiments 163-201, wherein the reagent is or comprises streptavidin, avidin, an analog or mutein of streptavidin that reversibly binds biotin, a biotin analog or a biologically active fragment thereof; an analog or mutein of avidin or streptavidin that reversibly binds a streptavidin-binding peptide; a reagent that comprises at least two chelating groups K, wherein the at least two chelating groups are capable of binding to a transition metal ion; an agent capable of binding to an oligohistidine affinity tag; an agent capable of binding to a glutathione-S-transferase; calmodulin or an analog thereof; an agent capable of binding to calmodulin binding peptide (CBP); an agent capable of binding to a FLAG-peptide; an agent capable of binding to an HA-tag; an agent capable of binding to maltose binding protein (MBP); an agent capable of binding to an HSV epitope; an agent capable of binding to a myc epitope; or an agent capable of binding to a biotinylated carrier protein.

203. The method of any of embodiments 163-202, wherein:

the reagent is or comprises a streptavidin analog or mutein or an avidin analog or mutein that reversibly binds to biotin or a biologically active fragment;

the reagent is or comprises a streptavidin analog or mutein or an avidin analog or mutein that reversibly binds to a biotin analog or a biologically active fragment; and/or the reagent is or comprises a streptavidin analog or mutein or an avidin analog or mutein that reversibly binds to a streptavidin-binding peptide.

204. The method of any of embodiments 163-203, wherein the reagent is an oligomer or polymer of streptavidin, avidin, an analog or mutein of streptavidin that reversibly binds biotin or a biologically active fragment; a streptavidin or avidin analog or mutein that reversibly binds a streptavidin-binding peptide; a reagent that comprises at least two chelating groups K, wherein the at least two chelating groups are capable of binding to a transition metal ion; an agent capable of binding to an oligohistidine affinity tag; an agent capable of binding to a glutathione-S-transferase; calmodulin or an analog thereof; an agent capable of binding to calmodulin binding peptide (CBP); an agent capable of binding to a FLAG-peptide; an agent capable of binding to an HA-tag; an agent capable of binding to maltose binding protein (MBP); an agent capable of binding to an HSV epitope; an agent capable of binding to a myc epitope; or an agent capable of binding to a biotinylated carrier protein.

205. The method of any of embodiments 163-204, wherein the reagent comprises an oligomer or polymer of streptavidin, avidin, a streptavidin analog or mutein or and an avidin analog or mutein.

206. The method of embodiment 204 or embodiment 205, wherein individual molecules of the oligomer or polymer are crosslinked by a polysaccharide or a bifunctional linker.

207. The method of any of embodiments 163-206, wherein the plurality of binding sites comprises at least 2, 4, 8, 12, 16, 20, 24, 28, 32, 36, 40, 44, 48, 52, 56, 60, 64, 72 or more binding sites.

208. The method of any of embodiments 202-207, wherein the streptavidin-binding peptide is selected from the group consisting of Trp-Ser-His-Pro-Gln-Phe-Glu-Lys (SEQ ID NO: 8), Trp-Ser-His-Pro-Gln-Phe-Glu-Lys-(GlyGlyGly-Ser)$_3$-Trp-Ser-His-Pro-Gln-Phe-Glu-Lys (SEQ ID NO: 17), Trp-Ser-His-Pro-Gln-Phe-Glu-Lys-(GlyGlyGlySer)$_2$-Trp-Ser-His-Pro-Gln-Phe-Glu-Lys (SEQ ID NO: 18) and Trp-Ser-His-Pro-Gln-Phe-Glu-Lys-(GlyGlyGlySer)$_2$Gly-Gly-Ser-Ala-Trp-Ser-His-Pro-Gln-Phe-Glu-Lys (SEQ ID NO: 19).

209. The method of any of embodiments 163-208, wherein:

the reagent comprises a streptavidin analog or mutein comprising the amino acid corresponding to positions 44 to 47 with reference to positions in streptavidin in the sequence of amino acids set forth in SEQ ID NO:1; or the streptavidin analog or mutein comprises the amino acid sequence Val$^{44}$-Thr$^{45}$-Ala$^{46}$-Arg$^{47}$ at sequence positions corresponding to positions 44 to 47 with reference to positions in streptavidin in the sequence of amino acids set forth in SEQ ID NO:1.

210. The method of any of embodiments 163-209, wherein the streptavidin analog or mutein comprises:

a) the sequence of amino acids set forth in any of SEQ ID NOS: 3-6, 27 or 28;

b) a sequence of amino acids that exhibits at least 85%, 86%, 87%, 88%, 89%, 89%, 90%, 91%, 92%, 93%, 94%, 95%, 96%, 97%, 98%, 99% or more sequence identity to any of SEQ ID NOS:3-6, 27 or 28 and contains the amino acid sequence corresponding to Val$^{44}$-Thr$^{45}$-Ala$^{46}$-Arg$^{47}$ or Ile$^{44}$-Gly$^{45}$-Ala$^{46}$-Arg$^{47}$ and that reversibly binds to biotin or a biologically active form thereof, a biotin analog or mutein or a biologically active fragment thereof or a streptavidin-binding peptide; or c) a functional fragment of a) or b) that reversibly binds to biotin or a biologically active form thereof, a biotin analog or mutein or a biologically active fragment thereof or a streptavidin-binding peptide.

211. The method of embodiment 209 or embodiment 210, wherein the streptavidin analog or mutein further comprises an amino acid replacement or replacements at a position corresponding to 117, 120 and/or 121 with reference to positions in streptavidin in the sequence of amino acids set forth in SEQ ID NO:1.

212. The method of embodiment 211, wherein:
the amino acid replacement or replacements are selected from among Glu117, Asp117, Arg117, Ser120, Ala120, Gly120, Trp121, Tyr121 or Phe121; or
the amino acid replacement or replacements are selected from one or more of Glu117, Gly120 or Tyr121; or
the amino acid replacements are selected from Glu117, Gly120 or Tyr121.

213. The method of any of embodiments 163-212, wherein the streptavidin analog or mutein comprises:
a) the sequence of amino acids set forth in SEQ ID NO: 27 or 28;
b) a sequence of amino acids that exhibits at least 85%, 86%, 87%, 88%, 89%, 89%, 90%, 91%, 92%, 93%, 94%, 95%, 96%, 97%, 98%, 99% or more sequence identity to SEQ ID NOS:28 and contains the amino acid sequence corresponding to Val$^{44}$, Thr$^{45}$, Ala$^{46}$, Arg$^{47}$, Glu$^{117}$, Gly$^{120}$ and Tyr$^{121}$ and reversibly binds to biotin or a biologically active fragment, a biotin analog or mutein or a biologically active fragment thereof or a streptavidin-binding peptide; or
c) a functional fragment of a) or b) that reversibly binds to biotin or a biologically active fragment, a biotin analog or mutein or a biologically active fragment thereof or a streptavidin-binding peptide.

214. The method of any of embodiments 163-213, wherein the binding partner C1 and/or the binding partner C2, independently, comprises a streptavidin-binding peptide selected from the group consisting of Trp-Ser-His-Pro-Gln-Phe-Glu-Lys (SEQ ID NO: 8), Trp-Ser-His-Pro-Gln-Phe-Glu-Lys-(GlyGlyGlySer)$_3$-Trp-Ser-His-Pro-Gln-Phe-Glu-Lys (SEQ ID NO: 17), Trp-Ser-His-Pro-Gln-Phe-Glu-Lys-(GlyGlyGlySer)$_2$-Trp-Ser-His-Pro-Gln-Phe-Glu-Lys (SEQ ID NO: 18) and Trp-Ser-His-Pro-Gln-Phe-Glu-Lys-(GlyGlySer)$_2$Gly-Gly-Ser-Ala-Trp-Ser-His-Pro-Gln-Phe-Glu-Lys (SEQ ID NO: 19).

215. The method of any of embodiments 163-214, further comprising disrupting the reversible binding between the first and/or second receptor-binding agent and the reagent.

216. The method of embodiment 215, wherein said disruption comprises introducing to the cells a composition comprising a substance capable of reversing the bond between the receptor-binding agent, which can be the first receptor-binding agent, and/or the second-receptor-binding agent and the reagent.

217. The method of embodiment 216, wherein the substance is a free binding partner and/or is a competition agent.

218. The method of embodiment 216 or embodiment 217, wherein the substance in the composition is not detrimental to the T cells or to the target cells and/or wherein the addition of said substance does not reduce the percentage of surviving T cells or target cells to less than 90%, 80%, 70%, 60%, or 50%, as compared to incubation of the T cells or target cells, respectively, under comparable or the same conditions, without the substance.

219. The method of any of embodiments 215-218, wherein said disruption terminates or lessens the signal induced or modulated by one or both of the receptor-binding agent or second receptor-binding agent in the T cells or the target cells.

220. The method of any of embodiments 215-219, wherein:
the reagent is or comprises a streptavidin, avidin, a streptavidin analog or mutein or and an avidin analog or mutein or biologically active fragments thereof; and
the substance comprises a streptavidin-binding peptide, biotin or a biologically active fragment, optionally a D-biotin, or a biotin analog or biologically active fragment.

221. The method of embodiment 220, wherein:
the substance is a streptavidin-binding peptide is selected from the group consisting of Trp-Ser-His-Pro-Gln-Phe-Glu-Lys (SEQ ID NO: 8), Trp-Ser-His-Pro-Gln-Phe-Glu-Lys-(GlyGlyGlySer)$_3$-Trp-Ser-His-Pro-Gln-Phe-Glu-Lys (SEQ ID NO: 17), Trp-Ser-His-Pro-Gln-Phe-Glu-Lys-(GlyGlyGlySer)$_2$-Trp-Ser-His-Pro-Gln-Phe-Glu-Lys (SEQ ID NO: 18) and Trp-Ser-His-Pro-Gln-Phe-Glu-Lys-(GlyGlyGlySer)$_2$Gly-Gly-Ser-Ala-Trp-Ser-His-Pro-Gln-Phe-Glu-Lys (SEQ ID NO: 19); and/or
the substance is C1, C2 or C3 or an analog thereof.

222. The method of any of embodiments 163-221, wherein:
the induction or modulation of the signal results in an altered activity selected from among chemotaxis, adhesion, cytokine production, proliferation (expansion), cytotoxic activity, metabolic activity compared to the target cells, optionally T cells, in the composition in the absence of the induction or modulation of the signal; and/or
the altered functional activity is selected from among chemotaxis, adhesion, cytokine production, proliferation (expansion), cytotoxic activity, metabolic activity compared to the functional activity of target cells, optionally T cells, in the composition prior to the incubation; and/or
the cultured target cells exhibit an altered activity selected from among chemotaxis, adhesion, cytokine production, proliferation (expansion), cytotoxic activity, metabolic activity compared to the functional activity of target cells, optionally T cells, in the composition prior to the incubation.

223. The method of embodiment 222, wherein the activity is altered at least 2-fold, 3-fold, 4-fold, 5-fold, 6-fold, 7-fold, 8-fold, 9-fold, 10-fold or greater.

224. The method of any of embodiments 163-223, further comprising introducing a recombinant nucleic acid molecule into T cells or target cells of the population, which nucleic acid molecule encodes a recombinant protein, whereby cells express the recombinant protein.

225. The method of embodiment 224, wherein the recombinant receptor is a chimeric antigen receptor or transgenic T cell receptor (TCR).

226. The method of any of embodiments 163-225, wherein the method is performed in vitro or ex vivo.

227. The method of any of embodiments 163-226, further comprising administering the cultured cells to a subject having a disease or condition.

228. A composition, comprising a plurality of cultured T cells or target cells produced by the method of any of embodiments 163-227, and optionally a pharmaceutically acceptable excipient.

229. The composition of embodiment 228, wherein after addition of the substance, the cells have not been incubated in vitro or ex vivo at a temperature greater than 30° C. for more than 24 hours, more than 48 hours, more than 72 hours or more than 96 hours.

230. An article of manufacture, comprising:
a) a reagent comprising a plurality of binding sites capable of binding to a receptor-binding agent; and
b) the receptor-binding agent which i) is reversibly bound to the reagent and ii) is capable of specifically binding to a molecule on the surface of target cells in a manner that induces or modulates a signal in the cells or alters a functional activity in the cells, wherein the molecule is not CD28, CD3, CD137 or CD40.

231. The article of manufacture of embodiment 230, wherein the receptor-binding agent specifically binds to a cytokine receptor, specifically binds to a chemokine receptor, is or comprises an adhesion molecule or is a factor that induces cytokine production, chemokine production and/or expression of an adhesion molecule.

232. The article of manufacture of embodiment 230 or embodiment 231, wherein the receptor-binding agent specifically binds to a cytokine receptor selected from among IL-2R, IL-1R, IL-15R, IFN-gammaR, TNF-alphaR, IL-4R, IL-10R, Type I IFNR, IL-12R, IL-15R, IL-17R, TNFR1, TNFR2, IL-7R, IL-21R and CD132 (IL receptor common gamma chain).

233. The article of manufacture of any of embodiments 230-232, wherein:
the receptor-binding agent is a ligand that specifically binds to a cytokine receptor selected from among IL-2R, IL-1R, IL-15R, IFN-gammaR, TNF-alphaR, IL-4R, IL-10R, Type I IFNR, IL-12R, IL-15R, IL-17R, TNFR1, TNFR2, IL-7R, IL-21R and CD132 (IL receptor common gamma chain); and/or
the receptor-binding agent is a ligand selected from among IL-2, IL-1, IL-15, IFN-gamma, TNF-alpha, IL-4, IL-10, IL-12, IL-15, IL-17, TNF, IL-7, IL-21 and IL-9, or is a biologically active fragment thereof.

234. The article of manufacture of any of embodiments 230-232, wherein:
the receptor-binding agent specifically binds to a cytokine selected from among IL-12R, IFN-gammaR, IL-4R and IL-17R; or
the receptor-binding agent is a ligand selected from among IL-2, IL-4, IL-7, IL-10, IL-15 and IL-17 or is a biologically active fragment thereof.

235. The article of manufacture of embodiment 68 or embodiment 69, wherein the receptor-binding agent specifically binds to a chemokine receptor selected from among CCR1, CCR2, CCR3, CCR4, CCR5, CCR7, CCR9, CXCR1, CXCR3 and CXCR4.

236. The article of manufacture of embodiment 230, embodiment 231 or embodiment 235, wherein:
the receptor-binding agent is a ligand that specifically binds to a cytokine receptor selected from among CCR1, CCR2, CCR3, CCR4, CCR5, CCR7, CCR9, CXCR1, CXCR3 and CXCR4; or the receptor-binding agent is a ligand selected from among CXCL9, CXCL10, CCL19, CCL21 and CCL25 or is a biologically active fragment thereof.

237. The article of manufacture of any of embodiment 68, embodiment 69, embodiment 235 or embodiment 236, wherein:
the receptor-binding agent specifically binds to a cytokine selected from among CXCR3, CCR7, CXCR1 and CXCR4; or
the receptor-binding agent is a ligand selected from among CXCL9, CXCL10, CCL19, CCL21 and CCL25 or is a biologically active fragment thereof.

238. The article of manufacture of embodiment 230 or embodiment 231, wherein the adhesion molecule is selected from among CD44, CD31, CD18/CD11a (LFA-1), CD29, CD54 (ICAM-1), CD62L (L-selectin), and CD29/CD49d (VLA-4), CD106 (VCAM-1) or is a biologically active fragment thereof.

239. The article of manufacture of embodiment 238, wherein the adhesion molecule is selected from among LFA-1, L-selectin, VCAM-1 and VLA-4 or is a biologically active fragment thereof.

240. The article of manufacture of embodiment 230 or embodiment 231, wherein the factor is a nuclear factor.

241. The article of manufacture of embodiment 230, embodiment 231 or embodiment 240, wherein the factor is a retinoic acid receptor-related orphan receptor gamma (RORgamma) or RORalpha.

242. The article of manufacture of any of embodiments 230-241, wherein:
the receptor-binding agent or agent comprises a binding partner C1; and
the plurality of binding sites comprises two or more binding site, Z1, which each are capable of binding to the binding partner C1 to form the reversible bond between the receptor-binding agent or agent and the reagent.

243. The article of manufacture of any of embodiments 230-241, wherein the receptor-binding agent is an additional receptor-binding agent and the molecule is an additional molecule, and the reagent further comprises: c) a plurality of binding sites capable of reversibly binding to a first receptor-binding agent and d) the first receptor-binding agent which i) is reversibly bound to the reagent and ii) is capable of specifically binding to a first molecule on the surface of a T cell.

244. The article of manufacture of embodiment 243, wherein the first receptor-binding agent specifically binds to a member of a TCR/CD3 complex and/or the first receptor-binding agent specifically binds to CD3.

245. The article of manufacture of embodiment 243 or embodiment 244, wherein the incubation is further carried out in the presence of a second receptor-binding agent, which is capable of specifically binding to a second molecule on the surface of one or more of the T cells, which second molecule is optionally capable of inducing or modulating a signal in target cells in the composition to enhance, dampen or modify a signal delivered through the first molecule.

246. The article of manufacture of embodiment 245, wherein:
the second signal is a signal other than a TCR/CD3 complex-associated signal;
the second signal is capable of enhancing or potentiating a TCR/CD3 complex-associated signal; or
the second molecule is a costimulatory molecule, accessory molecule, cytokine receptor, chemokine receptor, immune checkpoint molecule or is a member of the TNF family or the TNF receptor family.

247. The article of manufacture of any of embodiment 245 or embodiment 246, wherein the second molecule is selected from among CD28 or CD137.

248. The article of manufacture of any of embodiments 245-247, wherein the second molecule is CD28.

249. The article of manufacture of any of embodiments 230-248, wherein the reagent is immobilized, or is capable of being immobilized, on a support for at least a portion of the incubation, whereby the receptor-binding agent (additional, first and/or second) is immobilized, or is capable of being immobilized on the support.

250. The article of manufacture of embodiment 249, wherein:
the support is or comprises a stationary phase; and/or
the support is or comprises a solid support.

251. The article of manufacture of any of embodiments 230-248, wherein:
the reagent is not, and is not bound to or associated with, a solid support, stationary phase, a bead, a microparticle, a magnetic particle, and/or a matrix during said incubation; and/or
the reagent is flexible, does not contain a metal or magnetic core, is comprised entirely or primarily of organic multimer, is not spherical, is not substantially spherical or uniform in shape and/or is not rigid;
the reagent has a size that is less than 20 nm, less than 10 nm, less than 5 nm or less than 1 nm; or
the reagent has a density of less than 1.2 g/cm$^3$ or less than 1.0 g/cm$^3$.

252. The article of manufacture of any of embodiments 230-251, wherein the receptor-binding agent, which can be the additional receptor-binding agent, the first receptor-binding agent and/or the second receptor-binding agent each individually are selected from among an antibody fragment, a monovalent antibody fragment, a proteinaceous binding molecule with antibody-like binding properties, a molecule containing Ig domains, and binding fragments thereof.

253. The article of manufacture of any of embodiments 230-252, wherein:
the receptor-binding agent, which can be the additional receptor-binding agent, the first receptor-binding agent and/or the second receptor-binding agent comprise an antibody fragment;
the receptor-binding agent, which can be the additional receptor-binding agent, the first receptor-binding agent and/or the second receptor-binding agent comprise a Fab fragment;
the receptor-binding agent, which can be the additional receptor-binding agent, the first receptor-binding agent and/or the second receptor-binding agent are is a divalent antibody fragment selected from among a F(ab')$_2$-fragment and a divalent single-chain Fv (scFv) fragment; or
the receptor-binding agent, which can be the additional receptor-binding agent, the first receptor-binding agent and/or the second receptor-binding agent is a monovalent antibody fragment selected from among a Fab fragment, an Fv fragment and an scFv fragment.

254. The article of manufacture of any of embodiments 230-253, wherein:
the reagent is or comprises streptavidin, avidin, a streptavidin analog or mutein or and an avidin analog or mutein; or
the reagent comprises an oligomer or polymer of streptavidin, avidin, a streptavidin analog or mutein or and an avidin analog or mutein.

255. A kit, comprising the article of manufacture of any of embodiments 230-254 and optionally instructions for use.

256. The kit of embodiment 255, further comprising a substance capable of reversing the bond between the receptor-binding agent and the reagent 257. The kit of embodiment 256, wherein the substance comprises a streptavidin-binding peptide, biotin or a biologically active fragment, optionally a D-biotin, or a biotin analog or biologically active fragment.

VIII. Examples

The following examples are included for illustrative purposes only and are not intended to limit the scope of the invention.

Example 1: Generation of a Soluble Stimulatory Reagent, Containing Multimerized Anti-CD3 and Anti-CD28 Fab Fragments Reversibly Bound to an Oligomeric Streptavidin Mutein Reagent Stimulatory agents (anti-CD3 and anti-CD28 Fab fragments) were multimerized by reversibly binding to a multimerization reagent, which was an oligomeric streptavidin mutein. The reagent contained multiple binding sites for peptide tags, which were present on the Fab fragments. The oligomeric streptavidin mutein was prepared by polymerizing the streptavidin mutein designated Strep-Tactin® m1 (a streptavidin homo-tetramer containing the mutein sequence of amino acids set forth in SEQ ID NO:6, see e.g. U.S. Pat. No. 6,103,493 and Voss and Skerra (1997) Protein Eng., 1:975-982) with sulfo-SMCC (sulfosuccinimidyl 4-(N-maleimidomethyl)cyclohexane-1-carboxylate, product #22122 Thermo Scientific) and iminothiolan (product #26101 Thermo Scientific) according to the manufacturer's instructions (Thermo Scientific). The oligomeric streptavidin mutein molecules were separated from monomeric (unreacted) and dimeric streptavidin mutein by size exclusion chromatography.

Anti-CD3 and anti-CD28 Fab fragments were reversibly bound to the oligomeric streptavidin mutein via a streptavidin peptide-binding partner fused to each Fab fragment. The anti-CD3 Fab fragment was derived from the CD3 binding monoclonal antibody produced by the hybridoma cell line OKT3 (ATCC® CRL-8001™; see also U.S. Pat. No. 4,361,549), and contained the heavy chain variable domain and light chain variable domain of the anti-CD3 antibody OKT3 described in Arakawa et al J. Biochem. 120, 657-662 (1996). These sequences are set forth in SEQ ID NOs:31 and 32, respectively. The anti-CD28 Fab fragment was derived from antibody CD28.3 (deposited as a synthetic single chain Fv construct under GenBank Accession No. AF451974.1; see also Vanhove et al., BLOOD, 15 Jul. 2003, Vol. 102, No. 2, pages 564-570) and contained the heavy and light chain variable domains of the anti-CD28 antibody CD28.3 set forth in SEQ ID NOS: 33 and 34, respectively. The Fab fragments were individually fused at the carboxy-terminus of their heavy chain to a streptavidin peptide-binding sequence containing a sequential arrangement of two streptavidin binding modules having the sequence of amino acids SAWSHPQFEK(GGGS)$_2$GGSAWSHPQFEK (SEQ ID NO: 16). The peptide-tagged Fab fragments were recombinantly produced (see International Patent App. Pub. Nos. WO 2013/011011 and WO 2013/124474).

To effect reversible binding, peptide-tagged anti-CD3 and anti-CD28 Fab fragments were mixed with the multimerizing reagent, at approximately room temperature, thereby reversibly binding them to the reagent via interaction between twin-strep-tags on the Fab fragments, which were binding partners capable of reversibly binding to binding sites on the reagent, Specifically, in this study, approximately 0.5 µg of the anti-CD3 peptide tagged Fab fragment and approximately 0.5 µg of the anti-CD28 peptide-tagged Fab fragment were added to approximately 3 µg of soluble oligomeric Strep-Tactin® at room temperature. In some cases, the peptide-tagged Fab fragments were pre-mixed prior to immobilization onto the soluble oligomeric mutein streptavidin backbone, which, in some instances, can result in a more uniform distribution of the different Fab molecules. The resulting soluble anti-CD3/anti-CD28 multimerized agent was used to stimulate T cells. In some cases, the resulting soluble anti-CD3/anti-CD28 multimerized agent was stored on ice prior to stimulation of cells.

Example 2: Assessment of T Cell Expansion Following Temporally-Controlled Stimulation of T Cells by Incubation with a Reversible Agent T cells were incubated with the reagent described in Example 1, containing multimerized, reversibly bound agents (anti-CD3/anti-CD28 Fab fragments). Interaction between the multimerizedanti-CD3 and anti-CD28 Fabs and the cells was disrupted at various time-points after initiation, by addition of D-biotin. D-biotin competes with the strep-tag on the agents for binding to the binding partner on the streptavidin mutein, thereby disrupting binding.

In more detail, T cells were selected from a sample of fresh peripheral blood mononuclear cells (PBMCs) obtained from a Ficoll gradient, based on surface expression of CD3, CD4 or CD8. Approximately 500,000 T cells (either CD3+, CD4+ or CD8+) were seeded in 48-well plates in 1 mL complete RPMI medium, supplemented with 50 U/mL IL-2. The reagent (containing reversibly bound anti-CD3/anti-CD28 Fabs) described in Example 1 was added on the day of cell culture initiation (day 0), generally at least 20 minutes prior to stimulation. To another sample of cells were added with anti-CD3/anti-CD28 beads (which were anti-CD3- and anti-CD28-mAb coated magnetic beads, in which binding was not disruptable by the addition of D-Biotin, thus providing a control to confirm that any effects observed with D-biotin addition were due to specific binding and disruption in the case of the multimerized agents). Untreated (unstimulated) cells served as negative control.

Figure 5A:
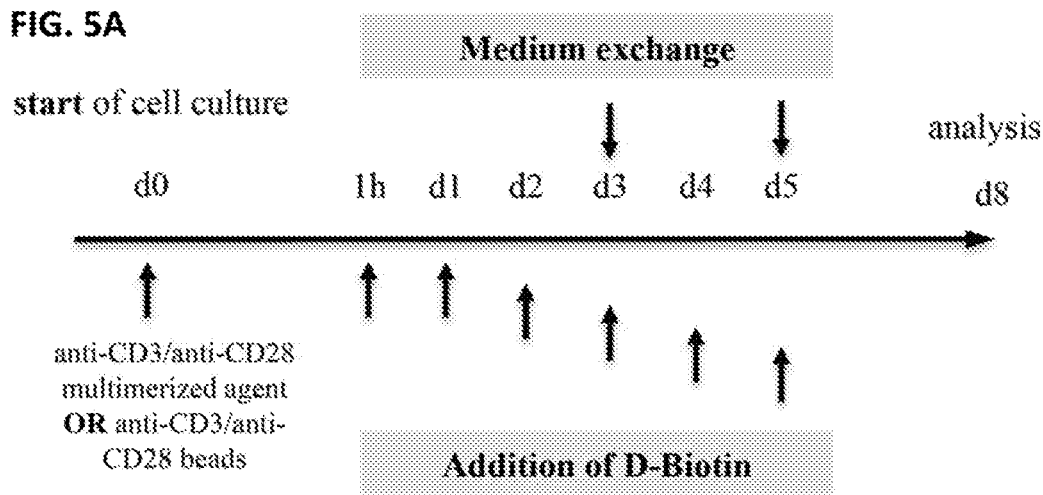
FIG. 5A is a schematic representation of the experimental conditions and timeline, including time points of D-Biotin addition and medium exchange during cell culture.
Figure 5B:
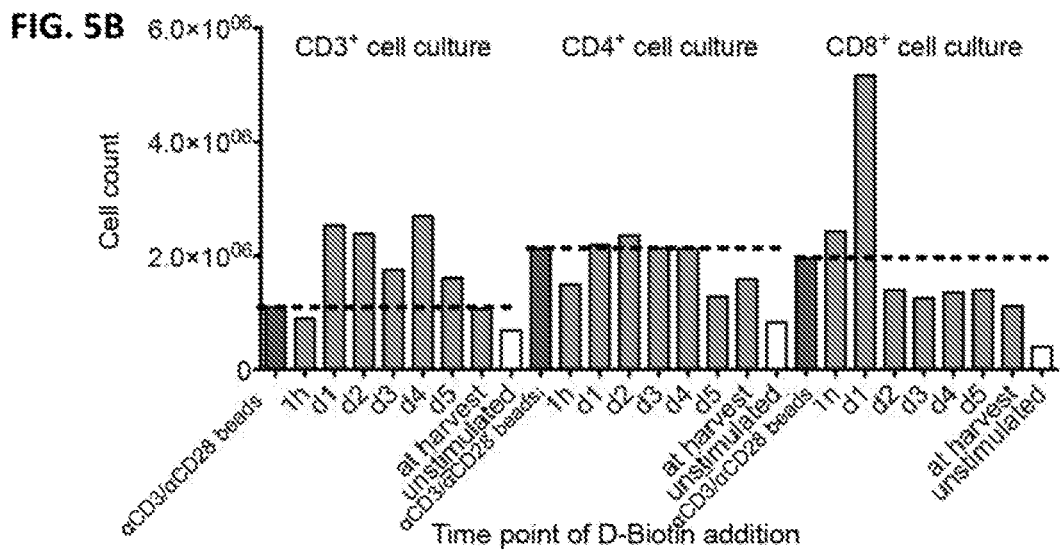
FIG. 5B shows total cell counts (degree of expansion) for $CD3^+$, $CD4^+$, and $CD8^+$ cells after stimulation under the indicated conditions, including with the addition of D-Biotin at different time-points. For comparison, the dashed horizontal lines indicate the number of $CD3^+$, $CD4^+$ or $CD8^+$ cells expanded in the positive control (anti-CD3/anti-CD28 beads).
Figure 5C:
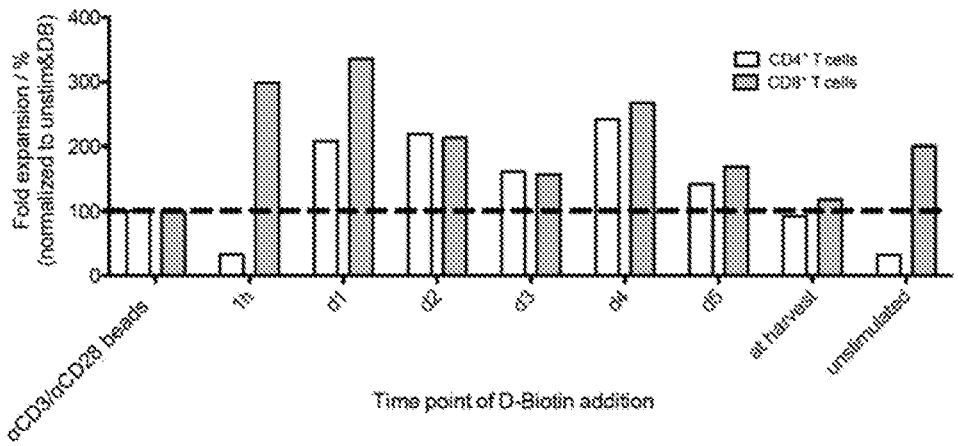
FIG. 5C shows fold expansion of $CD4^+$ and $CD8^+$ when normalized to the unstimulated control.

Cells were incubated at 37° C. for a total of eight days. As shown in FIG. 5A, D-Biotin was added at various time-points to compositions of cells (final concentration of 1 mM) that had been incubated with the multimerized anti-CD3/anti-CD28 stimulatory agents in order to disrupt the reversible binding of the multimeric stimulatory agent complex to the cells, to lessen or attenuate the signaling delivered to the cells through the multimerized anti-CD3 and anti-CD28 Fabs. Specifically, D-Biotin was added to the culture wells (at either one (1) hour, one day, two days, three days, four days or five days post-initiation of the incubation, or at harvest (day 8)) to a final concentration of 1 mM, without resuspension of cells. The cells were then incubated for 30 minutes at room temperature, followed by continued incubation at 37° C., where applicable, until day 8. Culture media was exchanged on days three and five. Individual test wells were resuspended to harvest cells, individually transferred to microcentrifuge tubes and analyzed for cell count to assess expansion of the cells and/or by flow cytometry for surface expression of CD4 or CD8. Exemplary results are depicted in FIGS. 5B and 5C. Data are representative of three independent experiments encompassing duplicates for each tested condition and controls.

As shown in FIG. 5B, incubation of T cells with the multimerized anti-CD3/anti-CD28 agents, followed by disruption by D-Biotin addition at various time-points, resulted in an increase in T cell numbers, consistent with T cell expansion and/or persistence to a degree at least comparable to and, in some cases, improved compared to incubation for eight days without disruption of binding. The results showed that addition of D-Biotin at early time points to dissociate the Fabs from the multimerization reagent (such as generally within one day for CD8+ cells or within 4 days for CD3+ cells) resulted in, at harvest at day 8 post-initiation of stimulation, higher total $CD3^+$ and $CD8^+$ cell numbers compared to stimulations in which the signal was not disrupted. In particular, when CD8+ T cells were stimulated for 1 day with the soluble anti-CD3/anti-CD28 multimerized reagent prior to addition of D-Biotin to disrupt the interaction and dampen the stimulatory signal, T cell numbers at harvest were almost 3-fold greater compared to the expansion of the T cells in the presence of anti-CD3/anti-CD28 reagents without disruption of binding. For CD4+ cells, the number of cells at harvest was generally comparable to those observed following stimulation in the presence of anti-CD3/anti-CD28 without disruption, particularly at time points when the anti-CD3/anti-CD28 signaling complex was temporally controlled by disruption of the multimerized complex at days 1 and 4 after stimulation with the anti-CD3/anti-CD28 multimerized reagent.

To assess relative effects on CD4+ and CD8+ subsets under the various conditions, the proportion of CD4+ or CD8+ T cells in the population of stimulated CD3+ cells was determined by flow cytometry. As shown in FIG. 5C, incubation of $CD3^+$ cell cultures with the anti-CD3/CD28 multimerized agents led to a relatively higher proportion of $CD8^+$ cells as compared to CD4+ cells at harvest, when disruption was effected at a relatively earlier time-point, such as within one day after initiating stimulation, and as compared to other conditions.

Figure 6A:
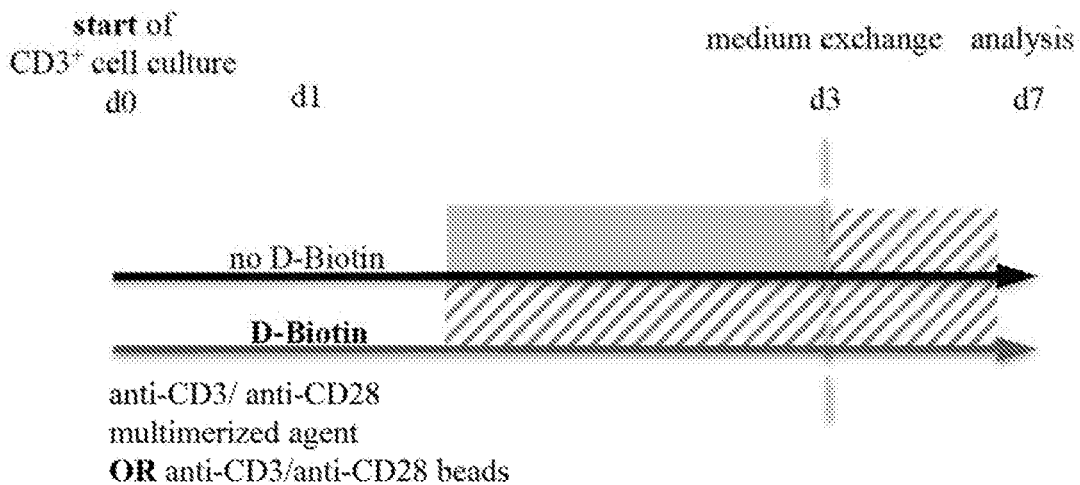
FIG. 6A is a schematic representation of the experimental conditions and timeline, including time points of D-Biotin addition and medium exchange during cell culture.

Example 3: Assessment of T Cell Expansion and Phenotype Following Temporally-Controlled Activation of CD3+ T Cells by Incubation with a Reversible Agent The impact of temporal control of T cell stimulation using the reagent described in Examples 1 and 2, via disruption with D-Biotin, was assessed. In this study, bulk CD3+ T cells were selected as described in Example 1 and 2 and incubated with the multimerized CD3/CD28 agent or one of the various control reagents. As shown in FIG. 6A, D-Biotin was added to certain samples, and not others, as described in Example 2, and the cells cultured through day 8 (with media exchange on day 3) post-initiation of stimulation. Untreated (unstimulated) cells served as negative control. Cells were incubated at 37° C. with media exchange on day three. After seven days, individual test wells were resuspended to harvest cells, individually transferred to microcentrifuge tubes and analyzed for cell count to assess persistence and/or expansion of the cells, and/or by flow cytometric analysis to assess surface expression of various markers (e.g., CD4, CD8, CD62L and CD127) and/or nuclear expression of Ki-67 and T-bet. Exemplary results are depicted in FIGS. 6B-6F. Data are representative of three independent experiments encompassing duplicates for each tested condition and controls.

Figure 6B:
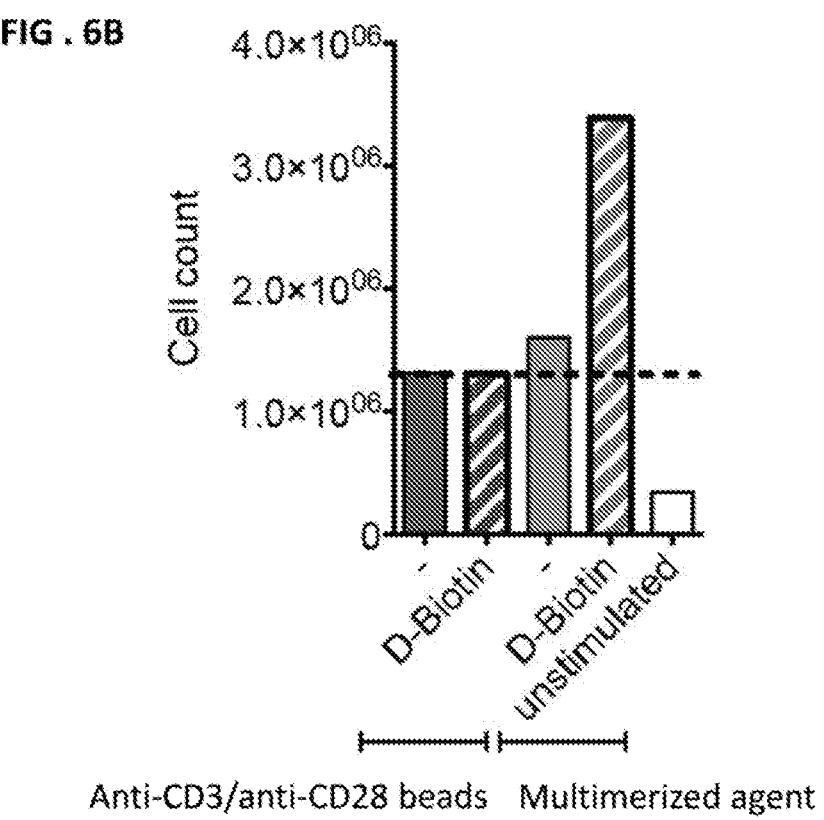
FIG. 6B shows the cell count (degree of expansion) in cultures at day 7 under the indicated conditions. The dashed horizontal line indicates the number of cells expanded in the anti-CD3/anti-CD28 beads positive control without D-Biotin addition.

As shown in FIG. 6B, the results showed a greater number of CD3+ T cells at harvest following stimulation of cells with the soluble anti-CD3/anti-CD28 multimerized reagent, temporally controlled by disruption at day 1 post-initiation, as compared to cells cultured under similar conditions with such reagents, without temporal control of the signal (i.e., no D-Biotin addition). There were observed approximately 3-fold greater numbers of CD3+ T cells at harvest following stimulation with temporal control via D-Biotin addition one day after initiating incubation with the soluble anti-CD3/anti-CD28 multimerized reagent, compared to cells stimulated in the presence of anti-CD3/anti-CD28 beads or the soluble reagent, without disruption of reversible binding. Additionally, the addition of D-Biotin had no substantial effect on the cell numbers at harvest in the case of cultures stimulated with anti-CD3/anti-CD28 beads, indicating that the effects observed with D-Biotin addition to the soluble reagent were due to its ability to specifically bind and disrupt binding of the components of this reagent.

Figure 6C:
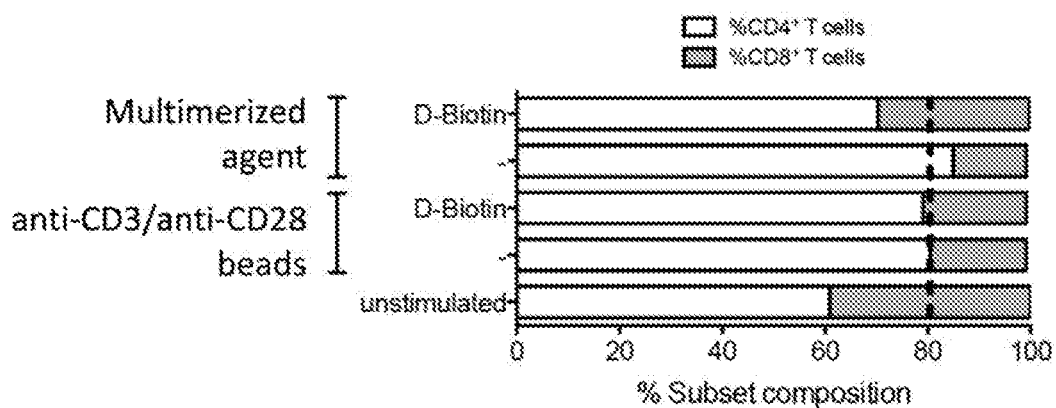
FIG. 6C shows the proportion of CD4+ and CD8+ cells in the cultures of FIG. 6B. The dashed horizontal line indicates the fraction of CD4+ and CD8+ cells in the positive control without D-Biotin addition.
Figure 6D:
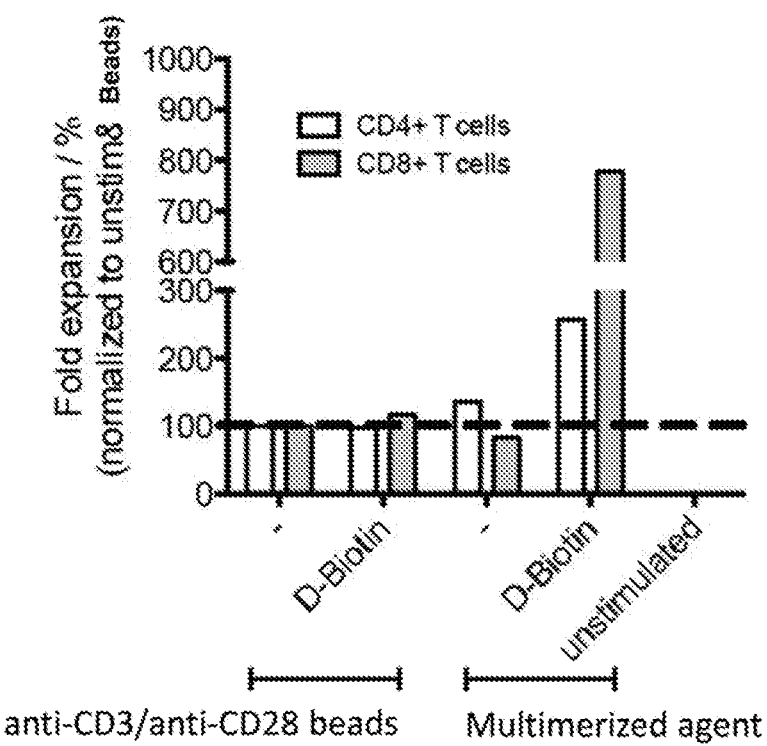
FIG. 6D shows the number of CD4+ or CD8+ cells normalized to the numbers of CD4+ or CD8+ cells in the unstimulated control. The horizontal line represents the numbers of CD4+ or CD8+ cells expanded in the positive anti-CD3/anti-CD28 beads control without D-Biotin addition.

Within the CD3+ expanded population, there was observed a higher proportion of CD8+ cells at harvest, following culture with the soluble reagent and temporal control using D-Biotin disruption at day one, as compared to the other tested conditions (FIG. 6C). As shown in FIG. 6D, normalizing the CD4+ and CD8+ subsets within the CD3+ T cell population to the ratio of CD4+ and CD8+ T cells in the unstimulated controls, the results showed that when binding of the soluble reagent was disrupted at day 1 using D-Biotin, the relative degree of expansion (and/or survival) of the CD8+ T cells as compared to CD4+ T cells was greater as compared to other tested conditions. The results demonstrate that in a mixed cell culture (e.g., bulk T cells), temporal control of the signal, e.g., by disruption of multimerized agent binding using a competition substance, can be used to tailor or adjust the relative expansion and/or persistence of particular subpopulations compared to others (e.g., CD4+ vs CD8+).

Figure 6E:
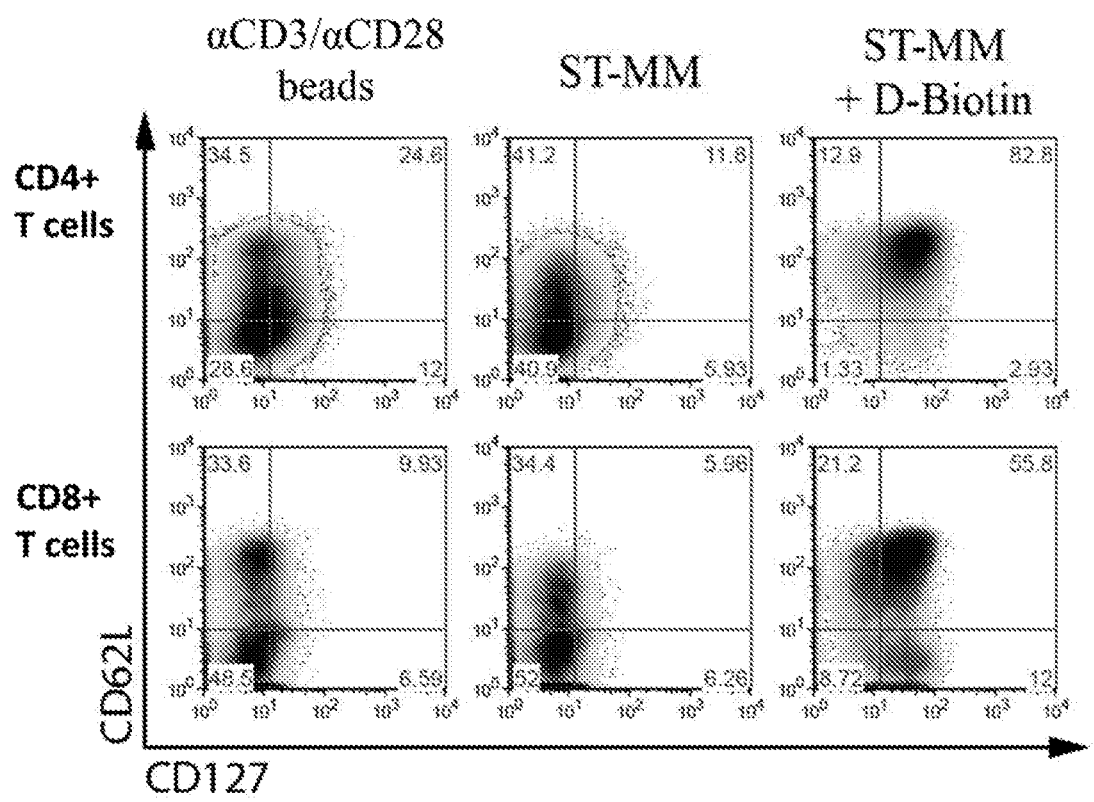
FIG. 6E shows flow cytometric analysis of CD62L and CD127 surface expression for both CD4+ and CD8+ T cell populations in cultures at day 7 for the indicated conditions.
Figure 6F:
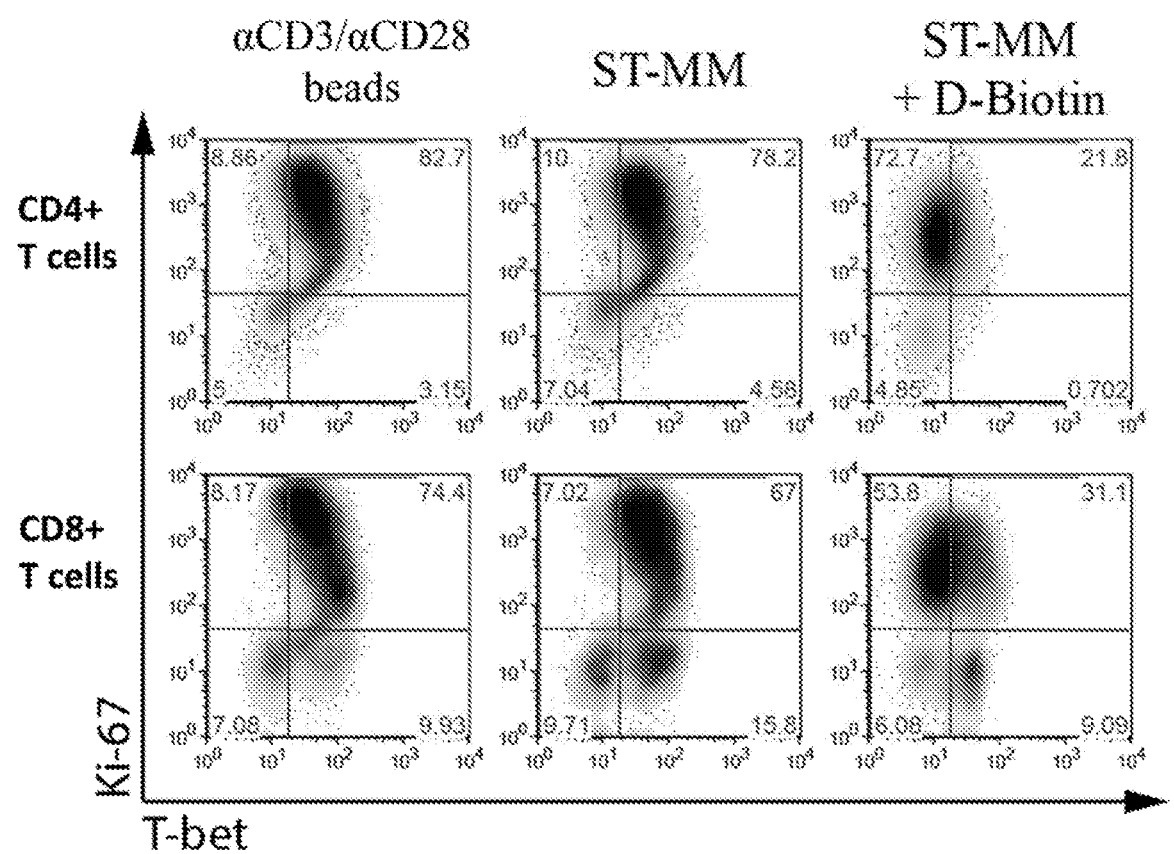
FIG. 6F shows flow cytometric analysis of Ki-67 and T-bet expression for both CD4+ and CD8+ T cell populations in cultures at day 7 for the indicated conditions. ST-MM is anti-CD3/anti-CD28 Fab multimerized mutein streptavidin agent.

Results from this study also showed that the ability to temporally control the CD3/CD28 signal using this reversible reagent also could be used to impact the relative representation, in the composition at harvest, of various cell populations with different activation, differentiation and phenotypic profiles. For example, as shown in FIG. 6E, stimulating CD3+ T cells with soluble anti-CD3/anti-CD28 multimerized reagent over eight days, with addition of D-Biotin at day one, resulted in a final composition in which a higher percentage of CD4+ cells and a higher percentage of CD8+ cells showed high surface expression of CD62L and CD127, as compared to other conditions, in which cells were cultured over the same period without temporal control by disruption. Similarly, as shown in FIG. 6F, as compared to conditions in which signal was not disrupted, following stimulation with the multimerized reagent with disruption at day 1, a higher percentage of both CD4+ and CD8+ cells at harvest were positive for the marker Ki-67 (at slightly lower levels than high-staining populations), indicative of proliferation, and exhibited low levels of T-bet staining. These findings are consistent with a conclusion that the ability to temporally control the signal using embodiments of the provided reagents can result in an increase in a less-differentiated, long-lived population T cells such as long-lived memory T cells. Without being bound by theory, higher expression of CD62L and of CD127 is generally observed on less-differentiated and/or relatively longer-lived T cell populations, such as naïve and long-lived memory populations such as central memory ($T_{CM}$) and less-differentiated memory T cells such as so-called stem memory T cells ($T_{SCM}$). By contrast, these markers are generally lower on effector cells or terminally differentiated effector memory T cells. Ki-67 positivity indicates cell proliferation, suggesting at least some cells within the increased population may represent long-lived, less differentiated memory cells, as opposed to naïve T cells. T-bet staining generally increases upon activation and reduced in less-differentiated cells, and has been reported as being lower in long-lived central memory T cells, and even lower in $T_{SCM}$ cells. Thus, the results indicated that in this study, temporal control of signal by disrupting the multimerized reagent at day 1, resulted in an increase (compared with similar stimulation without disruption) in persistence, expansion and/or emergence of cells having a phenotypic marker profile similar to that present on long-lived, less-differentiated memory cells. Thus, an increased percentage of cells harvested following temporally-controlled stimulation using the reversible reagent may exhibit features of long-lived memory cells, including T stem memory cells ($T_{SCM}$).

Figure 7B:
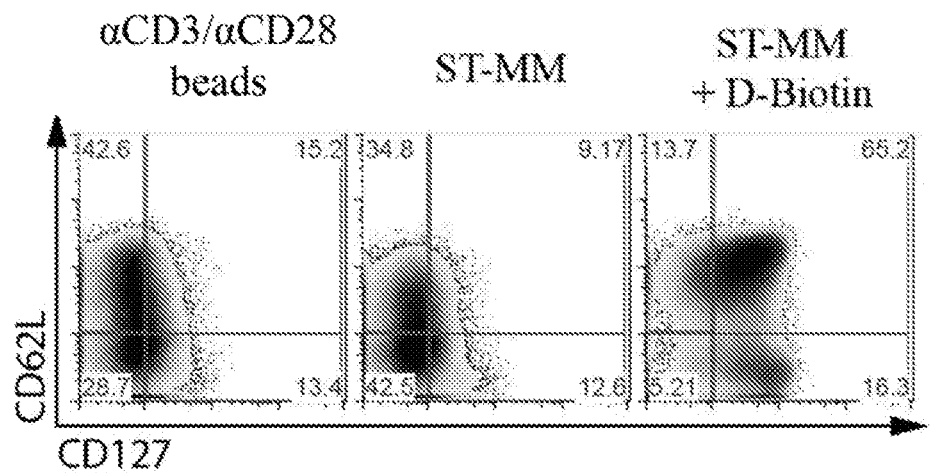
FIG. 7B shows flow cytometric analysis of CD62L and CD127 surface expression in cultures at day 7 for the indicated conditions.
Figure 7C:
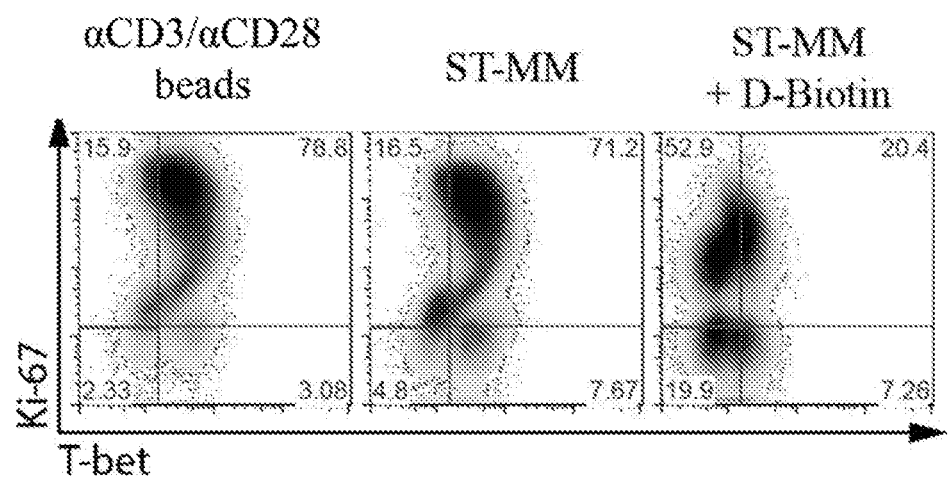
FIG. 7C shows flow cytometric analysis of Ki-67 and T-bet expression in cultures at day 7 for the indicated conditions. ST-MM is anti-CD3/anti-CD28 Fab multimerized mutein streptavidin agent.

Example 4: Assessment of T Cell Expansion and Phenotype Following Temporally-Controlled Activation of CD8+ T Cells by Incubation with a Reversible Agent To assess impact on CD8+ cells without substantial presence of CD4+ cells, a study was carried out essentially as in Example 3, but in which the cultured cells had been enriched for CD8+ cells, as opposed to stimulation of bulk CD3+ cells. Exemplary results are depicted in FIGS. 7A-7C. Data are representative of three independent experiments encompassing duplicates for each tested condition and controls.

As shown in FIG. 7A, as was the case for CD3+ bulk cultures, cell numbers indicated an increased survival and/or expansion of cells following disruption of signal at day 1, as compared to the corresponding conditions when no D-Biotin was added or signal was otherwise not disrupted. The increases in cell number and relative expansion or persistence were similar to that observed for bulk CD3+ cells, and again, addition of D-Biotin to the Dynabead® control sample indicated specificity of the effect due to disruption of binding of the multimerized reagent components.

As shown in FIGS. 7B and 7C, even in the absence of substantial CD4+ cells, the temporally-controlled conditions in this study resulted in increased representation of T cells at harvest exhibiting phenotypic properties similar to long-lived memory and/or less-differentiated cells.

Example 5: Assessment of T Cell Stimulation Following Stimulation of T Cells with a Soluble Multimerized Reagent Functionalized to Target CD3 and Various Co-Stimulatory Molecules Additional studies were carried out evaluating cells following incubation with alternative stimulatory agents and combinations thereof, illustrating that for some embodiments of the provided reagents, modular properties of the reagents can be used to design or adjust the output compositions to promote desired outcomes or phenotypes. Various multimerized agents containing anti-CD3 Fabs and one or two additional Fabs were generated as described in Example 1, except that in addition to the anti-CD3 and anti-CD28 Fabs described, additional Fabs were used that were capable of delivering, modulating, or augmenting a signal in T cells (anti-CD90, anti-CD95, anti-CD137 and anti-CD154). For different conditions, the Fabs were reversibly bound to the reagent in various double and triple combinations.

Functionalizing the reagent with the various Fabs was carried out essentially as described in Example 1, with mixing at room temperature the Fabs and the oligomeric reagent. For multimerizing two different Fabs (double-Fab combinations), approximately 3 μg of oligomeric Strep-Tactin® were mixed with approximately 0.5 μg of each Fab; for multimerizing three different Fabs on the same reagent, (triple-Fab combinations), approximately 4.5 μg of soluble oligomeric Strep-Tactin® with approximately 0.5 μg of each Fab for generation of triple Fab multimerized agents, containing anti-CD3 Fab, anti-CD28 Fab and one of the additional Fabs (targeting CD90, CD95, CD137 or CD154). The resulting soluble multimerized reagents were used directly to stimulate T cells, and optionally, were stored on ice prior to stimulation of cells.

CD3+ T cells were isolated as described in Example 1, and 500,000 CD3+ T cells seeded in 48-well plates in 1 mL complete cell culture medium supplemented with 50 U/mL IL-2. Cells were stimulated either with one of the various soluble Fab-multimerized agents or with anti-CD3/anti-CD28 beads (anti-CD3- and anti-CD28-mAb coated beads). Untreated (unstimulated) cells served as negative control. Cells were incubated at 37° C. with media exchange on day two post-initiation. After six days, individual test wells were resuspended to harvest cells, individually transferred to microcentrifuge tubes and analyzed for cell count to assess expansion of the cells and/or by flow cytometric analysis for surface expression of CD4, CD8, CD45RO, CD45RA, CD69 or CD62L. Exemplary results are depicted in FIGS. 8A-8F. Data are representative of three independent experiments encompassing duplicates for each tested condition and controls.

Figure 8A:
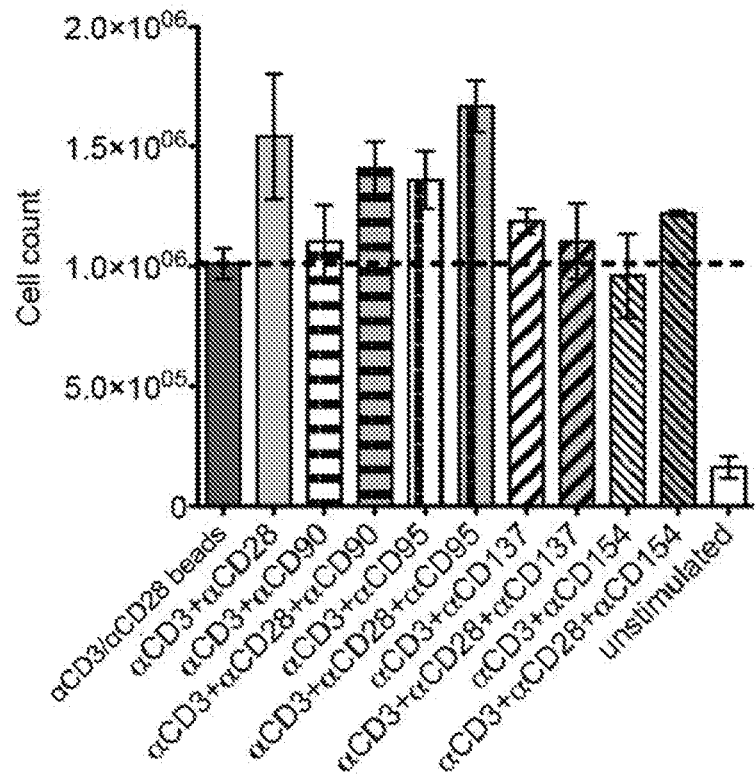
FIG. 8A shows the cell count (degree of expansion) in cultures at day 6 under the indicated conditions. The dashed horizontal line indicates the number of cells expanded in the positive control (anti-CD3/anti-CD28 beads).
Figure 8B:
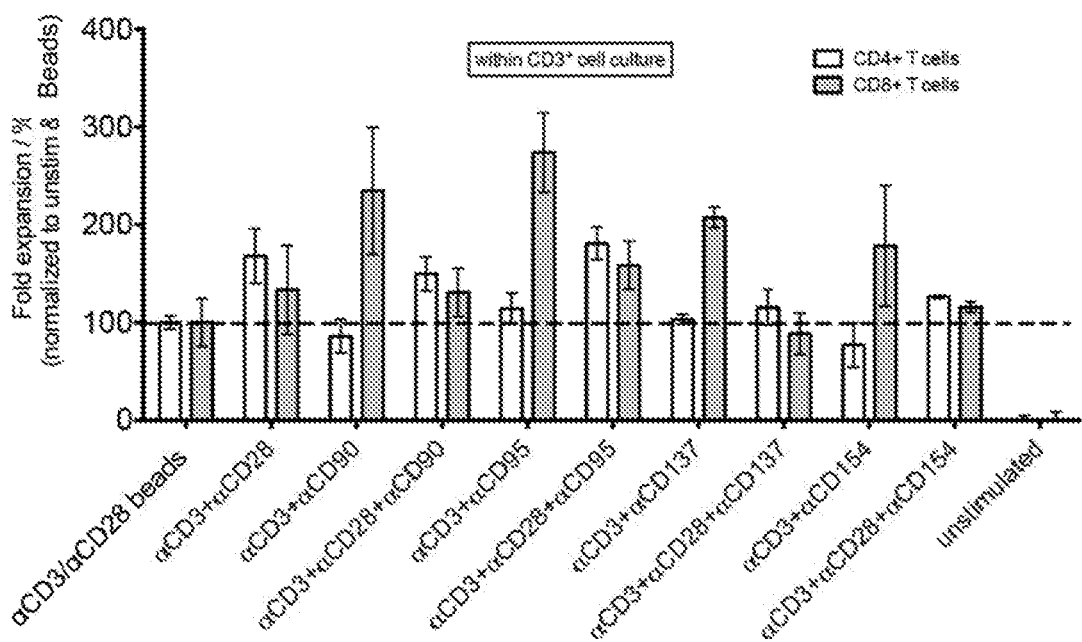
FIG. 8B shows the number of CD4+ or CD8+ cells normalized to the unstimulated control in cultures at day 6 under the indicated conditions. The resulting numbers of CD4+ or CD8+ cells expanded in the positive control (anti-CD3/anti-CD28 beads) were set to 100% as indicated by the dashed horizontal line.

As shown in FIG. 8A, stimulation of CD3+ T cells with each of the Fab-multimerized agents resulted in a cell count at harvest (indicative of expansion and/or persistence) that was at least comparable to stimulation with anti-CD3/anti-CD28 anti-CD3/anti-CD28 beads, and, in some cases, higher. Stimulation with Fab-multimerized agents that did not contain anti-CD28 Fab shifted the T cell composition of the expanded culture towards a higher proportion of CD8+ cells compared to stimulation of cells with a reagent that included an anti-CD28 Fab, such as by stimulation with anti-CD3/anti-CD28 beads or soluble anti-CD3/anti-CD28 multimerized agent. For example, as shown in FIG. 8B, normalizing the CD4+ and CD8+ subsets within the CD3+ T cell population to the ratio of CD4+ and CD8+ T cells in the unstimulated controls, the results showed that the relative increase in number of the CD8+ T cells was greater than the relative increase in CD4+ T cells for cultures were stimulated with multimeric reagents containing multimerized anti-CD3 Fab and either multimerized anti-CD90, anti-CD95, anti-CD137 or anti-CD154 Fabs, but not those stimulated with such reagents containing multimerized anti-CD3 and anti-CD28 Fabs or those with anti-CD3/anti-CD28 beads, or those containing three multimerized Fabs in which one of the multimerized Fabs was anti-CD28 Fab) did not lead to a greater proportion of CD8+ cells in the expanded T cell composition.

Figure 8E:
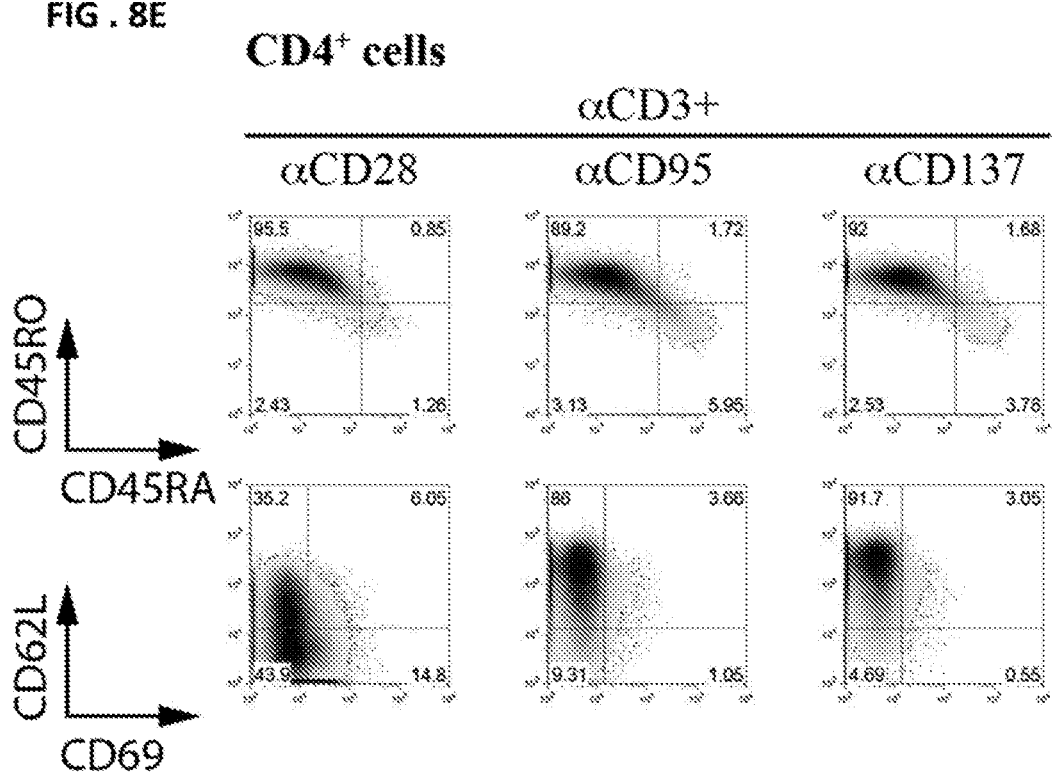
FIG. 8E and FIG. 8F depict the flow cytometric analysis of CD62L and CD69 surface expression or CD45RO and CD45RA surface expression in either the CD4+(FIG. 8E) or CD8+(FIG. 8F) cells within exemplary CD3+ cells cultured for 6 days under the indicated conditions.
Figure 8F:
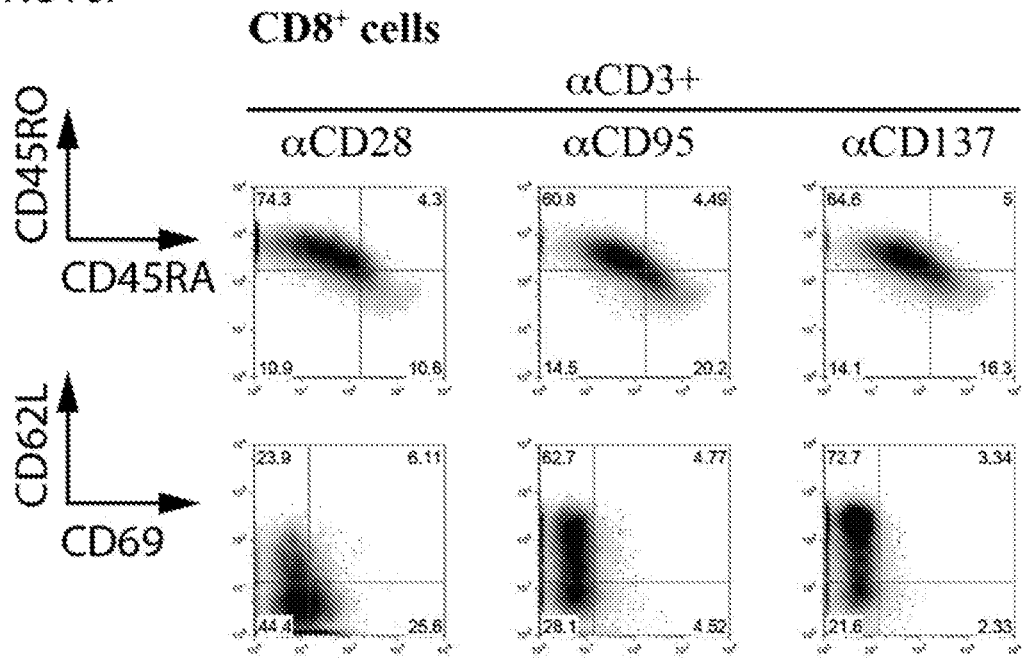

As shown in FIGS. 8C and 8D, under the conditions in this study, use of multimerized Fab combinations other than those including anti-CD28 Fabs, appeared to result in a relatively larger percentage of cells that were CD62L+, as compared to similar stimulatory conditions and agents including anti-CD28 Fab. This effect was observed in both CD4++ (FIG. 8C) and CD8+ (FIG. 8D) populations of cells at harvest, after normalizing the respective subsets, within the CD3+ T cell population. FIG. 8E (CD4+ T cells) and 8F (CD8+ T cells), show expression of CD62L, CD69, CD45RA, and CD45RO in the various conditions. These results demonstrate that in embodiments provided herein, the modular nature of the reagents allows the tailoring of the reagent for desired outcomes, cell populations, and phenotypes, including through the use of different combinations of stimulatory agents (including those targeting various second or accessory signaling molecules, including those other than CD28 (e.g., CD90, CD95, CD137 or CD154). In some aspects, such tailoring can be used to shift cultures toward production of a desired phenotype, such as to promote cells with a less differentiated surface phenotype, such as long-lived memory T cells.

Example 6: Effect of the Mutein Streptavidin Backbone of a Soluble Anti-CD3/Anti-CD28 Multimerized Reagent on T Cell Stimulation An alternative streptavidin mutein, which is a streptavidin homo-tetramer containing the mutein sequence of amino acids set forth in SEQ ID NO:27, see e.g. International Published PCT Appl. Nos. WO 2014/076277), was used to generate a soluble oligomeric reagent using methods that were substantially the same as described in Example 1. Anti-CD3 and anti-CD28 Fab fragments were immobilized to the soluble oligomeric streptavidin mutein (ST-MM B, via a streptavidin peptide-binding partner fused to each Fab fragment, substantially as described in Example 1. Stimulation of T cells with the resulting anti-CD3/CD28 Fab-multimerized reagent (ST-MM B) was compared to stimulation of T cells with the anti-CD3/CD28 Fab-multimerized reagent generated in Example 1 (designated ST-MM A for comparison herein).

CD3+ T cells were selected from a sample of fresh peripheral blood mononuclear cells (PBMCs) obtained from a Ficoll gradient. Approximately 500,000 CD3+ T cells were seeded in 48-well plates in 1 mL complete cell culture medium supplemented with 50 U/mL IL-2. Cells were stimulated with either soluble anti-CD3/anti-CD28 multimerized reagent (ST-MM A) generated as described in Example 1, soluble anti-CD3/anti-CD28 multimerized reagent (ST-MM B) or with anti-CD3/anti-CD28 beads (anti-CD3- and anti-CD28- mAb coated beads; positive control). Untreated (unstimulated) cells served as negative control. Cells were incubated at 37° C. without media exchange. After five days, individual test wells were resuspended to harvest cells, individually transferred to microcentrifuge tubes and analyzed for cell count to assess expansion of the cells and/or by flow cytometric analysis for surface expression of CD4, CD8, CD69 or CD62L. Exemplary results are depicted in FIGS. 9A-9D. Data are representative of three independent experiments encompassing duplicates for each tested condition and controls.

Figure 9A:
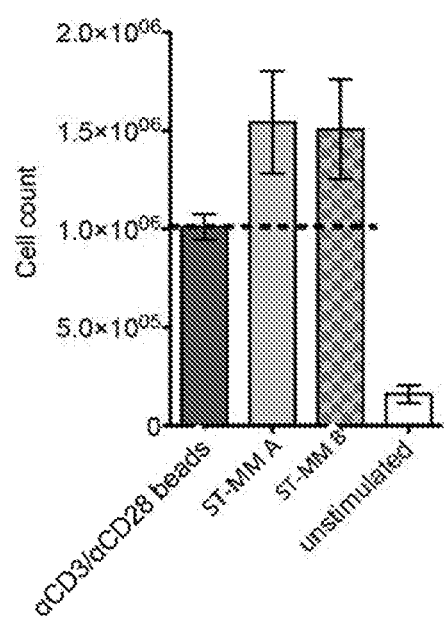
FIG. 9A shows the cell count (degree of expansion) in cultures at day 5 under the indicated conditions. The dashed horizontal line indicates the number of cells expanded in the positive control (anti-CD3/anti-CD28 beads).
Figure 9B:
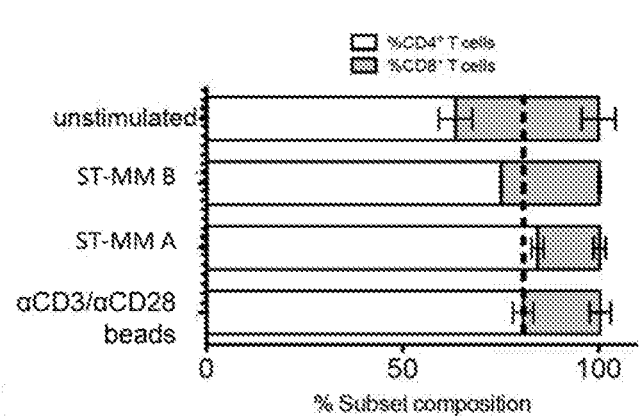
FIG. 9B s shows the proportion of CD4+ and CD8+ cells in the cultures of FIG. 9A. The dashed horizontal line indicates the fraction of CD4+ and CD8+ cells in the positive control (anti-CD3/anti-CD28 beads).

As shown in FIG. 9A, the results showed that stimulation of CD3+ T cells with either soluble anti-CD3/anti-CD28 multimerized reagent (ST-MM A) or soluble anti-CD3/anti-CD28 multimerized reagent (ST-MM B) resulted in comparable expansion of cells, which was greater than achieved with stimulation with anti-CD3/anti-CD28 beads. The results in FIG. 9B showed that stimulation of cells with the soluble anti-CD3/anti-CD28 multimerized reagent (ST-MM B) led to a small increase in the proportion of CD8+ cells in the T cell composition of the expanded culture compared to stimulation of cells with the soluble anti-CD3/anti-CD28 multimerized reagent (ST-MM A). As shown in FIG. 9C, normalizing the CD4+ and CD8+ subsets within the CD3+ T cell population to the ratio of CD4+ and CD8+ T cells in the unstimulated controls, the results showed that expansion of the CD8+ T cells was substantially greater than the expansion of CD4+ T cells in cells that were stimulated with the soluble anti-CD3/anti-CD28 multimerized reagent (ST-MM B) compared to with the soluble anti-CD3/anti-CD28 multimerized reagent (ST-MM A) or with anti-CD3/anti-CD28 beads. The results in FIG. 9D also showed that cells stimulated with soluble anti-CD3/anti-CD28 multimerized reagent (ST-MM A) shifted the T cell composition of the expanded culture towards a higher proportion of CD62L+ cells compared to cells stimulated with either the soluble anti-CD3/anti-CD28 multimerized reagent (ST-MM A) or with anti-CD3/anti-CD28 beads.

Figure 10A:
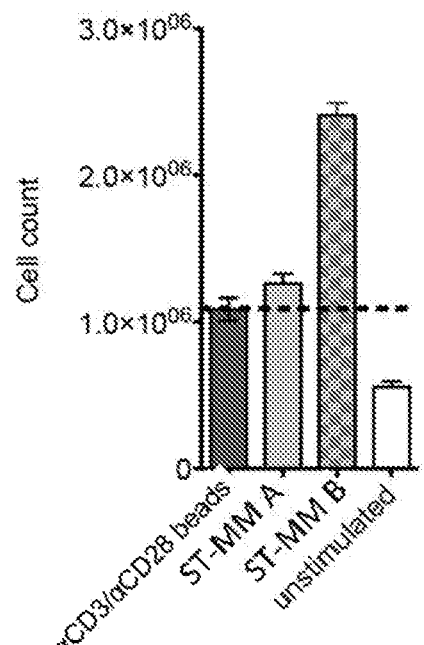
FIG. 10(A-B) shows features resulting from stimulation of CD8+ T cells with either an oligomeric mutein streptavidin (Strep-Tactin®; ST-MM A) reagent or an oligomeric mutein streptavidin (Strep-Tactin® XT; ST-MM B) reagent, each reversibly bound by anti-CD3 and anti-CD28. FIG.
FIG. 10B shows flow cytometric analysis of CD62L, CD69 and CD8 surface expression in cultures at day 6 for the indicated conditions.
Figure 10B:
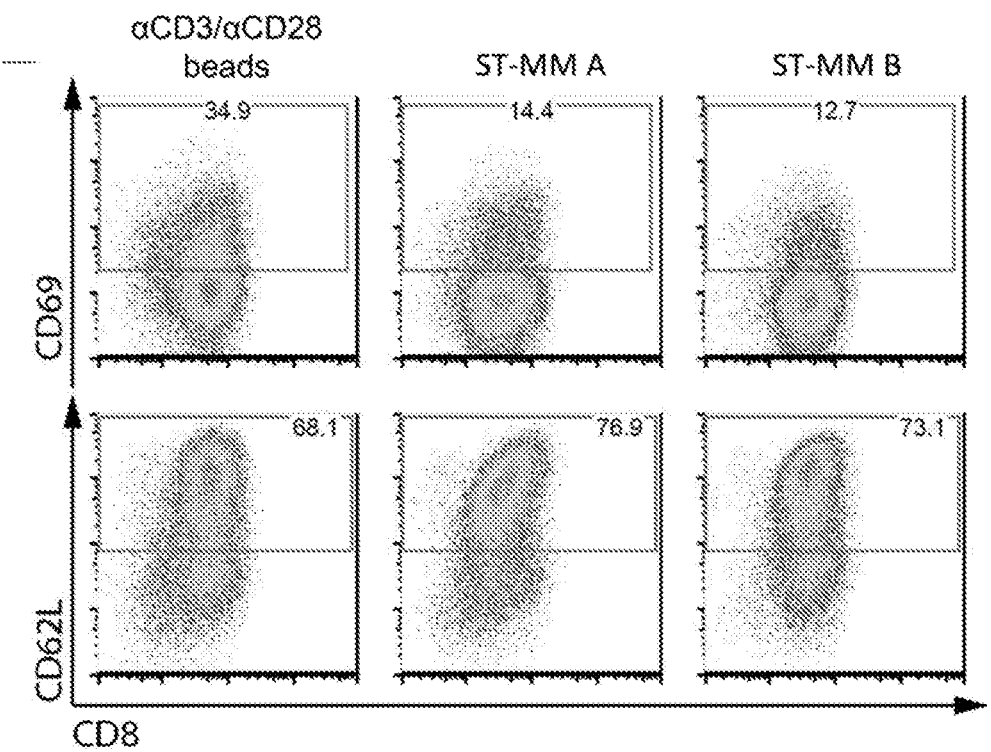

To assess the effects of the reagent ST-MM B specifically on CD8+ cells, similar experiments were performed as above, except that the stimulation was allowed to proceed until day six and a medium exchange was included. In particular, approximately 500,000 CD8+ T cells were seeded in 48-well plates in 1 mL complete cell culture medium supplemented with 50 U/mL IL-2. Cells were stimulated with either soluble anti-CD3/anti-CD28 multimerized reagent (ST-MM A) generated as described in Example 1, soluble anti-CD3/anti-CD28 multimerized reagent (ST-MM B) or with anti-CD3/anti-CD28 beads (anti-CD3- and anti-CD28-mAb coated beads; positive control). Untreated (unstimulated) cells served as negative control. Cells were incubated at 37° C. with media exchange at day four. After six days, individual test wells were resuspended to harvest cells, individually transferred to microcentrifuge tubes and analyzed for cell count to assess expansion of the cells and/or by flow cytometric analysis for surface expression of CD8, CD69 or CD62L. Exemplary results are depicted in FIGS. 10A and 10B. Data are representative of three independent experiments encompassing duplicates for each tested condition and controls.

As shown in FIG. 10A, the results showed that stimulation of CD8+ T cells with soluble anti-CD3/anti-CD28 multimerized reagent (ST-MM B) resulted in a greater than 2-fold increase in cell counts compared to CD8+ T cells stimulated with soluble anti-CD3/anti-CD28 multimerized reagent (ST-MM A) or with anti-CD3/anti-CD28 beads. The results in FIG. 10B show surface phenotypes of the cells, including degree of surface expression of CD62L+ and CD69+ T cell composition in T cells expanded with soluble anti-CD3/anti-CD28 multimerized reagent (ST-MM B) versus to T cells expanded with either soluble anti-CD3/anti-CD28 multimerized reagent (ST-MM A) or with anti-CD3/anti-CD28 beads.

Example 7: Stimulation/Expansion of CD3+ T Responder Cells with αCD3/αCD28 Fab Fragments that were Reversibly Immobilized on Beads Coated with the Streptavidin Mutein Strep-Tactin®

300,000 CD3+CD62L-responder T cells (Tresp, isolated by serial magnetic enrichment from a non-mobilized donor apheresis product) were labeled with 3 µM CFSE and stimulated with 5 µl of a 15 µl preparation of Streptactin® beads (10 mg magnetic particles/ml, loaded with 35 µg Streptactin®/mg beads) either loaded with 0.5 µg αCD3 Fab fragment alone, 0.5 µg αCD28 Fab fragment alone, or a mixture of 0.5 µg αCD3 Fab fragment and 0.5 µg αCD28 Fab.

The αCD3 Fab fragment used was derived from the CD3 binding monoclonal antibody produced by the hybridoma cell line OKT3. The hybridoma cell line OKT3 and the OKT3 antibody are described in U.S. Pat. No. 4,361,549, the cell line has been deposited under accession number ATCC® CRL-8001™). The αCD28 Fab used was derived from the monoclonal anti-human CD28 antibody CD28.3 (Vanhove et al., BLOOD, 15 Jul. 2003, Vol. 102, No. 2, pages 564-570). The nucleotide sequence of the variable domains of this antibody CD28.3 has been deposited in GenBank in the form of a synthetic single chain Fv construct anti-human CD28 antibody scFv28.3 under GenBank accession number AF451974.1 (set forth in SEQ ID NOS: 33 and 34).

Both Fab fragments were recombinantly produced in E. coli as described in International Patent App. Pub. No. WO2013/011011 and WO 2013/124474 carrying as constant domains (CH1 and Ckappa) an IgG1 consensus sequence. The heavy chain of both Fab fragments was carboxy-terminally fused with a sequential arrangement of two streptavidin binding modules (SAWSHPQFEK(GGGS)$_2$GGSAWSHPQFEK)(SEQ ID NO: 16), that is commercially available as "Twin-Strep-Tag®" from IBA GmbH, Göttingen, Germany). The αCD3 Fab fragment was used as first agent with the streptavidin binding peptide serving as binding partner C1 and the αCD28 Fab fragment was used as second agent with the streptavidin binding peptide serving as binding partner C2. The (tetrameric) streptavidin mutein "Strep-Tactin®" serves as the reagent on which both Fab fragments were reversibly immobilized.

Figure 11C:
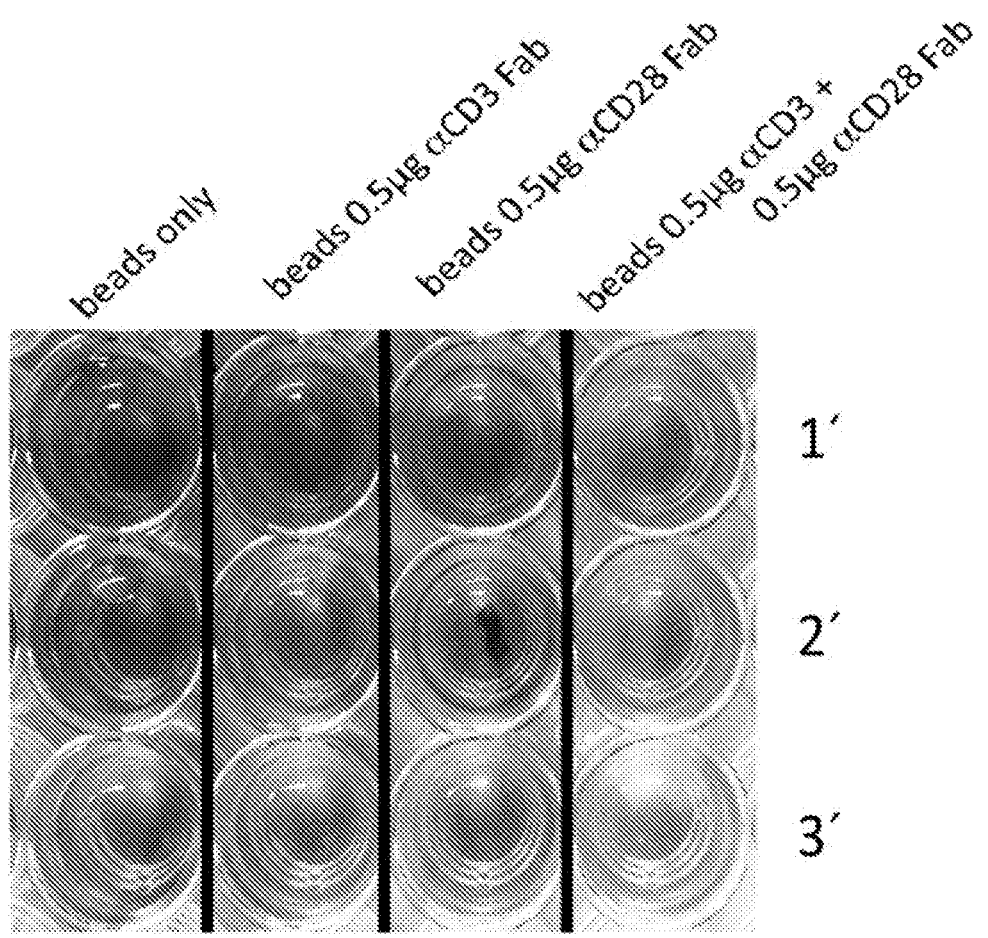
FIG. 11C shows a picture of the culture dish after 4 days of stimulation.

In the expansion experiment, Tresp cells stimulated with blank beads (no Fab) served as negative control. Tresp cells were seeded in triplets in 48-well plates along with 300,000 CD3 cells autologous feeder cells (irradiated with 30Gy) in 3 ml complete cell culture medium (RPMI (Gibco) supplemented with 10% (v/v) fetal calf serum, L-glutamine, b-mercapto ethanol, HEPES, penicillin, streptomycine and gentamycine) supplemented with 10 U/ml interleukin 2 (IL-2). The cells were incubated at 37° C. without media exchange and analyzed after 4 days by FACS analysis. FACS staining and analysis was done after 10 min incubation with 100 µM D-biotin. One representative plot for each condition is shown in FIG. 11A. Plots show live CD3+ cells that were stained with propidium iodide (PI) for live/dead discrimination. FIG. 11A is a histogram showing size-distribution (forward scatter) of stimulated cells. FIG. 11A shows that a specific cell population of Tresp cells was stimulated and expanded (increase in size/number compared to the unstimulated "beads only" control) when incubated in the presence of beads on which a mixture of 0.5 µg αCD3 Fab fragment and 0.5m αCD28 Fab was immobilized, after being stimulated in vitro with αCD3/αCD28 Fab fragments that were reversibly immobilized on beads coated with the streptavidin mutein Strep-Tactin®. FIG. 11B depicts histograms of the dilution of the proliferation dye CFSE representing the degree of proliferation according to the number of cells per cell division (indicated on top of FIG. 11B, 0 represents undivided cells; 5 represents cells that have gone through at least 5 divisions). It can be seen from FIG. 11B that the population of T cells stimulated with the beads on which a mixture of 0.5m αCD3 Fab fragment and 0.5 µg αCD28 Fab was immobilized have mostly gone through three cell divisions and represent a more uniform proliferation pattern than with a single stimulus alone (small number of cells within the undivided peak "0"). The increased absolute amount of proliferation (more cells have proliferated uniformly after 4d stimulation with αCD3 and αCD28 functionalized beads) is also represented by a more intense consumption of media as depicted by an indicator color change to yellow (depicted as lighter liquid in wells in FIG. 11C).

Example 8: Stimulation/Expansion of CD3+ T Responder Cells with αCD3/αCD28 Fab Fragments that were Reversibly Immobilized on Soluble Strep-Tactin In this example CD3+ T responder cells (isolated by magnetic selection from a sample of fresh PBMCs obtained from a Ficoll gradient) were expanded after in vitro stimulation with αCD3/αCD28 Fab fragments that were reversibly immobilized on soluble oligomeric Strep-Tactin® acting as a soluble reagent. The oligomeric streptavidin mutein was obtained by polymerizing Strep-Tactin® with sulfo SMCC (sulfosuccinimidyl 4-(N-maleimidomethyl)cyclohexane-1-carboxylate, product #22122 Thermo Scientific) and iminothiolan (product #26101 Thermo Scientific) according to the protocol of the manufacturer (Thermo Scientific). The oligomeric streptavidin muteins were separated from monomeric (unreacted) and dimeric streptavidin muteins by size exclusion chromatography and the so obtained fraction of the oligomeric streptavidin mutein (n≥3) was used as soluble reagent.

Figure 12A:
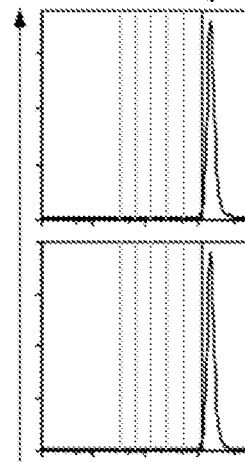
Figure 12B:
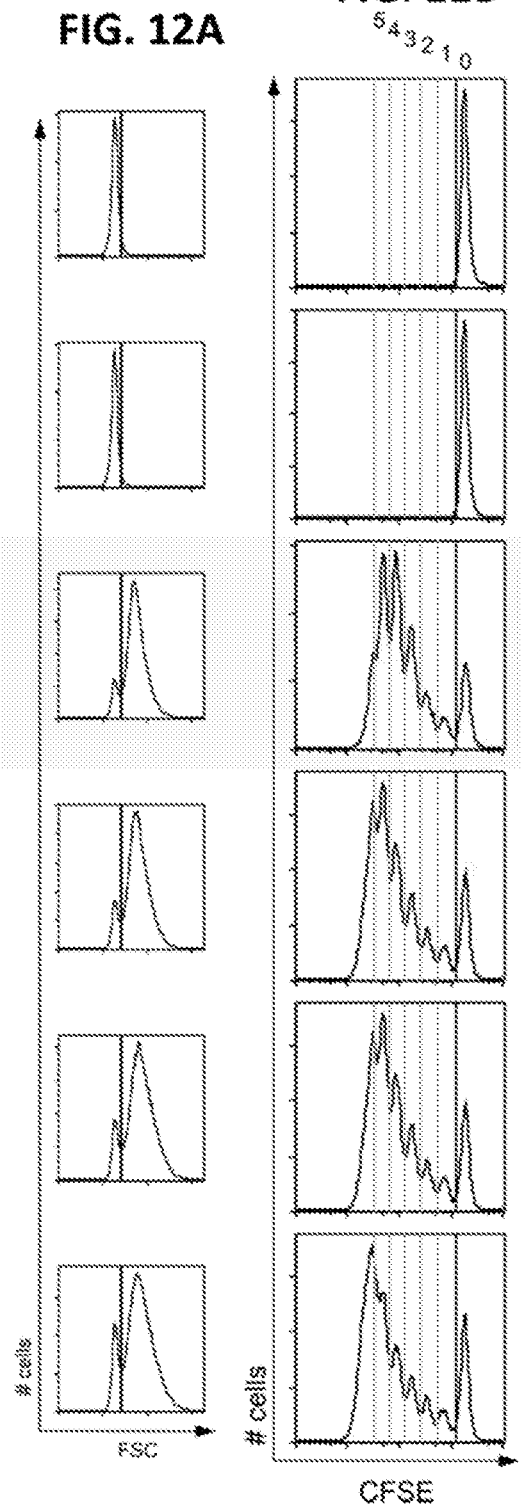
Figure 12C:
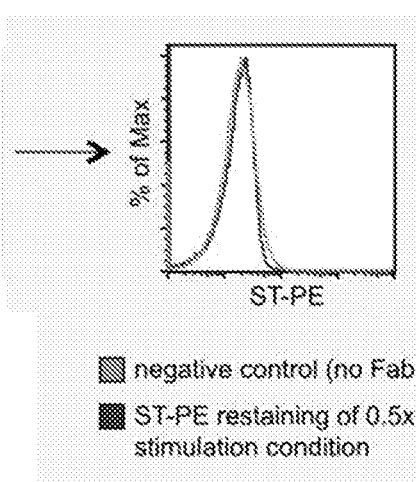
FIG. 12C shows cells after culture that were liberated by stimulation reagents after treated with 1 mM D-biotin and washed. The dissociation and removal of monomeric Fab fragments was analyzed by restaining with oligomeric streptavidin mutein labeled with phycoerythrine (ST-PE) as a fluorescent label and a representative histogram is shown.
Figure 12D:
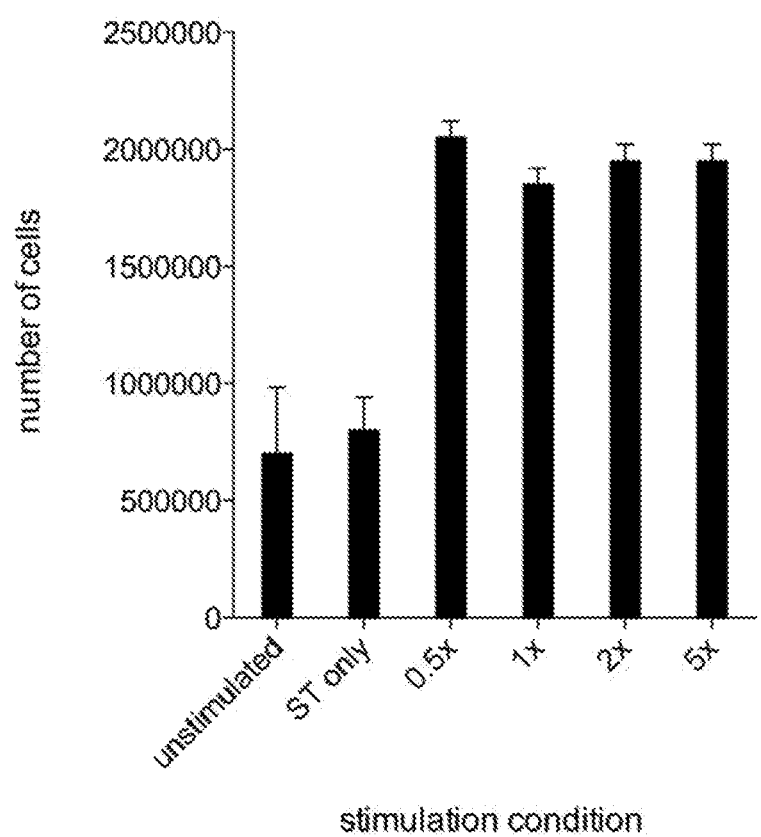
FIG. 12D shows the absolute number of live (trypan blue negative) cells after 5 days was counted using a Neubauer counting chamber and plotted against the respective stimulation condition. Median cell numbers are shown in FIG. 12D; error bars indicate standard deviation (SD).
Figure 12E:
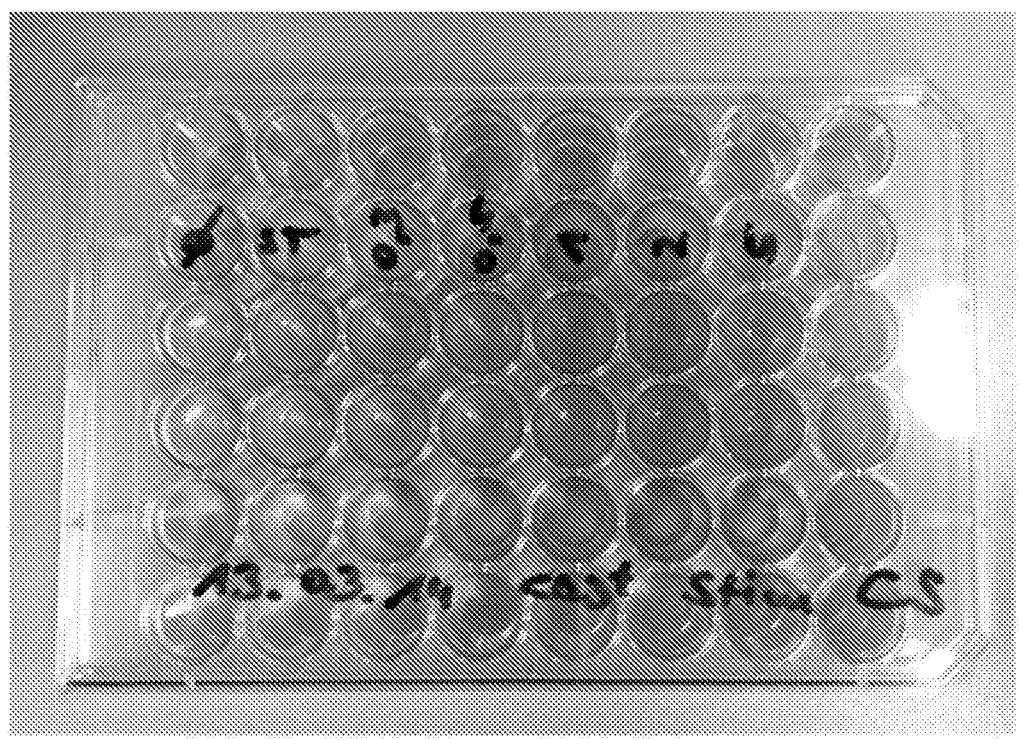
FIG. 12E shows a picture of the culture dish after 5 days of stimulation.

For the in vitro expansion, 300,000 CD3+ responder T cells (Tresp) were labeled with 2 µM Carboxyfluorescein succinimidyl ester (CFSE) and stimulated with varying amounts of a preparation of soluble oligomeric streptavidin mutein on which a combination of the above described αCD3 OKT3 Fab fragment and the αCD28 Fab fragment of the antibody 28.3 (both carrying the above-mentioned Twin-Strep-Tag® as streptavidin binding peptide at the heavy chain) were immobilized. ("1×" corresponds to 3 µg oligomeric streptavidin mutein functionalized with 0.5m of the αCD3- and 0.5m αCD28 monomeric Fab fragment, the numbers "0.5×", "2×" and "5×" indicate the respective n-fold amount of "1×"). Tresp cells either left unstimulated or were stimulated with blank oligomeric streptavidin mutein (no Fab) served as negative controls. Tresp cells were seeded in duplicates in 48-well plates along with 300,000 CD3 negative autologous feeder cells (irradiated with 30Gy) in 1 ml cell culture medium supplemented with 20 U/ml IL-2. Cells were incubated at 37° C. without media exchange and proliferation was analyzed according to CFSE dilution after 5 days by FACS analysis. FIG. 12A shows the increase in the size distribution of proliferating cells after 5 days in culture compared to the negative controls. FIG. 12B shows that CD3+ Tresp cells were properly stimulated and proliferated vigorously when incubated with soluble oligomeric streptavidin mutein (as compared to solid Streptactin magnetic particles in Example 7 and FIG. 11(A-C)) on which a mixture of αCD3 Fab and αCD28 Fab fragments were immobilized. The results in FIGS. 12A and 12B indicate that under these in vitro conditions most of the CD3+ T responder cells divided (2 to 5 cell divisions) after engagement of the surface CD28 and TCR/CD3 complex with the αCD3 and αCD28 Fab fragments that were reversibly immobilized on soluble oligomeric streptavidin mutein. After in vitro expansion the soluble multimerized agents were dissociated and removed after D-biotin treatment. The dissociation and removal of monomeric Fab fragments was flow-cytometrically analyzed by restaining cells with phycoerythrine label Strep-Tactin®) (ST-PE). A representative histogram (dark grey histogram) is shown compared to the appropriate ST-PE only negative control (light grey histogram). It can be seen from FIG. 12C that both Fab fragments had completely dissociated and were entirely removed from the expanded cells. FIG. 12D shows the absolute number of live (trypan blue negative) cells after 5 days. The number was counted using a Neubauer counting chamber and plotted against the respective stimulation condition. Median cell numbers are shown in FIG. 12D; error bars indicate standard deviation (SD). FIG. 12D shows that all which mixtures of αCD3 Fab fragments and αCD28 Fab fragments that were immobilized on a soluble oligomeric streptavidin mutein reagent were equally effective in expanding the CD3+ cells and resulted in an approx. 4-fold increase of absolute cell numbers.

Example 9: Kinetics of Proliferation of Purified CD4+ and CD8+ T Responder Cells Stimulated In Vitro with Reversible αCD3/αCD28 Fab-Streptamer Multimers without Medium Exchange In this example the expansion kinetics of proliferation of purified CD4+ and CD8+ T responder cells (Tresp) that were stimulated in vitro with αCD3/αCD28 Fab fragments that were reversibly immobilized soluble oligomeric streptavidin muteins were examined. For this purpose, soluble oligomeric Strep-Tactin® mutein of two different sizes served as soluble reagent. The first kind of oligomeric Strep-Tactin® was the fraction of the oligomeric streptavidin mutein (n≥3) obtained in Example 8 (also referred herein as "conventional oligomeric streptavidin mutein backbone", illustrated by the triangle symbol with the tip on top in FIG. 13(A-B)). The second kind of this oligomeric streptavidin mutein used as soluble reagent was an oligomeric streptavidin mutein (n≥3) that was reacted with biotinylated human serum albumin (also referred herein as "large oligomeric streptavidin mutein backbone).

In this example 500,000 purified CD4+ or CD8+ responder T cells (Tresp) were separately stimulated with these two different Streptamer multimers as explained above, i.e. with either the oligomeric streptavidin mutein backbone of Example 8 (using a solution with a concentration of 1 mg oligomeric streptavidin mutein/ml)) or with the large oligomeric streptavidin mutein backbones (0.1 mg/ml). 30 of the both different backbones were either loaded with a combination of 0.5 µg of the αCD3 Fab and 0.5 µg αCD28 Fab used in the earlier Examples that carried a streptavidin binding peptide SAWSHPQFEK(GGGS)$_2$GGSAWSHPQFEK (SEQ ID NO: 16) at the C-terminus of the heavy chain of the Fab fragment. In addition, 4.5 µl of the conventional oligomeric streptavidin mutein backbone was loaded with 0.5 µg αCD3 Fab fragment, 0.5 µg αCD8 Fab fragment (IBA GmbH Göttingen, that also carries at the C-terminus of the Fab fragment the streptavidin binding peptide SAWSHPQFEK(GGGS)$_2$GGSAWSHPQFEK (SEQ ID NO: 16) and 0.5 µg αCD28 Fab fragment. Untreated (unstimulated) Tresp cells served as negative control and Tresp cells stimulated with commercially available anti-CD3/anti-CD28 beads (beads on which αCD3 and αCD28 monoclonal antibodies are irreversible immobilized) as positive control. Tresp cells were seeded in duplicates in 48-well plates in 1 ml cell culture medium (RPMI 1640 (Gibco) supplemented with 10% (v/v fetal calf serum, 0.025% (w/v) L-glutamine, 0.025% (w/v) L-arginine, 0.1% (w/v) HEPES, 0.001% (w/v) gentamycine, 0.002% (w/v) streptomycine, 0.002% (w/v) peniciline) supplemented with 30 U/ml IL-2. Cells were incubated at 37° C. without media exchange and cell count was analyzed after 1, 3 and 6 days. In the experiments of FIG. 13(A-B) the expansion was carried out without medium exchange. The results for the CD4+ T responder cells are shown in FIG. 13A, the results for the CD8+ T responder cells are shown in FIG. 13B, with the graphs representing degree of proliferation according to the number of cells harvested per time point for CD4+ Tresp (FIG. 13A) and for CD8+ Tresp in FIG. 13B.

Figure 13A:
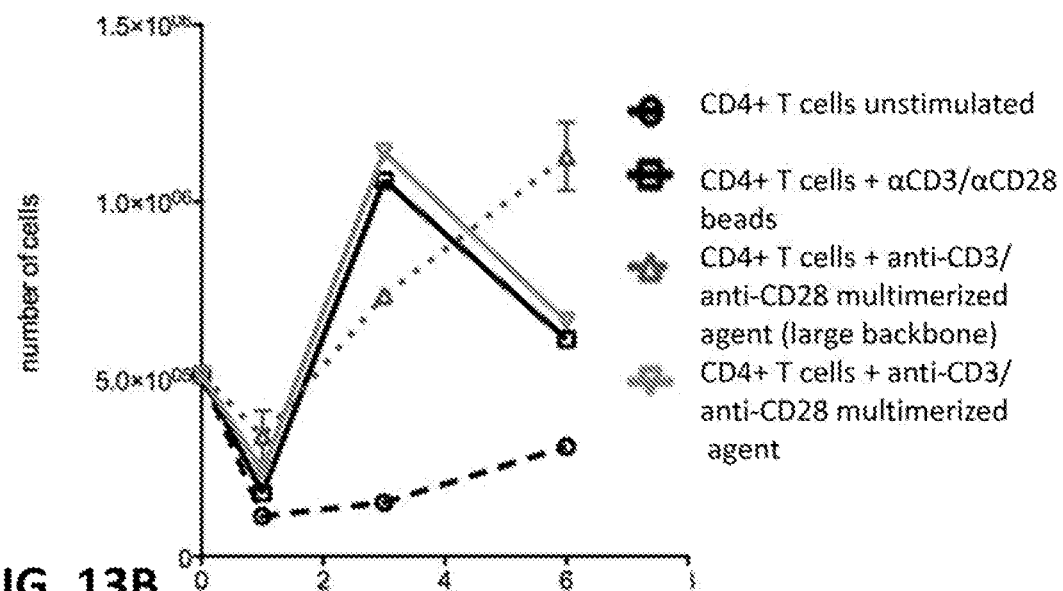
FIG. 13(A-B) shows the expansion kinetics of proliferation of purified CD4+ and CD8+ T responder cells (Tresp) that were stimulated in vitro either with αCD3/αCD28 Fab fragments or with αCD3/αCD28/αCD8 Fab that were reversibly immobilized on two kinds of a soluble oligomeric streptavidin mutein acting as soluble reagent. The first kind of oligomeric streptavidin mutein was the fraction of the oligomeric streptavidin mutein (n≥3) obtained in Example 3 (also referred herein as "conventional" or "smaller" oligomeric streptavidin mutein backbone, illustrated by the triangle symbol with the tip down in FIG. 13(A-B)), the second kind of this oligomeric streptavidin mutein used as soluble reagent was an oligomer that was obtained by reacting the soluble oligomeric streptavidin mutein with biotinylated human serum albumin (HSA). This HSA based soluble reagent is also referred herein as "larger" oligomeric streptavidin mutein backbone). In the experiments of FIG. 13(A-B) the expansion was carried out without medium exchange. The results for the CD4+ T responder cells are shown in FIG. 13A, the results for the CD8+ T responder cells are shown in FIG. 13B. In this context, it is noted that the experimentally used soluble reagents that were functionalized by reversibly binding first agents, and optionally second and third agents are referred to in the FIGS. as "multimerized agents."

As can be seen from FIG. 13A the "smaller" soluble reagent on which αCD3 Fab and αCD28 Fab fragments were reversibly immobilized provided for the same amount of expansion of CD4+ T cells as anti-CD3/anti-CD28 beads (which are so far the standard reagent for the expansion of T cells), while the "larger" soluble multimerized agent provided for even better expansion compared to Dynabead.

This improvement might be caused by the soluble "larger" multimerized being able to bind to more T cells at the same time than the "smaller" multimerized agent, thereby being able to stimulate more CD4+ T cells than the "smaller" multimerized agent.

Figure 13B:
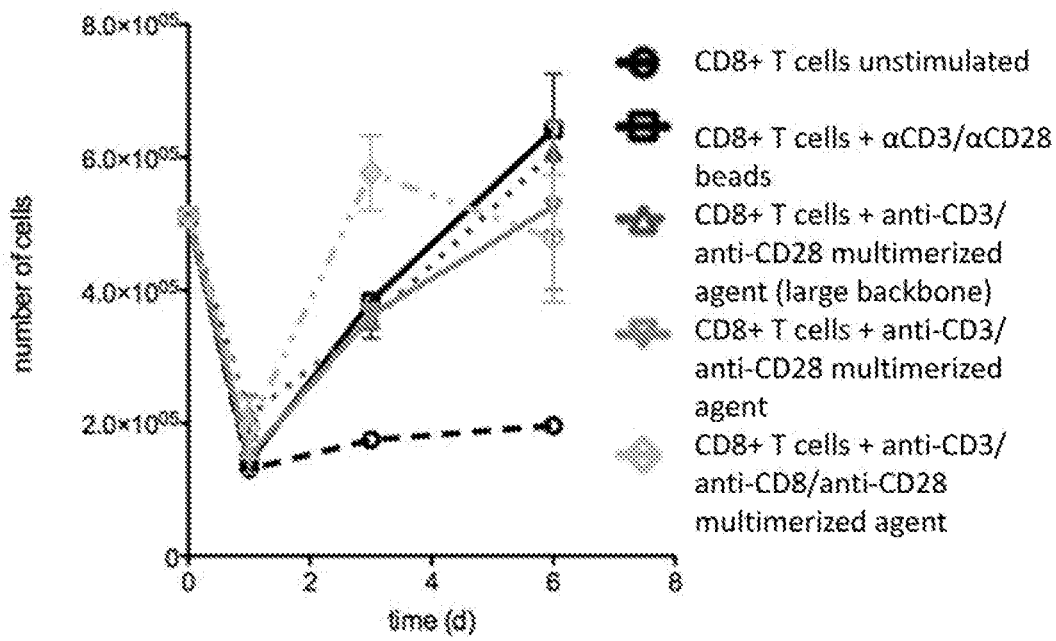

As evident from FIG. 13B, using the soluble multimerized agents disclosed herein, CD8+ T cells could be expanded within the first 3 days at least as efficiently as with anti-CD3/anti-CD28 beads. Notably, in this time period, the expansion experiment that used a soluble reagent that in addition to αCD3 Fab and αCD28 Fab fragments (as first and second agent) carried reversibly immobilized thereon αCD8 Fab fragment, showed the best degree of expansion under these culturing conditions. This indicates that it is possible by using a stimulus that is specific for a particular sub-population of cells (here the αCD8 Fab fragment) to increase or modulate the selectivity of the expansion, thereby being able to obtain larger amounts of a desired cell (sub)-population.

Thus, summarizing the above, Example 9 shows that the functionality of the soluble multimerized agent in terms of triggering expansion of T cells is comparable to the current standard methodology of using anti-CD3/anti-CD28 beads for this purpose. However, since the stimulation can be controlled (and terminated, if wanted) by adding a competitor such as biotin in the case of a streptavidin based reversible interaction between the first and second agent and the reagent, the compositions and methods described herein provide a significant advantage over the anti-CD3/anti-CD28 beads technology since the expansion conditions can be optimized (it would for example be possible to stop the stimulation in the experiment of FIG. 13B after 3 days). In addition, since the soluble reagent can be easily removed from the reaction (for example, by immobilizing the reagent on a biotinylated column after the expansion reaction), the expansion methods disclosed herein can be carried out and automated in closed systems that are, for example, needed for GMP production of cells for therapeutic purposes, without having to deal with the removal of beads such as anti-CD3/anti-CD28 beads.

Example 10: Kinetics of Proliferation of Purified CD4+ and CD8+ T Responder Cells Stimulated In Vitro with Reversible αCD3/αCD28 Fab-Streptamer Multimers with Medium Exchange In this example the expansion kinetics of proliferation of purified CD4+ and CD8+ T responder cells (Tresp) that were stimulated in vitro with αCD3/αCD28 Fab fragments that were reversibly immobilized on soluble oligomeric streptavidin muteins were examined. For this purpose, soluble oligomeric Strep-Tactin® mutein of two different sizes served as soluble reagent. The first kind of oligomeric Strep-Tactin® was the fraction of the oligomeric streptavidin mutein (n≥3) obtained in Example 8 (also referred herein as "conventional oligomeric streptavidin mutein backbone", illustrated by the triangle symbol with the tip down in FIG. 14(A-B)). The second kind of this oligomeric streptavidin mutein used as soluble reagent was obtained by reacting the oligomeric Strep-tactin (n≥3) obtained in Example 8 with biotinylated human serum albumin. This soluble oligomeric reagent is also referred herein as "large oligomeric streptavidin mutein backbone."

In this example, 400,000 purified CD4+ or CD8+ responder T cells (Tresp) were separately stimulated with these two different oligomeric streptavidin muteins as explained above, i.e. with either the oligomeric streptavidin mutein backbone of Example 8 (1.0 mg/ml) or with the large oligomeric streptavidin mutein backbones (0.1 mg/ml). 30 of both the different backbones were either loaded with a combination of 0.5 μg αCD3 Fab and 0.5 μg αCD28 Fab fragments described above. In addition, 4.5 μl of the oligomeric streptavidin mutein backbone of Example 8 was loaded with 0.5 μg αCD3, 0.5 μg αCD8 Fab and 0.5 μg αCD28 Fab fragment as described above. Untreated (un-stimulated) Tresp cells served as negative control and Tresp cells stimulated with anti-CD3/anti-CD28 beads (on which αCD3 and αCD28 monoclonal antibodies are irreversible immobilized) as positive control. Tresp cells were seeded in duplicates in 48-well plates in 1 ml cell culture medium supplemented with 30 U/ml IL-2. Cells were incubated at 37° C. with media exchange on day 3 and cell count was analyzed after 1, 3 and 6 days. The results for the CD4+ T responder cells are shown in FIG. 14A, the results for the CD8+ T responder cells are shown in FIG. 14B, with the graphs representing degree of proliferation according to the number of cells harvested per time point for CD4+ Tresp (FIG. 14A) and for CD8+ Tresp in (FIG. 14B).

Figure 14A:
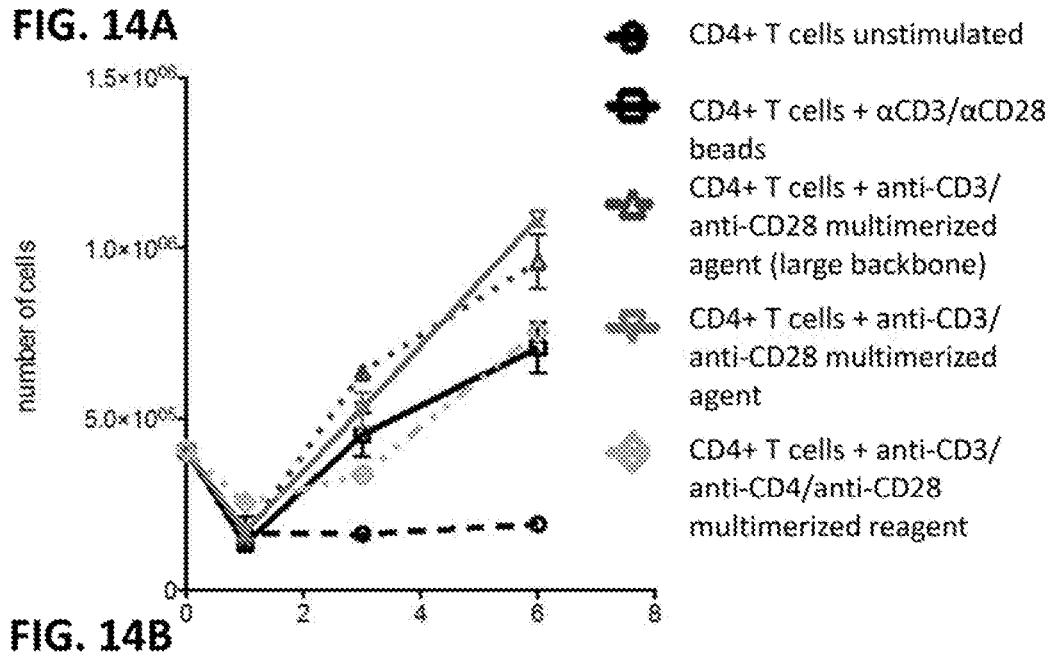
FIG. 14(A-B) shows the expansion kinetics of proliferation of purified CD4+ and CD8+ T responder cells (Tresp) that were stimulated in vitro with αCD3/αCD28 Fab fragments that were reversibly immobilized fragments that were reversibly immobilized with two kinds of soluble oligomeric streptavidin mutein acting as soluble reagent. The first kind of oligomeric Strep-Tactin® was the fraction of the oligomeric streptavidin mutein (n≥3) obtained in Example 3 (also referred herein as "conventional oligomeric streptavidin mutein backbone", illustrated by the triangle symbol with the tip on top in FIG. 14(A-B)), the second kind of this oligomeric streptavidin mutein used as soluble reagent was the HSA based soluble reagent, the above-mentioned "large backbone"). In the experiments of FIG. 14(A-B) the expansion was carried out with medium exchange. The results for the CD4+ T responder cells are shown in FIG. 14A, the results for the CD8+ T responder cells are shown in FIG. 14B.

As can be seen from FIG. 14A the soluble reagents on which αCD3 Fab and αCD28 Fab fragments were reversibly immobilized (the multimerized agents) provided for better expansion of CD4+ T cells than anti-CD3/anti-CD28 beads.

Figure 14B:
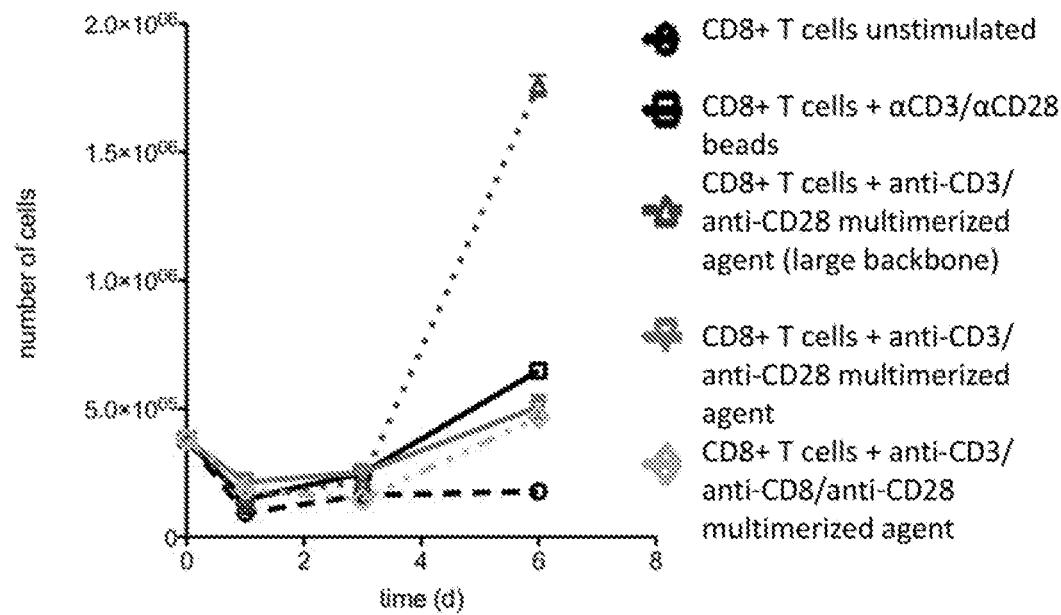

As evident from FIG. 14B, using the multimerized agents, CD8+ T cells could be expanded within the first 6 days at least as efficiently as with anti-CD3/anti-CD28 beads. Notably, in this time period, the expansion experiment that used the larger soluble reagent that carried αCD3 Fab and αCD28 Fab fragments (as first and second agent) showed the best degree of expansion under these culturing conditions. This might again be caused by the soluble "larger" multimerized agent being able to bind to more T cells at the same time than the "smaller" multimerized agent, thereby being able to stimulate more CD4+ T cells than the "smaller" multimerized agent.

Figure 15A:
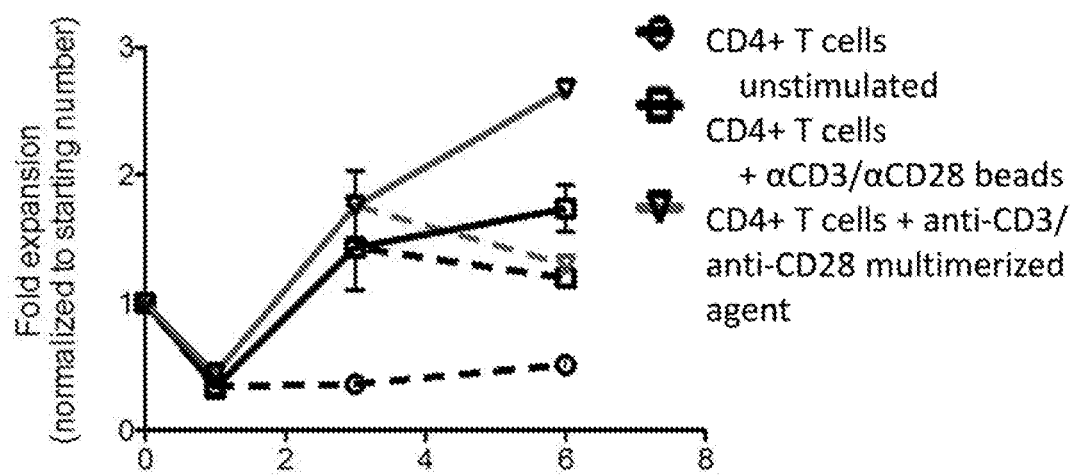
FIG. 15(A-B) shows the combined data from the results obtained in FIGS. 13 and 14 for the expansion kinetics of proliferation of purified CD4+ and CD8+ T responder cells, with FIG. 15A depicting the results for CD4+ T cells and FIG. 15B depicting the results for the CD8+ T cells. Straight lines are used for the culturing with medium exchange on day 3, while dashed lines depict the values obtained for the degree of expansion without media exchange on day 3. The data shown in FIG. 15(A-B) are normalized on the input cell number. Only data for the Tresp stimulated with the oligomeric streptavidin mutein (n≥3), the Tresp stimulated with the commercially available anti-CD3/anti-CD28 beads (positive control) and the unstimulated T cells (negative control) are shown but no data on the reagent with the "large backbone".
Figure 15B:
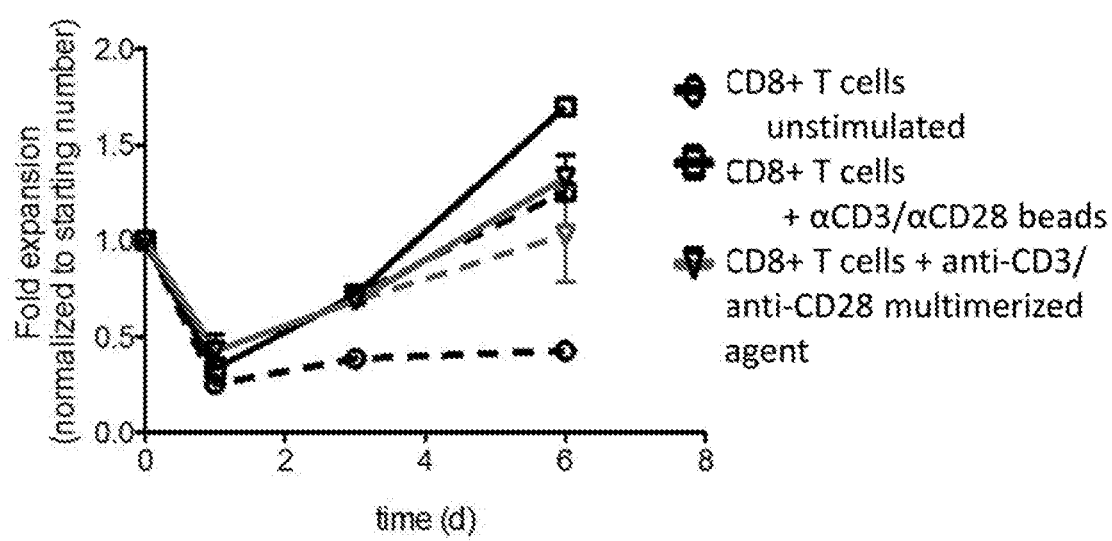

Example 11: Expansion Kinetics of Purified CD4+ and CD8+ T Cell Cultures with or without Medium Exchange In this Example the combined data from Examples 9 and 10 were normalized on input cell number for the "smaller" multimerized agent and positive and negative control. No normalization data was obtained on the "larger" multimerized agent. As explained in Examples 9 and 10, 400,000 to 500,000 CD4+ or CD8+ responder T cells (Tresp) were stimulated with 30 of a preparation of multimerized agent (1 mg/ml; on which 0.5 μg αCD3 Fab fragment and 0.5 μg αCD28 Fab fragment were immobilized). Untreated (un-stimulated) Tresp cells served as negative control and Tresp cells stimulated with anti-CD3/anti-CD28 beads as positive control. Tresp cells were seeded in duplicates in 48-well plates in 1 ml cell culture medium supplemented with 30 U/ml IL-2. Cells were incubated at 37° C. with media exchange (straight lines in FIG. 15(A-B)) or without media exchange (dashed lines in FIG. 15(A-B)) on day 3 and cell count was analyzed after 1, 3 and 6 days. As evident from the normalized data of FIG. 15A, the "smaller" soluble reagent on which αCD3 Fab and αCD28 Fab fragments were reversibly immobilized yielded an about 2.5 fold expansion of CD4+ T cells, while the expansion using anti-CD3/anti-CD28 beads yielded an about 1.8 fold expansion rate. Thus, the use of a multimerized agent even provides for an improvement in the expansion of CD4+ T cells over anti-CD3/anti-CD28 beads. Similarly, FIG. 15B, confirms that CD8+ T cells could be expanded using the multimerized agents within the first 3 days at least as efficiently as with anti-CD3/anti-CD28 beads.

Example 12: Expansion Kinetics & Phenotype of Polyclonal Activated/Expanded Bulk CD3+ Central Memory T Cells ($T_{CM}$)

Figure 16A:
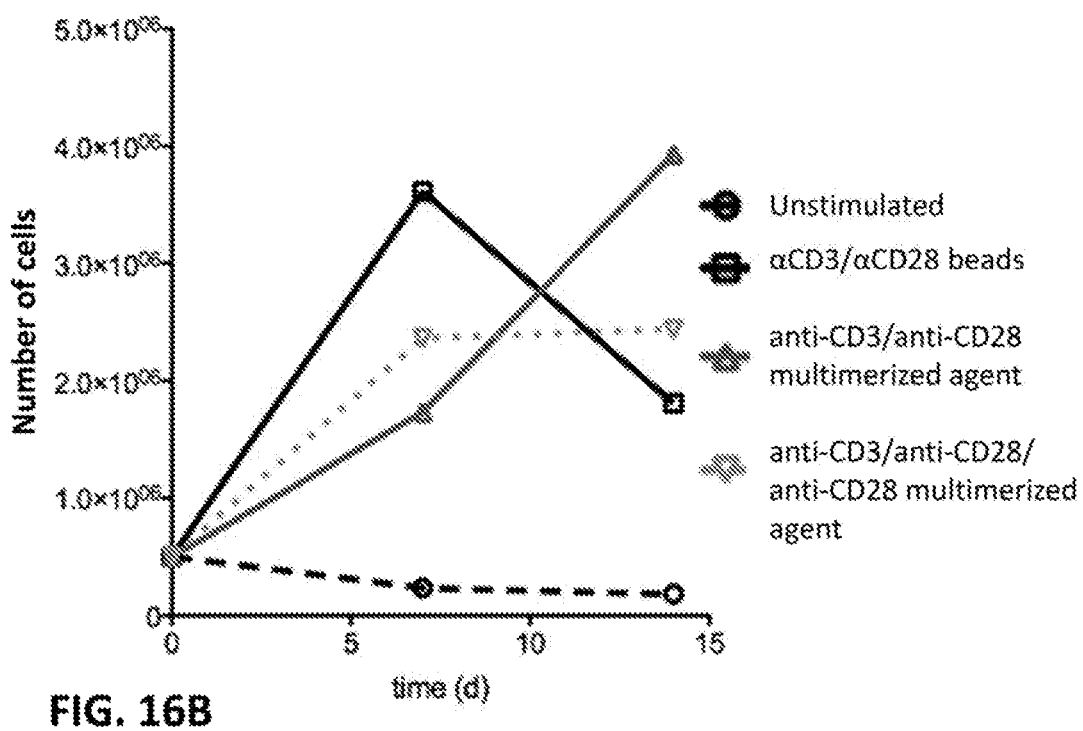
FIG. 16(A-C) shows the expansion kinetics and phenotype of CD3+ central memory T cells ($T_{CM}$) (CD3+CD62L+ CD45RA-$T_{CM}$) polyclonally stimulated in vitro with αCD3/ αCD28 Fab fragments that were reversibly immobilized on the soluble oligomeric streptavidin mutein (with n≥3) described in Example 3. The graphs shown in FIG. 16(A-C) represent the degree of proliferation according to the number of cells harvested per time point, with FIG. 16A showing the proliferation in only IL-2 supplemented media and in FIG. 16B showing the proliferation in IL-2 and IL-15 supplemented media.
FIG. 16C shows a flow-cytometric analysis of CD62L and CD127 surface expression after 14 days of culture in these variable cytokine milieus.
Figure 16B:
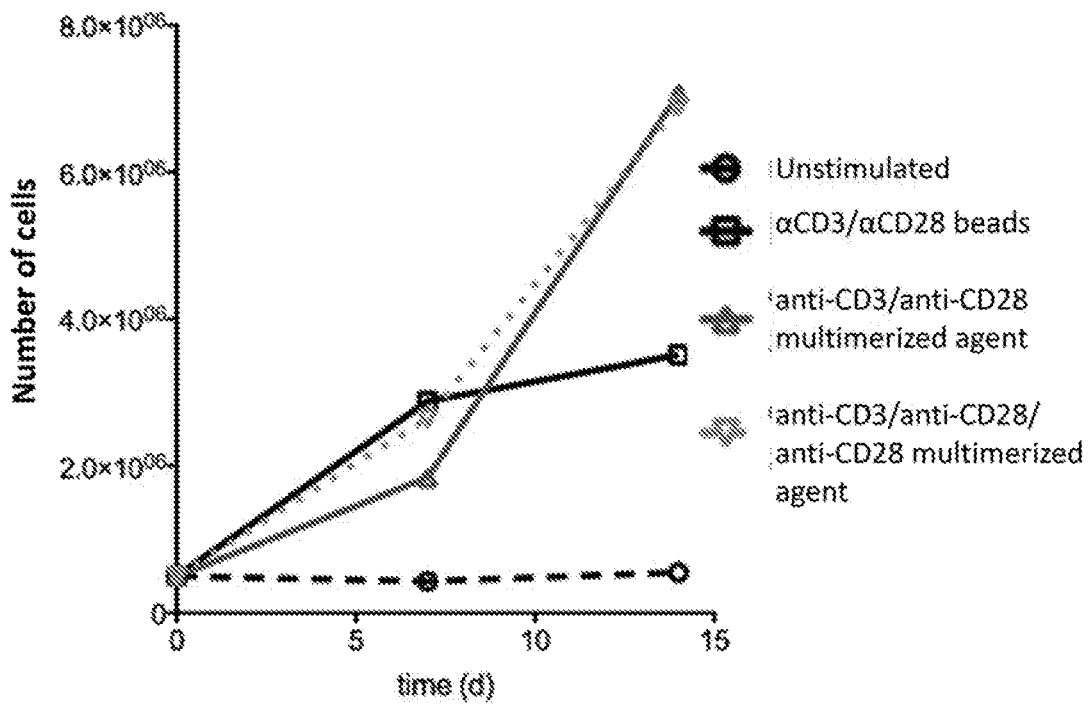
Figure 16C:
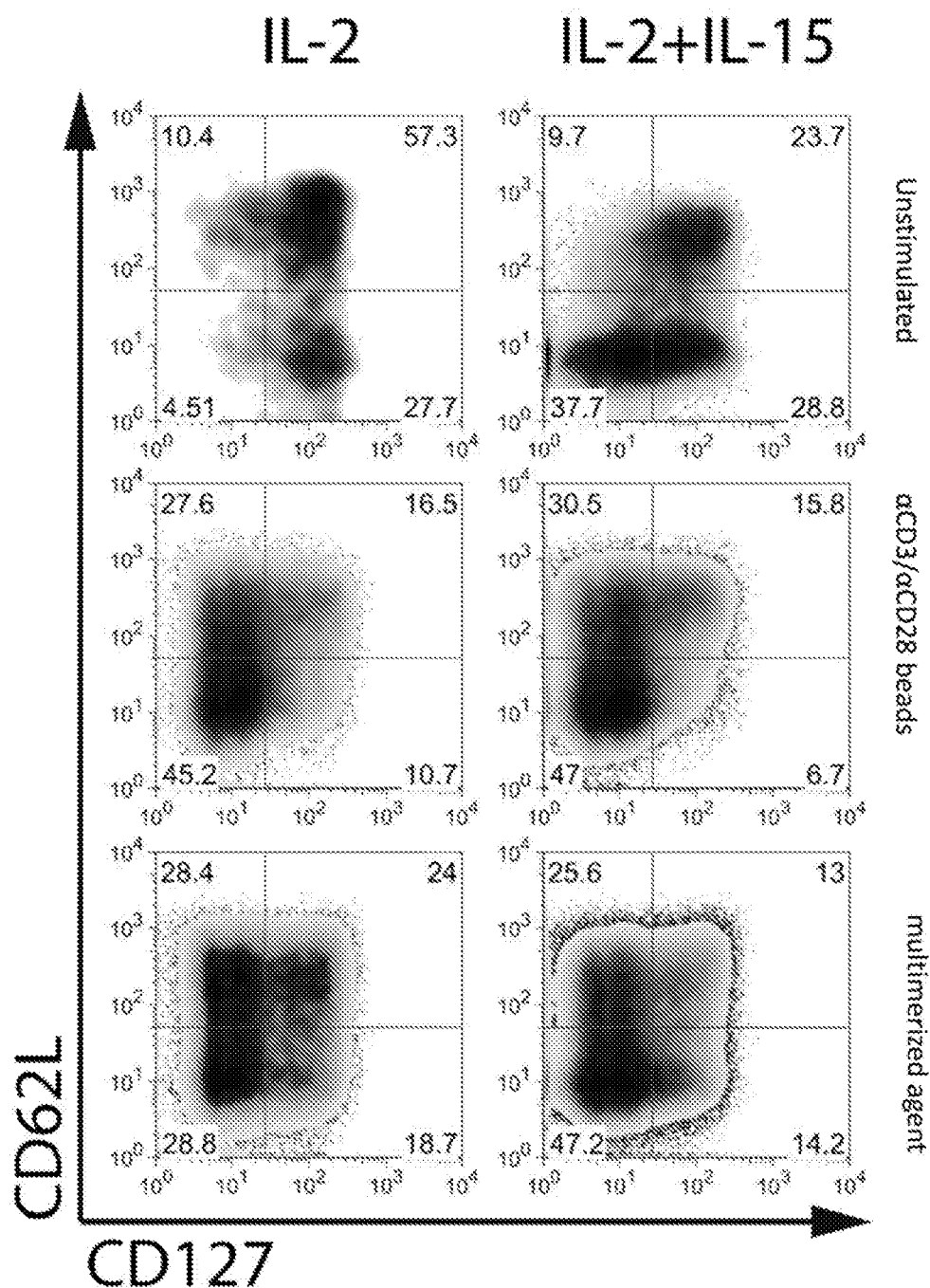

In this Example, 500,000 CD3+CD62L+CD45RA-responder $T_{CM}$ cells (Tresp) were stimulated with 3 μl of a preparation of the soluble oligomeric streptavidin mutein of Example 8 (1 mg/ml) that was either loaded with a combination of 0.5 μg αCD3 Fab and 0.5 μg αCD28 Fab. Furthermore, 4.5 μl of a preparation of oligomeric streptavidin mutein loaded with 0.5 μg αCD3, 0.5 μg αCD8 Fab and 0.5 μg αCD28 Fab was used as an additional stimulation condition. Untreated (unstimulated) Tresp cells served as negative control and Tresp cells stimulated with anti-CD3/anti-CD28 beads (on which αCD3 and αCD28 monoclonal antibodies are irreversible immobilized) as positive control. Tresp cells were seeded in 48-well plates in 1 ml cell culture medium supplemented with 30 U/ml IL-2 only or 30 U/ml IL-2 and 5 ng/ml IL-15. Cells were incubated at 37° C. with media exchange every 3 days and cell count was analyzed after 7 and 14 days. Graphs represent degree of proliferation according to the number of cells harvested per time point, in FIG. 16A only IL-2 supplemented media and in FIG. 16B IL-2 and IL-15 supplemented media. As can be seen from both FIG. 16A and FIG. 16B, the soluble reagent that has reversibly bound thereon αCD3 Fab fragment and αCD28 Fab fragment yields better cell expansion than the anti-CD3/anti-CD28 beads. As further shown by the flow-cytometric analysis of CD62L and CD127 surface expression after 14 days of culture in variable cytokine milieus of FIG. 16C, the experimental approaches using multimerized agents retain, under both conditions chosen here, a higher content of CD127-expressing long-lived memory T cells than expansion with anti-CD3/anti-CD28 beads. This illustrates a further advantage of the methods of the present compositions and methods described herein.

Example 13: Yield and Phenotype of Expanded CD8+ T Cells—Size Variation of Soluble Reagent and Addition of αCD8-Fab Addition for Stimulation In this Example, the expansion of purified CD8+ T responder cells stimulated in vitro with αCD3/αCD28 Fab fragments that were reversibly immobilized soluble oligomeric streptavidin muteins were examined. In addition, the effect of adding αCD8-Fab to the reagent for increasing the specificity of the expansion for CD8+ T cells was examined.

Figure 17B:
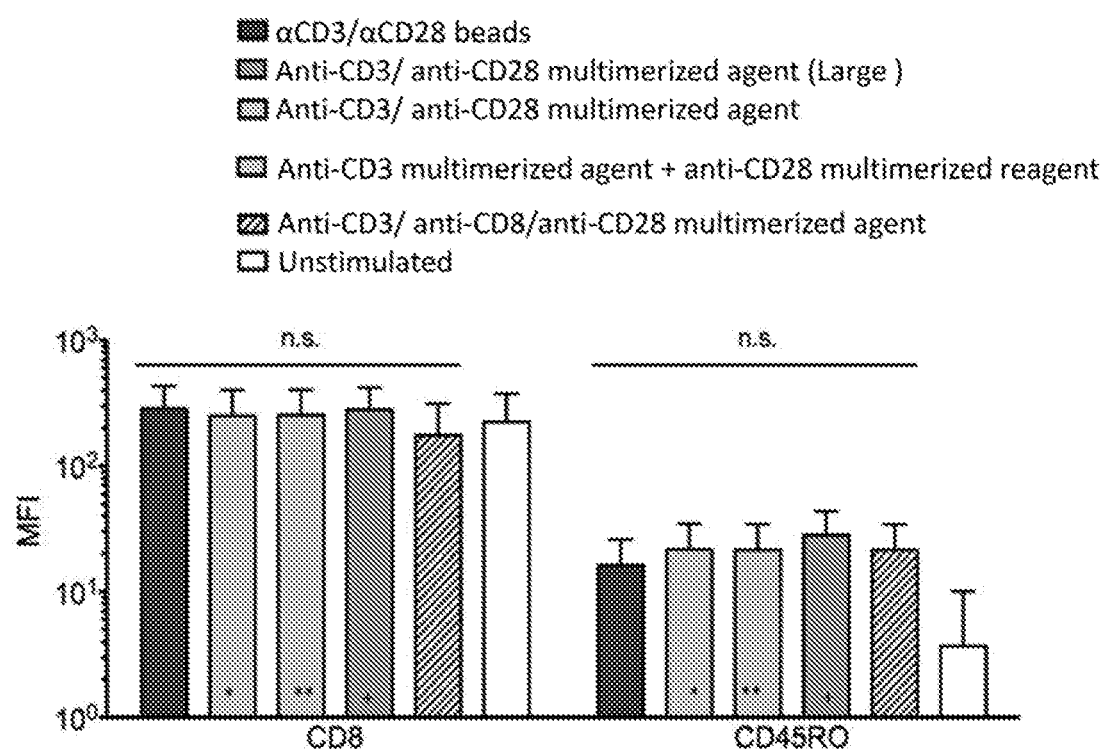
FIG. 17B shows flow-cytometric analysis of the surface expression of CD8 and the T cell surface molecule CD45RO (that is indicative of T cell proliferation and activation) after cell culture. The various stimulating conditions were compared using one-way ANOVA and no significant difference (n.s.) was detected.

For this purpose, 300,000 purified CD8+ responder T cells (Tresp) were separately stimulated with two different Streptactin based reagents, namely either the small multimerized agent of Example 8 (1 mg/ml) or the larger multimerized agent described above (0.1 mg/ml). 30 of both oligomeric streptavidin mutein reagent backbones were either loaded with a combination of the 0.5 μg αCD3 Fab and 0.5 μg αCD28 Fab fragments described above to form the multimerized agents. In addition, 4.5 μl of the smaller oligomeric streptavidin mutein backbone was loaded with 0.5 μg αCD3, 0.5 μg αCD8 Fab and 0.5 μg αCD28 Fab fragments described above. Furthermore 30 of the "smaller" oligomeric streptavidin mutein backbone only functionalized with 0.5 μg αCD3 Fab fragment alone or 0.5 μg αCD28 Fab fragment alone was used. Unstimulated Tresp cells served as negative control and Tresp stimulated with anti-CD3/anti-CD28 beads served as positive control. Tresp cells were seeded in duplicates in 48-well plates in 1 ml cell culture medium supplemented with 30 U/ml IL-2. Cells were incubated at 37° C. with media exchange after 3 days and analyzed after 6 days. FIG. 17A depicts the degree of proliferation according to the number of cells harvested at day 6 compared to the negative controls and normalized to the positive control. FIG. 17A shows that the expansion of the CD8+ T cells using the multimerized agents result in higher yields of the CD8+ T cells than expansion using anti-CD3/anti-CD28 beads. The FACS analysis of CD8 surface expression and CD45RO surface expression (FIG. 17B) after cell culture shows that the same phenotype of CD8+ T cells were expanded by either the multimerized agents or anti-CD3/anti-CD28 beads (the various stimulating conditions were compared using one-way ANOVA and no significant difference (n.s.) was detected). The improved yield of the CD8+ cells using the expansion methods disclosed herein compared to the anti-CD3/anti-CD28 beads might be due to the fact that the soluble multimerized agents can access their target receptors on the cell surface better than the antibodies that are immobilized on the anti-CD3/anti-CD28 beads. This improved yield might become very advantageous when expanding rare population of cells from an initial sample.

In addition, comparing the yield of expansion achieved with the reagent on which both the 0.5 μg αCD3 Fab and 0.5 μg αCD28 Fab fragments were jointly immobilized (second column from the left in FIG. 17B) to the yield using two reagents which were functionalized only with the αCD3 Fab fragment alone or the αCD28 Fab fragment alone (third column from the left in FIG. 17B), it can be seen that both experiments had the same expansion efficiency. Thus, these experiments show that using one reagent on which both the first agent and the second agent are jointly immobilized is functionally equivalent to using for the expansion two separate reagents which are loaded with only the first agent and the second agent, respectively.

Example 14: Yield & Phenotype of Expanded CD8+ T Cells—Titration of Separate Soluble Reagents with Different Ratios of αCD3- and αCD28 Fab Fragment Immobilized Thereon In this Example, the yield and the phenotype of expanded CD8+ T responder cells (Tresp) that were stimulated in vitro with αCD3/αCD28 Fab fragments that were reversibly immobilized in different amounts on soluble oligomeric streptavidin muteins were examined.

For this purpose 300,000 CD8+ responder T cells (Tresp) were stimulated with varying amounts of a mixture of preparations of the "small" oligomeric streptavidin muteins (1 mg/ml) functionalized with αCD3 Fab alone and αCD28 Fab alone ("1×" corresponds to 1.5 μg oligomeric streptavidin mutein functionalized with 0.5 μg αCD3 alone and 1.5 μg oligomeric streptavidin mutein functionalized with 0.5 μg αCD28 Fab fragment alone), or 30 of a preparation of the oligomeric streptavidin mutein loaded with 0.5 μg αCD3 Fab and 0.5 μg αCD28 Fab, or 4.5 μl of a preparation of the oligomeric streptavidin mutein loaded with 0.5 μg αCD3, 0.5 μg strep-tagged αCD8 and 0.5 μg αCD28 Fab. Untreated Tresp cells served as negative control and Tresp stimulated with anti-CD3/anti-CD28 beads as positive control. Tresp cells were seeded in 48-well plates in 1 ml cell culture medium supplemented with 30 U/ml IL-2. Cells were incubated at 37° C. without media exchange and analyzed after 5 days. FIG. 18A depicts the degree of proliferation according to the number of cells harvested at day 5 compared to the negative controls and normalized to the positive control. FIG. 18A shows that the expansion of the CD8+ T cells using the various multimerized agents result in higher yields of the CD8+ T cells than expansion using anti-CD3/anti-CD28 beads (especially the cumulative total reagent amount of the 5× condition resulted in an optimal expansion of cells especially over time/increase in total cells by beginning cell division). The FACS analysis of CD8 surface expression and CD45RO (FIG. 18B) surface expression after cell culture shows that the same phenotype of CD8+ T cells were expanded by either the multimerized agents or by the commercially available anti-CD3/anti-CD28 beads.

Figure 19A:
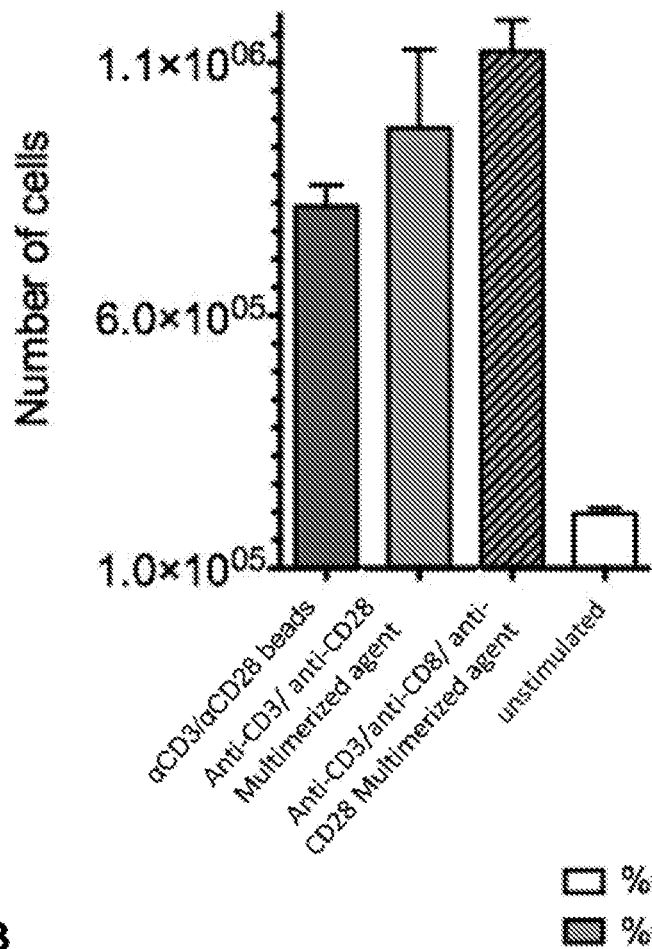
FIG. 19A shows a graph of the cell count (degree of expansion) in cultures in each condition.
Figure 19B:
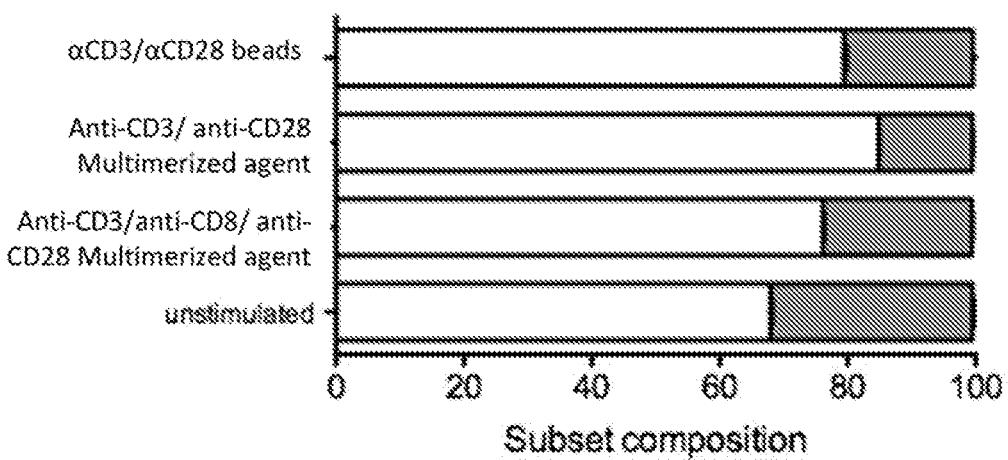
FIG. 19B shows the proportion of CD4+ and CD8+ cells in each stimulation condition.

Example 15: Yield and Subset Composition of Expanded CD3+ T Cells with Addition of αCD8-Fab for Stimulation The experiment shows the expansion of purified CD3+ T responder cells stimulated in vitro with αCD3/αCD28 Fab fragments that were reversibly immobilized on the soluble oligomeric streptavidin muteins of Example 8 that served as a soluble reagent. In one experiment, in addition to αCD3/αCD28 Fab fragments, an αCD8 Fab fragment commercially available from IBA GmbH, Göttingen, Germany (catalogue number 6-8000-203) was immobilized on the soluble oligomeric streptavidin mutein in order to test whether it is possible to preferentially stimulate a specific T cell subpopulation in vitro with the reversible αCD3/αCD28 multimerized agents. In more detail, 500,000 purified CD3+ responder T cells (Tresp) were stimulated with 30 of a preparation of oligomeric streptavidin muteins (1 mg/ml) loaded with a combination of 0.5 µg of the αCD3 Fab and 0.5 µg of the αCD28 Fab. As an alternative approach, 4.5 µl of the oligomeric streptavidin muteins were loaded with 0.5 µg αCD3, 0.5 µg strep-tagged αCD8 Fab and 0.5 µg strep-tagged αCD28 Fab. Unstimulated Tresp cells served as negative control and Tresp stimulated with anti-CD3/anti-CD28 beads (beads on which αCD3 and αCD28 monoclonal antibodies are irreversible immobilized) served as positive control. As can be seen from FIG. 19A, the reagent that is reversibly loaded with the αCD3 Fab fragment, the αCD28 Fab fragment and also the αCD8 Fab fragment provided the highest number of expanded CD3+ T cells. With approximately 1×10⁶ the number of expanded cells the yield was about 30% higher than for expansion of these T cells using commercially available anti-CD3/anti-CD28 beads. In addition and more important, as shown in FIG. 19B with this reagent that caries the αCD3 Fab fragment, the αCD28 Fab fragment and the αCD8 Fab fragment, the amount of CD8+ T cells were the highest, compared to both the expansion with anti-CD3/anti-CD28 beads or a soluble reagent that caries only the αCD3 Fab fragment and the αCD28 Fab fragment as first and second agent as described herein. Thus, also this experiment shows the advantage of the compositions and methods described herein that in addition to a first agent that provides a primary activation signal to the desired cell population and optionally a second agent that provides a co-stimulatory signal, a further agent that is specific for the activation of the desired cell population can be immobilized on the reagent. Thus, by so doing, the compositions and methods described herein provide for the possibility of preferentially expanding or selectively enriching any desired cell population or subpopulation from a sample that, for example, comprises a variety of different subpopulations.

Example 16: Analysis of the Differential Intracellular Calcium Mobilization in Jurkat Cells Real-time low-cytometric analysis of the differential intracellular calcium mobilization induced in Jurkat cells that are either labeled with the αCD3 antibody clone OKT3 or with Fab fragments of OKT3 being multimerized with Strep-Tactin® was examined here.

For this purpose, Jurkat cells were loaded with the calcium-sensitive dye Indo-1-AM and calcium release was triggered by injection of either αCD3 monoclonal antibody OKT3 (produced by the hybridoma cell line OKT3, see above, black squares) or αCD3 Fab fragments (derived from the parental cell line OKT3) that were multimerized by reversible binding of its streptavidin binding peptide to soluble Strep-Tactin fluorescently conjugated with phycoerythrin. In the case of the intact multimeric OKT3 Fab-Strep-Tactin complexes, the calcium release was triggered over an identical time period as with the parental antibody clone (dark grey triangles). Activation of cells could be completely avoided by injection of D-biotin treated, pre-dissociated Fab-Strep-Tactin complexes (light grey circles) identical to injection of the PBS negative control (inverted white triangles). Application of ionomycin served as positive control for calcium influx. Time-resolved changes in intracellular $Ca^{2+}$ concentration were monitored by flow-cytometry based on the change in FL6/FL7 ratio. It can be seen from FIG. 20A that both the parental antibody OKT3 as well as the multimerized monovalent Fab fragment of OKT3 effected calcium release, meaning that the multimerized monovalent Fab fragment of OKT3 is essentially as functional as the parental antibody. Notably, the multimeric OKT3 Fab fragment was not able to trigger calcium release if biotin was added to Strep-tactin on which the OKT3 Fab fragment was immobilized prior to the addition of the Streptactin-OKT3 Fab fragment. In this case, the biotin disrupted the reversible bond formed between Strep-tactin as multimerization agent and the OKT3 Fab fragment. The monovalent Fab fragment was therefore displaced from the multimerisation agent and after dissociation was not able to trigger calcium release by binding to CD3 of the Jurkat cells.

Figure 20A:
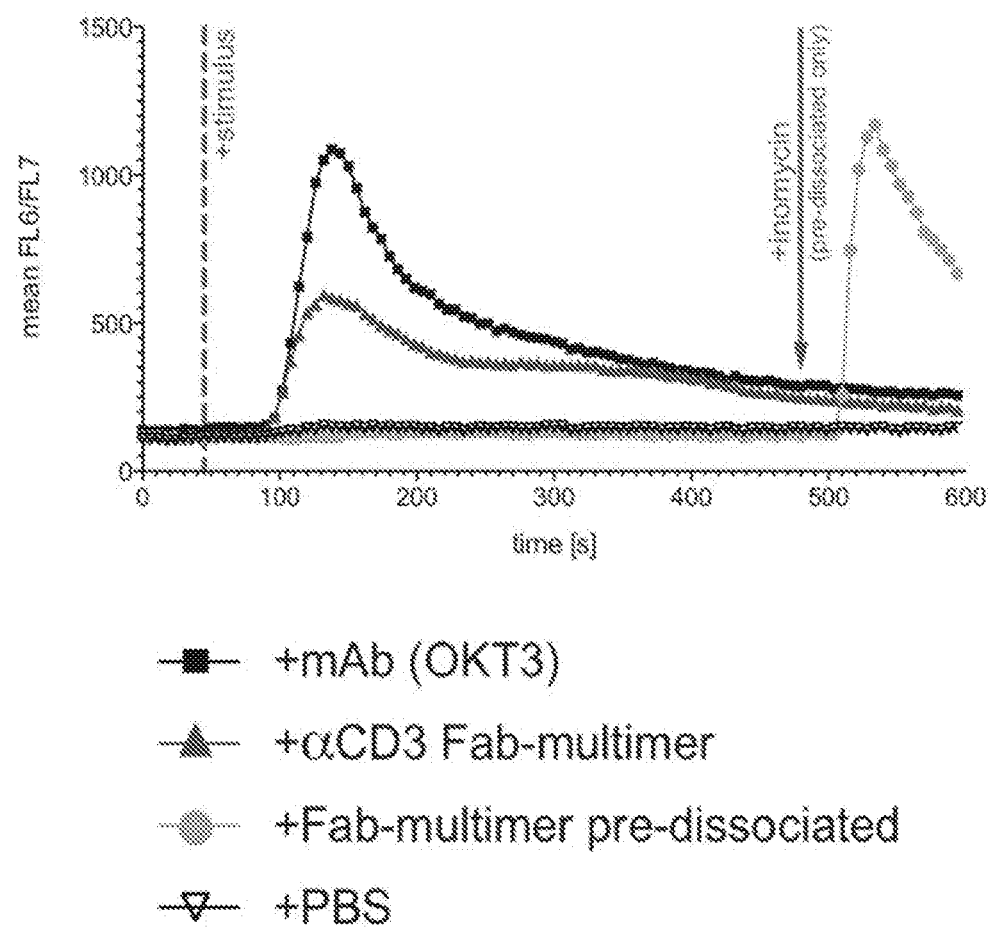
FIG. 20(A-B) shows the results of the differential intracellular calcium mobilization in Jurkat cells that are either labelled with the αCD3 antibody OKT3 or with Fab fragments of OKT3 being multimerized with Strep-Tactin® (also referred to as Fab multimers herein). For the experiment in FIG. 20A, Jurkat cells were loaded with the calcium-sensitive dye Indo-1-AM and calcium release was triggered by injection of either αCD3 mAb OKT3 (black squares) or αCD3 OKT3 Fab multimers (derived from the parental cell line OKT3) with or without prior D-biotin disruption (dark grey triangles and light grey circles respectively) compared to injection of PBS (inverted white triangles). Application of ionomycin served as positive control. Time-resolved changes in intracellular $Ca^{2+}$ concentration were monitored by flow-cytometry based on the change in FL6/FL7 ratio. For the experiment in FIG. 20B, Indo-1-AM-labeled Jurkat cells were activated by different αCD3 stimuli as described in Example 11; OKT3: upper graph and αCD3 Fab-multimer: middle graph) followed by subsequent (t=140s) D-biotin mediated disruption of αCD3 Fab-multimer signaling. αCD3 Fab-multimer pre-dissociated with D-biotin (lower graph) and ionomycin served as negative or positive control. Data are representative of three different experiments.
Figure 20B:
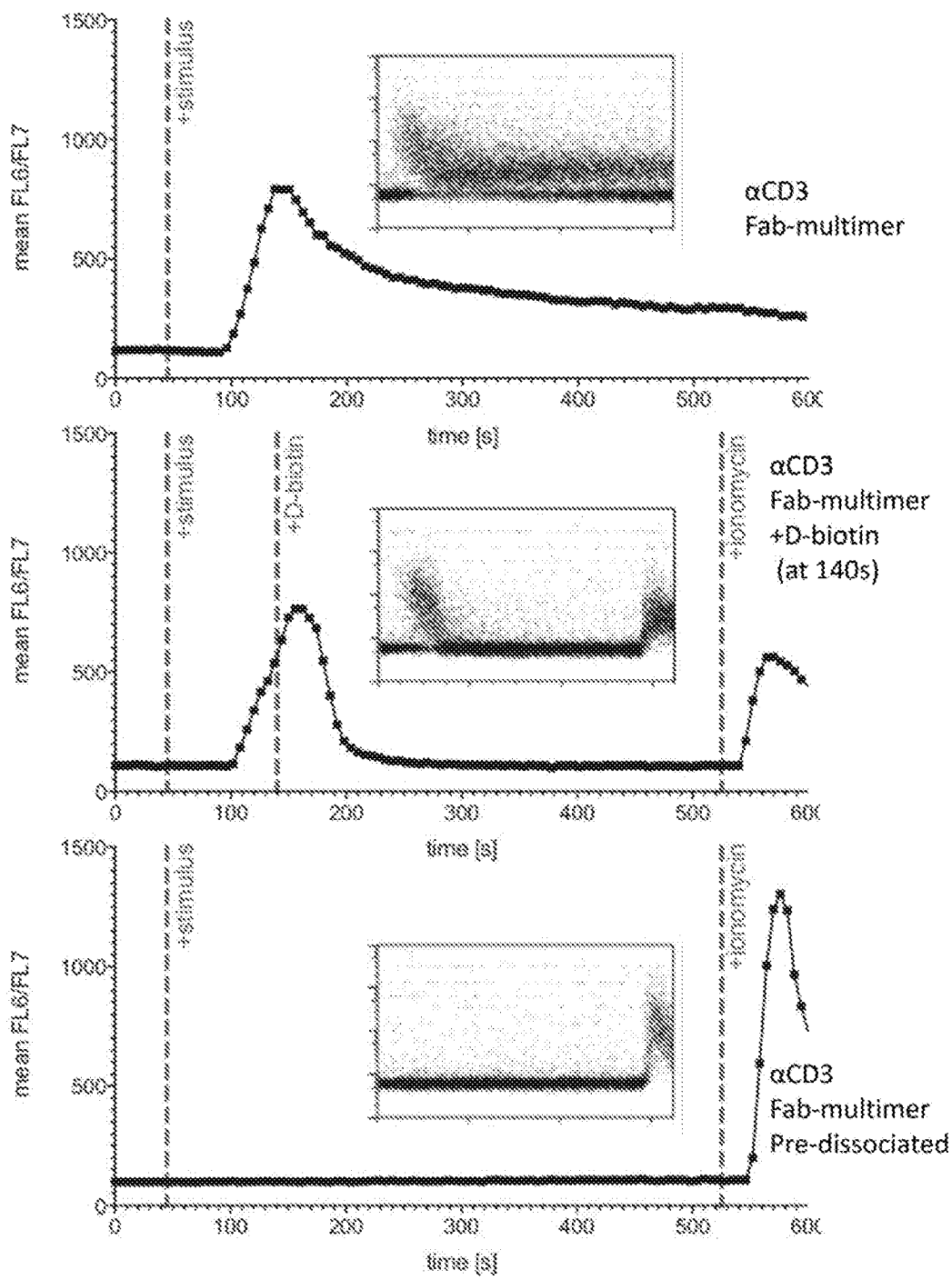

In the experiments shown in FIG. 20B indo-1-AM-labeled Jurkat cells were activated by OKT3 derived αCD3 Fab-Strep-Tactin-complexes as described in FIG. 20A. Injection of intact (upper graph) or pre-dissociated complexes (lower graph) served as positive or negative controls respectively. In addition, stimulation of cells with intact Fab-Strep Tactin-complexes followed by subsequent injection of D-biotin (near the peak activation at t=140s) resulted in abrupt disruption of αCD3 Fab-multimer signaling (middle graph). Injection of ionomycin into the pre-dissociated Fab complex group served as positive control. Data are representative of three different experiments. Importantly, FIG. 20B shows that the addition of D-biotin to the sample rapidly displaces the Fab fragment from the Strep-tactin multimerization agent, thereby effectively terminating the calcium release even under ongoing calcium stimulation and demonstrating that the dissociated OKT3 Fab fragment is not any longer biologically active. Likewise, the multimeric OKT3 Fab fragment was also not able to trigger calcium release when biotin was added to the Strep-tactin- OKT3 Fab fragment multimer prior to the addition of the Streptactin-OKT3 Fab sample to the Jurkat cells.

Example 17: Reversible Staining of Cells by αCD3 Fab-Multimers

Figure 21:
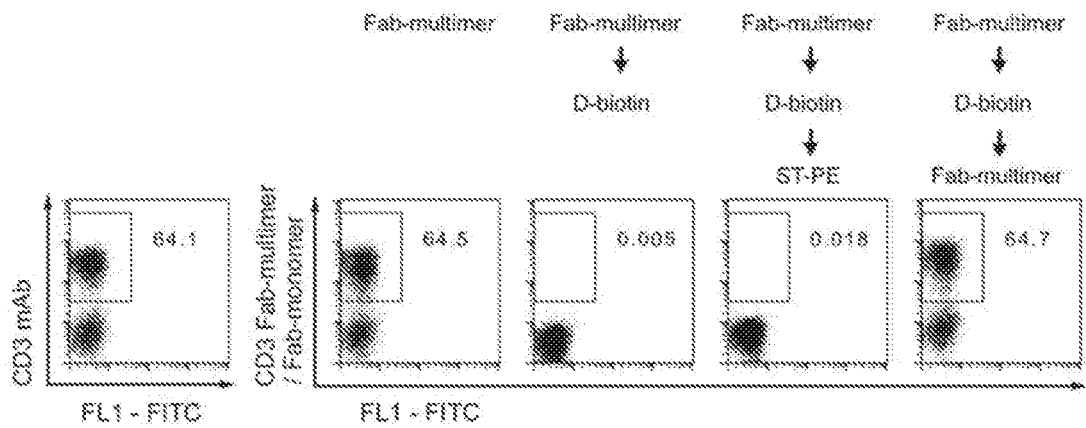
FIG. 21 shows the result of the reversible staining of cells by anti-CD3 OKT3 Fab-multimers. Freshly isolated PBMCs were stained with either a monoclonal antibody (left dot plot, parental clone for the Fab-multimers) or cognate PE-labeled Fab-multimers and analyzed either before (second dot plot from the left) or after treatment with D-biotin (middle dot plot). Remaining Fab monomers were then detected after subsequent washing steps using fresh PE-labeled Strep-Tactin® (second dot plot from the right). Secondary Fab-multimer staining of reversibly stained cells served as control (right dot plot). Only live ($PI^{negative}$) cells are shown. Numbers in dot plots indicate the percentage of cells within gates.

This Example examines the reversible staining of cells by αCD3 Fab-multimers. Freshly isolated PBMCs were stained with either the αCD3 monoclonal antibody clone OKT3 (left dot plot, parental clone for the Fab-multimers) or cognate phycoerythrine (PE)-labeled OKT3 Fab-multimers and analyzed either before (second dot plot from the left) or after treatment with D-biotin (middle dot plot). Remaining Fab monomers were then detected after subsequent washing steps using fresh PE-labeled Strep-Tactin® (second dot plot from the right). Secondary Fab-multimer staining of reversibly stained cells served as control (right dot plot). Only live CD3 cells which are negative in staining with propidium iodide (PI) for live/dead discrimination are shown in FIG. 21. Numbers in dot plots indicate the percentage of cells within gates. This experiment shows that the staining of CD3+ PBMCs with an anti-CD3 Fab fragment multimerized with Streptactin as multerization reagent is fully reversible by addition of D-biotin and that the monovalent Fab fragment alone does not bind to the CD3 molecule present on PBMCs.

Example 18: Reversible Isolation of Cells by αCD28 Fab-Multimers

Figure 22:
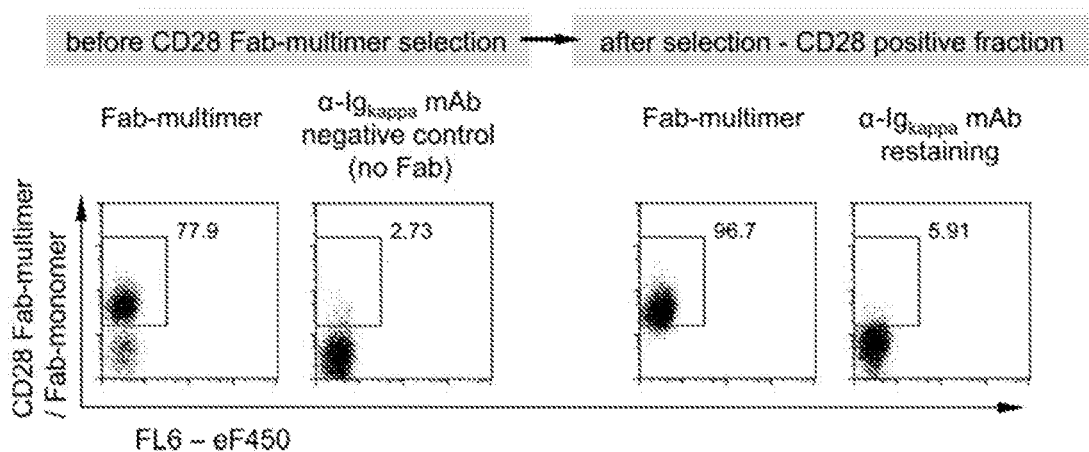
FIG. 22 shows the isolation of cells by reversible binding of anti-CD28 Fab fragments multimerized with Strep-Tactin® labeled with phycoerythrine as a fluorescent label. CD28+ cells were selected/isolation by Fab-multimer magnetic cell selection from freshly isolated PMBCs as described in International Patent App. Pub. No. WO2013/011011. Before selection cells were control stained with either the cognate fluorescent αCD28-multimers (left dot plot) or with an antibody directed against the immunoglobulin kappa light chain (second dot plot from the left, α-Ig kappa mAb). After selection, cells were treated with D-biotin and subsequently washed to remove magnetic beads and Fab-monomers. Liberated CD28+ cells were subsequently (re-)stained either with αCD28 Fab-multimers (second dot plot from the right) or with the α-Ig kappa mAb (right dot plot) to detect potentially remaining Fab-monomers. Only live (PI$^{negative}$) CD3+ cells are shown. Numbers in dot plots indicate the percentage of cells within gates.
Figure 24A:
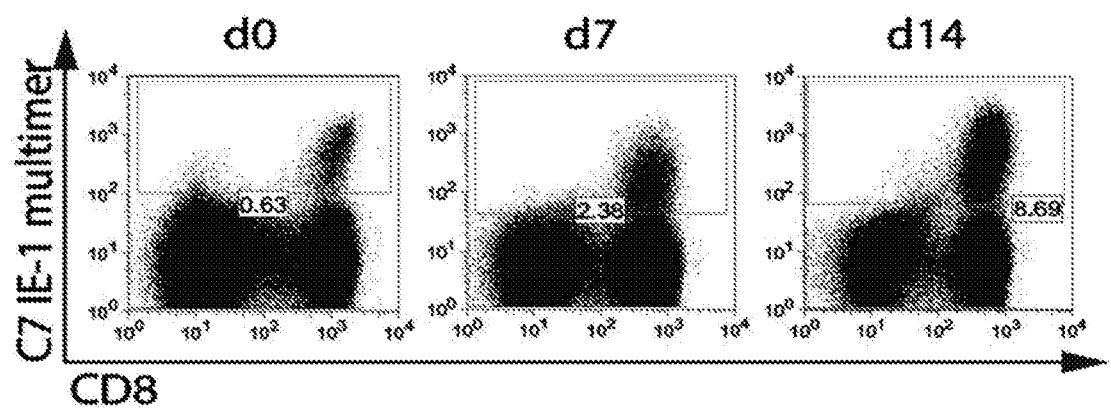
FIG. 24A shows exemplary flow-cytometric analysis for the fraction of the Ag-specific cells that were proliferated using the peptide:MHC-I complex specific for this HLA-C7/IE-1 epitope as first agent that provides a primary activation signal to the cells reversibly immobilized on the soluble oligomeric streptavidin mutein. The graphs in FIG. 24B to FIG. 24E illustrates the expansion kinetics of further Ag-specificities according to the number of specific peptide: MHCI multimer-positive cells harvested per time point in analogy to FIG. 24A using distinct complexes of an antigen-specific peptide with the MHC I molecule as first agent that provides a primary activation signal to the cells reversibly immobilized on the soluble oligomeric streptavidin mutein. In more detail.
Figure 24B:
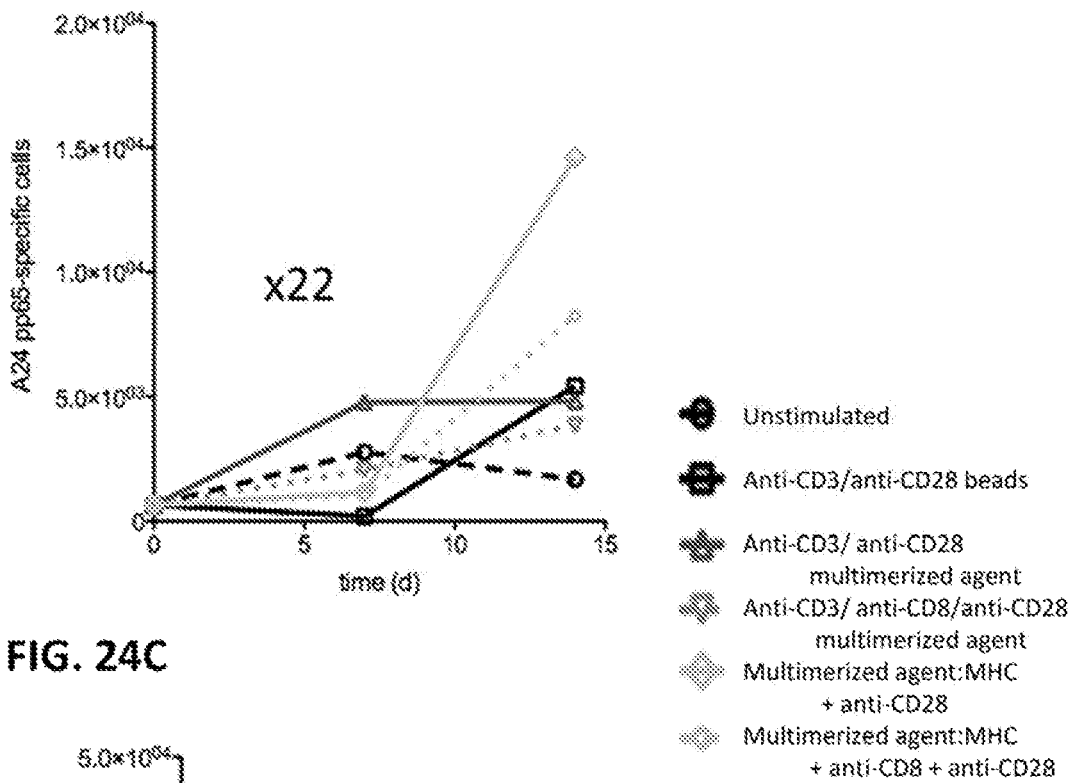
FIG. 24B shows the expansion of Ag-specific cells that were expanded using the peptide:MHC-I complex specific for the pp65 epitope of CMV (amino acids 341-350 (QYDPVAALF)(SEQ ID NO: 39) restricted by HLA-A2402)
Figure 24C:
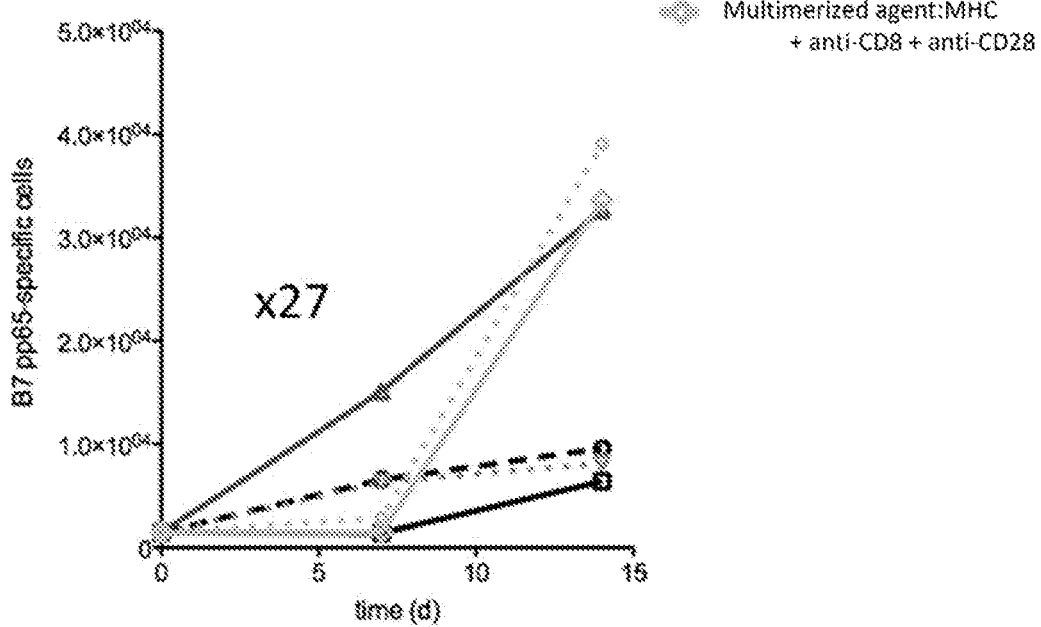
FIG. 24C shows the expansion of Ag-specific cells that were expanded using another peptide:MHC-I complex specific for the pp65 epitope of CMV (amino acids 265-274 (RPHERNGFTV)(SEQ ID NO: 40) restricted by HLA-B702)
Figure 24D:
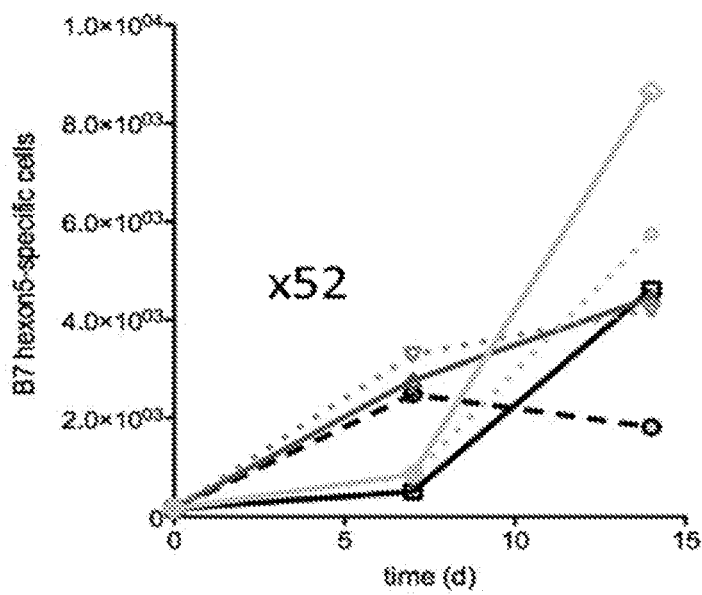
FIG. 24D shows the expansion of Ag-specific cells that were proliferated using the peptide:MHC-I complex specific for the hexon 5 epitope of adenovirus (amino acids 114-124 (CPYSGTAYNSL)(SEQ ID NO: 41) restricted by HLA-B702)
Figure 24E:
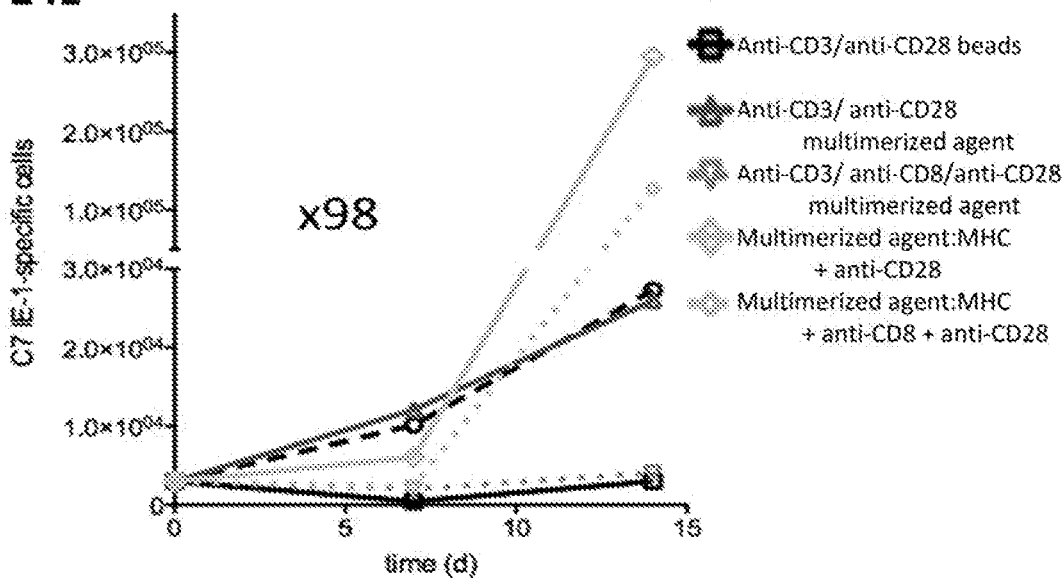
FIG. 24E shows the expansion of Ag-specific cells that were proliferated using the peptide:MHC-I complex specific for the HLA-B7/IE-1$_{309-317}$ epitope of CMV (CRVLCCYVL (SEQ ID NO: 38); exemplary FACS data see above FIG. 24A). All peptide:MHC molecules bearing the Twin Strep®-Tag are commercially available from IBA GmbH. In this context, the amino acid sequences of the HLA-A*2402, HLA-B*0702 and HLA-C*0702 molecules that carry the "Twin-Strep-Tag®" as their C-terminus are shown as SEQ ID NO: 42, 43 and 44 in the accompanying Sequence Listings, while the amino acid sequence of the β$_2$ microglobulin (which forms together with the a chain, that means the HLA encoded molecules the respective MHC I molecule) is shown as SEQ ID NO: 45 in the accompanying Sequence Listing. In addition.
Figure 24F:
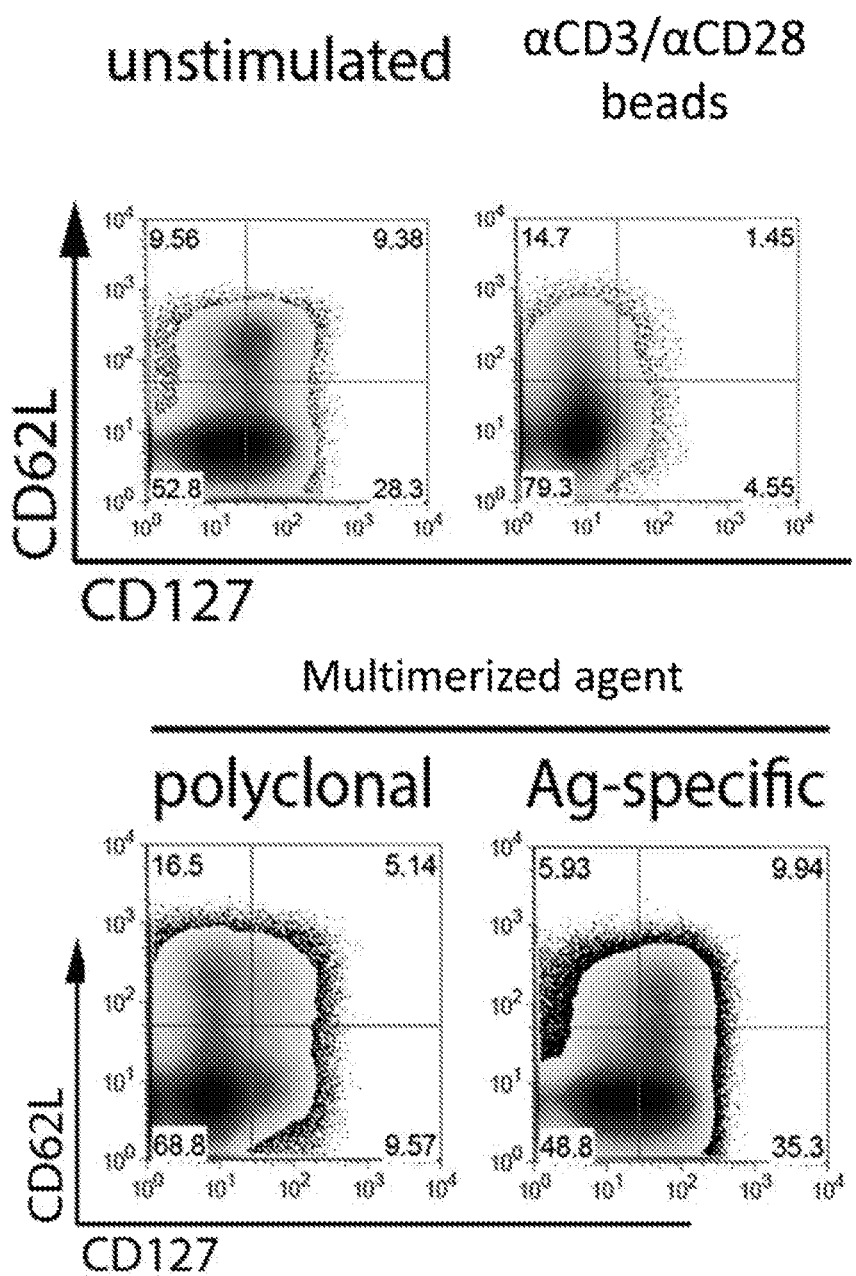
FIG. 24F shows exemplary flow-cytometric analysis of CD62L and CD127 surface expression after 14 days of culture for HLA-B7/Hexon5$_{114-124}$ stimulated/expanded cells from FIG. 24D.

This Example shows the isolation of cells by reversible binding of anti-CD28 Fab fragments multimerized with Strep-Tactin® magnetic particles (the magnetic particles are available from IBA GmbH Göttingen, Germany). The Fab fragments derived from the antibody CD28.3 described in Example 7 above were used for this purpose. CD28+ cells were selected/isolation by Fab-multimer magnetic cell selection from freshly isolated PMBCs as essentially described in International Patent App. Pub. No. WO2013/011011. The results are shown in FIG. 22. Before selection cells were control stained with either the cognate fluorescent αCD28-multimers (left dot plot) or with an antibody directed against the immunoglobulin kappa light chain (second dot plot from the left, α-Ig kappa mAb) as a control staining. After selection, CD28+ cells were treated with D-biotin and subsequently washed to remove magnetic beads and Fab-monomers. Liberated CD28+ cells were subsequently (re-) stained either with αCD28 Fab-multimers (second dot plot from the right) or with the α-Ig kappa mAb (right dot plot) to detect potentially remaining Fab-monomers. Only live ($PI^{negative}$) CD3+ cells are shown. Numbers in dot plots indicate the percentage of cells within gates. FIG. 22 shows that CD28+ cells can be isolated from PMBC using such multimerized anti-CD28 Fab fragment and that all isolation reagents including the anti-CD28 Fab-monomers can be removed after selection.

Example 19: Early Cluster Formation after Activation of Purified CD4+ and CD8+ T Responder Cells Stimulated In Vitro with Reversible αCD3/αCD28 Fab-Streptamer Multimers In this Example, 400,000 CD4+ or CD8+ responder T cells (Tresp) were stimulated with 30 of a preparation of oligomeric Streptactin multimerization reagent (1 mg/ml) loaded with a combination of 0.5 μg αCD3- and 0.5 μg αCD28 Fab. Untreated (unstimulated) Tresp cells served as negative control and Tresp cells stimulated with anti-CD3/anti-CD28 beads as positive control. Tresp cells were seeded in duplicates in 48-well plates in 1 ml cell culture medium supplemented with 30 U/ml IL-2. Cells were incubated at 37° C. and microscopically analyzed after 1 and 2 days. Stimulation of CD4+ Tresp (FIG. 23A) and CD8+ Tresp (FIG. 23B) are shown for anti-CD3/anti-CD28 beads (middle row) and multimerized agent (lower row) respectively. The photographs represent degree of cluster formation: For better visibility exemplary clusters are indicated by circles for the stimulation with soluble streptavidin mutein oligomers in FIG. 23A and FIG. 23B. Clusters within the Dynabead stimulation are readily visibly by accumulation of dark stimulatory particles. As evident, both for CD4+ and CD8+ T cells early clusters formed when using the expansion method of the invention that employs a soluble oligomeric multimerization reagent.

Example 20: Selective Antigen-Specific Expansion of $T_{CM}$ Responder Cells Out of Bulk CD3+ Central Memory T Cells (Kinetics & Phenotype)

In this Example, the kinetics and the phenotype of selective Antigen specific (Ag-specific) expansion out of purified CD3+CD62L+CD45RA-$T_{CM}$ responder cells was examined.

In more detail, CD3+CD62L+CD45RA-$T_{CM}$ responder cells were stimulated in vitro with both a peptide:MHC molecule complex (that acts as first agent that provides a primary activation signal to the cells) and an αCD28 Fab fragment (that acts as second reagent that stimulates an accessory molecule on the surface of the cells). Both the complex of antigen specific peptide with the MHC molecule and the αCD28 Fab fragment were reversibly immobilized on the soluble oligomeric streptavidin mutein (with n≥3) described in Example 8. The peptide that was used for the antigen specific expansion was the peptide CRVLCCYVL (SEQ ID NO: 38), amino acids 309-317 of the immediate-early 1 protein (described in Ameres et al., PLOS Pathogens, May 2013, vol. 9, issue 5, e1003383) representing an HLA-C7/IE-1 epitope that is specific for cytomegalovirus (CMV). The MHC I molecule that presents the peptide carries at the C-terminus of the a chain (heavy chain) the streptavidin binding peptide (SAWSHPQFEK(GGGS)$_2$GG-SAWSHPQFEK, (SEQ ID NO: 16) that is commercially available as "Twin-Strep-Tag®" from IBA GmbH, Göttingen, Germany).

For this purpose, 500,000 CD3+CD62L+CD45RA-responder $T_{CM}$ cells (Tresp) were stimulated Ag-specifically using 3 μl of a preparation of soluble oligomeric Streptactin multimerization reagent functionalized with 0.5 μg of the peptide:MHC class I complexes equipped with the streptavidin binding peptide and with 0.5 μg of the αCD28 Fab described above. As an alternative, 4.5 μl of a of preparation of the Streptactin multimerization reagent were loaded with 0.5 μg of these peptide:MHC class I complexes, 0.5 μg CD8 αFab and 0.5 μg αCD28 Fab. For comparison, polyclonal stimulation was performed, using 3 μl of a preparation of Streptactin multimerization reagent (1 mg/ml) either loaded with a combination of 0.5 μg αCD3 Fab and 0.5 μg αCD28 Fab. Again as the alternative stimulation condition described above, 4.5 μl of a preparation of Streptactin multimerization reagent reversibly loaded with 0.5 μg αCD3 Fab, 0.5 μg αCD8 Fab and 0.5 μg αCD28 Fab was used. Untreated (unstimulated) Tresp cells served as negative control and Tresp cells stimulated polyclonal with anti-CD3/anti-CD28 beads (beads on which αCD3 and αCD28 monoclonal antibodies are irreversible immobilized) as positive control. Tresp cells were seeded in 48-well plates in 1 ml cell culture medium supplemented with 30 U/ml IL-2 and 5 ng/ml IL-15. Cells were incubated at 37° C. with media exchange every 3 days and cell count was analyzed after 7 and 14 days. Exemplary results are shown in FIG. 24 (A-F). The exemplary flow-cytometric analysis for the fraction of Ag-specific cells that was stimulated/expanded via the soluble strept-tactin oligomer on which the peptide:MHC-I complex for an HLA-C7/IE-1 epitope (for CMV) was immobilized (FIG. 24A) show that these antigen-specific T cells were specifically expanded. The graphs of FIG. 24B to FIG. 24E (that represent the degree of expansion of distinct Ag-specificities according to the number of peptide:MHCI multimer-positive cells harvested per time point in analogy to the expansion experiment shown in FIG. 24A) show that, the multerimerization reagent that uses the respective complex of the Ag-specific peptide and MHC 1 molecule provided for the highest number of expanded cells (ranging from an twentyfold increase in the number of cells for the Ag-specific cells that recognize the pp65 epitope of CMV (amino acids 341-350 (QYDPVAALF, (SEQ ID NO: 39)) restricted by HLA-A2402) (see FIG. 24B) to an 98 fold increase in the number of Ag-specific cells that recognize the HLA-B7/IE-1$_{309-317}$ epitope (CRVLCCYVL (SEQ ID NO: 38)) of CMV (see FIG. 24E), thereby showing that the expansion method of the present invention is fully applicable to the expansion of Ag-specific cells. Finally, the exemplary flow-cytometric analysis of CD62L and CD127 surface expression after 14 days of culture for HLA-B7/Hexon5 epitope (for adenovirus) shown in FIG. 24F further confirms that experimental approaches using the soluble multimerization reagents of the present invention retain a higher content of CD127-expressing long-lived memory T cells in polyclonal and Ag-specific stimulatory conditions.

Example 21: Selective Ag-Specific Expansion Kinetics & Phenotype of Bulk Central Memory T Cells This Example examines the kinetics of selective Ag-specific expansion out of purified CD3+CD62L+CD45RA-$T_{CM}$ responder cells that were stimulated in vitro with a) antigen specific peptide MHC I complexes and b) αCD28 Fab fragments that were reversibly immobilized as first and second agent on soluble oligomeric streptavidin muteins.

Figure 25:
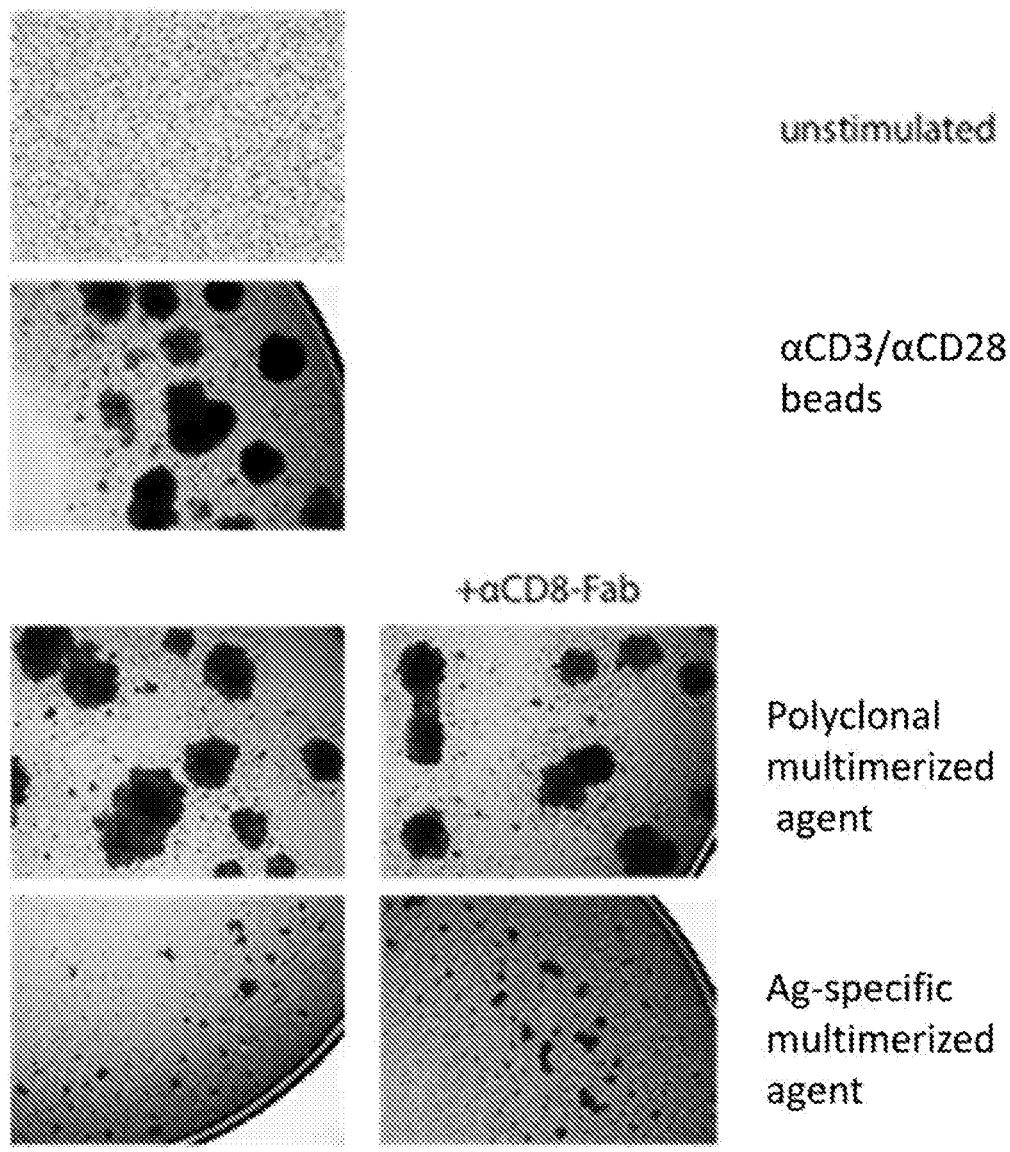
FIG. 25 shows the kinetics of selective Ag-specific expansion out of purified CD3+CD62L+CD45RA-$T_{CM}$ responder cells that were stimulated in vitro with a) antigen specific peptide MHC I complexes and b) αCD28 Fab fragments that were reversibly immobilized as first and second agent on soluble oligomeric streptavidin muteins. For this purpose 500,000 CD3+CD62L+CD45RA-responder $T_{CM}$ cells (Tresp) were stimulated Ag-specifically using 3 µl of a preparation of Streptactin multimerization reagent functionalized with 0.5 µg peptide:MHC class I complexes equipped with a streptavidin binding peptide (the specific peptide represents amino acids 114-124 (CPYSGTAYNSL, SEQ ID NO: 41) of the Hexon 5 protein of the adenovirus restricted by HLA-B0702, see above) and 0.5 µg αCD28 Fab. As an alternative, 4.5 µl of a preparation of Streptactin multimerization reagent loaded with 0.5 µg this peptide:MHC class I complex, 0.5 µg αCD8 Fab and 0.5 µg αCD28 Fab. For comparison, polyclonal stimulation was performed, using 3 µl of a preparation of Streptactin multimerization reagent (1 mg/ml) either loaded with a combination of 0.5 µg αCD3 Fab and 0.5 µg αCD28 Fab. Again as the alternative stimulation condition described above, 4.5 µl of a preparation of Streptactin multimers loaded with 0.5 µg αCD3 Fab, 0.5 µg αCD8 Fab and 0.5 µg αCD28 Fab was used. Untreated (unstimulated) Tresp cells served as negative control and Tresp cells stimulated polyclonal with anti-CD3/anti-CD28 beads as positive control. Tresp cells were seeded in 48-well plates in 1 ml cell culture medium supplemented with 30 U/ml IL-2 and 5 ng/ml IL-15. Cells were incubated at 37° C. with media exchange every 3 days and cell count was analyzed after 7 and 14 days. The photographs shown in FIG. 25 represent the degree of cluster formation on day 5 for Ag-specific stimulation as exemplified for the HLA-B7/Hexon 5 epitope of adenovirus.

For this purpose 500,000 CD3+CD62L+CD45RA-responder $T_{CM}$ cells (Tresp) were stimulated Ag-specifically using 3 μl of a preparation of Streptactin multimerization reagent functionalized with 0.5 μg peptide:MHC class I complexes equipped with a streptavidin binding peptide (the specific peptide represents amino acids 114-124 (CPYSGTAYNSL, SEQ ID NO: 41) of the Hexon 5 protein of adenovirus restricted by HLA-B07) and 0.5 μg αCD28 Fab. As an alternative, 4.5 μl of a preparation of Streptactin multimerization reagent loaded with 0.5 μg this peptide:MHC class I complex, 0.5 μg αCD8 Fab and 0.5 μg αCD28 Fab. For comparison, polyclonal stimulation was performed, using 3 μl of a preparation of Streptactin multimerization reagent (1 mg/ml) either loaded with a combination of 0.5 μg αCD3 Fab and 0.5 μg αCD28 Fab. Again as the alternative stimulation condition described above, 4.5 μl of a preparation of Streptactin multimers loaded with 0.5 μg αCD3 Fab, 0.5 μg αCD8 Fab and 0.5 μg αCD28 Fab was used. Untreated (unstimulated) Tresp cells served as negative control and Tresp cells stimulated polyclonal with anti-CD3/anti-CD28 beads as positive control. Tresp cells were seeded in 48-well plates in 1 ml cell culture medium supplemented with 30 U/ml IL-2 and 5 ng/ml IL-15. Cells were incubated at 37° C. with media exchange every 3 days and cell count was analyzed after 7 and 14 days. The pictures shown in FIG. 25 represent degree of cluster formation on day 5, exemplary Ag-specific stimulation is illustrated for the HLA-B7/Hexon 5 epitope of adenovirus. As can be seen from FIG. 25, such adenovirus antigen specific cells could be specifically expanded from the original CD3+CD62L+CD45RA-$T_{CM}$ responder population.

Example 22: Activation of Intracellular Signaling Cascades after Streptamer Multimers Stimulation of αCD19-CAR Transduced Jurkat Cells In this Example the activation of intracellular signaling cascades of transduced Jurkat cells that have been modified to express a tumor-specific chimeric antigen receptor (CAR), namely here CD19 and that were stimulated using the oligomeric Strep-Tactin® of Example 8 as soluble multimerization reagent was examined.

Figure 26A:
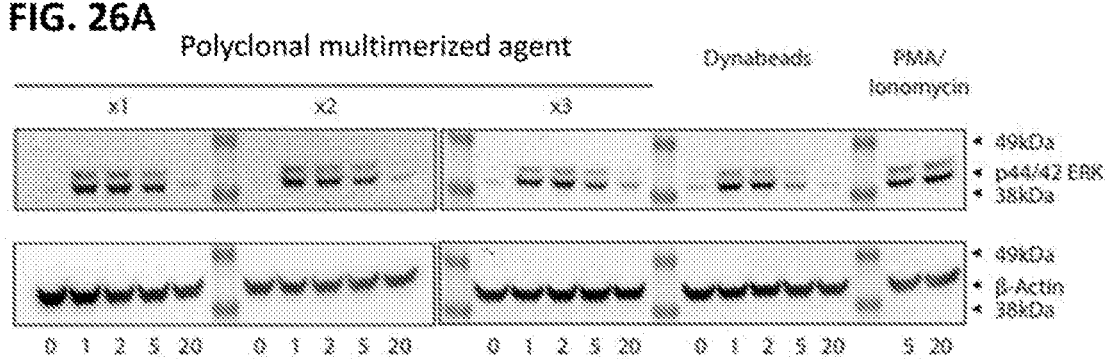
FIG. 26(A-B) shows the activation of intracellular signaling cascades of transduced Jurkat cells that have been modified to express an αCD19 chimeric antigen receptor (CAR), and that were stimulated using the oligomeric Strep-Tactin® of Example 3 as soluble multimerization reagent. The specificity of a CAR is typically derived from a scFv region assembled from the antigen-binding region of a monoclonal antibody (mAb) that specifically binds a target/tumor associated antigen such as CD19 and links it to T cell specific signaling (described in Hudecek et al., Clin Cancer Res. 2013 Jun. 15; 19(12): 3153-3164. In the experiments the extracellular domain (ECD) of CD19, which contains the natural ligand of the αCD19 CAR as well as the polyclonal αIgG F(ab)$_2$ fragment that recognizes the IgG4 spacer (donkey-anti-human F(ab)$_2$ is commercially available from Jackson Immuno Research) within the αCD19-CAR were also used in this experiment as first agent that provides a primary activation signal to the jurkat cells. The reversibly immobilization to the soluble oligomeric streptavidin mutein was provided by the streptavidin peptide SAWSHPQFEK(GGGS)$_2$GGSAWSHPQFEK (SEQ ID NO: 16) that was fused to the C-terminus of the ECD of CD19 or by the biotinylated (Fab)$_2$ fragment of the αIgG (since the streptavidin mutein "m2" binds biotin with reduced affinity, this binding is reversible and can for example be displaced by addition of an excess of free biotin). In the control experiment of FIG. 26A, 300,000 CD3+ Jurkat responder cells (Jresp) were stimulated with varying amounts of a mixture of preparations of oligomeric Streptactin (1 mg/ml) that was functionalized with the αCD3 Fab and the αCD28 Fab ("×1" corresponds to 3 μg multimerized Streptactin functionalized with 0.5 μg αCD3 Fab and 0.5 μg αCD28 Fab—polyclonal multimerized agent). In the experiment of FIG. 26B 3 μl of a preparation of the oligomeric Streptactin was functionalized with 0.5 μg (×1) or 1 μg (×2) of the extracellular domain (ECD) of CD19 or with 3 μl of a preparation of the oligomeric Streptactin loaded with 0.5 μg (×1) or 1 μg (×2) αIgG that recognizes the IgG4 spacer (which are both CAR-specific multimerized agent). Jresp stimulated with anti-CD3/anti-CD28 beads (beads on which αCD3 and αCD28 monoclonal antibodies are irreversible immobilized) or PMA and ionomycin served as positive controls. Jresp cells were seeded in 1.5 ml Eppendorf tubes in 200 μl cell culture medium supplemented with 30 U/ml IL-2. Cells were incubated at 37° C. and put on ice and lysed after 0 min to 20 min of stimulation. Detection of phosphorylated ERK indicates active MAPK signaling, staining of the housekeeper β-Actin indicates loading of equal amounts of total protein per condition and time point.
Figure 26B:
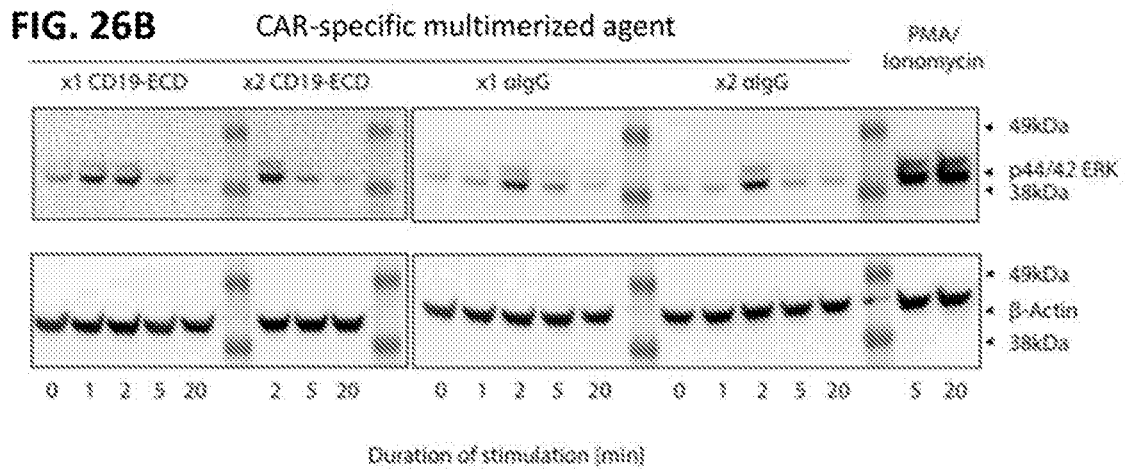

For this purpose, 300,000 Jurkat responder cells (Jresp) were stimulated with (A) varying amounts of a mixture of preparations of Streptactin multimerization reagent (1 mg/ml) functionalized with αCD3 Fab and αCD28 Fab fragments described here ("×1" corresponds to 3 μg Strep-tactin mulerization reagent functionalized with 0.5 μg αCD3- and 0.5 μg αCD28 Fab—this provides a "polyclonal Streptactin based multimerization reagent"), or (B) 3 μl of a preparation of Streptactin multimerization reagent functionalized with 0.5 μg (×1) or 1 μg (×2) of the extracellular domain (ECD) of CD19 (the natural ligand for the αCD19-CAR—this provides a "CAR-specific Streptactin based multimerization reagent"), or 3 μl of a preparation of Streptactin multimerization reagent loaded with 0.5 μg (×1) or 1 μg (×2) αIgG recognizing the IgG4 spacer within the αCD19-CAR—this also provides a "CAR-specific Streptavidin mutein based multimerization reagent". ECD of CD19 equipped with a hexahistidine tag was obtained from Sino Biological/Life technologies (SEQ ID NO: 47) and was functionalized for binding to the streptavidin based multimerization reagent by mixing the ECD of CD19 with the adapter molecule His-STREPPER (IBA GmbH, Germany, Order number 2-0920-005) at a molecular ratio of 1:1 and incubating for 15 min at room temperature. The His-STREPPER adapter molecule contains a chelating portion that binds to the hexahistidine tag and a streptavidin binding peptide, thereby temporarily providing the target molecule, here the ECD of CD19 with a streptavidin binding peptide that can reversibly bind to a streptavidin mutein based multimerization reagent. Jresp stimulated with anti-CD3/anti-CD28 beads (beads having irreversibly immobilized thereon αCD3- and αCD28-monoclonal antibodies) or PMA and Ionomycin served as positive controls. Jresp cells were seeded in 1.5 ml Eppendorf tubes in 200 μl cell culture medium supplemented with 30 U/ml IL-2. Cells were incubated at 37° C. and put on ice and lysed after 0 min to 20 min of stimulation. Detection of phosphorylated ERK indicates active MAPK signaling, staining of the housekeeper β-Actin indicates loading of equal amounts of total protein per condition and time point. As can be seen from the comparison of FIG. 26A showing activation of the Jurkat cells via the "polyclonal Streptactin multimerization reagent" and FIG. 26B showing activation of the Jurkat cells via the two "CAR-specific Streptactin based multimerization reagents", the Jurkat cells can be activated/expanded via the binding of the CD19 extracellular domain to the CD19 specific chimeric antigen receptor. Since genetic down-stream processing of T cells is almost exclusively performed on pre-selected cell populations, a generic activation via cross-linking of introduced CARs via the IgG4 spacer domain (this is conserved within various CARs with different specificities) broadens the applicability for reversible cell stimulation/expansion in these in vitro cell-processing situations.

Thus, this experiment shows that in principle any cell population that is activated by binding of an agent (ligand) that provides a primary activation signal to the cell population can be expanded using a first agent reversibly immobilized on a multimerization reagent as described here.

Example 23: Parallel Antigen-Specific Expansion of $T_{CM}$ Responder Cells Out of a Single Pool In this Example, the kinetics of parallel Antigen specific (Ag-specific) expansion out of a single pool of T responder cells stimulated in vitro with multiple reversible peptide:MHC/αCH28 Fab-Streptamer multimers is examined.

500,000 CD3+CD62L+CD45RA-responder $T_{CM}$ cells (Tresp) are simultaneously stimulated for multiple Ag-specificities using for each specificity, 3 µl of Streptactin multimers functionalized with 0.5 µg of the respective peptide:MHC class I complexes that carries a streptavidin binding peptide and 0.5 µg αCD28 Fab that also carries a streptavidin binding peptide. As an alternative approach, 4.5 µl of Streptactin based multimerization reagent functionalized with 0.5 µg peptide:MHC class I complexes carrying a streptavidin binding peptide, 0.5 µg αCD8 Fab and 0.5 µg αCD28 Fab as described here are used for each specificity. For comparison, polyclonal stimulation is performed, using 3 µl of a preparation of Streptactin based multimerization reagent (1 mg/ml) either reversibly loaded with a combination of 0.5 µg αCD3 Fab and 0.5 µg αCD28 Fab. Again as the alternative stimulation condition described above, 4.5 µl of a preparation of the Streptactin based multimerization reagent reversibly loaded with 0.5 µg αCD3 Fab, 0.5 µg αCD8 Fab and 0.5 µg αCD28 Fab (each of them carrying a streptavidin binding peptide can be used. Untreated (unstimulated) Tresp cells serve as negative control and Tresp cells stimulated polyclonal with anti-CD3/anti-CD28 beads (αCD3- and αCD28-mAb coated beads) as positive control. Tresp cells are seeded in 48-well plates in 1 ml cell culture medium supplemented with 30 U/ml IL-2 and 5 ng/ml IL-15. Cells are incubated at 37° C. with media exchange every 3 days and cell count are analyzed after 7 and 14 days.

Example 24: Preferential Proliferation of CD8+ T Cells Among CD3+ T Responder Cells Stimulated In Vitro with Streptavidin Based Multimerization Reagents Reversibly Functionalized with αCD3/αCD8/αCD28 Fab Fragments 300,000 CD3+ responder T cells (Tresp) are stimulated with 30 of a preparation of Streptactin multimerization (1 mg/ml) or a preparation of a multimerization reagent using the large Streptactin backbone (0.1 mg/ml) either loaded with a combination of 0.5 µg αCD3 Fab and 0.5 µg αCD28 Fab, or 4.5 µl of a preparation of Streptactin based multimerization reagent loaded with 0.5 µg αCD3, 0.5 µg αCD8 Fab and 0.5 µg αCD28 Fab, or 3 µl of a mixture of preparations of Streptactin based multimerization reagent with 0.5 µg αCD3 Fab alone and 0.5 µg αCD28 Fab alone (each Fab fragment again carries a streptavidin binding peptide). Untreated Tresp cells serve as negative control and Tresp stimulated with anti-CD3/anti-CD28 beads (αCD3- and αCD28-mAb coated beads) as positive control. Tresp cells are seeded in duplicates in 48-well plates in 1 ml cell culture medium supplemented with 30 U/ml IL-2. Cells are incubated at 37° C. with media exchange after 3 days and analyzed after 6 days.

Example 25: Preferential Proliferation of CD8+ T Cells Among CD3+ T Responder Cells Stimulated In Vitro with Streptavidin Based Multimerization Reagents Reversibly Functionalized with αCD3 Fab and αCD28 Fab Fragments 300,000 CD3+ responder T cells (Tresp) are stimulated with varying amounts of a mixture of preparations of Streptactin based multimerization reagent (1 mg/ml) functionalized with αCD3 Fab fragment alone and αCD28 Fab fragment alone (1.5 µg Streptactin based multimerization reagent functionalized with 0.5 µg αCD3 Fab fragment alone and 1.5 µg Streptactin based multimerization reagent functionalized with 0.5 µg αCD28 Fab fragment alone), or varying amounts of a mixture of preparations of Streptactin based multimerization reagent functionalized with αCD3 Fab fragment and αCD28 Fab fragment with or without αCD8 Fab fragment (each Fab fragment again carries a streptavidin binding peptide) (3 µg Streptactin based multimerization reagent functionalized with 0.5 µg αCD3- and 0.5 µg αCD28 Fab fragment—without αCD8 Fab fragment, or 4.5 µl of a preparation of Streptactin multimerization reagent loaded with 0.5 µg αCD3 Fab fragment, 0.5 µg αCD8 Fab fragment and 0.5 µg αCD28 Fab fragment, wherein Fab fragment again carries a streptavidin binding peptide). Untreated Tresp cells serve as negative control and Tresp stimulated with anti-CD3/anti-CD28 beads (αCD3- and αCD28- mAb coated beads) as positive control. Tresp cells are seeded in 48-well plates in 1 ml cell culture medium supplemented with 30 U/ml IL-2. Cells are incubated at 37° C. with media exchange after 3 days and analyzed after 6 days.

Example 26: Biotin-Mediated Disruption of Stimulation by Analysis of Intracellular Calcium Mobilization in Primary T Cells The impact of disrupting cell stimulation via a reversible multimerized reagent (by D-Biotin addition) on stimulation of primary human T cells was monitored by assessing Ca2+ flux. CD3-purified T cells from healthy donor peripheral blood mononuclear cells (PBMCs) were loaded with a calcium sensor dye, incubated with a reagent containing multimerized anti-CD3/anti-CD28 Fab fragments reversibly bound on an oligomeric streptavidin mutein reagent, and assessed for Ca2+ flux by flow cytometric analysis. The anti-CD3/anti-CD28 multimerized agent was added at 60s and the culture was either left undisturbed or treated with D-Biotin addition at 200s. To confirm induction of calcium flux of the T cells was still possible after having disrupted the signal by dissociation of the Fab fragments from the multimerization reagent, ionomycin was added at 400s.

Figure 27:
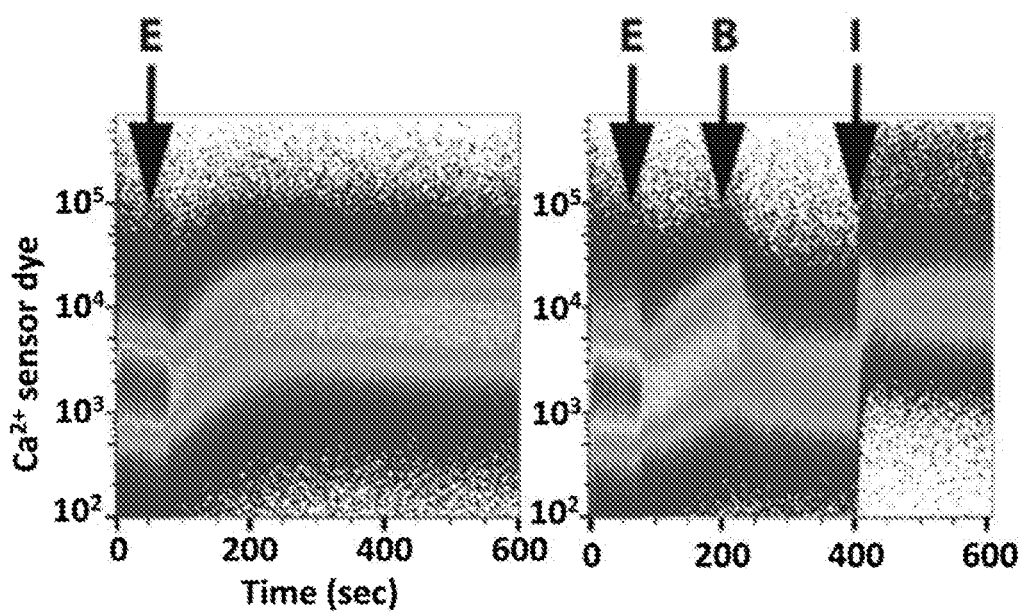
FIG. 27 shows the impact of adding D-Biotin on $Ca^{2+}$-flux in CD3+ T cells following stimulation with αCD3/αCD28 Fabs that were reversibly bound to an oligomeric mutein streptavidin reagent as assessed by flow cytometry. The multimerized reagent was added to cultures at 60s (arrow "E"), and cultures were either left undisturbed (left panel) or further treated by addition of D-Biotin at 200s (arrow "B") and addition of ionomycin at 400s (arrow "I").

As shown in FIG. 27, dissociation by addition of D-Biotin was able to disrupt the signal delivered to the cell via the anti-CD3/anti-CD28 multimerized agent as shown by a decrease in intracellular Ca2+ levels, following the increase of Ca2+ levels induced by the reagent. The addition of ionomycin following D-Biotin-mediated disruption of signaling restored intracellular Ca2+ to levels observed prior to addition of D-Biotin, indicating that the cells remained responsive and healthy following the dissociation of the reagent dissociation and disruption of signaling and were able to flux calcium and in response to ionomycin exhibited intracellular levels that were similar levels as compared to those observed following the initial stimulation.

Figure 28A:
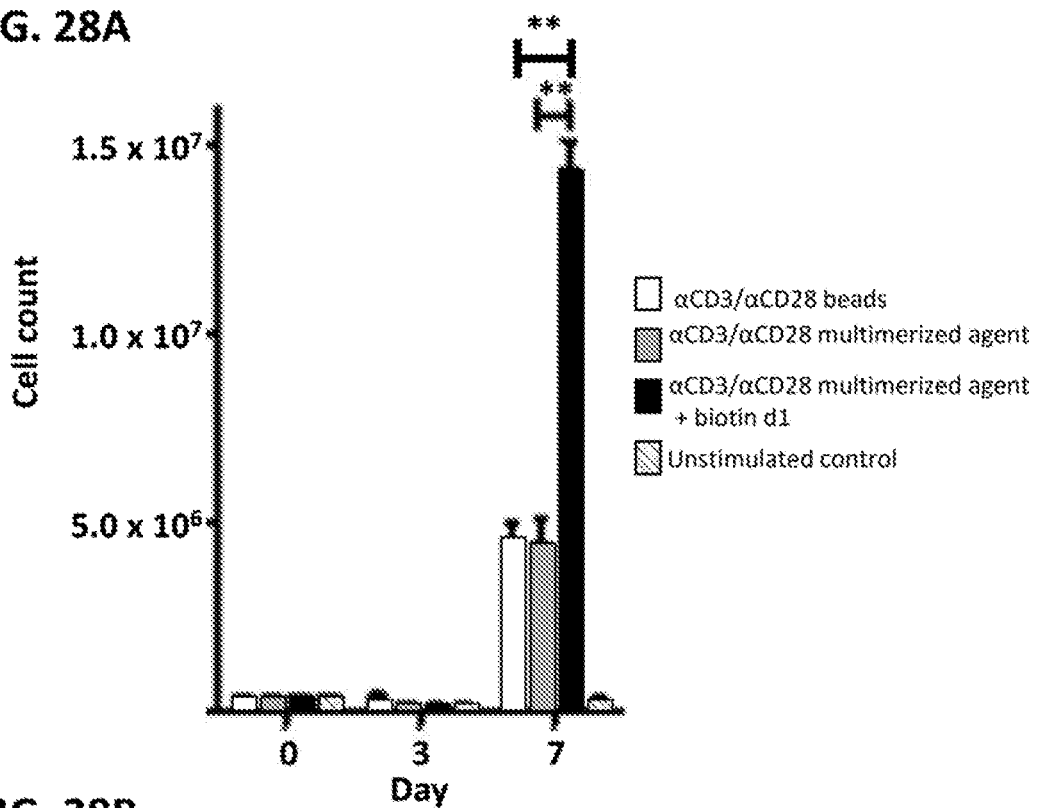
FIG. 28A shows the cell count (degree of expansion) resulting from activation of CD3+ T cells following stimulation with the multimerized agent reversibly bound with αCD3/αCD28 Fabs (with or without D-Biotin addition at day 1) or stimulation with control anti-CD3/anti-CD28 beads as assessed at day 0, 3 and 7 in culture. Unstimulated cells were included as a negative control. **: p≤0.05, two-tailed paried t test.
Figure 28B:
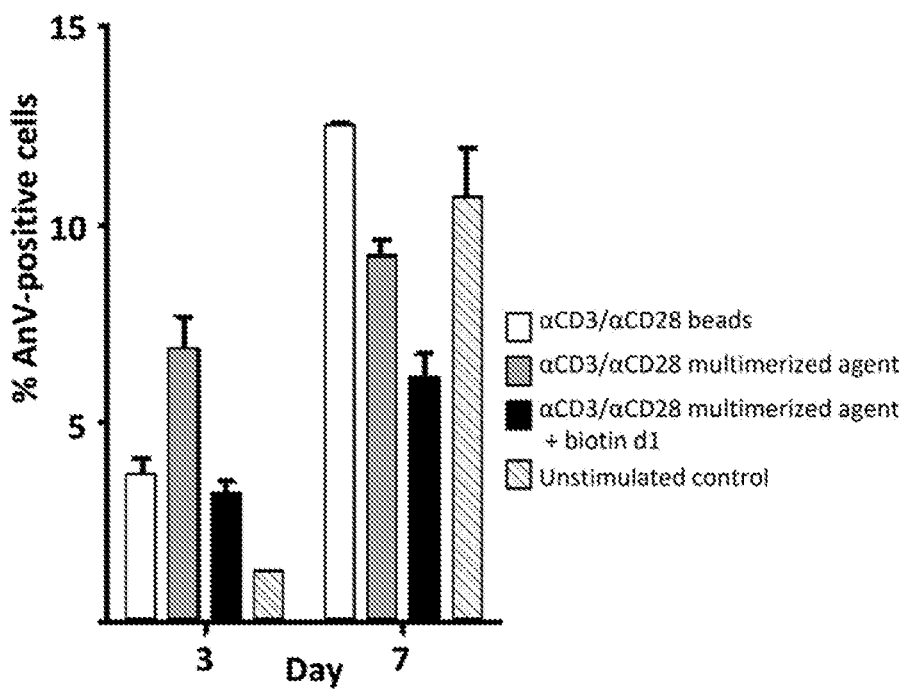
FIG. 28B shows the percent of annexin V-positive cells (indicating apoptosis) resulting from activation of CD3+ T cells following stimulation with the multimerized agent reversibly bound with αCD3/αCD28 Fabs (with or without D-Biotin addition at day 1) or stimulation with control anti-CD3/anti-CD28 beads as assessed at day 3 and 7 in culture. Unstimulated cells were included as a negative control. **: p≤0.05, two-tailed paried t test.

Example 27: Assessment of T Cell Expansion Following Temporally-Controlled Activation of T Cells by Incubation with Reversible Agent Following incubation with, and dissociation of, the anti-CD3/anti-CD28 signal, expansion of T cells isolated from healthy donor PBMCs was assessed. T cells were incubated for 7 days following the addition of a reagent containing multimerized anti-CD3/anti-CD28 Fab fragments reversibly bound to an oligomeric streptavidin mutein reagent. At day 1 of culture, either D-biotin was added to dissociate the multimerized agent or the cells were left undisturbed (no D-Biotin addition at day 1). As a control, cells were incubated with anti-CD3/anti-CD28 magnetic beads for the 7 days. The total cell count and fraction of annexin V-positive cells was assessed at day 0, 3 or 7 of culture. As shown in FIGS. 28A and 28B, CD3+ T cells cultured with the anti-CD3/anti-CD28 multimerized agent dissociated at day 1 (biotin added at day 1) showed enhanced expansion and reduced apoptosis (as indicated by decreased annexin V staining) compared to both the culture in which cells were incubated for the full seven days with the multimerized agent (without D-Biotin addition) and compared to the cultures in which cells were incubated with the control anti-CD3/anti-CD28 beads.

Figure 29:
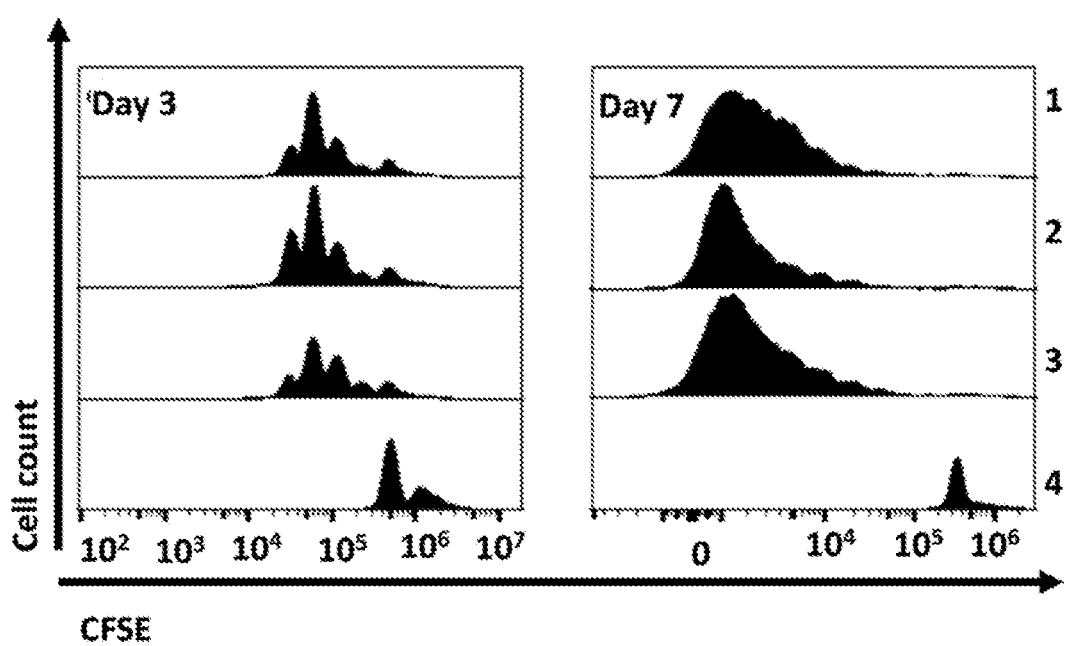
FIG. 29 shows cell cycle entry and proliferation resulting from activation of CD3+ T cells following stimulation with the multimerized agent reversibly bound with αCD3/αCD28 Fabs (with or without D-Biotin addition at day 2) or stimulation with control anti-CD3/anti-CD28 beads assessed by measuring CFSE dilution at day 3 (d3) and day 7 (d7) in culture. Unstimulated cells were included as a negative control.

In another assay, isolated CD3+ T cells, CD4+ T cells or CD8+ T cells were labeled with CFSE dye and proliferation was assessed after stimulation as described above, except with the addition of biotin at day 2. Proliferation was determined by flow cytometry based on the extent of dilution of the CFSE dye. As shown in FIG. 29, CD3+ cells stimulated with the anti-CD3/anti-CD28 multimerized agent with dissociation at d.1 (biotin added) displayed enhanced proliferation, particularly at day 3, as compared to cells stimulated with the multimerized agent but without disruption of the signal (no biotin).

Example 28: Assessment of Metabolic Activity in T Cells Following Temporally-Controlled Activation by Incubation with a Reversible Agent Metabolic activity of cells as an indicator of cell proliferation was assessed by colorimetric monitoring of cleavage of the stable tetrazolium salt WST-1 to a soluble formazan dye complex. Because the cleavage of this agent generally depends on glycolytic production of NAD(P)H in viable cells, the extent of formazan dye generally can be directly correlated to the number of metabolically active cells in a culture. In this study, CD4-, or CD8-purified T cells were incubated with the anti-CD3/anti-CD28 multimerized Fab fragments reversibly bound on an oligomeric streptavidin mutein reagent (with or without D-Biotin addition at day 2) or a control anti-CD3/anti-CD28 magnetic bead reagent. After culture of the cells at day 1, day 2 or day 3, the cells were incubated with the WST-1 reagent and levels of metabolic activity were assessed by measuring the absorbance at 450 nm as a readout. The results were normalized to the number of cells in the culture being assayed and depicted as the ratio of WST-1 per cell number.

Figure 30:
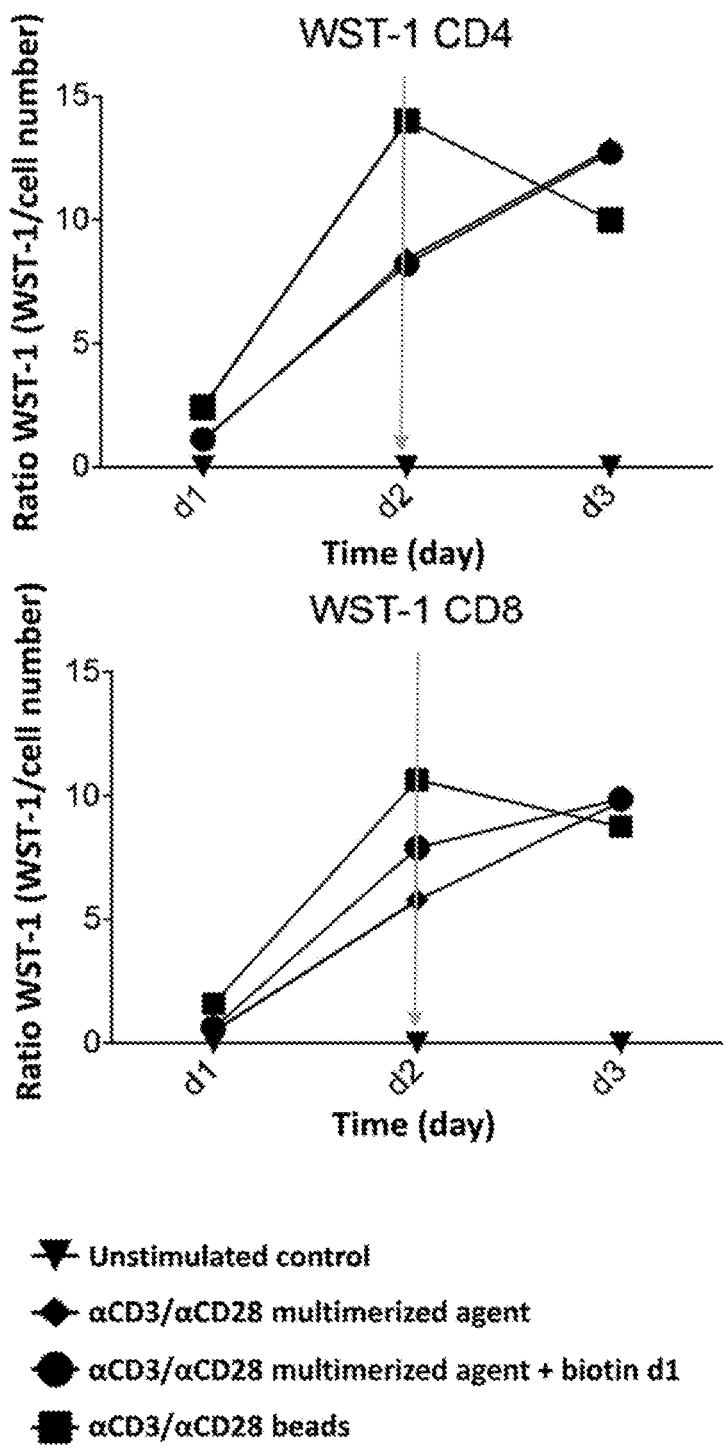
FIG. 30 shows the metabolic activity of CD4− or CD8− purified T cells following stimulation with the multimerized agent reversibly bound with αCD3/αCD28 Fabs (with or without D-Biotin addition at day 2) or stimulation with control anti-CD3/anti-CD28 beads as assessed by WST-1 assay at 24 hours and 72 hours in culture. Unstimulated cells were included as a negative control.

As shown in FIG. 30, the results indicated that controlled stimulation of T cells with the anti-CD3/anti-CD28 multimeric reagent resulted in increased levels of a signal indicative of metabolic activity and cell expansion, over the course of incubation in this study, even when biotin was added at d.2 to dissociate the reagent and disrupt signaling.

Example 29: Impact of Disruption of Signaling Via Anti-CD3/Anti-CD28 Multimeric Agent on Expansion Capacity of T Cells Upon Restimulation CD3+ cells labeled with CFSE dye were cultured in the presence of a reversible reagent containing multimerized, anti-CD3/anti-CD28 Fab fragments, reversibly bound on an oligomeric form of a streptavidin mutein. At day 1, D-Biotin was added to some samples as indicated in FIG. 31. Under some conditions as indicated, cells were sorted at day 3 for CFSE$^{low}$ (non-divided) cells. Sorted cells were either cultured without further addition of stimulus (sort purified (see FIG. 31)) or were further admixed with additional anti-CD3/anti-CD28 multimerized agent (sort purified, re-stimulation (see FIG. 31)). Unsorted cells (cells not sorted based on CFSE levels at day 3) also were assessed in parallel. Expansion of the cells, normalized to unstimulated cells, was monitored up to day 15.

As shown in FIG. 31, cells incubated with the multimeric reagent were observed to continue to expand through the duration of the study, up to day 15 for all of the conditions tested. Even in samples in which signaling induced by the multimeric agent was disrupted at day 1, and those in which cells were sort-purified without further addition of the reagent, continued to proliferate over this period of time. This result indicated that incubation with the oligomeric stimulatory reagent, even if for only 1 day, was able to induceprolonged T cell expansion over a period of 15 days. This effect was observed even in samples in which cells had been sort-purified at day 3, to isolate cells which had not yet divided, and in which there was no further stimulation by re-addition of that or any stimulating reagent. The result was consistent with a conclusion that the reversible oligomeric stimulatory agent was capable of inducing prolonged T cell expansion, for several days following disruption of binding to the reagent and/or following purification of non-divided cells, without the induction of additional reagent, an effect not observed in this assay under conditions in which cells were stimulated with beads.

Example 30: Assessment of T Cell Surface Markers Following Temporally-Controlled Activation by Incubation with a Reversible Agent Expression of various T cell markers was assessed following stimulation of T cells subjected to various conditions, including various types of retroviral-mediated transduction, by incubating them with the reversibly binding anti-CD3/anti-CD28 multimerized agent, with or without dissociation at day 1, induced by addition of D-Biotin). CD3-purified T cells from healthy donor-derived peripheral blood mononuclear cells (PBMCs), transduced with one of various retroviral vector particles each encoding a different chimeric antigen receptor, expanded in culture, frozen, and thawed. The cells were incubated for 7 days following addition of the reagent described in Example 1 containing multimerized, anti-CD3/anti-CD28 Fab fragments, which were multimerized by reversible binding to an oligomeric streptavidin mutein. At day 1 of culture, D-biotin was added to dissociate the multimerized agent from the cells in some samples, while in others cells and reagent were left undisturbed (no D-Biotin addition at day 1). In other samples, cells were incubated with anti-CD3/anti-CD28 magnetic beads for the 7 days. The percentage of cells positive for surface and/or intracellular expression of each of a number of T cell activation and/or other phenotypic markers were assessed at various times.

For example, at day 7, the cells were assayed for expression of markers Ki-67 and T-bet by flow cytometry as described. As in other studies described herein, following stimulation with the reversible oligomeric reagent, when the reagent was dissociated to disrupt signaling at day 1, the cells were observed to retained positivity for Ki67 but to have reduced expression of T-bet. This result indicated that under various conditions, temporal control by dissociation of the reagent could be used to generate an output composition of cells having a less-differentiated or stem-like phenotype, more long-lived and/or central memory and/or stem central memory phenotype.

Other markers assessed included CD25 and CD69 and markers CD45RA, CD45RO, CD27, CD127, and CXCR3, was assessed by flow cytometry at day 3 and day 7. Results are shown in FIG. 32 and are consistent with the observation that disruption of binding of the reversible stimulatory reagent at day 1 of the culture period as resulted in a greater percentage of the T cells in the resulting output composition having features of a phenotypic profile generally observed on less-differentiated and/or relatively longer-lived and/or stem-like T cell populations, such as central memory ($T_{CM}$) and less-differentiated memory T cells such as so-called stem memory T cells ($T_{SCM}$). These studies were further consistent with the observation that temporal-controlled of stimulation using the oligomeric reagent by addition of D-Biotin at early time points (within 4 days) resulted in cell compositions having an increase in cells with a phenotypic profile consistent with or similar to that present in a less-differentiated, long-lived population of T cells such as long-lived memory T cells.

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

SEQUENCES

| No. | Sequence | Description |
|---|---|---|
| 1 | DPSKDSKAQVSAAEAGITGTWYNQLGSTFIVTAGADGALTGTYESAV GNAESRYVLTGRYDSAPATDGSGTALGWTVAWKNNYRNAHSATTWSG QYVGGAEARINTQWLLTSGTTEANAWKSTLVGHDTFTKVKPSAASID AAKKAGVNNGNPLDAVQQ | Streptavidin Species: *Streptomyces avidinii* UniProt No. P22629 |
| 2 | EAGITGTWYNQLGSTFIVTAGADGALTGTYESAVGNAESRYVLTGRY DSAPATDGSGTALGWTVAWKNNYRNAHSATTWSGQYVGGAEARINTQ WLLTSGTTEANAWKSTLVGHDTFTKVKPSAAS | Minimal streptavidin Species: *Streptomyces avidinii* |
| 3 | DPSKDSKAQVSAAEAGITGTWYNQLGSTFIVTAGADGALTGTYVTAR GNAESRYVLTGRYDSAPATDGSGTALGWTVAWKNNYRNAHSATTWSG QYVGGAEARINTQWLLTSGTTEANAWKSTLVGHDTFTKVKPSAASID AAKKAGVNNGNPLDAVQQ | Mutein Streptavidin Val44-Thr45-Ala46-Arg47 Species: *Streptomyces avidinii* |
| 4 | EAGITGTWYNQLGSTFIVTAGADGALTGTYVTARGNAESRYVLTGRY DSAPATDGSGTALGWTVAWKNNYRNAHSATTWSGQYVGGAEARINTQ WLLTSGTTEANAWKSTLVGHDTFTKVKPSAAS | Mutein Streptavidin Val44-Thr45-Ala46-Arg47 Species: *Streptomyces avidinii* |
| 5 | DPSKDSKAQVSAAEAGITGTWYNQLGSTFIVTAGADGALTGTYIGAR GNAESRYVLTGRYDSAPATDGSGTALGWTVAWKNNYRNAHSATTWSG QYVGGAEARINTQWLLTSGTTEANAWKSTLVGHDTFTKVKPSAASID AAKKAGVNNGNPLDAVQQ | Mutein Streptavidin Ile44-Gly45-Ala-46-Arg47 Species: *Streptomyces avidinii* |
| 6 | EAGITGTWYNQLGSTFIVTAGADGALTGTYIGARGNAESRYVLTGRY DSAPATDGSGTALGWTVAWKNNYRNAHSATTWSGQYVGGAEARINTQ WLLTSGTTEANAWKSTLVGHDTFTKVKPSAAS | Mutein Streptavidin Ile44-Gly45-Ala-46-Arg47 Species: *Streptomyces avidinii* |
| 7 | Trp-Arg-His-Pro-Gln-Phe-Gly-Gly | Streptavidin binding peptide, Strep-tag ® |
| 8 | WSHPQFEK | Strep-tag ® II |
| 9 | His-Pro-Xaa | Streptavidin Binding peptide Xaa is selected from glutamine, asparagine and methionine |
| 10 | His-Pro-Gln-Phe | Streptavidin-binding peptide |

-continued

| No. | Sequence | Description |
|---|---|---|
| 11 | Xaa$_1$-Xaa$_2$-His-Pro-Gln-Phe-Xaa$_3$-Xaa$_4$ | Streptavidin-binding peptide Xaa$_1$ is Trp, Lys or Arg; Xaa$_2$ is any amino acid; Xaa$_3$ is Gly or Glu Xaa$_4$ is Gly, Lys or Arg |
| 12 | -Trp-Xaa$_1$-His-Pro-Gln-Phe-Xaa$_2$-Xaa$_3$- | Streptavidin-binding peptide Xaa$_1$ is any amino acid; Xaa$_2$ is Gly or Glu Xaa$_3$ is Gly, Lys or Arg |
| 13 | Trp-Ser-His-Pro-Gln-Phe-Glu-Lys-(Xaa)n-Trp-Ser-His-Pro-Gln-Phe-Glu-Lys- | Sequential modules of streptavidin-binding peptide Xaa is any amino acid; n is either 8 or 12 |
| 14 | Trp-Ser-His-Pro-Gln-Phe-Glu-Lys-(GlyGlyGlySer)n-Trp-Ser-His-Pro-Gln-Phe-Glu-Lys | Sequential modules of streptavidin-binding peptide n is 2 or 3 |
| 15 | SAWSHPQFEKGGGSGGGSGGGSWSHPQFEK | Twin-Strep-tag |
| 16 | SAWSHPQFEKGGGSGGGSGGSAWSHPQFEK | Twin-Strep-tag |
| 17 | WSHPQFEKGGGSGGGSGGGSWSHPQFEK | Twin-Strep-tag |
| 18 | WSHPQFEKGGGSGGGSWSHPQFEK | Twin-Strep-tag |
| 19 | WSHPQFEKGGGSGGGSGGSAWSHPQFEK | Twin-Strep-tag |
| 20 | Tyr-Pro-Tyr-Asp-Val-Pro-Asp-Tyr-Ala | HA-tag |
| 21 | Tyr-Thr-Asp-Ile-Glu-Met-Asn-Arg-Leu-Gly-Lys | VSV-G-tag |
| 22 | Gln-Pro-Glu-Leu-Ala-Pro-Glu-Asp-Pro-Glu-Asp | HSV-tag |
| 23 | Ala-Ser-Met-Thr-Gly-Gly-Gln-Gln-Met-Gly | T7 epitope |
| 24 | Gln-Pro-Glu-Leu-Ala-Pro-Glu-Asp-Pro-Glu-Asp | HSV epitope |
| 25 | Glu-Gln-Lys-Leu-Ile-Ser-Glu-Glu-Asp-Leu | Myc epitope |
| 26 | Gly-Lys-Pro-Ile-Pro-Asn-Pro-Leu-Leu-Gly-Leu-Asp-Ser-Thr | V5-tag |
| 27 | EAGITGTWYNQLGSTFIVTAGADGALTGTYVTARGNAESRYVLTGRYDSAPATDGSGTALGWTVAWKNNYRNAHSATTWSGQYVGGAEARINTQWLLTSGTTEENAGYSTLVGHDTFTKVKPSAAS | Mutein Streptavidin Ile44-Gly45-Ala-46-Arg47 and Glu117, Gly120, Try121 (mutein m1-9) Species: *Streptomyces avidinii* |
| 28 | DPSKDSKAQVSAAEAGITGTWYNQLGSTFIVTAGADGALTGTYVTARGNAESRYVLTGRYDSAPATDGSGTALGWTVAWKNNYRNAHSATTWSGQYVGGAEARINTQWLLTSGTTEENAGYSTLVGHDTFTKVKPSAAS | Mutein Streptavidin Ile44-Gly45-Ala-46-Arg47 and Glu117, Gly120, Try121 (mutein m1-9) Species: *Streptomyces avidinii* |

| No. | Sequence | Description |
|---|---|---|
| 29 | AMQVQLKQSG PGLVQPSQSL SITCTVSGFS LTTFGVHWVR QSPGKGLEWLGVIWASGITD YNVPFMSRLS ITKDNSKSQV FFKLNSLQPD DTAIYYCAKNDPGTGFAYWG QGTLVTVSAG STKGPSVFPL APSSKSTSGG TAALGCLVKDYFPEPVTVSW NSGALTSGVH TFPAVLQSSG LYSLSSVVTV PSSSLGTQTYICNVNHKPSN TKVDKKVEPK SCGSAWSHPQ FEKGGGSGGG SGGSAWSHPQFEK | Variable Heavy chain of Fab fragment m13B8.2 |
| 30 | AMDIQMTQSP ASLSASVGET VTFTCRASEM IYSYLAWYQQ KQGKSPQLLVHDAKTLAEGV PSRFSGGGSG TQFSLKINTL QPEDFGTYYC QAHYGNPPTFGGGTKLEIKR GIAAPSVFIF PPSDEQLKSG TASVVCLLNN FYPREAKVQWKVDNALQSGN SQESVTEQDS KDSTYSLSST LTLSKADYEK HKVYACEVTHQGLSSPVTKS FNRGECGS | Variable Light chain of Fab Fragment m13B8.2 |
| 31 | Gln Val Gln Leu Gln Gln Ser Gly Ala Glu Leu Ala Arg Pro Gly Ala Ser Val Lys Met Ser Cys Lys Ala Ser Gly Tyr Thr Phe Thr Arg Tyr Thr Met His Trp Val Lys Gln Arg Pro Gly Gln Gly Leu Glu Trp Ile Gly Tyr Ile Asn Pro Ser Arg Gly Tyr Thr Asn Tyr Asn Gln Lys Phe Lys Asp Lys Ala Thr Leu Thr Thr Asp Lys Ser Ser Ser Thr Ala Tyr Met Gln Leu Ser Ser Leu Thr Ser Glu Asp Ser Ala Val Tyr Tyr Cys Ala Arg Tyr Tyr Asp Asp His Tyr Cys Leu Asp Tyr Trp Gly Gln Gly Thr Thr Leu Thr Val Ser Ser | Variable Heavy chain of anti-CD3 antibody OKT3 |
| 32 | Gln Ile Val Leu Thr Gln Ser Pro Ala Ile Met Ser Ala Ser Pro Gly Glu Lys Val Thr Met Thr Cys Ser Ala Ser Ser Ser Val Ser Tyr Met Asn Trp Tyr Gln Gln Lys Ser Gly Thr Ser Pro Lys Arg Trp Ile Tyr Asp Thr Ser Lys Leu Ala Ser Gly Val Pro Ala His Phe Arg Gly Ser Gly Ser Gly Thr Ser Tyr Ser Leu Thr Ile Ser Gly Met Glu Ala Glu Asp Ala Ala Thr Tyr Tyr Cys Gln Gln Trp Ser Ser Asn Pro Phe Thr Phe Gly Ser Gly Thr Lys Leu Glu Ile Asn | Variable Light chain of anti-CD3 antibody OKT3 |
| 33 | Leu Gln Gln Ser Gly Ala Glu Leu Val Lys Pro Gly Ala Ser Val Arg Leu Ser Cys Lys Ala Ser Gly Tyr Thr Phe Thr Glu Tyr Ile Ile His Trp Ile Lys Leu Arg Ser Gly Gln Gly Leu Glu Trp Ile Gly Trp Phe Tyr Pro Gly Ser Asn Asp Ile Gln Tyr Asn Ala Lys Phe Lys Gly Lys Ala Thr Leu Thr Ala Asp Lys Ser Ser Ser Thr Val Tyr Met Glu Leu Thr Gly Leu Thr Ser Glu Asp Ser Ala Val Tyr Phe Cys Ala Arg Arg Asp Asp Phe Ser Gly Tyr Asp Ala Leu Pro Tyr Trp Gly Gln Gly Thr Met Val Thr Val | Variable Heavy chain of anti-CD28 antibody CD28.3 |
| 34 | Asp Ile Gln Met Thr Gln Ser Pro Ala Ser Leu Ser Val Ser Val Gly Glu Thr Val Thr Ile Thr Cys Arg Thr Asn Glu Asn Ile Tyr Ser Asn Leu Ala Trp Tyr Gln Gln Lys Gln Gly Lys Ser Pro Gln Leu Leu Ile Tyr Ala Ala Thr His Leu Val Glu Gly Val Pro Ser Arg Phe Ser Gly Ser Gly Ser Gly Thr Gln Tyr Ser Leu Lys Ile Thr Ser Leu Gln Ser Glu Asp Phe Gly Asn Tyr Tyr Cys Gln His Phe Trp Gly Thr Pro Cys Thr Phe Gly Gly Gly Thr Lys Leu Glu Ile Lys Arg | Variable Light chain of anti-CD28 antibody CD28.3 |
| 35 | His-Asn-His-Arg-His-Lys-His-Gly-Gly-Gly-Cys | MAT tag |
| 36 | Gln Val Thr Leu Lys Glu Ser Gly Pro Gly Ile Leu Gln Pro Ser Gln Thr Leu Ser Leu Thr Cys Ser Phe Ser Gly Phe Ser Leu Arg Thr Ser Gly Met Gly Val Gly Trp Ile Arg Gln Pro Ser Gly Lys Gly Leu Glu Trp Leu Ala His Ile Trp Trp Asp Asp Asp Lys Arg Tyr Asn Pro Ala Leu Lys Ser Arg Leu Thr Ile Ser Lys Asp Thr Ser Ser Asn Gln Val Phe Leu Lys Ile Ala Ser Val Asp Thr Ala Asp Thr Ala Thr Tyr Tyr Cys Ala Gln Ile Asn Pro Ala Trp Phe Ala Tyr Trp Gly Gln Gly Thr Leu Val Thr Val Ser Ser | αCD16 antibody 3G8 VH |
| 37 | Asp Ile Val Leu Thr Gln Ser Pro Ala Ser Leu Ala Val Ser Leu Gly Gln Arg Ala Thr Ile Ser Cys Lys Ala Ser Gln Ser Val Asp Phe Asp Gly Asp Ser Phe Met Asn Trp Tyr Gln Gln Lys Pro Gly Gln Pro Pro Lys Leu Leu Ile Tyr Thr Thr Ser Asn Leu Glu Ser | αD16 antibody 3G8 VL |

| No. | Sequence | Description |
|---|---|---|
| | Gly Ile Pro Ala Arg Phe Ser Ala Ser Gly Ser Gly<br>Thr Asp Phe Thr Leu Asn Ile His Pro Val Glu Glu<br>Glu Asp Thr Ala Thr Tyr Tyr Cys Gln Gln Ser Asn<br>Glu Asp Pro Tyr Thr Phe Gly Gly Gly Thr Lys Leu<br>Glu Ile Lys | |
| 38 | CRVLCCYVL | antigen-specific peptide |
| 39 | QYDPVAALF | pp65 epitope of CMV (amino acids 341-350) |
| 40 | RPHERNGFTV | pp65 epitope of CMV (amino acids 265-274 |
| 41 | CPYSGTAYNSL | hexon 5 epitope of adenovirus (amino acids 114-124) |
| 42 | Met Gly Ser His Ser Met Arg Tyr Phe Ser Thr Ser<br>Val Ser Arg Pro Gly Arg Gly Glu Pro Arg Phe Ile<br>Ala Val Gly Tyr Val Asp Asp Thr Gln Phe Val Arg<br>Phe Asp Ser Asp Ala Ala Ser Gln Arg Met Glu Pro<br>Arg Ala Pro Trp Ile Glu Gln Glu Gly Pro Glu Tyr<br>Trp Asp Glu Glu Thr Gly Lys Val Lys Ala His Ser<br>Gln Thr Asp Arg Glu Asn Leu Arg Ile Ala Leu Arg<br>Tyr Tyr Asn Gln Ser Glu Ala Gly Ser His Thr Leu<br>Gln Met Met Phe Gly Cys Asp Val Gly Ser Asp Gly<br>Arg Phe Leu Arg Gly Tyr His Gln Tyr Ala Tyr Asp<br>Gly Lys Asp Tyr Ile Ala Leu Lys Glu Asp Leu Arg<br>Ser Trp Thr Ala Ala Asp Met Ala Ala Gln Ile Thr<br>Lys Arg Lys Trp Glu Ala Ala His Val Ala Glu Gln<br>Gln Arg Ala Tyr Leu Glu Gly Thr Cys Val Asp Gly<br>Leu Arg Arg Tyr Leu Glu Asn Gly Lys Glu Thr Leu<br>Gln Arg Thr Asp Pro Pro Lys Thr His Met Thr His<br>His Pro Ile Ser Asp His Glu Ala Thr Leu Arg Cys<br>Trp Ala Leu Gly Phe Tyr Pro Ala Glu Ile Thr Leu<br>Thr Trp Gln Arg Asp Gly Glu Asp Gln Thr Gln Asp<br>Thr Glu Leu Val Glu Thr Arg Pro Ala Gly Asp Gly<br>Thr Phe Gln Lys Trp Ala Ala Val Val Val Pro Ser<br>Gly Glu Glu Gln Arg Tyr Thr Cys His Val Gln His<br>Glu Gly Leu Pro Lys Pro Leu Thr Leu Arg Trp Glu<br>Pro Pro Pro Ser Gly Ser Ser Ala Trp Ser His Pro<br>Gln Phe Glu Lys Gly Gly Gly Ser Gly Gly Gly Ser<br>Gly Gly Gly Ser Ser Ala Trp Ser His Pro Gln Phe<br>Glu Lys | HLA-A*2402 |
| 43 | Met Gly Ser His Ser Met Arg Tyr Phe Tyr Thr Ser<br>Val Ser Arg Pro Gly Arg Gly Glu Pro Arg Phe Ile<br>Ser Val Gly Tyr Val Asp Asp Thr Gln Phe Val Arg<br>Phe Asp Ser Asp Ala Ala Ser Pro Arg Glu Glu Pro<br>Arg Ala Pro Trp Ile Glu Gln Glu Gly Pro Glu Tyr<br>Trp Asp Arg Asn Thr Gln Ile Tyr Lys Ala Gln Ala<br>Gln Thr Asp Arg Glu Ser Leu Arg Asn Leu Arg Gly<br>Tyr Tyr Asn Gln Ser Glu Ala Gly Ser His Thr Leu<br>Gln Ser Met Tyr Gly Cys Asp Val Gly Pro Asp Gly<br>Arg Leu Leu Arg Gly His Asp Gln Tyr Ala Tyr Asp<br>Gly Lys Asp Tyr Ile Ala Leu Asn Glu Asp Leu Arg<br>Ser Trp Thr Ala Ala Asp Thr Ala Ala Gln Ile Thr<br>Gln Arg Lys Trp Glu Ala Ala Arg Glu Ala Glu Gln<br>Arg Arg Ala Tyr Leu Glu Gly Glu Cys Val Glu Trp<br>Leu Arg Arg Tyr Leu Glu Asn Gly Lys Asp Lys Leu<br>Glu Arg Ala Asp Pro Pro Lys Thr His Val Thr His<br>His Pro Ile Ser Asp His Glu Ala Thr Leu Arg Cys<br>Trp Ala Leu Gly Phe Tyr Pro Ala Glu Ile Thr Leu<br>Thr Trp Gln Arg Asp Gly Glu Asp Gln Thr Gln Asp<br>Thr Glu Leu Val Glu Thr Arg Pro Ala Gly Asp Arg<br>Thr Phe Gln Lys Trp Ala Ala Val Val Val Pro Ser<br>Gly Glu Glu Gln Arg Tyr Thr Cys His Val Gln His<br>Glu Gly Leu Pro Lys Pro Leu Thr Leu Arg Trp Glu<br>Pro Pro Pro Ser Gly Ser Ser Ala Trp Ser His Pro<br>Gln Phe Glu Lys Gly Gly Gly Ser Gly Gly Gly Ser<br>Gly Gly Gly Ser Ser Ala Trp Ser His Pro Gln Phe<br>Glu Lys | HLA-B*0702 |

| No. | Sequence | Description |
|---|---|---|
| 44 | Met Ala Leu Thr Glu Thr Trp Ala Cys Ser His Ser<br>Met Arg Tyr Phe Asp Thr Ala Val Ser Arg Pro Gly<br>Arg Gly Glu Pro Arg Phe Ile Ser Val Gly Tyr Val<br>Asp Asp Thr Gln Phe Val Arg Phe Asp Ser Asp Ala<br>Ala Ser Pro Arg Gly Glu Pro Arg Ala Pro Trp Val<br>Glu Gln Glu Gly Pro Glu Tyr Trp Asp Arg Glu Thr<br>Gln Lys Tyr Lys Arg Gln Ala Gln Ala Asp Arg Val<br>Ser Leu Arg Asn Leu Arg Gly Tyr Tyr Asn Gln Ser<br>Glu Asp Gly Ser His Thr Leu Gln Arg Met Ser Gly<br>Cys Asp Leu Gly Pro Asp Gly Arg Leu Leu Arg Gly<br>Tyr Asp Gln Ser Ala Tyr Asp Gly Lys Asp Tyr Ile<br>Ala Leu Asn Glu Asp Leu Arg Ser Trp Thr Ala Ala<br>Asp Thr Ala Ala Gln Ile Thr Gln Arg Lys Leu Glu<br>Ala Ala Arg Ala Ala Glu Gln Leu Arg Ala Tyr Leu<br>Glu Gly Thr Cys Val Glu Trp Leu Arg Arg Tyr Leu<br>Glu Asn Gly Lys Glu Thr Leu Gln Arg Ala Glu Pro<br>Pro Lys Thr His Val Thr His His Pro Leu Ser Asp<br>His Glu Ala Thr Leu Arg Cys Trp Ala Leu Gly Phe<br>Tyr Pro Ala Glu Ile Thr Leu Thr Trp Gln Arg Asp<br>Gly Glu Asp Gln Thr Gln Asp Thr Glu Leu Val Glu<br>Thr Arg Pro Ala Gly Asp Gly Thr Phe Gln Lys Trp<br>Ala Ala Val Val Pro Ser Gly Gln Glu Gln Arg<br>Tyr Thr Cys His Met Gln His Glu Gly Leu Gln Glu<br>Pro Leu Thr Leu Ser Trp Glu Pro Ser Ser Gln Pro<br>Thr Ile Gly Ser Ala Trp Ser His Pro Gln Phe Glu<br>Lys Gly Gly Ser Gly Gly Gly Ser Gly Gly Ser<br>Ala Trp Ser His Pro Gln Phe Glu Lys | HLA-C*0702 |
| 45 | Met Ile Gln Arg Thr Pro Lys Ile Gln Val Tyr Ser<br>Arg His Pro Ala Glu Asn Gly Lys Ser Asn Phe Leu<br>Asn Cys Tyr Val Ser Gly Phe His Pro Ser Asp Ile<br>Glu Val Asp Leu Leu Lys Asn Gly Glu Arg Ile Glu<br>Lys Val Glu His Ser Asp Leu Ser Phe Ser Lys Asp<br>Trp Ser Phe Tyr Leu Leu Tyr Tyr Thr Glu Phe Thr<br>Pro Thr Glu Lys Asp Glu Tyr Ala Cys Arg Val Asn<br>His Val Thr Leu Ser Gln Pro Lys Ile Val Lys Trp<br>Asp Arg Asp Met | $\beta_2$ microglobulin |
| 46 | WREPGRMELN | 10 amino acid tag from the collagen-binding domain of von Willebrand factor |
| 47 | PEEPLVVKVEEGDNAVLQCLKGTSDGPTQQLTWSRESPLKPFLKLSL<br>GLPGLGIHMRPLAIWLFIFNVSQQMGGFYLCQPGPPSEKAWQPGWTV<br>NVEGSGELFRWNVSDLGGLGCGLKNRSSEGPSSPSGKLMSPKLYVWA<br>KDRPEIWEGEPPCLPPRDSLNQSLSQDLTMAPGSTWLSCGVPPDSV<br>SRGPLSWTHVHPKGPKSLLSLELKDDRPARDMWVMETGLLLPRATAQ<br>DAGKYYCHRGNLTMSFHLEITARPVLWHWLLRTGGWKAHHHHHHHH<br>H | human CD19 extracellular domain with His-Tag |
| 48 | QVTLKESGPGILQPSQTLSLTCSFSGFSLRTSGMGVGWIRQPSGKGL<br>EWLAHIWWDDDKRYNPALKSRLTISKDTSSNQVFLKIASVDTADTAT<br>YYCAQINPAWFAYWGQGTLVTVSS | αCD16 antibody 3G8 VH |
| 49 | DIVLTQSPASLAVSLGQRATISCKASQSVDFDGDSFMNWYQQKPGQP<br>PKLLIYTTSNLESGIPARFSASGSGTDFTLNIHPVEEEDTATYYCQQ<br>SNEDPYTFGGGTKLEIK | αCD16 antibody 3G8 VL |
| 50 | APTSSSTKKTQLQLEHLLLDLQMILNGINNYKNPKLTRMLTFKFYMP<br>KKATELKHLQCLEEELKPLEEVLNLAQSKNFHLRPRDLISNINVIVL<br>ELKGSETTFMCEYADETATIVEFLNRWITFCQSIISTLT | IL-2 |
| 51 | DCDIEGKDGKQYESVLMVSIDQLLDSMKEIGSNCLNNEFNFFKRHIC<br>DANKEGMFLFRAARKLRQFLKMNSTGDFDLHLLKVSEGTTILLNCTG<br>QVKGRKPAALGEAQPTKSLEENKSLKEQKKLNDLCFLKRLLQEIKTC<br>WNKILMGTKEH | IL-7 |
| 52 | QGQDRHMIRMRQLIDIVDQLKNYVNDLVPEFLPAPEDVETNCEWSAF<br>SCFQKAQLKSANTGNNERIINVSIKKLKRKPPSTNAGRRQKHRLTCP<br>SCDSYEKKPPKEFLERFKSLLQKMIHQHLSSRTHGSEDS | IL-21 |

-continued

| No. | Sequence | Description |
|---|---|---|
| 53 | SAPFSPLSNVKYNFMRIIKYEFILNDALNQSIIRANDQYLTAAALHN LDEAVKFDMGAYKSSKDDAKITVILRISKTQLYVTAQDEDQPVLLKE MPEIPKTITGSETNLLFFWETHGTKNYFTSVAHPNLFIATKQDYWVC LAGGPPSITDFQILENQA | IL-1alpha |
| 54 | APVRSLNCTLRDSQQKSLVMSGPYELKALHLQGQDMEQQVVFSMSFV QGEESNDKIPVALGLKEKNLYLSCVLKDDKPTLQLESVDPKNYPKKK MEKRFVFNKIEINNKLEFESAQFPNWYISTSQAENMPVFLGGTKGGQ DITDFTMQFVSS | IL-1beta |
| 55 | GIHVFILGCFSAGLPKTEANWVNVISDLKKIEDLIQSMHIDATLYTE SDVHPSCKVTAMKCFLLELQVISLESGDASIHDTVENLIILANNSLS SNGNVTESGCKECEELEEKNIKEFLQSFVHIVQMFINTS | IL-15 |
| 56 | QDPYVKEAENLKKYFNAGHSDVADNGTLFLGILKNWKEESDRKIMQS QIVSFYFKLFKNFKDDQSIQKSVETIKEDMNVKFFNSNKKKRDDFEK LTNYSVTDLNVQRKAIHELIQVMAELSPAAKTGKRKRSQMLFRG | IFNγ |
| 57 | MSTESMIRDVELAEEALPKKTGGPQGSRRCLFLSLFSFLIVAGATTL FCLLHFGVIGPQREEFPRDLSLISPLAQAVRSSSRTPSDKPVAHVVA NPQAEGQLQWLNRRANALLANGVELRDNQLVVPSEGLYLIYSQVLFK GQGCPSTHVLLTHTISRIAVSYQTKVNLLSAIKSPCQRETPEGAEAK PWYEPIYLGGVFQLEKGDRLSAEINRPDYLDFAESGQVYFGIIAL | TNFα |
| 58 | HKCDITLQEIIKTLNSLTEQKTLCTELTVTDIFAASKNTTEKETFCR AATVLRQFYSHHEKDTRCLGATAQQFHRHKQLIRFLKRLDRNLWGLA GLNSCPVKEANQSTLENFLERLKTIMREKYSKCSS | IL-4 |
| 59 | SPGQGTQSENSCTHFPGNLPNMLRDLRDAFSRVKTFFQMKDQLDNLL LKESLLEDFKGYLGCQALSEMIQFYLEEVMPQAENQDPDIKAHVNSL GENLKTLRLRLRRCHRFLPCENKSKAVEQVKNAFNKLQEKGIYKAMS EFDIFINYIEAYMTMKIRN | IL-10 |
| 60 | CDLPQTHSLGSRRTLMLLAQMRKISLFSCLKDRHDFGFPQEEFGNQF QKAETIPVLHEMIQQIFNLFSTKDSSAAWDETLLDKFYTELYQQLND LEACVIQGVGVTETPLMKEDSILAVRKYFQRITLYLKEKKYSPCAWE VVRAEIMRSFSLSTNLQESLRSKE | IFNα2 |
| 61 | MSYDVLRYQQRSSNLACQKLLGQLPGTPQYCLEDRMNFEVPEEIMQP PQFQKEDAVLIIHEMLQQIFGILRRNFSSTGWNETVIKTILVELDGQ MDDLETILEEIMEEENFPRGDMTILHLKKYYLSILQYLKSKEYRSCA WTVVQVEILRNFSFLNRLTDYLRN | IFNβ1 |
| 62 | RNLPVATPDPGMFPCLHHSQNLLRAVSNMLQKARQTLEFYPCTSEEI DHEDITKDKTSTVEACLPLELTKNESCLNSRETSFITNGSCLASRKT SFMMALCLSSIYEDLKMYQVEFKTMNAKLLMDPKRQIFLDQNMLAVI DELMQALNFNSETVPQKSSLEEPDFYKTKIKLCILLHAFRIRAVTID RVMSYLNAS | IL-12α |
| 63 | IWELKKDVYVVELDWYPDAPGEMVVLTCDTPEEDGITWTLDQSSEVL GSGKTLTIQVKEFGDAGQYTCHKGGEVLSHSLLLLHKKEDGIWSTDI LKDQKEPKNKTFLRCEAKNYSGRFTCWWLTTISTDLTFSVKSSRGSS DPQGVTCGAATLSAERVRGDNKEYEYSVECQEDSACPAAEESLPIEV MVDAVHKLKYENYTSSFFIRDIIKPDPPKNLQLKPLKNSRQVEVSWE YPDTWSTPHSYFSLTFCVQVQGKSKREKKDRVFTDKTSATVICRKNA SISVRAQDRYYSSSWSEWASVPCS | IL-12β |
| 64 | GITIPRNPGCPNSEDKNFPRTVMVNLNIHNRNTNTNPKRSSDYYNRS TSPWNLHRNEDPERYPSVIWEAKCRHLGCINADGNVDYHMNSVPIQQ EILVLRREPPHCPNSFRLEKILVSVGCTCVTPIVHHVA | IL-17 |
| 65 | TPVVRKGRCSCISTNQGTIHLQSLKDLKQFAPSPSCEKIEIIATLKN GVQTCLNPDSADVKELIKKWEKQVSQKKKQKNGKKHQKKKVLKVRKS QRSRQKKTT | CXCL9 |
| 66 | VPLSRTVRCTCISISNQPVNPRSLEKLEIIPASQFCPRVEIIATMKK KGEKRCLNPESKAIKNLLKAVSKERSKRSP | CXCL10 |
| 67 | GTNDAEDCCLSVTQKPIPGYIVRNFHYLLIKDGCRVPAVVFTTLRGR QLCAPPDQPWVERIIQRLQRTSAKMKRRSS | CCL19 |
| 68 | SDGGAQDCCLKYSQRKIPAKVVRSYRKQEPSLGCSIPAILFLPRKRS QAELCADPKELWVQQLMQHLDKTPSPQKPAQGCRKDRGASKTGKKGK GSKGCKRTERSQTPKGP | CCL21 |

| No. | Sequence | Description |
|---|---|---|
| 69 | QGVFEDCCLAYHYPIGWAVLRRAWTYRIQEVSGSCNLPAAIFYLPKR HRKVCGNPKSREVQRAMKLLDARNKVFAKLHHNTQTFQAGPHAVKKL SSGNSKLSSSKFSNPISSSKRNVSLLISANSGL | CCL25 |
| 70 | GGGS | Linker peptide |
| 71 | YNLDVRGARSFSPPRAGRHFGYRVLQVGNGVIVGAPGEGNSTGSLYQ CQSGTGHCLPVTLRGSNYTSKYLGMTLATDPTDGSILACDPGLSRTC DQNTYLSGLCYLFRQNLQGPMLQGRPGFQECIKGNVDLVFLFDGSMS LQPDEFQKILDFMKDVMKKLSNTSYQFAAVQFSTSYKTEFDFSDYVK RKDPDALLKHVKHMLLLTNTFGAINYVATEVFREELGARPDATKVLI IITDGEATDSGNIDAAKDIIRYIIGIGKHFQTKESQETLHKFASKPA SEFVKILDTFEKLKDLFTELQKKIYVIEGTSKQDLTSFNMELSSSGI SADLSRGHAVVGAVGAKDWAGGFLDLKADLQDDTFIGNEPLTPEVRA GYLGYTVTWLPSRQKTSLLASGAPRYQHMGRVLLFQEPQGGGHWSQV QTIHGTQIGSYFGGELCGVDVDQDGETELLLIGAPLFYGEQRGGRVF IYQRRQLGFEEVSELQGDPGYPLGRFGEAITALTDINGDGLVDVAVG APLEEQGAVYIFNGRHGGLSPQPSQRIEGTQVLSGIQWFGRSIHGVK DLEGDGLADVAVGAESQMIVLSSRPVVDMVTLMSFSPAEIPVHEVEC SYSTSNKMKEGVNITICFQIKSLIPQFQGRLVANLTYTLQLDGHRTR RRGLFPGGRHELRRNIAVTTSMSCTDFSFHFPVCVQDLISPINVSLN FSLWEEEGTPRDQRAQGKDIPPILRPSLHSETWEIPFEKNCGEDKKC EANLRVSFSPARSRALRLTAFASLSVELSLSNLEEDAYWVQLDLHFP PGLSFRKVEMLKPHSQIPVSCEELPEESRLLSRALSCNVSSPIFKAG HSVALQMMFNTLVNSSWGDSVELHANVTCNNEDSDLLEDNSATTIIP ILYPINILIQDQEDSTLYVSFTPKGPKIHQVKHMYQVRIQPSIHDHN IPTLEAVVGVPQPPSEGPITHQWSVQMEPPVPCHYEDLERLPDAAEP CLPGALFRCPVVFRQEILVQVIGTLELVGEIEASSMFSLCSSLSISF NSSKHFHLYGSNASLAQVVMKVDVVYEKQMLYLYVLSGIGGLLLLLL IFIVLYKVGFFKRNLKEKMEAGRGVPNGIPAEDSEQLASGQEAGDPG CLKPLHEKDSESGGGKD | LFA-1α (homo sapiens) |
| 72 | QECTKFKVSSCRECIESGPGCTWCQKLNFTGPGDPDSIRCDTRPQLL MRGCAADDIMDPTSLAETQEDHNGGQKQLSPQKVTLYLRPGQAAAFN VTFRRAKGYPIDLYYLMDLSYSMLDDLRNVKKLGGDLLRALNEITES GRIGFGSFVDKTVLPFVNTHPDKLRNPCPNKEKECQPPFAFRHVLKL TNNSNQFQTEVGKQLISGNLDAPEGGLDAMMQVAACPEEIGWRNVTR LLVFATDDGFHFAGDGKLGAILTPNDGRCHLEDNLYKRSNEFDYPSV GQLAHKLAENNIQPIFAVTSRMVKTYEKLTEIIPKSAVGELSEDSSN VVQLIKNAYNKLSSRVFLDHNALPDTLKVTYDSFCNSGVTHRNQPRG DCDGVQINVPITFQVKVTATECIQEQSFVIRALGFTDIVTVQVLPQC ECRCRDQSRDRSLCHGKGFLECGICRCDTGYIGKNCECQTGRSSQE LEGSCRKDNNSIICSGLGDCVCGQCLCHTSDVPGKLIYGQYCECDTI NCERYNGQVCGGPGRGLCFCGKCRCHPGFEGSACQCERTTEGCLNPR RVECSGRGRCRCNVCECHSGYQLPLCQECPGCPSPCGKYISCAECLK FEKGPFGKNCSAACPGLQLSNNPVKGRTCKERDSEGCWVAYTLEQQD GMDRYLIYVDESRECVAGPNIAAIVGGTVAGIVLIGILLLVIWKALI HLSDLREYRRFEKEKLKSQWNNDNPLFKSATTTVMNPKFAES | LFA-1β (homo sapiens) |
| 73 | DFLAHHGTDCWTYHYSEKPMNWQRARRFCRDNYTDLVAIQNKAEIEY LEKTLPFSRSYYWIGIRKIGGIWTWVGTNKSLTEEAENWGDGEPNNK KNKEDCVEIYIKRNKDAGKWNDDACHKLKAALCYTASCQPWSCSGHG ECVEIINNYTCNCDVGYYGPQCQFVIQCEPLEAPELGTMDCTHPLGN FSFSSQCAFSCSEGTNLTGIEETTCGPFGNWSSPEPTCQVIQCEPLS APDLGIMNCSHPLASFSFTSACTFICSEGTELIGKKKTICESSGIWS NPSPICQKLDKSFSMIKEGDYNPLFIPVAVMVTAFSGLAFIIWLARR LKKGKKSKRSMNDPY | L-selectin (homo sapiens) |
| 74 | FKIETTPESRYLAQIGDSVSLTCSTTGCESPFFSWRTQIDSPLNGKV TNEGTTSTLTMNPVSFGNEHSYLCTATCESRKLEKGIQVEIYSFPKD PEIHLSGPLEAGKPITVKCSVADVYPFDRLEIDLLKGDHLMKSQEFL EDADRKSLETKSLEVTFTPVIEDIGKVLVCRAKLHIDEMDSVPTVRQ AVKELQVYISPKNTVISVNPSTKLQEGGSVTMTCSSEGLPAPEIFWS KKLDNGNLQHLSGNATLTLIAMRMEDSGIYVCEGVNLIGKNRKEVEL IVQEKPFTVEISPGPRIAAQIGDSVMLTCSVMGCESPSFSWRTQIDS PLSGKVRSEGTNSTLTLSPVSFENEHSYLCTVTCGHKKLEKGIQVEL YSFPRDPEIEMSGGLVNGSSVTVSCKVPSVYPLDRLEIELLKGETIL ENIEFLEDTDMKSLENKSLEMTFIPTIEDTGKALVCQAKLHIDDMEF EPKQRQSTQTLYVNVAPRDTTVLVSPSSILEEGSSVNMTCLSQGFPA PKILWSRQLPNGELQPLSENATLTLISTKMEDSGVYLCEGINQAGRS RKEVELIIQVTPKDIKLTAFPSESVKEGDTVIISCTCGNVPETWIIL KKKAETGDTVLKSIDGAYTIRKAQLKDAGVYECESKNKVGSQLRSLT LDVQGRENNKDYFSPELLVLYFASSLIIPAIGMIIYFARKANMKGSY SLVEAQKSKV | VCAM-1 (homo sapiens) |

-continued

| No. | Sequence | Description |
|---|---|---|
| 75 | YNVDTESALLYQGPHNTLFGYSVVLHSHGANRWLLVGAPTANWLANA SVINPGAIYRCRIGKNPGQTCEQLQLGSPNGEPCGKTCLEERDNQWL GVTLSRQPGENGSIVTCGHRWKNIFYIKNENKLPTGGCYGVPPDLRT ELSKRIAPCYQDYVKKFGENFASCQAGISSFYTKDLIVMGAPGSSYW TGSLFVYNITTNKYKAFLDKQNQVKFGSYLGYSVGAGHFRSQHTTEV VGGAPQHEQIGKAYIFSIDEKELNILHEMKGKKLGSYFGASVCAVDL NADGFSDLLVGAPMQSTIREEGRVFVYINSGSGAVMNAMETNLVGSD KYAARFGESIVNLGDIDNDGFEDVAIGAPQEDDLQGAIYIYNGRADG ISSTFSQRIEGLQISKSLSMFGQSISGQIDADNNGYVDVAVGAFRSD SAVLLRTRPVVIVDASLSHPESVNRTKFDCVENGWPSVCIDLTLCFS YKGKEVPGYIVLFYNMSLDVNRKAESPPRFYFSSNGTSDVITGSIQV SSREANCRTHQAFMRKDVRDILTPIQIEAAYHLGPHVISKRSTEEFP PLQPILQQKKEKDIMKKTINFARFCAHENCSADLQVSAKIGFLKPHE NKTYLAVGSMKTLMLNVSLFNAGDDAYETTLHVKLPVGLYFIKILEL EEKQINCEVTDNSGVVQLDCSIGYIYVDHLSRIDISFLLDVSSLSRA EEDLSITVHATCENEEEMDNLKHSRVTVAIPLKYEVKLTVHGFVNPT SFVYGSNDENEPETCMVEKMNLTFHVINTGNSMAPNVSVEIMVPNSF SPQTDKLFNILDVQTTTGECHFENYQRVCALEQQKSAMQTLKGIVRF LSKTDKRLLYCIKADPHCLNFLCNFGKMESGKEASVHIQLEGRPSIL EMDETSALKFEIRATGFPEPNPRVIELNKDENVAHVLLEGLHHQRPK RYFTIVIISSSLLLGLIVLLLISYVMWKAGFFKRQYKSILQEENRRD SWSYINSKSNDD | VLA-4 (homo sapiens) |
| 76 | YNLDVRGARSFSPPRAGRHFGYRVLQVGNGVIVGAPGEGNSTGSLYQ CQSGTGHCLPVTLRGSNYTSKYLGMTLATDPTDGSILACDPGLSRTC DQNTYLSGLCYLFRQNLQGPMLQGRPGFQECIKGNVDLVLFLFDGSMS LQPDEFQKILDFMKDVMKKLSNTSYQFAAVQFSTSYKTEFDFSDYVK RKDPDALLKHVKHMLLLTNTFGAINYVATEVFREELGARPDATKVLI IITDGEATDSGNIDAAKDIIRYIIGIGKHFQTKESQETLHKFASKPA SEFVKILDTFEKLKDLFTELQKKIYVIEGTSKQDLTSFNMELSSSGI SADLSRGHAVVGAVGAKDWAGGFLDLKADLQDDTFIGNEPLTPEVRA GYLGYTVTWLPSRQKTSLLASGAPRYQHMGRVLLFQEPQGGGHWSQV QTIHGTQIGSYFGGELCGVDVDQDGETELLLIGAPLFYGEQRGGRVF IYQRRQLGFEEVSELQGDPGYPLGRFGEAITALTDINGDGLVDVAVG APLEEQGAVYIFNGRHGGLSPQPSQRIEGTQVLSGIQWFGRSIHGVK DLEGDGLADVAVGAESQMIVLSSRPVVDMVTLMSFSPAEIPVHEVEC SYSTSNKMKEGVNITICFQIKSLIPQFQGRLVANLTYTLQLDGHRTR RRGLFPGGRHELRRNIAVTTSMSCTDFSFHFPVCVQDLISPINVSLN FSLWEEEGTPRDQRAQGKDIPPILRPSLHSETWEIPFEKNCGEDKKC EANLRVSFSPARSRALRLTAFASLSVELSLSNLEEDAYWVQLDLHFP PGLSFRKVEMLKPHSQIPVSCEELPEESRLLSRALSCNVSSPIFKAG HSVALQMMFNTLVNSSWGDSVELHANVTCNNEDSDLLEDNSATTIIP ILYPINILIQDQEDSTLYVSFTPKGPKIHQVKHMYQVRIQPSINHVN IPTLEAVVGVPQPPSEGPITHQWSVQMEPPVPCHYEDLERLPDAAEP CLPGALFRCPVVFRQEILVQVIGTLELVGEIEASSMFSLCSSLSISF NSSKHFHLYGSNASLAQVVMKVDVVYEKQML | LFA-1α Extracellular domain (ECD) |
| 77 | QECTKFKVSSCRECIESGPGCTWCQKLNFTGPGDPDSIRCDTRPQLL MRGCAADDIMDPTSLAETQEDHNGGQKQLSPQKVTLYLRPGQAAAFN VTFRRAKGYPIDLYYLMDLSYSMLDDLRNVKKLGGDLLRALNEITES GRIGFGSFVDKTVLPFVNTHPDKLRNPCPNKEKECQPPFAFRHVLKL TNNSNQFQTEVGKQLISGNLDAPEGGLDAMMQVAACEPEEIGWRNVTR LLVFATDDGFHFAGDGKLGAILTPNDGRCHLEDNLYKRSNEFDYPSV GQLAHKLAENNIQPIFAVTSRMVKTYEKLTEIIPKSAVGELSEDSSN VVQLIKNAYNKLSSRVFLDHNALPDTLKVTYDSFCSNGVTHRNQPRG DCDGVQINVPITFQVKVTATECIQEQSFVIRALGFTDIVTVQVLPQC ECRCRDQSRDRSLCHGKGFLECGICRCDTGYIGKNCECQTQGRSSQE LEGSCRKDNNSIICSGLGDCVCGQCLCHTSDVPGKLIYGQYCECDTI NCERYNGQVCGGPGRGLCFCGKCRCHPGFEGSACQCERTTEGCLNPR RVECSGRGRCRCNVCECHSGYQLPLCQECPGCPSPCGKYISCAECLK FEKGPPGKNCSAACPGLQLSNNPVKGRTCKERDSEGCWVAYTLEQQD GMDRYLIYVDESRECVAGPN | LFA-1β Extracellular Domain (ECD) |
| 78 | WTYHYSEKPMNWQRARRFCRDNYTDLVAIQNKAEIEYLEKTLPFSRS YYWIGIRKIGGIWTWVGTNKSLTEEAENWGDGEPNNKKNKEDCVEIY IKRNKDAGKWNDDACHKLKAALCYTASCQPWSCSGHGECVEIINNYT CNCDVGYYGPQCQFVIQCEPLEAPELGTMDCTHPLGNFSFSSQCAFS CSEGTNLTGIEETTCGPFGNWSSPEPTCQVIQCEPLSAPDLGIMNCS HPLASFSFTSACTFICSEGTELIGKKKTICESSGIWSNPSPICQKLD KSFSMIKEGDYN | L-selectin Extracellular Domain (ECD) |
| 79 | FKIETTPESRYLAQIGDSVSLTCSTTGCESPFFSWRTQIDSPLNGKV TNEGTTSTLTMNPVSFGNEHSYLCTATCESRKLEKGIQVEIYSFPKD PEIHLSGPLEAGKPITVKCSVADVYPFDRLEIDLLKGDHLMKSQEFL EDADRKSLETKSLEVTFTPVIEDIGKVLVCRAKLHIDEMDSVPTVRQ | VCAM-1 Extracellular Domain (ECD) |

| No. | Sequence | Description |
|---|---|---|
| | AVKELQVYISPKNTVISVNPSTKLQEGGSVTMTCSSEGLPAPEIFWS<br>KKLDNGNLQHLSGNATLTLIAMRMEDSGIYVCEGVNLIGKNRKEVEL<br>IVQEKPFTVEISPGPRIAAQIGDSVMLTCSVMGCESPSFSWRTQIDS<br>PLSGKVRSEGTNSTLTLSPVSFENEHSYLCTVTCGHKKLEKGIQVEL<br>YSFPRDPEIEMSGGLVNGSSVTVSCKVPSVYPLDRLEIELLKGETIL<br>ENIEFLEDTDMKSLENKSLEMTFIPTIEDTGKALVCQAKLHIDDMEF<br>EPKQRQSTQTLYVNVAPRDTTVLVSPSSILEEGSSVNMTCLSQGFPA<br>PKILWSRQLPNGELQPLSENATLTLISTKMEDSGVYLCEGINQAGRS<br>RKEVELIIQVTPKDIKLTAFPSESVKEGDTVIISCTCGNVPETWIIL<br>KKKAETGDTVLKSIDGAYTIRKAQLKDAGVYECESKNKVGSQLRSLT<br>LDVQGRENNKDYFSPE | |
| 80 | NVDTESALLYQGPHNTLFGYSVVLHSHGANRWLLVGAPTANWLANAS<br>VINPGAIYRCRIGKNPGQTCEQLQLGSPNGEPCGKTCLEERDNQWLG<br>VTLSRQPGENGSIVTCGHRWKNIFYIKNENKLPTGGCYGVPPDLRTE<br>LSKRIAPCYQDYVKKFGENFASCQAGISSFYTKDLIVMGAPGSSYWT<br>GSLFVYNITTNKYKAFLDKQNQVKFGSYLGYSVGAGHFRSQHTTEVV<br>GGAPQHEQIGKAYIFSIDEKELNILHEMKGKKLGSYFGASVCAVDLN<br>ADGFSDLLVGAPMQSTIREEGRVFVYINSGSGAVMNAMETNLVGSDK<br>YAARFGESIVNLGDIDNDGFEDVAIGAPQEDDLQGAIYIYNGRADGI<br>SSTFSQRIEGLQISKSLSMFGQSISGQIDADNNGYVDVAVGAFRSDS<br>AVLLRTRPVVIVDASLSHPESVNRTKFDCVENGWPSVCIDLTLCFSY<br>KGKEVPGYIVLFYNMSLDVNRKAESPPRFYFSSNGTSDVITGSIQVS<br>SREANCRTHQAFMRKDVRDILTPIQIEAAYHLGPHVISKRSTEEFPP<br>LQPILQQKKEKDIMKKTINFARFCAHENCSADLQVSAKIGFLKPHEN<br>KTYLAVGSMKTLMLNVSLFNAGDDAYETTLHVKLPVGLYFIKILELE<br>EKQINCEVTDNSGVVQLDCSIGYIYVDHLSRIDISFLLDVSSLSRAE<br>EDLSITVHATCENEEEMDNLKHSRVTVAIPLKYEVKLTVHGFVNPTS<br>FVYGSNDENEPETCMVEKMNLTFHVINTGNSMAPNVSVEIMVPNSFS<br>PQTDKLFNILDVQTTTGECHFENYQRVCALEQQKSAMQTLKGIVRFL<br>SKTDKRLLYCIKADPHCLNFLCNFGKMESGKEASVHIQLEGRPSILE<br>MDETSALKFEIRATGFPEPNPRVIELNKDENVAHVLLEGLHHQRPKR<br>YFT | VLA-4 Extracellular Domain (ECD) |
| 81 | QGCPTLAGILDINFLINKMQEDPASKCHCSANVTSCLCLGIPSDNCT<br>RPCFSERLSQMTNTTMQTRYPLIFSRVKKSVEVLKNNKCPYFSCEQP<br>CNQTTAGNALTFLKSLLEIFQKEKMRGMRGKI | IL-9 |

What is claimed:

1. A method for culturing T cells, the method comprising:
(a) incubating a composition comprising CD3+ T cells in the presence of a first receptor-binding agent and a second receptor-binding agent, wherein:
the first receptor-binding agent (i) is reversibly bound to a soluble reagent via a first binding partner comprised by the first receptor-binding agent and (ii) comprises an anti-CD3 antibody or antibody fragment or a proteinaceous CD3 binding molecule that specifically binds to a CD3 molecule on the surface of the CD3+ T cells in a manner that induces a TCR/CD3 complex-associated signal in CD3+ T cells in the composition,
the second receptor-binding agent (i) is reversibly bound to the reagent via a second binding partner comprised by the second receptor-binding agent and (ii) comprises an anti-CD28 antibody or antibody fragment or a proteinaceous CD28 binding molecule that specifically binds to a CD28 molecule on the surface of the CD3+ T cells in a manner that induces a costimulatory signal in CD3+ T cells in the composition,
the reagent is soluble in a culture medium and is not immobilized on a solid support, and
the incubation effects the stimulation or expansion of T cells in the composition; and
(b) disrupting the reversible binding between the first receptor-binding agent and the reagent and the second receptor-binding agent and the reagent on any of days 1-5 after initiation of said incubation, thereby generating cultured CD3+ T cells wherein the reagent comprises a streptavidin mutein or an avidin mutein that reversibly binds to biotin, a biotin analog, or a streptavidin-binding peptide.

2. The method of claim 1, wherein the CD3+ T cells are primary cells from a subject.

3. The method of claim 1, wherein the reagent comprises an oligomer or polymer of a streptavidin mutein.

4. The method of claim 1, wherein the reagent comprises a streptavidin mutein comprising the amino acid sequence Val$^{44}$-Thr$^{45}$-Ala$^{46}$-Arg$^{47}$ or Ile$^{44}$-Gly$^{45}$-Ala$^{46}$-Arg$^{47}$ at sequence positions corresponding to positions 44 to 47 with reference to positions in streptavidin in the sequence of amino acids set forth in SEQ ID NO: 1.

5. The method of claim 1, wherein the reagent comprises a streptavidin mutein that comprises:
(a) the sequence of amino acids set forth in any of SEQ ID NOS: 3-6, 27 and 28;
(b) a sequence of amino acids that exhibits at least 85%, 86%, 87%, 88%, 89%, 90%, 91%, 92%, 93%, 94%, 95%, 96%, 97%, 98%, 99%, or more sequence identity to any of SEQ ID NOS: 3-6, 27 and 28; contains the amino acid sequence corresponding to Val$^{44}$-Thr$^{45}$-Ala$^{46}$-Arg$^{47}$ or Ile$^{44}$-Gly$^{45}$-Ala$^{46}$-Arg$^{47}$ at sequence positions corresponding to positions 44 to 47 with reference to positions in streptavidin in the sequence of amino acids set forth in SEQ ID NO:1; and reversibly binds to biotin, a biotin analog, or a streptavidin-binding peptide; or
(c) a functional fragment of (a) or (b) that reversibly binds to biotin, a biotin analog, or a streptavidin-binding peptide.

6. The method of claim 1, wherein:
the first binding partner comprises a streptavidin-binding peptide selected from the group consisting of Trp-Ser-His-Pro-Gln-Phe-Glu-Lys (SEQ ID NO: 8), Trp-Ser-His-Pro-Gln-Phe-Glu-Lys-(GlyGlyGlySer)3-Trp-Ser-His-Pro-Gln-Phe-Glu-Lys (SEQ ID NO: 17), Trp-Ser-His-Pro-Gln-Phe-Glu-Lys-(GlyGlyGlySer)2-Trp-Ser-His-Pro-Gln-Phe-Glu-Lys (SEQ ID NO: 18), Trp-Ser-His-Pro-Gln-Phe-Glu-Lys-(GlyGlyGlySer)2Gly-Gly-Ser-Ala-Trp-Ser-His-Pro-Gln-Phe-Glu-Lys (SEQ ID NO: 19), Trp-Arg-His-Pro-Gln-Phe-Gly-Gly (SEQ ID NO: 7), SAWSHPQFEKGGGSGGGSGGGSWSHPQFEK (SEQ ID NO: 15), and SAWSHPQFEK(GGGS)$_2$GG-SAWSHPQFEK (SEQ ID NO: 16); and
the reagent comprises a streptavidin mutein that reversibly binds to the streptavidin-binding peptide.

7. The method of claim 1, wherein said disruption comprises introducing to the CD3+ T cells a composition comprising a substance capable of reversing the bond between the first receptor-binding agent and the reagent and the second receptor-binding agent and the reagent.

8. The method of claim 7, wherein:
the reagent comprises a streptavidin mutein; and
the substance comprises a streptavidin-binding peptide, biotin, or a biotin analog.

9. The method of claim 1, wherein said disruption is carried out between about 1 day and about 3 days after initiation of said incubation.

10. The method of claim 1, wherein said disruption is carried out about 2 days after initiation of said incubation.

11. The method of claim 1, wherein the first binding partner comprises a streptavidin-binding peptide comprising the sequence set forth in SEQ ID NO: 16, and the reagent comprises a streptavidin mutein that reversibly binds to the streptavidin-binding peptide.

12. The method of claim 7, wherein:
the reagent comprises a streptavidin mutein; and
the substance comprises D-biotin.

13. The method of claim 1, wherein the first receptor-binding agent comprises an anti-CD3 antibody or antibody fragment, and the second receptor-binding agent comprises an anti-CD28 antibody or antibody fragment.

14. The method of claim 1, wherein the first receptor-binding agent comprises an anti-CD3 antibody fragment, and the second receptor-binding agent comprises an anti-CD28 antibody fragment.

15. The method of claim 13, wherein the reagent comprises a streptavidin mutein comprising the amino acid sequence Val$^{44}$-Thr$^{45}$-Ala$^{46}$-Arg$^{47}$ or Ile$^{44}$-Gly$^{45}$-Ala$^{46}$-Arg$^{47}$ at sequence positions corresponding to positions 44 to 47 with reference to positions in streptavidin in the sequence of amino acids set forth in SEQ ID NO:1.

16. The method of claim 13, wherein the reagent comprises a streptavidin mutein that comprises:

(a) the sequence of amino acids set forth in any of SEQ ID NOS: 3-6, 27 and 28;
(b) a sequence of amino acids that exhibits at least 85%, 86%, 87%, 88%, 89%, 90%, 91%, 92%, 93%, 94%, 95%, 96%, 97%, 98%, 99%, or more sequence identity to any of SEQ ID NOS: 3-6, 27 and 28; contains the amino acid sequence corresponding to $Val^{44}$-$Thr^{45}$-$Ala^{46}$-$Arg^{47}$ or $Ile^{44}$-$Gly^{45}$-$Ala^{46}$-$Arg^{47}$ at sequence positions corresponding to positions 44 to 47 with reference to positions in streptavidin in the sequence of amino acids set forth in SEQ ID NO:1; and reversibly binds to biotin, a biotin analog, or a streptavidin-binding peptide; or
(c) a functional fragment of (a) or (b) that reversibly binds to biotin, a biotin analog, or a streptavidin-binding peptide.

17. The method of claim 13, wherein:
the first binding partner comprises a streptavidin-binding peptide comprising the sequence set forth in any of SEQ ID NOs: 7, 8, and 15-19;
the second binding partner comprises a streptavidin-binding peptide comprising the sequence set forth in any of SEQ ID NOs: 7, 8, and 15-19; and
the reagent comprises a streptavidin mutein that reversibly binds to the streptavidin-binding peptides of the first and second binding partners.

18. The method of claim 13, wherein the first and second binding partners each comprise a streptavidin-binding peptide comprising the sequence set forth in SEQ ID NO: 16, and the reagent comprises a streptavidin mutein that reversibly binds to the streptavidin-binding peptide.

19. The method of claim 13, wherein said disruption is carried out between about 1 day and about 3 days after initiation of said incubation.

20. The method of claim 13, wherein said disruption is carried out about 2 days after initiation of said incubation.

21. The method of claim 13, wherein:
the reagent comprises a streptavidin mutein; and
said disruption comprises introducing to the CD3+ T cells a composition comprising a streptavidin-binding peptide, biotin, or a biotin analog capable of reversing the bond between the first and second receptor-binding agents and the reagent.

22. The method of claim 13, wherein:
the reagent comprises a streptavidin mutein; and
said disruption comprises introducing to the CD3+ T cells a composition comprising D-biotin.

23. The method of claim 18, wherein said disruption is carried out between about 1 day and about 3 days after initiation of said incubation.

24. The method of claim 18, wherein said disruption is carried out about 2 days after initiation of said incubation.

25. The method of claim 18, wherein said disruption comprises introducing to the CD3+ T cells a composition comprising a streptavidin-binding peptide, biotin, or a biotin analog capable of reversing the bond between the first and second receptor-binding agents and the reagent.

26. The method of claim 18, wherein said disruption comprises introducing to the CD3+ T cells a composition comprising D-biotin.

27. The method of claim 1, wherein:
the second binding partner comprises a streptavidin-binding peptide selected from the group consisting of Trp-Ser-His-Pro-Gln-Phe-Glu-Lys (SEQ ID NO: 8), Trp-Ser-His-Pro-Gln-Phe-Glu-Lys-(GlyGlyGlySer)3-Trp-Ser-His-Pro-Gln-Phe-Glu-Lys (SEQ ID NO: 17), Trp-Ser-His-Pro-Gln-Phe-Glu-Lys-(GlyGlyGlySer)2-Trp-Ser-His-Pro-Gln-Phe-Glu-Lys (SEQ ID NO: 18), Trp-Ser-His-Pro-Gln-Phe-Glu-Lys-(GlyGlyGlySer) 2Gly-Gly-Ser-Ala-Trp-Ser-His-Pro-Gln-Phe-Glu-Lys (SEQ ID NO: 19), Trp-Arg-His-Pro-Gln-Phe-Gly-Gly (SEQ ID NO: 7), SAWSHPQFEKGGGSGGGSGGGSWSHPQFEK (SEQ ID NO: 15), and SAWSHPQFEK(GGGS)$_2$GG-SAWSHPQFEK (SEQ ID NO: 16); and
the reagent comprises a streptavidin mutein that reversibly binds to the streptavidin-binding peptide.

28. The method of claim 4, wherein the streptavidin mutein comprises the sequence of amino acids set forth in any of SEQ ID NOS: 3-6, 27 and 28.

29. The method of claim 15, wherein the streptavidin mutein comprises the sequence of amino acids set forth in any of SEQ ID NOS: 3-6, 27 and 28.

30. The method of claim 17, wherein the streptavidin mutein comprises the sequence of amino acids set forth in any of SEQ ID NOS: 3-6, 27 and 28.

31. The method of claim 23, wherein the streptavidin mutein comprises the sequence of amino acids set forth in any of SEQ ID NOS: 3-6, 27 and 28.

32. The method of claim 14, wherein the antibody fragment is a divalent antibody fragment selected from a F(ab')$_2$-fragment and a divalent single-chain Fv (scFv) fragment.

33. The method of claim 14, wherein the antibody fragment is a monovalent antibody fragment selected from a Fab fragment, an Fv fragment, and an scFv fragment.

34. The method of claim 14, wherein the antibody fragment is a Fab fragment.

35. The method of claim 1, wherein each of the first and second receptor-binding agent comprises a proteinaceous binding molecule with antibody-like binding properties independently selected from aptamers, muteins based on a polypeptide of the lipocalin family, glubodies, proteins based on the ankyrin scaffold, proteins based on the crystalline scaffold, adnectins, and avimers.

36. The method of claim 30, wherein said disruption comprises introducing to the CD3+ T cells a composition comprising biotin or a biotin analog capable of reversing the bond between the first and second receptor-binding agents and the reagent.

37. The method of claim 30, wherein said disruption comprises introducing to the CD3+ T cells a composition comprising D-biotin.

38. The method of claim 17, wherein the streptavidin mutein comprises the amino acid sequence $Val^{44}$-$Thr^{45}$-$Ala^{46}$-$Arg^{47}$ or $Ile^{44}$-$Gly^{45}$-$Ala^{46}$-$Arg^{47}$ at sequence positions corresponding to positions 44 to 47 with reference to positions in streptavidin in the sequence of amino acids set forth in SEQ ID NO:1.

39. The method of claim 38, wherein said disruption comprises introducing to the CD3+ T cells a composition comprising biotin or a biotin analog capable of reversing the bond between the first and second receptor-binding agents and the reagent.

40. The method of claim 38, wherein said disruption comprises introducing to the CD3+ T cells a composition comprising D-biotin.

41. The method of claim 34, wherein the reagent comprises a streptavidin mutein comprising the amino acid sequence $Val^{44}$-$Thr^{45}$-$Ala^{46}$-$Arg^{47}$ or $Ile^{44}$-$Gly^{45}$-$Ala^{46}$-$Arg^{47}$ at sequence positions corresponding to positions 44 to 47 with reference to positions in streptavidin in the sequence of amino acids set forth in SEQ ID NO:1.

42. The method of claim 34, wherein the reagent comprises a streptavidin mutein comprising the sequence of amino acids set forth in any of SEQ ID NOS: 3-6, 27 and 28.

43. The method of claim 34, wherein:
the first binding partner comprises a streptavidin-binding peptide comprising the sequence set forth in any of SEQ ID NOs: 7, 8, and 15-19;
the second binding partner comprises a streptavidin-binding peptide comprising the sequence set forth in any of SEQ ID NOs: 7, 8, and 15-19; and
the reagent comprises a streptavidin mutein that reversibly binds to the streptavidin-binding peptides of the first and second binding partners.

44. The method of claim 34, wherein the first binding partner comprises a streptavidin-binding peptide comprising the sequence set forth in SEQ ID NO: 16, and the reagent comprises a streptavidin mutein that reversibly binds to the streptavidin-binding peptide.

45. The method of claim 43, wherein the streptavidin mutein comprises the amino acid sequence $Val^{44}$-$Thr^{45}$-$Ala^{46}$-$Arg^{47}$ or $Ile^{44}$-$Gly^{45}$-$Ala^{46}$-$Arg^{47}$ at sequence positions corresponding to positions 44 to 47 with reference to positions in streptavidin in the sequence of amino acids set forth in SEQ ID NO:1.

46. The method of claim 43, wherein the streptavidin mutein comprises the sequence of amino acids set forth in any of SEQ ID NOS: 3-6, 27 and 28.

47. The method of claim 43, wherein said disruption comprises introducing to the CD3+ T cells a composition comprising biotin or a biotin analog capable of reversing the bond between the first and second receptor-binding agents and the reagent.

48. The method of claim 43, wherein said disruption comprises introducing to the CD3+ T cells a composition comprising D-biotin.

49. The method of claim 36, wherein the first and second binding partners each comprise a streptavidin-binding peptide comprising the sequence set forth in SEQ ID NO: 16.

50. The method of claim 37, wherein the first and second binding partners each comprise a streptavidin-binding peptide comprising the sequence set forth in SEQ ID NO: 16.

51. The method of claim 17, wherein said disruption comprises introducing to the CD3+ T cells a composition comprising biotin or a biotin analog capable of reversing the bond between the first and second receptor-binding agents and the reagent.

52. The method of claim 17, wherein said disruption comprises introducing to the CD3+ T cells a composition comprising D-biotin.

53. The method of claim 39, wherein the first and second binding partners each comprise a streptavidin-binding peptide comprising the sequence set forth in SEQ ID NO: 16.

54. The method of claim 40, wherein the first and second binding partners each comprise a streptavidin-binding peptide comprising the sequence set forth in SEQ ID NO: 16.

\* \* \* \* \*